(12) United States Patent
Kang et al.

(10) Patent No.: US 12,178,860 B2
(45) Date of Patent: Dec. 31, 2024

(54) HYALURONIDASE ENZYME FORMULATIONS FOR HIGH VOLUME ADMINISTRATION

(71) Applicant: Halozyme, Inc., San Diego, CA (US)

(72) Inventors: David W. Kang, San Diego, CA (US); Robert J. Connor, San Diego, CA (US); Tara Nekoroski, San Diego, CA (US); Todd J. Leadens, II, San Diego, CA (US); Baylor Frantz, San Diego, CA (US); Scott Beacher, San Diego, CA (US); Kevin Swanson, San Diego, CA (US); Mike Travanty, San Diego, CA (US)

(73) Assignee: Halozyme, Inc., San Diego, CA (US)

( * ) Notice: Subject to any disclaimer, the term of this patent is extended or adjusted under 35 U.S.C. 154(b) by 0 days.

(21) Appl. No.: 18/395,001

(22) Filed: Dec. 22, 2023

(65) Prior Publication Data

US 2024/0207375 A1    Jun. 27, 2024

Related U.S. Application Data

(60) Provisional application No. 63/476,830, filed on Dec. 22, 2022, provisional application No. 63/485,108, filed on Feb. 15, 2023, provisional application No. 63/507,125, filed on Jun. 9, 2023, provisional application No. 63/516,732, filed on Jul. 31, 2023, provisional application No. 63/518,057, filed on Aug. 7, 2023, provisional application No. 63/520,524, filed on Aug. 18, 2023.

(51) Int. Cl.
  *A61K 9/00* (2006.01)
  *A61K 38/47* (2006.01)
  *A61K 45/06* (2006.01)

(52) U.S. Cl.
  CPC ............ *A61K 38/47* (2013.01); *A61K 9/0019* (2013.01); *A61K 45/06* (2013.01); *C12Y 302/01035* (2013.01)

(58) Field of Classification Search
  CPC . A61P 43/00; C12Y 302/01035; C07K 16/00; C07K 14/5418; C07K 2317/622; C07K 9/00; C07K 2/00; C07K 14/545; C07K 14/5434
  USPC ..................................................... 424/94.62
  See application file for complete search history.

(56) References Cited

U.S. PATENT DOCUMENTS

| | | | |
|---|---|---|---|
| 7,572,613 B2 | 8/2009 | Klein | |
| 7,767,429 B2 | 8/2010 | Bookbinder et al. | |
| 7,829,081 B2 | 11/2010 | Bookbinder et al. | |
| 7,846,431 B2 | 12/2010 | Bookbinder et al. | |
| 7,871,607 B2 | 1/2011 | Bookbinder et al. | |
| 8,105,586 B2 | 1/2012 | Bookbinder et al. | |
| 8,167,866 B2 | 5/2012 | Klein | |
| 8,187,855 B2 | 5/2012 | Baker et al. | |
| 8,202,517 B2 | 6/2012 | Bookbinder et al. | |
| 8,257,699 B2 | 9/2012 | Bookbinder et al. | |
| 8,343,487 B2 | 1/2013 | Baker et al. | |
| 8,431,124 B2 | 4/2013 | Bookbinder et al. | |
| 8,431,380 B2 | 4/2013 | Bookbinder et al. | |
| 8,450,470 B2 | 5/2013 | Bookbinder et al. | |
| 8,580,252 B2 | 11/2013 | Bookbinder et al. | |
| 8,765,685 B2 | 7/2014 | Bookbinder et al. | |
| 8,772,246 B2 | 7/2014 | Bookbinder et al. | |
| 8,795,654 B2 | 8/2014 | Uvarkina et al. | |
| 8,927,249 B2 | 1/2015 | Wei et al. | |
| 9,084,743 B2 | 7/2015 | Teschner et al. | |
| 9,284,543 B2 | 3/2016 | Wei et al. | |
| 9,393,370 B2 | 7/2016 | Auld et al. | |
| 9,447,401 B2 | 9/2016 | Wei et al. | |
| 9,677,061 B2 | 6/2017 | Bookbinder et al. | |
| 9,677,062 B2 | 6/2017 | Bookbinder et al. | |
| 9,993,529 B2 | 6/2018 | Yang et al. | |
| 10,029,052 B2 | 7/2018 | Auld et al. | |
| 10,137,104 B2 | 11/2018 | Maneval et al. | |
| 10,265,410 B2 | 4/2019 | Shepard et al. | |
| 10,301,376 B2 | 5/2019 | Schiff et al. | |
| 10,610,351 B2 | 4/2020 | McCawley et al. | |
| 10,865,400 B2 | 12/2020 | Wei et al. | |
| 11,041,149 B2 | 6/2021 | Wei et al. | |
| 11,066,656 B2 | 7/2021 | Wei et al. | |
| 2009/0022727 A1 | 1/2009 | Houston | |
| 2009/0311237 A1 | 12/2009 | Frost et al. | |

(Continued)

FOREIGN PATENT DOCUMENTS

| | | |
|---|---|---|
| EP | 2300046 B1 | 12/2014 |
| WO | 2010077297 A1 | 7/2010 |

(Continued)

OTHER PUBLICATIONS

Devos et al., (Proteins: Structure, Function and Genetics, 2000, vol. 41: 98-107.*

(Continued)

*Primary Examiner* — Robert B Mondesi
*Assistant Examiner* — Mohammad Y Meah
(74) *Attorney, Agent, or Firm* — Morgan, Lewis & Bockius LLP

(57) ABSTRACT

In one aspect, the present disclosure provides a formulation comprising a hyaluronidase enzyme and a therapeutically effective amount of an active ingredient. In another aspect, the present disclosure provides a method of administering a high volume of the formulation in a single administration to treat a disease or disorder in a subject.

12 Claims, 199 Drawing Sheets
Specification includes a Sequence Listing.

(56) References Cited

U.S. PATENT DOCUMENTS

| | | |
|---|---|---|
| 2010/0130958 A1 | 5/2010 | Kang et al. |
| 2013/0022592 A1 | 1/2013 | Vaughn et al. |
| 2013/0344048 A1 | 12/2013 | Wasserman et al. |
| 2019/0284263 A1 | 9/2019 | Smith et al. |
| 2020/0232605 A1 | 7/2020 | McCawley et al. |
| 2021/0155913 A1 | 5/2021 | Park et al. |
| 2021/0363270 A1 | 11/2021 | Park et al. |
| 2022/0096603 A1 | 3/2022 | Kiani et al. |
| 2022/0133861 A1 | 5/2022 | Sweis et al. |
| 2022/0233693 A1 | 7/2022 | Huang et al. |
| 2022/0289864 A1 | 9/2022 | Park et al. |
| 2022/0296816 A1 | 9/2022 | Coyne |
| 2024/0009401 A1 | 1/2024 | Coyne |

FOREIGN PATENT DOCUMENTS

| | | |
|---|---|---|
| WO | 2013/102144 A2 | 7/2013 |
| WO | 2020/022791 A1 | 1/2020 |
| WO | 2020/197230 A1 | 10/2020 |
| WO | 2021030210 A1 | 2/2021 |
| WO | 2021/150079 A1 | 7/2021 |
| WO | 2022/031093 A1 | 2/2022 |
| WO | 2022203994 A1 | 9/2022 |
| WO | 2023018952 A1 | 2/2023 |
| WO | 2023/042096 A1 | 3/2023 |

OTHER PUBLICATIONS

Whisstock et al., (Quarterly Reviews of Biophysics 2003, vol. 36 (3): 307-340.*

Witkowski et al., (Biochemistry 38:11643-11650, 1999.*

Kisselev L., (Structure, 2002, vol. 10: 8-9.*

International Search Report and Written Opinion issued in International Patent Application No. PCT/US2023/085807, mailed Apr. 11, 2024, 12 pages.

Badkar, Advait V. et al., "Subcutaneous Delivery of High-Dose/Volume Biologies: Current Status and Prospect for Future Advancements," Drug Design, Development, and Therapy, 2021.

Hylenex recombinant (hyaluronidase human injection), Halozyme Therapeutics, Inc., https://www.accessdata.fda.gov/drugsatfda_docs/label/2008/021859s005lbl.pdf, Approved 2005, revised Apr. 2021. Accessed Dec. 23, 2023.

Gammagard Liquid (immune globulin infusion [human] 10%), Baxalta US Inc, https://www.shirecontent.com/PI/PDFs/Gamliquid_USA_ENG.pdf. Published Mar. 2021. Accessed Dec. 23, 2023.

NCT05059977, "A Study of TAK-881 in Healthy Adults," https://clinicaltrials.gov/search?term=NCT05059977, Accessed Dec. 23, 2023.

NCT04578535, "A Study to Assess the Tolerability, Safety, and Pharmacokinetics of Subcutaneous Immune Globulin Infusion 10% (Human) With Recombinant Human Hyaluronidase (HyQvia/HyQvia) With Ramp-up and No. Ramp-up Dosing in Healthy Adult Participants," https://clinicaltrials.gov/search?term=NCT04578535, Accessed Dec. 23, 2023.

Frost G., "Recombinant Human Hyaluronidase (rHuPH20): An Enabling Platform for Subcutaneous Drug and Fluid Administration," Expert Opin. Drug Deliv., 2007, 4(4):427-440.

HyQvia [Immune Globulin Infusion 10% (Human) with Recombinant Human Hyaluronidase] Solution for subcutaneous administration. Baxalta US Inc., https://www.fda.gov/media/89844/download, Approved 2014, revised Mar. 2021. Accessed Dec. 23, 2023.

Printz, Marie A., "A Phase I Study to Evaluate the Safety, Tolerability, Pharmacokinetics, and Pharmacodynamics of Recombinant Human Hyaluronidase PH20 Administered Intravenously in Healthy Volunteers," Curr Ther Res Clin Exp., Aug. 19, 2020, 93:100604.

Printz, Marie A., "Risk Factors, Hyaluronidase Expression, and Clinical Immunogenicity of Recombinant Human Hyaluronidase PH20, an Enzyme Enabling Subcutaneous Drug Administration." AAPS J., Oct. 20, 2022, 24(6):110.

Rosengren S., "Clinical Immunogenicity of rHuPH20, a Hyaluronidase Enabling Subcutaneous Drug Administration," AAPS J., Sep. 2015, 17(5):1144-56.

* cited by examiner

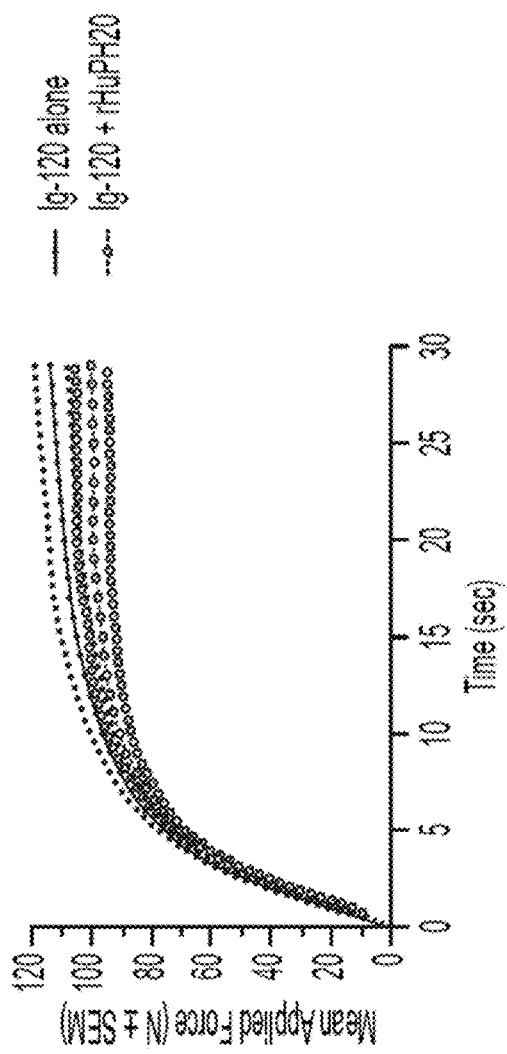
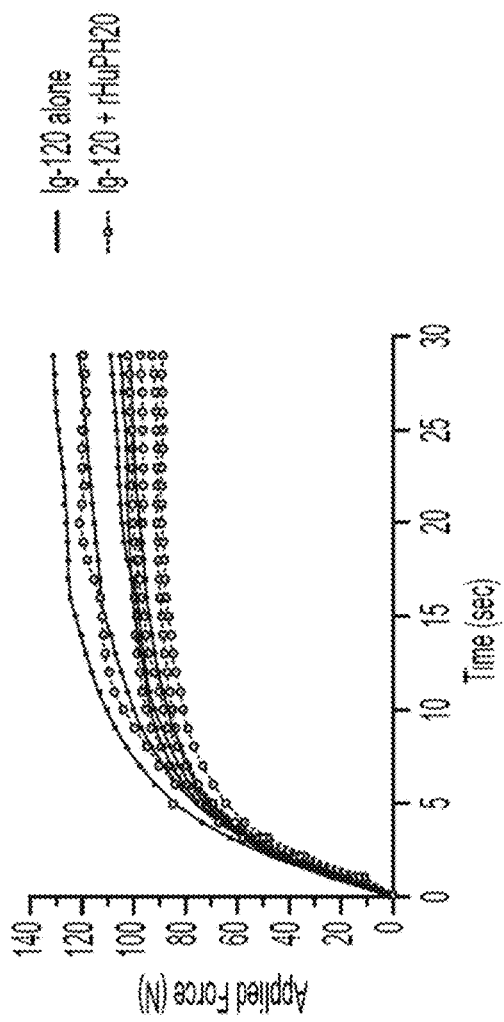
FIG. 1
FIG. 2

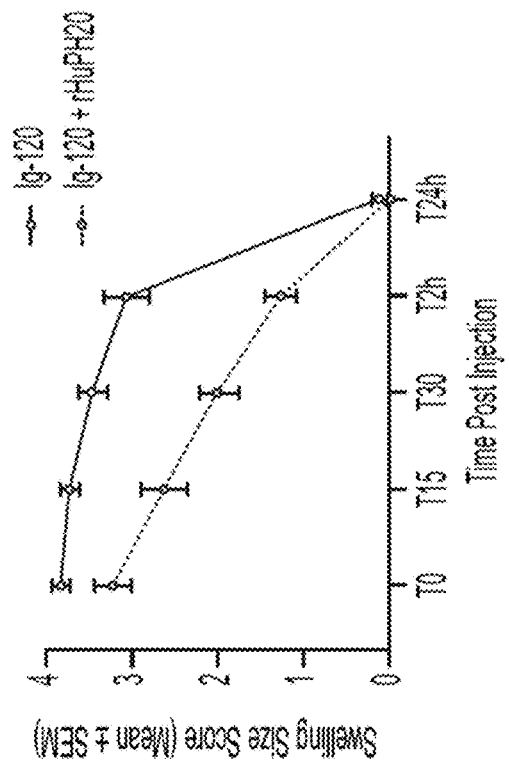
FIG. 12
FIG. 13
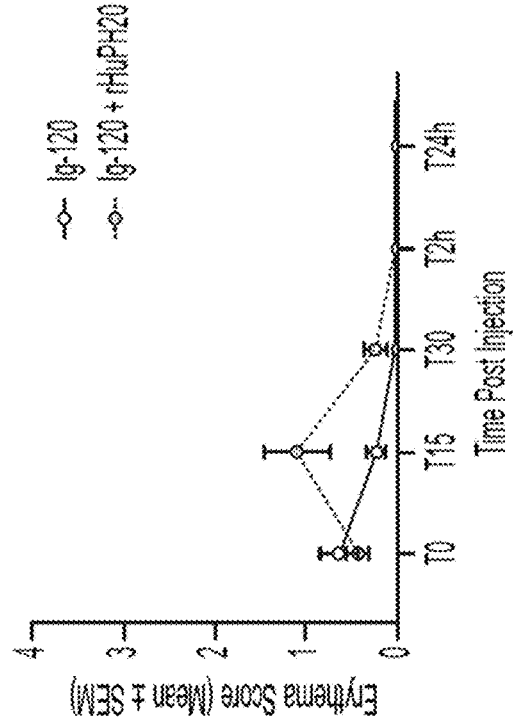
FIG. 14

Sample: 120 g/L Human Ig (unspiked)

Lot Number: 1032-17
Formulation Buffer: 20 mM Histidine, 130 mM NaCl, 0.05% Polysorbate-80, pH 6.5
Storage Temperature: 2-8°C
Sample Prep. Reference: NB01032 p. 1-29
DOM: 21Sep2020  Retest Date: Not Determined

| Test Description | Test Method | Results Reference | Results |
|---|---|---|---|
| Protein Concentration | ATM146 [1] | NB01032 p. 28 | 121.0 mg/mL |
| Endotoxin | No official method used [2] | NB01032 p. 28 | 12.7 EU/mL |
| Enzyme Activity | TM051 (VV-QUAL-00675) | NB01037 p. 12 | N/A – Unspiked sample |
| pH | No official method used [2,3] | NB01032 p. 28 | 6.79 |
| Conductivity | No official method used [2,3] | NB01032 p. 28 | 13.186 mS/cm |
| Density | No official method used [2,3] | NB01032 p. 28 | 1.0381 g/cm³ |
| Osmolality | No official method used [2,3] | NB01037 p. 13 | 376 mOsm/kg |
| Viscosity | No official method used [2,3] | NB00986 p. 70 | 4.6 mPa.s at 20°C |

N/A = Not applicable
[1] ATM146 used for guidance only.
[2] For a complete description of method used, refer to notebook reference.
[3] All measurements were performed on equipment that was either calibrated per Halozyme calibration schedule or on equipment that was calibrated on day of measurement with appropriate standards.

FIG. 15A rHuPH20
Lot Number: 462-022

10 mg/mL rHuPH20, 10 mM Histidine, 130 mM NaCl, pH 6.5

Manufacturer: Halozyme Inc., USA
Storage: -80°C ± 10°C
DOM: Dec. 30, 2014
Retest Date: February 2023

| Test Description | Test Method | Notebook Pages | Result |
|---|---|---|---|
| Enzyme Activity | VV-QUAL-00638 (TM010) | NB 01032 p. 74 | 1,229,456 U/mL |
| Purity by RP-HPLC | ATM026 | NB 01027 p. 90 | rHuPH20: 93.8%<br>Oxidized Form: 5.0%<br>Hydrolyzed Form: 1.2% |
| Purity by SE-HPLC | ATM012 | NB 01027 p. 91 | Main Peak: 99.1%<br>HMW Peak: 0.9% |

FIG. 15B

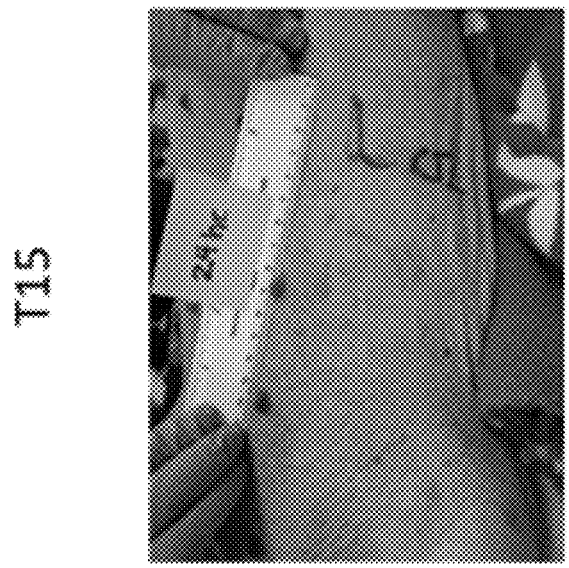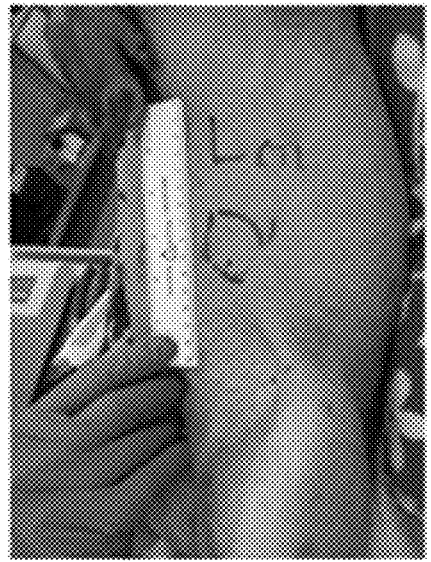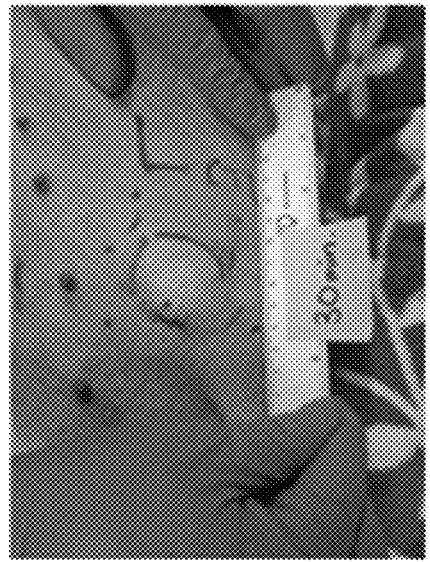
FIG. 16A

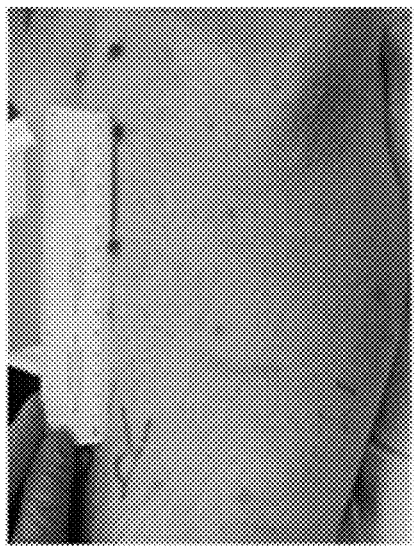
FIG. 16B

AID #1114R: Ig-120
FIG. 17A

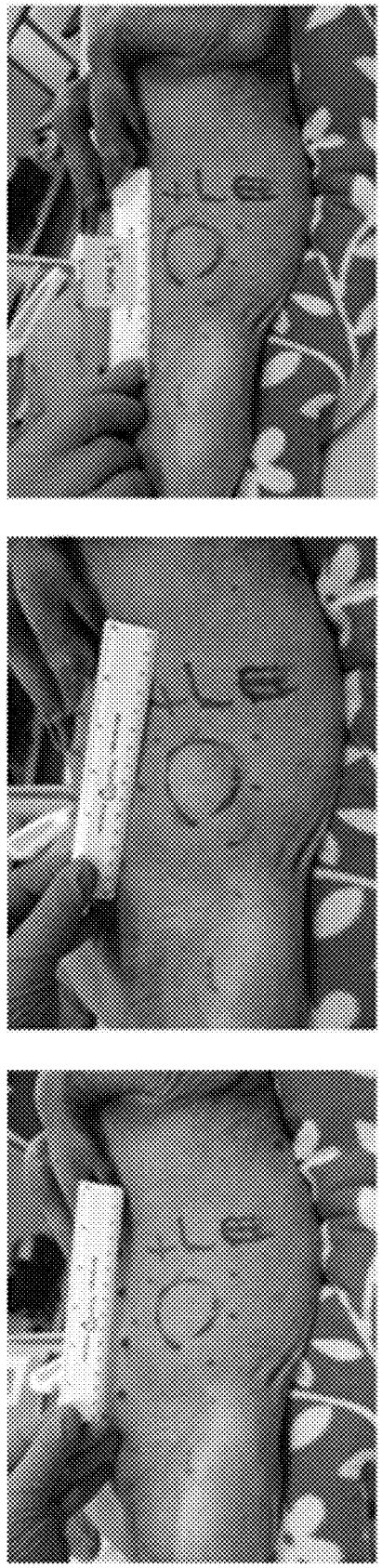
FIG. 17B

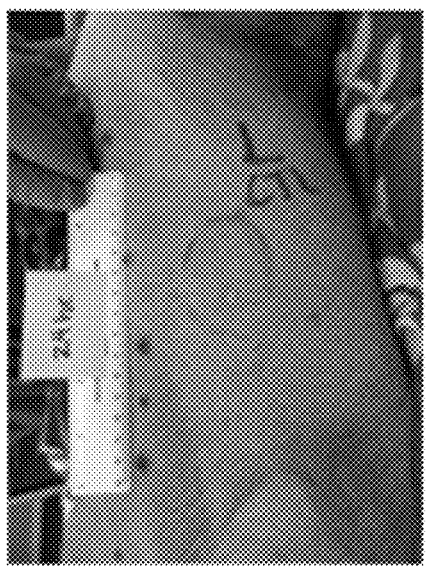
FIG. 18A

FIG. 18B

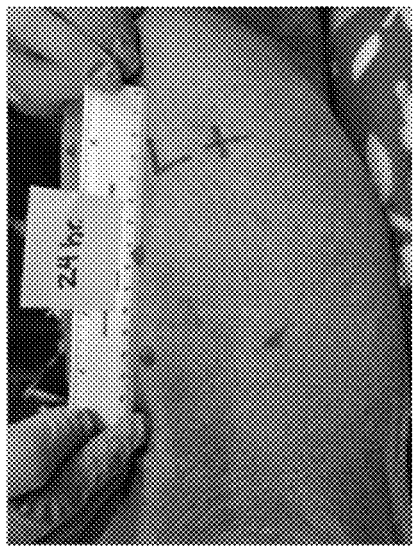
AID #1184L: Ig-120
FIG. 19A

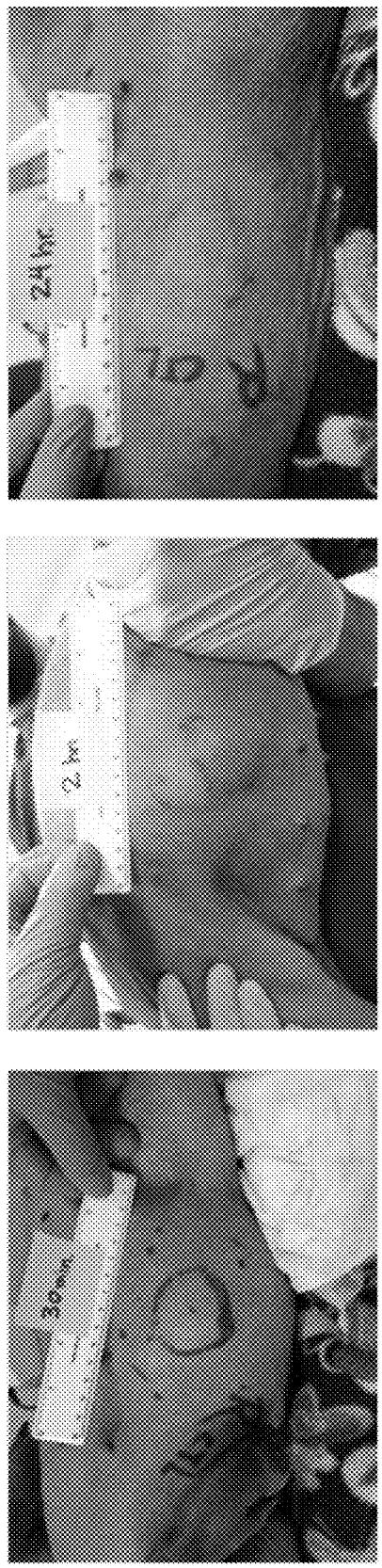
FIG. 19B

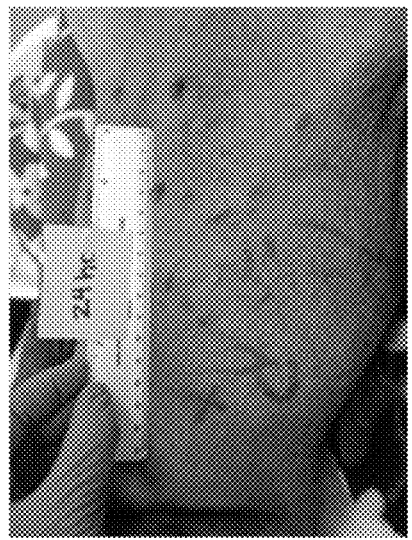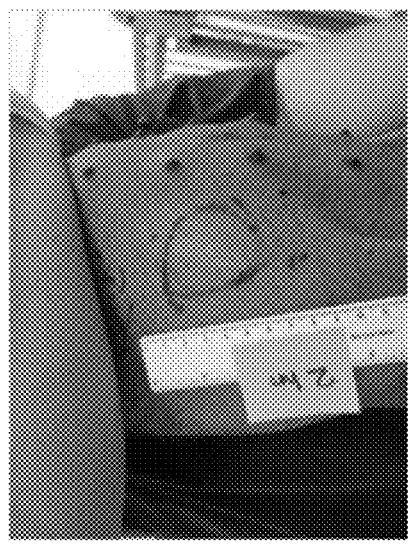
FIG. 20A

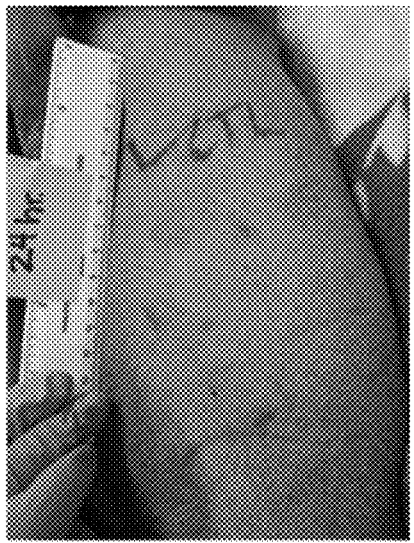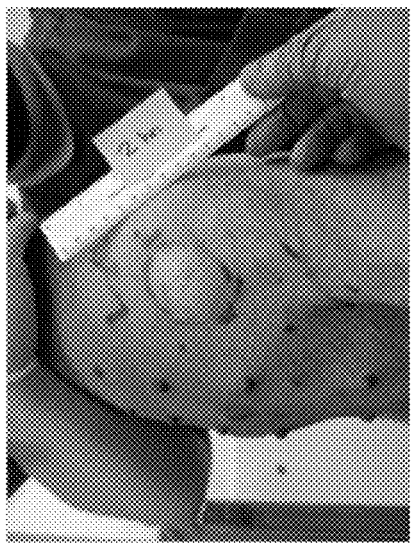
FIG. 20B

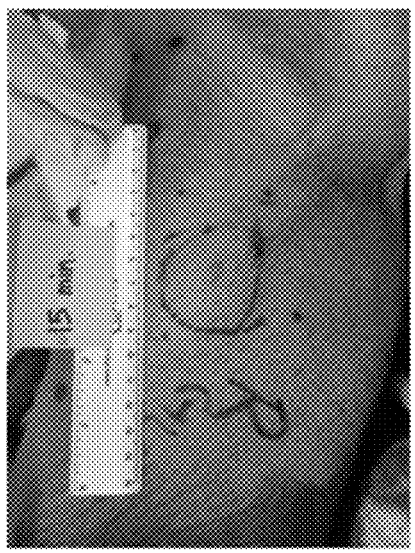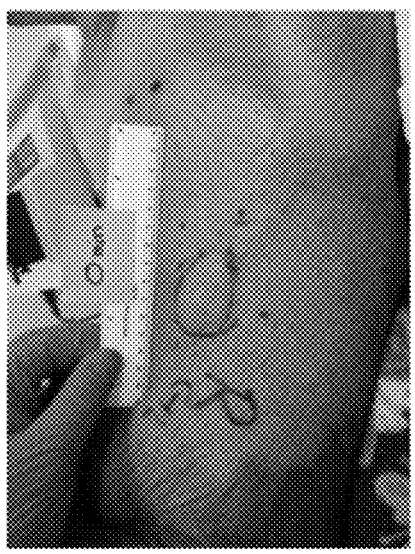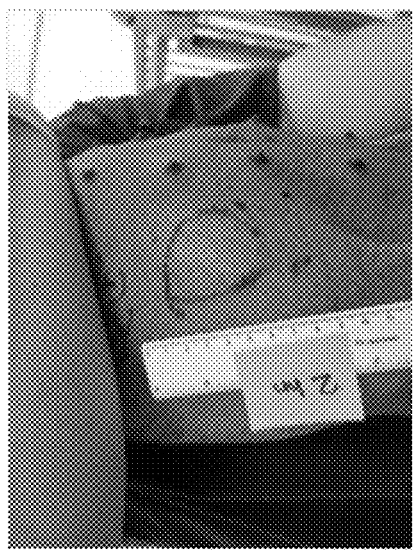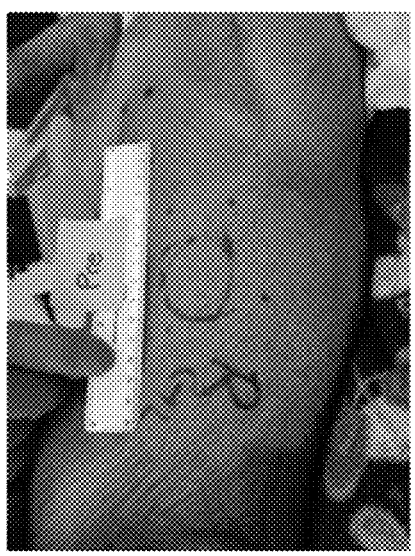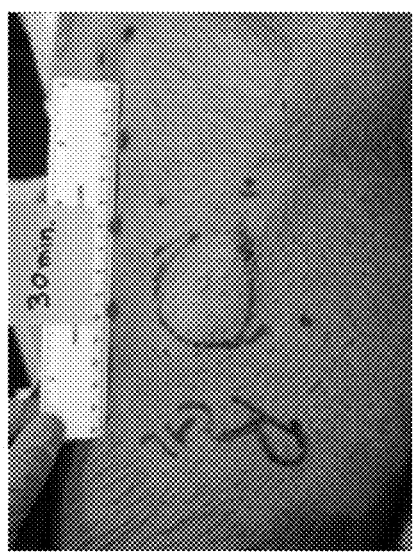
AID #1188R: Ig-120
FIG. 21A

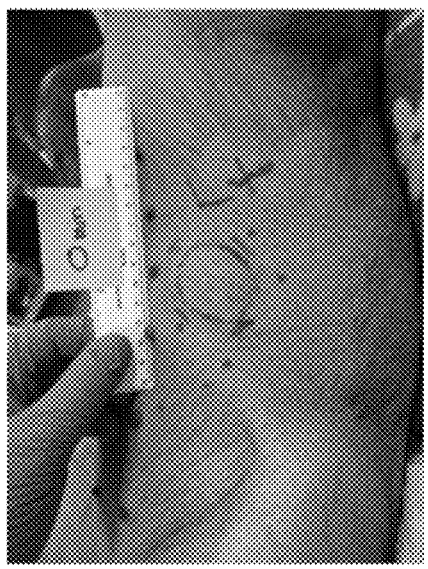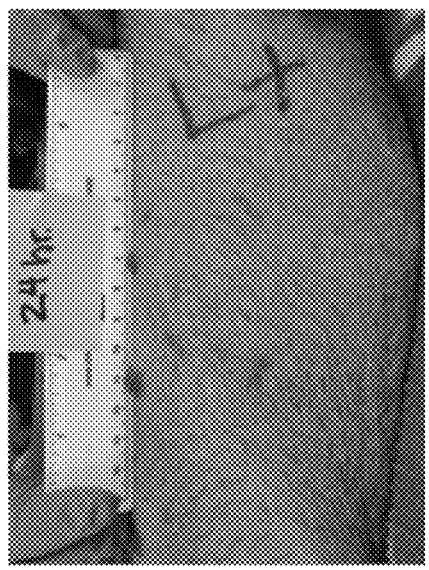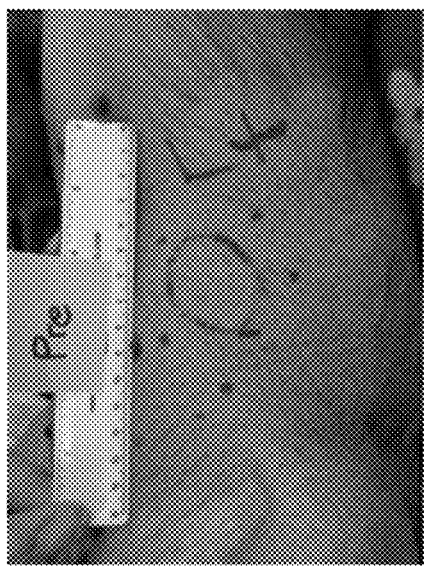
FIG. 21B

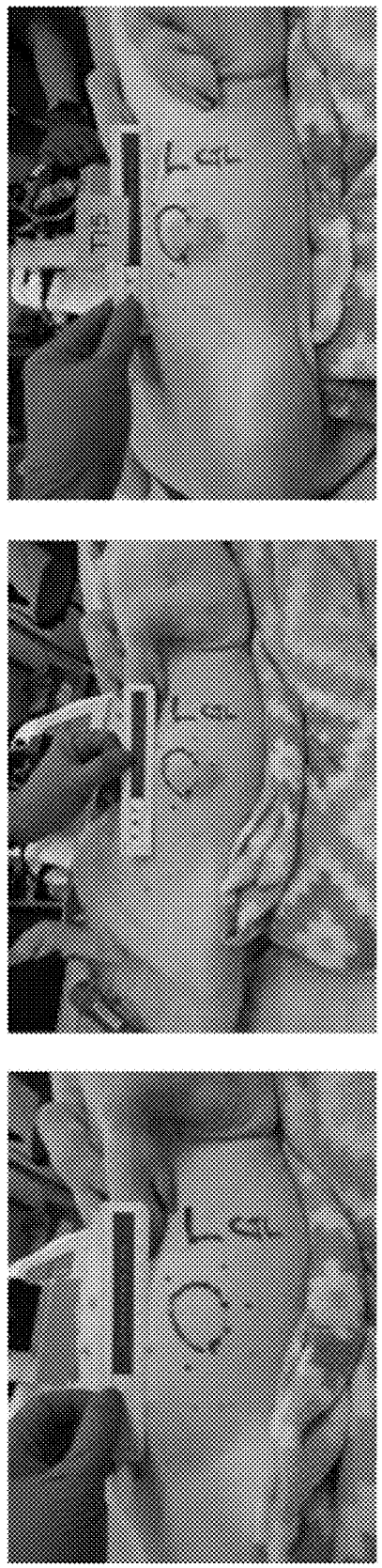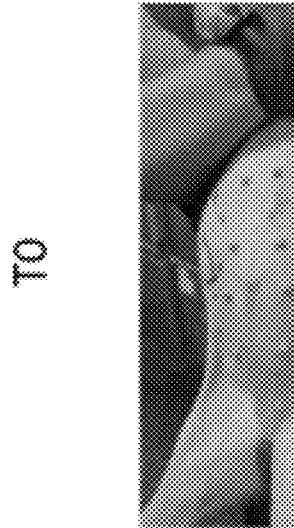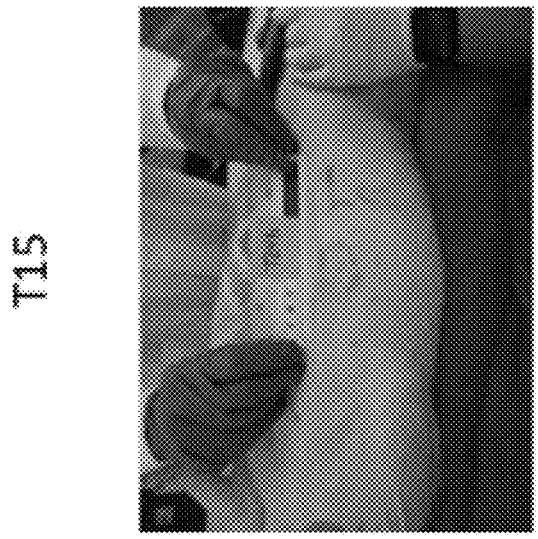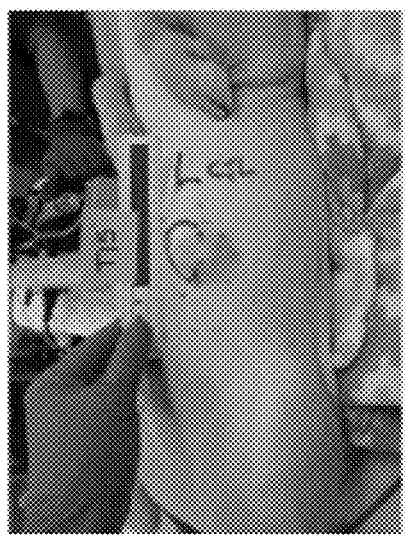
FIG. 36A

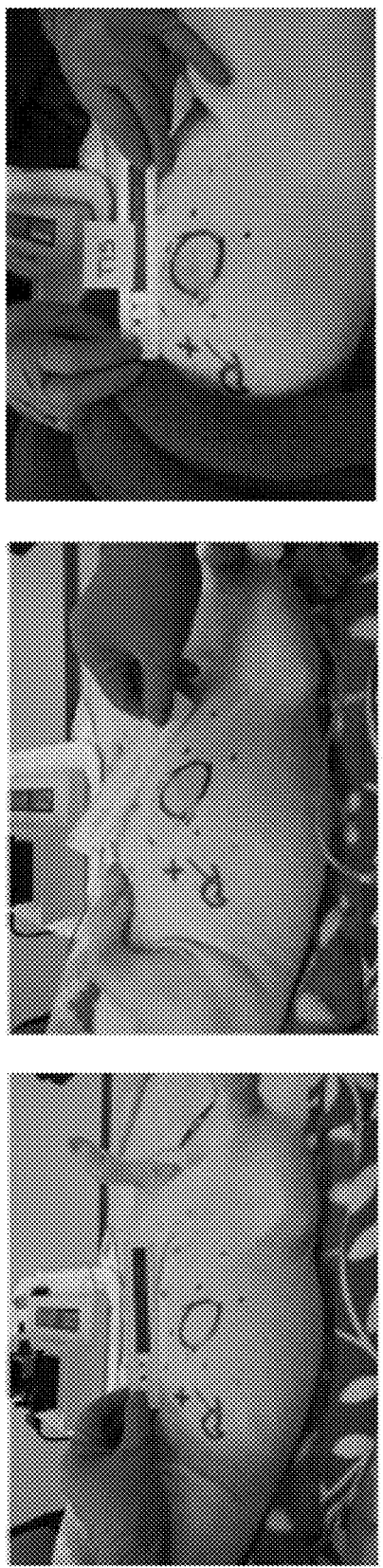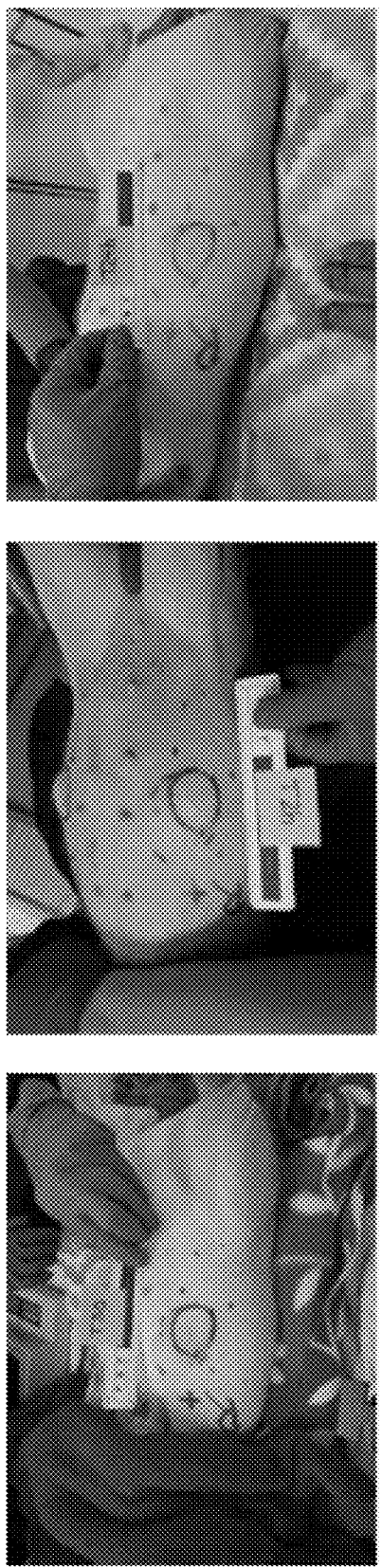
FIG. 36B

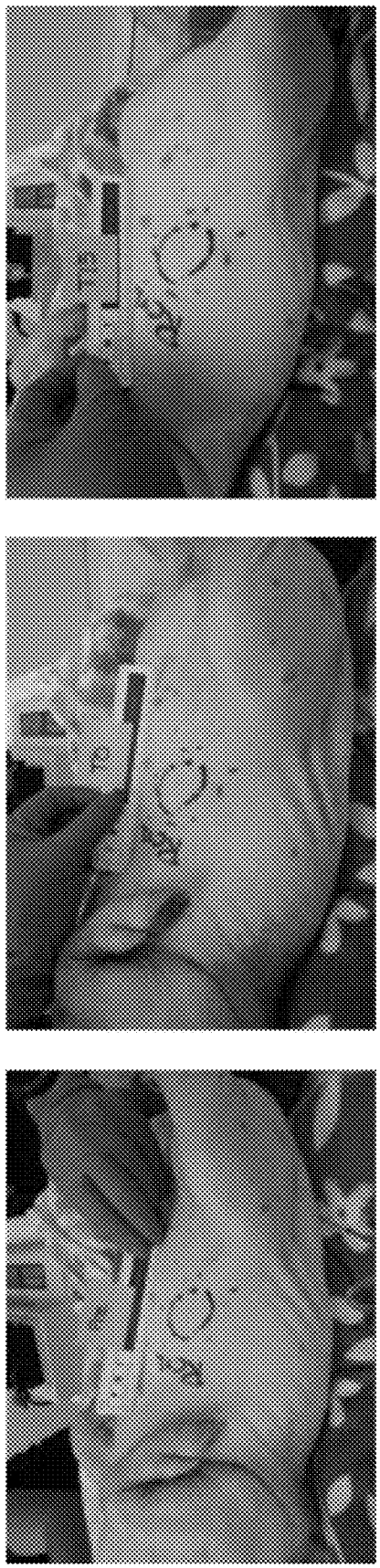
FIG. 37

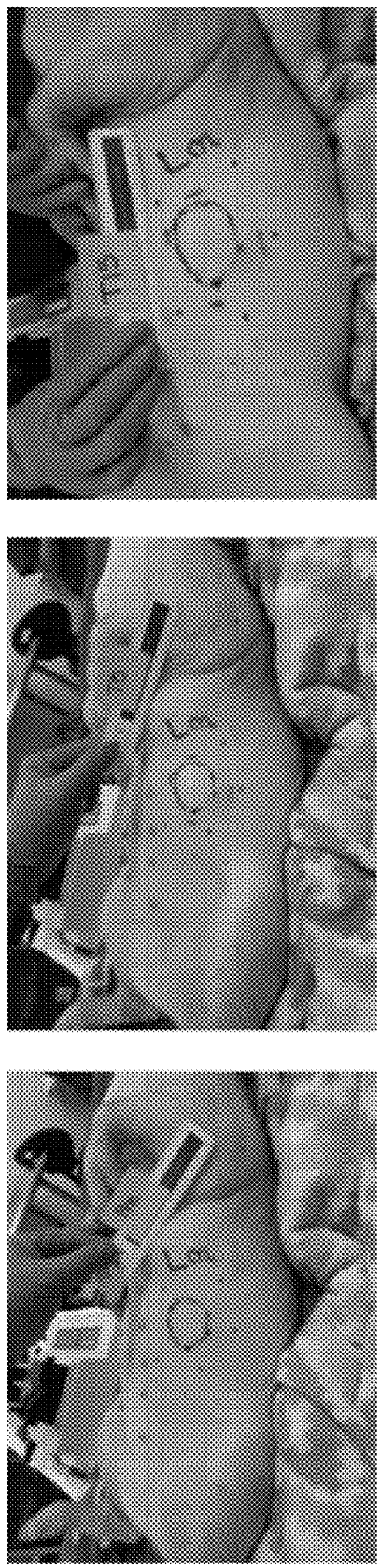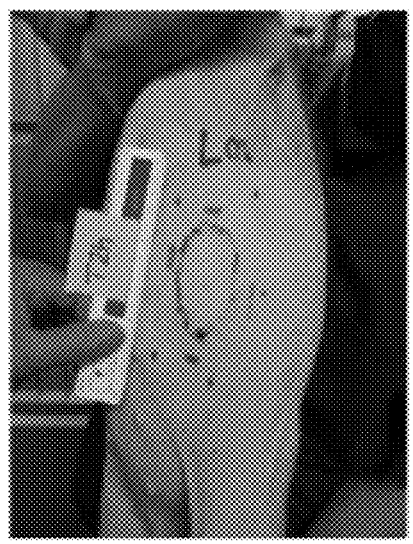
FIG. 39A

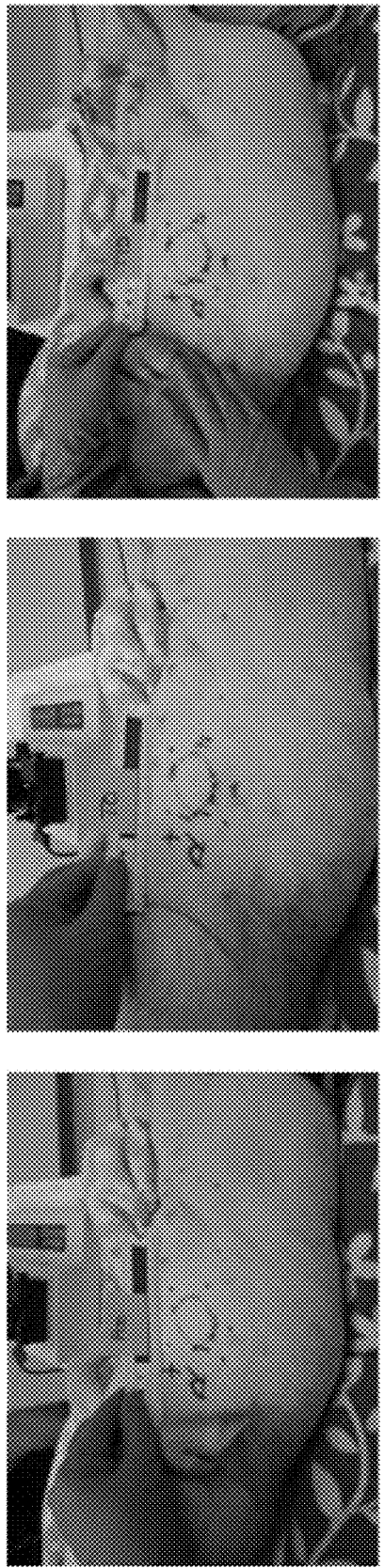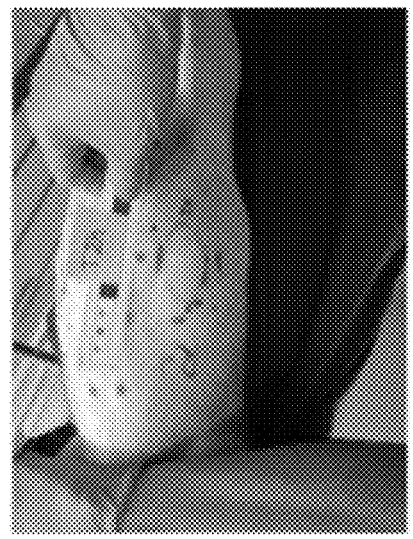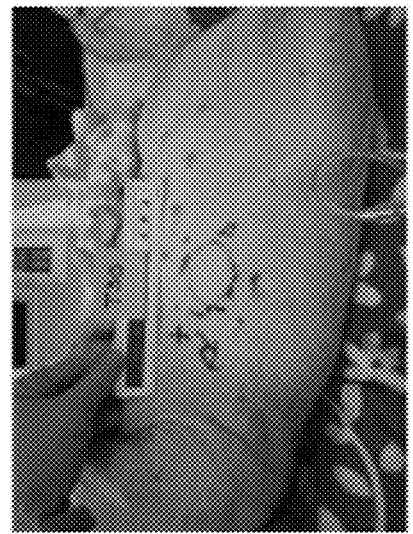
FIG. 39B

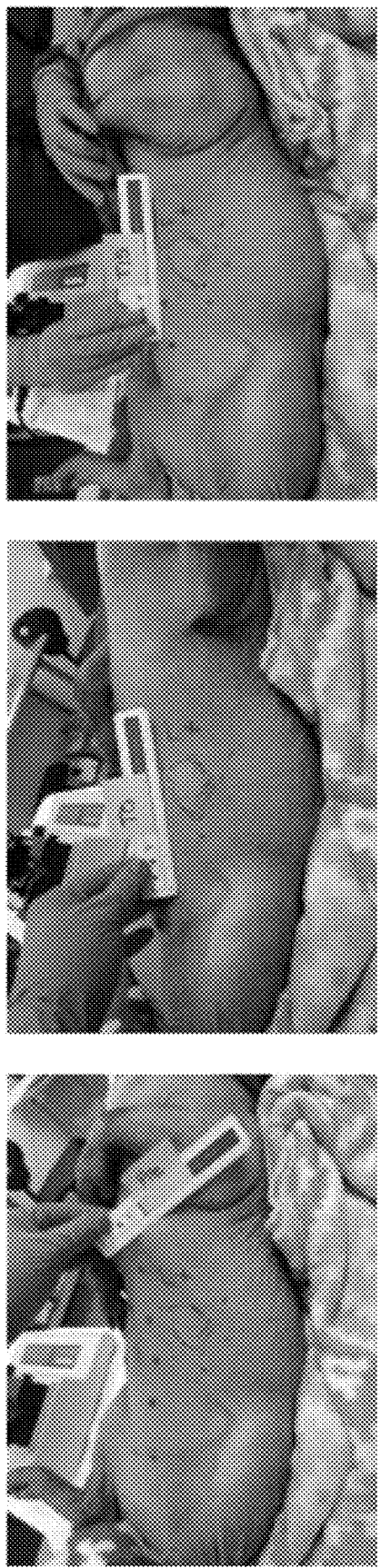
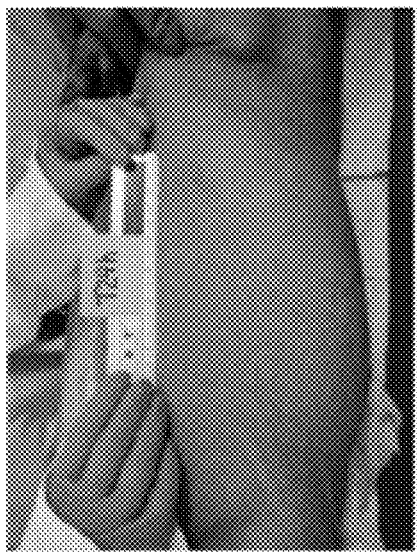
FIG. 40B

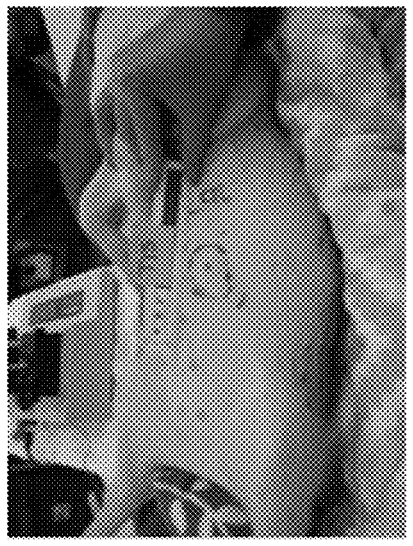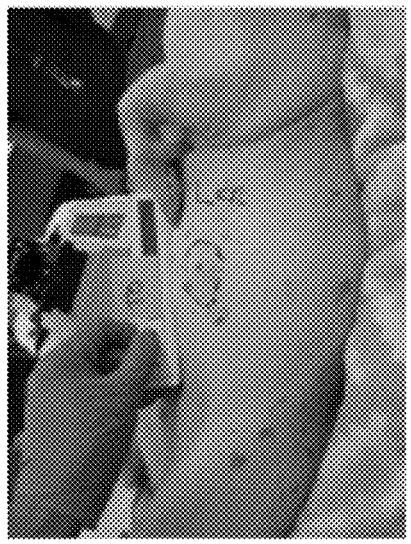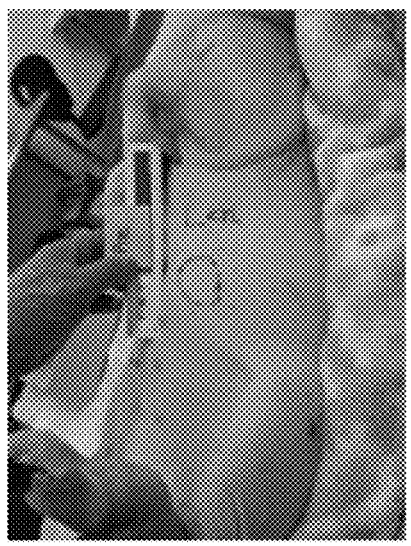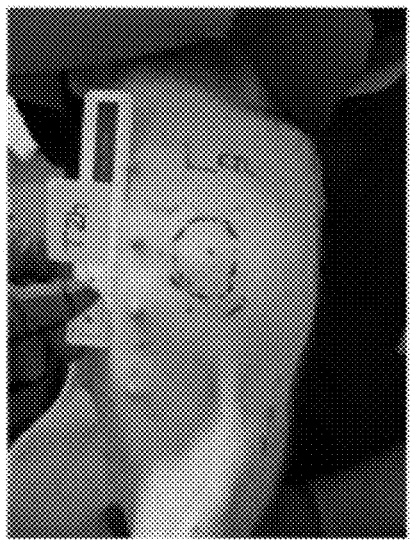
FIG. 41A

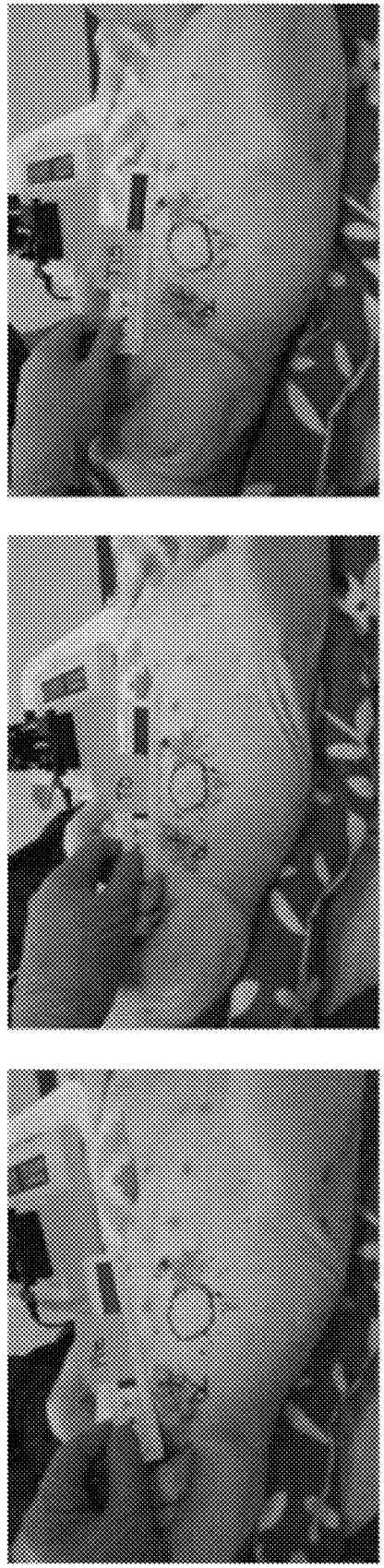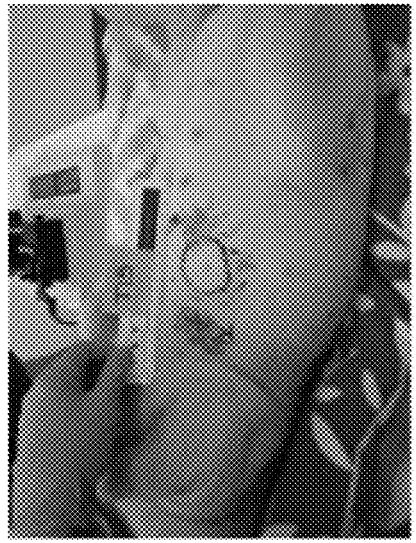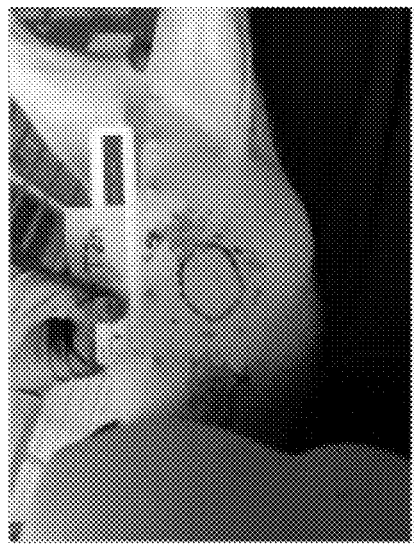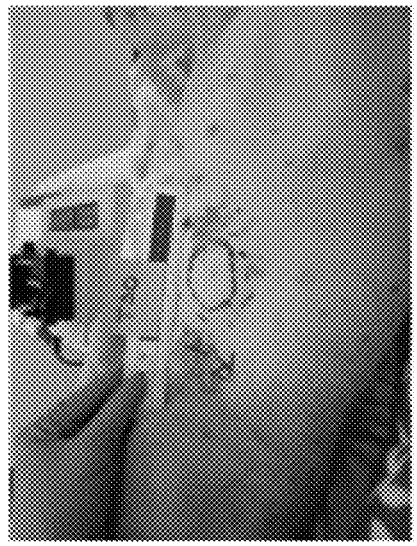
FIG. 41B

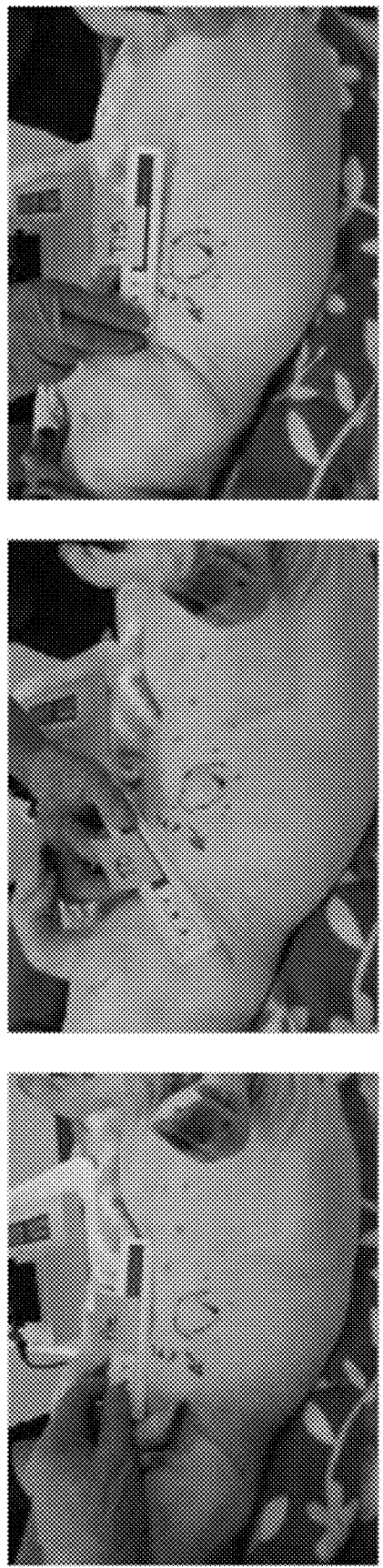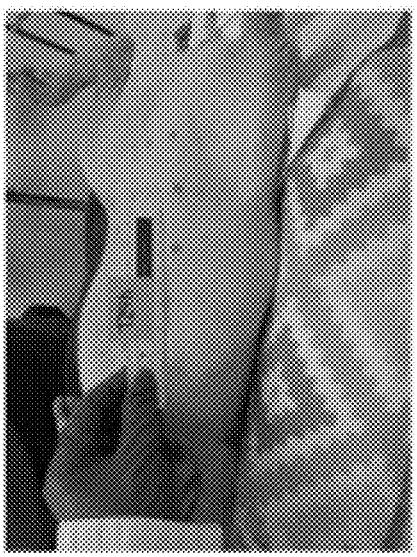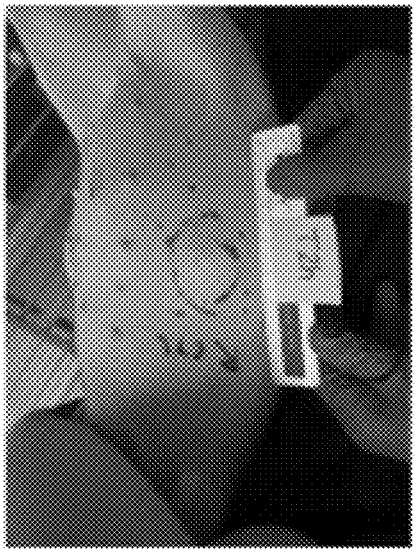
FIG. 42A

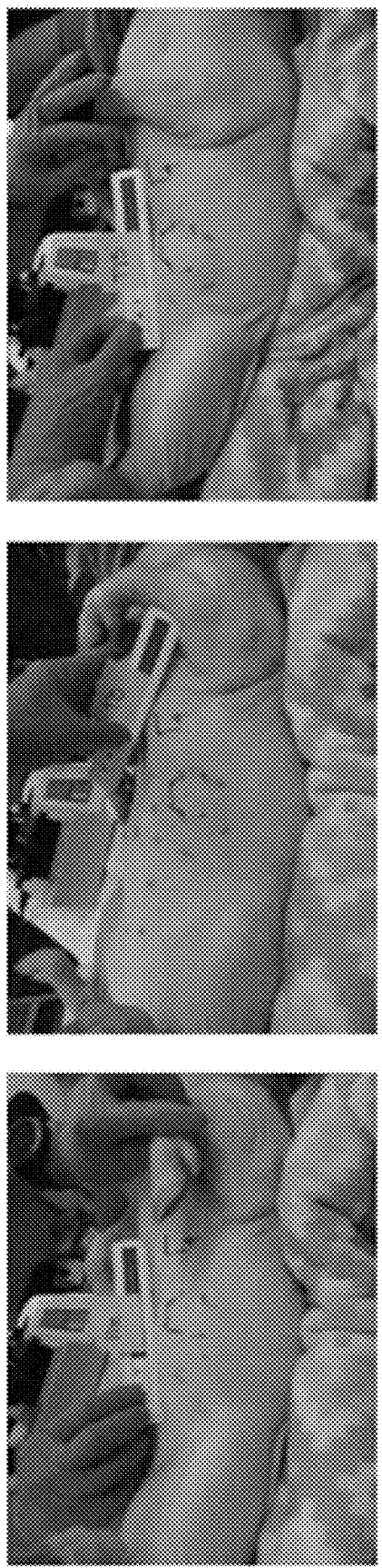
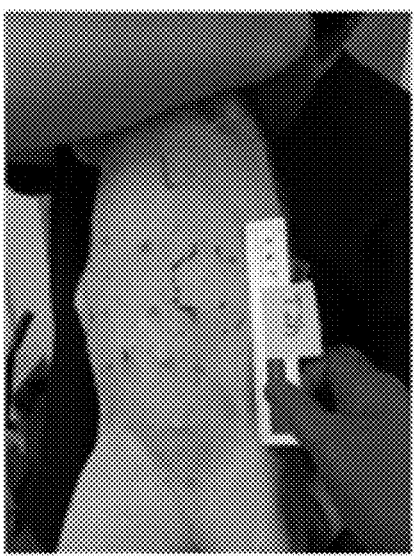
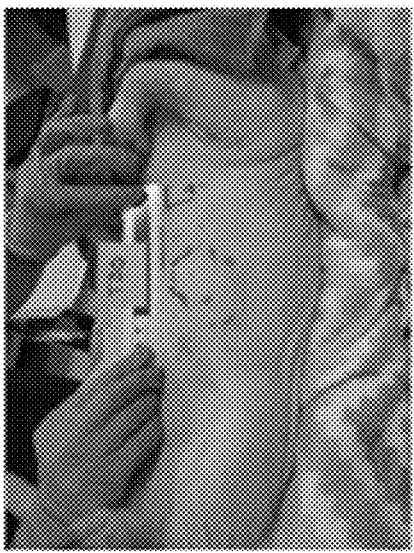
FIG. 42B

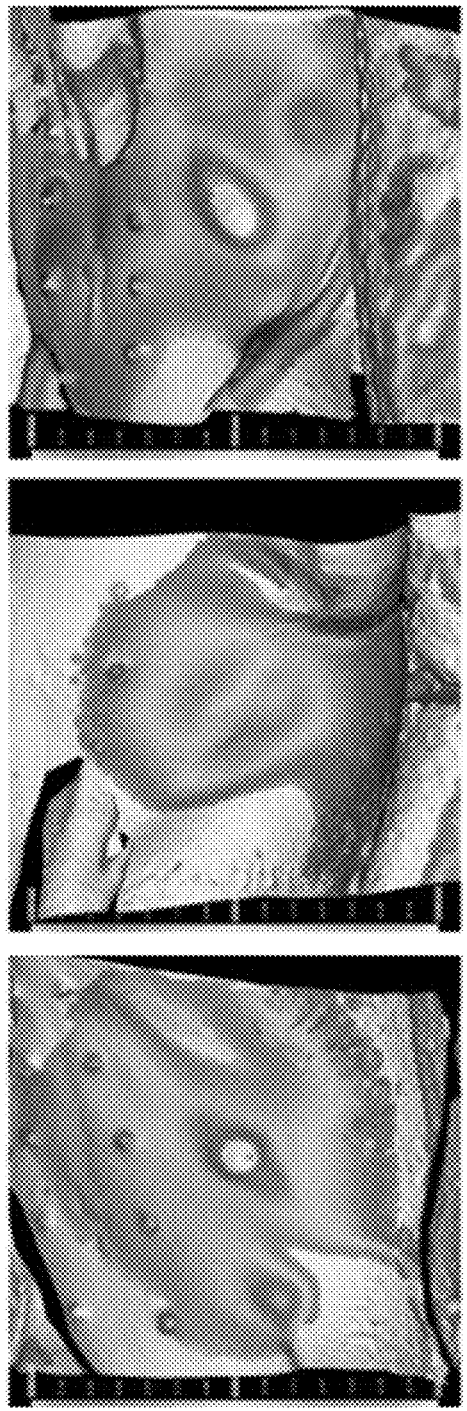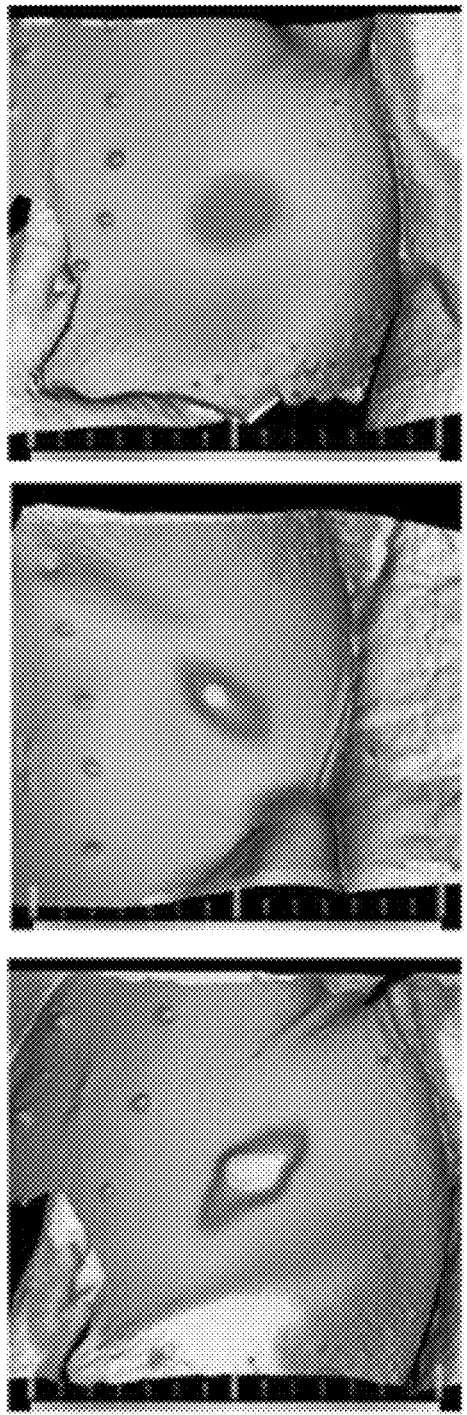
FIG. 51A

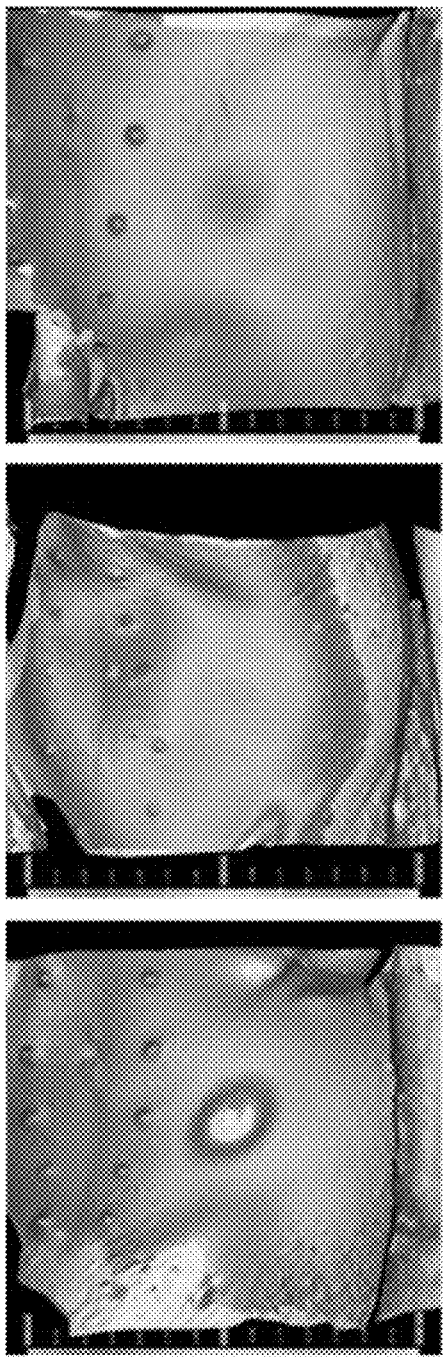
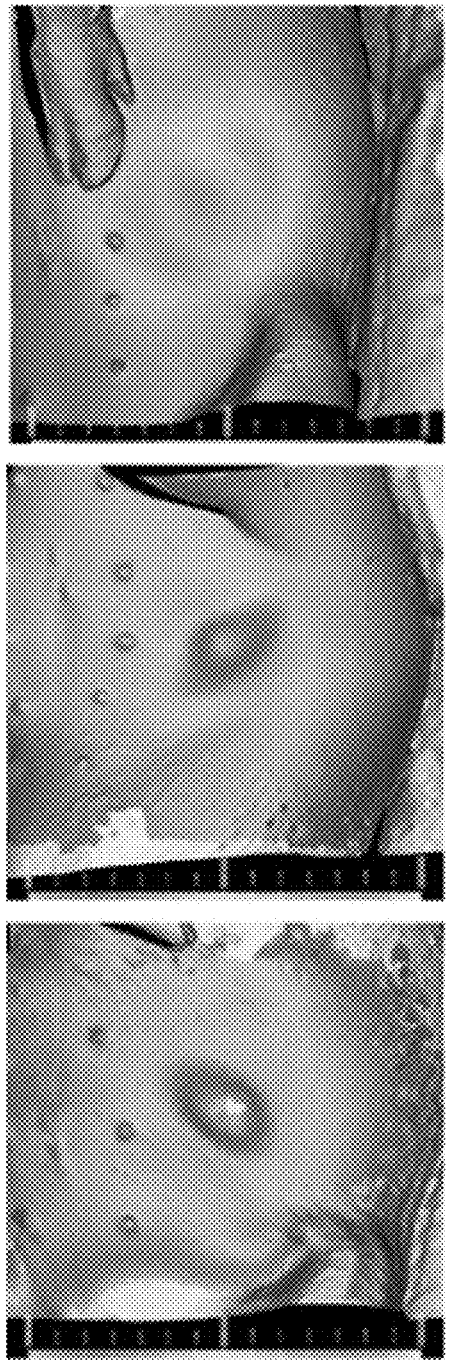
FIG. 51B

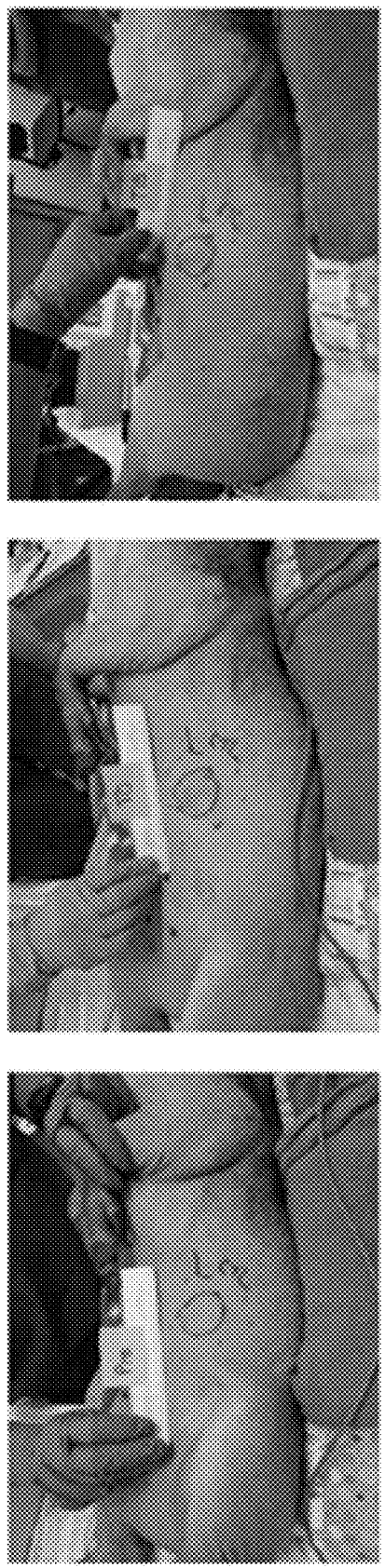
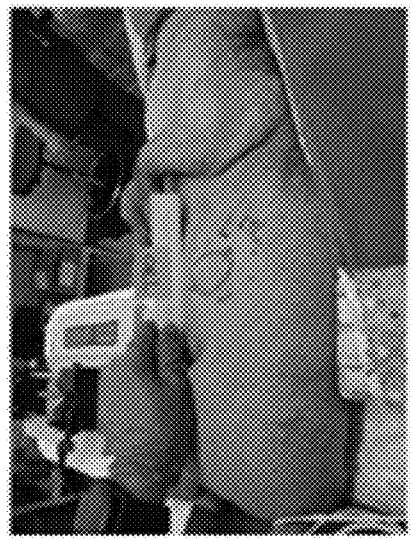
FIG. 59A

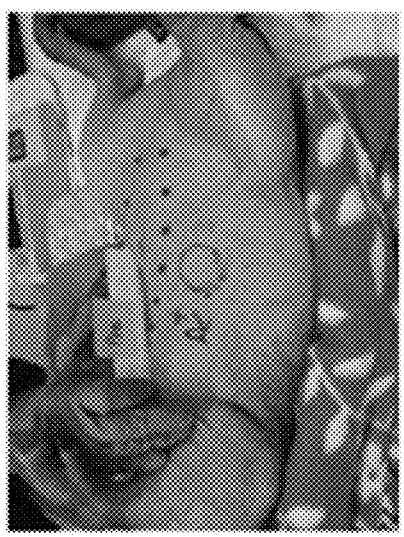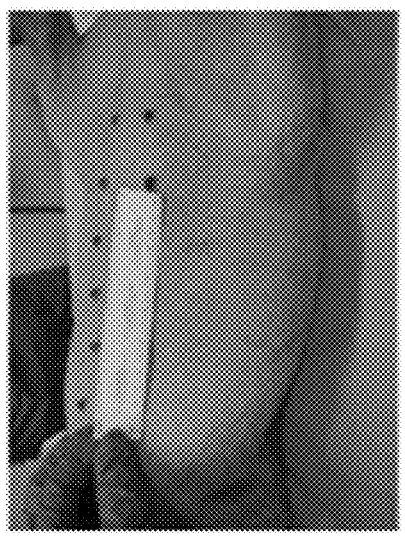
FIG. 59B

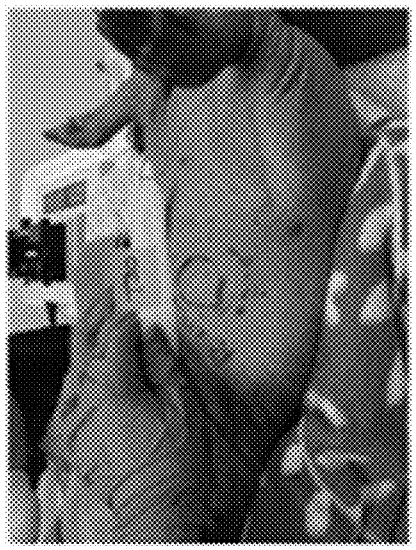
FIG. 60A

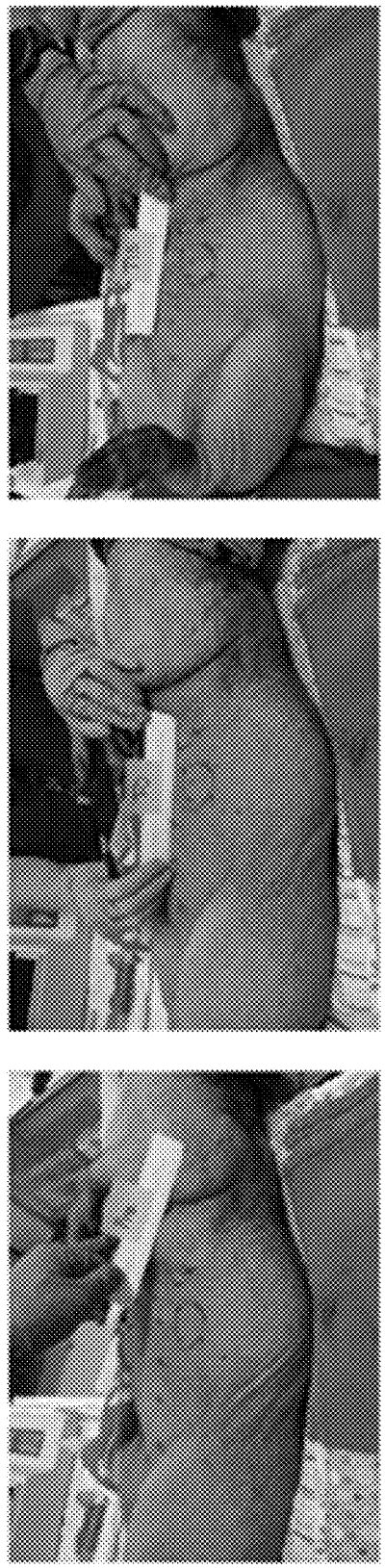
FIG. 60B

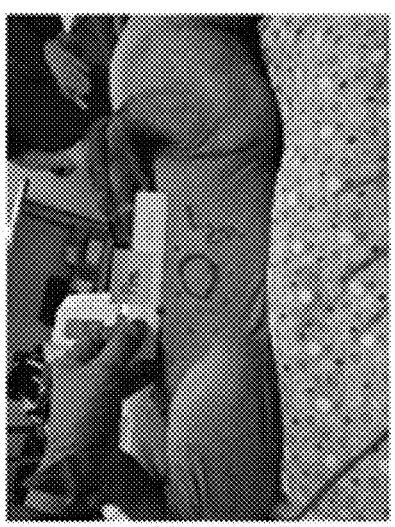
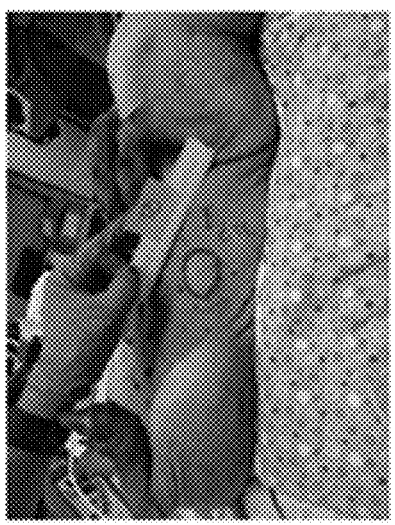
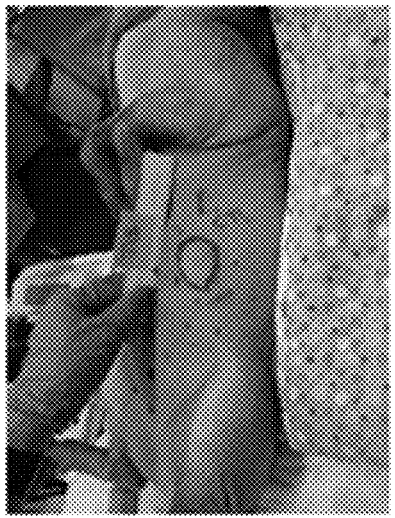
FIG. 61A

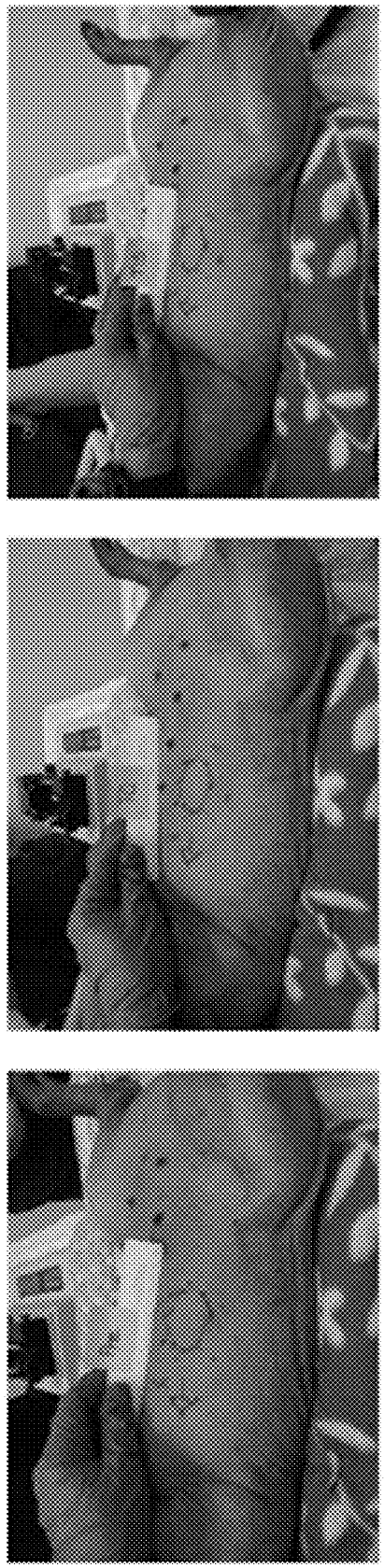
FIG. 61B

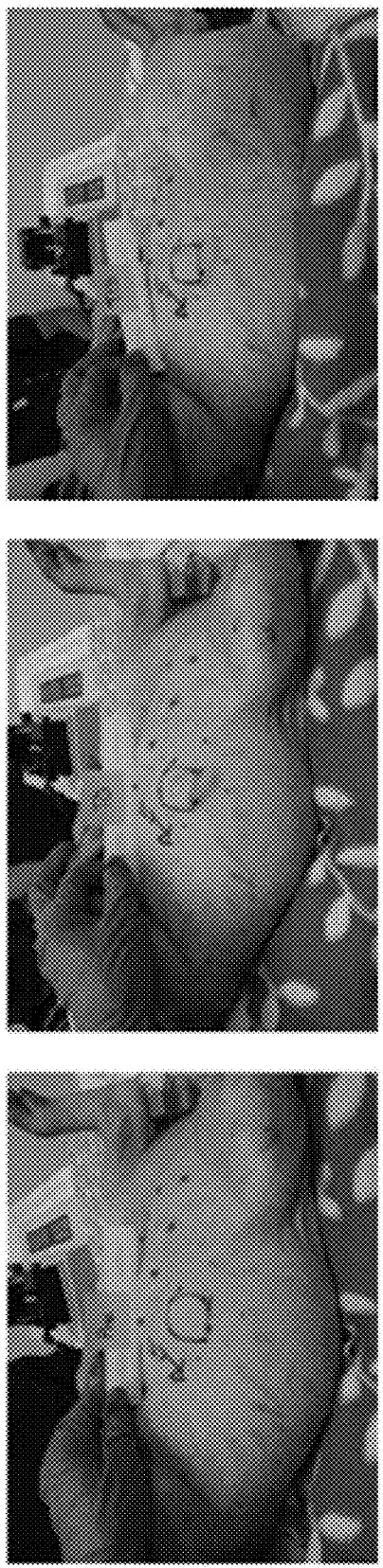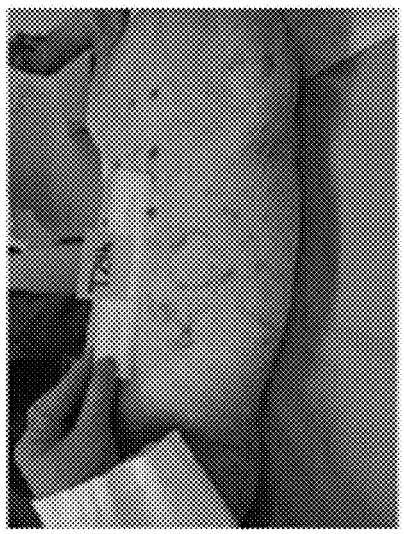
FIG. 62A

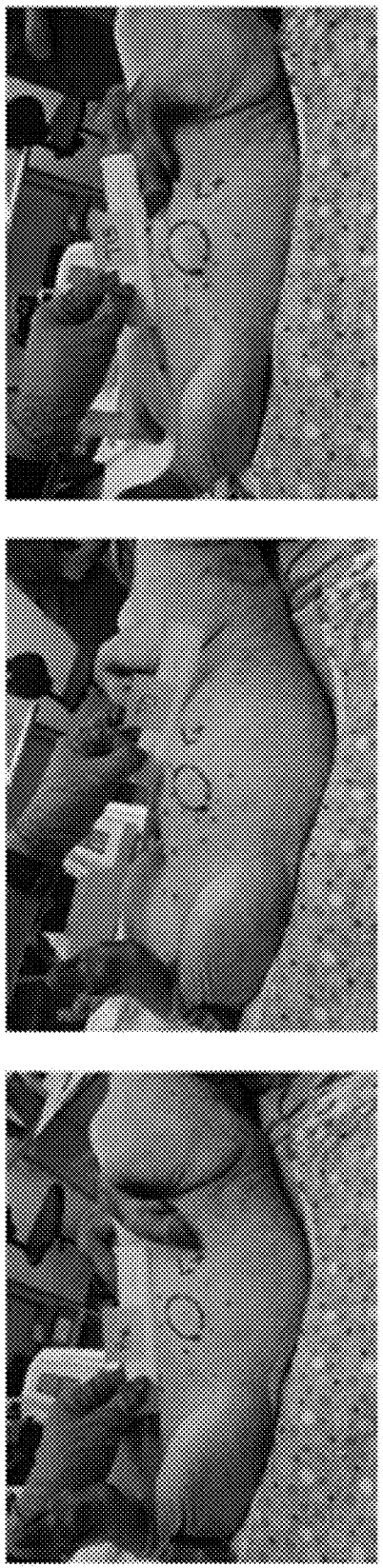
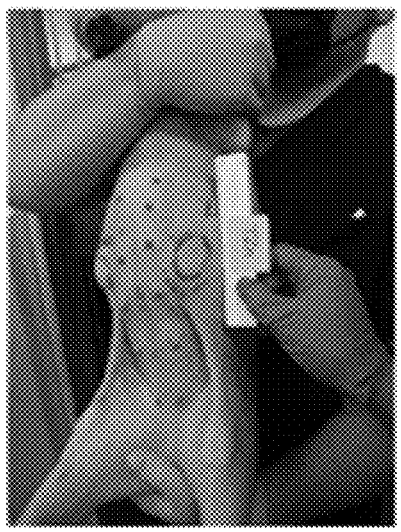
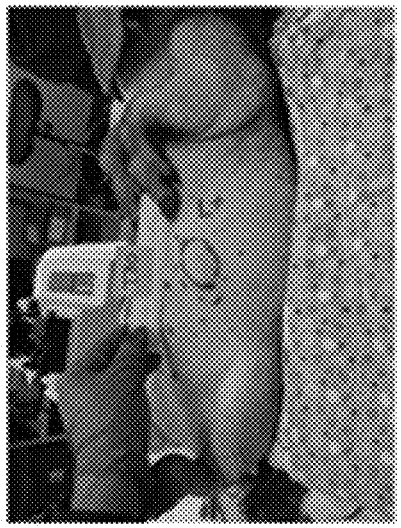
FIG. 62B

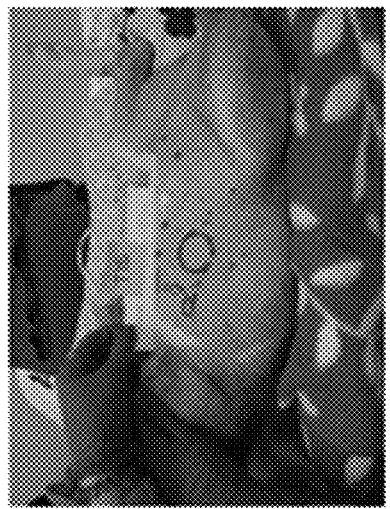
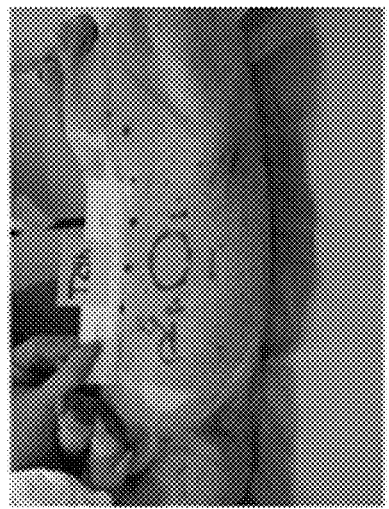
FIG. 64A

FIG. 64B

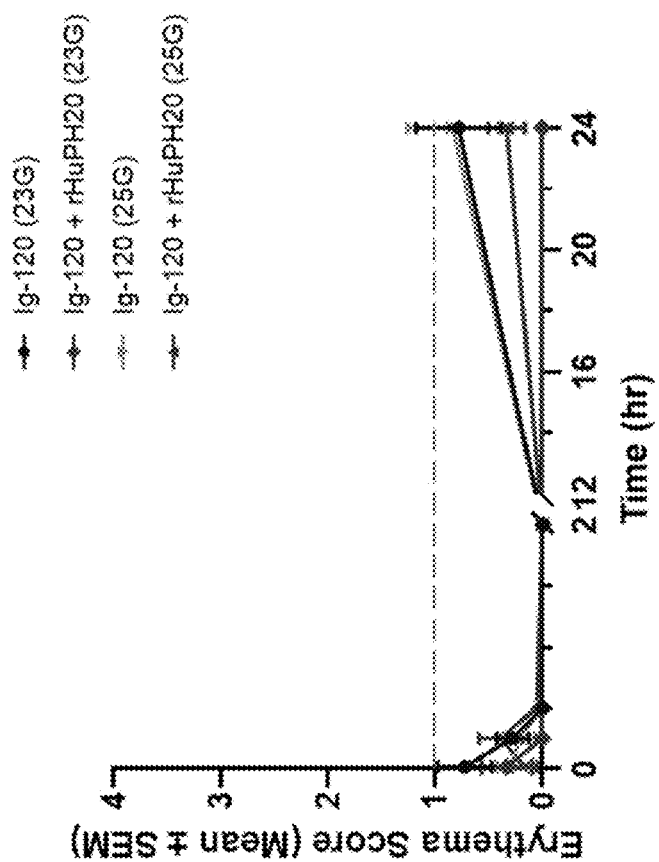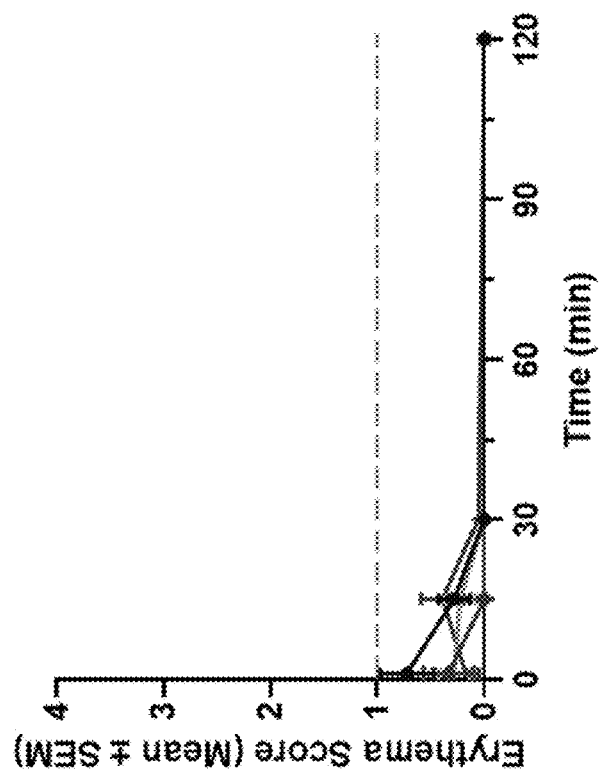
FIG. 78

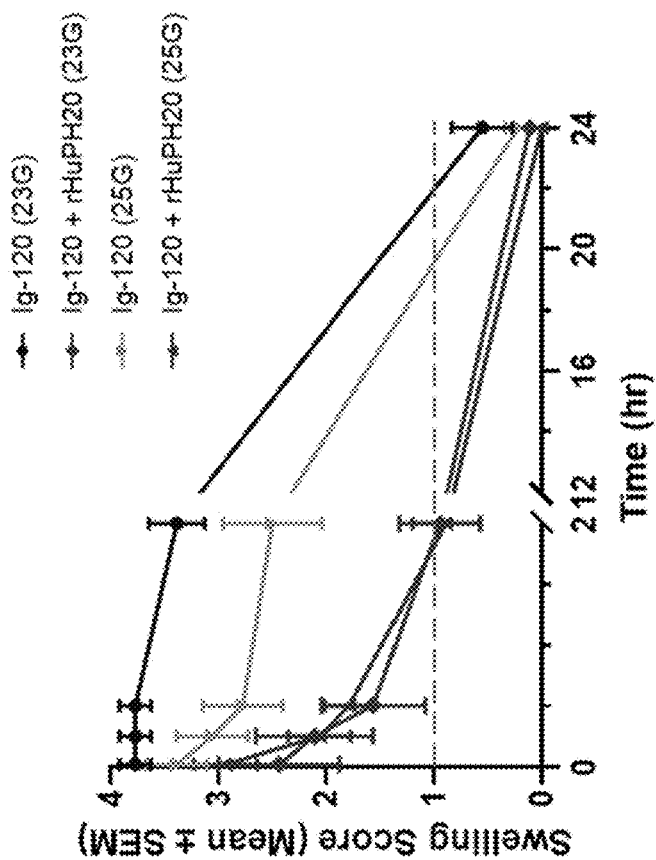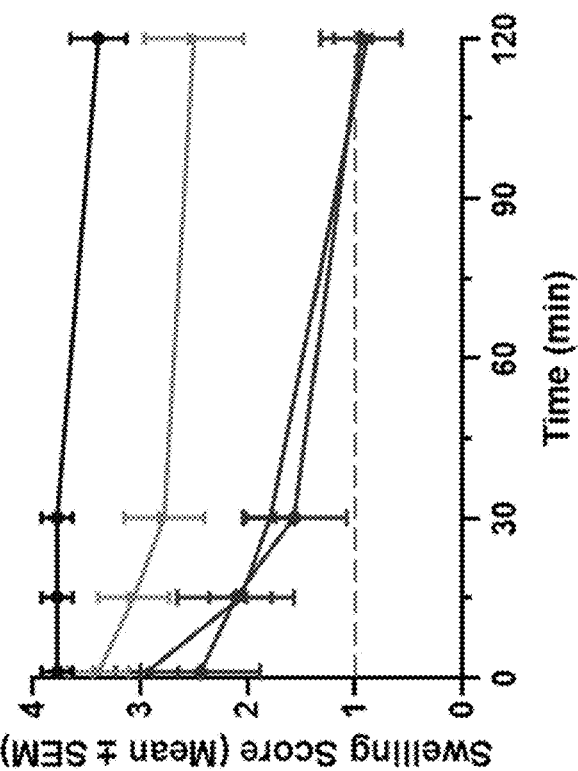
FIG. 79

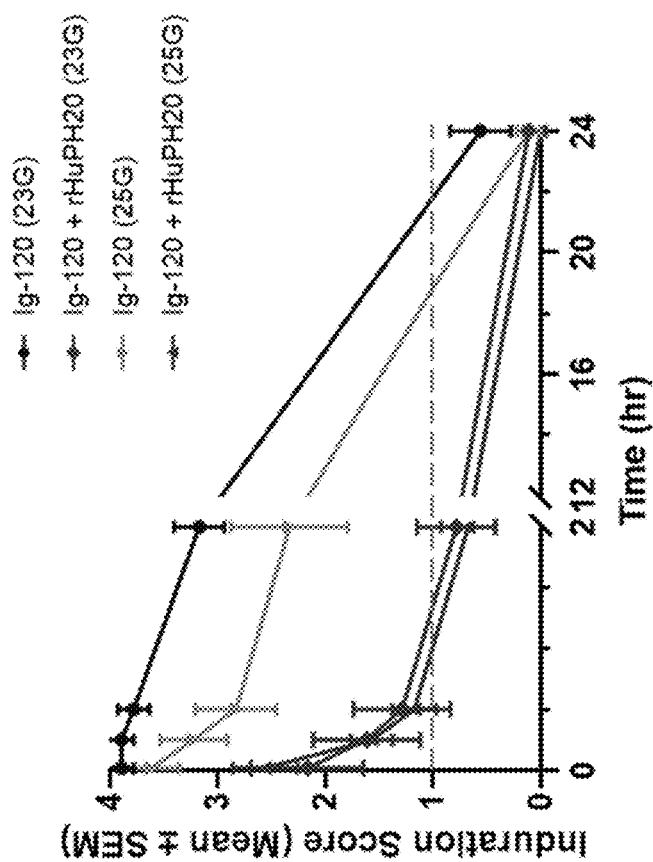
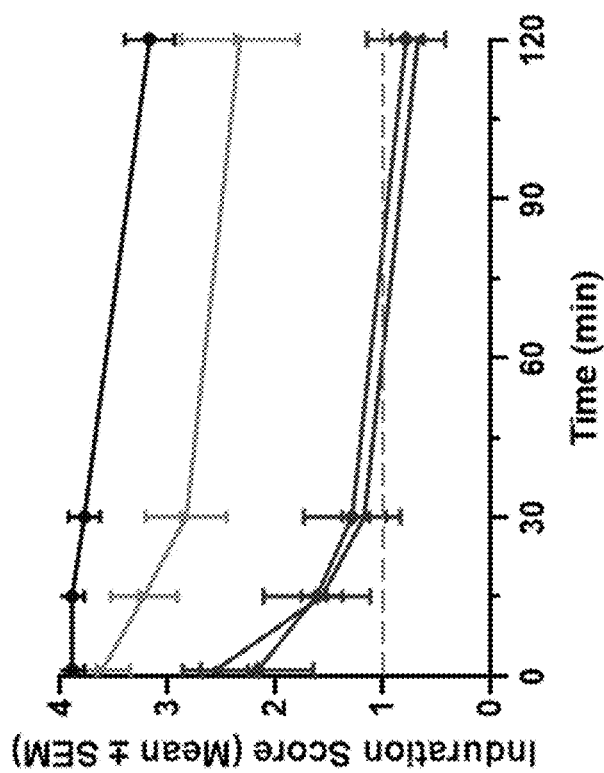
FIG. 80

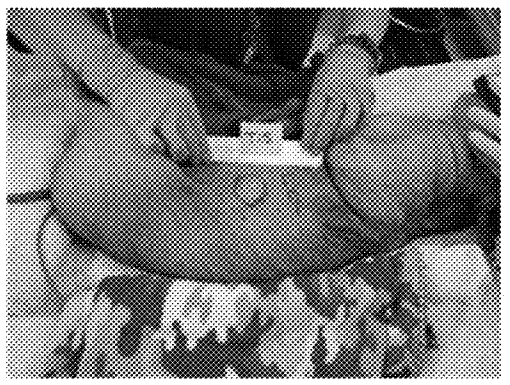 T15
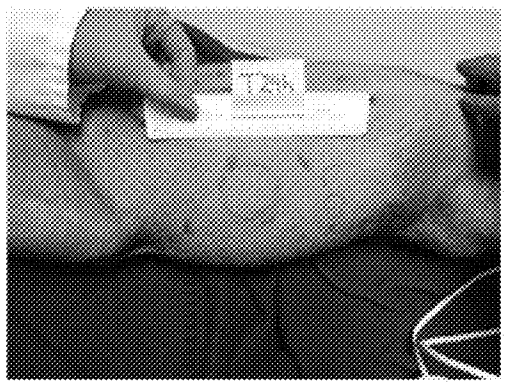 T24h
 T0
 T2h
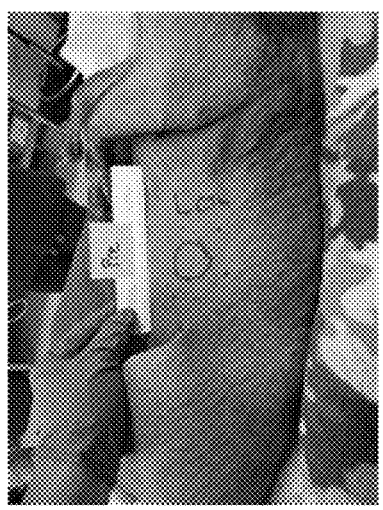 Pre-injection
FIG. 81A

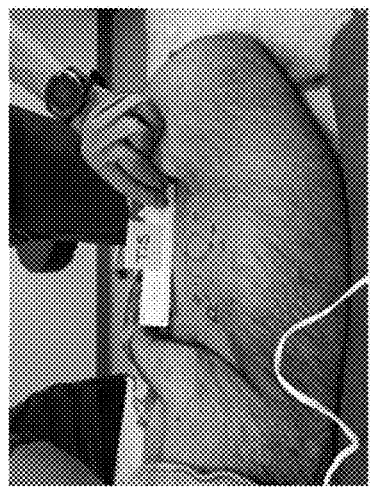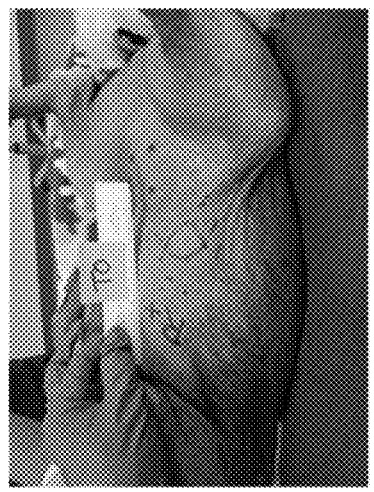
FIG. 81B

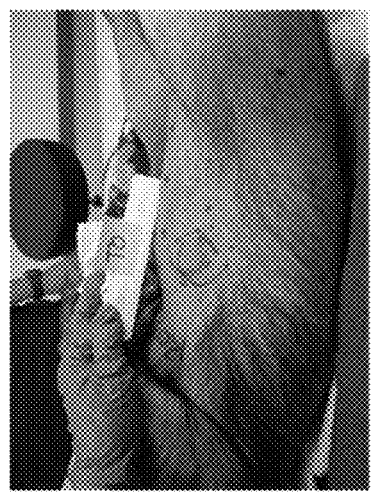
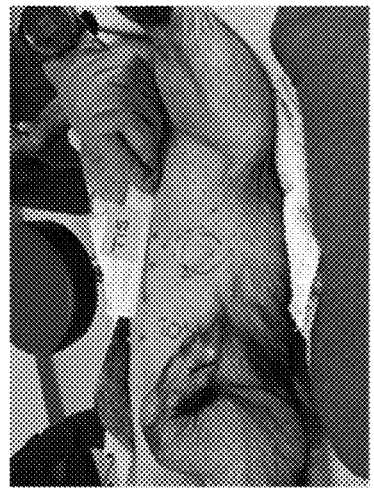
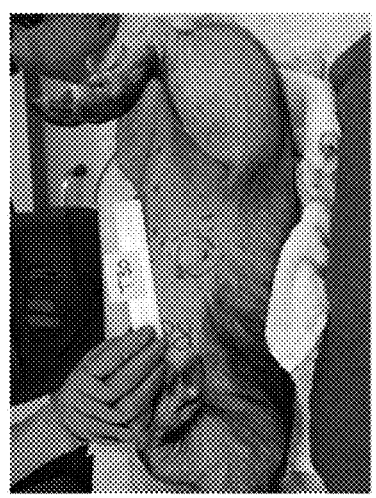
FIG. 82A

Pre-injection
T0
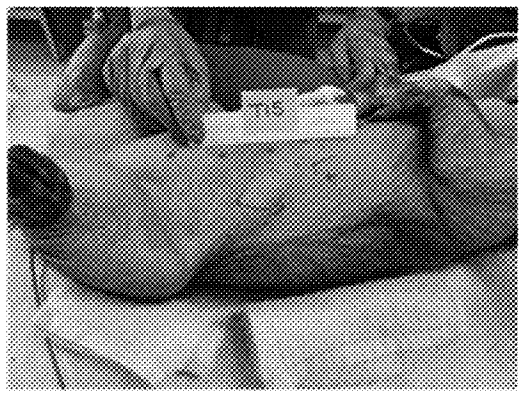
T15
T30
T2h
T24h
FIG. 82B

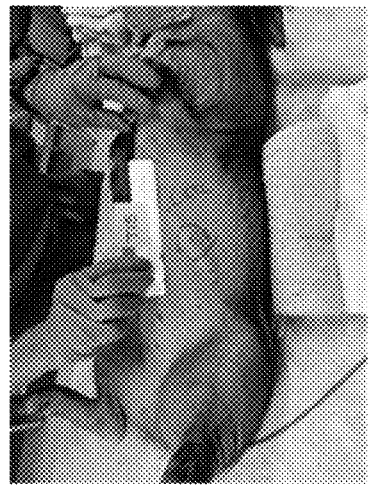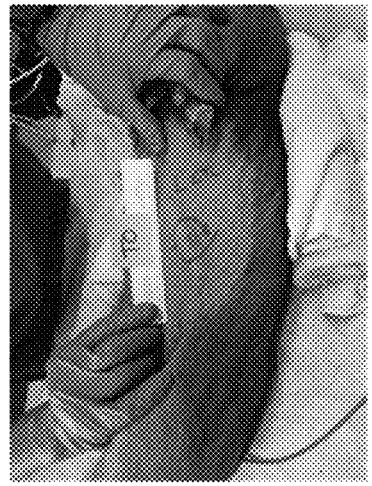
FIG. 83A

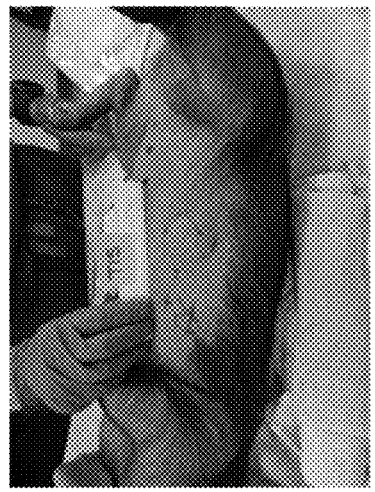  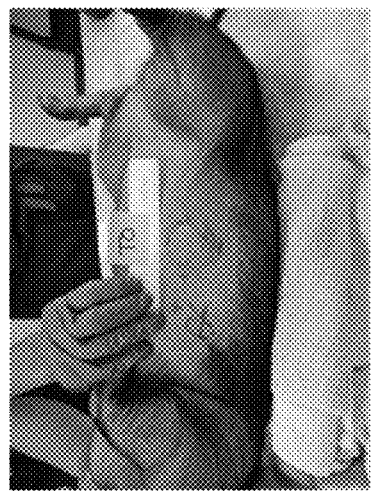   
FIG. 83B

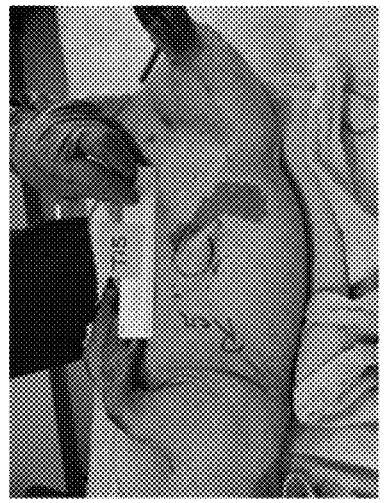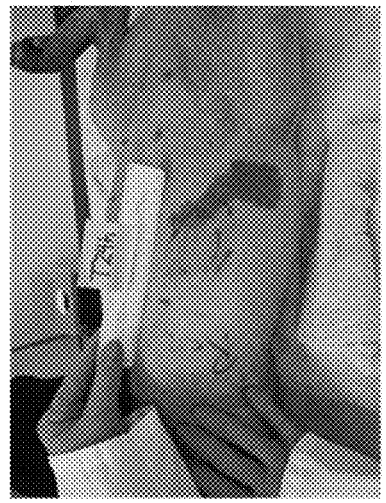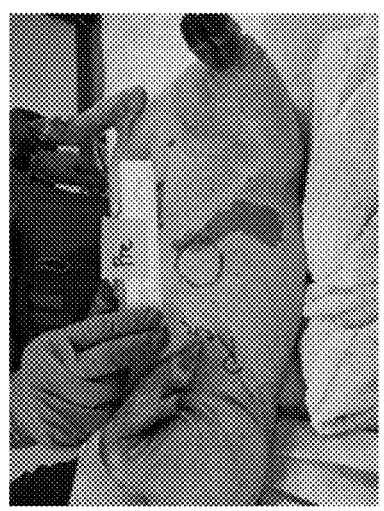
FIG. 84A

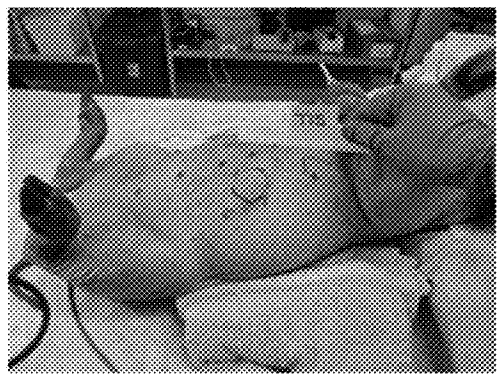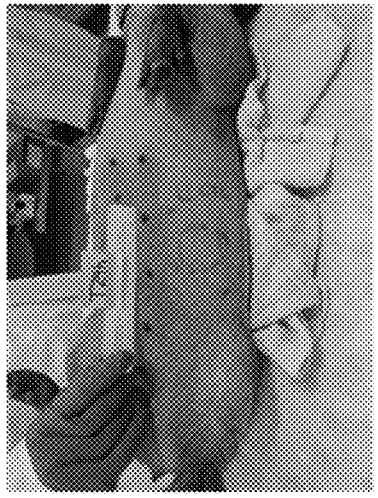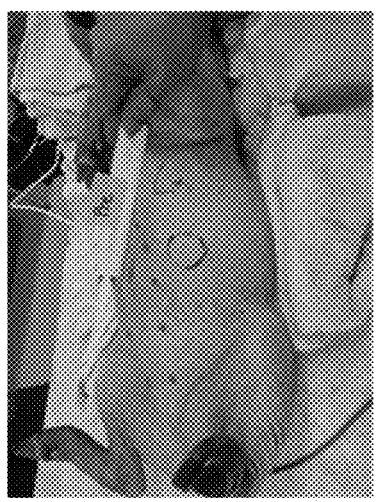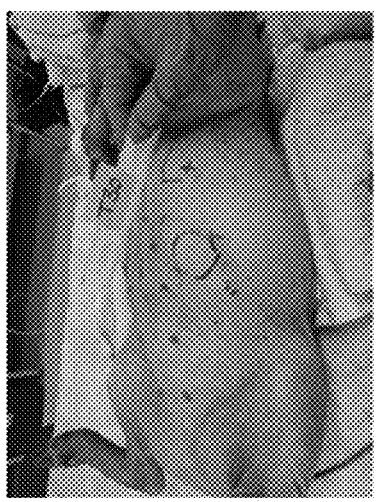
FIG. 84B

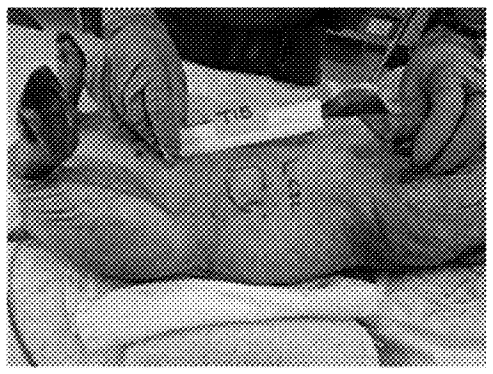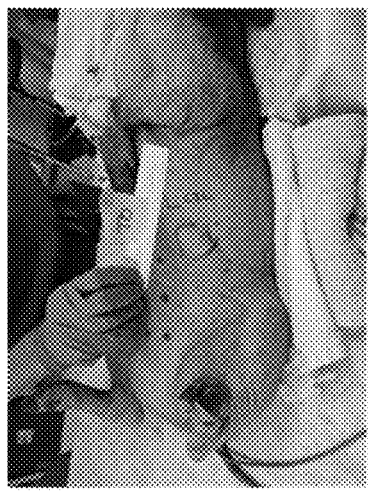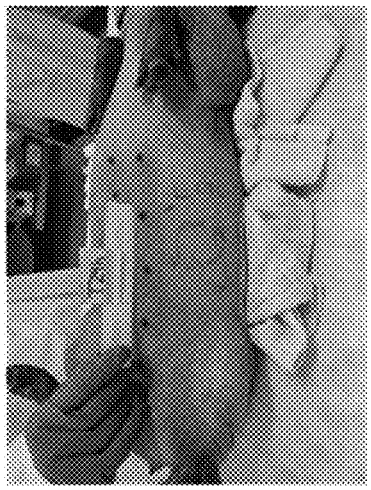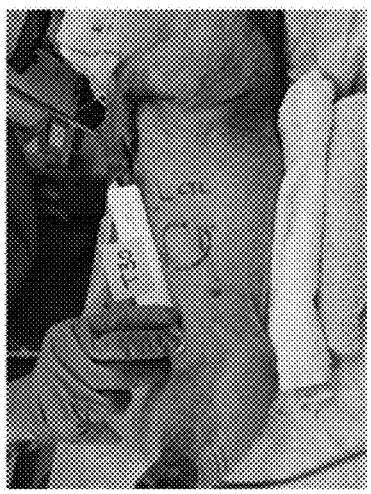
FIG. 85A

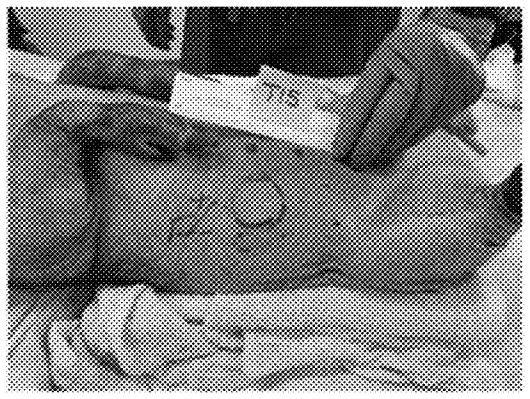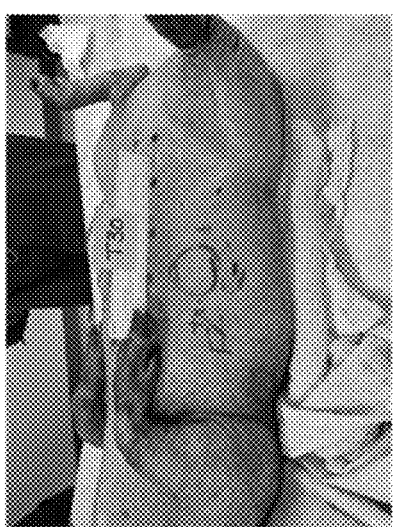
FIG. 85B

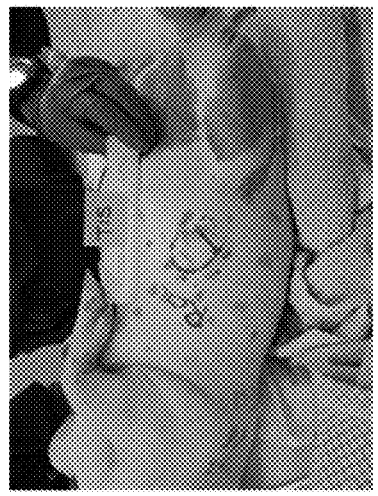
FIG. 86A

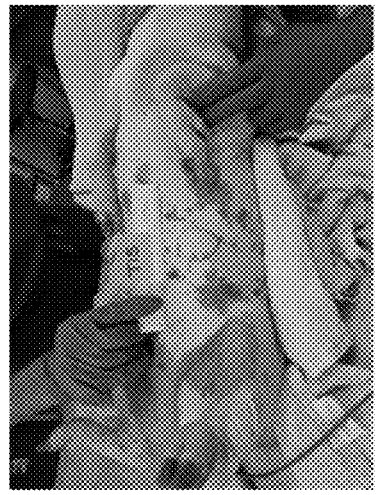
FIG. 86B

Lot Number: SSRM-1
rHuPH20 System Suitability Reference Material
Halozyme Part Number H981

1 mg/mL rHuPH20, 10 mM Histidine, 130 mM NaCl, 0.02% Polysorbate 80, 10 mM L-Methionine, pH 6.5

Manufacturer: Halozyme, Inc. USA

DOM: Jan. 27, 2015
(1 mL Fill Volume)

Retest Date: February 2023[1]
Storage: ≤ -70°C

| Test | Acceptance Criteria | Result |
|---|---|---|
| Protein Concentration | 0.85 – 1.25 mg/mL | 1.01 mg/mL |
| Enzyme Activity | 75 – 150 kU/mL | 120 kU/mL |
| Specific Activity | Report Result in kU/mg | 119 kU/mg |
| Purity by RP-HPLC | rHuPH20: ≥ 90.0% | 94.3% |
| | Hydrolyzed rHuPH20 (Clip): ≤ 5.0% | 0.3% |
| | Oxidized rHuPH20: ≤ 10.0% | 5.4% |
| | Unidentified Peaks: ≤ 3.0% | Not Detected |
| | Total Impurities: ≤ 10.0% | 5.7% |
| Purity by SE-HPLC | rHuPH20: ≥ 95.0% rHuPH20 | 99.5% |
| | High Molecular Weight Species: ≤ 5.0% | 0.5% |
| | Unidentified Peaks: ≤ 3.0% | Not Detected |
| | Total Impurities: ≤ 5.0% | 0.5% |
| pH | 6.0 to 7.0 | 6.5 |

FIG. 87

ENHANZE™ Drug Product (EDP)
Recombinant Hyaluronidase (rHuPH20), 0.5 mL/vial, 1.0 mg/mL in
10 mM L-Histidine, 130 mM NaCl, 10 mM L-Methionine, 0.02% Polysorbate 80,
pH 6.5 (FNH216), Store at 5°C ± 3°C Lot: 1-FIN-3792  Date of Manufacture: October 6, 2021  Expiration Date: October 2026  Version: 1

| Test | Method | Acceptance Criteria | Result |
|---|---|---|---|
| Appearance and Description | 1-P-QM-WI-9032305 | Clear and Colorless Solution | Clear and Colorless Solution |
| pH | 1-P-QM-WI-9032242 | 6.5 ± 0.5 | 6.5 |
| Concentration by A280 | 1-P-QM-WI-9092620 | 1.0 ± 0.10 mg/mL | 0.97 mg/mL |
| Enzyme Activity Assay and Identification | 1-P-QM-WI-9049053 | 75 – 150 kU/mL<br>Positive Identification (Hyaluronidase) | 106 kU/mL<br>Positive Identification (Hyaluronidase) |
| Specific Activity[1] | Calculation | Report Results (kU/mg) | 110 kU/mg |
| Osmolality | 1-P-QM-WI-9032244 | 250 – 310 mOsm/kg | 262 mOsm/kg |
| Purity by RP-HPLC | 1-P-QM-WI-9032232 | rHuPH20 (by area normalization) ≥ 90.0%<br>Hydrolyzed rHuPH20: ≤ 5.0%<br>Oxidized (Ox1) rHuPH20: ≤ 10.0%<br>Oxidized (Ox2) rHuPH20: ≤ 3.0%<br>Unidentified Peaks: ≤ 3.0%<br>Total Impurities: ≤ 10.0% | 96.2%<br>0.9%<br>2.9%<br>BLOQ[3]<br>ND[3]<br>3.7% |
| Purity by SE-HPLC | 1-P-QM-WI-9032231 | rHuPH20: ≥ 95.0%<br>High Molecular Weight Species: ≤ 5.0%<br>Unidentified Peaks: ≤ 3.0%<br>Total Impurities: ≤ 3.0% | 99.7%<br>BLOQ[3]<br>BLOQ[3]<br>BLOQ[3] |
| Endotoxin | 1-P-QM-WI-9014312 | ≤ 1 EU/mg | <0.05 EU/mg[3] |
| Sterility[2] | 1-P-QM-WI-9014676 | No growth | No Growth |
| Particulate Matter | 1-P-QM-WI-9013477 | ≤ 6000 particles/container for ≥ 10 μm<br>≤ 600 particles/container for ≥ 25 μm | 17 particles/container for ≥ 10 μm<br>0 particles/container for ≥ 25 μm |

[1] Specific activity = enzyme activity/protein concentration. [2] Testing managed by Ampcacto Bio-Pharma per VV-QUAL-00653. [3] BLOQ = Below Limit of Quantitation. ND = Not Detected. Endotoxin is tested beginning, middle, end, and all results are <0.05 EU/mg. Catalent Drug Substance Lot Number: 3803339 (BMF 112)

FIG. 112

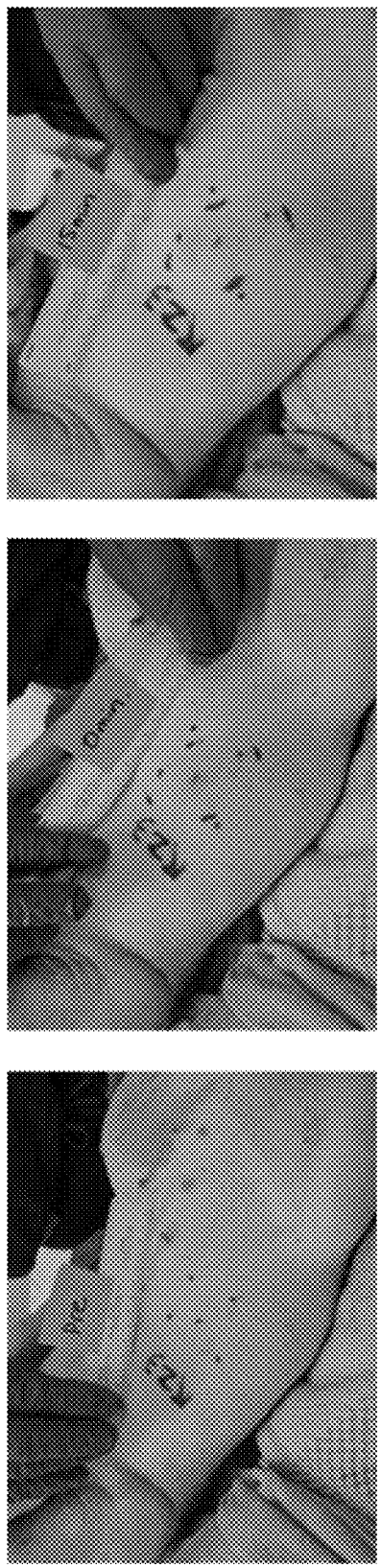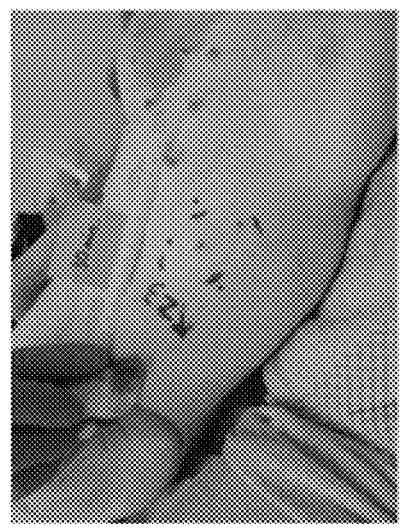
FIG. 118B

FIG. 119A

| Parameter | Result |
|---|---|
| Number of Subjects | 24 |
| Gender | Male = 9<br>Female = 15 |
| Ethnicity | Hispanic or Latino = 13<br>Not Hispanic of Latino = 11 |
| Race | Black or African American = 4<br>White = 17<br>Other = 3 |
| Age Range | 19-62 years of age |

FIG. 127

| Cohort | Injection Visit 1 (syringe pump) | N | Injection Visit 2 (HVAI) | N |
|---|---|---|---|---|
| A | 5 ml / 30 sec | 12 | 10 mL / 30 sec | 12 |
| B | 10 mL / 30 sec | 12 | 10 mL / 30 sec | 11* |

All subjects have completed Follow-Up Visit 1
* 1 subject not dosed due to + COVID test

FIG. 128

| Cohort | Delivery Method | Injection Duration (range)* | Injection Duration Mean |
|---|---|---|---|
| Cohort A | Syringe Pump | 30 seconds | 30 sec |
| Cohort B | HVAI | 22 – 34 seconds | 27.91 sec |

* Pump programmed to deliver full dose in 30 seconds

FIG. 129

Pain Scores

| Time After injection V1 | N | Pain Scores | | | | | Not Done |
|---|---|---|---|---|---|---|---|
| | | 0 | 1 | 2 | 3 | 4 | |
| 5 Min Prior to Needle Placement | 24 | 24 | 0 | 0 | 0 | 0 | 0 |
| After Needle Placement, Prior to Injection | 24 | 18 | 2 | 0 | 1 | 0 | 3 |
| Immediately After Injection | 24 | 3 | 0 | 1 | 0 | 0 | 20 |
| 5 Min After Injection | 24 | 17 | 5 | 1 | 0 | 1 | 0 |
| 10 Min Post Injection | 24 | 17 | 4 | 3 | 0 | 0 | 0 |
| 15 Min Post Injection | 24 | 17 | 5 | 2 | 0 | 0 | 0 |
| 30 Min Post Injection | 24 | 18 | 5 | 1 | 0 | 0 | 0 |
| 45 Min Post Injection | 24 | 21 | 2 | 1 | 0 | 0 | 0 |
| 60 Min Post Injection | 24 | 22 | 1 | 1 | 0 | 0 | 0 |
| 90 Min Post Injection | 24 | 24 | 0 | 0 | 0 | 0 | 0 |
| 120 Min Post Injection | 24 | 23 | 1 | 0 | 0 | 0 | 0 |
| 180, 240, 300, 360 Min Post Injection | 24 | 24 | 0 | 0 | 0 | 0 | 0 |

FIG. 130

Pain Scores / Repeat HVAI

| Time After injection V2 | N | Pain Scores | | | | | |
| --- | --- | --- | --- | --- | --- | --- | --- |
| | | 0 | 1 | 2 | 3 | 4+ | Not Done |
| 5 Min Prior to Needle Placement | 23 | 22 | 0 | 0 | 1 | 0 | 0 |
| After Needle Placement, Prior to Injection | 23 | 17 | 5 | 1 | 0 | 0 | 0 |
| Immediately After Injection | 23 | 5 | 5 | 7 | 2 | 2 = 6 | 2 |
| 5 Min After Injection | 23 | 13 | 7 | 2 | 0 | 1 = 4 | 0 |
| 10 Min Post Injection | 23 | 15 | 6 | 1 | 1 | 0 | 0 |
| 15 Min Post Injecton | 22 | 13 | 7 | 0 | 1 | 1 = 10 | 1 |
| 30 Min Post Injection | 23 | 18 | 3 | 1 | 1 | 0 | 0 |
| 45 Min Post Injection | 23 | 21 | 2 | 0 | 0 | 0 | 0 |
| 60 Min Post Injection | 23 | 22 | 1 | 0 | 0 | 0 | 0 |
| 90 Min Post Injection | 23 | 22 | 1 | 0 | 0 | 0 | 0 |
| 120 Min Post Injection | 23 | 23 | 0 | 0 | 0 | 0 | 0 |
| 180, 240, 300, 360 Min Post Injection | 23 | 23 | 0 | 0 | 0 | 0 | 1 ND @ 360 min |

22/23 subjects replied "Yes" to the question "would you have this injection again with HVAI"

FIG. 131

| Time After injection V1 | N | Erythema | | | | | |
|---|---|---|---|---|---|---|---|
| | | 0 None | 1 Very Slight | 2 Well-Defined | 3 Moderate to Severe | 4 | Not Done |
| 5 Min Prior to Needle Placement | 24 | 3 | 1 | 0 | 0 | 0 | 0 |
| Immediately After Injection | 24 | 0 | 0 | 0 | 0 | 0 | 24 |
| 5 Min After Injection | 24 | 1 | 13 | 10 | 0 | 0 | 0 |
| 10 Min Post Injection | 24 | 2 | 11 | 11 | 0 | 0 | 0 |
| 15 Min Post Injection | 24 | 1 | 11 | 12 | 0 | 0 | 0 |
| 30 Min Post Injection | 24 | 1 | 11 | 11 | 0 | 0 | 1 |
| 45 Min Post Injection | 24 | 1 | 16 | 7 | 0 | 0 | 0 |
| 60 Min Post Injection | 24 | 9 | 15 | 0 | 0 | 0 | 0 |
| 90 Min Post Injection | 24 | 19 | 5 | 0 | 0 | 0 | 0 |
| 120 Min Post Injection | 24 | 24 | 0 | 0 | 0 | 0 | 0 |
| 180, 240, 300, 360 Min Post Injection | 24 | 24 | 0 | 0 | 0 | 0 | 0 |

FIG. 133

| Time After injection V2 | N | Erythema | | | | | |
|---|---|---|---|---|---|---|---|
| | | 0 None | 1 Very Slight | 2 Well-Defined | 3 Moderate to Severe | 4 | Not Done |
| 5 Min Prior to Needle Placement | 23 | 23 | 0 | 0 | 0 | 0 | 0 |
| Immediately After Injection | 23 | 7 | 14 | 0 | 0 | 0 | 2 |
| 5 Min After Injection | 23 | 1 | 14 | 6 | 2 | 0 | 0 |
| 10 Min Post Injection | 23 | 1 | 11 | 11 | 0 | 0 | 0 |
| 15 Min Post Injection | 23 | 0 | 12 | 11 | 0 | 0 | 0 |
| 30 Min Post Injection | 23 | 0 | 12 | 11 | 0 | 0 | 0 |
| 45 Min Post Injection | 23 | 2 | 16 | 5 | 0 | 0 | 0 |
| 60 Min Post Injection | 23 | 5 | 15 | 3 | 0 | 0 | 0 |
| 90 Min Post Injection | 23 | 20 | 3 | 0 | 0 | 0 | 0 |
| 120 Min Post Injection | 23 | 23 | 0 | 0 | 0 | 0 | 0 |
| 180, 240, 300, 360 Min Post Injection | 23 | 23 | 0 | 0 | 0 | 0 | 0 |

FIG. 134

| Time After injection V1 | N | Edema | | | | | |
|---|---|---|---|---|---|---|---|
| | | 0 None | 1 Very Slight Swelling | 2 Slight Swelling | 3 | 4 | Not Done |
| 5 Min Prior to Needle Placement | 24 | 24 | 0 | 0 | 0 | 0 | 0 |
| Immediately After Injection | 24 | 0 | 0 | 0 | 0 | 0 | 24 |
| 5 Min After Injection | 24 | 13 | 7 | 4 | 0 | 0 | 0 |
| 10 Min Post Injection | 24 | 10 | 11 | 3 | 0 | 0 | 0 |
| 15 Min Post Injection | 24 | 9 | 9 | 6 | 0 | 0 | 0 |
| 30 Min Post Injection | 24 | 10 | 11 | 2 | 0 | 0 | 1 |
| 45 Min Post Injection | 24 | 13 | 10 | 1 | 0 | 0 | 0 |
| 60 Min Post Injection | 24 | 17 | 6 | 1 | 0 | 0 | 0 |
| 90 Min Post Injection | 24 | 23 | 1 | 0 | 0 | 0 | 0 |
| 120 Min Post Injection | 24 | 21 | 3 | 0 | 0 | 0 | 0 |
| 180, 240, 300, 360 Min Post Injection | 24 | 24 | 0 | 0 | 0 | 0 | 0 |

FIG. 135

| Time After injection V2 | N | Edema | | | | | |
|---|---|---|---|---|---|---|---|
| | | 0 None | 1 Very Slight Swelling | 2 Slight Swelling | 3 | 4 | Not Done |
| 5 Min Prior to Needle Placement | 23 | 23 | 0 | 0 | 0 | 0 | 0 |
| Immediately After Injection | 23 | 14 | 5 | 2 | 0 | 0 | 2 |
| 5 Min After Injection | 23 | 9 | 11 | 2 | 0 | 0 | 0 |
| 10 Min Post Injection | 23 | 8 | 8 | 7 | 0 | 0 | 0 |
| 15 Min Post Injection | 23 | 8 | 8 | 7 | 0 | 0 | 0 |
| 30 Min Post Injection | 23 | 10 | 6 | 7 | 0 | 0 | 0 |
| 45 Min Post Injection | 23 | 11 | 9 | 3 | 0 | 0 | 0 |
| 60 Min Post Injection | 23 | 14 | 8 | 1 | 0 | 0 | 0 |
| 90 Min Post Injection | 23 | 20 | 3 | 0 | 0 | 0 | 0 |
| 120 Min Post Injection | 23 | 21 | 2 | 0 | 0 | 0 | 0 |
| 180, 240, 300, 360 Min Post Injection | 23 | 23 | 0 | 0 | 0 | 0 | 0 |

FIG. 136

| Time After injection V1 | N | Induration | | | | | |
|---|---|---|---|---|---|---|---|
| | | 0 No Firmness | 1 Slightly Firm | 2 Mildly Firm | 3 | 4 | Not Done |
| 5 Min Prior to Needle Placement | 24 | 24 | 0 | 0 | 0 | 0 | 0 |
| Immediately After Injection | 24 | 0 | 0 | 0 | 0 | 0 | 24 |
| 5 Min After Injection | 24 | 15 | 7 | 2 | 0 | 0 | 0 |
| 10 Min Post Injection | 24 | 14 | 7 | 3 | 0 | 0 | 0 |
| 15 Min Post Injection | 24 | 14 | 9 | 1 | 0 | 0 | 0 |
| 30 Min Post Injection | 24 | 13 | 9 | 1 | 0 | 0 | 1 |
| 45 Min Post Injection | 24 | 18 | 6 | 0 | 0 | 0 | 0 |
| 60 Min Post Injection | 24 | 21 | 2 | 1 | 0 | 0 | 0 |
| 90 Min Post Injection | 24 | 23 | 1 | 0 | 0 | 0 | 0 |
| 120 Min Post Injection | 24 | 23 | 1 | 0 | 0 | 0 | 0 |
| 180, 240, 360 Min Post Injection | 24 | 24 | 0 | 0 | 0 | 0 | 0 |
| 300 Min Post-Injection | 24 | 23 | 1 | 0 | 0 | 0 | 0 |

FIG. 137

| Time After injection V2 | N | Induration | | | | | |
|---|---|---|---|---|---|---|---|
| | | 0 No Firmness | 1 Slightly Firm | 2 Mildly Firm | 3 | 4 | Not Done |
| 5 Min Prior to Needle Placement | 23 | 23 | 0 | 0 | 0 | 0 | 0 |
| Immediately After Injection | 23 | 19 | 2 | 0 | 0 | 0 | 2 |
| 5 Min After Injection | 23 | 18 | 4 | 1 | 0 | 0 | 0 |
| 10 Min Post Injection | 23 | 19 | 3 | 1 | 0 | 0 | 0 |
| 15 Min Post Injection | 23 | 19 | 4 | 0 | 0 | 0 | 0 |
| 30 Min Post Injection | 23 | 20 | 3 | 0 | 0 | 0 | 0 |
| 45 Min Post Injection | 23 | 19 | 4 | 0 | 0 | 0 | 0 |
| 60 Min Post Injection | 23 | 19 | 4 | 0 | 0 | 0 | 0 |
| 90 Min Post Injection | 23 | 23 | 0 | 0 | 0 | 0 | 0 |
| 120 Min Post Injection | 23 | 23 | 0 | 0 | 0 | 0 | 0 |
| 180, 240, 300, 360 Min Post Injection | 23 | 24 | 0 | 0 | 0 | 0 | 0 |

FIG. 138

| Adverse Event | Severity | Causality | Status | Relationship to Dose |
|---|---|---|---|---|
| ISR #2 (INJECTION SITE #2 RASH) | MILD | DEFINITELY RELATED | RECOVERED/RESOLVED | DOSE NOT CHANGED |
| PRURITIS | MILD | PROBABLY RELATED | RECOVERED/RESOLVED | NOT APPLICABLE |
| PRURITUS | MILD | PROBABLY RELATED | RECOVERED/RESOLVED | NOT APPLICABLE |
| EAR INFECTION | MILD | UNLIKELY RELATED | ONGOING | DOSE NOT CHANGED |
| PRURITIS | MILD | DEFINITELY RELATED | RECOVERED/RESOLVED | NOT APPLICABLE |

FIG. 139

Example 5 – modeling of Inj. Visit #1 – Cohort B

| Cohort # | Needle | Mean Applied Force (N) ± SEM |
|---|---|---|
| 2 | 25G-Terumo | 42.6 ± 1.1 |

Cohort B – GGL + EDP (4000 U/mL)

| Cohort # | Needle | Mean Applied Force (N) ± SEM |
|---|---|---|
| B | 25G-Terumo | 38.7 ± 0.6 |

Example 5 – modeling of injection times

| Needle Gauge | Injection Time (sec ± SEM) | |
|---|---|---|
| | 25G-Terumo | 25G-BD |
| | 19.8 ± 0.5 | 30.0 ± 1.1 |

Using this modeling, the 25G-BD needle was chosen to use with the HVAI device to provide a delivery time of ~30s.

*Predicted injection times for HVAI devices**

| Needle Gauge | Projected Injection Time (sec) | |
|---|---|---|
| | 25G-Terumo | 25G-BD |
| | ~18.0 | ~27.2 |

*Predicted Injection time = (38.7 * Injection time from 23027)/42.6

FIG. 142

| | Time After injection V2 | Pain Scores | | | | | | | | | | | |
|---|---|---|---|---|---|---|---|---|---|---|---|---|---|
| N | | 0 | 1 | 2 | 3 | 4 | 5 | 6 | 7 | 8 | 9 | 10 | Not Done |
| 23 | 5 Min Prior to Needle Placement | 22 | 0 | 0 | 1 | 0 | 0 | 0 | 0 | 0 | 0 | 0 | 0 |
| 23 | After Needle Placement, Prior to Injection | 17 | 5 | 1 | 0 | 0 | 0 | 0 | 0 | 0 | 0 | 0 | 0 |
| 23 | Immediately After Injection | 5 | 5 | 7 | 2 | 0 | 0 | 2 | 0 | 0 | 0 | 0 | 2 |
| 23 | 5 Min After Injection | 13 | 7 | 2 | 0 | 1 | 0 | 0 | 0 | 0 | 0 | 0 | 0 |
| 23 | 10 Min Post Injection | 15 | 6 | 1 | 1 | 0 | 0 | 0 | 0 | 0 | 0 | 0 | 0 |
| 22 | 15 Min Post Injection | 13 | 7 | 0 | 1 | 0 | 0 | 0 | 0 | 0 | 0 | 0 | 1 |
| 23 | 30 Min Post Injection | 18 | 3 | 1 | 1 | 0 | 0 | 0 | 0 | 0 | 0 | 0 | 0 |
| 23 | 45 Min Post Injection | 21 | 2 | 0 | 0 | 0 | 0 | 0 | 0 | 0 | 0 | 0 | 0 |
| 23 | 60 Min Post Injection | 22 | 1 | 0 | 0 | 0 | 0 | 0 | 0 | 0 | 0 | 0 | 0 |
| 23 | 90 Min Post Injection | 22 | 1 | 0 | 0 | 0 | 0 | 0 | 0 | 0 | 0 | 0 | 0 |
| 23 | 120 Min Post Injection | 23 | 0 | 0 | 0 | 0 | 0 | 0 | 0 | 0 | 0 | 0 | 0 |
| 23 | 180 Min Post Injection | 23 | 0 | 0 | 0 | 0 | 0 | 0 | 0 | 0 | 0 | 0 | 0 |
| 23 | 240 Min Post Injection | 23 | 0 | 0 | 0 | 0 | 0 | 0 | 0 | 0 | 0 | 0 | 0 |
| 23 | 300 Min Post Injection | 23 | 0 | 0 | 0 | 0 | 0 | 0 | 0 | 0 | 0 | 0 | 0 |
| 23 | 360 Min Post Injection | 22 | 0 | 0 | 0 | 0 | 0 | 0 | 0 | 0 | 0 | 0 | 1 |

FIG. 149A

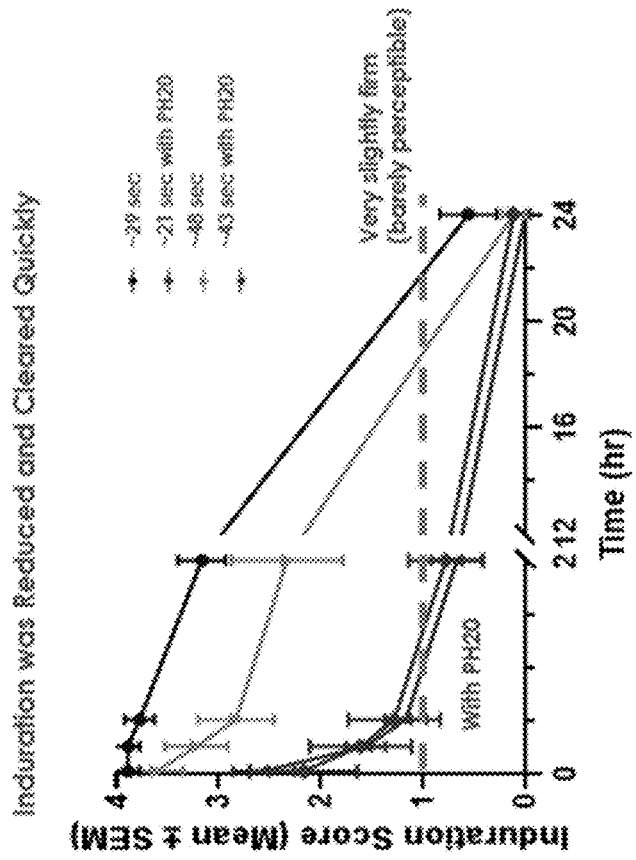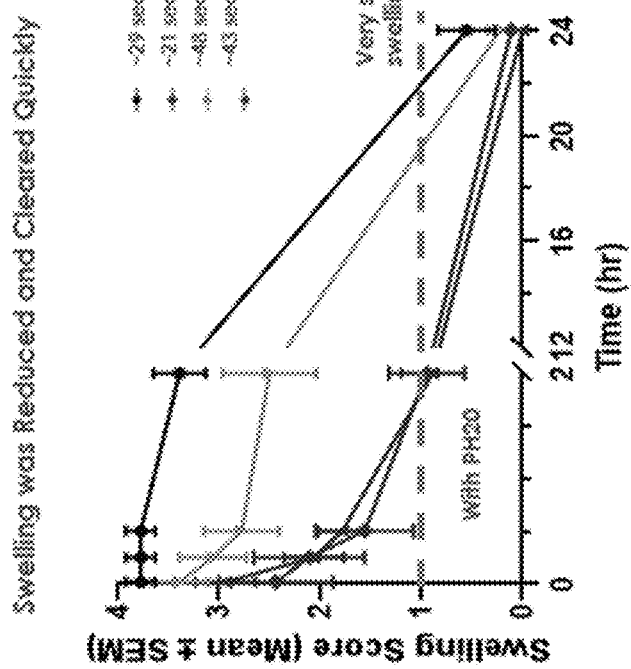
FIG. 151

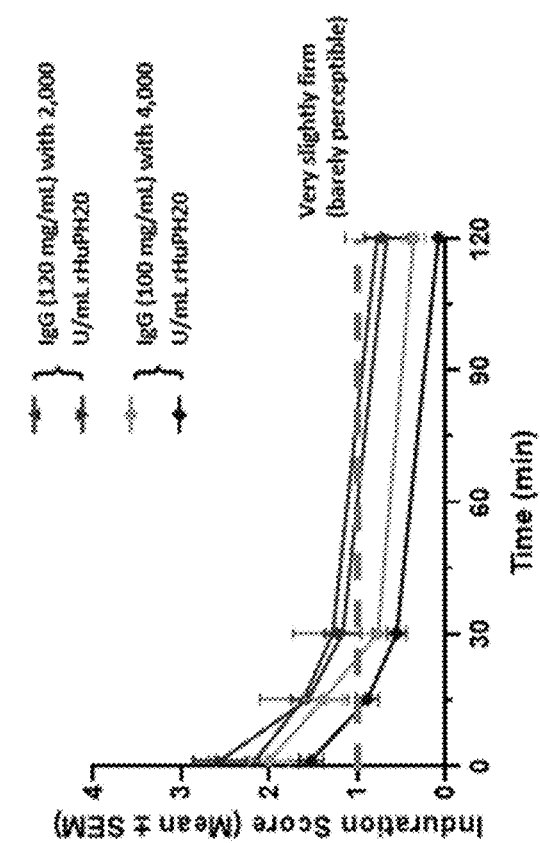
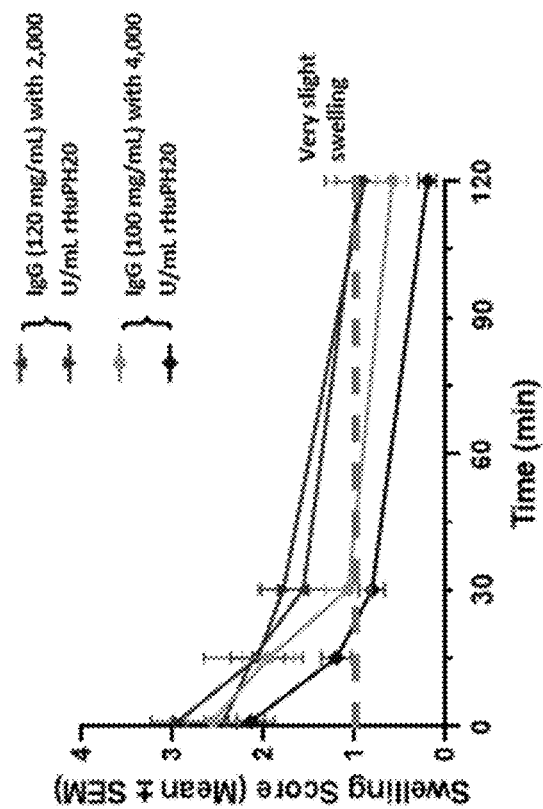
FIG. 153

Example of How Needle Was Selected for Halo 104-105 Clinical Trial

*Example 4 – Preclinical Modeling of Inj. Visit #1 – Cohort B*

- 10 mL of GGL + EDP was administered at 20 mL/min to the mini-pig (25G-Terumo needle)
- Applied force was measured during injection and used to compare to Halo 104-105 data Data from mini-pig model (Example 4)

| Example | Needle | Mean Applied Force (N) ± SEM |
|---|---|---|
| 4 | 25G-Terumo | 42.6 ± 1.1 |

*Example 8 – Preclinical injection times of GGL + EDP Using HVAI*

- 10 mL of GGL + EDP was administered using the HVAI
- Injection times were measured Data from mini-pig model (Example 8)

| Example | Injection Time (sec ± SEM) | |
|---|---|---|
|  | 25G-Terumo | 25G-BD |
| 5 | 19.8 ± 0.5 | 30.0 ± 1.1 |

*Example 6 – Clinical Testing – Inj. Visit #1 – Cohort B – Applied Force*

- 10 mL of GGL + EDP was administered at 20 mL/min to human subjects (25G-Terumo needle)
- Applied force was measured during injection and used to compare to Halo 104-105 data Data from Halo 104-105 model

| Example | Needle | Mean Applied Force (N) ± SEM |
|---|---|---|
| 6 | 25G-Terumo | 38.7 ± 0.6 |

*Predicted 104-105 Injection time = (38.7 *Inj. Time from mini-pig model/42.6) = 90.8% of times from mini-pig study (Example 8)

*Predicted injection times for HVAI devices**

| Needle Gauge | Projected Injection Time (sec) | |
|---|---|---|
|  | 25G-Terumo | 25G-BD |
|  | ~18.0 | ~27.2 |

Using this predictive modeling, the 25G-BD needle was chosen to use with the HVAI device to provide a delivery time of ~30s.

FIG. 173

```
                             SEQUENCE LISTING

Sequence total quantity: 47
SEQ ID NO: 1            moltype = AA  length = 509
FEATURE                 Location/Qualifiers
REGION                  1..509
                        note = precursor human PH20
source                  1..509
                        mol_type = protein
                        organism = Homo sapiens
SEQUENCE: 1
MGVLKFKHIF FRSFVKSSGV SQIVFTFLLI PCCLTLNFRA PPVIPNVPFL WAWNAPSEFC   60
LGKFDEPLDM SLFSFIGSPR INATGQGVTI FYVDRLGYYP YIDSITGVTV NGGIPQKISL  120
QDHLDKAKKD ITFYMPVDNL GMAVIDWEEW RPTWARNWKP KDVYKNRSIE LVQQQNVQLS  180
LTEATEKAKQ EFEKAGKDFL VETIKLGKLL RPNHLWGYYL FPDCYNHHYK KPGYNGSCFN  240
VEIKRNDDLS WLWNESTALY PSIYLNTQQS PVAATLYVRN RVREAIRVSK IPDAKSPLPV  300
FAYTRIVFTD QVLKFLSQDE LVYTFGETVA LGASGIVIWG TLSIMRSMKS CLLLDNYMET  360
ILNPYIINVT LAAKMCSQVL CQEQGVCIRK NWNSSDYLHL NPDNFAIQLE KGGKFTVRGK  420
PTLEDLEQFS EKFYCSCYST LSCKEKADVK DTDAVDVCIA DGVCIDAFLK PPMETEEPQI  480
FYNASPSTLS ATMFIVSILF LIISSVASL                                   509

SEQ ID NO: 2            moltype = AA  length = 447
FEATURE                 Location/Qualifiers
REGION                  1..447
                        note = Mature PH20 36-482
source                  1..447
                        mol_type = protein
                        organism = Homo sapiens
SEQUENCE: 2
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFY                                     447

SEQ ID NO: 3            moltype = AA  length = 442
FEATURE                 Location/Qualifiers
REGION                  1..442
                        note = soluble rHuPh20 36-477
source                  1..442
                        mol_type = protein
                        organism = Homo sapiens
SEQUENCE: 3
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EE                                          442

SEQ ID NO: 4            moltype = AA  length = 443
FEATURE                 Location/Qualifiers
REGION                  1..443
                        note = soluble rHuPH20 36-478
source                  1..443
                        mol_type = protein
                        organism = Homo sapiens
SEQUENCE: 4
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
```

```
DVCIADGVCI DAFLKPPMET EEP                                                     443

SEQ ID NO: 5              moltype = AA  length = 444
FEATURE                   Location/Qualifiers
REGION                    1..444
                          note = Mature PH20 36-479
source                    1..444
                          mol_type = protein
                          organism = Homo sapiens
SEQUENCE: 5
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQ                                          444

SEQ ID NO: 6              moltype = AA  length = 445
FEATURE                   Location/Qualifiers
REGION                    1..445
                          note = Mature PH20 36-480
source                    1..445
                          mol_type = protein
                          organism = Homo sapiens
SEQUENCE: 6
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQI                                         445

SEQ ID NO: 7              moltype = AA  length = 446
FEATURE                   Location/Qualifiers
REGION                    1..446
                          note = Mature PH20 36-481
source                    1..446
                          mol_type = protein
                          organism = Homo sapiens
SEQUENCE: 7
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIF                                        446

SEQ ID NO: 8              moltype = AA  length = 482
FEATURE                   Location/Qualifiers
REGION                    1..482
                          note = HuPH20 precursor 1-482
source                    1..482
                          mol_type = protein
                          organism = Homo sapiens
SEQUENCE: 8
MGVLKFKHIF FRSFVKSSGV SQIVFTFLLI PCCLTLNFRA PPVIPNVPFL WAWNAPSEFC    60
LGKFDEPLDM SLFSFIGSPR INATGQGVTI FYVDRLGYYP YIDSITGVTV NGGIPQKISL   120
QDHLDKAKKD ITFYMPVDNL GMAVIDWEEW RPTWARNWKP KDVYKNRSIE LVQQQNVQLS   180
LTEATEKAKQ EFEKAGKDFL VETIKLGKLL RPNHLWGYYL FPDCYNHHYK KPGYNGSCFN   240
VEIKRNDDLS WLWNESTALY PSIYLNTQQS PVAATLYVRN RVREAIRVSK IPDAKSPLPV   300
FAYTRIVFTD QVLKFLSQDE LVYTFGETVA LGASGIVIWG TLSIMRSMKS CLLLDNYMET   360
ILNPYIINVT LAAKMCSQVL CQEQGVCIRK NWNSSDYLHL NPDNFAIQLE KGGKFTVRGK   420
PTLEDLEQFS EKFYCSCYST LSCKEKADVK DTDAVDVCIA DGVCIDAFLK PPMETEEPQI   480
FY                                                                  482

SEQ ID NO: 9              moltype = AA  length = 495
FEATURE                   Location/Qualifiers
REGION                    1..495
                          note = HuPH20 precursor 1-495
source                    1..495
                          mol_type = protein
                          organism = Homo sapiens
SEQUENCE: 9
```

```
MGVLKFKHIF FRSFVKSSGV SQIVFTFLLI PCCLTLNFRA PPVIPNVPFL WAWNAPSEFC    60
LGKFDEPLDM SLFSFIGSPR INATGQGVTI FYVDRLGYYP YIDSITGVTV NGGIPQKISL   120
QDHLDKAKKD ITFYMPVDNL GMAVIDWEEW RPTWARNWKP KDVYKNRSIE LVQQQNVQLS   180
LTEATEKAKQ EFEKAGKDFL VETIKLGKLL RPNHLWGYYL FPDCYNHHYK KPGYNGSCFN   240
VEIKRNDDLS WLWNESTALY PSIYLNTQQS PVAATLYVRN RVREAIRVSK IPDAKSPLPV   300
FAYTRIVFTD QVLKFLSQDE LVYTFGETVA LGASGIVIWG TLSIMRSMKS CLLLDNYMET   360
ILNPYIINVT LAAKMCSQVL CQEQGVCIRK NWNSSDYLHL NPDNFAIQLE KGGKFTVRGK   420
PTLEDLEQFS EKFYCSCYST LSCKEKADVK DTDAVDVCIA DGVCIDAFLK PPMETEEPQI   480
FYNASPSTLS ATMFI                                                   495

SEQ ID NO: 10           moltype = AA  length = 496
FEATURE                 Location/Qualifiers
REGION                  1..496
                        note = HuPH20 precursor 1-496
source                  1..496
                        mol_type = protein
                        organism = Homo sapiens
SEQUENCE: 10
MGVLKFKHIF FRSFVKSSGV SQIVFTFLLI PCCLTLNFRA PPVIPNVPFL WAWNAPSEFC    60
LGKFDEPLDM SLFSFIGSPR INATGQGVTI FYVDRLGYYP YIDSITGVTV NGGIPQKISL   120
QDHLDKAKKD ITFYMPVDNL GMAVIDWEEW RPTWARNWKP KDVYKNRSIE LVQQQNVQLS   180
LTEATEKAKQ EFEKAGKDFL VETIKLGKLL RPNHLWGYYL FPDCYNHHYK KPGYNGSCFN   240
VEIKRNDDLS WLWNESTALY PSIYLNTQQS PVAATLYVRN RVREAIRVSK IPDAKSPLPV   300
FAYTRIVFTD QVLKFLSQDE LVYTFGETVA LGASGIVIWG TLSIMRSMKS CLLLDNYMET   360
ILNPYIINVT LAAKMCSQVL CQEQGVCIRK NWNSSDYLHL NPDNFAIQLE KGGKFTVRGK   420
PTLEDLEQFS EKFYCSCYST LSCKEKADVK DTDAVDVCIA DGVCIDAFLK PPMETEEPQI   480
FYNASPSTLS ATMFIV                                                  496

SEQ ID NO: 11           moltype = AA  length = 497
FEATURE                 Location/Qualifiers
REGION                  1..497
                        note = HuPH20 precursor 1-497
source                  1..497
                        mol_type = protein
                        organism = Homo sapiens
SEQUENCE: 11
MGVLKFKHIF FRSFVKSSGV SQIVFTFLLI PCCLTLNFRA PPVIPNVPFL WAWNAPSEFC    60
LGKFDEPLDM SLFSFIGSPR INATGQGVTI FYVDRLGYYP YIDSITGVTV NGGIPQKISL   120
QDHLDKAKKD ITFYMPVDNL GMAVIDWEEW RPTWARNWKP KDVYKNRSIE LVQQQNVQLS   180
LTEATEKAKQ EFEKAGKDFL VETIKLGKLL RPNHLWGYYL FPDCYNHHYK KPGYNGSCFN   240
VEIKRNDDLS WLWNESTALY PSIYLNTQQS PVAATLYVRN RVREAIRVSK IPDAKSPLPV   300
FAYTRIVFTD QVLKFLSQDE LVYTFGETVA LGASGIVIWG TLSIMRSMKS CLLLDNYMET   360
ILNPYIINVT LAAKMCSQVL CQEQGVCIRK NWNSSDYLHL NPDNFAIQLE KGGKFTVRGK   420
PTLEDLEQFS EKFYCSCYST LSCKEKADVK DTDAVDVCIA DGVCIDAFLK PPMETEEPQI   480
FYNASPSTLS ATMFIVS                                                 497

SEQ ID NO: 12           moltype = AA  length = 498
FEATURE                 Location/Qualifiers
REGION                  1..498
                        note = HuPH20 precursor 1-498
source                  1..498
                        mol_type = protein
                        organism = Homo sapiens
SEQUENCE: 12
MGVLKFKHIF FRSFVKSSGV SQIVFTFLLI PCCLTLNFRA PPVIPNVPFL WAWNAPSEFC    60
LGKFDEPLDM SLFSFIGSPR INATGQGVTI FYVDRLGYYP YIDSITGVTV NGGIPQKISL   120
QDHLDKAKKD ITFYMPVDNL GMAVIDWEEW RPTWARNWKP KDVYKNRSIE LVQQQNVQLS   180
LTEATEKAKQ EFEKAGKDFL VETIKLGKLL RPNHLWGYYL FPDCYNHHYK KPGYNGSCFN   240
VEIKRNDDLS WLWNESTALY PSIYLNTQQS PVAATLYVRN RVREAIRVSK IPDAKSPLPV   300
FAYTRIVFTD QVLKFLSQDE LVYTFGETVA LGASGIVIWG TLSIMRSMKS CLLLDNYMET   360
ILNPYIINVT LAAKMCSQVL CQEQGVCIRK NWNSSDYLHL NPDNFAIQLE KGGKFTVRGK   420
PTLEDLEQFS EKFYCSCYST LSCKEKADVK DTDAVDVCIA DGVCIDAFLK PPMETEEPQI   480
FYNASPSTLS ATMFIVSI                                                498

SEQ ID NO: 13           moltype = AA  length = 499
FEATURE                 Location/Qualifiers
REGION                  1..499
                        note = HuPH20 precursor 1-499
source                  1..499
                        mol_type = protein
                        organism = Homo sapiens
SEQUENCE: 13
MGVLKFKHIF FRSFVKSSGV SQIVFTFLLI PCCLTLNFRA PPVIPNVPFL WAWNAPSEFC    60
LGKFDEPLDM SLFSFIGSPR INATGQGVTI FYVDRLGYYP YIDSITGVTV NGGIPQKISL   120
QDHLDKAKKD ITFYMPVDNL GMAVIDWEEW RPTWARNWKP KDVYKNRSIE LVQQQNVQLS   180
LTEATEKAKQ EFEKAGKDFL VETIKLGKLL RPNHLWGYYL FPDCYNHHYK KPGYNGSCFN   240
VEIKRNDDLS WLWNESTALY PSIYLNTQQS PVAATLYVRN RVREAIRVSK IPDAKSPLPV   300
FAYTRIVFTD QVLKFLSQDE LVYTFGETVA LGASGIVIWG TLSIMRSMKS CLLLDNYMET   360
ILNPYIINVT LAAKMCSQVL CQEQGVCIRK NWNSSDYLHL NPDNFAIQLE KGGKFTVRGK   420
```

```
PTLEDLEQFS EKFYCSCYST LSCKEKADVK DTDAVDVCIA DGVCIDAFLK PPMETEEPQI    480
FYNASPSTLS ATMFIVSIL                                                499

SEQ ID NO: 14           moltype = AA  length = 500
FEATURE                 Location/Qualifiers
REGION                  1..500
                        note = HuPH20 precursor 1-500
source                  1..500
                        mol_type = protein
                        organism = Homo sapiens
SEQUENCE: 14
MGVLKFKHIF FRSFVKSSGV SQIVFTFLLI PCCLTLNFRA PPVIPNVPFL WAWNAPSEFC     60
LGKFDEPLDM SLFSFIGSPR INATGQGVTI FYVDRLGYYP YIDSITGVTV NGGIPQKISL    120
QDHLDKAKKD ITFYMPVDNL GMAVIDWEEW RPTWARNWKP KDVYKNRSIE LVQQQNVQLS    180
LTEATEKAKQ EFEKAGKDFL VETIKLGKLL RPNHLWGYYL FPDCYNHHYK KPGYNGSCFN    240
VEIKRNDDLS WLWNESTALY PSIYLNTQQS PVAATLYVRN RVREAIRVSK IPDAKSPLPV    300
FAYTRIVFTD QVLKFLSQDE LVYTFGETVA LGASGIVIWG TLSIMRSMKS CLLLDNYMET    360
ILNPYIINVT LAAKMCSQVL CQEQGVCIRK NWNSSDYLHL NPDNFAIQLE KGGKFTVRGK    420
PTLEDLEQFS EKFYCSCYST LSCKEKADVK DTDAVDVCIA DGVCIDAFLK PPMETEEPQI    480
FYNASPSTLS ATMFIVSILF                                                500

SEQ ID NO: 15           moltype = AA  length = 1314
FEATURE                 Location/Qualifiers
REGION                  1..1314
                        note = Synthetic Sequence
source                  1..1314
                        mol_type = protein
                        organism = synthetic construct
SEQUENCE: 15
PHEARGALAP ROPROVALIL EPROASNVAL PROPHELEUT RPALATRPAS NALAPROSER     60
GLUPHECYSL EUGLYLYSPH EASPGLUPRO LEUASPMETS ERLEUPHESE RPHEILEGLY    120
SERPROARGI LEASNALATH RGLYGLNGLY VALTHRILEP HETYRVALAS PARGLEUGLY    180
TYRTYRPROT YRILEASPSE RILETHRGLY VALTHRVALA SNGLYGLYIL EPROGLNLYS    240
ILESERLEUG LNASPHISLE UASPLYSALA LYSLYSASPI LETHRPHETY RMETPROVAL    300
ASPASNLEUG LYMETALAVA LILEASPTRP GLUGLUTRPA RGPROTHRTR PALAARGASN    360
TRPLYSPROL YSASPPVALTY RLYSASNARG SERILEGLUL EUVALGLNGL NGLNASNVAL    420
GLNLEUSERL EUTHRGLUAL ATHRGLULYS ALALYSGLNG LUPHEGLULY SALAGLYLYS    480
ASPPHELEUV ALGLUTHRIL ELYSLEUGLY LYSLEULEUA RGPROASNHI SLEUTRPGLY    540
TYRTYRLEUP HEPROASPCY STYRASNHIS HISTYRLYSL YSPROGLYTY RASNGLYSER    600
CYSPHEASNV ALGLUILELY SARGASNASP ASPLEUSERT RPLEUTRPAS NGLUSERTHR    660
ALALALEUTYRP ROSERILETY RLEUASNTHR GLNGLNSERP ROVALALAAL ATHRLEUTYR    720
VALARGASNA RGVALARGGL UALAILEARG VALSERLYSI LEPROASPAL ALYSSERPRO    780
LEUPROVALP HEALATYRTH RARGILEVAL PHETHRASPG LNVALLEULY SPHELEUSER    840
GLNASPGLUL EUVALTYRTH RPHEGLYGLU THRVALALAL EUGLYALASE RGLYILEVAL    900
ILETRPGLYS ERTRPGLUAS NTHRARGTHR LYSGLUSERC YSGLNALAIL ELYSGLUTYR    960
METASPTHRT HRLEUASNPR OTYRILEILE ASNVALTHRL EUALAALALY SMETCYSSER   1020
GLNVALLEUC YSGLNGLUGL NGLYVALCYS ILEARGLYSA SNTRPASNSE RSERASPTYR   1080
LEUHISLEUA SNPROASPAS NPHEALAILE GLNLEUGLUL YSGLYGLYLY SPHETHRVAL   1140
ARGGLYLYSP ROTHRLEUGL UASPLEUGLU GLNPHESERG LULYSPHETY RCYSSERCYS   1200
TYRSERTHRL EUSERCYSLY SGLULYSALA ASPVALLYSA SPTHRASPAL AVALASPVAL   1260
CYSILEALAA SPGLYVALCY SILEASPALA PHESEQUENC ELISTINGFA MILY         1314

SEQ ID NO: 16           moltype = AA  length = 474
FEATURE                 Location/Qualifiers
REGION                  1..474
                        note = Mature full-length human PH20
source                  1..474
                        mol_type = protein
                        organism = Homo sapiens
SEQUENCE: 16
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS PSTLSATMFI VSILFLIISS VASL          474

SEQ ID NO: 17           moltype = AA  length = 430
FEATURE                 Location/Qualifiers
REGION                  1..430
                        note = Mature human PH20 36-465
source                  1..430
                        mol_type = protein
                        organism = Homo sapiens
SEQUENCE: 17
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
```

```
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTAV    420
DVCIADGVCI                                                           430

SEQ ID NO: 18             moltype = AA  length = 431
FEATURE                   Location/Qualifiers
REGION                    1..431
                          note = mature human PH20 36-466
source                    1..431
                          mol_type = protein
                          organism = Homo sapiens
SEQUENCE: 18
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTAV    420
DVCIADGVCI D                                                         431

SEQ ID NO: 19             moltype = AA  length = 432
FEATURE                   Location/Qualifiers
REGION                    1..432
                          note = mature human PH20 36-467
source                    1..432
                          mol_type = protein
                          organism = Homo sapiens
SEQUENCE: 19
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTAV    420
DVCIADGVCI DA                                                        432

SEQ ID NO: 20             moltype = AA  length = 433
FEATURE                   Location/Qualifiers
REGION                    1..433
                          note = mature human PH20 36-468
source                    1..433
                          mol_type = protein
                          organism = Homo sapiens
SEQUENCE: 20
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTAV    420
DVCIADGVCI DAF                                                       433

SEQ ID NO: 21             moltype = AA  length = 434
FEATURE                   Location/Qualifiers
REGION                    1..434
                          note = mature PH20 36-469
source                    1..434
                          mol_type = protein
                          organism = Homo sapiens
SEQUENCE: 21
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTAV    420
DVCIADGVCI DAFL                                                      434

SEQ ID NO: 22             moltype = AA  length = 435
FEATURE                   Location/Qualifiers
REGION                    1..435
                          note = mature human PH20 36-470
```

```
source                  1..435
                        mol_type = protein
                        organism = Homo sapiens
SEQUENCE: 22
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLK                                                   435

SEQ ID NO: 23           moltype = AA   length = 436
FEATURE                 Location/Qualifiers
REGION                  1..436
                        note = mature human PH20 36-471
source                  1..436
                        mol_type = protein
                        organism = Homo sapiens
SEQUENCE: 23
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKP                                                  436

SEQ ID NO: 24           moltype = AA   length = 437
FEATURE                 Location/Qualifiers
REGION                  1..437
                        note = mature human PH20 36-472
source                  1..437
                        mol_type = protein
                        organism = Homo sapiens
SEQUENCE: 24
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPP                                                 437

SEQ ID NO: 25           moltype = AA   length = 438
FEATURE                 Location/Qualifiers
REGION                  1..438
                        note = mature human PH20 36-473
source                  1..438
                        mol_type = protein
                        organism = Homo sapiens
SEQUENCE: 25
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPM                                                438

SEQ ID NO: 26           moltype = AA   length = 439
FEATURE                 Location/Qualifiers
REGION                  1..439
                        note = mature human PH20 36-474
source                  1..439
                        mol_type = protein
                        organism = Homo sapiens
SEQUENCE: 26
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
```

```
DVCIADGVCI DAFLKPPME                                                    439

SEQ ID NO: 27           moltype = AA  length = 440
FEATURE                 Location/Qualifiers
REGION                  1..440
                        note = mature human PH20 36-475
source                  1..440
                        mol_type = protein
                        organism = Homo sapiens
SEQUENCE: 27
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET                                                440

SEQ ID NO: 28           moltype = AA  length = 441
FEATURE                 Location/Qualifiers
REGION                  1..441
                        note = mature human PH20 36-476
source                  1..441
                        mol_type = protein
                        organism = Homo sapiens
SEQUENCE: 28
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET E                                              441

SEQ ID NO: 29           moltype = AA  length = 448
FEATURE                 Location/Qualifiers
REGION                  1..448
                        note = mature human PH20 36-483
source                  1..448
                        mol_type = protein
                        organism = Homo sapiens
SEQUENCE: 29
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYN                                       448

SEQ ID NO: 30           moltype = AA  length = 449
FEATURE                 Location/Qualifiers
REGION                  1..449
                        note = mature human PH20 36-484
source                  1..449
                        mol_type = protein
                        organism = Homo sapiens
SEQUENCE: 30
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNA                                      449

SEQ ID NO: 31           moltype = AA  length = 450
FEATURE                 Location/Qualifiers
REGION                  1..450
                        note = mature human PH20 36-485
source                  1..450
                        mol_type = protein
                        organism = Homo sapiens
SEQUENCE: 31
LNFRAPPVIP NVPFLWAWNA PSEFCLGKFD EPLDMSLFSF IGSPRINATG QGVTIFYVDR    60
```

```
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS                                    450

SEQ ID NO: 32           moltype = AA   length = 451
FEATURE                 Location/Qualifiers
REGION                  1..451
                        note = mature human PH20 36-486
source                  1..451
                        mol_type = protein
                        organism = Homo sapiens
SEQUENCE: 32
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS P                                  451

SEQ ID NO: 33           moltype = AA   length = 452
FEATURE                 Location/Qualifiers
REGION                  1..452
                        note = mature human PH20 36-487
source                  1..452
                        mol_type = protein
                        organism = Homo sapiens
SEQUENCE: 33
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS PS                                 452

SEQ ID NO: 34           moltype = AA   length = 453
FEATURE                 Location/Qualifiers
REGION                  1..453
                        note = mature human PH20 36-488
source                  1..453
                        mol_type = protein
                        organism = Homo sapiens
SEQUENCE: 34
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS PST                                453

SEQ ID NO: 35           moltype = AA   length = 454
FEATURE                 Location/Qualifiers
REGION                  1..454
                        note = mature human PH20 36-489
source                  1..454
                        mol_type = protein
                        organism = Homo sapiens
SEQUENCE: 35
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS PSTL                               454

SEQ ID NO: 36           moltype = AA   length = 455
FEATURE                 Location/Qualifiers
REGION                  1..455
```

```
                              note = mature human PH20 36-490
source                        1..455
                              mol_type = protein
                              organism = Homo sapiens
SEQUENCE: 36
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNAS PSTLS                              455

SEQ ID NO: 37                 moltype = AA  length = 456
FEATURE                       Location/Qualifiers
REGION                        1..456
                              note = mature human PH20 36-491
source                        1..456
                              mol_type = protein
                              organism = Homo sapiens
SEQUENCE: 37
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNAS PSTLSA                             456

SEQ ID NO: 38                 moltype = AA  length = 457
FEATURE                       Location/Qualifiers
REGION                        1..457
                              note = mature human PH20 36-492
source                        1..457
                              mol_type = protein
                              organism = Homo sapiens
SEQUENCE: 38
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNAS PSTLSAT                            457

SEQ ID NO: 39                 moltype = AA  length = 458
FEATURE                       Location/Qualifiers
REGION                        1..458
                              note = mature human PH20 36-493
source                        1..458
                              mol_type = protein
                              organism = Homo sapiens
SEQUENCE: 39
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNAS PSTLSATM                           458

SEQ ID NO: 40                 moltype = AA  length = 459
FEATURE                       Location/Qualifiers
REGION                        1..459
                              note = mature human PH20 36-494
source                        1..459
                              mol_type = protein
                              organism = Homo sapiens
SEQUENCE: 40
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
```

```
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS PSTLSATMF                          459

SEQ ID NO: 41         moltype = AA  length = 460
FEATURE               Location/Qualifiers
REGION                1..460
                      note = mature human PH20 36-495
source                1..460
                      mol_type = protein
                      organism = Homo sapiens
SEQUENCE: 41
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS PSTLSATMFI                         460

SEQ ID NO: 42         moltype = AA  length = 461
FEATURE               Location/Qualifiers
REGION                1..461
                      note = mature human PH20 36-496
source                1..461
                      mol_type = protein
                      organism = Homo sapiens
SEQUENCE: 42
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS PSTLSATMFI V                       461

SEQ ID NO: 43         moltype = AA  length = 462
FEATURE               Location/Qualifiers
REGION                1..462
                      note = mature human PH30 36-497
source                1..462
                      mol_type = protein
                      organism = Homo sapiens
SEQUENCE: 43
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS PSTLSATMFI VS                      462

SEQ ID NO: 44         moltype = AA  length = 463
FEATURE               Location/Qualifiers
REGION                1..463
                      note = mature human PH20 36-498
source                1..463
                      mol_type = protein
                      organism = Homo sapiens
SEQUENCE: 44
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS PSTLSATMFI VSI                     463

SEQ ID NO: 45         moltype = AA  length = 464
FEATURE               Location/Qualifiers
REGION                1..464
                      note = mature human PH20 36-499
source                1..464
                      mol_type = protein
                      organism = Homo sapiens
SEQUENCE: 45
```

```
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNAS PSTLSATMFI VSIL                    464

SEQ ID NO: 46          moltype = AA  length = 465
FEATURE                Location/Qualifiers
REGION                 1..465
                       note = mature human PH20 36-500
source                 1..465
                       mol_type = protein
                       organism = Homo sapiens
SEQUENCE: 46
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNAS PSTLSATMFI VSILF                   465

SEQ ID NO: 47          moltype = AA  length = 447
FEATURE                Location/Qualifiers
REGION                 1..447
                       note = F204P
source                 1..447
                       mol_type = protein
                       organism = Homo sapiens
SEQUENCE: 47
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCPNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFY                                       447
```

HYALURONIDASE ENZYME FORMULATIONS FOR HIGH VOLUME ADMINISTRATION

CROSS-REFERENCE TO RELATED APPLICATIONS

The present application claims priority to U.S. Provisional Application No. 63/476,830, filed Dec. 22, 2022, U.S. Provisional Application No. 63/485,108, filed Feb. 15, 2023, U.S. Provisional Application No. 63/507,125, filed Jun. 9, 2023, U.S. Provisional Application No. 63/516,732, filed Jul. 31, 2023, U.S. Provisional Application No. 63/518,057, filed Aug. 7, 2023, and U.S. Provisional Application No. 63/520,524, filed Aug. 18, 2023, each of which is incorporated by reference herein in its entirety.

SEQUENCE LISTING

The instant application contains a Sequence Listing which has been submitted electronically in .XML format and is hereby incorporated by reference in its entirety. The .XML copy, created on Dec. 20, 2023, is named "063995-5088" and is 83 KB in size.

TECHNICAL FIELD

The present disclosure relates to a formulation comprising a hyaluronidase enzyme and an active ingredient wherein the formulation can be administered in high volumes to a subject in a need thereof while causing minimal side effects.

SUMMARY OF THE DISCLOSURE

In one embodiment, the present disclosure provides a method of treating a disease or disorder in a subject in need thereof, the method comprising administering to the subject via subcutaneous administration about 3 mL to about 50 mL of a formulation comprising a therapeutically effective amount of an active ingredient selected from a small molecule, a peptide fragment, a biologic, a nanoparticle, an antibody, an antibody fragment, and a small molecule antiviral, wherein the subcutaneous administration occurs via a high volume autoinjector with a starting delivery force of about 3 lbf to about 50 lbf, an ending delivery force of about 5 lbf to about 20 lbf, a starting pressure of about 50 psi to about 200 psi, and/or an ending pressure of about 20 psi to about 75 psi. In one embodiment, the formulation further comprises a hyaluronidase enzyme. In one embodiment, the hyaluronidase enzyme is a recombinant human hyaluronidase enzyme. In one embodiment, the hyaluronidase enzyme is recombinant human hyaluronidase PH20 enzyme. In one embodiment, the hyaluronidase enzyme has an activity of about 150 U/mL to about 150 kU/mL. In one embodiment, the hyaluronidase enzyme has an activity of about 500 U/mL to about 5,000 U/mL. In one embodiment, the hyaluronidase enzyme has an activity of about 1,500 U/mL to about 10,000 U/mL. In one embodiment, the active ingredient is a small molecule, a peptide fragment, a biologic, or a nanoparticle. In one embodiment, the active ingredient is an antibody, an antibody fragment, or a small molecule antiviral. In one embodiment, the method comprises administering to the subject about 10 mL to about 20 mL of the formulation. In one embodiment, the method comprises administering to the subject about 3 mL to about 15 mL of the formulation. In one embodiment, the method comprises administering to the subject about 3 mL, about 3.1 mL, about 3.2 mL, about 3.4 mL, about 3.5 mL, about 3.6 mL, about 3.7 mL, about 3.8 mL, about 3.9 mL, about 4 mL, about 4.1 mL, about 4.2 mL, about 4.3 mL, about 4.4 mL, about 4.5 mL, about 5 mL, about 5.1 mL, about 5.2 mL, about 5.3 mL, about 5.4 mL, about 5.5 mL, about 5.6 mL, about 5.7 mL, about 5.8 mL, about 5.9 mL, about 6 mL, about 6.1 mL, about 6.2 mL, about 6.3 mL, about 6.4 mL, about 6.5 mL, about 6.6 mL, about 6.7 mL, about 6.8 mL, about 6.9 mL, about 7 mL, about 7.1 mL, about 7.2 mL, about 7.3 mL about 7.4 mL, about 7.5 mL, about 7.6 mL, about 7.7 mL, about 7.8 mL, about 7.9 mL, about 8 mL, about 8.1 mL, about 8.2 mL, about 8.3 mL, about 8.4 mL, about 8.5 mL, about 8.6 mL, about 8.7 mL, about 8.8 mL, about 8.9 mL, about 9 mL, about 9.1 mL, about 9.2 mL, about 9.3 mL, about 9.4 mL, about 9.5 mL, about 9.6 mL, about 9.7 mL, about 9.8 mL, about 9.9 mL, about 10 mL, about 10.1 mL, about 10.2 mL, about 10.3 mL, about 10.4 mL, about 10.5 mL, about 10.6 mL, about 10.7 mL, about 10.8 mL, about 10.9 mL, about 11 mL, about 11.1 mL, about 11.2 mL, about 11.3 mL, about 11.4 mL, about 11.5 mL, about 11.6 mL, about 11.7 mL, about 11.8 mL, about 11.9 mL, about 12 mL, about 12.1 mL, about 12.2 mL, about 12.3 mL, about 12.4 mL, about 12.5 mL, about 12.6 mL, about 12.7 mL, about 12.8 mL, about 12.9 mL, about 13 mL, about 13.1 mL, about 13.2 mL, about 13.3 mL, about 13.4 mL, about 13.5 mL, about 13.6 mL, about 13.7 mL, about 13.8 mL, about 13.9 mL, about 14 mL, about 14.1 mL, about 14.2 mL, about 14.3 mL, about 14.4 mL, about 14.5 mL, about 14.6 mL, about 14.7 mL, about 14.8 mL, about 14.9 mL, about 15 mL, about 15.1 mL, about 15.2 mL, about 15.3 mL, about 15.4 mL, about 15.5 mL, about 15.6 mL, about 15.7 mL, about 15.8 mL, about 15.9 mL, about 16 mL, about 16.1 mL, about 16.2 mL, about 16.3 mL, about 16.4 mL, about 16.5 mL, about 16.6 mL, about 16.7 mL, about 16.8 mL, about 16.9 mL about 17 mL, about 17.1 mL, about 17.2 mL, about 17.3 mL, about 17.4 mL, about 17.5 mL, about 17.6 mL, about 17.7 mL, about 17.8 mL, about 17.9 mL, about 18 mL, about 18.1 mL, about 18.2 mL, about 18.3 mL, about 18.4 mL, about 18.5 mL, about 18.6 mL, about 18.7 mL, about 18.8 mL, about 18.9 mL, about 19 mL, about 19.1 mL, about 19.2 mL, about 19.3 mL, about 19.4 mL, about 19.5 mL, about 19.6 mL, about 19.7 mL, about 19.8 mL, about 19.9 mL, about 20 mL, about 20.1 mL, about 20.2 mL, about 20.3 mL, about 20.4 mL, about 20.5 mL, about 20.6 mL, about 20.7 mL, about 20.8 mL, about 20.9 mL, about 21 mL, about 21.1 mL, about 21.2 mL, about 21.3 mL, about 21.4 mL, about 21.5 mL, about 21.6 mL, about 21.7 mL, about 21.8 mL, about 21.9 mL, about 22 mL, about 22.1 mL, about 22.2 mL, about 22.3 mL, about 22.4 mL, about 22.5 mL, about 22.6 mL, about 22.7 mL, about 22.8 mL, about 22.9 mL, about 23 mL, about 23.1 mL, about 23.2 mL, about 23.3 mL, about 23.4 mL, about 23.5 mL, about 23.6 mL, about 23.7 mL, about 23.8 mL, about 23.9 mL, about 24 mL, about 24.1 mL, about 24.2 mL, about 24.3 mL, about 24.4 mL, about 24.5 mL, about 24.6 mL, about 24.7 mL, about 24.8 mL, about 24.9 mL, or about 25 mL. In one embodiment, the method comprises administering the formulation using a high volume autoinjector. In one embodiment, the method comprises administering the formulation with a starting delivery force of about 3 lbf to about 50 lbf using a high volume autoinjector. In one embodiment, the method comprises administering the formulation with an ending delivery force of about 5 lbf to about 20 lbf using a high volume autoinjector. In one embodiment, the method comprises administering the formulation with a starting pressure of about 50 psi to about 200 psi using a high volume autoinjector. In one embodiment, the method comprises administering the formulation with an ending pressure of about 20 psi to about 75 psi using a high volume autoinjector. In one embodiment, the formulation is in a prefilled syringe. In one embodiment, the prefilled syringe contains about 3 mL, about 3.1 mL, about 3.2 mL, about 3.4 mL, about 3.5 mL, about 3.6 mL, about 3.7 mL, about 3.8 mL, about 3.9 mL, about 4 mL, about 4.1 mL, about 4.2 mL, about 4.3 mL, about 4.4 mL, about 4.5 mL, about 5 mL, about 5.1 mL, about 5.2 mL, about 5.3 mL, about 5.4 mL, about 5.5 mL, about 5.6 mL, about 5.7 mL, about 5.8 mL, about 5.9 mL, about 6 mL, about 6.1 mL, about 6.2 mL, about 6.3 mL, about 6.4 mL, about 6.5 mL, about 6.6 mL, about 6.7 mL, about 6.8 mL, about 6.9 mL, about 7 mL, about 7.1 mL, about 7.2 mL, about 7.3 mL about 7.4 mL, about 7.5 mL, about 7.6 mL, about 7.7 mL, about 7.8 mL, about 7.9 mL, about 8 mL, about 8.1 mL, about 8.2 mL, about 8.3 mL, about 8.4 mL, about 8.5 mL, about 8.6 mL, about 8.7 mL, about 8.8 mL, about 8.9 mL, about 9 mL, about 9.1 mL, about 9.2 mL, about 9.3 mL, about 9.4 mL, about 9.5 mL, about 9.6 mL, about 9.7 mL, about 9.8 mL, about 9.9 mL, about 10 mL, about 10.1 mL, about 10.2 mL, about 10.3 mL, about 10.4 mL, about 10.5 mL, about 10.6 mL, about 10.7 mL, about 10.8 mL, about 10.9 mL, about 11 mL, about 11.1 mL, about 11.2 mL, about 11.3 mL, about 11.4 mL, about 11.5 mL, about 11.6 mL, about 11.7 mL, about 11.8 mL, about 11.9 mL, about 12 mL, about 12.1 mL, about 12.2 mL, about 12.3 mL, about 12.4 mL, about 12.5 mL, about 12.6 mL, about 12.7 mL, about 12.8 mL, about 12.9 mL, about 13 mL, about 13.1 mL, about 13.2 mL, about 13.3 mL, about 13.4 mL, about 13.5 mL, about 13.6 mL, about 13.7 mL, about 13.8 mL, about 13.9 mL, about 14 mL, about 14.1 mL, about 14.2 mL, about 14.3 mL, about 14.4 mL, about 14.5 mL, about 14.6 mL, about 14.7 mL, about 14.8 mL, about 14.9 mL, about 15 mL, about 15.1 mL, about 15.2 mL, about 15.3 mL, about 15.4 mL, about 15.5 mL, about 15.6 mL, about 15.7 mL, about 15.8 mL, about 15.9 mL, about 16 mL, about 16.1 mL, about 16.2 mL, about 16.3 mL, about 16.4 mL, about 16.5 mL, about 16.6 mL, about 16.7 mL, about 16.8 mL, about 16.9 mL about 17 mL, about 17.1 mL, about 17.2 mL, about 17.3 mL, about 17.4 mL, about 17.5 mL, about 17.6 mL, about 17.7 mL, about 17.8 mL, about 17.9 mL, about 18 mL, about 18.1 mL, about 18.2 mL, about 18.3 mL, about 18.4 mL, about 18.5 mL, about 18.6 mL, about 18.7 mL, about 18.8 mL, about 18.9 mL, about 19 mL, about 19.1 mL, about 19.2 mL, about 19.3 mL, about 19.4 mL, about 19.5 mL, about 19.6 mL, about 19.7 mL, about 19.8 mL, about 19.9 mL, about 20 mL, about 20.1 mL, about 20.2 mL, about 20.3 mL, about 20.4 mL, about 20.5 mL, about 20.6 mL, about 20.7 mL, about 20.8 mL, about 20.9 mL, about 21 mL, about 21.1 mL, about 21.2 mL, about 21.3 mL, about 21.4 mL, about 21.5 mL, about 21.6 mL, about 21.7 mL, about 21.8 mL, about 21.9 mL, about 22 mL, about 22.1 mL, about 22.2 mL, about 22.3 mL, about 22.4 mL, about 22.5 mL, about 22.6 mL, about 22.7 mL, about 22.8 mL, about 22.9 mL, about 23 mL, about 23.1 mL, about 23.2 mL, about 23.3 mL, about 23.4 mL, about 23.5 mL, about 23.6 mL, about 23.7 mL, about 23.8 mL, about 23.9 mL, about 24 mL, about 24.1 mL, about 24.2 mL, about 24.3 mL, about 24.4 mL, about 24.5 mL, about 24.6 mL, about 24.7 mL, about 24.8 mL, about 24.9 mL, or about 25 mL of the formulation. In one embodiment, the prefilled syringe comprises a needle having a gauge of about 20 to about 33. In one embodiment, the prefilled syringe comprises a 20 gauge needle, a 21 gauge needle, a 22 gauge needle, a 23 gauge needle, a 24 gauge needle, a 25 gauge needle, a 26 gauge needle, a 27 gauge needle, a 28 gauge needle, a 29 gauge needle, a 30 gauge needle, a 31 gauge needle, a 32 gauge needle, or a 33 gauge needle. In one embodiment, the method comprises administering the formulation at a rate of about 0.08 to about 1.00 mL/sec. In one embodiment, the method comprises administering the formulation at a rate of at least about 0.08 to about 1.0 mL/sec. In one embodiment, the method comprises administering the formulation at a rate of at least or faster than about 0.08 to about 1.00 mL/sec. In one embodiment, the administration takes about 10 seconds to about 40 seconds. In one embodiment, the administration takes at least about 10 seconds to about 40 seconds. In one embodiment, the administration takes at least or less than about 10 seconds to about 40 seconds. In one embodiment, the administration takes about 15 seconds to about 30 seconds. In one embodiment, the administration takes at least about 15 seconds to about 30 seconds. In one embodiment, the administration takes at least or less than about 15 seconds to about 30 seconds. In one embodiment, the method comprises administering about 5 mL of the formulation at a rate of about 0.14 mL/sec to about 0.21 mL/sec. In one embodiment, the method comprises administering about 10 mL of the formulation at a rate of about 0.32 mL/sec to about 0.42 mL/sec. In one embodiment, the formulation has a viscosity of about 1 cP to about 50 cP. In one embodiment, administration of the formulation requires less applied force when compared to a similar formulation that does not comprise a hyaluronidase enzyme. In one embodiment, the method comprises administering about 5 mL of the formulation at a rate of about 0.14 mL/sec to about 0.21 mL/sec with an applied force of about 10 N to about 45 N. In one embodiment, the method comprises administering the formulation to the subject using a prefilled syringe comprising a 25 gauge needle. In one embodiment, the method comprises administering about 10 mL of the formulation to the subject at a rate of about 0.32 mL/sec to about 0.42 mL/sec with an applied force of about 25 N to about 50 N. In one embodiment, the method comprises administering the formulation to the subject using a prefilled syringe comprising a 25 gauge needle. In one embodiment, administration of the formulation is faster when compared to a similar formulation that does not comprise a hyaluronidase enzyme. In one embodiment, administration of the formulation causes fewer side effects in the subject when compared to a similar formulation that does not comprise a hyaluronidase enzyme. In one embodiment, administration of the formulation causes less pain and discomfort in the subject when compared to a similar formulation that does not comprise a hyaluronidase enzyme. In one embodiment, administration of the formulation causes less back leakage at the injection site when compared to a similar formulation that does not comprise a hyaluronidase enzyme. In one embodiment, the back leakage at the injection site is about 85% to about 30% less when compared to a similar formulation that does not comprise a hyaluronidase enzyme. In one embodiment, administration of the formulation causes less swelling volume and/or swelling height at the injection site when compared to a similar formulation that does not comprise a hyaluronidase enzyme. In one embodiment, the formulation causes about 35% to about 5% less swelling and/or swelling height the injection site when compared to a similar formulation that does not comprise a hyaluronidase enzyme. In one embodiment, administration of the formulation yields a lower bleb swelling size, less bleb induration, and/or quicker bleb resolution when compared to a similar formulation that does not comprise a hyaluronidase enzyme. In one embodiment, administration of the formulation yields more consistent delivery times when compared to a similar formulation that does not comprise a hyaluronidase enzyme. In one embodiment, the subject is human. In one embodiment, the administering comprises the subject self-administering the formulation. In one embodiment, the administering comprises a healthcare provider or a caregiver administering the formulation to the subject. In one embodiment, the subcutaneous administration comprises a single injection. In one embodiment, the subcutaneous administration comprises two or more injections. In one embodiment, the subcutaneous administration is delivered via an on body device.

In another aspect, the present disclosure provides a pharmaceutical kit comprising a high volume autoinjector and about 3 mL to about 50 mL of a formulation comprising a therapeutically effective amount of an active ingredient selected from a small molecule, a peptide fragment, a biologic, a nanoparticle, an antibody, an antibody fragment, and a small molecule antiviral. In one embodiment, the formulation further comprises a hyaluronidase enzyme. In one embodiment, the kit further comprises instructions for administering a hyaluronidase enzyme to a subject in need thereof. In one embodiment, the kit further comprises instructions for administering a hyaluronidase enzyme to a subject in need thereof concurrently or sequentially with the formulation comprising the active ingredient. In one embodiment, the high volume autoinjector is configured to subcutaneously administer the formulation to a subject at a rate of about 0.05 mL/sec to about 1.0 mL/sec. In one embodiment, the high volume autoinjector is configured to subcutaneously administer the formulation from a prefilled syringe having a volume of about 3 mL to about 15 mL. In one embodiment, the prefilled syringe comprises a needle having a gauge of about 20 to about 33. In one embodiment, the high volume autoinjector is configured to subcutaneously administer the formulation to a subject at a rate of about 0.05 mL/sec to about 0.10 mL/sec. In one embodiment, the high volume autoinjector is configured to subcutaneously administer the formulation to a subject at a rate of about 0.10 mL/sec to about 0.20 mL/sec. In one embodiment, the high volume autoinjector is configured to subcutaneously administer the formulation to a subject at a rate of about 0.20 mL/sec to about 0.30 mL/sec. In one embodiment, the high volume autoinjector is configured to subcutaneously administer the formulation to a subject at a rate of about 0.30 mL/sec to about 0.40 mL/sec. In one embodiment, the high volume autoinjector is configured to subcutaneously administer the formulation to a subject at a rate of about 0.40 mL/sec to about 0.50 mL/sec. In one embodiment, the high volume autoinjector is configured to subcutaneously administer the formulation to a subject at a rate of about 0.50 mL/sec to about 0.60 mL/sec. In one embodiment, the high volume autoinjector is configured to subcutaneously administer the formulation to a subject at a rate of about 0.60 mL/sec to about 0.70 mL/sec. In one embodiment, the high volume autoinjector is configured to subcutaneously administer the formulation to a subject at a rate of about 0.70 mL/sec to about 0.80 mL/sec. In one embodiment, the high volume autoinjector is configured to subcutaneously administer the formulation to a subject at a rate of about 0.80 mL/sec to about 0.90 mL/sec. In one embodiment, the high volume autoinjector is configured to subcutaneously administer the formulation to a subject at a rate of about 0.90 mL/sec to about 1.00 mL/sec. In one embodiment, the high volume autoinjector is configured to subcutaneously administer the formulation to a subject with an applied force of about 10 N to about 200 N. In one embodiment, the high volume autoinjector is configured to subcutaneously administer the formulation to a subject with an applied force of about 10 N to about 45 N. In one embodiment, the high volume autoinjector is configured to subcutaneously administer the formulation to a subject with an applied force of about 25 N to about 50 N. In one embodiment, the high volume autoinjector is configured for self-administration of the formulation by the subject.

BRIEF DESCRIPTION OF THE DRAWINGS

The following detailed description of embodiments of the hyaluronidase enzyme formulations for high volume administration, will be better understood when read in conjunction with the appended drawings of exemplary embodiments.

FIG. 1 is a chart of applied force (N) during injection (Mean±SEM) of Ig-120 and Ig-120+rHuPH20.

FIG. 2 is a chart of individual applied force (N) during injection of Ig-120 and Ig-120+rHuPH20.

FIG. 7A: Composite images of minipigs treated with Ig-120. FIG. 7B: Composite 3D images of minipigs treated with Ig-120+rHuPH20.

FIG. 12 is a chart of the qualitative assessment of post-injection erythema.

FIG. 13 is a chart of the qualitative assessment of post-injection swelling size.

FIG. 14 is a chart of the qualitative assessment of post-injection induration (firmness).

FIGS. 15A-15B are certificates of analysis of the Ig-120 and rHuPH20 used in Examples 2-4 of the disclosure. FIG. 15A is the certificate of analysis for the Ig-120. FIG. 15B is the certification of analysis for the rHuPH20.

FIGS. 16A-16B provide photographs of minipig AID #1107 before and at different intervals after the 10 mL injection procedure. FIG. 16A provides images of the injection site following Ig-120 injection. FIG. 16B provides images of the injection site following Ig-120+rHuPH20 injection.

FIGS. 17A-17B provide photographs of minipig AID #1114 before and at different intervals after the 10 mL injection procedure. FIG. 17A provides images of the injection site following Ig-120 injection. FIG. 17B provides images of the injection site following Ig-120+rHuPH20 injection.

FIGS. 18A-18B provide photographs of minipig AID #1181 before and at different intervals after the 10 mL injection procedure. FIG. 18A provides images of the injection site following Ig-120 injection. FIG. 18B provides images of the injection site following Ig-120+rHuPH20 injection.

FIGS. 19A-19B provide photographs of minipig AID #1184 before and at different intervals after the 10 mL injection procedure. FIG. 19A provides images of the injection site following Ig-120 injection. FIG. 19B provides images of the injection site following Ig-120+rHuPH20 injection.

FIGS. 20A-20B provide photographs of minipig AID #1185 before and at different intervals after the 10 mL injection procedure. FIG. 20A provides images of the injection site following Ig-120 injection. FIG. 20B provides images of the injection site following Ig-120+rHuPH20 injection.

FIGS. 21A-21B provide photographs of minipig AID #1188 before and at different intervals after the 10 mL injection procedure. FIG. 21A provides images of the injection site following Ig-120 injection. FIG. 21B provides images of the injection site following Ig-120+rHuPH20 injection.

FIG. 28A: Composite images of minipigs treated with Ig-120. FIG. 28B: Composite 3D images of minipigs treated with Ig-120+rHuPH20.

FIGS. 36A-36B provide photographs of minipig AID #1359 before and at different intervals after the 10 mL injection procedure. FIG. 36A provides images of the injection site following Ig-120 injection. FIG. 36B provides images of the injection site following Ig-120+rHuPH20 injection.

FIG. 37 provides photographs of the injection site of minipig AID #1361 before and at different intervals after the 10 mL Ig-120 injection procedure.

FIGS. 39A-39B provide photographs of minipig AID #1362 before and at different intervals after the 10 mL injection procedure. FIG. 39A provides images of the injection site following Ig-120 injection. FIG. 39B provides images of the injection site following Ig-120+rHuPH20 injection.

FIGS. 40A-40B provide photographs of minipig AID #1363 before and at different intervals after the 10 mL injection procedure. FIG. 40A provides images of the injection site following Ig-120 injection. FIG. 40B provides images of the injection site following Ig-120+rHuPH20 injection.

FIGS. 41A-41B provide photographs of minipig AID #1396 before and at different intervals after the 10 mL injection procedure. FIG. 41A provides images of the injection site following Ig-120 injection. FIG. 41B provides images of the injection site following Ig-120+rHuPH20 injection.

FIGS. 42A-42B provide photographs of minipig AID #1405 before and at different intervals after the 10 mL injection procedure. FIG. 42A provides images of the injection site following Ig-120 injection. FIG. 42B provides images of the injection site following Ig-120+rHuPH20 injection.

FIGS. 51A-51B are composite 3D images of the minipigs by treatment. FIG. 51A: Composite images of minipigs treated with Ig-120. FIG. 51B: Composite 3D images of minipigs treated with Ig-120+rHuPH20.

FIGS. 59A-59B provide photographs of minipig AID #1535 before and at different intervals after the 10 mL injection procedure. FIG. 59A provides images of the injection site following Ig-120 injection. FIG. 59B provides images of the injection site following Ig-120+rHuPH20 injection.

FIGS. 60A-60B provide photographs of minipig AID #1536 before and at different intervals after the 10 mL injection procedure. FIG. 60A provides images of the injection site following Ig-120 injection. FIG. 60B provides images of the injection site following Ig-120+rHuPH20 injection.

FIGS. 61A-61B provide photographs of minipig AID #1537 before and at different intervals after the 10 mL injection procedure. FIG. 61A provides images of the injection site following Ig-120 injection. FIG. 61B provides images of the injection site following Ig-120+rHuPH20 injection.

FIGS. 62A-62B provide photographs of minipig AID #1539 before and at different intervals after the 10 mL injection procedure. FIG. 62A provides images of the injection site following Ig-120 injection. FIG. 62B provides images of the injection site following Ig-120+rHuPH20 injection.

FIG. 63A provides images of the injection site following Ig-120 injection. FIG. 63B provides images of the injection site following Ig-120+rHuPH20 injection.

FIGS. 64A-64B provide photographs of minipig AID #1543 before and at different intervals after the 10 mL injection procedure. FIG. 64A provides images of the injection site following Ig-120 injection. FIG. 64B provides images of the injection site following Ig-120+rHuPH20 injection.

FIG. 78 are charts depicting a qualitative assessment of post-injection erythema.

FIG. 79 are charts depicting a qualitative assessment of post-injection swelling size.

FIG. 80 are charts depicting a qualitative assessment of post-injection induration (firmness).

FIGS. 81A-81B provide photographs of minipig AID #1865 before and at different intervals after the 10 mL injection procedure. FIG. 81A provides images of the injection site following Ig-120 injection. FIG. 81B provides images of the injection site following Ig-120+rHuPH20 injection.

FIGS. 82A-82B provide photographs of minipig AID #1866 before and at different intervals after the 10 mL injection procedure. FIG. 82A provides images of the injection site following Ig-120 injection. FIG. 82B provides images of the injection site following Ig-120+rHuPH20 injection.

FIGS. 83A-83B provide photographs of minipig AID #1867 before and at different intervals after the 10 mL injection procedure. FIG. 83A provides images of the injection site following Ig-120 injection. FIG. 83B provides images of the injection site following Ig-120+rHuPH20 injection.

FIGS. 84A-84B provide photographs of minipig AID #1869 before and at different intervals after the 10 mL injection procedure. FIG. 84A provides images of the injection site following Ig-120 injection. FIG. 84B provides images of the injection site following Ig-120+rHuPH20 injection.

FIGS. 85A-85B provide photographs of minipig AID #1870 before and at different intervals after the 10 mL injection procedure. FIG. 85A provides images of the injection site following Ig-120 injection. FIG. 85B provides images of the injection site following Ig-120+rHuPH20 injection.

FIGS. 86A-86B provide photographs of minipig AID #1926 before and at different intervals after the 10 mL injection procedure. FIG. 86A provides images of the injection site following Ig-120 injection. FIG. 86B provides images of the injection site following Ig-120+rHuPH20 injection.

FIG. 87 is a certificate of analysis of the rHuPH20 used in Example 4 of the disclosure.

FIG. 112 is a graph of the Qualitative Assessment of Post-Injection Induration (0-120 min).

FIG. 113A provides images of the injection site following GGL injection with a 25 G Terumo needle. FIG. 113B provides images of the injection site following GGL+EDP injection with a 25 G Terumo needle.

FIG. 114A provides images of the injection site following GGL+EDP injection with a 25 G BD needle. FIG. 114B provides images of the injection site following GGL+EDP injection with a 25 G BD needle.

FIG. 115A provides images of the injection site following GGL injection with a 25 G Terumo needle. FIG. 115B provides images of the injection site following GGL+EDP injection with a 23 G BD needle.

FIG. 116A provides images of the injection site following GGL+EDP injection with a 25 G BD needle. FIG. 116B provides images of the injection site following GGL+EDP injection with a 23 G BD needle.

FIG. 117A provides images of the injection site following GGL injection with a 25 G Terumo needle. FIG. 117B provides images of the injection site following GGL+EDP injection with a 25 G BD needle.

Figure 118A:
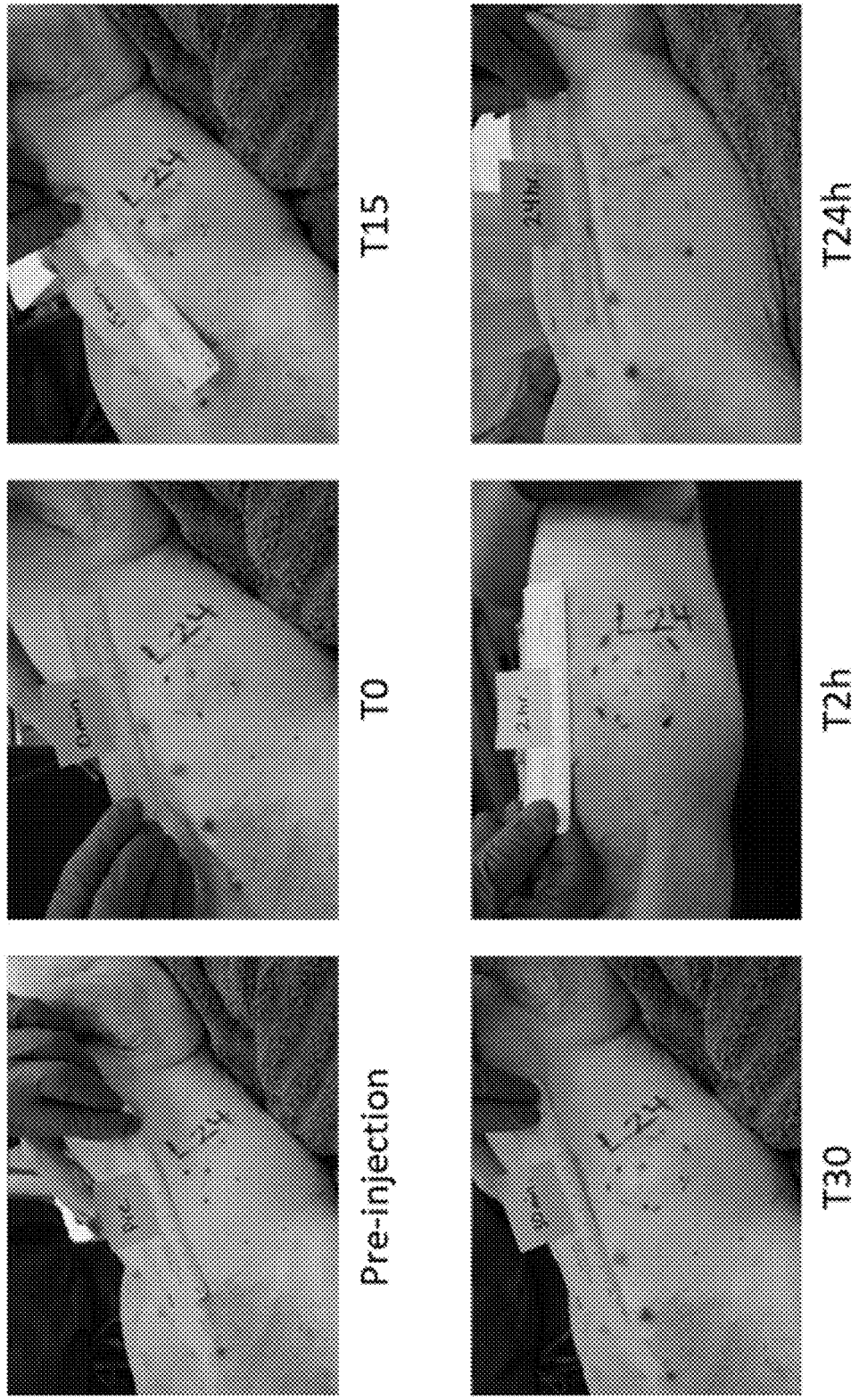

FIGS. 118A-118B provide photographs of minipig AID #2273 before and at different intervals after the 10 mL injection procedure. FIG. 118A provides images of the injection site following GGL+EDP injection with a 25 G Terumo needle. FIG. 118B provides images of the injection site following GGL+EDP injection with a 23 G BD needle.

Figure 119B:
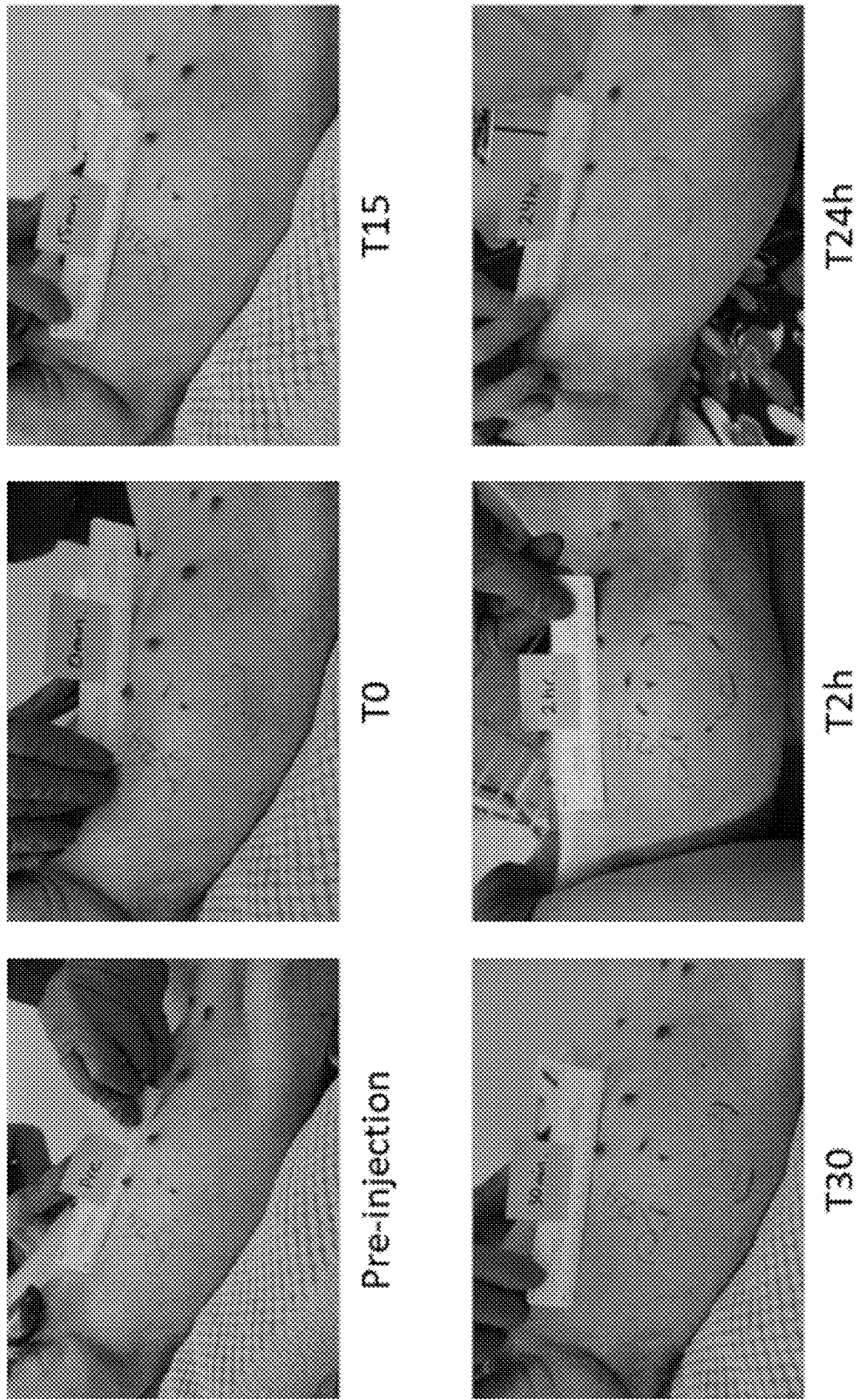

FIGS. 119A-119B provide photographs of minipig AID #2195 before and at different intervals after the 10 mL injection procedure. FIG. 119A provides images of the injection site following GGL injection with a 25 G Terumo needle. FIG. 119B provides images of the injection site following GGL+EDP injection with a 25 G Terumo needle.

Figure 120A:
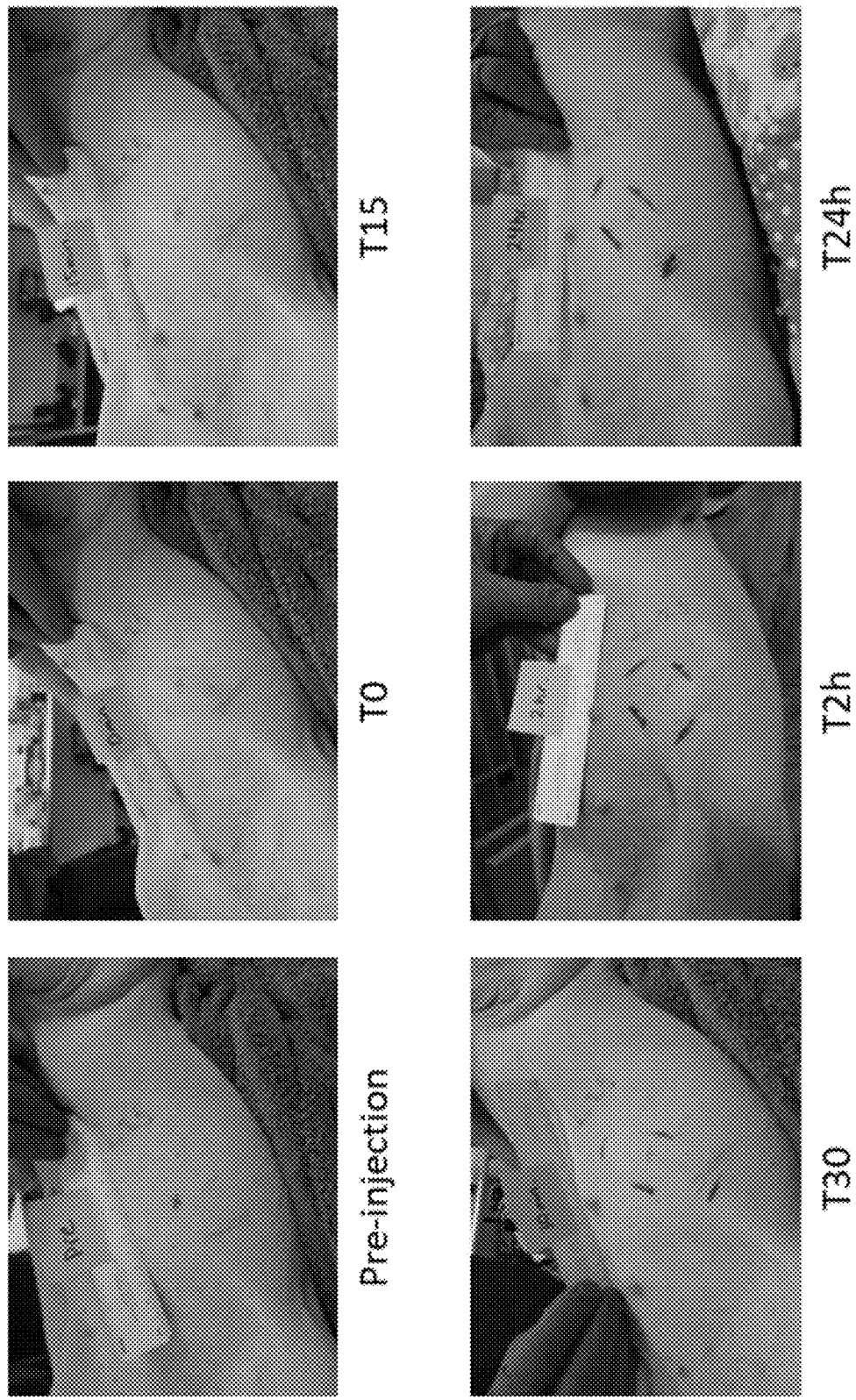
Figure 120B:
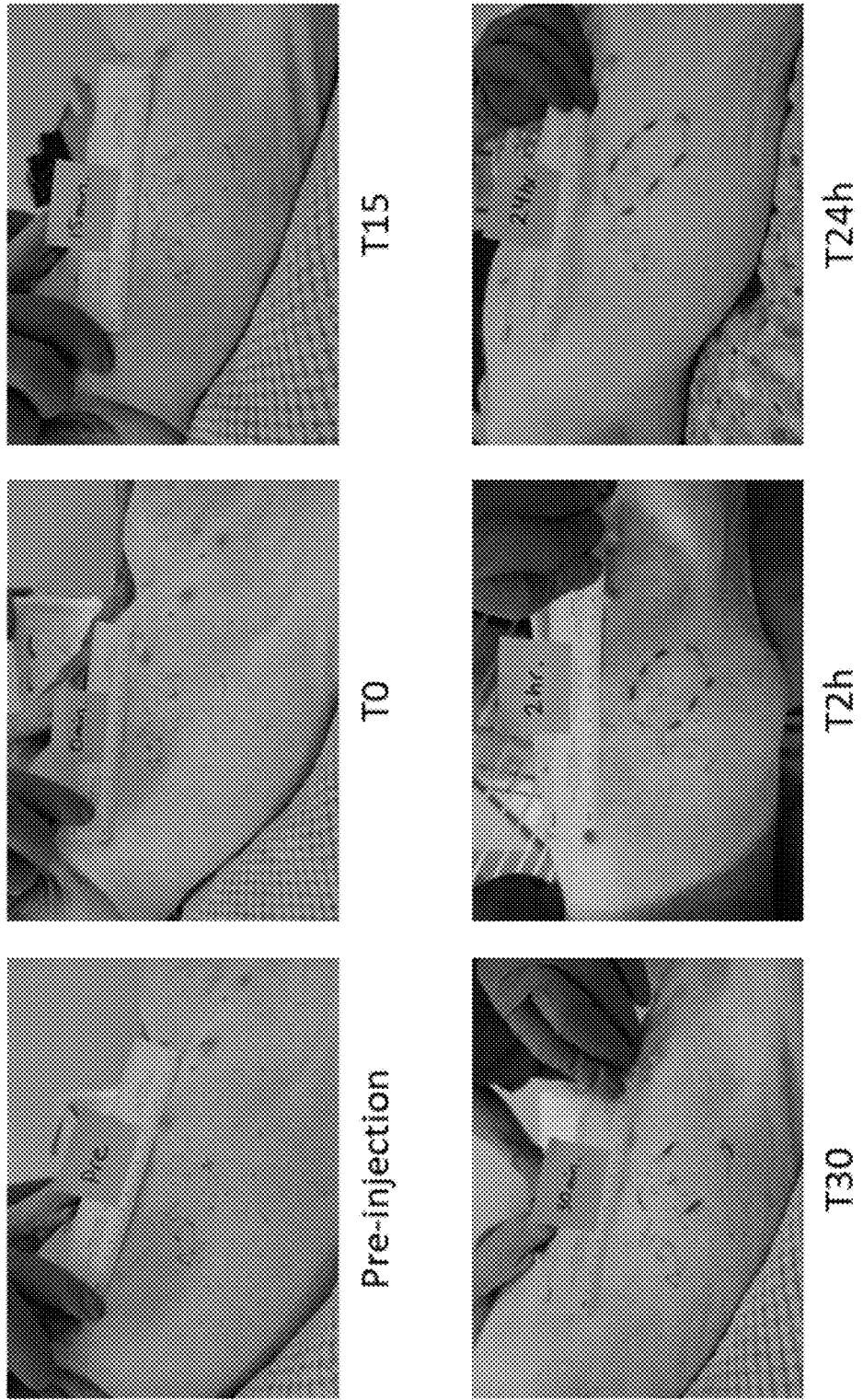

FIGS. 120A-120B provide photographs of minipig AID #2265 before and at different intervals after the 10 mL injection procedure. FIG. 120A provides images of the injection site following GGL+EDP injection with a 25 G BD needle. FIG. 120B provides images of the injection site following GGL+EDP injection with a 25 G Terumo needle.

Figure 121A:
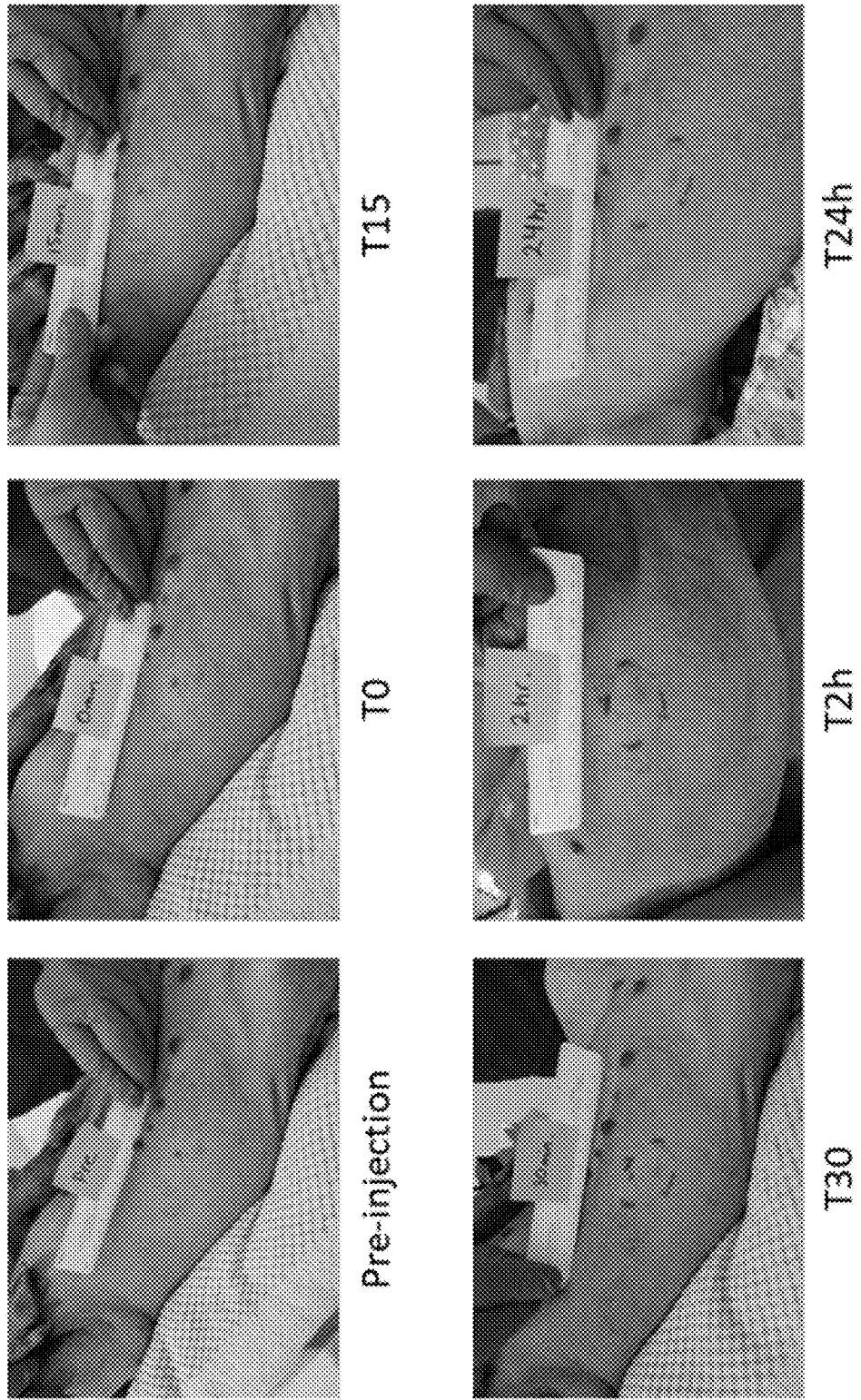
Figure 121B:
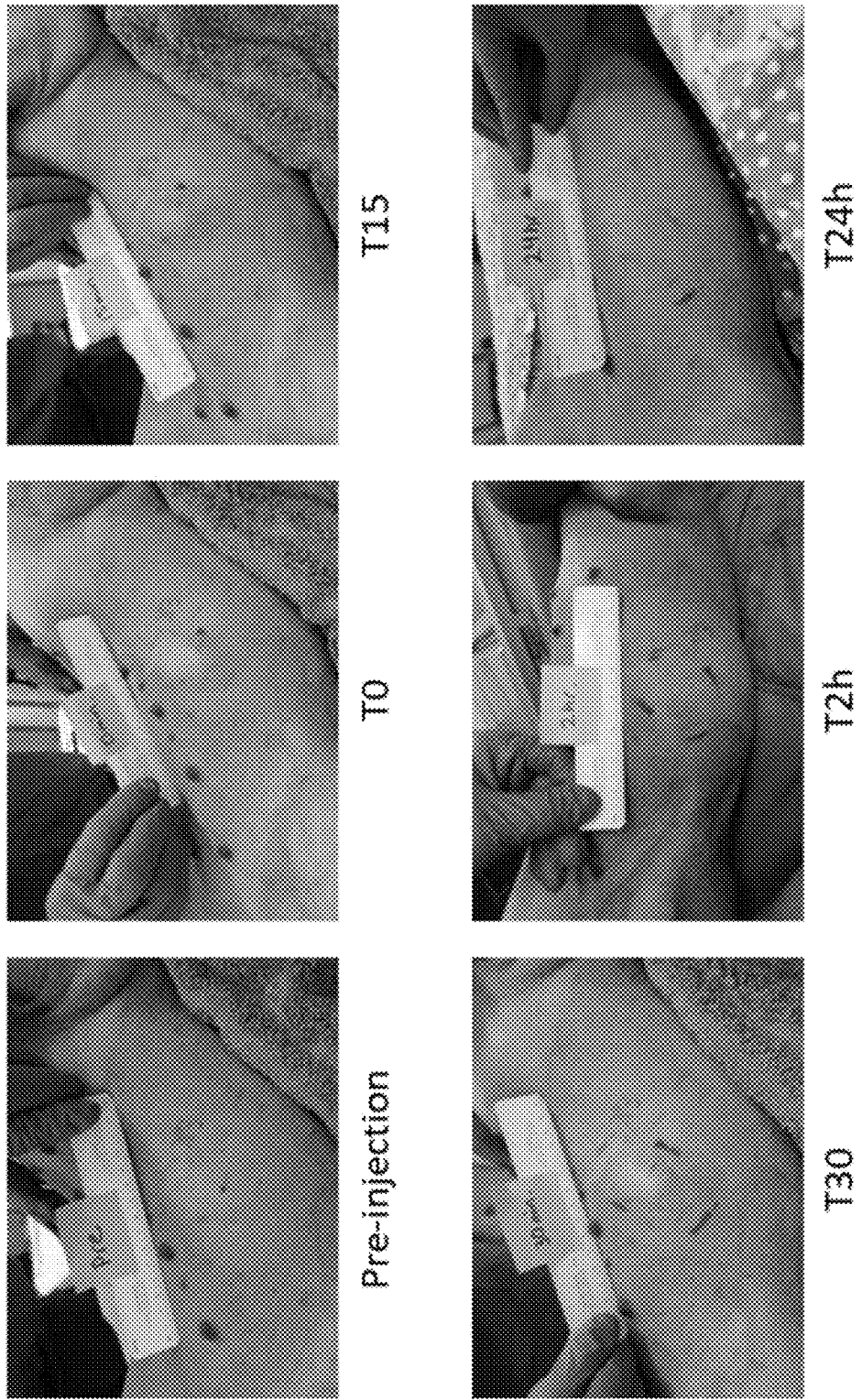

FIGS. 121A-121B provide photographs of minipig AID #2272 before and at different intervals after the 10 mL injection procedure. FIG. 121A provides images of the injection site following GGL injection with a 25 G Terumo needle. FIG. 121B provides images of the injection site following GGL+EDP injection with a 23 G BD needle.

Figure 122A:
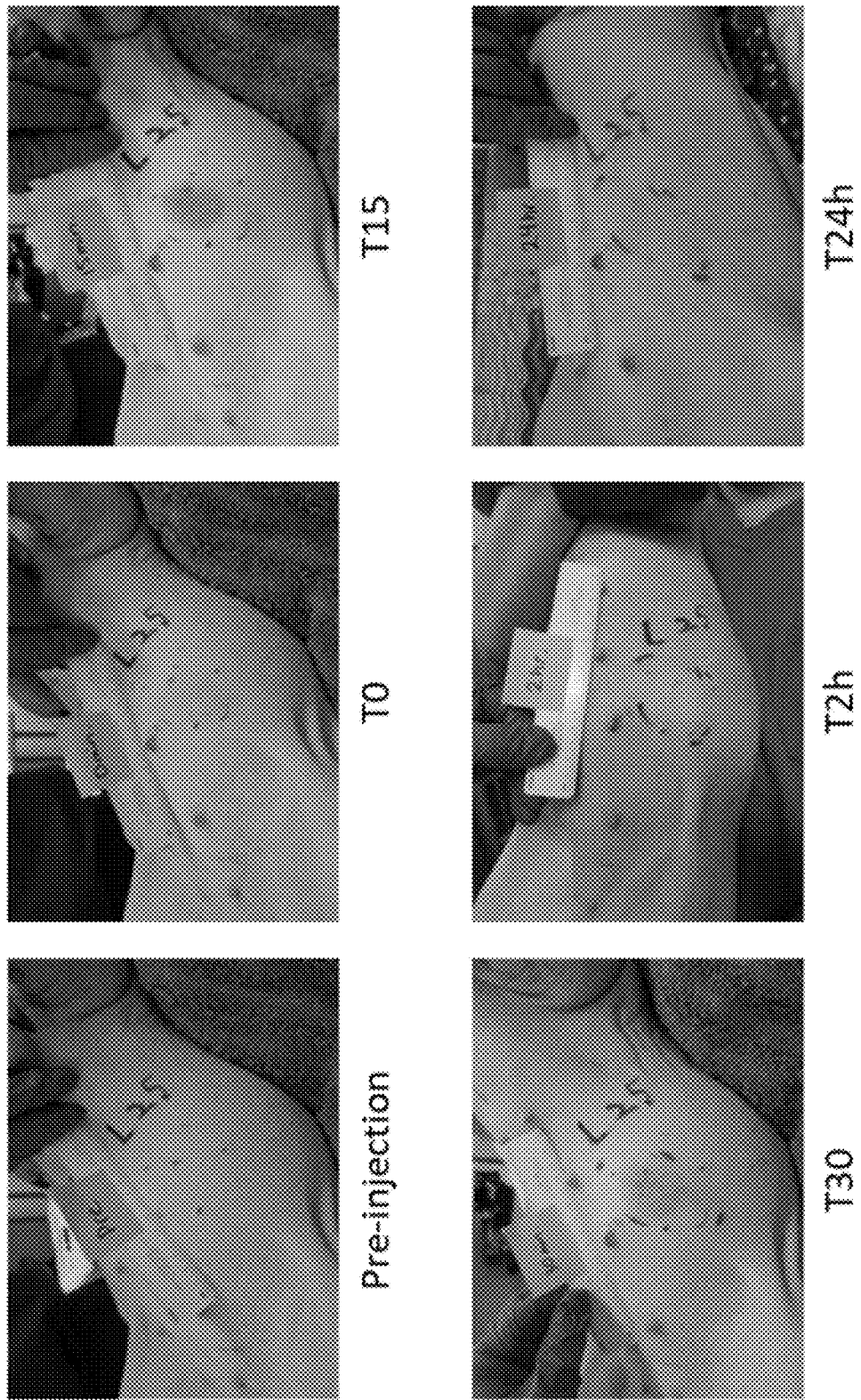
Figure 122B:
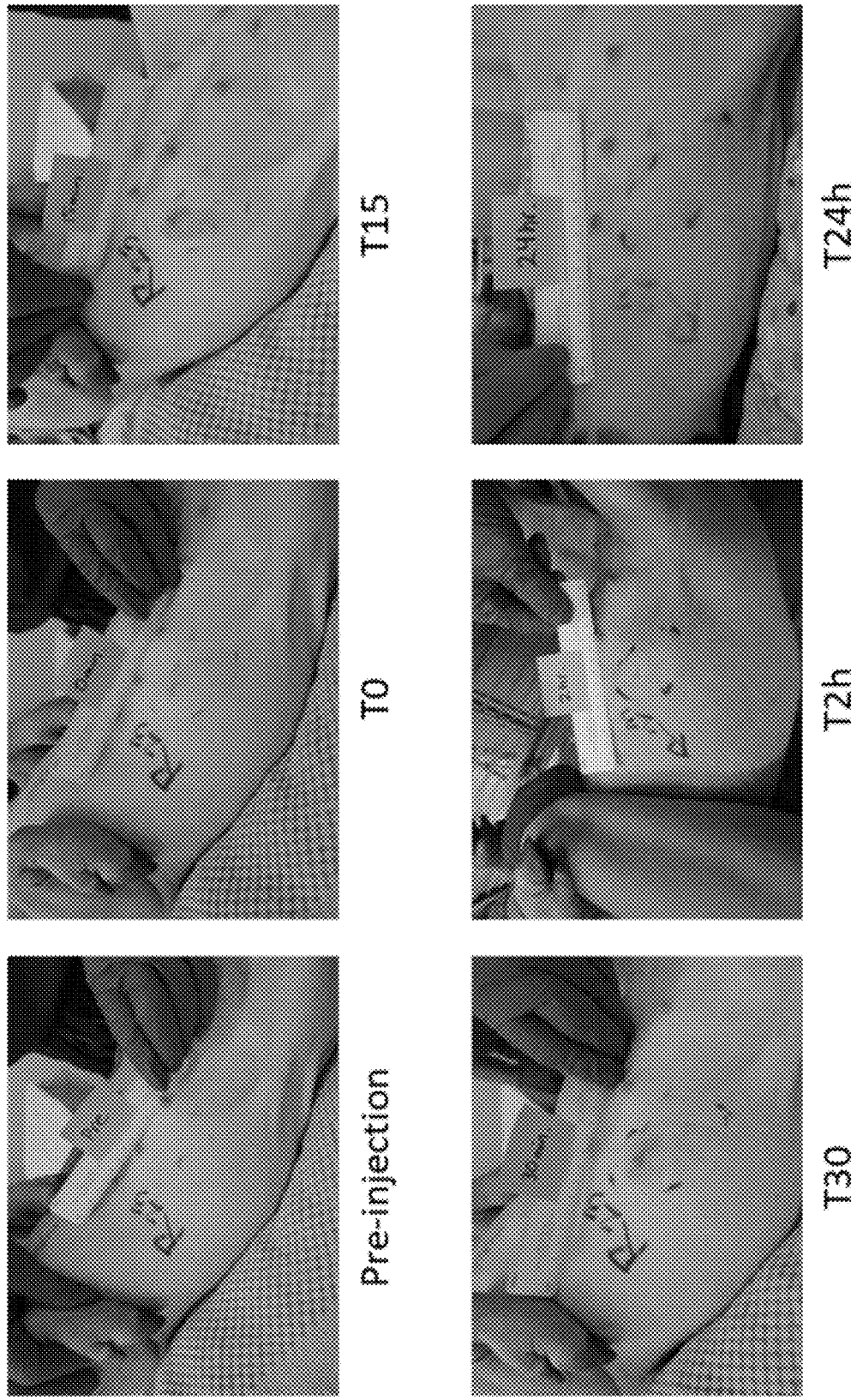

FIGS. 122A-122B provide photographs of minipig AID #2275 before and at different intervals after the 10 mL injection procedure. FIG. 122A provides images of the injection site following GGL+EDP injection with a 25 G BD needle. FIG. 122B provides images of the injection site following GGL+EDP injection with a 23 G BD needle.

Figure 123A:
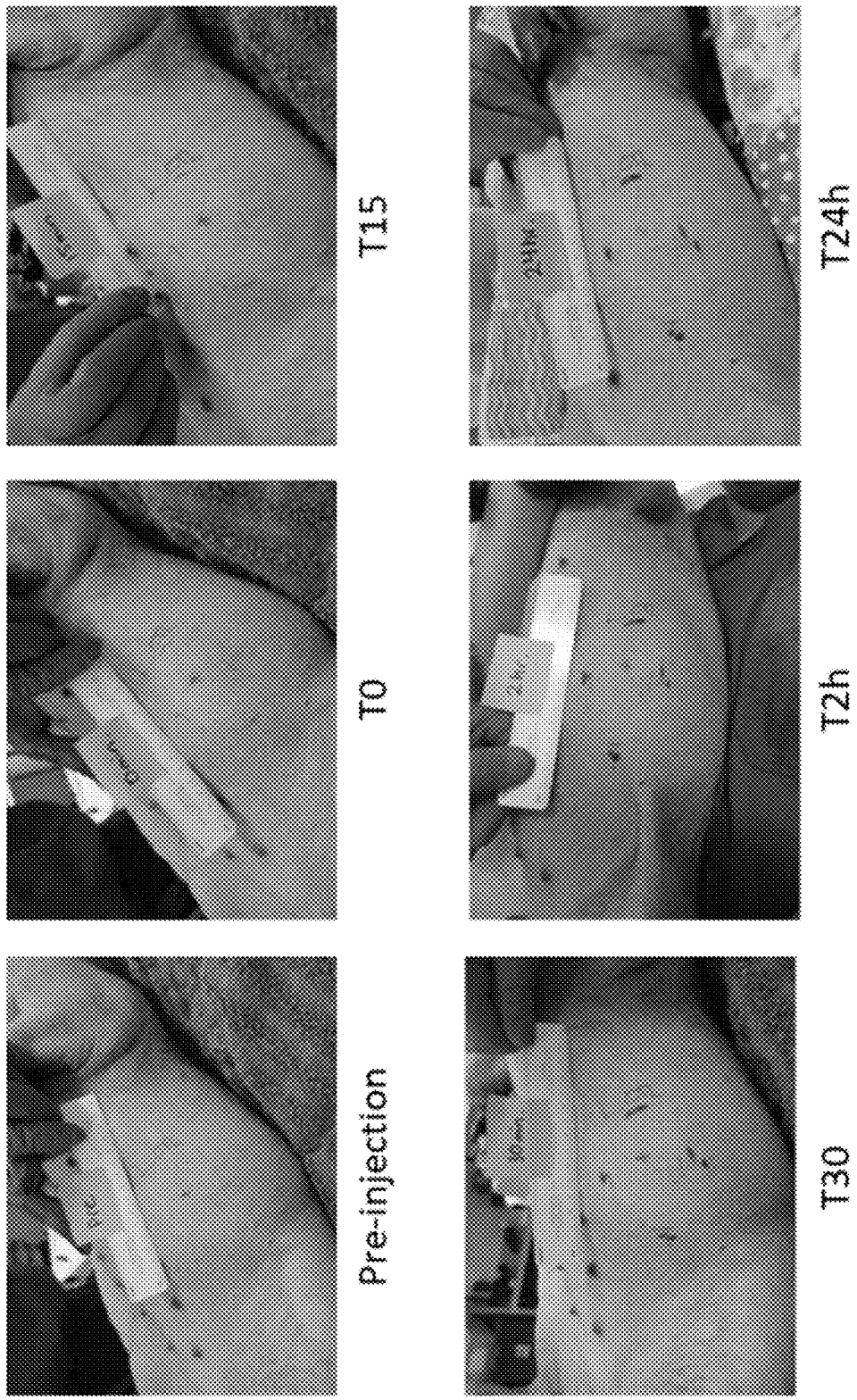
Figure 123B:
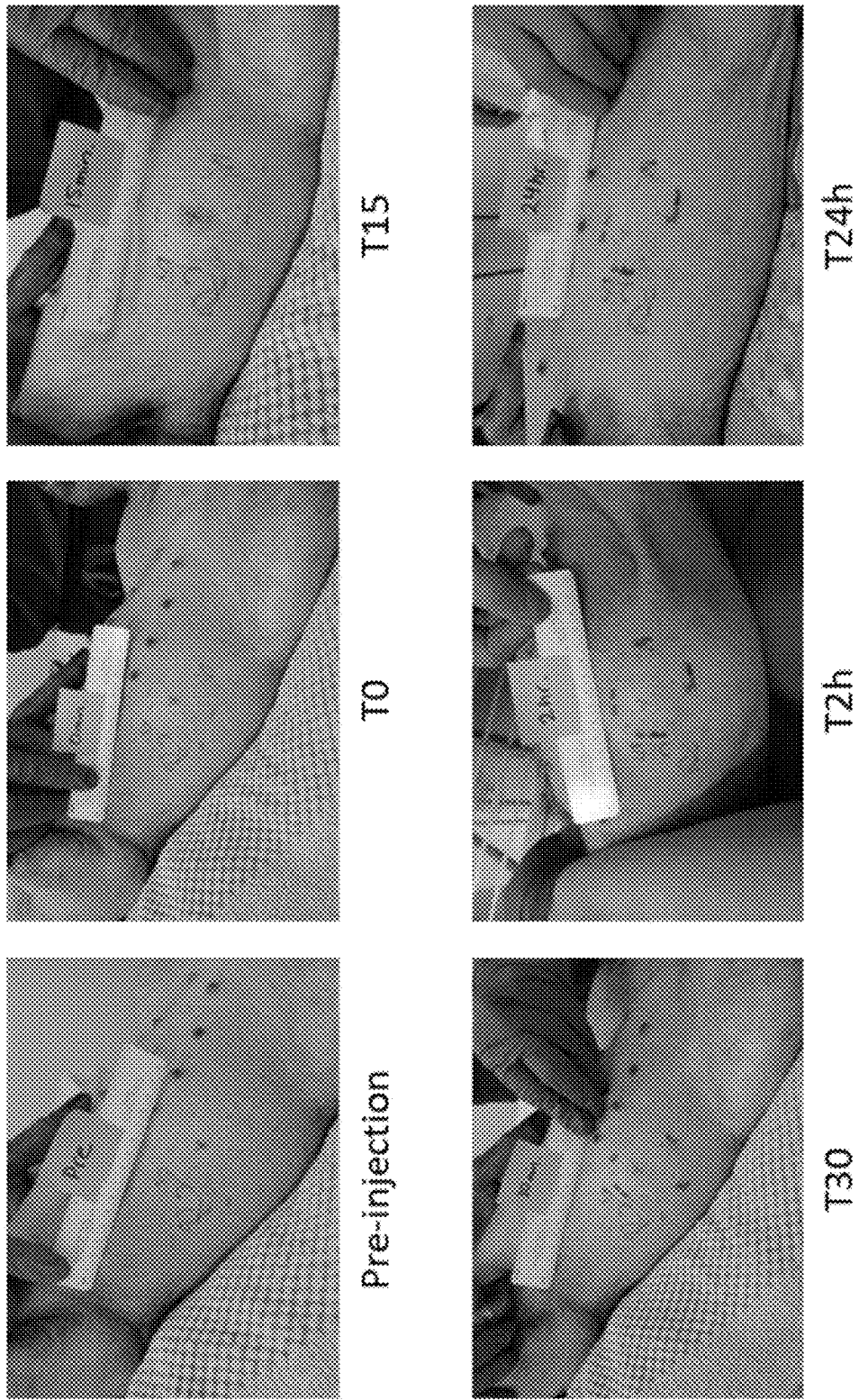

FIGS. 123A-123B provide photographs of minipig AID #2279 before and at different intervals after the 10 mL injection procedure. FIG. 123A provides images of the injection site following GGL injection with a 25 G Terumo needle. FIG. 123B provides images of the injection site following GGL+EDP injection with a 25 G BD needle.

Figure 124A:
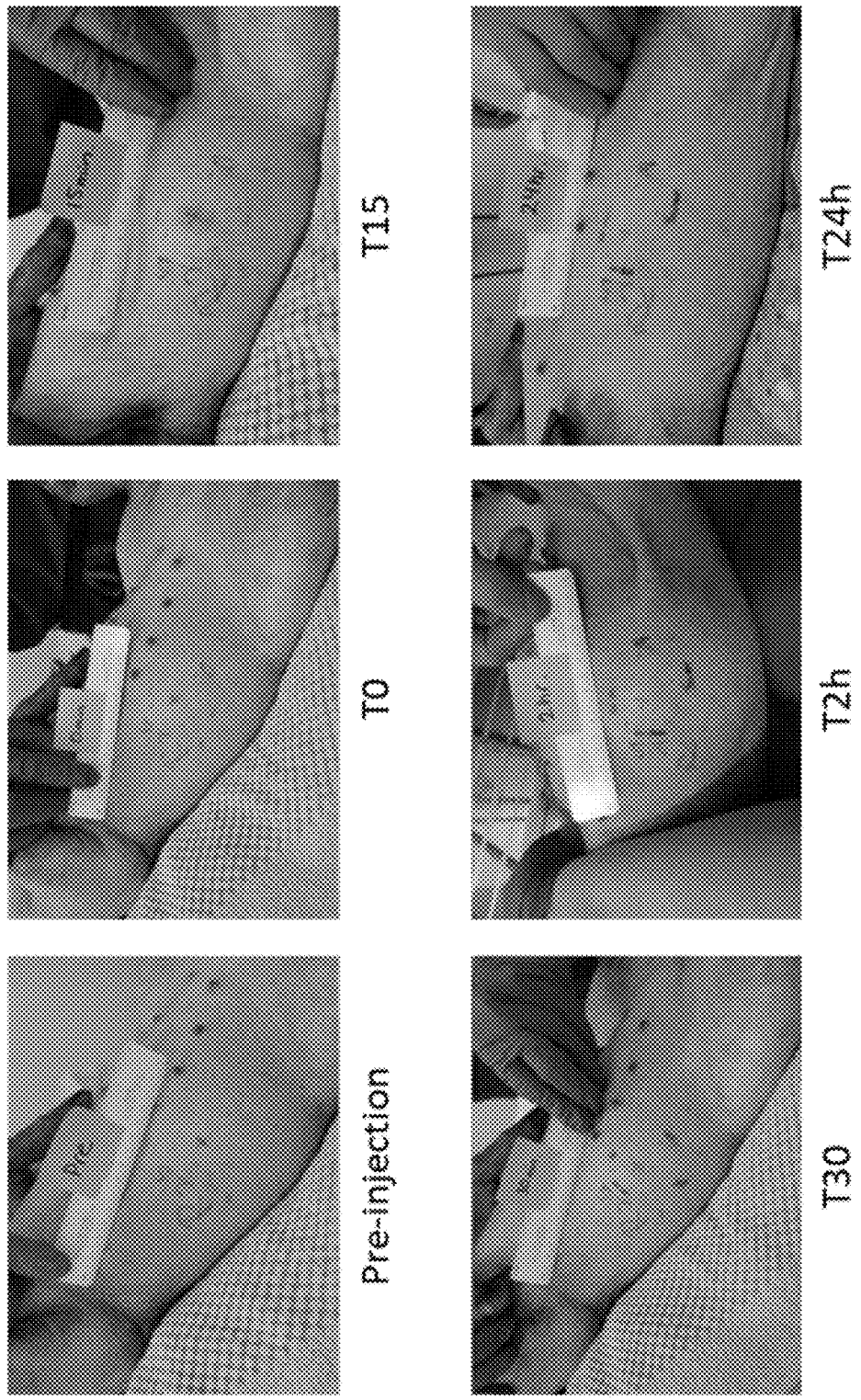
Figure 124B:
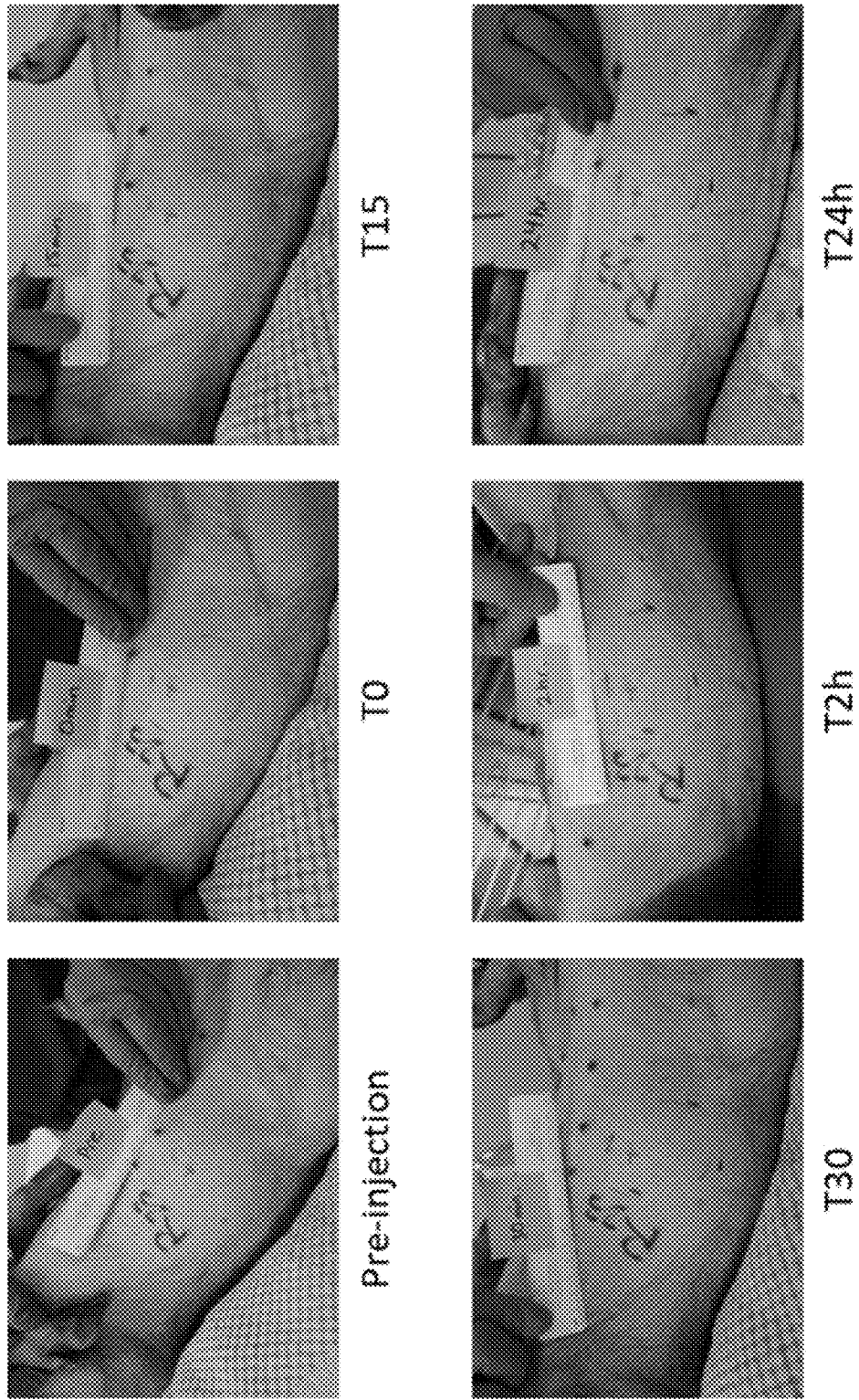

FIGS. 124A-124B provide photographs of minipig AID #2282 before and at different intervals after the 10 mL injection procedure. FIG. 124A provides images of the injection site following GGL+EDP injection with a 25 G BD needle. FIG. 124B provides images of the injection site following GGL+EDP injection with a 23 G BD needle.

Figure 125:
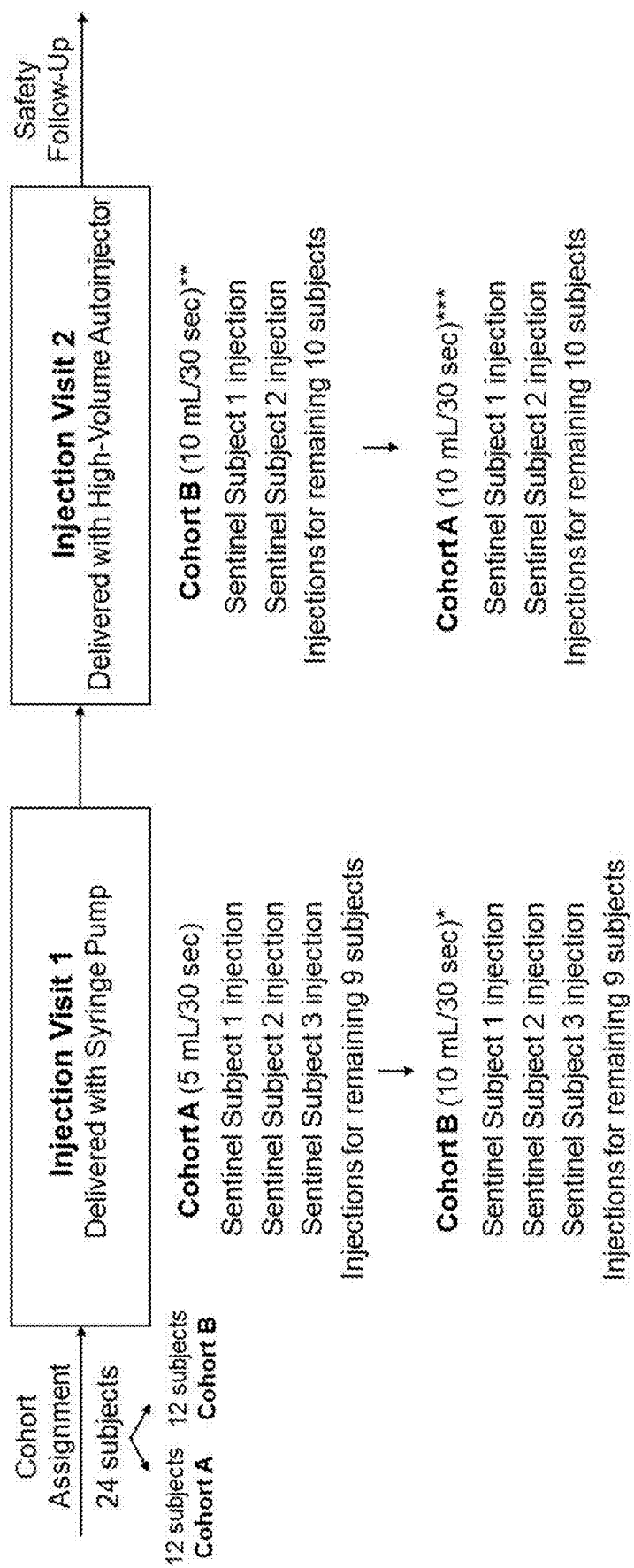

FIG. 125 is a study schema for the human trial in Example 6. Note: Sentinel subjects in each cohort are dosed at least 24 hours apart, and dosing of the remaining subjects in that cohort begins at least 24 hours after dosing of the last sentinel subject. *If Cohort B does not tolerate 10 mL/30 sec with the syringe pump, a Cohort C is added evaluating 10 mL/45 sec with the syringe pump on the same schedule as Days 5 through 8. If 10 mL/30 sec is tolerated using the syringe pump at Injection Visit 1 but Cohort B does not tolerate 10 mL/30 sec using the HVAI at Injection Visit 2, Cohort C is evaluated using the syringe pump at 10 mL/45 seconds on the same schedule as Days 5 through 8. If Cohort C tolerates 10 mL/45 sec using the syringe pump, the HVAI dose for Cohort B is 10 mL/45 sec. *If 10 mL/30 sec is tolerated using the HVAI (Injection Visit 2/Cohort B), then the volume for Cohort A at Injection Visit 2 increases to 10 mL/30 sec (or the highest tolerated volume/rate combination).

Figure 126:
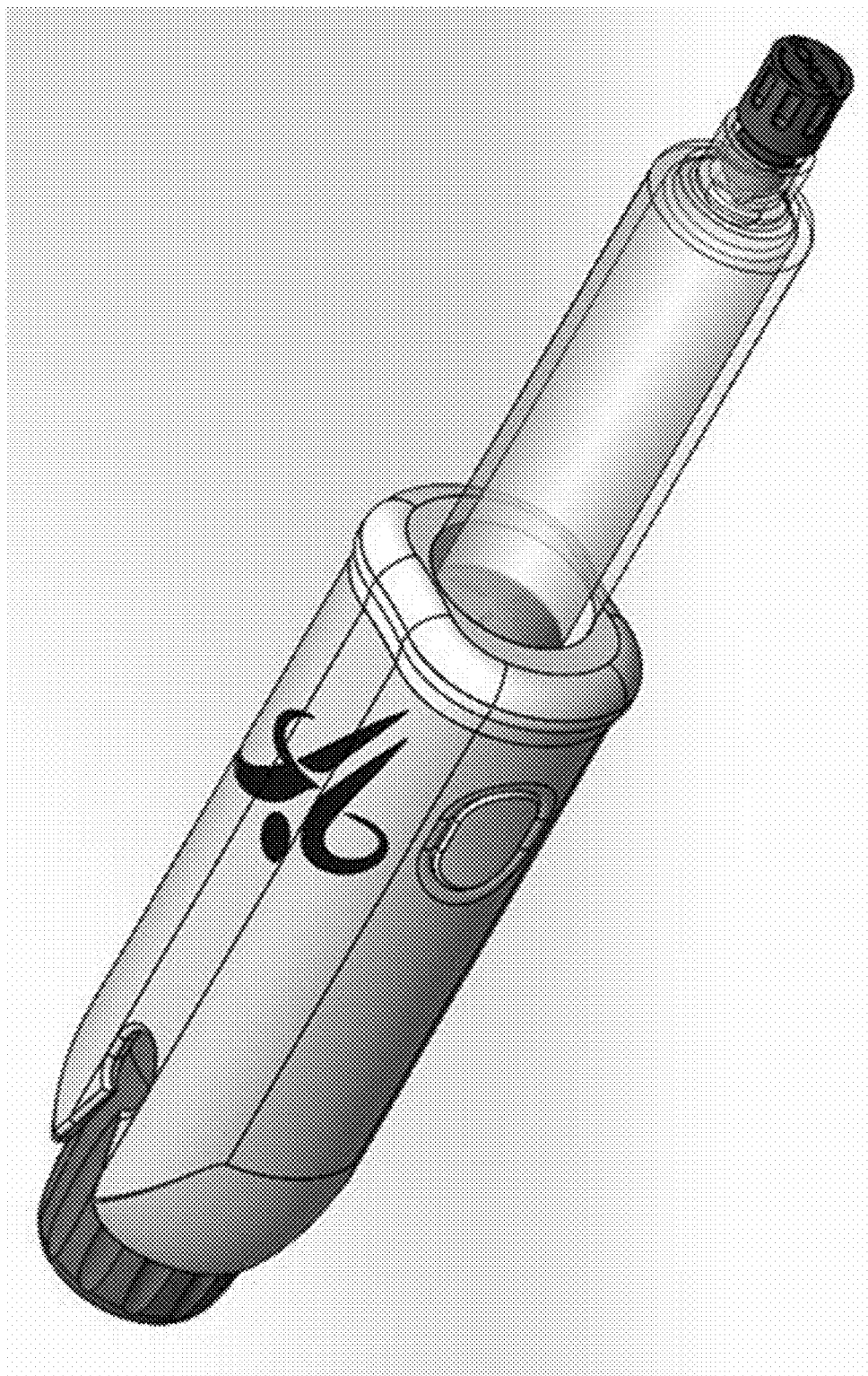

FIG. 126 is a diagram of an exemplary high volume autoinjector (HVAI). In this embodiment, the tip cap shown on the syringe is disposed of prior to filling the syringe with drug.

FIG. 127 provides the demographics of the patients in Example 6.

FIG. 128 provides the dosing groups and dispositions in Example 6.

FIG. 129 provides the injection duration for each cohort in Example 6.

Figure 132:

FIGS. 130-132 provide the pain scores from Example 6.

FIGS. 133-134 provide the Draize score/Erythema from Example 6.

FIGS. 135-136 provide the Draize score/Edema from Example 6.

FIGS. 137-138 provide the Draize score/Induration from Example 6.

FIG. 139 provides the adverse events from Example 6.

Figure 140A:
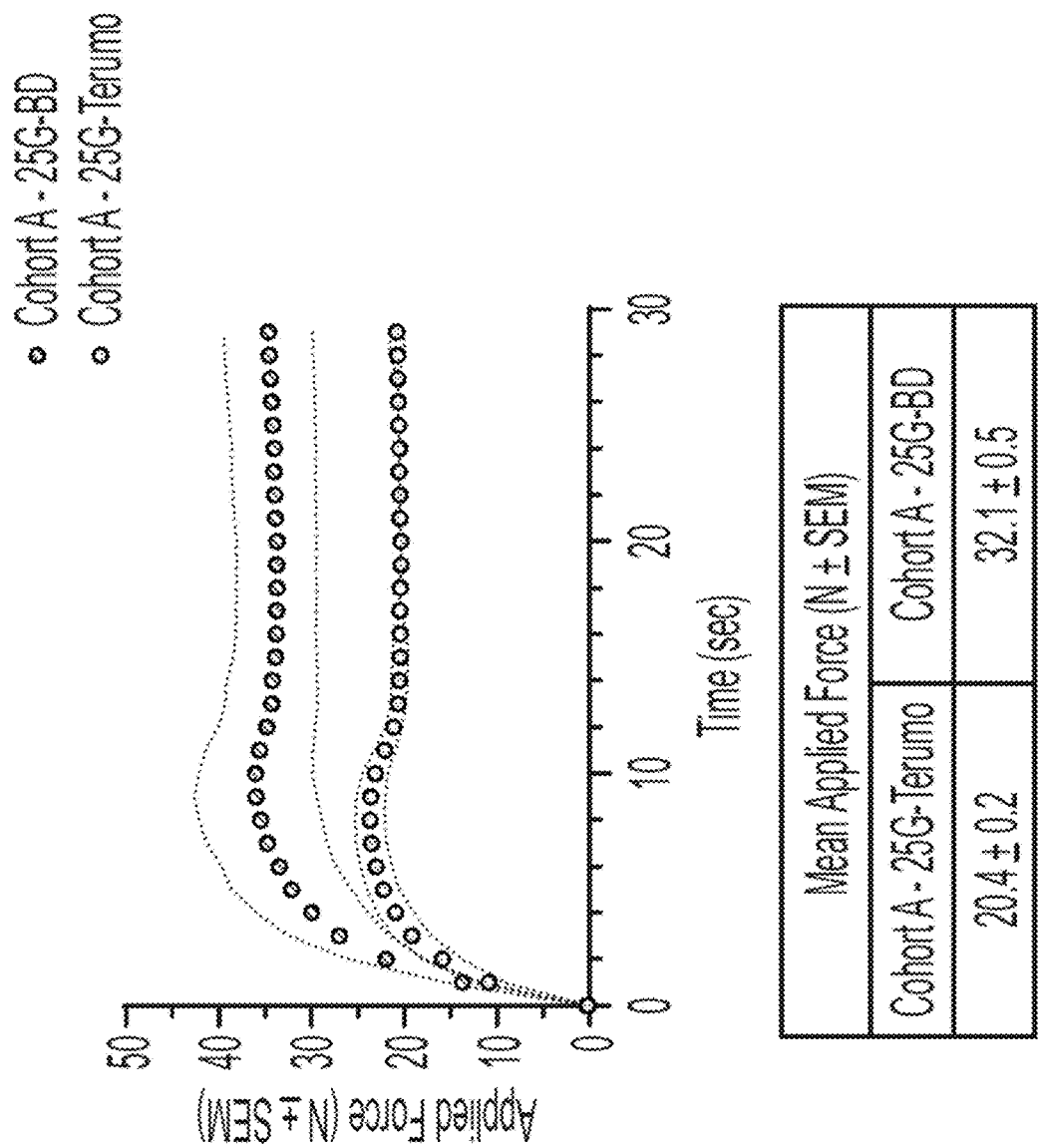
Figure 140B:
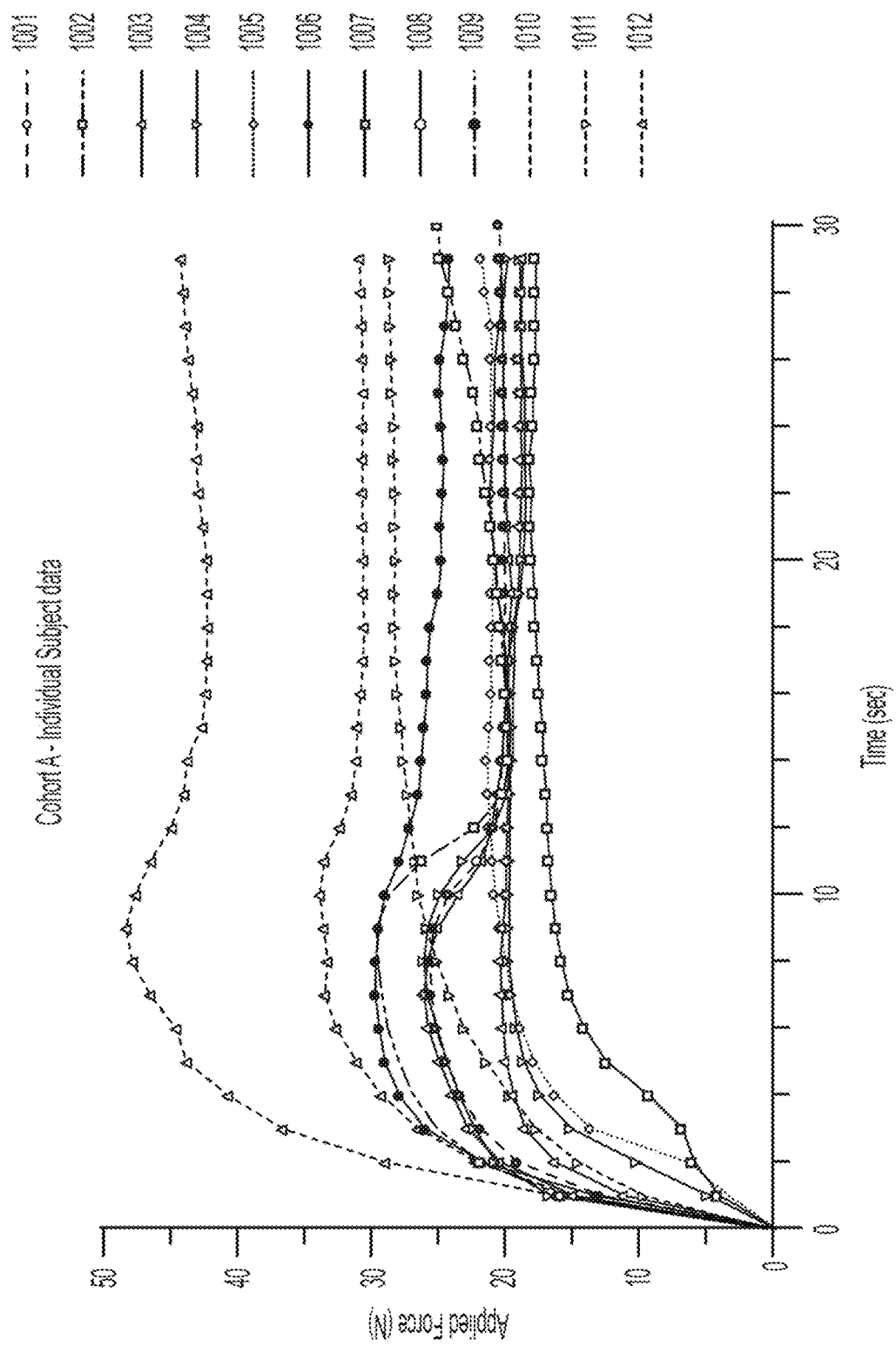

FIGS. 140A-140B provide a summary of the applied force data from Example 6, Cohort A (5 mL/30 s). Using the Hagen-Poiseuille equation, these results predict that increasing the flow rate by 2× will increase the pressure (and Force) by 2× as well. Thus, the predicted applied force for Cohort B (25 G-Terumo needle) was ~40.8 N.

Figure 141A:
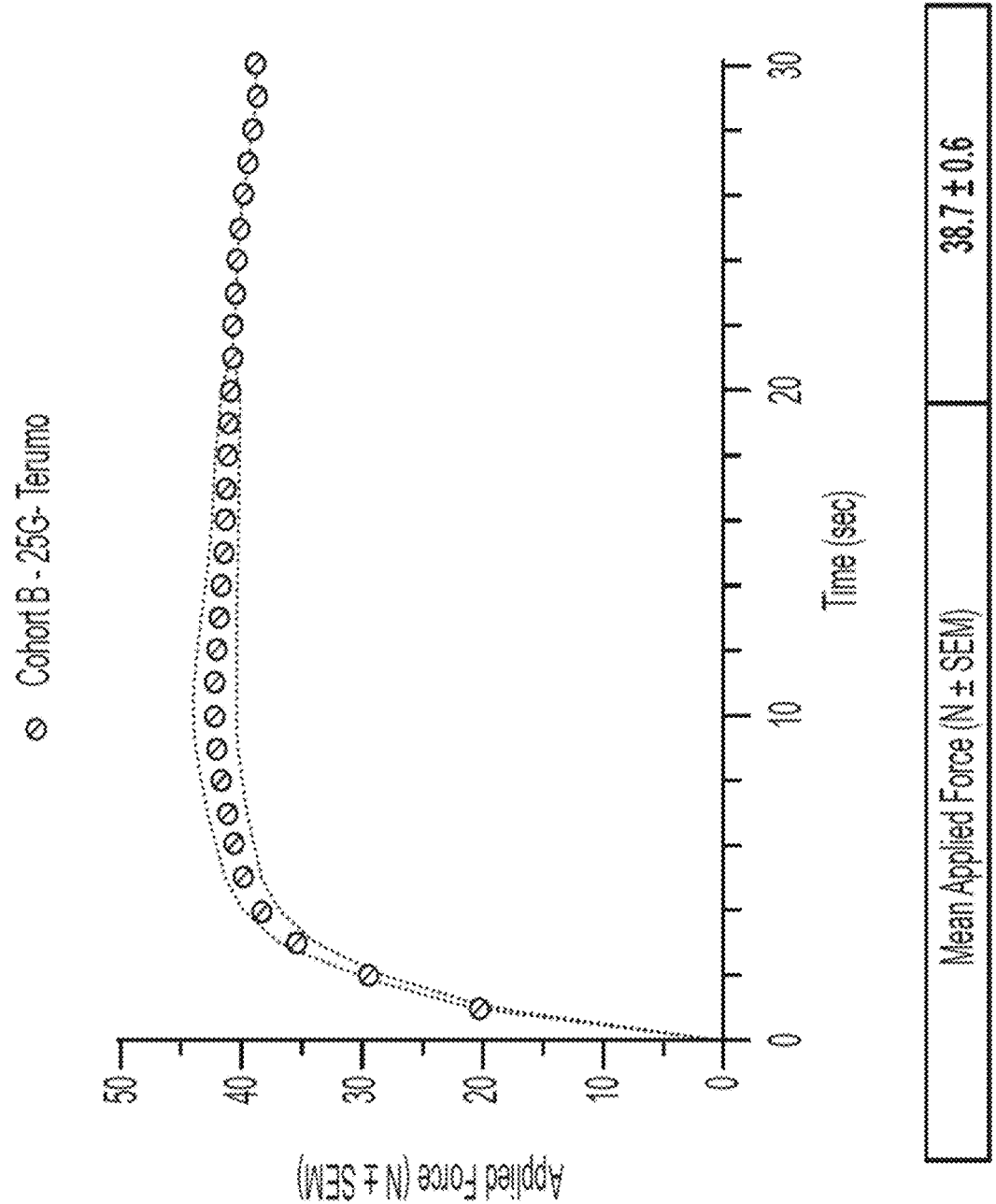
Figure 141B:
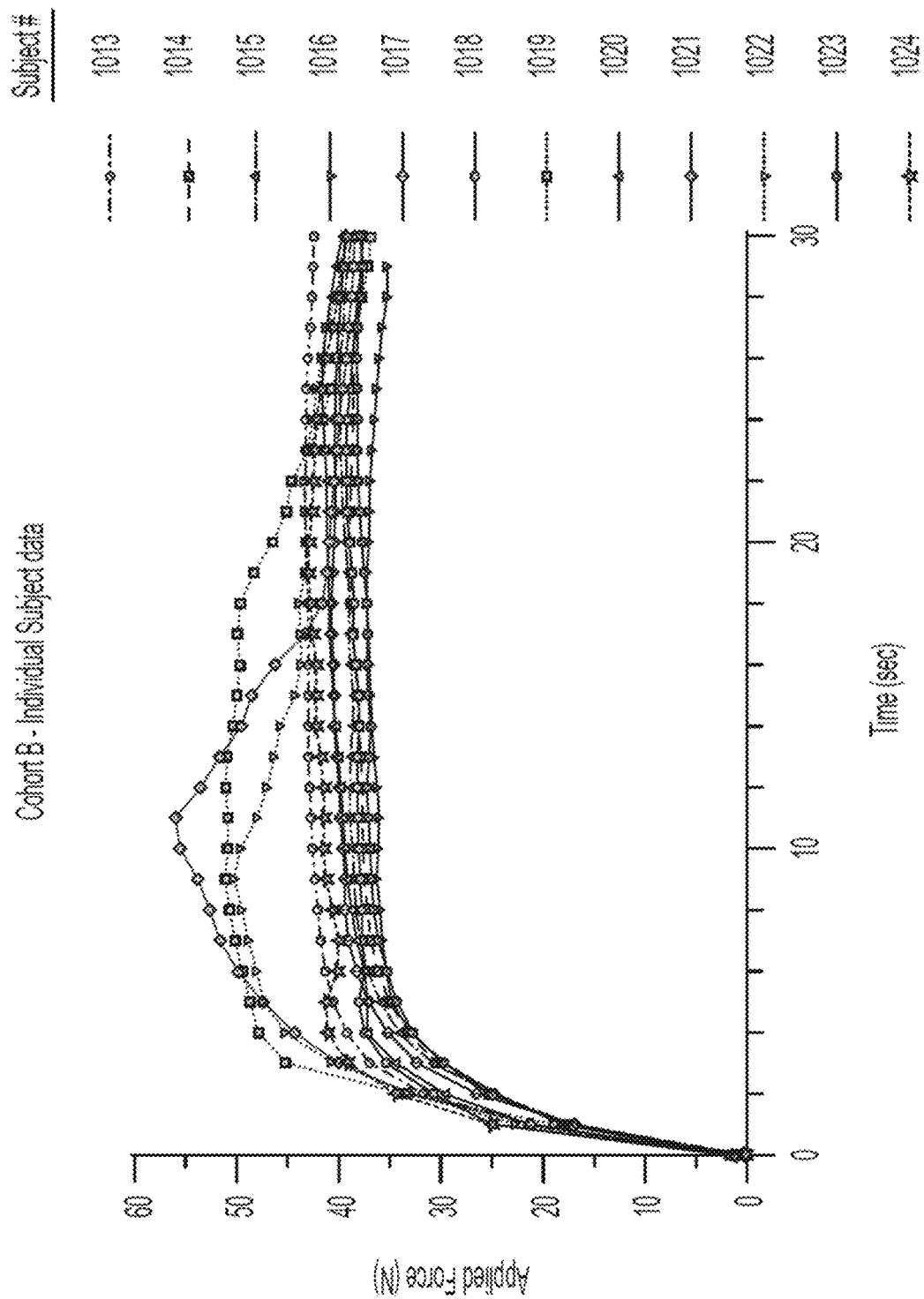

FIGS. 141A-141B provides a summary of the applied force data from Example 6, Cohort B (10 mL/30 s). The predicted applied force (AF) was approximately 2× that for Cohort B compared to Cohort A. Comparison of the clinical & nonclinical AF values allowed for prediction of HVAI performance using the various needle gauges.

FIG. 142 provides a comparison of applied forces between preclinical and clinical studies.

Figure 143:
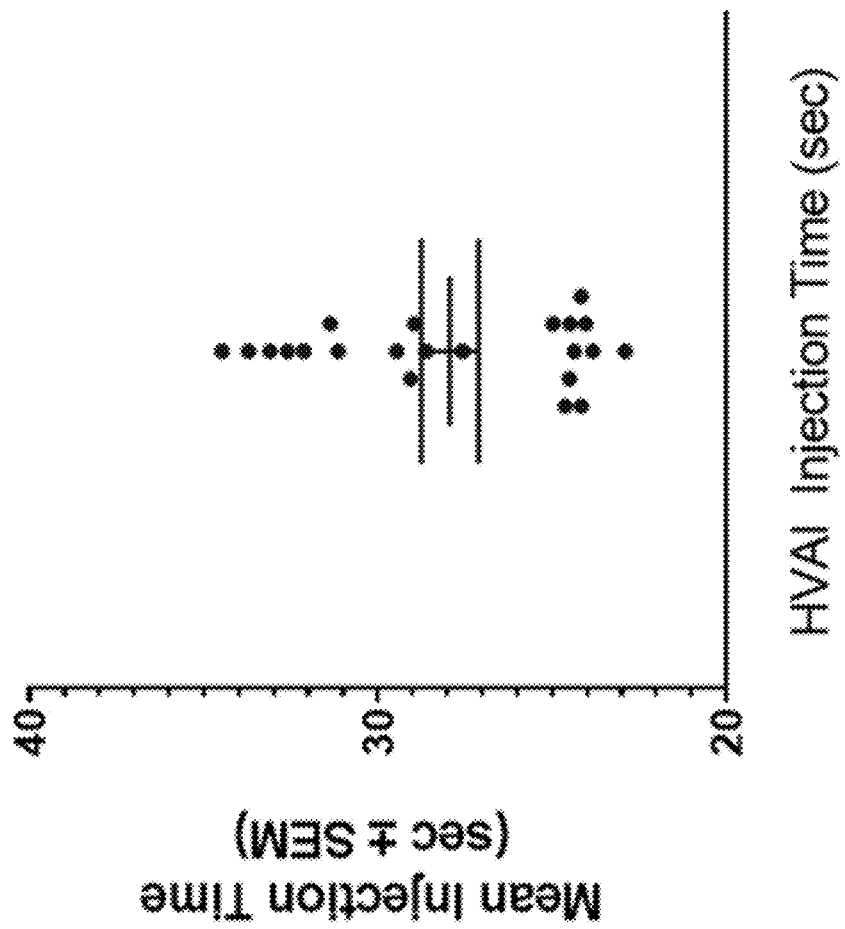

FIG. 143 depicts that the human clinical trial HVAI injections were completed and well tolerated.

Figure 144:
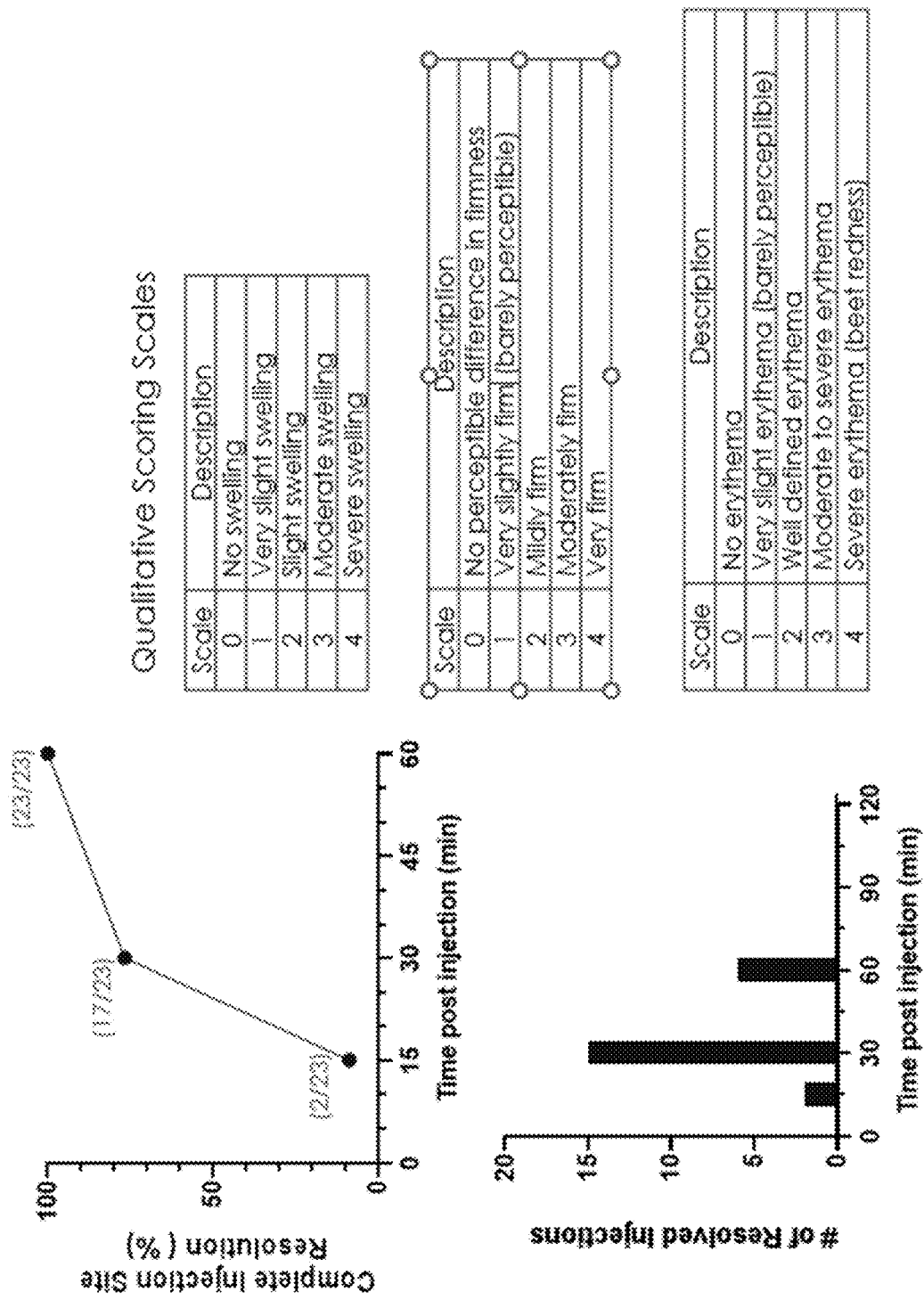

FIG. 144 depicts the rapid time to resolution for the human clinical trial HVAI injections.

Figure 145:
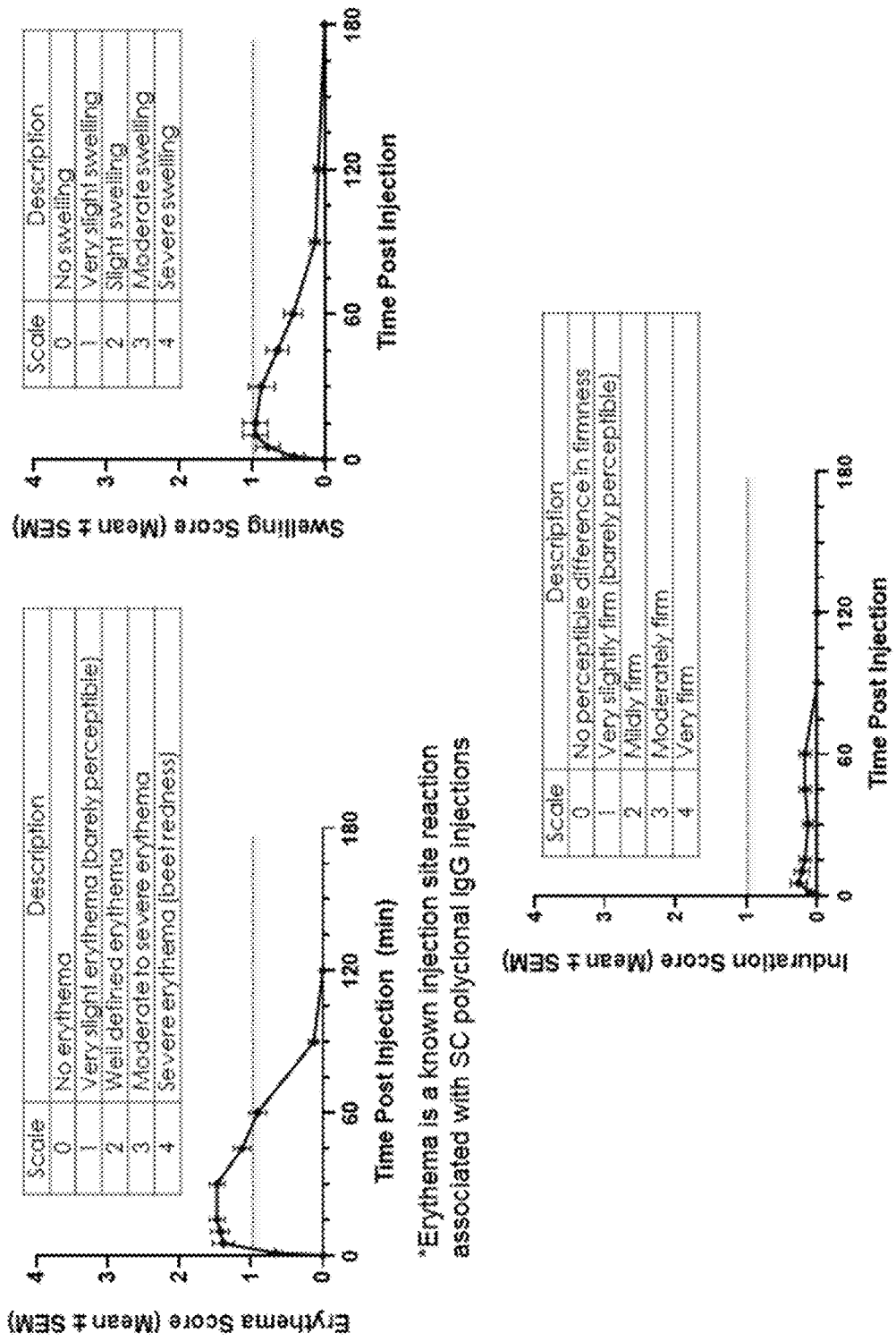

FIG. 145 provides modified-Draize scores for erythema, swelling, and induration with HVAI injections.

Figure 146A:
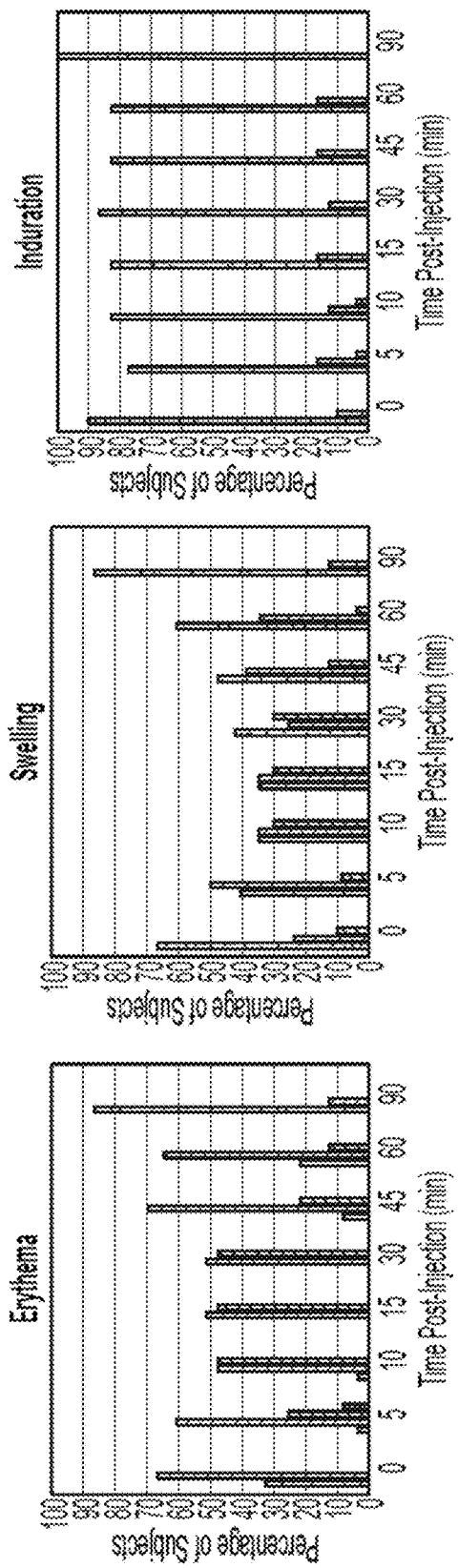
Figure 146B:
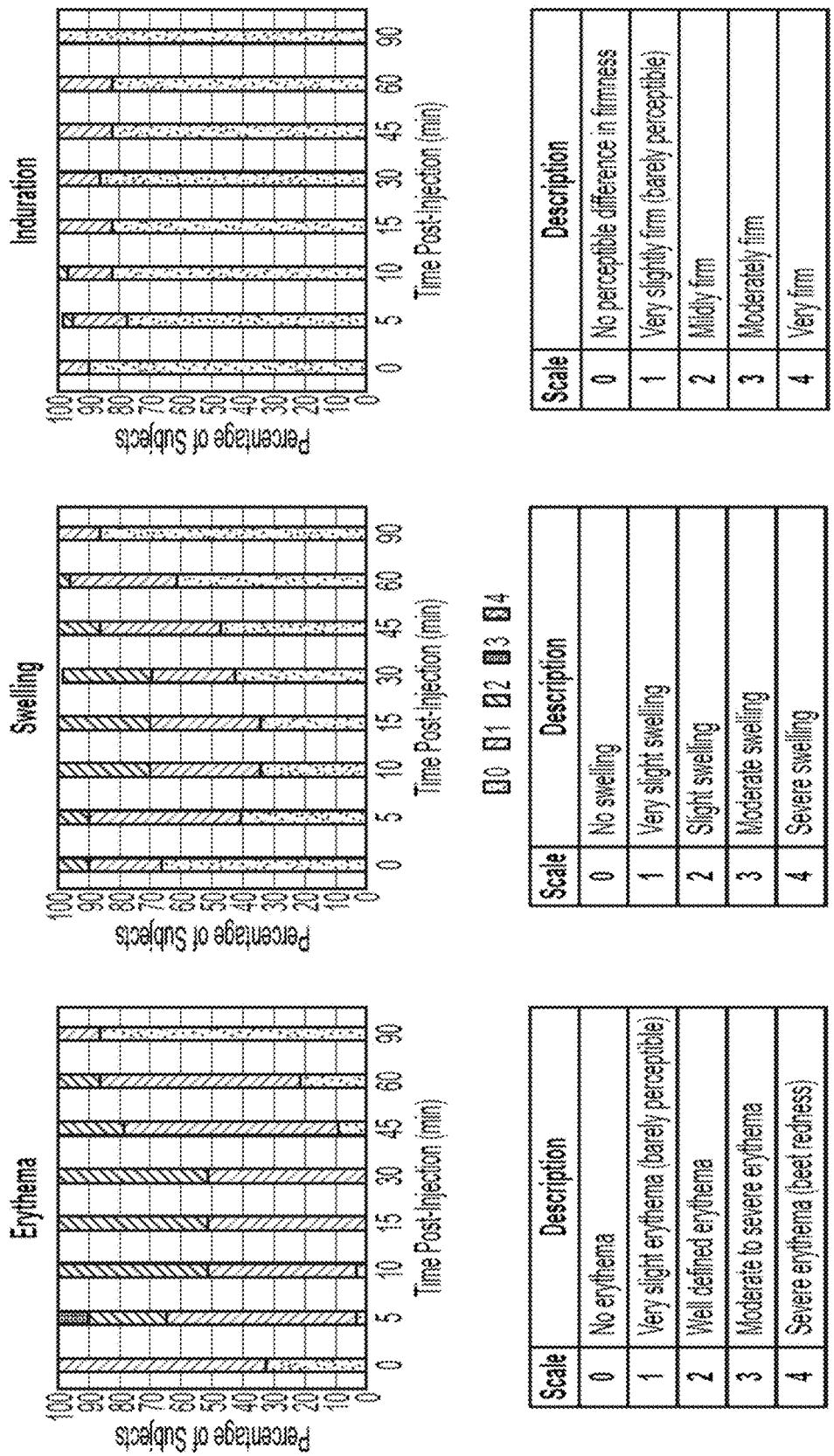
Figure 147:
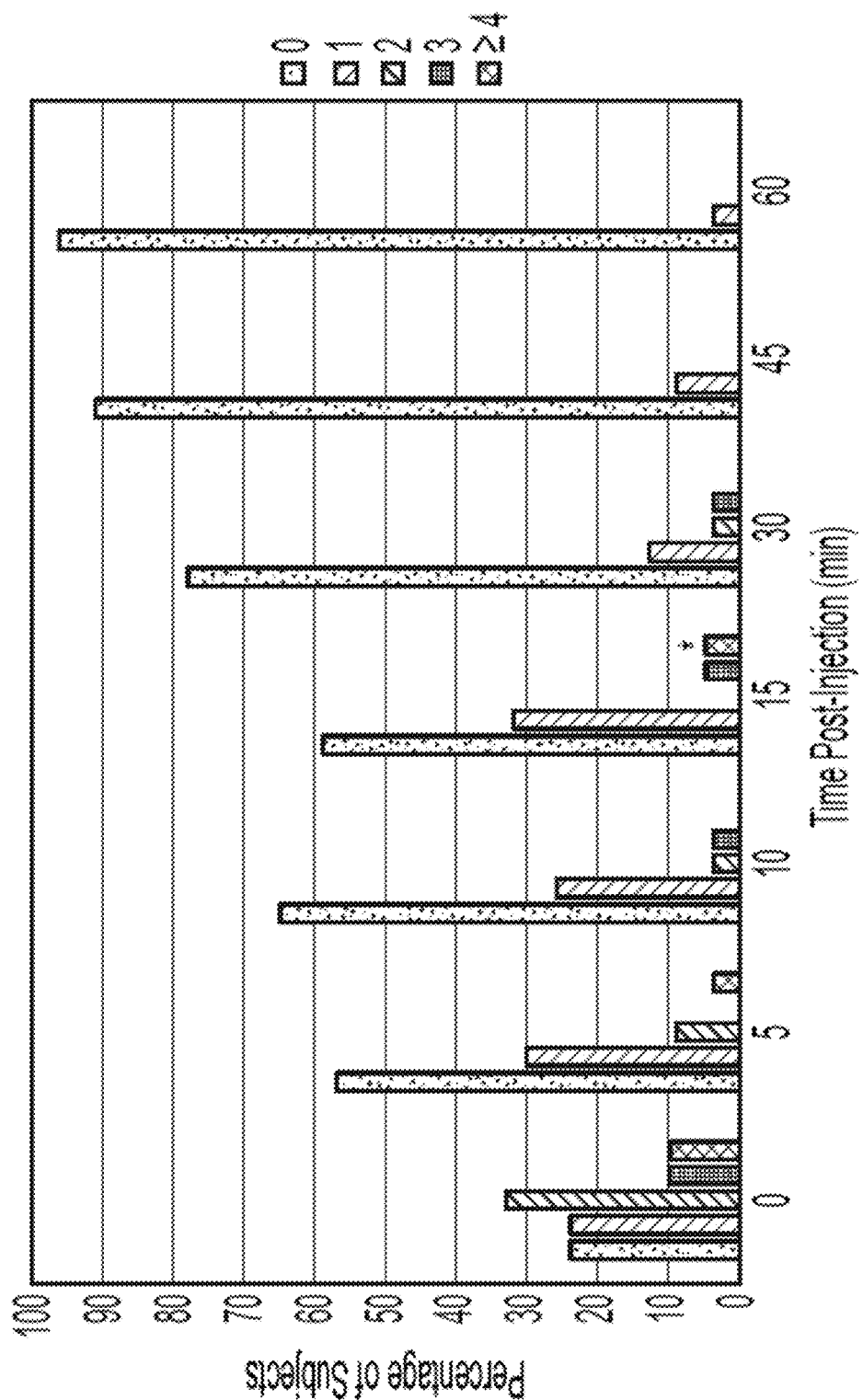
Figure 148:
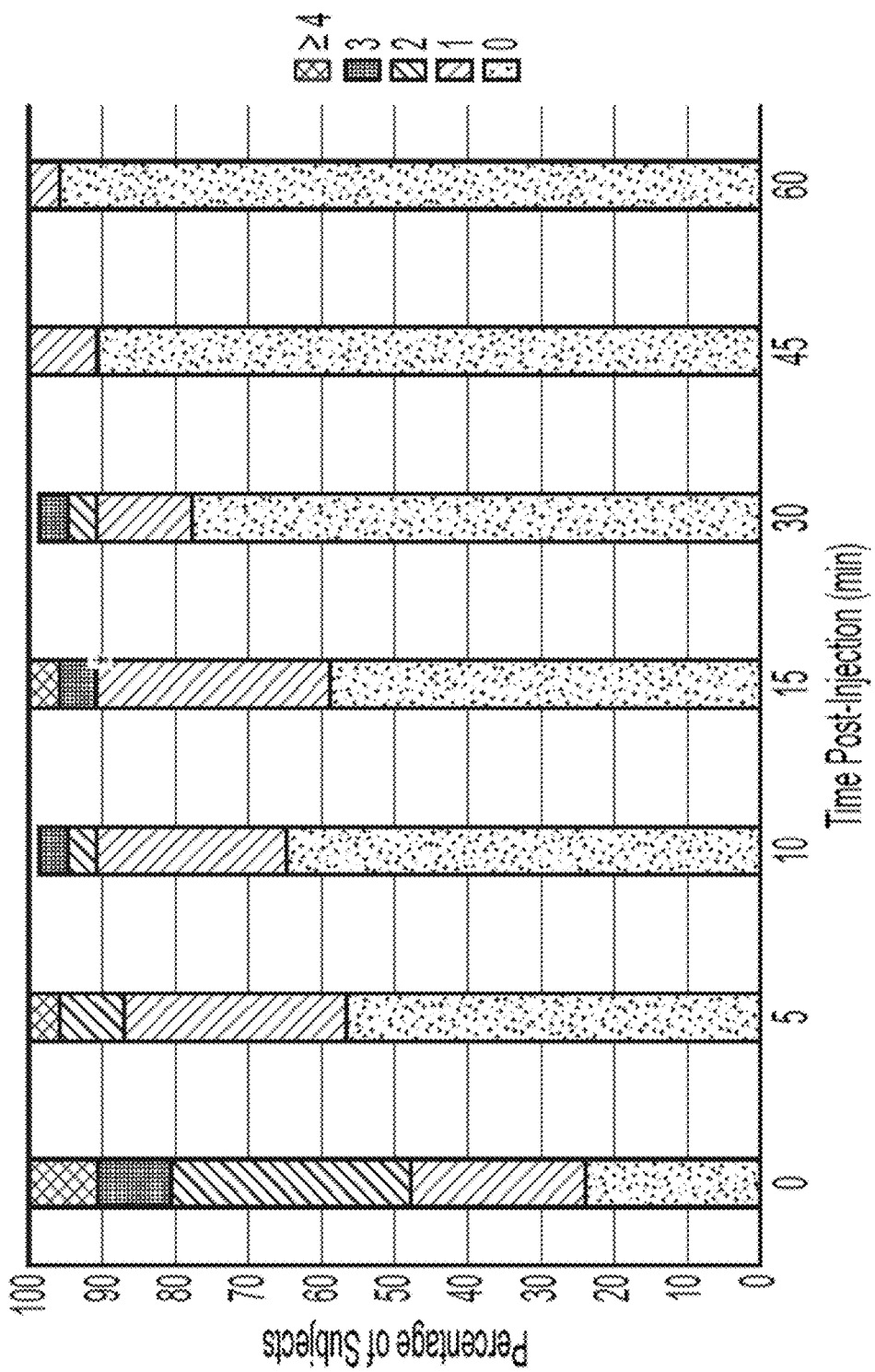
Figure 149B:
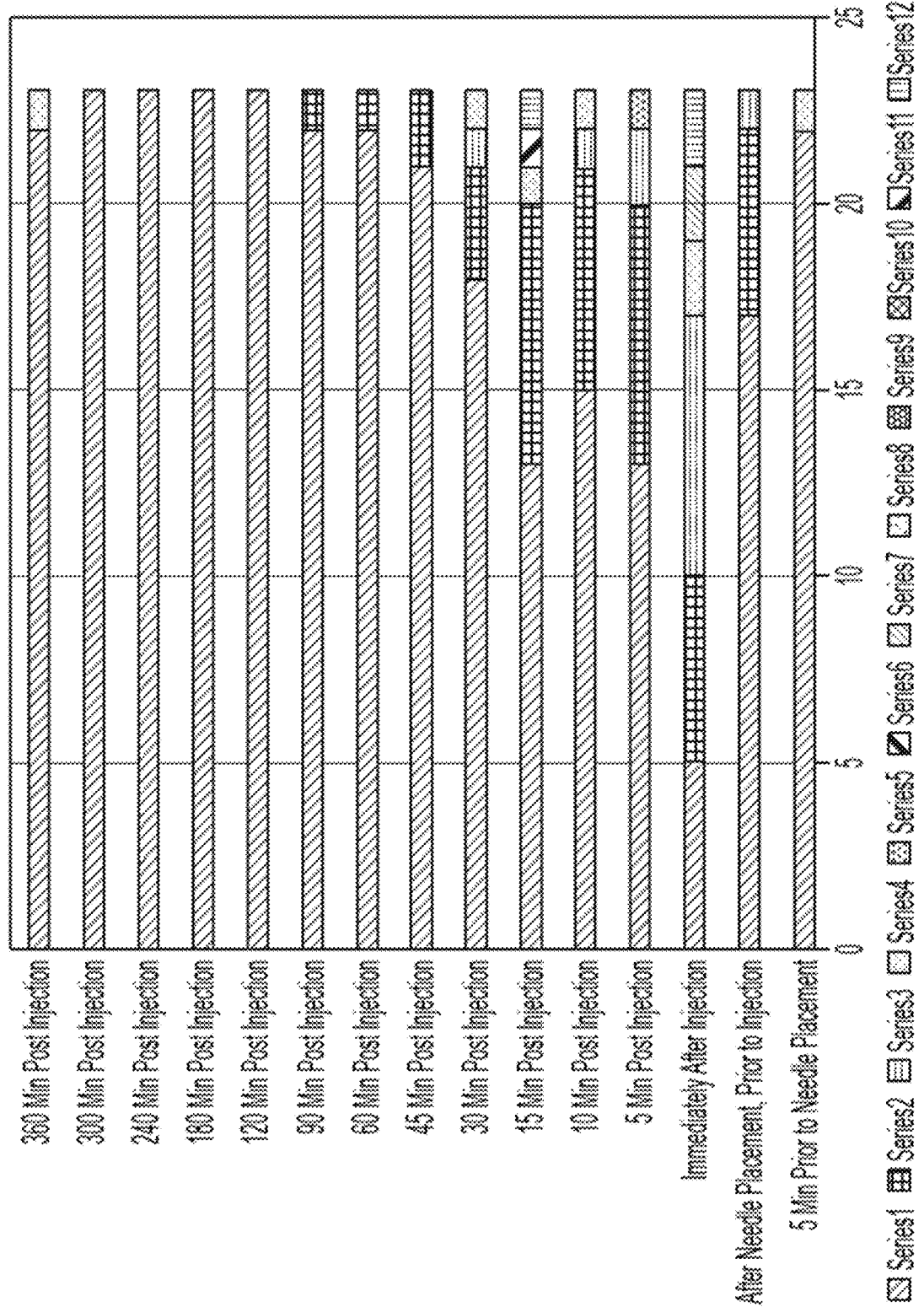

FIGS. 146A-146B provide data demonstrating that the modified-Draize score for erythema, swelling, and induration were low and resolved quickly (score≤1).

FIGS. 147-149B provide data using a numeric rating scale (NRS, 0-10 scale) demonstrating that subjects had minimal pain with the injection and rapid resolution of the pain.

Figure 150:
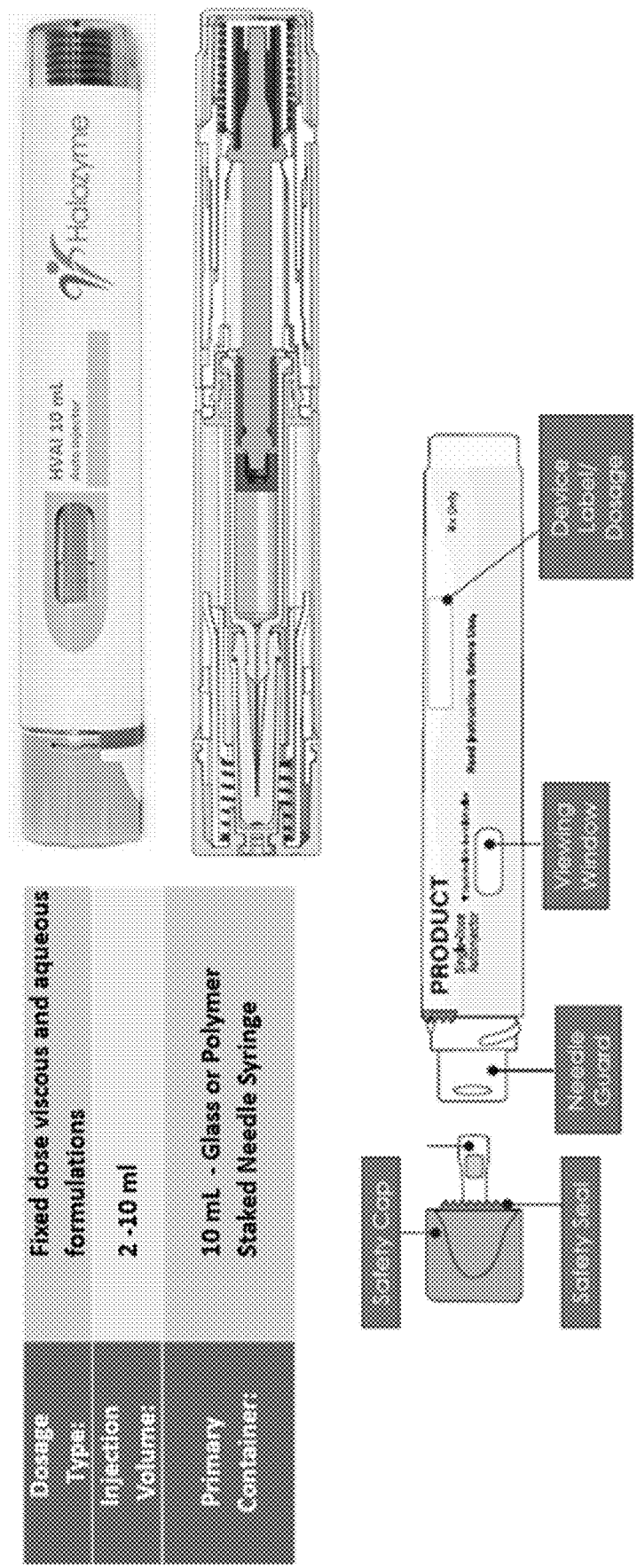

FIG. 150 is an illustrative rendering of a 2-step patient-friendly 10 mL HVAI concept based on a staked needle PFS primary container.

FIG. 151 is an overview of the swelling scores and induration scores of minipigs administered 10 mL IgG (120 mg/mL) with 2,000 U/mL rHuPH20 as fast as 30 mL/min. As illustrated, swelling and induction were both "very slight" within 30 minutes after the HVAI injection. The swelling and induration resolved rapidly after delivery. Injection times were about 30 sec for 25 G-BD and 19 sec for 25 G-Terumo.

Figure 152:
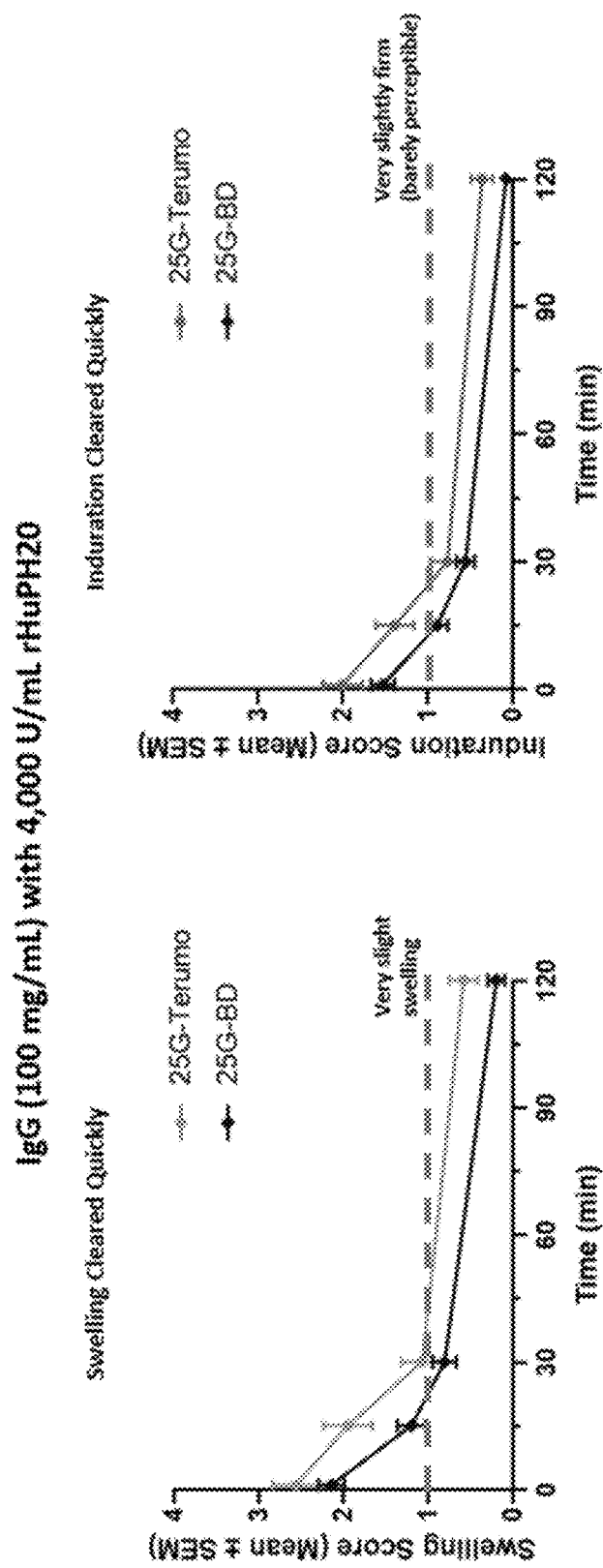

FIG. 152 is an overview of the swelling scores and induration scores of minipigs administered 10 mL IgG (100 mg/mL) with 4,000 U/mL rHuPH20 via HVAI in less than or equal to 30 seconds.

FIG. 153 is an overview of the swelling scores and induration scores of minipigs administered IgG-rHuPH20 (120 mg/mL-2,000 U/mL) to IgG-rHuPH20 (100 mg/mL-4,000 U/mL) via the HVAI.

Figure 154:
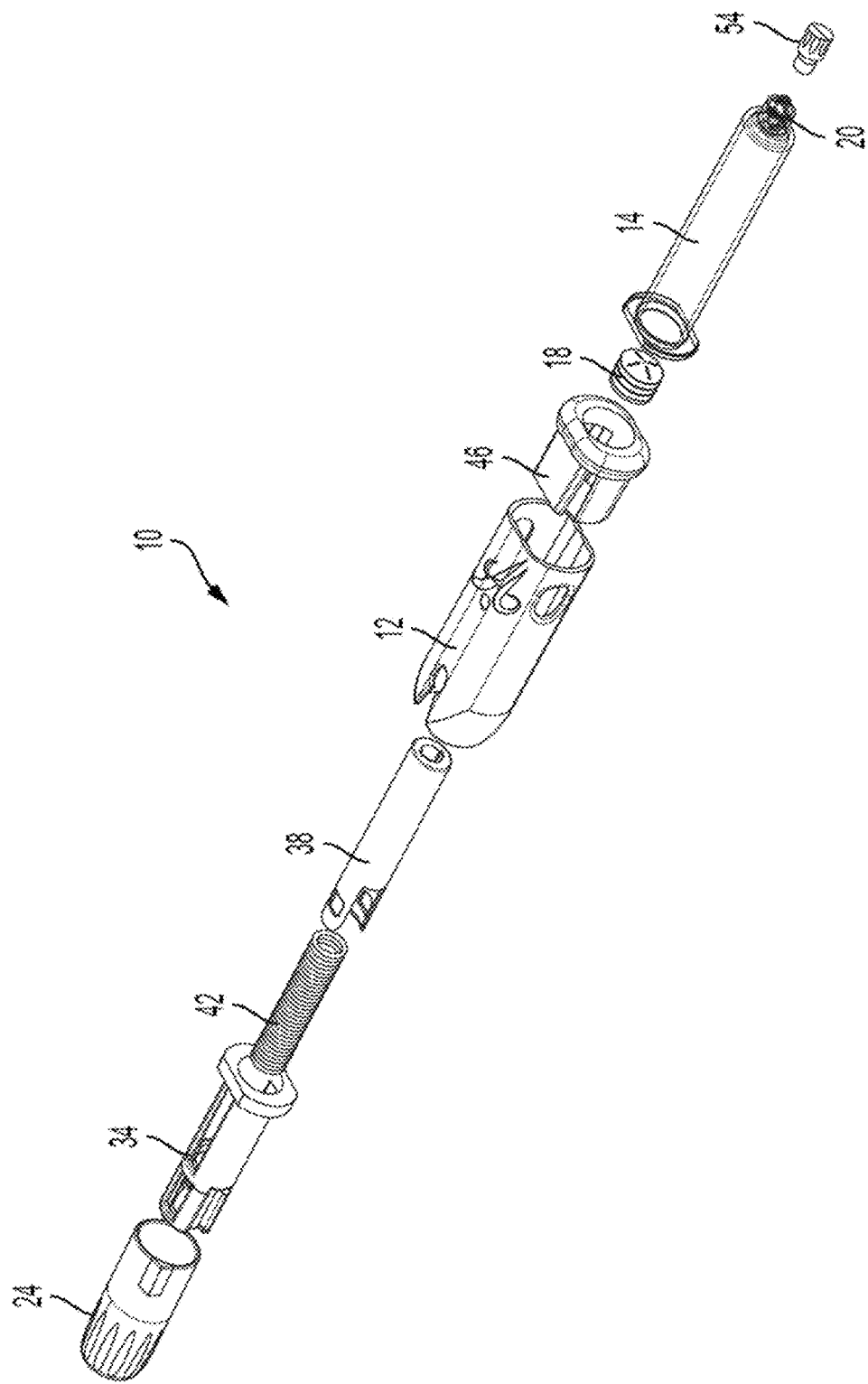

FIG. 154 is an exploded view a button actuated auto-injector in accordance with a first exemplary embodiment of the present invention.

Figure 155:
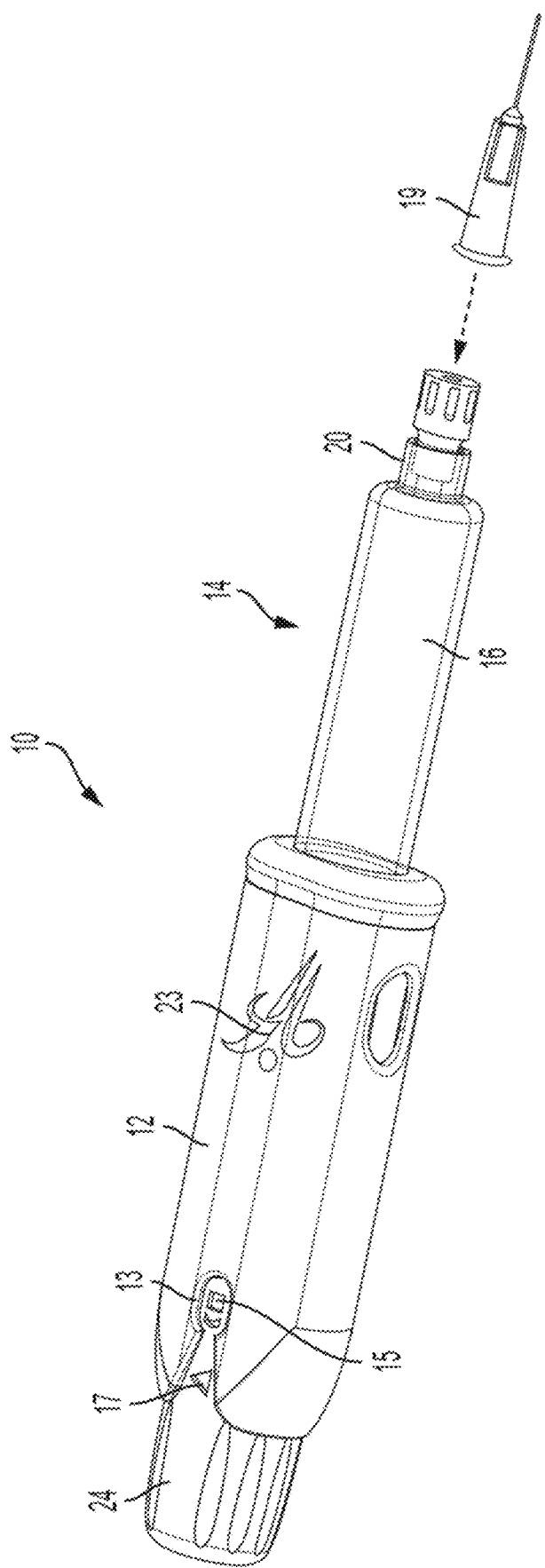

FIG. 155 is a perspective view of the button actuated auto-injector of FIG. 154.

Figure 156:
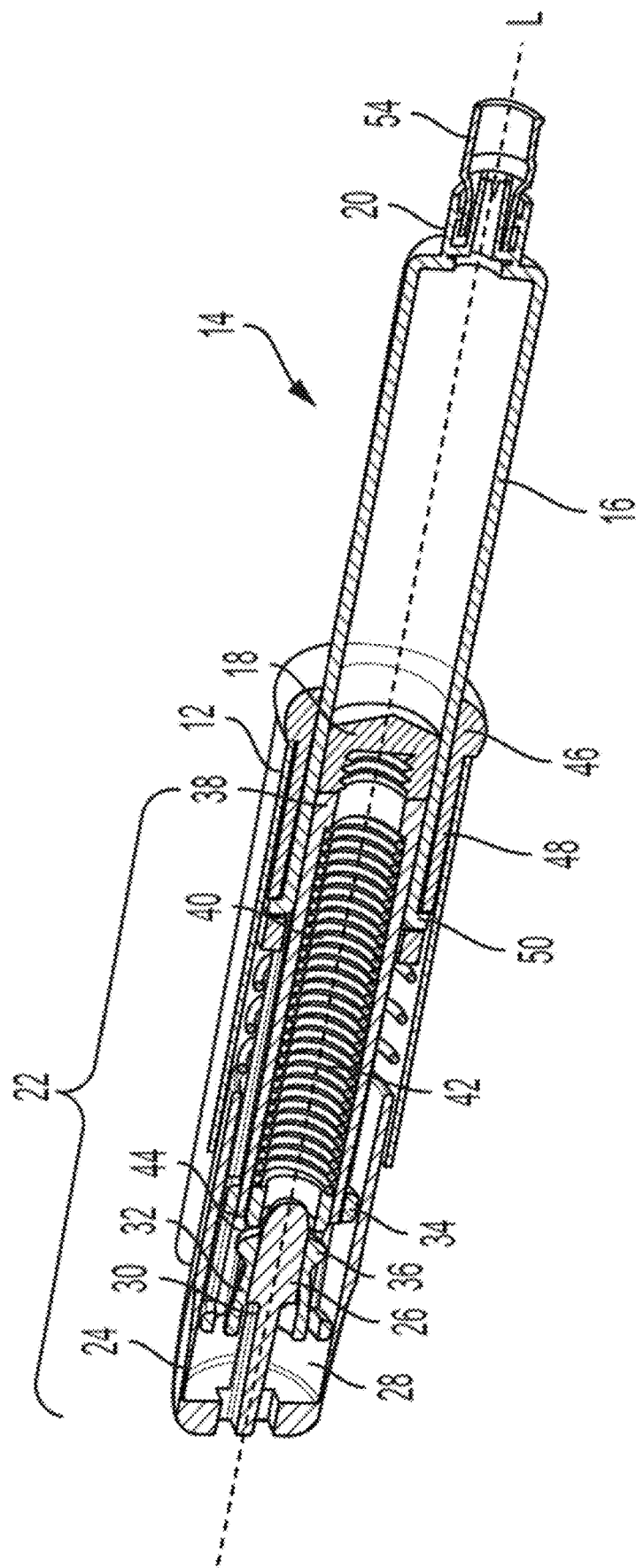

FIG. 156 is a cross-sectional view of the button actuated auto-injector of FIG. 154.

Figure 157:
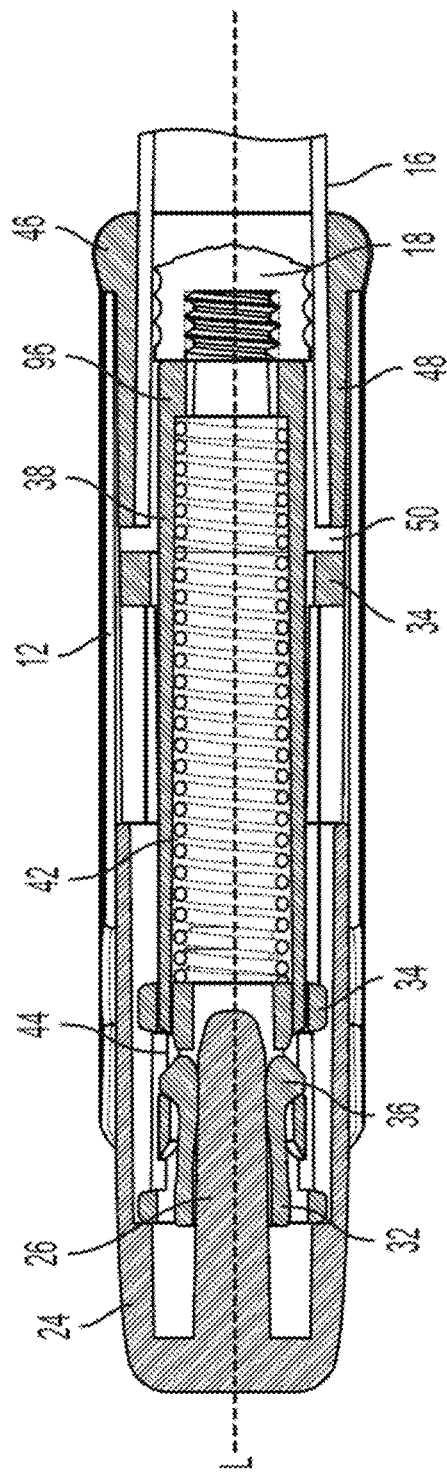

FIG. 157 is a partial cross-sectional view of the button actuated auto-injector of FIG. 154 in a locked configuration.

Figure 158:
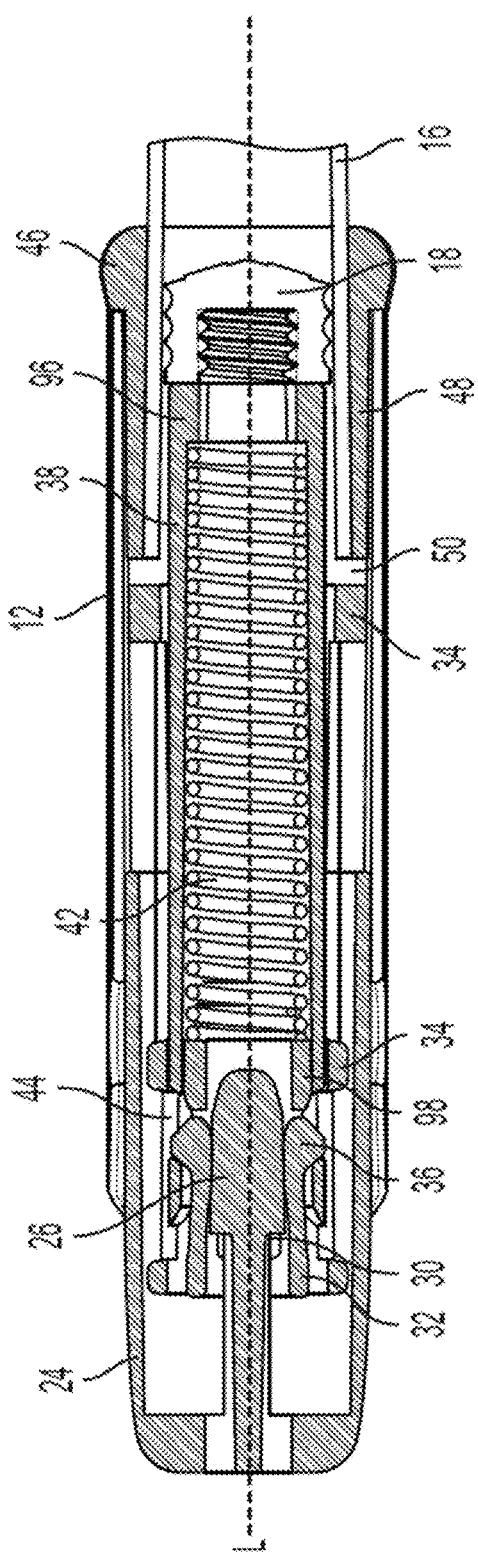

FIG. 158 is a partial cross-sectional view of the button actuated auto-injector of FIG. 154 in an unlocked configuration.

Figure 159:
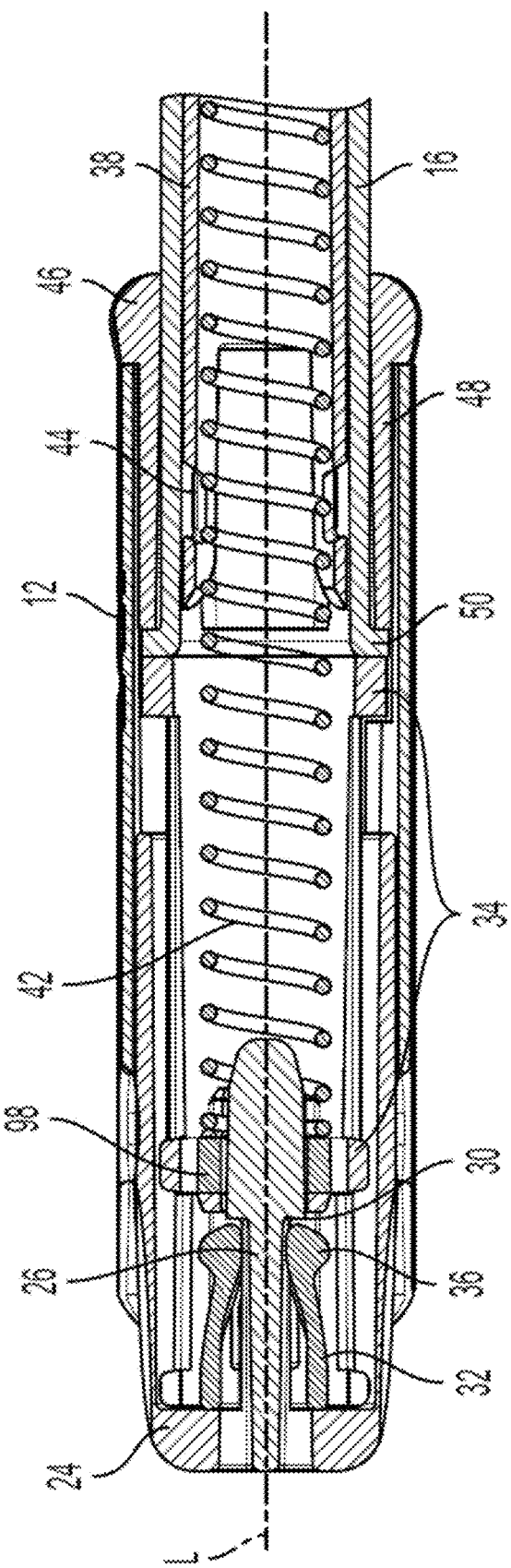

FIG. 159 is a partial cross-sectional view of the button actuated auto-injector of FIG. 154 in a discharged configuration.

Figure 160B:
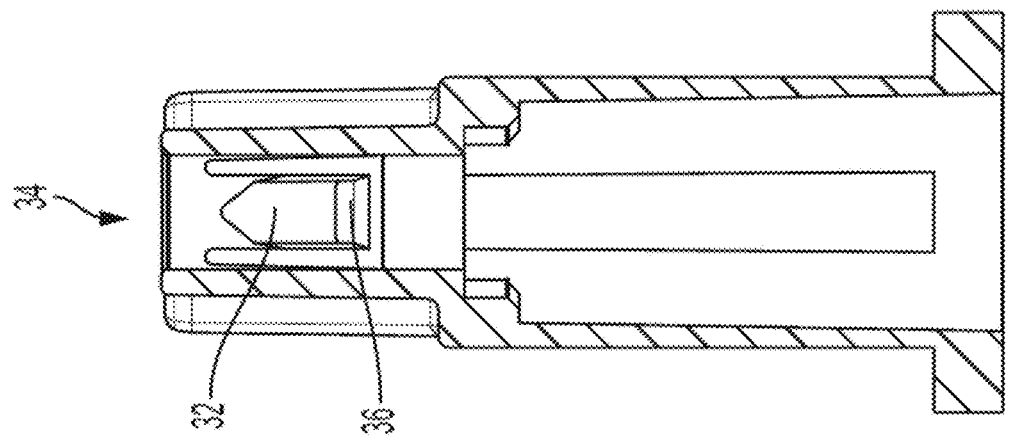
Figure 160A:
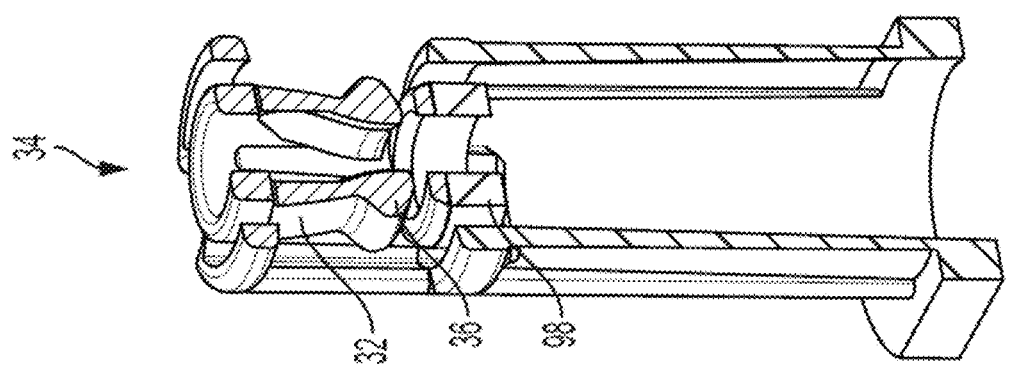

FIG. 160A is a cross sectional view of the latch of the button actuated auto-injector of FIG. 154.

FIG. 160 B is a cross sectional view of the latch of the button actuated auto-injector of FIG. 154.

Figure 161:
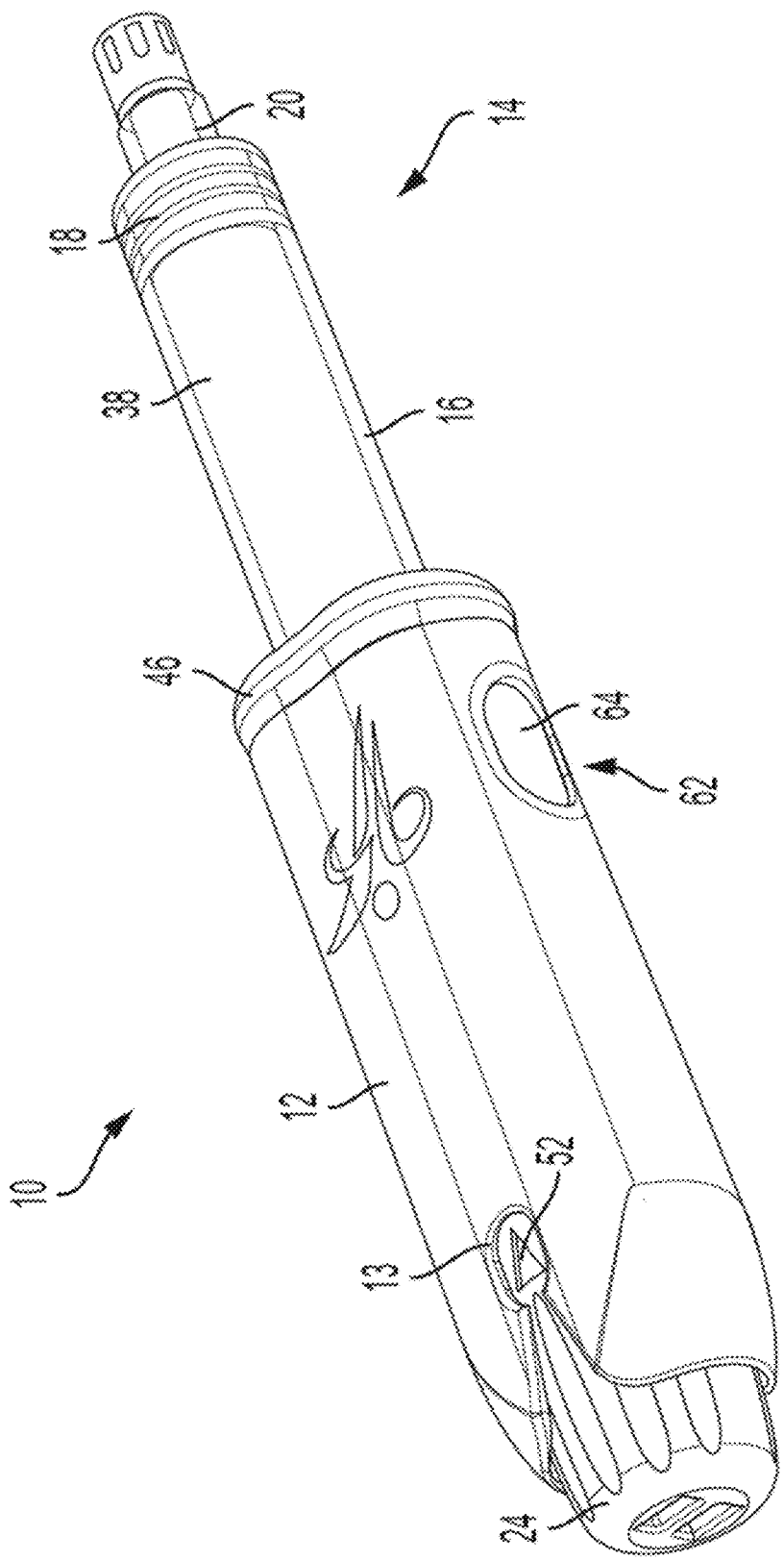

FIG. 161 is a perspective view of the button actuated auto-injector of FIG. 154 in a discharged configuration.

Figure 162B:
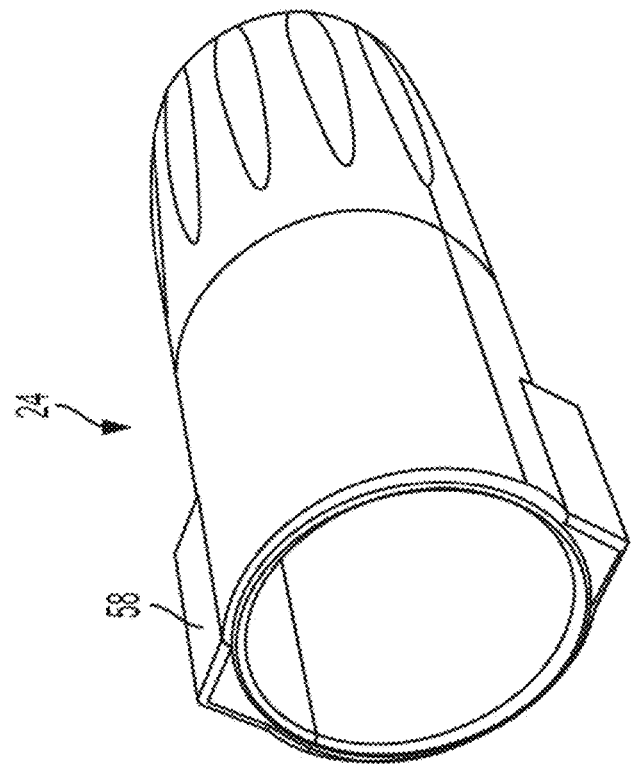
Figure 162A:
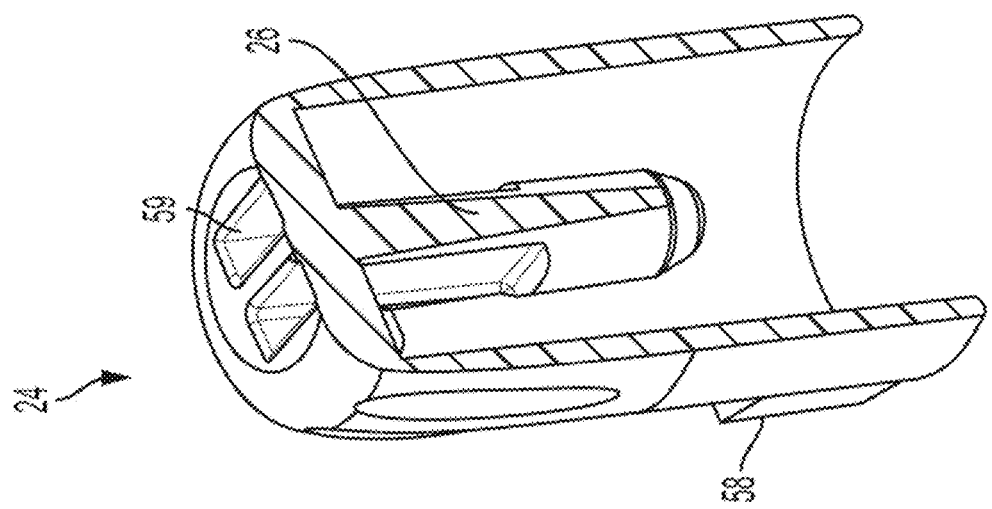

FIG. 162A is a cross-sectional view of a button of the button actuated auto-injector of FIG. 154.

FIG. 162B is a perspective view of a button of the button actuated auto-injector of FIG. 154.

Figure 163A:
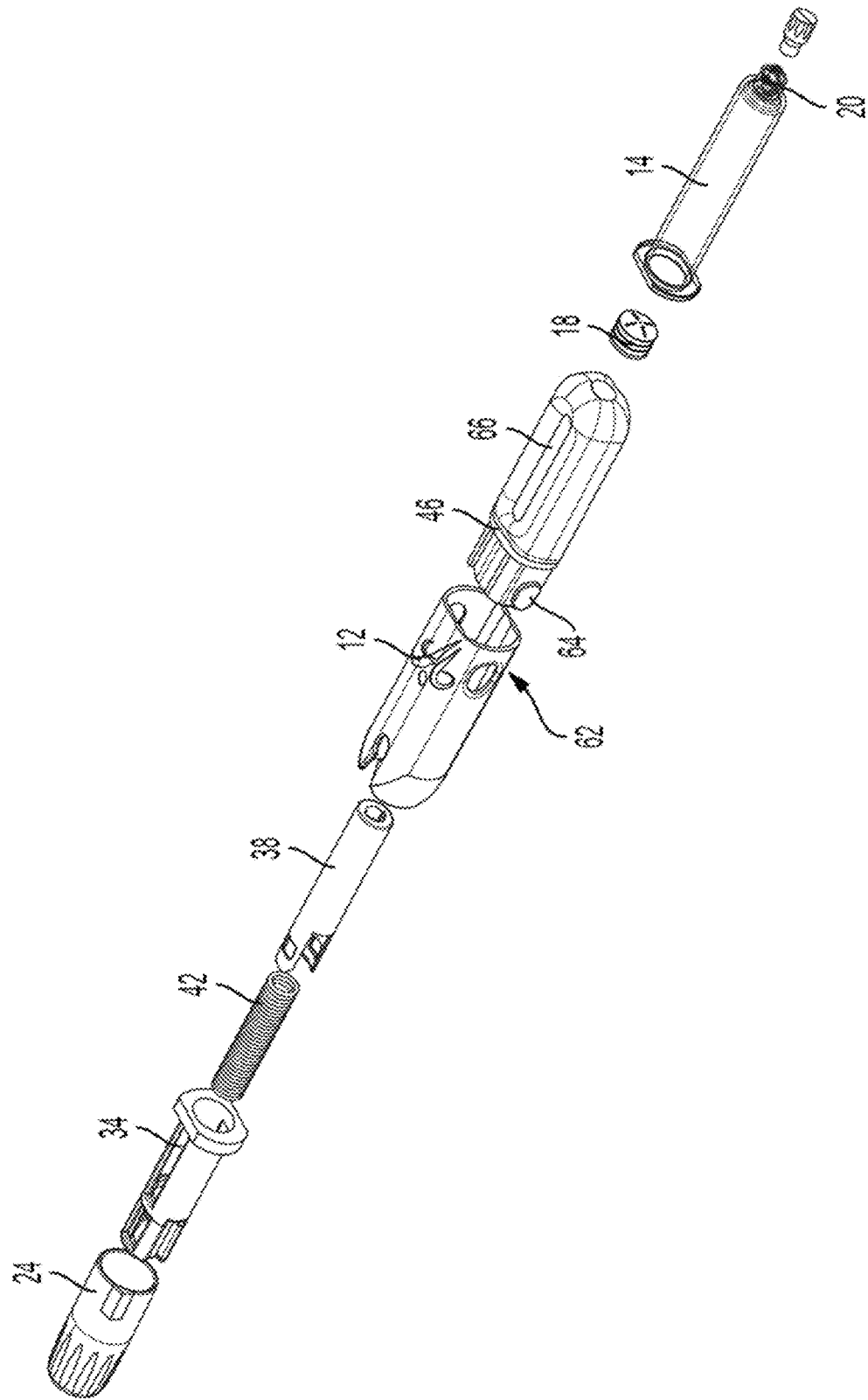

FIG. 163A is an exploded view of the button actuated auto-injector in accordance with a second exemplary embodiment of the present invention.

Figure 163C:
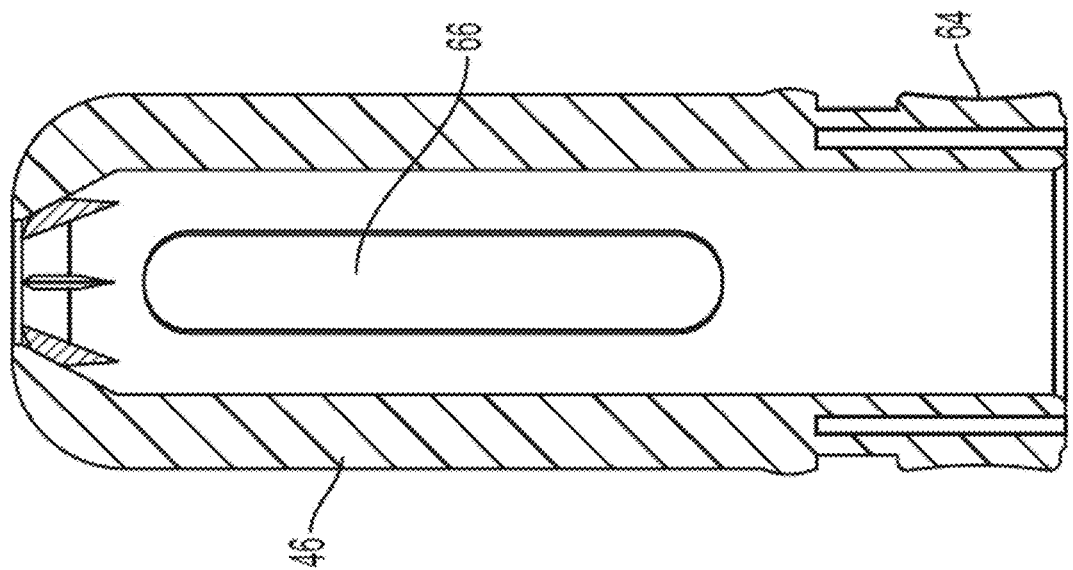
Figure 163B:
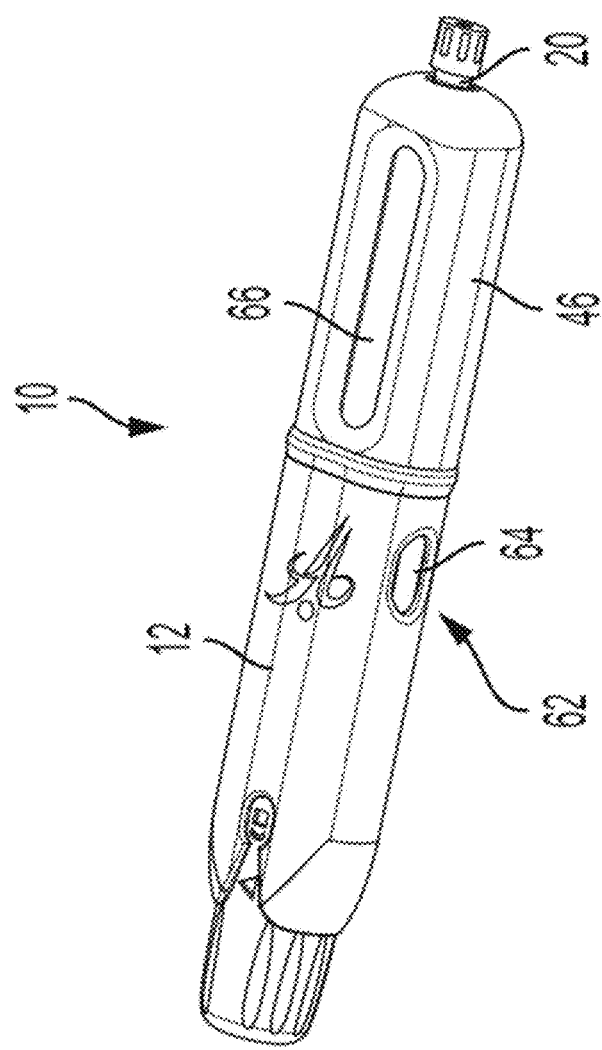

FIG. 163B is a perspective view of the button actuated auto-injector in accordance with a second exemplary embodiment of the present invention.

FIG. 163C is a cross-sectional view of the container support in accordance with a second exemplary embodiment of the present invention.

Figure 164A:
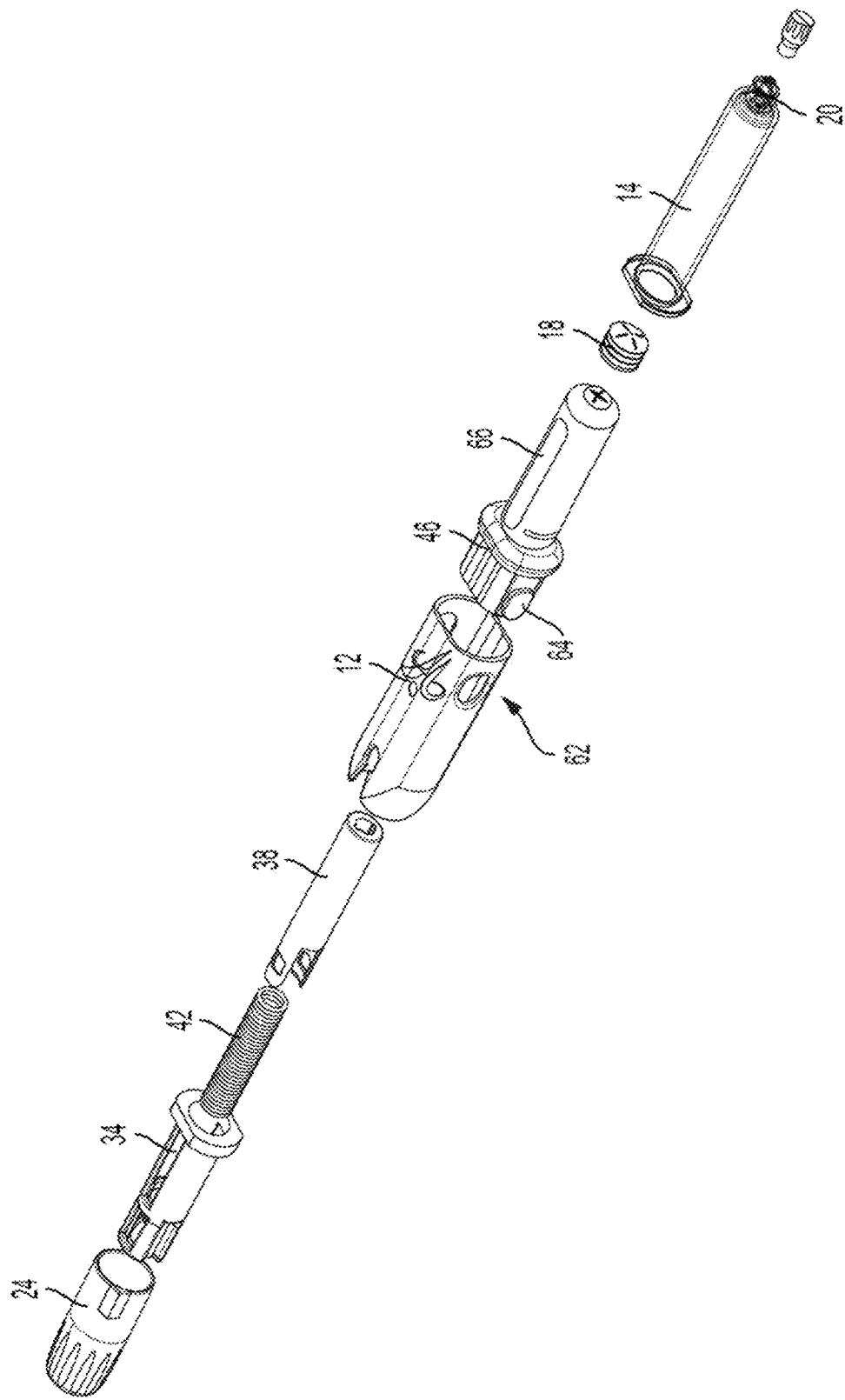

FIG. 164A is an exploded view of the button actuated auto-injector in accordance with a third exemplary embodiment of the present invention.

Figure 164C:
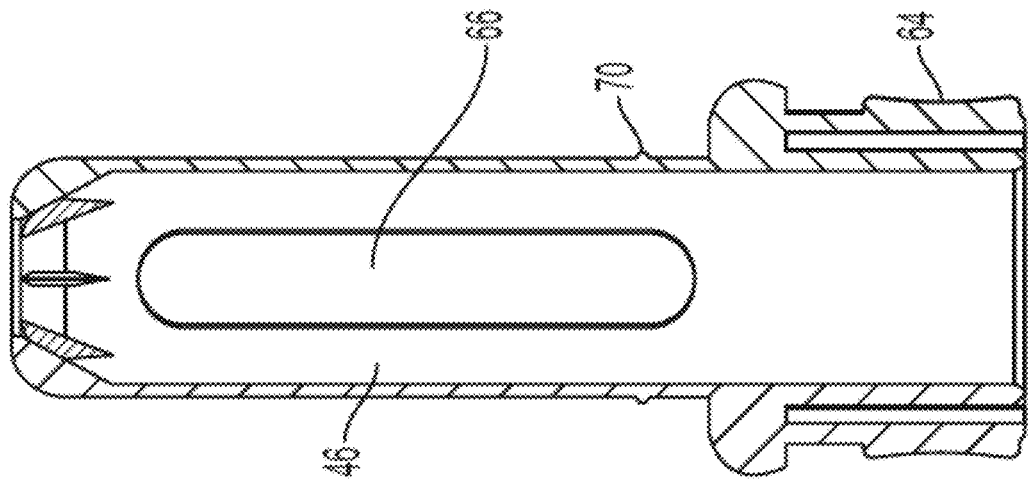
Figure 164B:
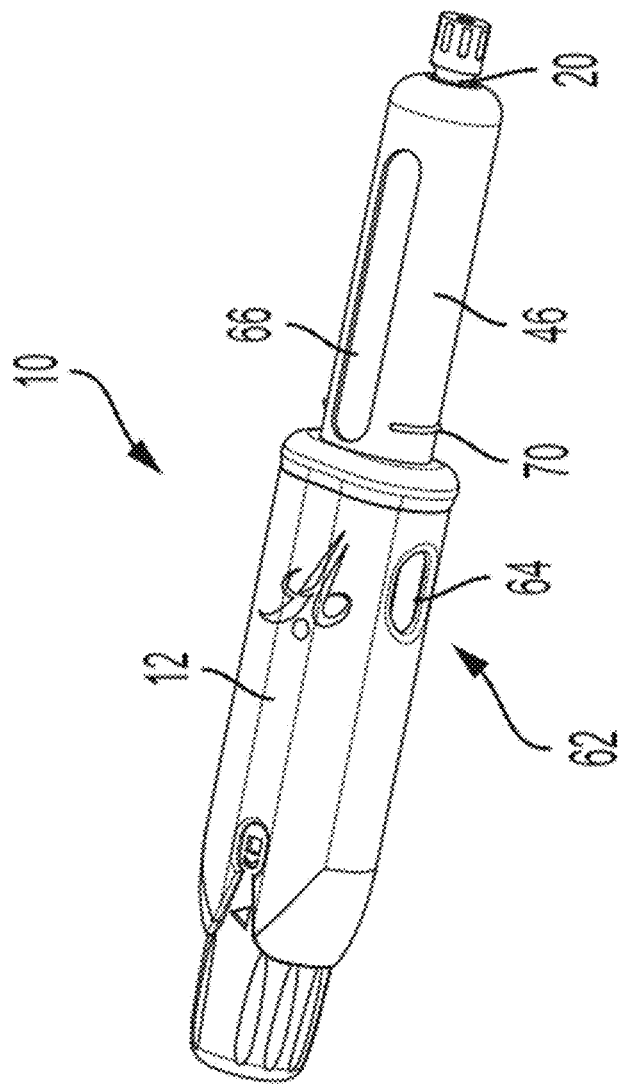

FIG. 164B is a perspective view of the button actuated auto-injector in accordance with a third exemplary embodiment of the present invention.

FIG. 164C is a cross-sectional view of the container support in accordance with a third exemplary embodiment of the present invention.

Figure 165:
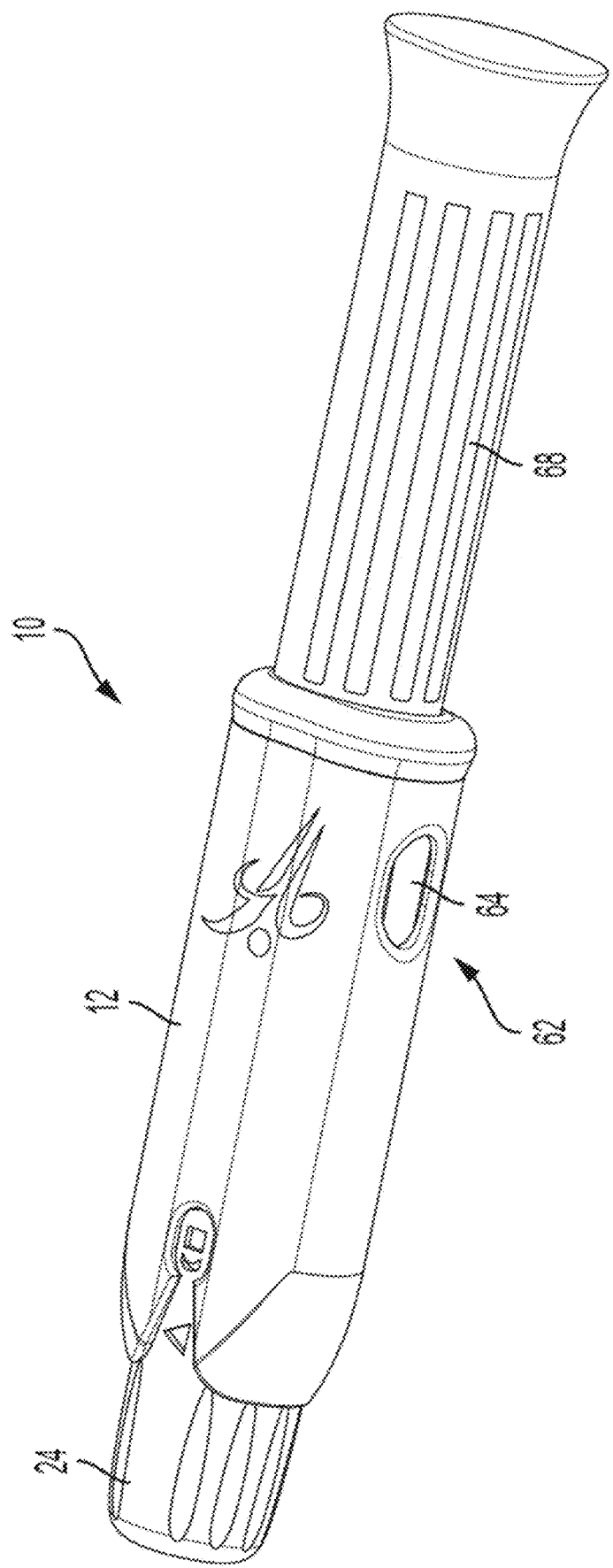

FIG. 165 is a perspective view of the button actuated auto-injector in accordance with a fourth exemplary embodiment of the present invention.

Figure 166:
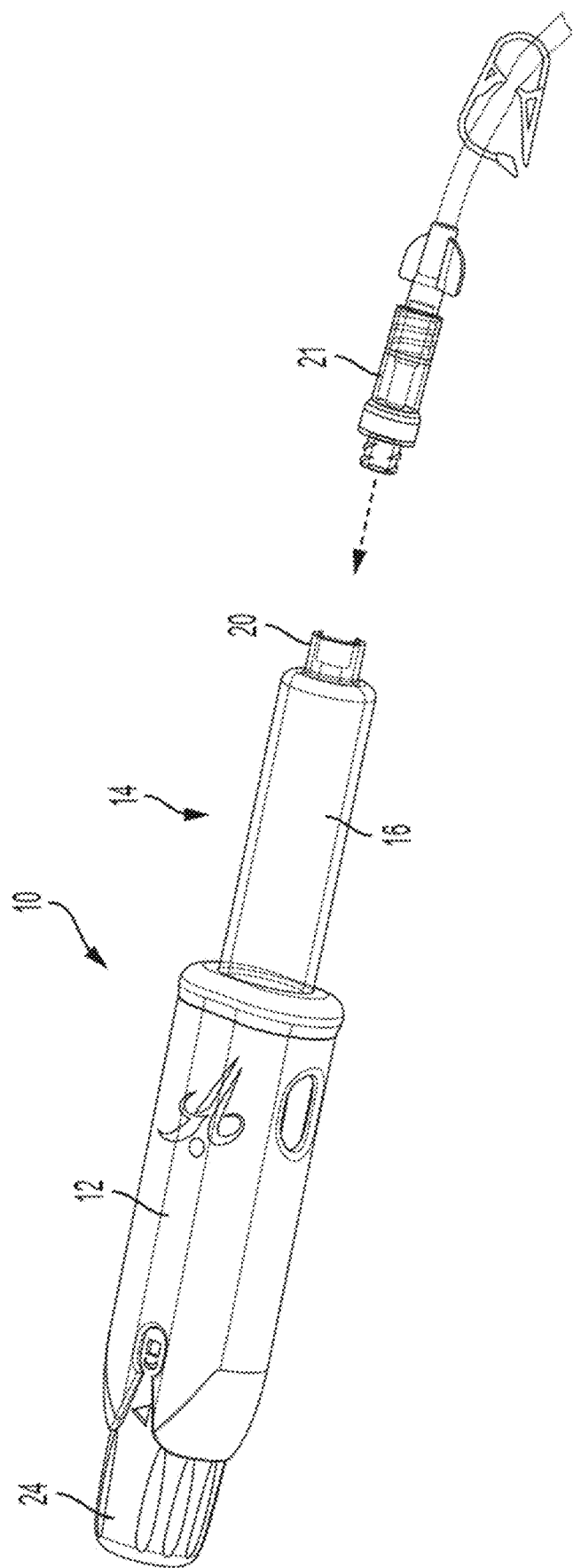

FIG. 166 is a perspective view of the button actuated auto-injector coupled to a tubing set in accordance with a fifth exemplary embodiment of the present invention.

Figure 167A:
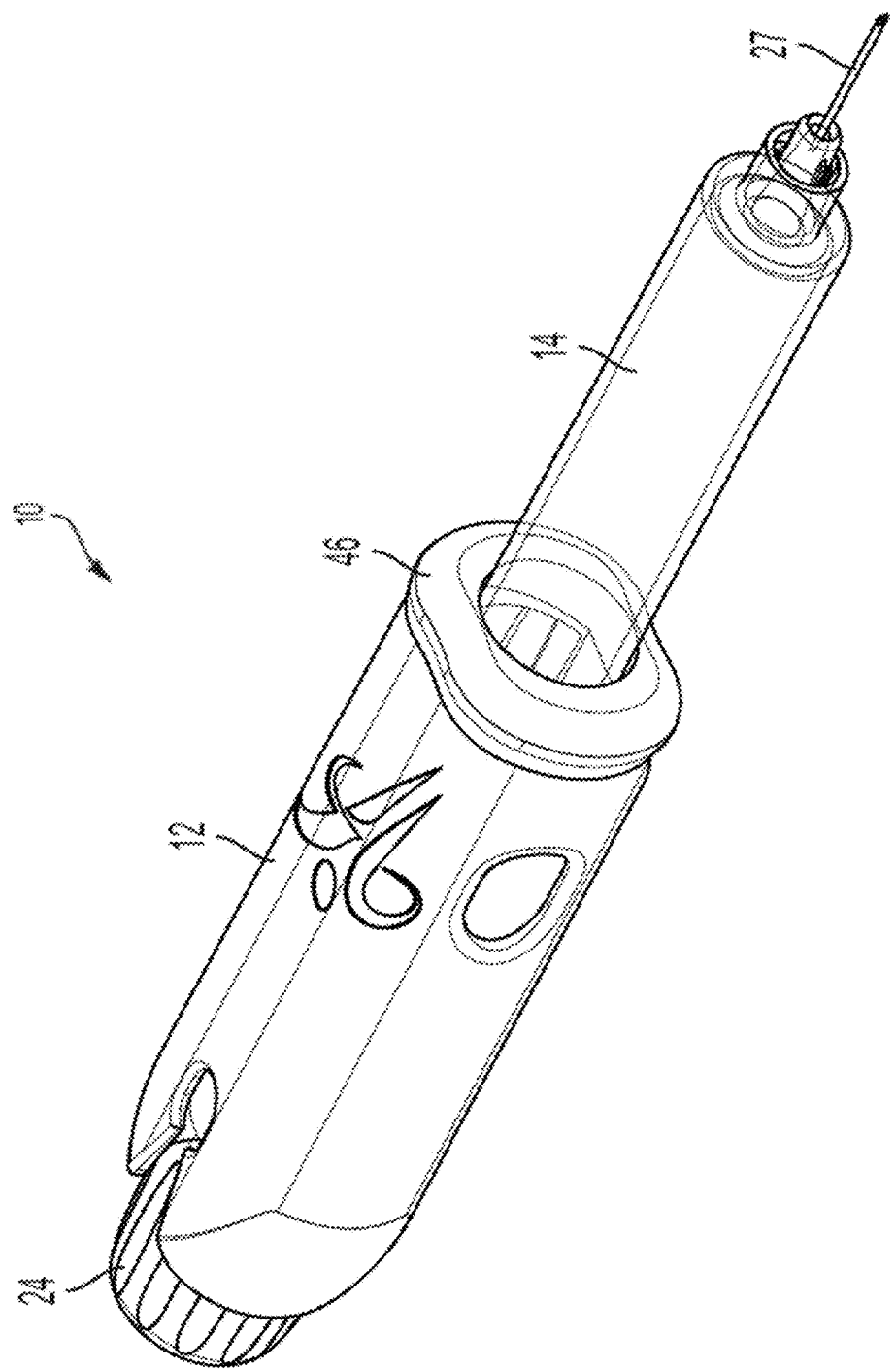

FIG. 167A is a perspective view of the button actuated auto-injector in accordance with a sixth exemplary embodiment of the present invention.

Figure 167B:
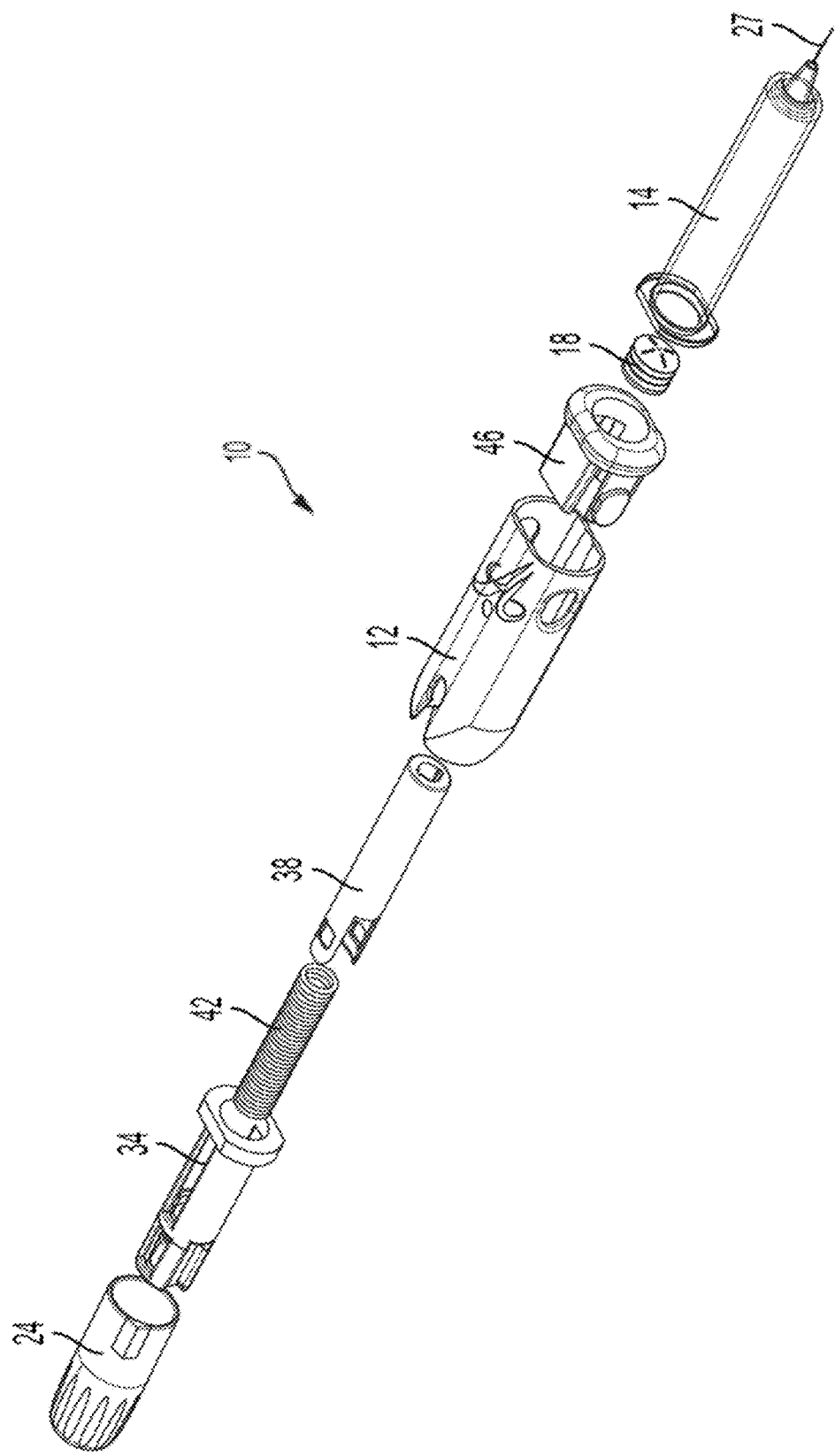

FIG. 167B is an exploded view of the button actuated auto-injector in accordance with a sixth exemplary embodiment of the present invention.

Figure 168:
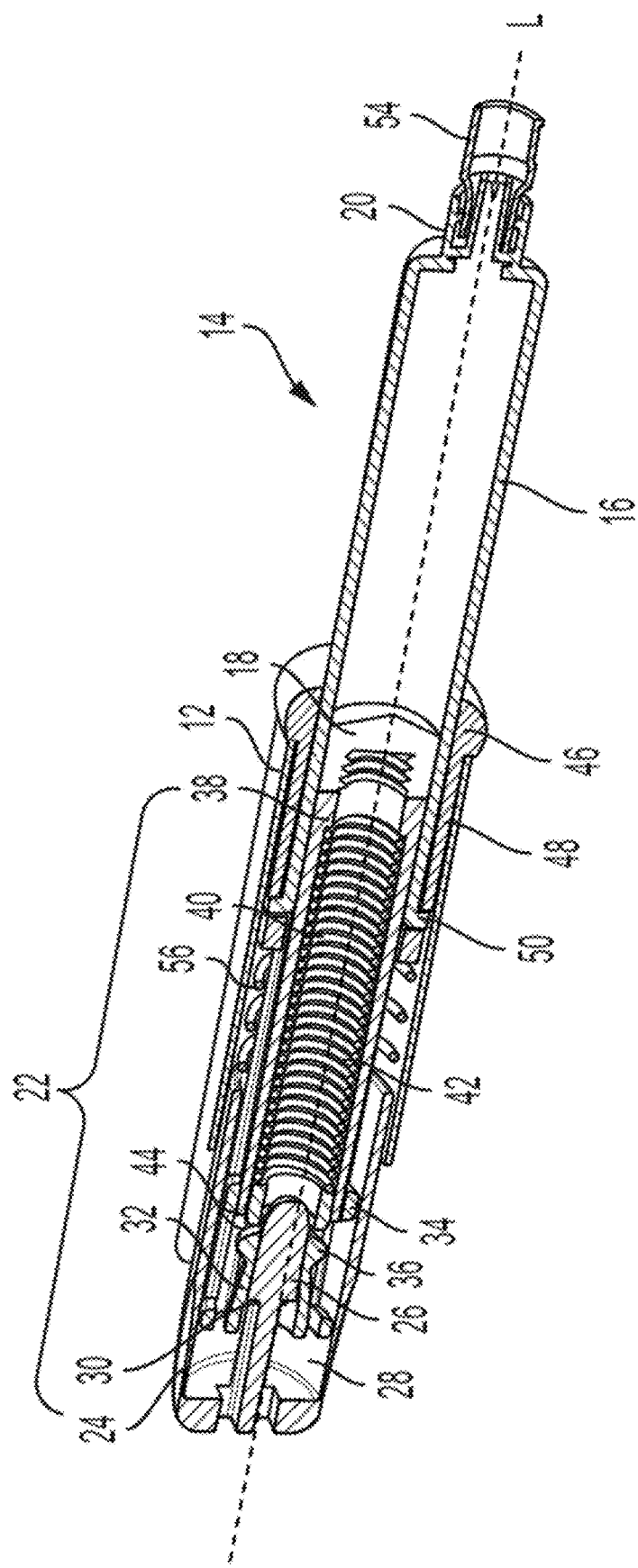

FIG. 168 is a cross-sectional view of the button actuated auto-injector in accordance with a seventh exemplary embodiment of the present invention.

Figure 169:
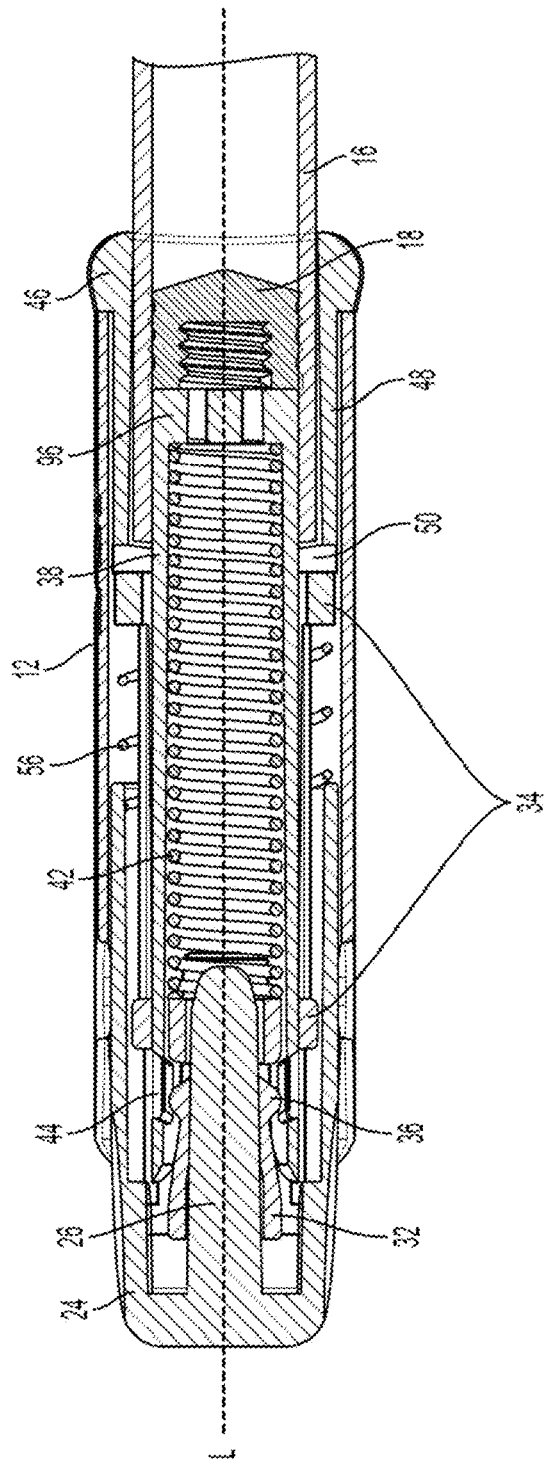

FIG. 169 is a partial cross-sectional view of the button actuated auto-injector in accordance with the seventh exemplary embodiment of the present invention in a locked configuration.

Figure 170:
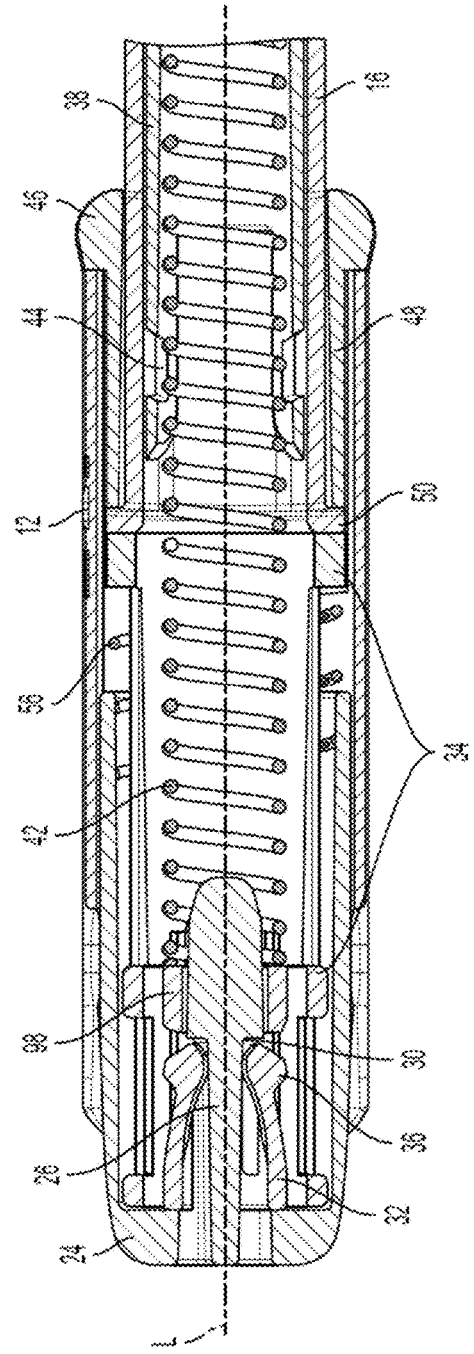

FIG. 170 is a partial cross-sectional view of the button actuated auto-injector in accordance with the seventh exemplary embodiment of the present invention in a discharged configuration.

Figure 171:
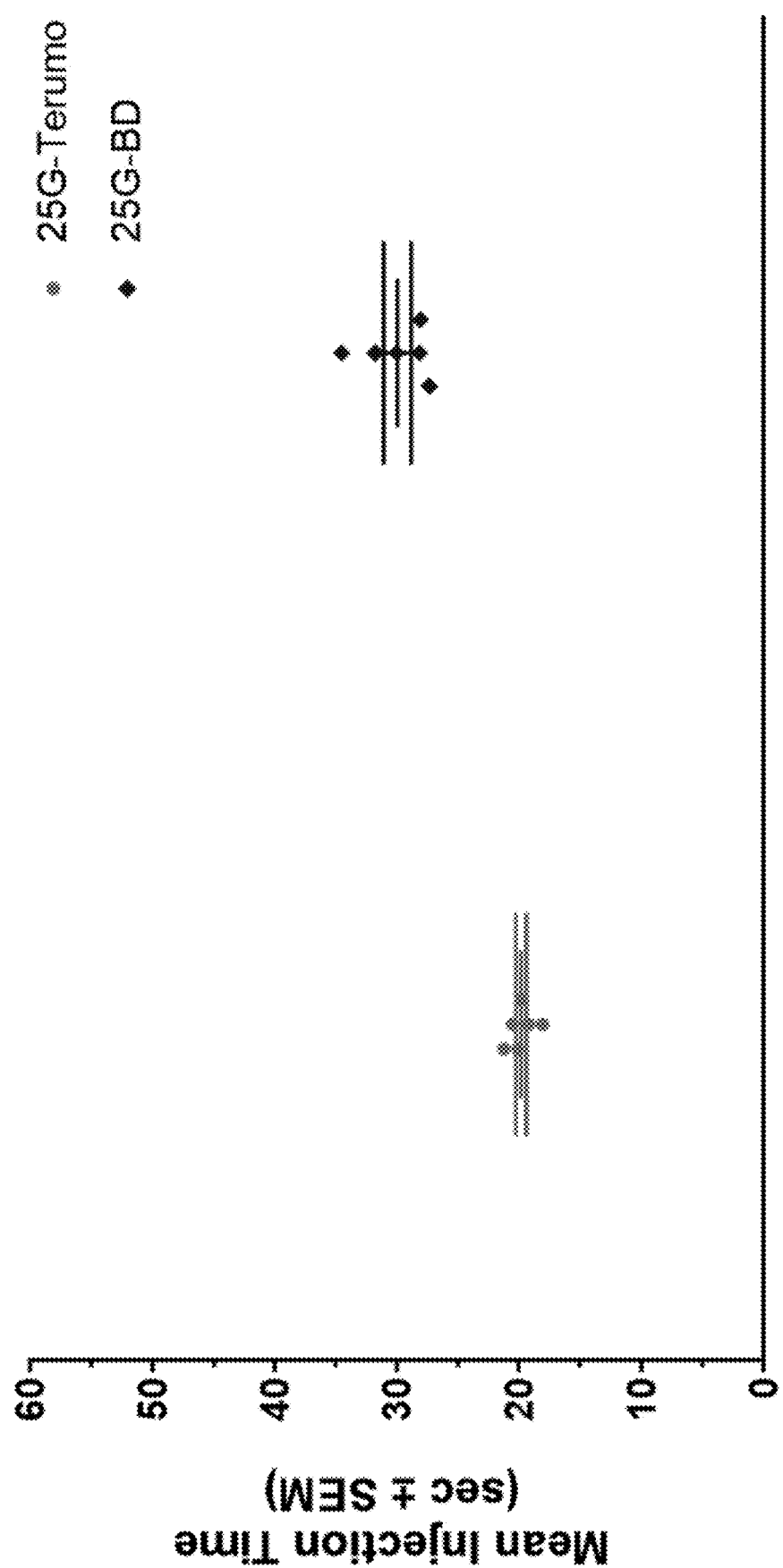

FIG. 171 is a graph of individual animal injection time data (mean±SEM).

Figure 172:
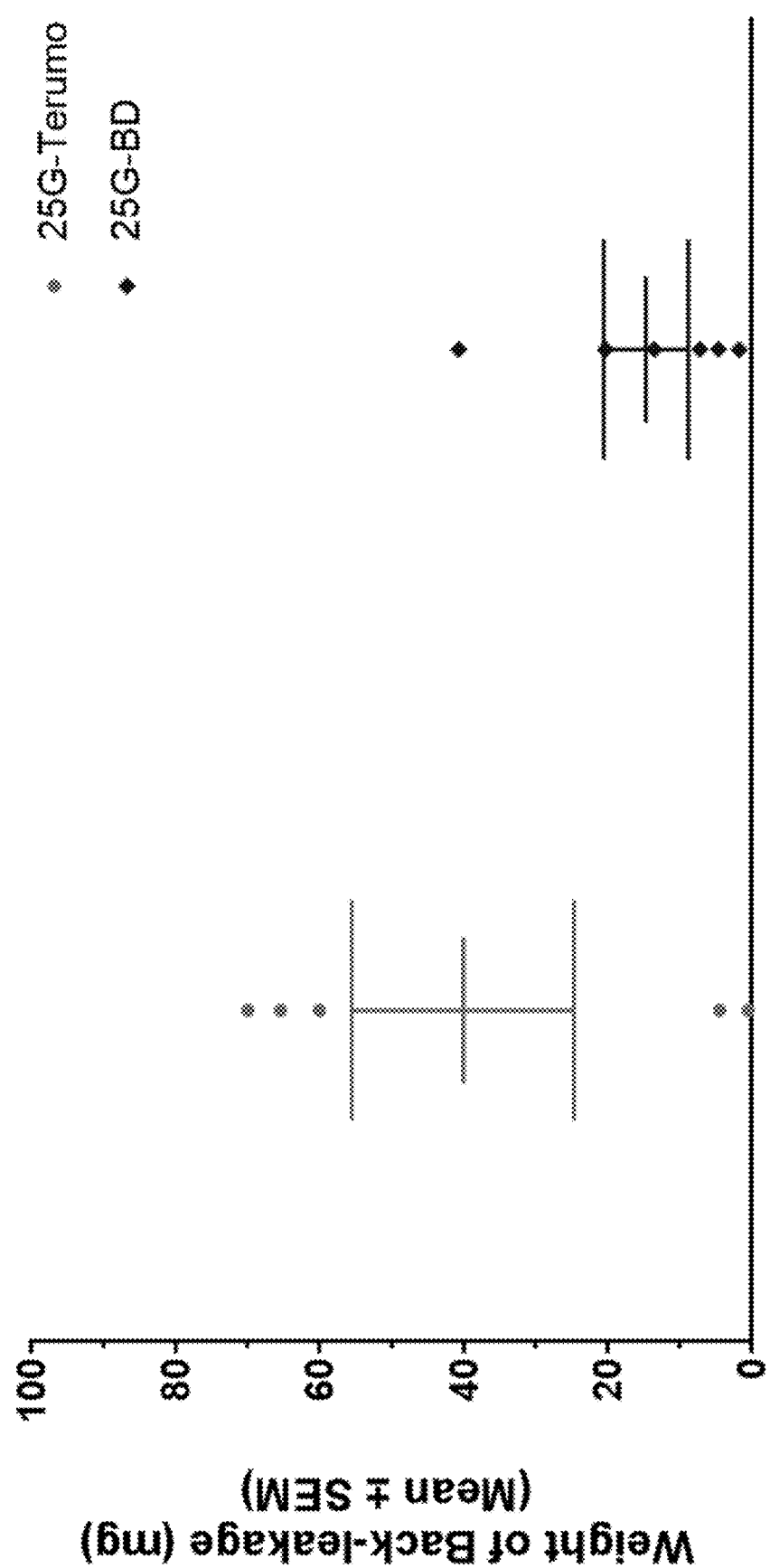

FIG. 172 is a graph of individual animal back leakage data (mean±SEM).

FIG. 173 provides an example of how the needle was selected for the human clinical trial in Example 6.

DETAILED DESCRIPTION

Definitions

Unless defined otherwise, all technical and scientific terms used herein have the same meaning as is commonly understood by one of skill in the art to which this invention belongs. All patents and publications referred to herein are incorporated by reference in their entireties.

As used herein, the terms "administer," "administration," or "administering" refer to (1) providing, giving, dosing, and/or prescribing by either a health practitioner or his authorized agent or under his or her direction according to the disclosure, and/or (2) putting into, taking, or consuming by a subject, for example a mammal, including a human, according to the disclosure.

The terms "co-administration," "co-administering," "administered in combination with," "administering in combination with," "simultaneous," and "concurrent," as used herein, encompass administration of two or more active pharmaceutical ingredients to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. In some embodiments, simultaneous administration in separate compositions and administration in a composition in which both agents are present are preferred.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc., which can readily be determined by one of ordinary skill in the art. The term also applies to a dose that will induce a particular response in target cells (e.g., the reduction of platelet adhesion and/or cell migration). The specific dose will vary depending on the subject to whom the dose is to be administered, the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying, or eliminating the onset of symptoms of a disease or condition, slowing, halting, or reversing the progression of a disease or condition, or any combination thereof.

As used herein, the terms "treat," "treatment," and/or "treating" may refer to the management of a disease, disorder, or pathological condition, or symptom thereof with the intent to cure, ameliorate, stabilize, and/or control the disease, disorder, pathological condition, or symptom thereof. Regarding control of the disease, disorder, or pathological condition more specifically, "control" may include the absence of condition progression, as assessed by the response to the methods recited herein, where such response may be complete (e.g., placing the disease in remission) or partial (e.g., lessening or ameliorating any symptoms associated with the condition). As used herein, the terms "prevent," "preventing," and/or "prevention" may refer to reducing the risk of developing a disease, disorder, or pathological condition.

As used herein, a soluble hyaluronidase is a hyaluronidase of form thereof that is not GPI anchored, and that is soluble under physiological conditions and is secreted upon expression. Soluble hyaluronidases include any that, upon expression, are secreted from a cell and exist in soluble form. Human PH20 hyaluronidase does not occur as a soluble hyaluronidase. It is known in the art that removal of all or a part of the GPI anchor results in soluble forms. Such soluble hyaluronidases include, but are not limited to, bacterial soluble hyaluronidases, non-human soluble hyaluronidases, such as bovine PH20 and ovine PH20, human soluble PH20, and variants thereof. Generally soluble forms of PH20 are produced using protein expression systems that facilitate correct N-glycosylation to ensure the polypeptide retains activity, since glycosylation is important for the catalytic activity and stability of hyaluronidases. Such cells include, for example Chinese Hamster Ovary (CHO) cells (e.g., DG44 CHO cells).

As used herein the term 'rHuPH20' refers to the soluble hyaluronidase composition produced upon expression in a mammalian cell, such as a CHO cell, or other cell that effects glycosylation, of nucleic acid encoding residues 36-482 of SEQ ID NO: 1. For expression in cells the encoding nucleic acid is linked to the native (residues 1-35 of SEQ ID NO: 1) or a heterologous signal sequence for trafficking and secretion of the encoded polypeptides. The resulting secreted soluble glycoprotein is a heterogeneous mixture of polypeptides, including polypeptides that terminate at residues 479, 480, 481, and 482, and are composed of residues 36-479, 36-480, 36-481, and 36-482 with reference to SEQ ID NO: 1. Shorter C-terminally truncated forms also may be included, in various abundance. Typically, rHuPH20 is produced in cells that facilitate correct N-glycosylation to retain activity, such as CHO cells (e.g., DG44 CHO cells). In some embodiments, one of the most abundant species is the 446 amino acid polypeptide corresponding to residues 36-481 of SEQ ID NO: 1. Also included are polypeptides that are soluble or secreted upon expression in a mammalian cell and have at least 90%, 91%, 92%, 93%, 94%, 95%, 96%, 97%, 98%, 99%, or more sequence identity with residues 36-482 of SEQ ID NO: 1.

As used herein, "combination therapy" refers to a treatment in which a subject if given two or more therapeutic agents, such as at least two or at least three therapeutic agents, for treating a single disease.

As used herein, "hyaluronidase activity" refers to the ability to enzymatically catalyze the cleavage of hyaluronic acid. The United States Pharmacopeia (USP) XXII assay for hyaluronidase determines hyaluronidase activity indirectly by measuring the amount of higher molecular weight hyaluronic acid, or hyaluronan, (HA) substrate remaining after the enzyme is allowed to react with the HA for 30 min at 37° ° C. (USP XXII-NF XVII (1990) 644-645 United States Pharmacopeia Convention, Inc, Rockville, MD). A Reference Standard solution can be used in an assay to ascertain the relative activity, in units, of any hyaluronidase. In vitro assays to determine the hyaluronidase activity of hyaluronidases, such as PH20, including soluble PH20 and esPH20, are known in the art and described herein. Exemplary assays include the microturbidity assay that measures cleavage of hyaluronic acid by hyaluronidase indirectly by detecting the insoluble precipitate formed when the uncleaved hyaluronic acid binds with serum albumin and the biotinylated-hyaluronic acid assay that measures the cleavage of hyaluronic acid indirectly by detecting the remaining biotinylated-hyaluronic acid non-covalently bound to microtiter plate wells with a streptavidin-horseradish peroxidase conjugate and a chromogenic substrate. Reference Standards can be used, for example, to generate a standard curve to determine the activity in Units of the hyaluronidase being tested.

"Pharmaceutically acceptable carrier" or "pharmaceutically acceptable excipient" or "physiologically compatible" carrier or carrier medium is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

As used herein, "specific activity" refers to Units of activity per mg protein. The milligrams of hyaluronidase is defined by the absorption of a solution of at 280 nm assuming a molar extinction coefficient of approximately 1.7, in units of $M^{-1}$ $cm^{-1}$.

As used herein, "neutral active" refers to the ability of a PH20 polypeptide to enzymatically catalyse the cleavage of hyaluronic acid at neutral pH (e.g., at or about pH 7.0).

As used herein, a "GPI-anchor attachment signal sequence" is a C-terminal sequence of amino acids that directs addition of a preformed GPI-anchor to the polypeptide within the lumen of the ER. GPI-anchor attachment signal sequences are present in the precursor polypeptides of GPI-anchored polypeptides, such as GPI-anchored PH20 polypeptides. The C-terminal GPI-anchor attachment signal sequence typically contains a predominantly hydrophobic region of 8-20 amino acids, preceded by a hydrophilic spacer region of 8-12 amino acids, immediately downstream of the @-site, or site of GPI-anchor attachment. GPI-anchor attachment signal sequences can be identified using methods well known in the art, such as but not limited to, in silico methods and algorithms (see, e.g., Udenfriend et al. (1995) Methods Enzymol. 250:571-582, Eisenhaber et al., (1999) J. Biol. Chem. 292: 741-758, Fankhauser et al., (2005) Bioinformatics 21:1846-1852, Omaetxebarria et al., (2007) Proteomics 7:1951-1960, Pierleoni et al., (2008) BMC Bioinformatics 9:392), including those that are readily available on bioinformatic websites, such as the ExPASy Proteomics tools site (e.g., the World Wide Web site expasy.ch/tools/).

As used herein, "sequence identity" refers to the relatedness between or among polypeptides among nucleic acid molecules. Sequence identity can be assessed by aligning two sequences and counting the number of differences between the aligned portion and the sequence to which it is compared. Whether any two molecules have nucleotide sequences or amino acid sequences that are at least 60%, 70%, 80%, 85%, 90%, 95%, 96%, 97%, 98% or 99% "identical" or "homologous" can be determined using known computer algorithms such as the "FASTA" program, using for example, the default parameters as in Pearson et al. (1988) Proc. Natl. Acad. Sci. USA 85:2444 (other programs include the GCG program package (Devereux, J., et al., Nucleic Acids Research 12(I):387 (1984)), BLASTP, BLASTN, FASTA (Altschul, S. F., et al., J Mol Biol 215:403 (1990)); Guide to Huge Computers, Martin J. Bishop, ed., Academic Press, San Diego, 1994, and Carrillo et al. (1988) SIAM J Applied Math 48:1073). For example, the BLAST function of the National Center for Biotechnology Information database can be used to determine identity. Other commercially or publicly available programs include, DNAStar "MegAlign" program (Madison, WI) and the University of Wisconsin Genetics Computer Group (UWG) "Gap" program (Madison WI). Percent homology or identity of proteins and/or nucleic acid molecules can be determined, for example, by comparing sequence information using a GAP computer program (e.g., Needleman et al. (1970) J. Mol. Biol. 48:443, as revised by Smith and Waterman ((1981) Adv. Appl. Math. 2:482). Briefly, the GAP program defines similarity as the number of aligned symbols (i.e., nucleotides or amino acids), which are similar, divided by the total number of symbols in the shorter of the two sequences. Default parameters for the GAP program can include: (1) a unary comparison matrix (containing a value of 1 for identities and 0 for non identities) and the weighted comparison matrix of Gribskov et al. (1986) Nucl. Acids Res. 14:6745, as described by Schwartz and Dayhoff, eds., ATLAS OF PROTEIN SEQUENCE AND STRUCTURE, National Biomedical Research Foundation, pp. 353 358 (1979); (2) a penalty of 3.0 for each gap and an additional 0.10 penalty for each symbol in each gap; and (3) no penalty for end gaps.

Therefore, as used herein, the term "identity" or "homology" represents a comparison between a test and a reference polypeptide or polynucleotide.

As used herein, the term at least "90% identical to" refers to percent identities from 90 to 99.99 relative to the reference nucleic acid or amino acid sequence of the polypeptide. Identity at a level of 90% or more is indicative of the fact that, assuming for exemplification purposes a test and reference polypeptide length of 100 amino acids are compared. No more than 10% (i.e., 10 out of 100) of the amino acids in the test polypeptide differs from that of the reference polypeptide. Similar comparisons can be made between test and reference polynucleotides. Such differences can be represented as point mutations randomly distributed over the entire length of a polypeptide or they can be clustered in one or more locations of varying length up to the maximum allowable, e.g., $^{10}/_{100}$ amino acid difference (approximately 90% identity). Differences are defined as nucleic acid or amino acid substitutions, insertions or deletions. At the level of homologies or identities above about 85-90%, the result should be independent of the program and gap parameters set; such high levels of identity can be assessed readily, often by manual alignment without relying on software.

As used herein, an "aligned sequence" refers to the use of homology (similarity and/or identity) to align corresponding positions in a sequence of nucleotides or amino acids. Typically, two or more sequences that are related by 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

As used herein, "denaturing condition" or "denaturation condition" refers to any condition or agent that, when exposed to a protein, affects or influences the degradation or denaturation of the protein, generally as a result of a loss or partial loss of the tertiary or secondary structure of the protein. Denaturing conditions can result in effects such as loss or reduction in activity, loss or reduction of solubility, aggregation and/or crystallization.

As used herein, "resistance to a denaturation condition" refers to any amount of decreased reduction or elimination of a property or activity of the protein associated with or caused by denaturation. For example, denaturation is associated with or causes increased crystallization or aggregation, reduced solubility or decreased activity. Hence, resistance to denaturation means that the protein exhibits decreased aggregation or crystallization, increased solubility or increased or greater activity (e.g., hyaluronidase activity) when exposed to a denaturing condition compared to a reference protein (e.g., unmodified enzyme).

As used herein, "stability of a modified PH20 hyaluronidase" means that it exhibits resistance to denaturation caused by a denaturation condition or denaturing agent.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, from 0% to 10%, from 0% to 5%, or the like, of the stated number or numerical range.

As used herein, the term "about" means that amounts, sizes, formulations, parameters, shapes and other quantities and characteristics are not, and need not be exact, but may be approximate and/or larger or smaller, as desired, reflecting tolerances, conversion factors, rounding off, measurement error and the like, and other factors known to those of skill in the art. In general, an amount, size, formulation, parameter, shape or other quantity or characteristic is "about" or "approximate" whether or not expressly stated to be such. The term "about" generally refers to a particular numeric value that is within an acceptable error range as determined by one of ordinary skill in the art, which will depend in part on how the numeric value is measured or determined, i.e., the limitations of the measurement system. For example, "about" can mean a range of +20%, +10%, or +5% of a given numeric value.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step, or material. The term "consisting of" excludes any element, step or material other than those specified in the claim and, in the latter instance, impurities ordinarily associated with the specified material(s). The term "consisting essentially of" limits the scope of a claim to the specified elements, steps, or material(s) and those that do not materially affect the basic and novel characteristic(s) of the claimed invention. All compounds, compositions, formulations, and methods described herein that embody the present invention can, in alternate embodiments, be more specifically defined by any of the transitional terms "comprising," "consisting essentially of," and "consisting of." The term "comprising" (and related terms such as "comprise" or "comprises" or "having" or "including") includes those embodiments such as, for example, an embodiment of any composition of matter, method, or process that "consist of" or "consist essentially of" the described features.

The present disclosure generally relates to automatic or manual triggering devices that are used in the delivery of high volumes of injectable fluid, such as medicament, (e.g., 2 ml, 3 ml, 5 ml, 10 ml or higher doses) for sub skin surface penetration (e.g., subcutaneous and intramuscular injections). Devices that deliver high volumes of medicament are prone to configuration restrictions as the delivery volume of the medicament increases, such as spring force limitations and syringe container breakage. Due to the current configurations of overall device design, and the limitations of the biological uptake factors that limit injection speed and volume, injection devices would be held for long durations, and often result in other delivery methods being used such as on-body delivery systems which are attached to the patient during delivery.

Increasingly, more biologics are allowing for at-home administration for patients. However, for many biologics, high doses and the resulting high volume of medicament that must be delivered often precludes self-administration because of the length of time required to hold the delivery device in place. Protein hyper-concentration can be used to reduce injection volume, but the resulting medicament often has a much higher viscosity than the traditional biologics. High powered injectors may allow delivery of these hyper-concentrated proteins. However, typical handheld injector designs only allow for up to 2.25 mL of a viscous medicament to be injected in 30 seconds.

With the development of enzymes which locally degrade hyaluronan (HA) in the subcutaneous (SC) space, thereby temporarily removing a barrier to fluid flow, the traditional limitations of biological uptake factors that limit injection speed and volume may be reduced. As such, higher volumes of viscous medicaments may be delivered. Accordingly, there is a need to provide a handheld device capable of delivering a high dose (e.g., 3 mL, 5 mL, 10 mL, 20 mL and up to 50 mL) of a viscous medicament in a delivery time appropriate for a handheld device.

Drug delivery technology of high doses of a viscous medicament is currently based on the proprietary recombinant human hyaluronidase PH20 enzyme (e.g., rHuPH20; Halozyme, Inc.) that facilitates SC delivery of co-administered therapeutics. rHuPH20 works by degrading the HA, thus decreasing the resistance to bulk fluid flow in the SC space, and permitting high volume SC drug delivery, dispersion, and absorption. Co-administration of rHuPH20 with injectable therapies can overcome administration time and volume barriers associated with existing SC therapeutic formulations and has been shown to reduce the burden on patients and healthcare providers compared with intravenous formulations. rHuPH20 has countless applications in the current field of injectable therapies by increasing the dispersion and absorption of other injected drugs, such as anticancer therapies (e.g., trastuzumab and rituximab), immunodeficiency treatment, in subcutaneous urography for improving resorption of radiopaque agents, and fluid delivery for rehydration.

Button actuated auto-injector or injector

Referring to the drawings in detail, wherein like reference numerals indicate like elements throughout, there is shown in FIGS. 154-170 a button actuated auto-injector or injector, generally designated 10, in accordance with a first exemplary embodiment of the present invention.

Referring to FIG. 154, an injector 10 as described below in more detail. The injector 10 may have a button 24, a latch 34, a spring 42, a ram 38, a housing 12, a container support 46, a stopper 18, a primary container 14, a flange 20 and a plug 54.

Referring to FIG. 155, an injector 10 is shown having a housing 12 configured for allowing a user to grip or handle the injector 10. The housing 12 may be shaped to fit into a user's hand for single-handed function. The housing 12 may have a generally oval cross-section to help position the injector 10 in the user's hand. The housing 12 may further include a ridge extending along a longitudinal axis L of the housing (as shown in FIG. 155) to help align or position the injector 10 in the user's hand. The housing 12 may substantially house the components shown in FIGS. 156-160B.

A primary container 14 containing an injectable fluid may be at least partially retained within the housing 12. As used herein, the fluid may comprise medicaments, drugs, biologics, solutions, gels, suspensions or other substances that may be delivered via a syringe or needle, and such terms may be used interchangeably as appearing in the specification and claims. The primary container 14 may be a prefilled syringe. In one embodiment, the primary container 14 is one of a prefilled cartridge, prefilled staked needle syringe, vial, or other injectable fluid containing vessel. The primary container 14 has a distal portion and a proximal portion opposite the distal portion. The primary container 14 may comprise a container portion 16 defining a fluid chamber containing a medicament. In one embodiment, the container portion 16 of the primary container 14 has a maximum volume of approximately 5 mL. In one embodiment, the container portion 16 of the primary container 14 has a maximum volume selected from approximately: 3 mL, 3.5 mL, 4 mL, 4.5 mL, 5.5 mL, 6 mL, 6.5 mL, 7 mL, 7.5 mL, 8 mL, 8.5 mL, 9 mL, 9.5 mL, 10 mL, 10.5 mL, 11 mL, 11.5 mL, 12 mL, 12.5 mL, 13 mL, 13.5 mL, 14 mL, 14.5 mL, 15 mL, 15.5 mL, 16 mL, 16.5 mL, 17 mL, 17.5 mL, 18 mL, 18.5 mL, 19 mL, 19.5 mL, 20 mL, 25 mL, 30 mL, 35 mL, 40 mL, 45 mL, and 50 mL.

As shown in FIG. 156, the primary container 14 may further comprise a stopper 18 movable within the fluid chamber relative to the primary container 14. Prior to use or triggering of the injector 10, the stopper 18 may be disposed at a distal end of the container portion 16. The stopper 18 may be a plunger that seals the medicament in the container portion 16. The stopper 18 may be made of a rubber material. In one embodiment, the stopper 18 is made of a plastic. In one embodiment, the stopper 18 is made of butyl rubber, polyisoprene, polytetrafluorethylene, high density polyethylene or other thermoset elastomers. As shown in FIGS. 155 and 156, a flange 20 may extent outwardly from the distal portion of the primary container 14. In one embodiment, the flange 20 is a Luer. In one embodiment, the flange 20 is a Luer-Lock. In another embodiment, the flange 20 may be couplable to a needle 19 in fluid communication with the medicament in the container portion 16. In some embodiments, the needle 19 may be a regular walled needle. In some embodiments, the needle 19 may be a thin walled needle. The needle 19 may be a 21-30 gauge needle. In one embodiment, the flange 20 may be couplable to a tubing set 21 (as shown in FIG. 166) in fluid communication with the medicament in the container portion 16. In one embodiment, as shown in FIGS. 167A and 167B a staked needle 27 is pre-attached and extending from the distal portion of the primary container 14. In one embodiment, a double-hub pen needle is attached to a drug cartridge with the needle piercing the septum of the cartridge to deliver the fluid. In one embodiment, the primary container bearing a septum is inserted into a stationary needle hub.

The needle 19 may be a 20 gauge needle, the needle 19 may be a 21 gauge needle, the needle 19 may be a 22 gauge needle, the needle 19 may be a 23 gauge needle, the needle 19 may be a 24 gauge needle, the needle 19 may be a 25 gauge needle, the needle 19 may be a 26 gauge needle, the needle 19 may be a 27 gauge needle, the needle 19 may be a 28 gauge needle, the needle 19 may be a 29 gauge needle, the needle 19 may be a 30 gauge needle, the needle 19 may be a 31 gauge needle.

The needle 19 may have a length selected from:
a) 1/8", 3/16", 1/4", 5/16, 3/8", 7/16", 1/2", 9/16", 5/8", 11/16", 3/4", 13/16", 7/8", 15/16", 1", 1 1/8", 1 3/16", 1 1/4", 1 5/16, 1 3/8", 1 7/16", 1 1/2".

The housing 12 may house at least a portion of the primary container 14. In one embodiment, the housing 12 only houses a proximal portion of the primary container 14. In one embodiment, the housing 12 may house the entire primary container 14. The portion of the housing 12 that receives the primary container 14 may have a shape generally the same as a proximal portion of the primary container 14 to prevent rotation of the primary container 14 relative to the housing 12. The primary container 14 may be prevented from moving relative to the housing 12 as described below in more detail.

The primary container 14 may be selected from:
a) a luer fit cyclic olefin copolymer (COC) syringe, a glass staked needle syringe, a polymer staked needle syringe, and a glass cartridge syringe.

The primary container 14 may be sized and shaped to hold a volume corresponding to a volume selected from:
a) 3 mL to 5 mL, 3 mL to 10 mL, 3 mL to 15 mL, 3 mL to 20 mL, 3 mL to 25 mL, 3 ml to 30 mL, 3 mL to 35 mL, 3 mL to 40 mL, 3 mL to 45 mL, 3 mL to 50 mL, 5 mL to 10 mL, 5 mL to 15 mL, 5 mL to 20 mL, 5 mL to 25 mL, 5 mL to 30 mL, 5 mL to 35 mL, 5 mL to 40 mL; 5 mL to 45 mL, 5 mL to 50 mL, 10 mL to 15 mL; 10 mL to 20 mL; 10 mL to 25 mL; 10 mL to 30 mL; 10 mL to 35 mL; 10 mL to 40 mL, 10 mL to 50 mL;
b) about 3 mL to about 5 mL, about 3 mL to about 10 mL, about 3 mL to about 15 mL, about 3 mL to about 20 mL, about 3 mL to about 25 mL, about 3 ml to about 30 mL, about 3 mL to about 35 mL, about 3 mL to about 40 mL, about 3 mL to about 45 mL, about 3 mL to about 50 mL, about 5 mL to about 10 mL, about 5 mL to about 15 mL, about 5 mL to about 20 mL, about 5 mL to about 25 mL, about 5 mL to about 30 mL, about 5 mL to about 35 mL, about 5 mL to about 40 mL; about 5 mL to about 45 mL, about 5 mL to about 50 mL, about 10 mL to about 15 mL; about 10 mL to about 20 mL; about 10 mL to about 25 mL; about 10 mL to about 30 mL; about 10 mL to about 35 mL; about 10 mL to about 40 mL, about 10 mL to about 50 mL;
c) at least about 3 mL, at least about 3.5 mL, at least about 4 mL, at least about 4.5 mL, at least about 5.5 mL, at least about 6 mL, at least about 6.5 mL, at least about 7 mL, at least about 7.5 mL, at least about 8 mL, at least about 8.5 mL, at least about 9 mL, at least about 9.5 mL, at least about 10 mL, at least about 10.5 mL, at least about 11 mL, at least about 11.5 mL, at least about 12 mL, at least about 12.5 mL, at least about 13 mL, at least about 13.5 mL, at least about 14 mL, at least about 14.5 mL, at least about 15 mL, at least about 15.5 mL, at least about 16 mL, at least about 16.5 mL, at least about 17 mL, at least about 17.5 mL, at least about 18 mL, at least about 18.5 mL, at least about 19 mL, at least about 19.5 mL, at least about 20 mL, at least about 25 mL, at least about 30 mL, at least about 35 mL, at least about 40 mL, at least about 45 mL, at least about 50 mL; and
d) at least 3 mL, at least 3.5 mL, at least 4 mL, at least 4.5 mL, at least 5.5 mL, at least 6 mL, at least 6.5 mL, at least 7 mL, at least 7.5 mL, at least 8 mL, at least 8.5 mL, at least 9 mL, at least 9.5 mL, at least 10 mL, at least 10.5 mL, at least 11 mL, at least 11.5 mL, at least 12 mL, at least 12.5 mL, at least 13 mL, at least 13.5 mL, at least 14 mL, at least 14.5 mL, at least 15 mL, at least 15.5 mL, at least 16 mL, at least 16.5 mL, at least 17 mL, at least 17.5 mL, at least 18 mL, at least 18.5 mL, at least 19 mL, at least 19.5 mL, at least 20 mL, at least 25 mL, at least 30 mL, at least 35 mL, at least 40 mL, at least 45 mL, at least 50 mL.

The injector 10 may be configured to deliver the entire amount or a portion of the predetermined amount of the medicament within primary container 14. The predetermined amount of the medicament may correspond with the volume contained in the primary container 14. In one embodiment, the injector 10 may expel an initial portion of the volume (priming volume) followed by a second step to expel the remaining portion of the volume (deliverable volume). In one embodiment, the medicament contained in the primary container 14 corresponds to a volume selected from:
  a) 3 mL to 5 mL, 3 mL to 10 mL, 3 mL to 15 mL, 3 mL to 20 mL, 3 mL to 25 mL, 3 ml to 30 mL, 3 mL to 35 mL, 3 mL to 40 mL, 3 mL to 45 mL, 3 mL to 50 mL, 5 mL to 10 mL, 5 mL to 15 mL, 5 mL to 20 mL, 5 mL to 25 mL, 5 mL to 30 mL, 5 mL to 35 mL, 5 mL to 40 mL; 5 mL to 45 mL, 5 mL to 50 mL, 10 mL to 15 mL; 10 mL to 20 mL; 10 mL to 25 mL; 10 mL to 30 mL; 10 mL to 35 mL; 10 mL to 40 mL, 10 mL to 50 mL;
  b) about 3 mL to about 5 mL, about 3 mL to about 10 mL, about 3 mL to about 15 mL, about 3 mL to about 20 mL, about 3 mL to about 25 mL, about 3 ml to about 30 mL, about 3 mL to about 35 mL, about 3 mL to about 40 mL, about 3 mL to about 45 mL, about 3 mL to about 50 mL, about 5 mL to about 10 mL, about 5 mL to about 15 mL, about 5 mL to about 20 mL, about 5 mL to about 25 mL, about 5 mL to about 30 mL, about 5 mL to about 35 mL, about 5 mL to about 40 mL; about 5 mL to about 45 mL, about 5 mL to about 50 mL, about 10 mL to about 15 mL; about 10 mL to about 20 mL; about 10 mL to about 25 mL; about 10 mL to about 30 mL; about 10 mL to about 35 mL; about 10 mL to about 40 mL, about 10 mL to about 50 mL;
  c) at least about 3 mL, at least about 3.5 mL, at least about 4 mL, at least about 4.5 mL, at least about 5.5 mL, at least about 6 mL, at least about 6.5 mL, at least about 7 mL, at least about 7.5 mL, at least about 8 mL, at least about 8.5 mL, at least about 9 mL, at least about 9.5 mL, at least about 10 mL, at least about 10.5 mL, at least about 11 mL, at least about 11.5 mL, at least about 12 mL, at least about 12.5 mL, at least about 13 mL, at least about 13.5 mL, at least about 14 mL, at least about 14.5 mL, at least about 15 mL, at least about 15.5 mL, at least about 16 mL, at least about 16.5 mL, at least about 17 mL, at least about 17.5 mL, at least about 18 mL, at least about 18.5 mL, at least about 19 mL, at least about 19.5 mL, at least about 20 mL, at least about 25 mL, at least about 30 mL, at least about 35 mL, at least about 40 mL, at least about 45 mL, at least about 50 mL; and
  d) at least 3 mL, at least 3.5 mL, at least 4 mL, at least 4.5 mL, at least 5.5 mL, at least 6 mL, at least 6.5 mL, at least 7 mL, at least 7.5 mL, at least 8 mL, at least 8.5 mL, at least 9 mL, at least 9.5 mL, at least 10 mL, at least 10.5 mL, at least 11 mL, at least 11.5 mL, at least 12 mL, at least 12.5 mL, at least 13 mL, at least 13.5 mL, at least 14 mL, at least 14.5 mL, at least 15 mL, at least 15.5 mL, at least 16 mL, at least 16.5 mL, at least 17 mL, at least 17.5 mL, at least 18 mL, at least 18.5 mL, at least 19 mL, at least 19.5 mL, at least 20 mL, at least 25 mL, at least 30 mL, at least 35 mL, at least 40 mL, at least 45 mL, at least 50 mL.

Flow rate of the injector 10 is heavily dependent on the viscosity and volume of the medicament. However, the injector 10 may deliver the full volume of the medicament at a rate of approximately 0.08-0.75 mL/sec. For example, this would provide target delivery rate ranges of 13-120 seconds for a 10 mL dose volume. The injector 10 may deliver 10 mL of the medicament at a rate of 0.33 mL/sec. In one embodiment, the injector 10 delivers the full deliverable volume of the medicament at a rate of:
  a) 0.5 mL/10 sec., 0.75 mL/10 sec., 1 mL/10 sec., 1.25 mL/10 sec., 1.5 mL/10 sec., 1.75 mL/10 sec, 2 mL/10 sec., 2.25 mL/10 sec, 2.5 mL/10 sec., 2.75 mL/10 sec, 3 mL/10 sec., 3.25 mL/10 sec, 3.5 mL/10 sec., 3.75 mL/10 sec, 4 mL/10 sec., 4.25 mL/10 sec, 4.5 mL/10 sec., 4.75 mL/10 sec, 5 mL/10 sec; b) 2 mL/30 sec., 2.5 mL/30 sec., 3 mL/30 sec., 3.5 mL/30 sec., 4 mL/30 sec., 4.5 mL/30 sec., 5 mL/30 sec., 5.5 mL/30 sec., 6 mL/30 sec., 6.5 mL/30 sec., 7 mL/30 sec., 7.5 mL/30 sec., 8 mL/30 sec., 8.5 mL/30 sec., 9 mL/30 sec., 9.5 mL/30 sec., 10 mL/30 sec., 10.5 mL/30 sec.; and
  c) 4 mL/min, 5 mL/min, 6 mL/min, 7 mL/min, 8 mL/min, 9 mL/min, 10 mL/min, 11 mL/min, 12 mL/min, 13 mL/min, 14 mL/min, 15 mL/min, 16 mL/min, 17 mL/min, 18 mL/min, 19 mL/min, 20 mL/min, 21 mL/min.

In one embodiment, the viscosity of the medicament may be selected from:
  a) 5 centipoise (cP), 6 cP, 7 cP, 8 cP, 9 cP, 10 cP, 11 cP, 12 cP, 13 cP, 14 cP, 15 cP, 16 cP, 17 cP, 18 cP, 19 cP, 20 cP, 21 cP, 22 cP, 23 cP, 24 cP, 25 cP, 26 cP, 27 cP, 28 cP, 29 cP, 30;
  b) about 5 cP to about 7 cP, about 5 cP to about 9 cP, about 5 cP to about 11 cP, about 5 cP to about 13 cP, about 5 cP to about 15 cP, about 5 cP to about 17 cP, about 5 cP to about 19 cP, about 5 cP to about 21 cP, about 5 cP to about 23 cP, about 5 cP to about 25 cP, about 5 cP to about 27 cP, about 5 cP to about 29 cP, about 10 cP to about 15 cP, about 10 cP to about 20 cP, about 10 cP to about 25 cP, about 10 cP to about 30 cP,
  c) at least about 5 cP, at least about 6 cP, at least about 7 cP, at least about 8 cP, at least about 9 cP, at least about 10 cP, at least about 11 cP, at least about 12 cP, at least about 13 cP, at least about 14 cP, at least about 15 cP, at least about 16 cP, at least about 17 cP, at least about 18 cP, at least about 19 cP, at least about 20 cP, at least about 21 cP, at least about 22 cP, at least about 23 cP, at least about 24 cP, at least about 25 cP, at least about 26 cP, at least about 27 cP, at least about 28 cP, at least about 29 cP, at least about 30; and
  d) at least about 5 cP, at least 6 cP, at least 7 cP, at least 8 cP, at least 9 cP, at least 10 cP, at least 11 cP, at least 12 cP, at least 13 cP, at least 14 cP, at least 15 cP, at least 16 cP, at least 17 cP, at least 18 cP, at least 19 cP, at least 20 cP, at least 21 cP, at least 22 cP, at least 23 cP, at least 24 cP, at least 25 cP, at least 26 cP, at least 27 cP, at least 28 cP, at least 29 cP, at least 30.

The user's experience may be improved if the injector 10 can deliver the full volume of the medicament as fast as possible. A faster delivery may result in less pain and discomfort for the patient. The injector 10 may deliver the full deliverable volume of the medicament in 5 seconds. The injector 10 may deliver the full deliverable volume of the medicament in 10 seconds. The injector 10 may deliver the full deliverable volume of the medicament in 15 seconds. The injector 10 may deliver the full deliverable volume of the medicament in 20 seconds. The injector 10 may deliver the full deliverable volume of the medicament in 25 seconds. The injector 10 may deliver the full deliverable volume of the medicament in 30 seconds. The injector 10 may deliver the full deliverable volume of the medicament in 35 seconds. The injector 10 may deliver the full deliverable volume of the medicament in 40 seconds. The injector 10 may deliver the full deliverable volume of the medicament in 45 seconds. The injector 10 may deliver the full deliverable volume of the medicament in 50 seconds. The injector 10 may deliver the full deliverable volume of the medicament in 55 seconds. The injector 10 may deliver the full deliverable volume of the medicament in 60 seconds. The injector 10 may deliver the full deliverable volume of the medicament in 70 seconds. The injector 10 may deliver the full deliverable volume of the medicament in 80 seconds. The injector 10 may deliver the full deliverable volume of the medicament in 90 seconds. The injector 10 may deliver the full deliverable volume of the medicament in 100 seconds. The injector 10 may deliver the full deliverable volume of the medicament in 110 seconds. The injector 10 may deliver the full deliverable volume of the medicament in 120 seconds.

Any number of indicia may be displayed on the injector 10. For example, a symbol 23 (as shown in FIG. 155) may be displayed on the housing 12 or an indicator regarding the status of the injector 10 may be displayed on a button 24 (as shown in FIG. 155). Referring to FIGS. 155 and 161, the housing 12 may include a cutout 13 extending therethrough to allow an indicator on the button 24 disposed within the housing 12 to be viewed. The cutout 13 may be located at a proximal portion of the housing 12. The cutout 13 may be a generally oval shape. The cutout 13 may expose a portion of the button 24 containing an indicia. The button 24 may be at least partially received within the proximal portion of the housing 12. The button 24 may include a lock indicator 15 thereon for indicating a lock status of the button and/or for indicating the injector 10 is in a locked configuration. The lock indicator 15 may be engraved, etched, printed or molded in the button 24. In one embodiment, the lock indicator 15 is a decal fixed to the button 24 with an adhesive. In one embodiment, the lock indicator 15 is applied onto the button 24 via spray painting, powder coating, silk screen, laser marking, pad printing, or heat staking. The lock indicator 15 may be a graphic of a lock signifying that the injector 10 is in the locked configuration. The lock indicator 15 may be any combination of shapes and/or words.

The button 24 may further include a rotation indicator 17 for indicating a direction the button 24 is movable about the longitudinal axis L. The rotation indicator 17 may be engraved in the button 24. In one embodiment, the rotation indicator 17 is a decal fixed to the button 24 with an adhesive. In one embodiment, the rotation indicator 17 is applied onto the button 24 via spray painting, powder coating, silk screen, laser marking, pad printing, or heat staking. The rotation indicator 17 may be an arrow signifying the direction the button 24 must be rotated relative to the housing 12 to transition from a locked configuration to an unlocked configuration. The rotation indicator 17 may be any combination of shapes and/or words. In one embodiment, the button contains an indication for partial dosing of the medicament, such as priming volume in the location of the lock indicator 15. The partial dosing indicator may be engraved, etched, printed or molded in the button 24. In one embodiment, the partial dosing indicator is a decal fixed to the button 24 with an adhesive. In one embodiment, the partial dosing indicator is applied onto the button 24 via spray painting, powder coating, silk screen, laser marking, pad printing, or heat staking.

To expel the medicament from the primary container 14, the injector 10 undergoes a series of sequential movements that results in a triggering event. The triggering event is initiated by a user moving the button 24 relative to the housing 12. Referring to FIGS. 156-160B, the injector 10 may further comprise a trigger mechanism 22. The trigger mechanism 22 may comprise the button 24, latch 34, ram 38 and spring 42 located at the proximal portion of the housing 12. The button 24 may be rotatably coupled to the housing 12 about a longitudinal axis L thereof. The button 24 may be rotatable between the unlocked configuration and the locked configuration, which may be indicated to the user by an indicia visible through the cutout 13. Rotation of the button 24 between the locked configuration and the unlocked configuration may not breach a sterile barrier of the primary container 14. This may allow the user to rotate the button 24 back to the locked configuration for use at a later time.

In the locked configuration, the button 24 may be prevented from moving distally along the longitudinal axis L of the housing 12 by a rim along an inner surface of the housing 12. In certain applications (i.e., lab testing), it may be necessary to remove the button 24. In one embodiment, the button 24 may be moved proximally along the longitudinal axis L of the housing 12. The button 24 may include a passthrough hole 59 extending through a proximal end thereof that allows for disassembly using appropriate equipment. In one embodiment, the button 24 is removable by inserting a disassembly tool (not shown) into the passthrough hole 59, thereby releasing the button 24 from the rim. In the unlocked configuration, the button 24 may be movable distally along the longitudinal axis L of the housing 12 to initiate a triggering event. The button 24 may be a generally cylindrical shape. A proximal end of the button 24 may be closed and a distal end of the button 24 may be open. The button 24 may have an internal cavity 28 defined therein. The button 24 may be the only feature of the injector 10 that is moveable relative to the housing 12 prior to the triggering event. An outer surface of the button 24 may have one or more ridges extending along a length thereof. In one embodiment, rotation of the button 24 to the unlocked position causes the device to expel the priming volume.

Referring to FIGS. 156-160B, the button 24 may comprise a barrel 26 extending distally from the proximal end within the internal cavity 28. The barrel 26 may have a proximal side and a distal side thereof. The barrel 26 may include a depression 30 extending radially inward on the barrel 26. The barrel 26 may be a generally cylindrical shape at the distal side. The barrel 26 may be a non-uniform generally cylindrical shape at the proximal side. The barrel 26 may have a radius less than a radius of the button 24. The radius of the barrel 26 may be one third the radius of the button 24. The barrel 26 may have a radius 0.1 to 0.5 inches. The depression 30 may be located on the proximal side of the barrel 26. In one embodiment, the barrel 26 includes two depressions 30 on opposite sides of the barrel 26 from each other. The distal side of the barrel 26 may have a smaller diameter than the proximal side of the barrel 26. The barrel 26 may extend distally only a portion of a length of the button 24. In one embodiment, the barrel 26 extends distally substantially along a length of the button 24.

Referring to FIGS. 160A-160B, the trigger mechanism 22 may further comprise a latch 34 for facilitating the triggering event. The latch 34 may have a proximal end and a distal end thereof. The latch 34 may have a generally cylindrical shape. The latch 34 may be disposed within the housing 12. The latch 34 may be fixed to the housing 12. The proximal end of the latch 34 may be disposed within the button 24.

The latch 34 may further comprise a latch arm 32. The latch arm 32 may extend distally along the longitudinal axis L from a proximal end of the latch 34. The latch arm 32 may be coupled to the latch 34. The latch arm 32 may be biased in an inward radial direction. The latch arm 32 may be prevented from deflecting in the inward radial direction by the barrel 26 prior to the triggering event. The latch arm 32 may include a protrusion 36. The protrusion 36 may extend radially outwardly from the latch arm 32. The depression 30 may be configured to align with the latch arm 32 in the unlocked configuration. When the button 24 is moved distally a predetermined distance along the longitudinal axis L in the unlocked configuration, the latch arm 32 may be received in the depression 30. In one embodiment, the latch arm 32 comprises two diametrically opposed latches.

Referring to FIGS. 156-160B, the trigger mechanism 22 may further comprise a ram 38. The ram 38 may comprise a proximal side and a distal side opposite the proximal side. The ram 38 may be disposed within the latch 34. The ram 38 may be configured to engage the stopper 18 at the distal side thereof. The ram 38 may be a generally cylindrical shape defining an internal cavity 40 therein. The spring 42 may be disposed in the internal cavity 40. In one embodiment, the spring 42 may be disposed on an outside of the ram 38. The spring 42 may have a proximal end and a distal end opposite the proximal end. The proximal end of the spring 42 may engage a collar 98 of the latch 34. The collar 98 may be a generally cylindrical shape. The collar 98 may be sized such that the barrel 26 is able to pass therethrough. A radius of the collar 98 may be the same as the spring 42 to ensure the collar 98 engages the spring 42. The distal end of spring 42 may engage a ram collar 96 located within the internal cavity 40 at the distal side of the ram 38. During a triggering event, the spring 42 may bias the ram 38 distally along the longitudinal axis L relative to the housing 12. In an exemplary embodiment, spring 42 includes a compression spring, however, other suitable energy source can be used, such as an electric pump, elastomer or compressed-gas spring, a compressed-gas cylinder 43, a gas generator, or other suitable energy storage members. The ram 38 may cause the stopper 18 to move distally along the longitudinal axis L relative to the primary container 14.

In some embodiments, the compressed-gas cylinder 43 (not shown) is used in combination with or in place of spring 42 as an energy source of the injector 10. The compressed-gas cylinder 43 may be disposed in the injector 10 at a proximate end. The compressed-gas cylinder 43 may store energy therein which may be selectively released upon a user's movement of the button 24 distally along the longitudinal axis L relative to the housing 12. A distal end of the compressed-gas cylinder 43 may engage the ram 38 to move the ram 38 relative to the primary container 14 thereby ejecting the medicament. In some embodiments, the compressed-gas cylinder 43 includes a pin 45 movable relative to the compressed-gas cylinder 43 and extendable from a distal end thereof when the injector 10 is actuated. The pin 45 may engage the ram 38 and move the ram 38 distally relative to the housing 12 when the injector 10 is actuated. The compressed-gas cylinder 43 may increase precision of medicament delivery by precisely controlling the force acting on the ram 38. The compressed-gas cylinder 43 may reduce vibration and noise during use compared to alternate embodiments (e.g., spring 42). In some embodiments, an injector 10 using the compressed-gas cylinder 43 has a length smaller along the longitudinal axis L than an injector 10 using an alternate embodiment of an energy source (e.g., spring 42).

Referring to FIGS. 156-160B, the ram 38 may comprise an aperture 44 extending therethrough. The aperture 44 may be located on the proximal side of the ram 38. The ram 38 may be prevented from moving distally relative to the housing 12 by the latch arm 32. The protrusion 36 may engage the aperture 44 to prevent the spring 42 from biasing the ram 38 distally.

Referring to FIGS. 157 and 158, in the unlocked configuration, movement of the button 24 distally along the longitudinal axis L relative to the housing 12 may allow the latch arm 32 to deflect radially inward into the depression 30 of the barrel 26 thereby initiating a triggering event. Radial deflection of the latch arm 32 may disengage the protrusion 36 from the aperture 44. The latch arm 32 disengaging the protrusion 36 may allow the spring 42 to bias the ram 38 distally along the longitudinal axis L relative to the housing 12. The ram 38 may move the stopper 18 distally along the longitudinal axis L relative to the primary container 14 to eject the medicament in a discharged configuration.

Referring to FIGS. 156-160B, the spring 42 may be a compression spring. The spring 42 may have a 5 mm diameter. The spring 42 may have a 6 mm diameter. The spring 42 may have a 7 mm diameter. The spring 42 may have an 8 mm diameter. The spring 42 may have a 9 mm diameter. The spring 42 may have a 10 mm diameter. The spring 42 may have a 11 mm diameter. The spring 42 may have a 12 mm diameter. The spring 42 may have a 13 mm diameter. The spring 42 may have a 14 mm diameter. The spring 42 may have a 15 mm diameter. The spring 42 may have a 0.75 mm wire diameter. The spring 42 may have a 1 mm wire diameter. The spring 42 may have a 1.25 mm wire diameter. The spring 42 may have a 1.5 mm wire diameter. The spring 42 may have a 1.75 mm wire diameter. The spring 42 may have a 2 mm wire diameter.

The spring may produce 8 lbf of force. The spring may produce 9 lbf of force. The spring may produce 10 lbf of force. The spring may produce 11 lbf of force. The spring may produce 12 lbf of force. The spring may produce 13 lbf of force. The spring may produce 14 lbf of force. The spring may produce 15 lbf of force. The spring may produce 16 lbf of force. The spring may produce 17 lbf of force. The spring may produce 18 lbf of force. The spring may produce 19 lbf of force. The spring may produce 20 lbf of force. The spring may produce 21 lbf of force. The spring may produce 22 lbf of force. The spring may produce 23 lbf of force. The spring may produce 24 lbf of force. The spring may produce 25 lbf of force. The spring may produce 26 lbf of force. The spring may produce 27 lbf of force. The spring may produce 28 lbf of force. The spring may produce 29 lbf of force. The spring may produce 30 lbf of force. The spring may produce 31 lbf of force. The spring may produce 32 lbf of force. The spring may produce 33 lbf of force. The spring may produce 34 lbf of force. The spring may produce 35 lbf of force. The spring may produce 36 lbf of force. The spring may produce 37 lbf of force. The spring may produce 38 lbf of force. The spring may produce 39 lbf of force. The spring may produce 40 lbf of force.

The spring 42 may generate up to 15 lbf of force prior to a triggering event. The spring 42 may generate up to 17.5 lbf of force prior to a triggering event. The spring 42 may generate up to 20 lbf of force prior to a triggering event. The spring 42 may generate up to 22.5 lbf of force prior to a triggering event. The spring 42 may generate up to 25 lbf of force prior to a triggering event. The spring 42 may generate up to 27.5 lbf of force prior to a triggering event. The spring 42 may generate up to 30 lbf of force prior to a triggering event. The spring 42 may generate up to 32.5 lbf of force prior to a triggering event. The spring 42 may generate up to 35 lbf of force prior to a triggering event. The spring 42 may generate up to 37.5 lbf of force prior to a triggering event. The spring 42 may generate up to 40 lbf of force prior to a triggering event.

The spring 42 may generate a residual force of 8 lbf of force after expelling the full volume of fluid from the primary container. The spring 42 may generate a residual force of 10 lbf of force after expelling the full volume of fluid from the primary container. The spring 42 may generate a residual force of 12 lbf of force after expelling the full volume of fluid from the primary container. The spring 42 may generate a residual force of 14 lbf of force after expelling the full volume of fluid from the primary container. The spring 42 may generate a residual force of 16 lbf of force after expelling the full volume of fluid from the primary container. The spring 42 may generate a residual force of 18 lbf of force after expelling the full volume of fluid from the primary container. The spring 42 may generate a residual force of 20 lbf of force after expelling the full volume of fluid from the primary container. The spring 42 may generate a residual force of 22 lbf of force after expelling the full volume of fluid from the primary container. The spring 42 may generate a residual force of 24 lbf of force after expelling the full volume of fluid from the primary container. The spring 42 may generate a residual force of 26 lbf of force after expelling the full volume of fluid from the primary container. The spring 42 may generate a residual force of 28 lbf of force after expelling the full volume of fluid from the primary container. The spring 42 may generate a residual force of 30 lbf of force after expelling the full volume of fluid from the primary container. The spring 42 may generate a residual force of 32 lbf of force after expelling the full volume of fluid from the primary container. The spring 42 may generate a residual force of 34 lbf of force after expelling the full volume of fluid from the primary container. The spring 42 may generate a residual force of 36 lbf of force after expelling the full volume of fluid from the primary container. The spring 42 may generate a residual force of 38 lbf of force after expelling the full volume of fluid from the primary container. The spring 42 may generate a residual force of 40 lbf of force after expelling the full volume of fluid from the primary container.

When the primary container 14 may be received in the housing 12, it must be fixed thereto to ensure the medicament is ejected as a result of the triggering event. If the primary container 14 were to rotate or move distally as a result of the triggering event, the consistency of delivery could be compromised. Referring to FIGS. 156-160B, the injector 10 further comprises a container support 46 coupled to the housing 12. The container support 46 may fix the primary container 14 to the housing 12. The container support 46 may prevent the primary container 14 from rotating about the longitudinal axis L relative to the housing 12. The container support 46 may axially support a proximal portion of the primary container 14 such that the distal portion of the primary container 14 is substantially unsupported in the axial direction. The container support 46 may extend distally along the longitudinal axis L to cover at least a portion of the primary container 14. In one embodiment, the container support 46 extends distally along the longitudinal axis L to cover the entire primary container 14. The container support 46 may include a window 66 (as shown in FIGS. 164A-164C and 165) exposing at least a portion of the primary container 14.

Referring to FIGS. 156-160B, the container support 46 comprises an extension 48 that extends proximally along the longitudinal axis L inside the housing 12. The extension 48 may engage a collar 50 at the proximal portion of the primary container 14. In some embodiments, a proximal end of the extension 48 may include a padding, cushion, rib or other feature to dampen the force exerted on the collar 50 during a triggering event to reduce the likelihood of breaking. The extension 48 may cause the collar 50 to engage the distal portion of the latch 34 thereby fixing the primary container 14 relative to the housing 12. The container support 46 may extend substantially around the entire circumference of the collar 50 of the primary container 14. In one embodiment, the container support 46 extends only partially around the circumference of the collar 50 of the primary container 14. The container support 46 may be coupled to the housing 12 through snap-fit coupling. In one embodiment, the container support 46 is threadedly coupled to the housing 12.

Referring to FIGS. 155, 156, and 161, the flange 20 may be a luer lock disposed at the distal end of the primary container 14. The flange 20 may be configured to couple to the needle 19 thereby establishing fluid communication from the primary container 14 to the needle 19. The flange 20 may receive a plug 54. The plug 54 may prevent the medicament from flowing out of the primary container 14. The plug 54 may be removed prior to the needle 19 being coupled to the luer lock. The needle 19 may be threadedly coupled to the flange 20 to establish fluid communication therethrough. In one embodiment shown in FIG. 166, a tubing set 21 is coupled to the flange 20 to establish fluid communication therethrough. In some embodiments, the housing 12 includes a safety cap (not shown) removably coupled to the distal end of the housing 12. The safety cap may include a safety seal in contact with the housing 12 when the safety cap is coupled to the housing 12 to prevent any contaminants (dust, dirt, liquids) from interacting with the needle 19 while the safety cap is coupled to the housing 12. The needle 19 may be exposed when the safety cap is removed.

Friction between the button 24 and the housing 12 may provide adequate resistance to prevent accidental or unintended movement of the button 24. In one embodiment, as shown in FIGS. 168-170, to prevent accidental or unintended movement of the button 24, a button spring 56 is included to bias the button proximally relative to the housing. Referring to FIGS. 156-160B, the button 24 may be at least partially disposed within the housing 12. The button 24 may be biased proximally along the longitudinal axis L relative to the housing 12 by the button spring 56. The button spring 56 may have a proximal end and a distal end thereof. The proximal end of the button spring 56 may engage the button 24. The distal end of the button spring 56 may engage the latch 34. The button spring 56 may produce 1 to 5 lbf of force.

Any time prior to an intended use, the injector 10 is preferably in the locked configuration to prevent an unintended or accidental triggering event. Referring to FIG. 157, an embodiment of the injector 10 of the present disclosure in the locked configuration is shown. In the locked configuration, the button 24 may be prevented from moving along the longitudinal axis L relative to the housing 12. The button 24 may only be rotatable about the longitudinal axis L in the locked configuration. The latch arm 32 may be configured to align with a portion of the button 24 that does not include a depression 30 on a proximal end thereof to ensure a triggering event is not initiated. The button 24 having no depression 30 aligned with the latch arm 32 may further prevent accidental discharge from a drop, misuse, or other handling. The barrel 26 may urge the latch arm 32 in an outward radial direction. In the locked configuration, the protrusion 36 of the latch arm 32 may engage the aperture 44 of the ram 38 to prevent the ram 38 from moving distally along the longitudinal axis L relative to the housing 12. In the locked configuration, the spring 42 may be in a compressed configuration. The spring 42 may be prevented from biasing the ram 38 distally along the longitudinal axis L relative to the housing 12 by the protrusion 36 engaging the aperture 44 of the ram 38.

When the injector 10 is to be used, the injector 10 may be transitioned into an unlocked configuration to enable a triggering event. Referring to FIG. 158, an embodiment of the injector 10 of the present disclosure in the unlocked configuration is shown. The injector 10 may be transitioned from the locked configuration to the unlocked configuration by rotating the button 24 about the longitudinal axis L. Rotation of the button 24 into the unlocked configuration may cause the button 24 to move distally along the longitudinal axis L relative to the housing 12. The button 24 moving distally along the longitudinal axis L relative to the housing 12 may prime the primary container 14 by removing any air in the container portion 16 prior to the triggering event. In the unlocked configuration, the spring 42 may be in the compressed configuration.

Rotation of the button 24 90° about the longitudinal axis L may transition the injector 10 from the locked configuration to the unlocked configuration. Rotation of the button 24 between 0°-89° about the longitudinal axis L may not transition the injector 10 from the locked configuration to the unlocked configuration. In one embodiment, rotation of the button 24 45° about the longitudinal axis L transitions the injector 10 from the locked configuration to the unlocked configuration. In one embodiment, rotation of the button 24 180° about the longitudinal axis L transitions the injector 10 from the locked configuration to the unlocked configuration. In one embodiment, rotation of the button 24 between 90°-180° about the longitudinal axis L transitions the injector 10 from the locked configuration to the unlocked configuration. In one embodiment, rotation of the button 24 between 45°-180° about the longitudinal axis L transitions the injector 10 from the locked configuration to the unlocked configuration.

In the unlocked configuration, the button 24 may be movable proximally along the longitudinal axis L relative to the housing 12. The depression 30 of the barrel 26 may be aligned with the latch arm 32 in the unlocked configuration. When the button 24 is moved proximally a predetermined distance along the longitudinal axis L relative to the housing 12, the latch arm 32 may be allowed to deflect radially inward into the depression 30 initiating the triggering event. The latch arm 32 deflecting radially inward may disengage the protrusion 36 of the latch arm 32 from the aperture 44 of the ram 38. The latch arm 32 disengaging the aperture 44 may allow the spring 42 to bias the ram 38 distally along the longitudinal axis L relative to the housing 12. Distal movement of the ram 38 along the longitudinal axis L relative to the housing 12 may move the stopper 18 through the container portion 16 of the primary container 14 forcing the medicament through the flange 20. The container support 46 engaging the collar 50 of the primary container 14 against the latch 34 may prevent the primary container 14 from moving distally along the longitudinal axis L relative to the housing 12 during the triggering event.

Following a triggering event, the injector 10 may be disabled to prevent a further actuation or trigger events. Referring to FIG. 159, an embodiment of the injector 10 of the present disclosure in a discharged configuration is shown. The button 24 may be fixed relative to the housing 12 in the discharged configuration. The latch arm 32 deflected in the depression 30 may prevent the button spring 56 from biasing the button 24 in a distal direction along the longitudinal axis L relative to the housing 12. During the triggering event, the ram 38 may move distally along the longitudinal axis L relative to the housing 12 such that the ram 38 is disposed entirely within the container portion 16 of the primary container 14 in the discharged configuration. In one embodiment, the ram 38 is partially disposed within the container portion 16 of the primary container 14 in the discharged configuration.

Referring to FIG. 161, an embodiment of the injector 10 of the present disclosure in a discharged configuration is shown. The primary container 14 may be made of a transparent material. The primary container 14 may be made of glass. In one embodiment, the primary container 14 is made of a plastic. In the discharged configuration, the ram 38 may be visible through the primary container 14. The ram 38 and stopper 18 may be visible through the primary container 14.

Referring to FIG. 161, the button 24 may include a trigger indicator 52. The trigger indicator 52 may be engraved in the button 24. The trigger indicator 52 may be a decal fixed to the button 24 with an adhesive. The trigger indicator 52 may be an arrow signifying the direction the button 24 must be moved relative to the housing 12 to initiate the triggering event. The trigger indicator 52 may be any combination of shapes and/or words. When the injector 10 is in the discharged configuration the trigger indicator 52 may be visible in the cutout 13.

Referring to FIG. 161, the container support 46 may include a release mechanism. The release mechanism may allow the user to disassemble the injector 10 to replace and reset any of the components thereof prior to a triggering event. The housing 12 may include an aperture 62 extending therethrough. The container support 46 may include a catch 64 extending radially outward from the extension 48 through the aperture 62 in an engaged configuration. The catch 64 may prevent the container support 46 from moving relative to the housing 12 in the engaged configuration. The catch 64 may allow the container support 46 to move relative to the housing 12 when the catch 64 is urged radially inward into a disengaged configuration. The container support 46 may be moved along the longitudinal axis L in the disengaged configuration. As shown in FIGS. 164A-164C and 165, the container support 46 may be removed and replaced with an alternate container support 46 embodiment. Removal of the container support 46 may allow for replacement of any of the components of the trigger mechanism 22 to accommodate different medicament viscosities and volumes.

FIGS. 160A-160B show an embodiment of the button 24 of the present disclosure. The button 24 may include a wing 58 protruding radially outward therefrom. The wing 58 may be located at a proximal portion of the button 24. The wing 58 may prevent the button 24 from being rotated about the longitudinal axis L beyond a predetermined threshold. An inner surface of the housing 12 may include a bumper 60 (not shown) that engages the wing 58 to prevent the wing 58 from passing therethrough when the button 24 is rotated about the longitudinal axis L. The wing 58 and bumper 60 may align when the injector 10 is in the locked configuration and in the unlocked configuration. When the wing 58 engages the bumper 60 in the unlocked configuration the inner surface of the housing 12 the latch arm 32 may be aligned with the depression 30 of the barrel 26. In one embodiment, there are two wings. In one embodiment, to overcome the bumper 60 and rotate from the locked to unlocked position a maximum torque of 1 in-lbs. to 15 in-lbs. is required.

The bumper 60 may allow the button 24 to be turned about the longitudinal axis L 90° before the wing 58 engages the bumper 60. In one embodiment, the bumper 60 allows the button 24 to be turned about the longitudinal axis L 45° before the wing 58 engages the bumper 60. In one embodiment, the bumper 60 allows the button 24 to be turned about the longitudinal axis L 180° before the wing 58 engages the bumper 60. In one embodiment, the bumper 60 allows the button 24 to be turned from 1°-180° about the longitudinal axis L before the wing 58 engages the bumper 60.

Referring to FIGS. 163A-163C, there is a second embodiment of the injector 10 shown. The injector 10 may be similar to the embodiment of the injector 10 shown in FIGS. 154-161 except that the container support 46 may cover substantially an entire length of the primary container 14. In one embodiment, the container support 46 partially covers the primary container 14.

As shown in FIGS. 163A-163C, the container support 46 may extend from a proximal portion of the housing 12 to the flange 20. The container support 46 may have a thickness generally the same as the housing 12. The container support 46 may include a window 66. The window 66 may be an aperture extending through the container support 46 to expose the primary container 14. The window 66 may be a generally oval shape. The window 66 may extend substantially along the entire length of the container support 46.

Referring to FIGS. 164A-164C, there is a third embodiment of the injector 10 shown. The injector 10 may be similar to the embodiment of the injector 10 shown in FIGS. 163A-163C except that the container support 46 may have a thickness generally the same as the container portion 16 of the primary container 14. In one embodiment, the container support 46 has a thickness that is less than a thickness of the housing 12.

As shown in FIGS. 164A-164C, the container support 46 may extend from a proximal portion of the housing 12 to the flange 20. The container support 46 may have a thickness generally less than the housing 12. The container support 46 may include a window 66. The window 66 may be an aperture extending through the container support 46 to expose the primary container 14. The window 66 may be a generally oval shape. The window 66 may extend substantially along the entire length of the container support 46.

Referring to FIG. 165, there is a fourth embodiment of the injector 10 shown. The injector 10 may be similar to the embodiment of the injector 10 shown in FIGS. 163A-163C except that the container support 46 may have a cap 68 covering the container support 46. The cap 68 may have a thickness that is less than a thickness of the housing 12. In one embodiment, the cap 68 has a thickness that is generally the same as a thickness of a housing 12.

Referring to FIG. 165, there is the cap 68 shown on the injector 10. The cap 68 may be removably coupled to the injector 10. The cap 68 may be a generally cylindrical shape. The cap 68 may have a proximal end and a distal end opposite the proximal end. The proximal end of the cap 68 may define an aperture. The distal end of the cap 68 may be generally flat. A diameter of the flat distal end of the cap 68 may be larger than a diameter of the proximal end of the cap 68. The flat distal end of the cap 68 may allow the injector 10 to stand in a vertical orientation.

The cap 68 may be sized to receive the container support 46 through the aperture at the proximal end. As shown in FIGS. 164A-164C, the container support 46 may include a lip 70 extending radially outward from the container support 46. The lip 70 may extend circumferentially around the container support 46. The lip 70 may only extent partially circumferentially around the container support 46. The lip 70 may be near a proximal end of the container support 46. The lip 70 may engage a cap lip 72 (not shown) on an inner surface of the cap 68 to couple the cap 68 and the container support 46. The cap 68 may cover the flange 20 of the primary container 14 to prevent damage or accidental removal of the plug 54 when the cap 68 is coupled to the container support 46.

Referring to FIG. 166, there is a fifth embodiment of the injector 10 shown. The injector 10 may be similar to the embodiment of the injector 10 shown in FIGS. 154-161 except that the flange 20 may couple to a tubing set 21 for applications where a needle 19 may be insufficient or inappropriate for delivery of the medicament. The plug 54 may be removed prior to the tubing set 21 being coupled to the luer lock. The tubing set 21 may be threadedly coupled to the flange 20 to establish fluid communication therethrough.

Referring to FIGS. 167A-167B, there is a sixth embodiment of the injector 10 shown. The injector 10 may be similar to the embodiment of the injector 10 shown in FIGS. 154-161 except that a staked needle 27 is pre-attached and extending from the distal portion of the primary container 14. The staked needle 27 may be in fluid communication with the primary container 14 containing the medicament.

Referring to FIGS. 168-170, there is a seventh embodiment of the injector 10 shown. The injector 10 may be similar to the embodiment of the injector 10 shown in FIGS. 154-161 except that the button spring 56 is included to bias the button 24 in the proximal direction to prevent an unintended or accidental triggering event. As discussed above in more detail, the button spring 56 may be disposed between the housing 12 and the latch 34, and engage a distal end of the latch 34 to bias the distal end of the button 24 in the proximal direction relative to the housing 12. In the discharged configuration, as shown in FIG. 170, the latch arm 32 may engage the depression 30 to prevent the button spring 56 from biasing the button 24 proximally relative to the housing.

Formulation for High Dose Injection

The present disclosure provides a formulation for a high dose injection comprising a hyaluronidase enzyme. In one embodiment, the formulation is an aqueous formulation. In one embodiment, the formulation comprises one or more pharmaceutically acceptable carriers.

Forms of Soluble Hyaluronidases

Soluble hyaluronidases include any that, upon expression, are secreted from a cell and exist in soluble form. Such soluble hyaluronidases include, for example, but are not limited to, bacterial soluble hyaluronidases, non-human soluble hyaluronidases, such as bovine PH20 and ovine PH20, human soluble PH20, and variants thereof. Generally soluble forms of PH20 are produced using protein expression systems that facilitate correct N-glycosylation to ensure the polypeptide retains activity, since glycosylation is important for the catalytic activity and stability of hyaluronidases. Such cells include, for example Chinese Hamster Ovary (CHO) cells (e.g., DG44 CHO cells).

Vorhyaluronidase alfa is a recombinant human hyaluronidase PH-20 analog corresponding to the amino acid sequence of human hyaluronidase PH-20 at positions 36-482. Vorhyaluronidase alfa is produced in Chinese hamster ovary cells. Vorhyaluronidase alfa is a glycoprotein (molecular weight: 60,000-65,000) consisting of 447 amino acid residues. In one embodiment, the soluble PH20 product is the composition produced by expression of nucleic acid encoding residues 36-482 in CHO cells resulting in a mixture of polypeptides with C-termini at residues 477, 478, 479, 480, 481, and 482.

Soluble PH20 hyaluronidase is available and sold, for example, under the trademark ENHANZER (CAS name of 36-482-Hyaluronoglucosaminidase PH20 (human)). ENHANZER is the mixture of polypeptides produced by expression of nucleic acid encoding amino acids 36-482 (SEQ ID NO: 2). The product is a mixture of polypeptides, produced by expression of nucleic acid encoding amino acids 36-477 (SEQ ID NO: 3), 36-478 (SEQ ID NO: 4), 36-479 (SEQ ID NO: 5), 36-480 (SEQ ID NO: 6), 36-481 (SEQ ID NO: 7), and 36-482 (SEQ ID NO: 2). ENHANZER technology provides to a drug delivery technology, employing the soluble hyaluronidases to facilitate the delivery of injected drugs and fluids. When co-formulated with other drugs or administered with other drugs, the ENHANZER technology reduces treatment burden for patients. It can allow for large volume subcutaneous injection with increased dispersion and absorption of co-administered therapies.

In one embodiment, one or more of N47, N131, N200, N219, N333, N358, or T440 in SEQ ID NOs: 2-7 are glycosylation sites. In one embodiment, one or more of Q444, I445, F446, or Y447 in SEQ ID NOs: 2-7 are partial processing sites. In one embodiment, one or more of C25-C316, C189-C203, C341-C352, C346-C400, C402-C408, or C423-C429 in SEQ ID NOs.: 2-7 are disulfides.

rHuPH20 refers to the composition produced upon expression in a cell, such as CHO cell, of nucleic acid encoding residues 36-482 of SEQ ID NO: 8, generally linked to the native or a heterologous signal sequence (residues 1-35 of SEQ ID NO: 8). rHuPH20 is produced by expression of a nucleic acid molecule, such as encoding amino acids 1-482 (set forth in SEQ ID NO: 8) in a mammalian cell. Translational processing removes the 35 amino acid signal sequence. As produced in the culture medium there is heterogeneity at the C-terminus such that the product, designated rHuPH20, includes a mixture of species that can include any one or more of the polypeptides 36-480, 36-481, and 36-482 of SEQ ID NO: 8, and some shorter polypeptides, in various abundance. rHuPH20 and forms of soluble hyaluronidase are produced in cells, such as CHO cells, for example DG44 CHO cells, that facilitate N-glycosylation. PH20 is a glycoprotein, and as known in the art, requires glycosylation retain activity. See, e.g., U.S. Pat. Nos. 8,927,249 and 9,284,543 (and PCT Publication No. WO 2010/077297), which describe the effects of glycosylation and partial glycosylation and elimination of glycosylation on the activity of soluble forms of PH20. These patents and publications also describe and exemplify soluble C-terminally truncated forms of PH20.

Forms of Soluble Human PH20

Soluble hyaluronidases include bovine and ovine PH20, and recombinant and humanized forms thereof. Human PH20 in nature includes a GPI anchor and exists linked to sperm cells; it is not soluble. C-terminally-truncated forms thereof are soluble. Soluble forms of recombinant human PH20 have been produced and can be used in the compositions, combinations and methods described herein. Descriptions of and production of such soluble forms of PH20 are described, for example, in U.S. Pat. Nos. 7,767,429, 8,202,517, 8,431,380, 8,431,124, 8,450,470, 8,765,685, 8,772,246, 7,871,607, 7,846,431, 7,829,081, 8,105,586, 8,187,855, 8,257,699, 8,580,252, 9,677,061, and 9,677,062, each incorporated by reference herein. The soluble hyaluronidases, thus include forms of human PH20, which are neutral active hyaluronidases and which require glycosylation for activity.

SEQ ID NO: 1 sets forth the sequence of the precursor polypeptides; the mature PH20 polypeptide (residues 36-509); soluble forms also include those with amino acid truncations at the N-terminal, such as deletions of the first one, two, three, or fours residues, such that the resulting polypeptides have an N-terminus, for example, at residue 36, 37, 38, 39, or 40, and a C-terminus at a residue from 465 to 500, and variants thereof, including, but not limited to, variants discussed below, variants known in the art, and allelic variants.

Hyaluronidases for use in the compositions, combinations and methods herein are soluble neutral active hyaluronidases. Exemplary thereof are the soluble C-terminally truncated forms of mature human PH20. Soluble forms that have hyaluronidase activity, include but are not limited to, those that are truncated at residues from 465 to 500 of SEQ ID NO: 1, and that are, upon expression, secreted. Exemplary thereof are polypeptides that have sequence 36-465, 36-466, 36-467, 36-468, 36-469, 35-470, 36-471, 36-472, 36-474, 36-475, 36-476, 35-477, 36-478, 36-479, 36-480, 36-481, 36-482, 36-483 35-484, 36-485, 36-486, 36-487, 36-488, 36-489, 36-490, 35-491, 36-492, 36-493, 36-494, 36-495, 36-496, 36-497, 35-498, 36-499, and 36-500 of SEQ ID NO: 1, as well as N-terminally truncated forms of each of the preceding that lack two to five residues at the N-terminus, such as for example 37-368, 38-468, and any others that exhibit hyaluronidase activity at neutral pH, such as pH in the range of 7.0-7.4.

Thus, such soluble forms include truncated forms of the mature form of human PH20 lacking all or a portion of the C-terminal GPI anchor, so long as the hyaluronidase is soluble and retains hyaluronidase activity. Soluble forms are secreted upon expression in mammalian cells, and are encoded with a signal sequence, such are residues 1-35 of SEQ ID NO. 1 or a heterologous signal sequence that is cleaved by the cell to effect secretion. Soluble forms are forms that, when expressed in a cell, lack the signal peptide. Also included among soluble hyaluronidases are variants of the soluble PH20 polypeptides that exhibit hyaluronidase activity. Variants include polypeptides having at least 60%, 70%, 80%, 85%, 90%, 91%, 92%, 93%, 94%, 95%, 96%, 97%, 98%, 99% or more sequence identity to any of the PH20 polypeptides 36-465, 36-466, 36-467, 36-468, 36-469, 35-470, 36-471, 36-472, 36-474, 36-475, 36-476, 35-477, 36-478, 36-479, 36-480, 36-481, 36-482, 36-483 35-484, 36-485, 36-486, 36-487, 36-488, 36-489, 36-490, 35-491, 36-492, 36-493, 36-494, 36-495, 36-496, 36-497, 35-498, 36-499, and 36-500 of SEQ ID NO: 1. Amino acid variants include conservative and non-conservative insertions, or deletions, or replacements, and include the modifications, singly or combinations of the modifications detailed, for example, in U.S. Pat. No. 11,041,149 and International PCT publication No. WO 2013/102144. U.S. Pat. No. 11,041,149 and International PCT publication No. WO 2013/102144 describe a systematic analysis and results identifying the effects of amino acid modifications at each residue in PH20 to thereby provide a structure/function map of PH20; a skilled person can identify replacement residues and consequent alterations in properties and activities, such as for effecting increases in enzymatic activity, stability in denaturing conditions, and also residues whose replacement or deletion decreases or eliminates enzymatic activity.

It is understood that residues that are important or otherwise required for the activity of a hyaluronidase, such as any described above or known to skill in the art, are generally invariant and, except for possible conservative amino acid substitutions, cannot be changed. These include, for example, active site residues. For example, amino acid residues 111, 113 and 176 (corresponding to residues in the mature PH20 polypeptide) of a human PH20 polypeptide, or soluble form thereof, are generally invariant and are not altered. Other residues that confer glycosylation and formation of disulfide bonds required for proper folding also can be invariant.

The soluble human PH20 hyaluronidase is GPI-anchored and is rendered soluble by truncation at the C-terminus by removal of all or a part of the GPI anchor. Such truncation can remove all of the GPI anchor attachment sequence or can remove only some of the GPI anchor attachment sequence. The resulting polypeptide, however, is soluble. In instances where the soluble hyaluronidase retains a portion of the GPI anchor attachment signal sequence, 1, 2, 3, 4, 5, 6, 7 or more amino acid residues in the GPI anchor attachment signal sequence can be retained, provided the polypeptide is soluble. Polypeptides containing one or more amino acids of the GPI anchor are termed extended soluble hyaluronidases. One of skill in the art can determine whether a polypeptide is GPI-anchored using methods well known in the art. Such methods include, but are not limited to, using known algorithms to predict the presence and location of the GPI anchor attachment signal sequence and @-site, and performing solubility analyses before and after digestion with phosphatidylinositol-specific phospholipase C (PI-PLC) or D (PI-PLD).

Extended soluble hyaluronidases, which terminate for example, at residues 495, 496, 497, 498, 499, and 500, with reference to SEQ ID NO: 1, such as those set forth in SEQ ID NO: 9 (residues 1-495), SEQ ID NO: 10 (residues 1-496), SEQ ID NO: 11 (residues 1-497), SEQ ID NO: 12 (residues 1-498), SEQ ID NO: 13 (residues 1-499), and SEQ ID NO: 14 (residues 1-500), can be produced by making C-terminal truncations to any naturally GPI-anchored hyaluronidase such that the resulting polypeptide is soluble and contains one or more amino acid residues from the GPI anchor attachment signal sequence (see, e.g., U.S. Pat. No. 8,927, 249). These include hyaluronidases that are neutral active, soluble, contain amino acid substitutions, and have at least 60%, 70%, 80%, 85%, 90%, 91%, 92%, 93%, 94%, 95% or more sequence identity to any of SEQ ID NOs: 9-14.

Typically, for use in the compositions, combinations, and methods herein, a soluble human hyaluronidase, such as a soluble human PH20, is used, such as a PH20 and variants having, for example, at least 91% or 95% or 98% sequence identity thereto, including those with 1 to 5 N-terminal residues deleted. Hyaluronidases used in the regimens, combinations, compositions, and methods herein can be recombinantly produced or can be purified or partially purified from natural sources, such as, for example, from testes extracts. Methods for production of recombinant proteins, including recombinant hyaluronidases, are well known in the art.

Recombinant soluble forms of human PH20 have been generated and can be used in the compositions, combinations and methods provided herein. For example, with reference to SEQ ID NO: 1, which sets forth the sequence of full length precursor PH20, which includes a signal sequence (residues 1-35), soluble forms include, but are not limited to, C-terminal truncated polypeptides of human PH20 set forth in SEQ ID NO: 1 having a C-terminal amino acid residue 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 or 500 of the sequence of amino acids set forth in SEQ ID NO: 1, or polypeptides that exhibit at least 85%, 90%, 91%, 92%, 93%, 94%, 95%, 96%, 97%, 98%, 99%, or more sequence identity thereto, when aligned with the unmodified sequence of the soluble PH20, have activity at neutral pH, and are soluble (secreted into the medium when expressed in a mammalian cell). Soluble forms of human PH20 generally include those that contain amino acids 36-464 set forth in SEQ ID NO: 1 and terminate at any of residues, 465-500, and optionally include a 1-3 amino acid deletion at the N-terminus (i.e. lack residues 36, 36-37, or 36-38 of SEQ ID NO: 1). For example, when expressed in mammalian cells, the 35 amino acid N-terminal signal sequence (residues 1-35 of SEQ ID NO: 1) is cleaved during processing, and a soluble form of the protein is secreted. Thus, the mature soluble polypeptides include those that contain amino acids 36 to 467, 468, 469, 470, 471, 472, 473, 474, 475, 476, 477, 478, 479, 480, 481, 482, 483, and up to and including 500 of SEQ ID NO: 1. Exemplary of soluble hyaluronidases are soluble human PH20 polypeptides that are 442, 443, 444, 445, 446 or 447 amino acids in length, such as set forth those set forth above, and variants thereof that have, for example, at least 85%, 86%, 87%, 88%, 89%, 90%, 91%, 92%, 93%, 94%, 95%, 96%, 97%, 98% or 99% sequence identity thereto and retains hyaluronidase activity. The generation of such soluble forms of recombinant human PH20 are described, for example, in U.S. Pat. Nos. 7,767,429, 8,202, 517, 8,431,380, 8,431,124, 8,450,470 8,765,685, 8,772,246, 7,871,607, 7,846,431, 7,829,081, 8,105,586, 8, 187,855, 8,257,699, 8,580,252, 9,677,061, and 9,677,062.

Generally soluble forms of PH20 are produced using protein expression systems that facilitate correct N-glycosylation to ensure the polypeptide retains activity, since glycosylation is important for the catalytic activity and stability of hyaluronidases. Such cells include, for example Chinese Hamster Ovary (CHO) cells (e.g. DG44 CHO cells).

The composition that recombinantly produced from mammalian cells, such as CHO cells, has been referred to rHuPH20. It refers to the composition produced upon expression in a cell, such as CHO cell, of nucleic acid encoding residues 36-482 of SEQ ID NO: 1, generally linked to the native (residues 1-35 of SEQ ID NO: 1) or a heterologous signal sequence. rHuPH20 is produced by expression of a nucleic acid molecule, such as encoding amino acids 1-482 (set forth in SEQ ID NO: 1) or 36 to 482 with a heterologous signal sequence. Post translational processing removes the 35 amino acid signal sequence, resulting in polypeptide or a mixture of polypeptides, including those set forth in SEQ ID NO: 2 (residues 36-482), SEQ ID NO: 3 (residues 36-477), SEQ ID NO: 4 (residues 36-478), SEQ ID NO: 5 (residues 36-479), SEQ ID NO: 6 (residues 36-480), and SEQ ID NO: 7 (residues 36-481). As produced in the culture medium there is heterogeneity at the C-terminus such that the product, designated rHuPH20, includes a mixture of species that can include any one or more of SEQ ID NOs: 3 and 44-49 in various abundance. Generally, the soluble hyaluronidases, rHuPH20 is produced in cells that facilitate correct N-glycosylation to retain activity, such as CHO cells (e.g. DG44 CHO cells). Human soluble PH20 hyaluronidase requires glycosylation for activity. When produced recombinantly from a vector encoding residues 36-582, the most abundant species is the 446 amino acid polypeptides corresponding to residues 36-481 of SEQ ID NO: 1. The particular distribution of resulting polypeptides can depend upon the particular method of production. An exemplary method for production of high levels of PH20 is detailed, for example in U.S. Pat. Nos. 8,187,855 and 8,343,487.

Glycosylation of Hyaluronidases

Glycosylation, including N- and O-linked glycosylation, of some hyaluronidases, including the soluble PH20 hyaluronidases, can be important for their catalytic activity and stability. For some hyaluronidases, removal of N-linked glycosylation can result in near complete inactivation of the hyaluronidase activity. For such hyaluronidases, the presence of N-linked glycans can be important for generating an active enzyme.

N-linked oligosaccharides fall into several primary types (oligomannose, complex, hybrid, sulfated), all of which have (Man) 3-GlcNAc-GlcNAc- cores attached via the amide nitrogen of Asn residues that fall within -Asn-Xaa-Thr/Ser-sequences (where Xaa is not Pro). Glycosylation at an -Asn-Xaa-Cys-site has been reported for coagulation protein C. In some instances, a hyaluronidase, such as a PH20 hyaluronidase, can contain N-glycosidic and O-glycosidic linkages. For example, PH20 has O-linked oligosaccharides as well as N-linked oligosaccharides. There are six potential N-linked glycosylation sites at N82, N166, N235, N254, N368, N393 of human PH20 exemplified in SEQ ID NO: 1.

Variants of PH20

As discussed above, variants of PH20 are known to those of skill in the art, or readily can be prepared in view of the skill and knowledge in the art. Variants include those with amino acid replacements, insertions, and deletions. Variants of the soluble PH20 polypeptides that have altered properties, such as increased stability and/or activity, have been produced. U.S. Pat. No. 9,447,401 and family members U.S. Pat. Nos. 10,865,400, 11,041,149 and 11,066,656 describe and provide a structure/function map of human PH20 detailing the effects of amino acid replacements at every residue in the catalytic domain of PH20. These patents provide about 7000 examples in which the effects of replacing each amino acid with 15 other amino acids on activity and stability were identified and described. By virtue of those patents, and earlier publications/patents, describing virtually all variants of soluble PH20 polypeptides are known in the art. A skilled person readily can prepare soluble hyaluronidases and variants thereof and know the properties of the resulting hyaluronidase.

Other variants also are known to those of skill in the art, and can be used in the combinations, regimens, and methods described herein. For example, see International PCT Publication Nos. WO2020/022791 and WO2020/197230, which are incorporated by reference, and which describe modified PH20 polypeptides. These polypeptides, which include variants of the PH20 polypeptides that generally span residues 38-468, and include replacements, insertions, and deletions. The variants include for example one or more amino acid residues changes S343E, I344N, M345T, M348K, K349E, L353A, L354I, N356E, and I361T (with reference to SEQ ID NO: 1), and others, including about 15 amino acid variations, and truncations at the N-terminus and C-terminus. Variants that contain such modifications and others are set forth in SEQ ID NOs: 60-115 of International PCT publication No. WO2020/022791. Exemplary of these polypeptides is the polypeptide of SEQ ID NO: 99, therein, and reproduced herein as SEQ ID NO: 15. International PCT Publication No. WO2021/150079 provides variant PH20 polypeptides described as having increased stability relative to unmodified PH20, such as those in rHuPH20. These variant polypeptides have been shown to have PH20 activity and are described as having use for subcutaneous co-administration with other agents.

In one embodiment, the variant of PH20 is a variant of human PH20 or rHuPH20 selected from any one of SEQ ID NOs: 16-47.

In one embodiment, the hyaluronidase enzyme is a human hyaluronidase enzyme. Exemplary human hyaluronidase enzymes include HYAL1, HYAL2, HYAL3, HYAL4, HYAL5 (also known as SPAM1 or PH20), and HYAL6 (also known as HYALP1). In one embodiment, the hyaluronidase enzyme is a recombinant hyaluronidase enzyme. In one embodiment, the hyaluronidase enzyme is a recombinant human hyaluronidase enzyme. In one embodiment, the hyaluronidase enzyme is a recombinant human hyaluronidase PH20 enzyme. Exemplary hyaluronidase enzymes that can be used in the disclosure can be found in the following patents and patent applications which are incorporated by reference herein in their entirety: U.S. 2022/0289864 (Alteogen), U.S. Pat. No. 9,084,743 (Baxter), U.S. Pat. No. 9,993,529 (Halozyme), U.S. Pat. No. 8,795,654, U.S. 2009/0311237 (Greg Frost), U.S. Pat. No. 9,284,543 (Halozyme), U.S. Pat. No. 10,265,410 (Halozyme), U.S. Pat. No. 10,137,104 (Halozyme), U.S. 2013/0022592, U.S. 2019/0284263 (Greg Frost), U.S. 11,065,309, WO 2017/185383, U.S. Pat. No. 11,041,149 (Halozyme), U.S. 2010/0003238 (Greg Frost), U.S. Pat. No. 8,343,487 (Halozyme), U.S. Pat. No. 10,301,376 (Baxalta), U.S. 2013/0344048, U.S. 2021/0363270 (Alteogen), U.S. 2021/0155913 (Alteogen), WO 2021/150079 (Dassault Systems SolidWorks), and WO 2022/031093 (Toshiba TEC Kabushiki Kaisha).

In one embodiment, the hyaluronidase enzyme has an activity of between about 150 U/mL to about 1,000 kU/mL, about 150 U/mL to about 900 kU/mL, about 150 U/mL to about 800 kU/mL, about 150 U/mL to about 700 kU/mL, about 150 U/mL to about 600 kU/mL, about 150 U/mL to about 500 kU/mL, about 150 U/mL to about 400 kU/mL, about 150 U/mL to about 300 kU/mL, about 150 U/mL to about 200 kU/mL, about 500 U/mL to about 200 kU/mL, about 1 kU/mL to about 200 kU/mL, about 10 kU/mL to about 200 kU/mL, about 25 kU/mL to about 200 kU/mL, about 50 kU/mL to about 200 kU/mL, about 100 kU/mL to about 200 kU/mL, about 100 kU/mL to about 150 kU/mL, or about 120 kU/mL. In one embodiment, the hyaluronidase enzyme has an activity of about 10 kU/mL for a 5 mL formulation or about 5 kU/mL for a 10 mL formulation. In one embodiment, the hyaluronidase enzyme has a minimum activity of about 150 U/mL and a maximum activity of about 110,000 U/mL (110 kU/mL). In one embodiment, the hyaluronidase enzyme is recombinant human hyaluronidase PH20 enzyme with an activity of about 120 kU/mL. In another embodiment, the hyaluronidase enzyme is recombinant human hyaluronidase PH20 enzyme with a minimum activity of about 150 U/mL and a maximum activity of about 110,000 U/mL.

In one embodiment, the concentration of hyaluronidase enzyme in the formulation is between about 10 U/mL to about 50,000 U/mL, about 10 U/mL to about 45,000 U/mL, about 10 U/mL to about 40,000 U/mL, about 10 U/mL to about 35,000 U/mL, about 10 U/mL to about 30,000 U/mL, about 10 U/mL to about 25,000 U/mL, about 10 U/mL to about 20,000 U/mL, about 10 U/mL to about 15,000 U/mL, about 10 U/mL to about 10,000 U/mL, about 100 U/mL to about 9,000 U/mL, about 100 U/mL to about 8,000 U/mL, about 100 U/mL to about 7,000 U/mL, about 100 U/mL to about 6,000 U/mL, about 100 U/mL to about 5,000 U/mL, about 500 U/mL to about 5,000 U/mL, about 500 U/mL to about 4,000 U/mL, about 500 U/mL to about 3,000 U/mL, about 1,000 U/mL to about 3,000 U/mL, about 1,500 U/mL to about 3,000 U/mL, about 1,500 U/mL to about 2,500 U/mL, or about 2,000 U/mL. In one embodiment, the formulation comprises about 1,500 U/mL to about 10,000 U/mL of hyaluronidase enzyme. In one embodiment, the formulation comprises about 1,500 U/mL to about 10,000 U/mL of recombinant human hyaluronidase PH20 enzyme. In one embodiment, the formulation comprises about 2,000 U/mL of recombinant human hyaluronidase PH20 enzyme. In one embodiment, the formulation comprises about 5,000 U/mL of recombinant human hyaluronidase PH20 enzyme. In another embodiment, the formulation comprises at least 4,000 U/mL of recombinant human hyaluronidase PH20 enzyme. In another embodiment, the formulation comprises at least 7,500 U/mL of recombinant human hyaluronidase PH20 enzyme. In another embodiment, the formulation comprises at least 10,000 U/mL of recombinant human hyaluronidase PH20 enzyme. In one embodiment, the formulation comprises about 4,000 U/mL of recombinant human hyaluronidase PH20 enzyme.

In one embodiment, the formulation comprises a hyaluronidase enzyme that permits a high volume of the formulation to be injected into a subject in need thereof at a high flow rate. In one embodiment, the formulation comprises a hyaluronidase enzyme at a concentration and/or activity that permits a high volume of the formulation to be injected into a subject in need thereof at a high flow rate.

In one embodiment, the formulation comprises one or more pharmaceutically acceptable additives including, but not limited to, carriers, excipients, fillers, preservatives, stabilizers, and antioxidants. The pharmaceutically acceptable additive can be any pharmaceutically acceptable additive known to a person of skill in the art for an injectable formulation. In one embodiment, the formulation comprises histidine. In one embodiment, the formulation comprises sodium chloride. In one embodiment, the formulation comprises polysorbate. In one embodiment, the polysorbate comprises polysorbate 80. In one embodiment, the formulation comprises between about 0.001% to about 5%, about 0.001% to about 4.5%, about 0.001% to about 4.0%, about 0.001% to about 3.5%, about 0.001% to about 3.0%, about 0.001% to about 2.5%, about 0.001% to about 2.0%, about 0.001% to about 1.5%, about 0.001% to about 1.0%, about 0.001% to about 0.5%, about 0.005% to about 0.5%, about 0.005% to about 0.1%, about 0.005% to about 0.05%, about 0.01% to about 0.05%, or about 0.02% polysorbate 80. In one embodiment, the formulation comprises an antioxidant. In one embodiment, the antioxidant comprises methionine. In one embodiment, the formulation comprises between about 0.5 mM to about 50 mM, about 0.5 mM to about 45 mM, about 0.5 mM to about 40 mM, about 0.5 mM to about 35 mM, about 0.5 mM to about 30 mM, about 0.5 mM to about 25 mM, about 0.5 mM to about 20 mM, about 5 mM to about 20 mM, about 5 mM to about 15 mM, or about 10 mM antioxidant. In one embodiment, the formulation comprises about 10 mM methionine. In one embodiment, the formulation comprises a carrier protein.

In one embodiment, the formulation has a pH of between about 4.0 to about 8.0, about 4.2 to about 8.0, about 4.4 to about 7.8, about 4.6 to about 7.8, about 4.6 to about 7.6, about 4.8 to about 7.8, about 5.0 to about 7.8, about 5.2 to about 7.8, about 5.4 to about 7.6, about 5.6 to about 7.4, about 5.8 to about 7.2, about 6.0 to about 7.0, about 6.2 to about 6.8, about 6.4 to about 6.6, or about 6.5. In one embodiment, the formulation has a pH of between about 4.6 to about 7.6. In one embodiment, the formulation has a pH of between about 4.0 to about 8.0.

In one embodiment, the formulation comprises an active ingredient. The active ingredient can be any active ingredient to treat a disease or disorder in a subject in need thereof provided that the active ingredient can be administered via injection to the subject in need thereof. In one embodiment, the active ingredient is selected from a small molecule, a peptide fragment, a biologic, a nanoparticle, an antibody, an antibody fragment, or a small molecule antiviral.

Methods of Treatment

In one aspect, the present disclosure provides a method of treating a disease or disorder in subject in need thereof, the method comprising administering to the subject via injection a formulation comprising a hyaluronidase enzyme and a therapeutically effective amount of an active ingredient. The formulation is described elsewhere herein. In one embodiment, the hyaluronidase enzyme is a recombinant human hyaluronidase PH20 enzyme. In one embodiment, the subject is a mammal. In one embodiment, the subject is a human. In one embodiment, the formulation is administered to the subject via a subcutaneous injection. In one embodiment, the formulation is self-administered. In another embodiment, the formulation is administered to the subject by a healthcare professional. In yet another embodiment, the formulation is administered to the subject by a layperson, such as a caregiver. In one embodiment, the formulation is administered using an autoinjector. In one embodiment, the formulation is administered using a HVAI. In one embodiment, the formulation is administered from a prefilled syringe using a HVAI. In another embodiment, the formulation is administered manually using a manually triggered injection device. In another embodiment, the formulation is administered from an on-body device.

In one embodiment, the formulation is administered to the abdomen or thigh of the subject. In one embodiment, the formulation is subcutaneously administered to the abdomen or thigh of the subject.

In one embodiment, the amount of the disclosed formulation administered to the subject is dependent on the subject being treated, the severity of the disorder or condition, the rate of administration, the disposition of the compounds, and/or the discretion of the prescribing physician. In one embodiment, an effective dosage of the active ingredient in the disclosed formulation is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect, for example by dividing such larger doses into several small doses for administration throughout the day.

In one embodiment, the disclosed formulation is administered to the subject in multiple doses. Dosing may be about once, twice, three times, four times, five times, six times, or more than six times per day. Dosing may be about once a month, once every two weeks, once a week, or once every other day. In one embodiment, the disclosed formulation is administered about once per day to about 6 times per day. In one embodiment, the administration of the disclosed formulation continues for less than about 7 days. In yet another embodiment the administration continues for more than about 6, 10, 14, 28 days, two months, six months, or one year. In some cases, continuous dosing is achieved and maintained as long as necessary.

In one embodiment, an effective dosage of the active ingredient in the disclosed formulation is in the range of about 1 mg/mL to about 500 mg/mL, about 10 mg/mL to about 450 mg/mL, about 20 mg/mL to about 400 mg/mL, about 30 mg/mL to about 350 mg/mL, about 50 mg/mL to about 300 mg/mL, about 75 mg/mL to about 250 mg/mL, about 100 mg/mL to about 200 mg/mL, or about 150 mg/mL.

In one embodiment, the formulation is administered using a HVAI fitted with a needle. In one embodiment, the needle is a 20 gauge needle, a 21 gauge needle, a 22 gauge needle, a 23 gauge needle, a 24 gauge needle, a 25 gauge needle, a 26 gauge needle, a 27 gauge needle, a 28 gauge needle, a 29 gauge needle, a 30 gauge needle, or a 31 gauge needle. In one embodiment, the needle is a 27 gauge regular wall needle×½", a 27 gauge regular wall×⅝" needle, a 27 gauge regular wall×¾" needle, a 27 gauge regular wall×1" needle, a 27 gauge thin wall×½" needle, a 27 gauge thin wall×⅝" needle, a 27 gauge thin wall×¾" needle, a 27 gauge thin wall×1" needle, a 25 gauge regular wall×½" needle, a 25 gauge regular wall×⅝" needle, a 25 gauge regular wall×¾" needle, a 25 gauge regular wall×1" needle, a 25 gauge thin wall×½" needle, a 25 gauge thin wall×⅝" needle, a 25 gauge thin wall×¾" needle, a 25 gauge thin wall×1" needle, a 23 gauge regular wall×½" needle, a 23 gauge regular wall×⅝" needle, a 23 gauge regular wall×¾" needle, or a 23 gauge regular wall×1" needle. In one embodiment, the needle is a 25 gauge thin wall×½" needle. In one embodiment, the needle is a 25 gauge thin wall×⅝" needle.

In one embodiment, a high volume of the formulation is administered to the subject. In one embodiment, a "high volume" is greater than 2.25 mL in a single administration. In one embodiment, 3 mL to 5 mL, 3 mL to 10 mL, 3 mL to 15 mL, 3 mL to 20 mL, 3 mL to 25 mL, 3 ml to 30 mL, 3 mL to 35 mL, 3 mL to 40 mL, 3 mL to 45 mL, 3 mL to 50 mL, 5 mL to 10 mL, 5 mL to 15 mL, 5 mL to 20 mL, 5 mL to 25 mL, 5 mL to 30 mL, 5 mL to 35 mL, 5 mL to 40 mL; 5 mL to 45 mL, 5 mL to 50 mL, 10 mL to 15 mL; 10 mL to 20 mL; 10 mL to 25 mL; 10 mL to 30 mL; 10 mL to 35 mL; 10 mL to 40 mL, or 10 mL to 50 mL are administered to the subject in a single administration. In one embodiment, about 3 mL to about 5 mL, about 3 mL to about 10 mL, about 3 mL to about 15 mL, about 3 mL to about 20 mL, about 3 mL to about 25 mL, about 3 ml to about 30 mL, about 3 mL to about 35 mL, about 3 mL to about 40 mL, about 3 mL to about 45 mL, about 3 mL to about 50 mL, about 5 mL to about 10 mL, about 5 mL to about 15 mL, about 5 mL to about 20 mL, about 5 mL to about 25 mL, about 5 mL to about 30 mL, about 5 mL to about 35 mL, about 5 mL to about 40 mL; about 5 mL to about 45 mL, about 5 mL to about 50 mL, about 10 mL to about 15 mL; about 10 mL to about 20 mL; about 10 mL to about 25 mL; about 10 mL to about 30 mL; about 10 mL to about 35 mL; about 10 mL to about 40 mL, or about 10 mL to about 50 mL are administered to the subject in a single administration. In one embodiment, at least about 3 mL, at least about 3.5 mL, at least about 4 mL, at least about 4.5 mL, at least about 5.5 mL, at least about 6 mL, at least about 6.5 mL, at least about 7 mL, at least about 7.5 mL, at least about 8 mL, at least about 8.5 mL, at least about 9 mL, at least about 9.5 mL, at least about 10 mL, at least about 10.5 mL, at least about 11 mL, at least about 11.5 mL, at least about 12 mL, at least about 12.5 mL, at least about 13 mL, at least about 13.5 mL, at least about 14 mL, at least about 14.5 mL, at least about 15 mL, at least about 15.5 mL, at least about 16 mL, at least about 16.5 mL, at least about 17 mL, at least about 17.5 mL, at least about 18 mL, at least about 18.5 mL, at least about 19 mL, at least about 19.5 mL, at least about 20 mL, at least about 25 mL, at least about 30 mL, at least about 35 mL, at least about 40 mL, at least about 45 mL, or at least about 50 mL are administered to the subject in a single administration. In one embodiment, at least 3 mL, at least 3.5 mL, at least 4 mL, at least 4.5 mL, at least 5.5 mL, at least 6 mL, at least 6.5 mL, at least 7 mL, at least 7.5 mL, at least 8 mL, at least 8.5 mL, at least 9 mL, at least 9.5 mL, at least 10 mL, at least 10.5 mL, at least 11 mL, at least 11.5 mL, at least 12 mL, at least 12.5 mL, at least 13 mL, at least 13.5 mL, at least 14 mL, at least 14.5 mL, at least 15 mL, at least 15.5 mL, at least 16 mL, at least 16.5 mL, at least 17 mL, at least 17.5 mL, at least 18 mL, at least 18.5 mL, at least 19 mL, at least 19.5 mL, at least 20 mL, at least 25 mL, at least 30 mL, at least 35 mL, at least 40 mL, at least 45 mL, or at least 50 mL are administered to the subject in a single administration.

In one embodiment, greater than about 2.25 mL, about 2.5 mL, about 3.0 mL, about 3.5 mL, about 4.0 mL, about 4.5 mL, about 5.0 mL, about 5.5 mL, about 6.0 mL, about 6.5 mL, about 7.0 mL, about 7.5 mL, about 8.0 mL, about 8.5 mL, about 9.5 mL, about 10 mL, about 12 mL, about 14 mL, about 16 mL, about 18 mL, or about 20 mL of the formulation is administered to the subject in a single administration. In one embodiment, greater than about 2.5 mL, about 3.0 mL, about 3.5 mL, about 4.0 mL, about 4.5 mL, about 5.0 mL, about 5.5 mL, about 6.0 mL, about 6.5 mL, about 7.0 mL, about 7.5 mL, about 8.0 mL, about 8.5 mL, about 9.5 mL, about 10 mL, about 12 mL, about 14 mL, about 16 mL, about 18 mL, or about 20 mL of the formulation is administered to the subject in about 10 seconds, about 12 seconds, about 16 seconds, about 18 seconds, about 20 seconds, about 22 seconds, about 24 seconds, about 26 seconds, about 28 seconds, about 30 seconds, about 32 seconds, about 34 seconds, about 36 seconds, about 38 seconds, about 40 seconds, about 42 seconds, about 44 seconds, about 46 seconds, about 48 seconds, about 50 seconds, about 52 seconds, about 54 seconds, about 56 seconds, about 58 seconds, about 60 seconds, about 65 seconds, about 70 seconds, about 75 seconds, about 80 seconds, about 85 seconds, about 90 seconds, about 95 seconds, about 100 seconds, about 105 seconds, about 110 seconds, about 115 seconds, or about 120 seconds.

In one embodiment, about 5 mL of the formulation can be administered to the subject in about 5 seconds, about 10 seconds, about 15 seconds, about 20 seconds, about 25 seconds, about 30 seconds, about 35 seconds, about 40 seconds, about 45 seconds, about 50 seconds, about 55 seconds, or about 60 seconds.

In one embodiment, about 10 mL of the formulation can be administered to the subject in about 5 seconds, about 10 seconds, about 15 seconds, about 20 seconds, about 25 seconds, about 30 seconds, about 35 seconds, about 40 seconds, about 45 seconds, about 50 seconds, about 55 seconds, or about 60 seconds.

In one embodiment, about 10.5 mL of the formulation can be administered to the subject in about 5 seconds, about 10 seconds, about 15 seconds, about 20 seconds, about 25 seconds, about 30 seconds, about 35 seconds, about 40 seconds, about 45 seconds, about 50 seconds, about 55 seconds, or about 60 seconds.

In some embodiments, the speed at which a high volume of the formulation can be administered to the subject depends on the gauge of the needle used to inject the formulation. In one embodiment, the formulation is administered to the subject using an autoinjector and a 23 gauge needle. In one embodiment, about 10 mL of the formulation can be administered to the subject in between about 5 seconds to about 45 seconds, about 5 seconds to about 40 seconds, about 10 seconds to about 40 seconds, about 10 seconds to about 35 seconds, about 15 seconds to about 35 seconds, about 15 seconds to about 30 seconds, about 20 seconds to 30 seconds, about 15 seconds to about 25 seconds, or about 20 seconds using an autoinjector and a 23 gauge needle. In one embodiment, about 5.5 mL of the formulation can be administered to the subject in between about 5 seconds to about 45 seconds, about 5 seconds to about 40 seconds, about 10 seconds to about 40 seconds, about 10 seconds to about 35 seconds, about 15 seconds to about 35 seconds, about 15 seconds to about 30 seconds, about 15 seconds to about 25 seconds, or about 20 seconds using an autoinjector and a 23 gauge needle. In one embodiment, about 5.5 mL of the formulation can be administered to the subject in between about 15 seconds to about 60 seconds, about 20 seconds to about 60 seconds, about 25 seconds to about 60 seconds, about 25 seconds to about 55 seconds, about 30 seconds to about 55 seconds, about 30 seconds to about 50 seconds, about 35 seconds to about 50 seconds, about 40 seconds to about 50 seconds, or about 45 seconds using an autoinjector and a 23 gauge needle. In another embodiment, the formulation is administered to the subject using an autoinjector and a 25 gauge needle. In one embodiment, about 10 mL of the formulation can be administered to the subject in between about 15 seconds to about 60 seconds, about 20 seconds to about 60 seconds, about 25 seconds to about 60 seconds, about 25 seconds to about 55 seconds, about 30 seconds to about 55 seconds, about 30 seconds to about 50 seconds, about 35 seconds to about 50 seconds, about 40 seconds to about 50 seconds, or about 45 seconds using an autoinjector and a 25 gauge needle. In one embodiment, about 5.5 mL of the formulation can be administered to the subject in between about 5 seconds to about 45 seconds, about 5 seconds to about 40 seconds, about 10 seconds to about 40 seconds, about 10 seconds to about 35 seconds, about 15 seconds to about 35 seconds, about 15 seconds to about 30 seconds, about 15 seconds to about 25 seconds, or about 20 seconds using an autoinjector and a 23 gauge needle. In one embodiment, about 5.5 mL of the formulation can be administered to the subject in between about 15 seconds to about 60 seconds, about 20 seconds to about 60 seconds, about 25 seconds to about 60 seconds, about 25 seconds to about 55 seconds, about 30 seconds to about 55 seconds, about 30 seconds to about 50 seconds, about 35 seconds to about 50 seconds, about 40 seconds to about 50 seconds, or about 45 seconds using an autoinjector and a 25 gauge needle. In another embodiment, the formulation is administered to the subject using an autoinjector and a 27 gauge needle. In one embodiment, about 10 mL of the formulation can be administered to the subject in between about 15 seconds to about 60 seconds, about 20 seconds to about 60 seconds, about 25 seconds to about 60 seconds, about 25 seconds to about 55 seconds, about 30 seconds to about 55 seconds, about 30 seconds to about 50 seconds, about 35 seconds to about 50 seconds, about 40 seconds to about 50 seconds, or about 45 seconds using an autoinjector and a 27 gauge needle. In one embodiment, about 5.5 mL of the formulation can be administered to the subject in between about 15 seconds to about 60 seconds, about 20 seconds to about 60 seconds, about 25 seconds to about 60 seconds, about 25 seconds to about 55 seconds, about 30 seconds to about 55 seconds, about 30 seconds to about 50 seconds, about 35 seconds to about 50 seconds, about 40 seconds to about 50 seconds, or about 45 seconds using an autoinjector and a 27 gauge needle.

In one embodiment, using a 23 gauge needle with a HVAI and the disclosed formulation provides about 40%, about 42%, about 44%, about 46%, about 48%, about 50%, about 52%, about 54%, about 56%, about 58%, or about 60% faster injection times than using a 25 gauge needle with a HVAI.

In one embodiment, the device has a variable delivery rate that can deliver the formulation faster at the start of the injection and slower at the completion of the injection. In another embodiment, the device has a variable delivery rate that delivers the formulation slower at the initiation of the injection and faster at the completion of the injection.

In one embodiment, the viscosity and volume of the disclosed formulation affect the time needed to inject the formulation into a subject. However, the full volume of the formulation can be delivered from a HVAI at a rate of approximately 0.08-1.0 mL/sec. For example, this would provide target delivery rate ranges of 10-120 seconds for a 10 mL dose volume. The HVAI may deliver 10 mL of the formulation at a rate of 0.33 mL/sec. In one embodiment, HVAI delivers the full deliverable volume of the formulation at a rate of: 0.5 mL/10 sec., 0.75 mL/10 sec., 1 mL/10 sec., 1.25 mL/10 sec., 1.5 mL/10 sec., 1.75 mL/10 sec, 2 mL/10 sec., 2.25 mL/10 sec, 2.5 mL/10 sec., 2.75 mL/10 sec, 3 mL/10 sec., 3.25 mL/10 sec, 3.5 mL/10 sec., 3.75 mL/10 sec, 4 mL/10 sec., 4.25 mL/10 sec, 4.5 mL/10 sec., 4.75 mL/10 sec, or about 5 mL/10 sec. In one embodiment, the HVAI delivers the full deliverable volume of the formulation at a rate of: 2 mL/30 sec., 2.5 mL/30 sec., 3 mL/30 sec., 3.5 mL/30 sec., 4 mL/30 sec., 4.5 mL/30 sec., 5 mL/30 sec., 5.5 mL/30 sec., 6 mL/30 sec., 6.5 mL/30 sec., 7 mL/30 sec., 7.5 mL/30 sec., 8 mL/30 sec., 8.5 mL/30 sec., 9 mL/30 sec., 9.5 mL/30 sec., 10 mL/30 sec., or 10.5 mL/30 sec. In one embodiment, delivers the full deliverable volume of the formulation at a rate of: 4 mL/min, 5 mL/min, 6 mL/min, 7 mL/min, 8 mL/min, 9 mL/min, 10 mL/min, 11 mL/min, 12 mL/min, 13 mL/min, 14 mL/min, 15 mL/min, 16 mL/min, 17 mL/min, 18 mL/min, 19 mL/min, 20 mL/min, 21 mL/min.

In one embodiment, the disclosed formulation is administered to the subject at a rate of about 0.05 mL/sec, about 0.06 mL/sec, about 0.07 mL/sec, about 0.08 mL/sec, about 0.09 mL/sec, about 0.10 mL/sec, about 0.11 mL/sec, about 0.12 mL/sec, about 0.13 mL/sec, about 0.14 mL/sec, about 0.15 mL/sec, about 0.16 mL/sec, about 0.17 mL/sec, about 0.18 mL/sec, about 0.19 mL/sec, about 0.20 mL/sec, about 0.21 mL/sec, about 0.22 mL/sec, about 0.23 mL/sec, about 0.24 mL/sec, about 0.25 mL/sec, about 0.31 mL/sec, about 0.32 mL/sec, about 0.33 mL/sec, about 0.34 mL/sec, about 0.35 mL/sec, about 0.36 mL/sec, about 0.37 mL/sec, about 0.38 mL/sec, about 0.39 mL/sec, about 0.4 mL/sec, about 0.41 mL/sec, about 0.42 mL/sec, about 0.43 mL/sec, about 0.44 mL/sec, about 0.45 mL/sec, about 0.46 mL/sec, about 0.47 mL/sec, about 0.48 mL/sec, about 0.49 mL/sec, about 0.50 mL/sec, about 0.51 mL/sec, about 0.52 mL/sec, about 0.53 mL/sec, about 0.54 mL/sec, about 0.55 mL/sec, about 0.56 mL/sec, about 0.57 mL/sec, about 0.58 mL/sec, about 0.59 mL/sec, about 0.60 mL/sec, about 0.61 mL/sec, about 0.62 mL/sec, about 0.63 mL/sec, about 0.64 mL/sec, about 0.65 mL/sec, about 0.66 mL/sec, about 0.67 mL/sec, 0.68 mL/sec, about 0.69 mL/sec, about 0.70 mL/sec, about 0.71 mL/sec, about 0.72 mL/sec, about 0.73 mL/sec, about 0.74 mL/sec, about 0.75 mL/sec, about 0.76 mL/sec, about 0.77 mL/sec, about 0.78 mL/sec, about 0.79 mL/sec, about 0.80 mL/sec, about 0.81 mL/sec, about 0.82 mL/sec, about 0.83 mL/sec, about 0.84 mL/sec, about 0.85 mL/sec, about 0.86 mL/sec, about 0.87 mL/sec, about 0.88 mL/sec, about 0.89 mL/sec, about 0.90 mL/sec, about 0.91 mL/sec, about 0.92 mL/sec, about 0.93 mL/sec, about 0.94 mL/sec, about 0.95 mL/sec, about 0.96 mL/sec, about 0.97 mL/sec, about 0.98 mL/sec, about 0.99 mL/sec, or about 1.0 mL/sec.

In one embodiment, the disclosed formulation is administered to the subject, using a prefilled syringe fitted with a needle having a gauge between 20 and 33, at a rate of about 0.05 mL/sec, about 0.06 mL/sec, about 0.07 mL/sec, about 0.08 mL/sec, about 0.09 mL/sec, about 0.10 mL/sec, about 0.11 mL/sec, about 0.12 mL/sec, about 0.13 mL/sec, about 0.14 mL/sec, about 0.15 mL/sec, about 0.16 mL/sec, about 0.17 mL/sec, about 0.18 mL/sec, about 0.19 mL/sec, about 0.20 mL/sec, about 0.21 mL/sec, about 0.22 mL/sec, about 0.23 mL/sec, about 0.24 mL/sec, about 0.25 mL/sec, about 0.26 mL/sec, about 0.27 mL/sec, about 0.28 mL/sec, about 0.29 mL/sec, about 0.30 mL/sec, about 0.31 mL/sec, about 0.32 mL/sec, about 0.33 mL/sec, about 0.34 mL/sec, about 0.35 mL/sec, about 0.36 mL/sec, about 0.37 mL/sec, about 0.38 mL/sec, about 0.39 mL/sec, about 0.4 mL/sec, about 0.41 mL/sec, about 0.42 mL/sec, about 0.43 mL/sec, about 0.44 mL/sec, about 0.45 mL/sec, about 0.46 mL/sec, about 0.47 mL/sec, about 0.48 mL/sec, about 0.49 mL/sec, about 0.50 mL/sec, about 0.51 mL/sec, about 0.52 mL/sec, about 0.53 mL/sec, about 0.54 mL/sec, about 0.55 mL/sec, about 0.56 mL/sec, about 0.57 mL/sec, about 0.58 mL/sec, about 0.59 mL/sec, about 0.60 mL/sec, about 0.61 mL/sec, about 0.62 mL/sec, about 0.63 mL/sec, about 0.64 mL/sec, about 0.65 mL/sec, about 0.66 mL/sec, about 0.67 mL/sec, 0.68 mL/sec, about 0.69 mL/sec, about 0.70 mL/sec, about 0.71 mL/sec, about 0.72 mL/sec, about 0.73 mL/sec, about 0.74 mL/sec, about 0.75 mL/sec, about 0.76 mL/sec, about 0.77 mL/sec, about 0.78 mL/sec, about 0.79 mL/sec, about 0.80 mL/sec, about 0.81 mL/sec, about 0.82 mL/sec, about 0.83 mL/sec, about 0.84 mL/sec, about 0.85 mL/sec, about 0.86 mL/sec, about 0.87 mL/sec, about 0.88 mL/sec, about 0.89 mL/sec, about 0.90 mL/sec, about 0.91 mL/sec, about 0.92 mL/sec, about 0.93 mL/sec, about 0.94 mL/sec, about 0.95 mL/sec, about 0.96 mL/sec, about 0.97 mL/sec, about 0.98 mL/sec, about 0.99 mL/sec, or about 1.0 mL/sec.

In one embodiment, the disclosed formulation is administered to the subject from a high volume autoinjector disclosed herein at a rate of about 0.05 mL/sec, about 0.06 mL/sec, about 0.07 mL/sec, about 0.08 mL/sec, about 0.09 mL/sec, about 0.10 mL/sec, about 0.11 mL/sec, about 0.12 mL/sec, about 0.13 mL/sec, about 0.14 mL/sec, about 0.15 mL/sec, about 0.16 mL/sec, about 0.17 mL/sec, about 0.18 mL/sec, about 0.19 mL/sec, about 0.20 mL/sec, about 0.21 mL/sec, about 0.22 mL/sec, about 0.23 mL/sec, about 0.24 mL/sec, about 0.25 mL/sec, about 0.26 mL/sec, about 0.27 mL/sec, about 0.28 mL/sec, about 0.29 mL/sec, about 0.30 mL/sec, about 0.31 mL/sec, about 0.32 mL/sec, about 0.33 mL/sec, about 0.34 mL/sec, about 0.35 mL/sec, about 0.36 mL/sec, about 0.37 mL/sec, about 0.38 mL/sec, about 0.39 mL/sec, about 0.4 mL/sec, about 0.41 mL/sec, about 0.42 mL/sec, about 0.43 mL/sec, about 0.44 mL/sec, about 0.45 mL/sec, about 0.46 mL/sec, about 0.47 mL/sec, about 0.48 mL/sec, about 0.49 mL/sec, about 0.50 mL/sec, about 0.51 mL/sec, about 0.52 mL/sec, about 0.53 mL/sec, about 0.54 mL/sec, about 0.55 mL/sec, about 0.56 mL/sec, about 0.57 mL/sec, about 0.58 mL/sec, about 0.59 mL/sec, about 0.60 mL/sec, about 0.61 mL/sec, about 0.62 mL/sec, about 0.63 mL/sec, about 0.64 mL/sec, about 0.65 mL/sec, about 0.66 mL/sec, about 0.67 mL/sec, 0.68 mL/sec, about 0.69 mL/sec, about 0.70 mL/sec, about 0.71 mL/sec, about 0.72 mL/sec, about 0.73 mL/sec, about 0.74 mL/sec, about 0.75 mL/sec, about 0.76 mL/sec, about 0.77 mL/sec, about 0.78 mL/sec, about 0.79 mL/sec, about 0.80 mL/sec, about 0.81 mL/sec, about 0.82 mL/sec, about 0.83 mL/sec, about 0.84 mL/sec, about 0.85 mL/sec, about 0.86 mL/sec, about 0.87 mL/sec, about 0.88 mL/sec, about 0.89 mL/sec, about 0.90 mL/sec, about 0.91 mL/sec, about 0.92 mL/sec, about 0.93 mL/sec, about 0.94 mL/sec, about 0.95 mL/sec, about 0.96 mL/sec, about 0.97 mL/sec, about 0.98 mL/sec, about 0.99 mL/sec, or about 1.0 mL/sec.

In one embodiment, the disclosed formulation is contained in a prefilled syringe fitted with a needle having a gauge between 20 and 33 wherein the prefilled syringe is contained in a high volume autoinjector disclosed herein and the formulation is administered to the subject at a rate of about 0.05 mL/sec, about 0.06 mL/sec, about 0.07 mL/sec, about 0.08 mL/sec, about 0.09 mL/sec, about 0.10 mL/sec, about 0.11 mL/sec, about 0.12 mL/sec, about 0.13 mL/sec, about 0.14 mL/sec, about 0.15 mL/sec, about 0.16 mL/sec, about 0.17 mL/sec, about 0.18 mL/sec, about 0.19 mL/sec, about 0.20 mL/sec, about 0.21 mL/sec, about 0.22 mL/sec, about 0.23 mL/sec, about 0.24 mL/sec, about 0.25 mL/sec, about 0.31 mL/sec, about 0.32 mL/sec, about 0.33 mL/sec, about 0.34 mL/sec, about 0.35 mL/sec, about 0.36 mL/sec, about 0.37 mL/sec, about 0.38 mL/sec, about 0.39 mL/sec, about 0.4 mL/sec, about 0.41 mL/sec, about 0.42 mL/sec, about 0.43 mL/sec, about 0.44 mL/sec, about 0.45 mL/sec, about 0.46 mL/sec, about 0.47 mL/sec, about 0.48 mL/sec, about 0.49 mL/sec, about 0.50 mL/sec, about 0.51 mL/sec, about 0.52 mL/sec, about 0.53 mL/sec, about 0.54 mL/sec, about 0.55 mL/sec, about 0.56 mL/sec, about 0.57 mL/sec, about 0.58 mL/sec, about 0.59 mL/sec, about 0.60 mL/sec, about 0.61 mL/sec, about 0.62 mL/sec, about 0.63 mL/sec, about 0.64 mL/sec, about 0.65 mL/sec, about 0.66 mL/sec, about 0.67 mL/sec, 0.68 mL/sec, about 0.69 mL/sec, about 0.70 mL/sec, about 0.71 mL/sec, about 0.72 mL/sec, about 0.73 mL/sec, about 0.74 mL/sec, about 0.75 mL/sec, about 0.76 mL/sec, about 0.77 mL/sec, about 0.78 mL/sec, about 0.79 mL/sec, about 0.80 mL/sec, about 0.81 mL/sec, about 0.82 mL/sec, about 0.83 mL/sec, about 0.84 mL/sec, about 0.85 mL/sec, about 0.86 mL/sec, about 0.87 mL/sec, about 0.88 mL/sec, about 0.89 mL/sec, about 0.90 mL/sec, about 0.91 mL/sec, about 0.92 mL/sec, about 0.93 mL/sec, about 0.94 mL/sec, about 0.95 mL/sec, about 0.96 mL/sec, about 0.97 mL/sec, about 0.98 mL/sec, about 0.99 mL/sec, or about 1.0 mL/sec.

In one embodiment, about 3 mL to about 50 mL of the formulation is administered to a subject via subcutaneous administration, wherein the subcutaneous administration occurs at a rate of about 0.10 mL/sec to about 1.0 mL/sec. In one embodiment, about 3 mL to about 15 mL of the formulation is administered to the subject via subcutaneous administration, wherein the subcutaneous administration occurs at a rate of about 0.10 mL/sec to about 1.0 mL/sec. In one embodiment, the formulation is administered subcutaneously to the subject from a prefilled syringe. In one embodiment, the prefilled syringe comprises a needle having a gauge of about 20 to about 31. In one embodiment, the prefilled syringe comprises a needle having a gauge of about 23, about 25, or about 27. In one embodiment, the formulation is administered to the subject from the prefilled syringe using a HVAI described elsewhere herein.

In one embodiment, about 5 mL of the formulation is administered to the subject at a rate of about 0.14 mL/sec to about 0.21 mL/sec. In one embodiment, about 5 mL of the formulation is administered to the subject at a rate of about 0.14 mL/sec to about 0.21 mL/sec from a prefilled syringe using a HVAI. In one embodiment, about 5 mL of the formulation is administered to the subject at a rate of about 0.28 mL/sec to about 0.42 mL/sec. In one embodiment, about 5 mL of the formulation is administered to the subject at a rate of about 0.28 mL/sec to about 0.42 mL/sec from a prefilled syringe using a HVAI. In one embodiment, about 10 mL of the formulation is administered to the subject at a rate of about 0.32 mL/sec to about 0.42 mL/sec. In one embodiment, about 10 mL of the formulation is administered to the subject at a rate of about 0.32 mL/sec to about 0.42 mL/sec from a prefilled syringe using a HVAI. In one embodiment, about 10.5 mL of the formulation is administered to the subject at a rate of about 0.40 mL/sec to about 1.0 mL/sec. In one embodiment, about 10.5 mL of the formulation is administered to the subject at a rate of about 0.40 mL/sec to about 1.0 mL/sec from a prefilled syringe using a HVAI. In one embodiment, about 10.5 mL of the formulation is administered to the subject at a rate of at least 0.7 mL/sec. In one embodiment, about 10.5 mL of the formulation is administered to the subject at a rate of at least 0.7 mL/sec from a prefilled syringe using a HVAI.

In one embodiment, about 5 mL, about 5.5 mL, about 6 mL, about 7 mL, about 8 mL, about 9 mL, about 10 mL, about 10.5 mL, about 11 mL, about 12 mL, about 13 mL, about 14 mL, or about 15 mL of the disclosed formulation can be administered to a subject in 15 seconds or less using a needle having a gauge of 20 to 31. In one embodiment, about 5 mL, about 5.5 mL, about 6 mL, about 7 mL, about 8 mL, about 9 mL, about 10 mL, about 10.5 mL, about 11 mL, about 12 mL, about 13 mL, about 14 mL, or about 15 mL of the disclosed formulation can be administered to a subject in 15 seconds or less using a 27 gauge needle. In one embodiment, about 10.5 mL of the disclosed formulation can be administered to a subject in 15 seconds or less using a 27 gauge needle. In one embodiment, the needle is connected to a syringe wherein the syringe is prefilled with the disclosed formulation. In one embodiment, the prefilled syringe is contained in an autoinjector. In one embodiment, the prefilled syringe is contained in the HVAI described elsewhere herein.

In one embodiment, about 3 mL to about 50 mL of the formulation disclosed herein is administered to the subject with a starting delivery force of about 1 lbf to about 200 lbf, about 1 lbf to about 190 lbf, about 1 lbf to about 180 lbf, about 1 lbf to about 170 lbf, about 1 lbf to about 160 lbf, about 1 lbf to about 150 lbf, about 1 lbf to about 140 lbf, about 1 lbf to about 130 lbf, about 1 lbf to about 120 lbf, about 1 lbf to about 110 lbf, 1 lbf to about 100 lbf, 1 lbf to about 100 lbf, about 1 lbf to about 90 lbf, about 1 lbf to about 80 lbf, about 1 lbf to about 70 lbf, about 1 lbf to about 60 lbf, about 1 lbf to about 50 lbf, about 1 lbf to about 40 lbf, about 1 lbf to about 30 lbf, or about 25 lbf from a prefilled syringe using a HVAI. In one embodiment, about 3 mL to about 50 mL of the formulation disclosed herein is administered to the subject with a starting delivery force of about 1 lbf, about 2 lbf, about 3 lbf, about 4 lbf, 5 lbf, about 6 lbf, about 7 lbf, about 8 lbf, about 9 lbf, about 10 lbf, about 11 lbf, about 12 lbf, about 13 lbf, about 14 lbf, about 15 lbf, about 16 lbf, about 17 lbf, about 18 lbf, about 19 lbf, about 20 lbf, about 21 lbf, about 22 lbf, about 23 lbf, about 24 lbf, about 25 lbf, about 26 lbf, about 27 lbf, about 28 lbf, about 29 lbf, about 30 lbf, about 31 lbf, about 32 lbf, about 33 lbf, about 34 lbf, about 35 lbf, about 36 lbf, about 37 lbf, about 38 lbf, about 39 lbf, about 40 lbf, about 41 lbf, about 42 lbf, about 43 lbf, about 44 lbf, about 45 lbf, about 46 lbf, about 47 lbf, about 48 lbf, about 49 lbf, about 50 lbf, about 51 lbf, about 52 lbf, about 53 lbf, about 54 lbf, about 55 lbf, about 56 lbf, about 57 lbf, about 58 lbf, about 59 lbf, about 60 lbf, about 61 lbf, about 62 lbf, about 63 lbf, about 64 lbf, about 65 lbf, about 66 lbf, about 67 lbf, about 68 lbf, about 69 lbf, about 70 lbf, about 71 lbf, about 72 lbf, about 73 lbf, about 74 lbf, about 75 lbf, about 76 lbf, about 77 lbf, about 78 lbf, about 79 lbf, about 80 lbf, about 81 lbf, about 82 lbf, about 83 lbf, about 84 lbf, about 85 lbf, about 86 lbf, about 87 lbf, about 88 lbf, about 89 lbf, about 90 lbf, about 91 lbf, about 92 lbf, about 93 lbf, about 94 lbf, about 95 lbf, about 96 lbf, about 97 lbf, about 98 lbf, about 99 lbf, about 100 lbf, about 101 lbf, about 102 lbf, about 103 lbf, about 104 lbf, about 105 lbf, about 106 lbf, about 107 lbf, about 108 lbf, about 109 lbf, about 110 lbf, about 111 lbf, about 112 lbf, about 113 lbf, about 114 lbf, about 115 lbf, about 116 lbf, about 117 lbf, about 118 lbf, about 119 lbf, about 120 lbf, about 121 lbf, about 122 lbf, about 123 lbf, about 124 lbf, about 125 lbf, about 126 lbf, about 127 lbf, about 128 lbf, about 129 lbf, about 130 lbf, about 131 lbf, about 132 lbf, about 133 lbf, about 134 lbf, about 135 lbf, about 136 lbf, about 137 lbf, about 138 lbf, about 139 lbf, about 140 lbf, about 141 lbf, about 142 lbf, about 143 lbf, about 144 lbf, about 145 lbf, about 146 lbf, about 147 lbf, about 148 lbf, about 149 lbf, about 150 lbf, about 151 lbf, about 152 lbf, about 153 lbf, about 154 lbf, about 155 lbf, about 156 lbf, about 157 lbf, about 158 lbf, about 159 lbf, about 160 lbf, about 161 lbf, about 162 lbf, about 163 lbf, about 164 lbf, about 165 lbf, about 166 lbf, about 167 lbf, about 168 lbf, about 169 lbf, about 170 lbf, about 171 lbf, about 172 lbf, about 173 lbf, about 174 lbf, about 175 lbf, about 176 lbf, about 177 lbf, about 178 lbf, about 179 lbf, about 180 lbf, about 181 lbf, about 182 lbf, about 183 lbf, about 184 lbf, about 185 lbf, about 186 lbf, about 187 lbf, about 188 lbf, about 189 lbf, about 190 lbf, about 191 lbf, about 192 lbf, about 193 lbf, about 194 lbf, about 195 lbf, about 196 lbf, about 197 lbf, about 198 lbf, about 199 lbf, or about 200 lbf from a prefilled syringe using a HVAI.

In one embodiment, the starting delivery force refers to the starting delivery force exerted on the subject's tissue upon administration of the formulation from a prefilled syringe using a HVAI. In one embodiment, the starting delivery force refers to the starting delivery force exerted the syringe stopper of the prefilled syringe in a HVAI as the disclosed formulation is delivered to a subject. In one embodiment, the starting delivery force refers to the starting delivery force exerted on the formulation upon administration of the formulation from a prefilled syringe using a HVAI. In one embodiment, the starting delivery force refers to the starting delivery force exerted on the prefilled syringe upon administration of the formulation from a prefilled syringe using a HVAI. In one embodiment, the starting delivery force refers to the starting delivery force generated by the HVAI device upon administration of the formulation from a prefilled syringe using a HVAI.

In one embodiment, about 3 mL to about 50 mL of the formulation disclosed herein is administered to the subject with an ending delivery force of about 1 lbf to about 200 lbf, about 1 lbf to about 190 lbf, about 1 lbf to about 180 lbf, about 1 lbf to about 170 lbf, about 1 lbf to about 160 lbf, about 1 lbf to about 150 lbf, about 1 lbf to about 140 lbf, about 1 lbf to about 130 lbf, about 1 lbf to about 120 lbf, about 1 lbf to about 110 lbf, 1 lbf to about 100 lbf, 1 lbf to about 100 lbf, about 1 lbf to about 90 lbf, about 1 lbf to about 80 lbf, about 1 lbf to about 70 lbf, about 1 lbf to about 60 lbf, about 1 lbf to about 50 lbf, about 1 lbf to about 40 lbf, about 1 lbf to about 30 lbf, about 5 lbf to about 30 lbf, or about 5 lbf to about 20 lbf from a prefilled syringe using a HVAI. In one embodiment, about 3 mL to about 50 mL of the formulation disclosed herein is administered to the subject with an ending delivery force of about 1 lbf, about 2 lbf, about 3 lbf, about 4 lbf, 5 lbf, about 6 lbf, about 7 lbf, about 8 lbf, about 9 lbf, about 10 lbf, about 11 lbf, about 12 lbf, about 13 lbf, about 14 lbf, about 15 lbf, about 16 lbf, about 17 lbf, about 18 lbf, about 19 lbf, about 20 lbf, about 21 lbf, about 22 lbf, about 23 lbf, about 24 lbf, about 25 lbf, about 26 lbf, about 27 lbf, about 28 lbf, about 29 lbf, about 30 lbf, about 31 lbf, about 32 lbf, about 33 lbf, about 34 lbf, about 35 lbf, about 36 lbf, about 37 lbf, about 38 lbf, about 39 lbf, about 40 lbf, about 41 lbf, about 42 lbf, about 43 lbf, about 44 lbf, about 45 lbf, about 46 lbf, about 47 lbf, about 48 lbf, about 49 lbf, about 50 lbf, about 51 lbf, about 52 lbf, about 53 lbf, about 54 lbf, about 55 lbf, about 56 lbf, about 57 lbf, about 58 lbf, about 59 lbf, about 60 lbf, about 61 lbf, about 62 lbf, about 63 lbf, about 64 lbf, about 65 lbf, about 66 lbf, about 67 lbf, about 68 lbf, about 69 lbf, about 70 lbf, about 71 lbf, about 72 lbf, about 73 lbf, about 74 lbf, about 75 lbf, about 76 lbf, about 77 lbf, about 78 lbf, about 79 lbf, about 80 lbf, about 81 lbf, about 82 lbf, about 83 lbf, about 84 lbf, about 85 lbf, about 86 lbf, about 87 lbf, about 88 lbf, about 89 lbf, about 90 lbf, about 91 lbf, about 92 lbf, about 93 lbf, about 94 lbf, about 95 lbf, about 96 lbf, about 97 lbf, about 98 lbf, about 99 lbf, about 100 lbf, about 101 lbf, about 102 lbf, about 103 lbf, about 104 lbf, about 105 lbf, about 106 lbf, about 107 lbf, about 108 lbf, about 109 lbf, about 110 lbf, about 111 lbf, about 112 lbf, about 113 lbf, about 114 lbf, about 115 lbf, about 116 lbf, about 117 lbf, about 118 lbf, about 119 lbf, about 120 lbf, about 121 lbf, about 122 lbf, about 123 lbf, about 124 lbf, about 125 lbf, about 126 lbf, about 127 lbf, about 128 lbf, about 129 lbf, about 130 lbf, about 131 lbf, about 132 lbf, about 133 lbf, about 134 lbf, about 135 lbf, about 136 lbf, about 137 lbf, about 138 lbf, about 139 lbf, about 140 lbf, about 141 lbf, about 142 lbf, about 143 lbf, about 144 lbf, about 145 lbf, about 146 lbf, about 147 lbf, about 148 lbf, about 149 lbf, about 150 lbf, about 151 lbf, about 152 lbf, about 153 lbf, about 154 lbf, about 155 lbf, about 156 lbf, about 157 lbf, about 158 lbf, about 159 lbf, about 160 lbf, about 161 lbf, about 162 lbf, about 163 lbf, about 164 lbf, about 165 lbf, about 166 lbf, about 167 lbf, about 168 lbf, about 169 lbf, about 170 lbf, about 171 lbf, about 172 lbf, about 173 lbf, about 174 lbf, about 175 lbf, about 176 lbf, about 177 lbf, about 178 lbf, about 179 lbf, about 180 lbf, about 181 lbf, about 182 lbf, about 183 lbf, about 184 lbf, about 185 lbf, about 186 lbf, about 187 lbf, about 188 lbf, about 189 lbf, about 190 lbf, about 191 lbf, about 192 lbf, about 193 lbf, about 194 lbf, about 195 lbf, about 196 lbf, about 197 lbf, about 198 lbf, about 199 lbf, or about 200 lbf from a prefilled syringe using a HVAI.

In one embodiment, the ending delivery force refers to the ending delivery force exerted on the subject's tissue upon administration of the formulation from a prefilled syringe using a HVAI. In one embodiment, the ending delivery force refers to the ending delivery force exerted the syringe stopper of the prefilled syringe in a HVAI as the disclosed formulation is delivered to a subject. In one embodiment, the ending delivery force refers to the ending delivery force exerted on the formulation upon administration of the formulation from a prefilled syringe using a HVAI. In one embodiment, the ending delivery force refers to the ending delivery force exerted on the prefilled syringe upon administration of the formulation from a prefilled syringe using a HVAI. In one embodiment, the ending delivery force refers to the ending delivery force generated by the HVAI device upon administration of the formulation from a prefilled syringe using a HVAI.

In one embodiment, about 3 mL to about 50 mL of the formulation disclosed herein is administered to the subject with a starting pressure of about 10 psi to about 500 psi, about 10 psi to about 475 psi, about 10 psi to about 450 psi, about 10 psi to about 400 psi, about 10 psi to about 375 psi, about 10 psi to about 350 psi, about 10 psi to about 325 psi, about 10 psi to about 300 psi, about 20 psi to about 300 psi, about 20 psi to about 275 psi, about 30 psi to about 275 psi, about 30 psi to about 250 psi, about 40 psi to about 250 psi, about 40 psi to about 225 psi, about 50 psi to about 225 psi, or about 50 psi to about 200 psi from a prefilled syringe using a HVAI. In one embodiment, about 3 mL to about 50 mL of the formulation disclosed herein is administered to the subject with a starting pressure of about 50 psi, about 55 psi, about 60 psi, about 65 psi, about 70 psi, about 75 psi, about 80 psi, about 85 psi, about 90 psi, about 95 psi, about 100 psi, about 105 psi, about 110 psi, about 115 psi, about 120 psi, about 125 psi, about 130 psi, about 135 psi, about 140 psi, about 145 psi, about 150 psi, about 155 psi, about 160 psi, about 165 psi, about 170 psi, about 175 psi, about 180 psi, about 185 psi, about 190 psi, about 195 psi, or about 200 psi from a prefilled syringe using a HVAI. In one embodiment, about 3 mL to about 50 mL of the formulation disclosed herein is administered to the subject with a starting pressure of about 50 psi, about 51 psi, about 52 psi, about 53 psi, about 54 psi, about 55 psi, about 56 psi, about 57 psi, about 58 psi, about 59 psi, about 60 psi, about 61 psi, about 62 psi, about 63 psi, about 64 psi, about 65 psi, about 66 psi, about 67 psi, about 68 psi, about 69 psi, about 70 psi, about 71 psi, about 72 psi, about 73 psi, about 74 psi, about 75 psi, about 76 psi, about 77 psi, about 78 psi, about 79 psi, about 80 psi, about 81 psi, about 82 psi, about 83 psi, about 84 psi, about 85 psi, about 86 psi, about 87 psi, about 88 psi, about 89 psi, about 90 psi, about 91 psi, about 92 psi, about 93 psi, about 94 psi, about 95 psi, about 96 psi, about 97 psi, about 98 psi, about 99 psi, about 100 psi, about 101 psi, about 102 psi, about 103 psi, about 104 psi, about 105 psi, about 106 psi, about 107 psi, about 108 psi, about 109 psi, about 110 psi, about 111 psi, about 112 psi, about 113 psi, about 114 psi, about 115 psi, about 116 psi, about 117 psi, about 118 psi, about 119 psi, about 120 psi, about 121 psi, about 122 psi, about 123 psi, about 124 psi, about 125 psi, about 126 psi, about 127 psi, about 128 psi, about 129 psi, about 130 psi, about 131 psi, about 132 psi, about 133 psi, about 134 psi, about 135 psi, about 136 psi, about 137 psi, about 138 psi, about 139 psi, about 140 psi, about 141 psi, about 142 psi, about 143 psi, about 144 psi, about 145 psi, about 146 psi, about 147 psi, about 148 psi, about 149 psi, about 150 psi, about 151 psi, about 152 psi, about 153 psi, about 154 psi, about 155 psi, about 156 psi, about 157 psi, about 158 psi, about 159 psi, about 160 psi, about 161 psi, about 162 psi, about 163 psi, about 164 psi, about 165 psi, about 166 psi, about 167 psi, about 168 psi, about 169 psi, about 170 psi, about 171 psi, about 172 psi, about 173 psi, about 174 psi, about 175 psi, about 176 psi, about 177 psi, about 178 psi, about 179 psi, about 180 psi, about 181 psi, about 182 psi, about 183 psi, about 184 psi, about 185 psi, about 186 psi, about 187 psi, about 188 psi, about 189 psi, about 190 psi, about 191 psi, about 192 psi, about 193 psi, about 194 psi, about 195 psi, about 196 psi, about 197 psi, about 198 psi, about 199 psi, or about 200 psi from a prefilled syringe using a HVAI.

In one embodiment, the starting pressure refers to the starting pressure exerted on the subject's tissue upon administration of the formulation from a prefilled syringe using a HVAI. In one embodiment, the starting pressure refers to the starting pressure exerted the syringe stopper of the prefilled syringe in a HVAI as the disclosed formulation is delivered to a subject. In one embodiment, the starting pressure refers to the starting pressure exerted on the formulation upon administration of the formulation from a prefilled syringe using a HVAI. In one embodiment, the starting pressure refers to the starting pressure exerted on the prefilled syringe upon administration of the formulation from a prefilled syringe using a HVAI. In one embodiment, the starting pressure refers to the starting pressure generated by the HVAI device upon administration of the formulation from a prefilled syringe using a HVAI.

In one embodiment about 3 mL to about 50 mL of the formulation disclosed herein is administered to the subject with an ending pressure of about 1 psi to about 250 psi, about 1 psi to about 225 psi, about 1 psi to about 200 psi, about 10 psi to about 200 psi, about 10 psi to about 175 psi, about 10 psi to about 150 psi, about 10 psi to about 125 psi, about 15 psi to about 125 psi, about 15 psi to about 100 psi, about 15 psi to about 80 psi, about 15 psi to about 75 psi, or about 20 psi to about 75 psi from a prefilled syringe using a HVAI. In one embodiment about 3 mL to about 50 mL of the formulation disclosed herein is administered to the subject with an ending pressure of about 20 psi, about 25 psi, about 30 psi, about 35 psi, about 40 psi, about 45 psi, about 50 psi, about 55 psi, about 60 psi, about 65 psi, about 70 psi, or about 75 psi from a prefilled syringe using a HVAI. In one embodiment about 3 mL to about 50 mL of the formulation disclosed herein is administered to the subject with an ending pressure of about 20 psi, about 21 psi, about 22 psi, about 23 psi, about 24 psi, about 25 psi, about 26 psi, about 27 psi, about 28 psi, about 29 psi, about 30 psi, about 31 psi, about 32 psi, about 33 psi, about 34 psi, about 35 psi, about 36 psi, about 37 psi, about 38 psi, about 39 psi, about 40 psi, about 41 psi, about 42 psi, about 43 psi, about 44 psi, about 45 psi, about 46 psi, about 47 psi, about 48 psi, about 49 psi, about 50 psi, about 51 psi, about 52 psi, about 53 psi, about 54 psi, about 55 psi, about 56 psi, about 57 psi, about 58 psi, about 59 psi, about 60 psi, about 61 psi, about 62 psi, about 63 psi, about 64 psi, about 65 psi, about 66 psi, about 67 psi, about 68 psi, about 69 psi, about 70 psi, about 71 psi, about 72 psi, about 73 psi, about 74 psi, or about 75 psi from a prefilled syringe using a HVAI.

In one embodiment, the ending pressure refers to the ending pressure exerted on the subject's tissue upon administration of the disclosed formulation from a prefilled syringe using a HVAI. In one embodiment, the ending pressure refers to the ending pressure exerted the syringe stopper of the prefilled syringe in a HVAI as the disclosed formulation is delivered to a subject. In one embodiment, the ending pressure refers to the ending pressure exerted on the formulation upon administration of the formulation from a prefilled syringe using a HVAI. In one embodiment, the ending pressure refers to the ending pressure exerted on the prefilled syringe upon administration of the formulation from a prefilled syringe using a HVAI. In one embodiment, the ending pressure refers to the ending pressure generated by the HVAI device upon administration of the formulation from a prefilled syringe using a HVAI.

In one embodiment, the administration of the formulation to the subject requires less applied force when compared to a similar formulation that does not comprise a hyaluronidase enzyme.

In one embodiment, about 3 mL to about 50 mL of the formulation disclosed herein is administered at a rate of about 0.05 mL/sec to about 1.0 mL/sec with an applied force of about 10 N to about 200 N about 20 N to about 150 N, about 10 N, about 20 N, about 30 N, about 40 N, about 50 N, about 60 N, about 70 N, about 80 N, about 90 N, about 100 N, about 110 N, about 120 N, about 130 N, about 140 N, about 150 N, about 160 N, about 170 N, about 180 N, about 190 N, or about 200 N.

In one embodiment, about 5 mL of the formulation is administered to the subject at a rate of about 0.14 mL/sec to about 0.21 mL/sec with an applied force of about 10 N to about 45 N. In one embodiment, about 5 mL of the formulation is administered to the subject at a rate of about 0.14 mL/sec to about 0.21 mL/sec using a 25 gauge needle with an applied force of about 10 N to about 45 N. In one embodiment, about 5 mL of the formulation is administered to the subject at a rate of about 0.14 mL/sec to about 0.21 mL/sec using a 25 gauge needle with an applied force of about 15 N to about 25 N. In another embodiment, about 5 mL of the formulation is administered to the subject at a rate of about 0.14 mL/sec to about 0.21 mL/sec using a 25 gauge needle with an applied force of about 22 N to about 40 N. In one embodiment, the about 10 mL formulation is administered to the subject at a rate of about 0.32 mL/sec to about 0.42 mL/sec with an applied force of about 25 N to about 50 N.

In one embodiment, the applied force at which the formulation is administered to the subject at a specific rate is dependent upon the gauge of the needle used to deliver the formulation to the subject. In one embodiment, the applied force at which the formulation is administered to the subject at a specific rate is dependent upon the gauge of the needle used to deliver the formulation to the subject and the inner diameter of the needle used to deliver the formulation to the subject. Therefore, in one embodiment, the use of a 25 gauge needle with a larger inner diameter (i.e., a thin wall needle such as a Terumo needle) will require less applied force to administer the disclosed formulation to a subject at a specific rate than the use of a 25 gauge needle with a smaller inner diameter (such as a BD needle). In one embodiment, about 5 mL of the formulation is administered to the subject at a rate of about 0.14 mL/sec to about 0.21 mL/sec using a 25 gauge needle with an applied force of about 15 N to about 25 N, wherein the needle is a thin wall needle (e.g., a Terumo needle). In another embodiment, about 5 mL of the formulation is administered to the subject at a rate of about 0.14 mL/sec to about 0.21 mL/sec using a 25 gauge needle with an applied force of about 22 N to about 40 N, wherein the needle is not a thin wall needle (e.g., a BD needle).

In one embodiment, the about 10 mL formulation is administered to the subject using a 25 gauge needle at a rate of about 0.32 mL/sec to about 0.42 mL/sec with an applied force of about 25 N to about 50 N.

In one embodiment, about 5 mL of the formulation is administered to the subject at a rate of about 0.14 mL/sec to about 0.21 mL/sec with an applied force of about 10 N, about 11 N, about 12 N, about 13 N, about 14 N, about 15 N, about 16 N, about 17 N, about 18 N, about 19 N, about 20, about 21 N, about 22 N, about 23 N, about 24 N, about 25 N, about 26 N, about 27 N, about 28 N, about 29 N, about 30 N, about 31 N, about 32 N, about 33 N, about 35 N, about 36 N, about 37 N, about 38 N, about 39 N, about 40 N, about 41 N, about 42 N, about 43 N, about 44 N, or about 45 N. In one embodiment, about 5 mL of the formulation is administered to the subject at a rate of about 0.14 mL/sec to about 0.21 mL/sec using a 25 gauge needle with an applied force of about 10 N, about 11 N, about 12 N, about 13 N, about 14 N, about 15 N, about 16 N, about 17 N, about 18

N, about 19 N, about 20, about 21 N, about 22 N, about 23 N, about 24 N, about 25 N, about 26 N, about 27 N, about 28 N, about 29 N, about 30 N, about 31 N, about 32 N, about 33 N, about 35 N, about 36 N, about 37 N, about 38 N, about 39 N, about 40 N, about 41 N, about 42 N, about 43 N, about 44 N, or about 45 N.

In one embodiment, the about 10 mL formulation is administered to the subject at a rate of about 0.32 mL/sec to about 0.42 mL/sec with an applied force of about 25 N, about 26 N, about 27 N, about 28 N, about 29 N, about 30 N, about 31 N, about 32 N, about 33 N, about 35 N, about 36 N, about 37 N, about 38 N, about 39 N, about 40 N, about 41 N, about 42 N, about 43 N, about 44 N, about 46 N, about 47 N, about 48 N, about 49 N, or about 50 N. In one embodiment, about 10 mL formulation is administered to the subject at a rate of about 0.32 mL/sec to about 0.42 mL/sec using a 25 gauge needle with an applied force of about 25 N, about 26 N, about 27 N, about 28 N, about 29 N, about 30 N, about 31 N, about 32 N, about 33 N, about 35 N, about 36 N, about 37 N, about 38 N, about 39 N, about 40 N, about 41 N, about 42 N, about 43 N, about 44 N, about 45 N, about 46 N, about 47 N, about 48 N, about 49 N, or about 50 N.

The HVAI may deliver the full deliverable volume of the formulation in 5 seconds, 10 seconds, 15 seconds, 20 seconds, 25 seconds, 30 seconds, 35 seconds, 40 seconds, 45 seconds, 50 seconds, 55 seconds, 60 seconds, 70 seconds, 80 seconds, 90 seconds, 100 seconds, 110 seconds, or 120 seconds.

In one embodiment, the hyaluronidase enzyme allows the formulation to be administered to the subject faster than a comparable formulation that does not comprise the hyaluronidase enzyme. In one embodiment, the disclosed formulation can be administered about 20%, about 22%, about 24%, about 26%, about 28%, about 30%, about 32%, about 34%, about 36%, about 38%, about 40%, about 42%, about 44%, about 46%, or about 48% faster than a comparable formulation that does not comprise the hyaluronidase enzyme when both are administered using the same HVAI fitted with a 23 gauge needle. In one embodiment, the disclosed formulation can be administered about 2%, about 4%, about 6%, about 8%, about 10%, about 12%, about 14%, about 16%, about 18%, or about 20% faster than a comparable formulation that does not comprise the hyaluronidase enzyme when both are administered using the same HVAI fitted with a 25 gauge needle.

In one embodiment, the injection of a high volume of the disclosed formulation in a subject leads to fewer side effects in the subject compared to an identical subject administered the same volume of a comparable formulation that does not comprise the hyaluronidase enzyme. In one embodiment, the injection of a high volume disclosed elsewhere herein with the disclosed formulation has reduced back leakage compared similar formulation that does not comprise the hyaluronidase enzyme. In one embodiment, the back leakage is reduced about 54%, about 56%, about 58%, about 60%, about 62%, about 64%, about 66%, about 68%, about 70%, about 72%, about 74%, about 76%, or about 78% when a high volume of the disclosed formulation is administered to a subject using a HVAI fitted with a 23 gauge needle compared to a similar formulation that does not comprise the hyaluronidase enzyme. In one embodiment, the back leakage is reduced about 62%, about 64%, about 68%, about 70%, about 72%, about 74%, about 76%, about 78%, about 80%, about 82%, about 84%, or about 86% when a high volume of the disclosed formulation is administered to a subject using a HVAI fitted with a 25 gauge needle compared to a similar formulation that does not comprise the hyaluronidase enzyme.

In one embodiment, the swelling (bleb) volume is reduced following the injection of the disclosed formulation into a subject when compared to a similar formulation that does not comprise the hyaluronidase enzyme. In one embodiment, the swelling height is reduced following the injection of the disclosed formulation when compared to a similar formulation that does not comprise the hyaluronidase enzyme. In one embodiment, the swelling size is reduced following the injection of the disclosed formulation when compared to a similar formulation that does not comprise the hyaluronidase enzyme. In one embodiment, the swelling area is reduced following the injection of the disclosed formulation when compared to a similar formulation that does not comprise the hyaluronidase enzyme. In one embodiment, the swelling induration following the initial injection of the disclosed formulation is minimized compared to a similar formulation that does not comprise the hyaluronidase enzyme. In one embodiment, the swelling resolves quicker when the disclosed formulation is injected compared to a similar formulation that does not comprise the hyaluronidase enzyme. In one embodiment, the disclosed formulation permits for more consistent delivery (i.e., time to delivery, reduction in bleb swelling volume, height and induration) from injection to injection, compared to a similar formulation that does not comprise the hyaluronidase enzyme. In one embodiment, the disclosed formulation permits for faster delivery of the full volume from a HVAI than a comparable formulation that does not comprise the hyaluronidase enzyme which results in less pain and discomfort for the subject.

Clauses of the disclosure.

Clause 1. A method of treating a disease or disorder in a subject in need thereof, the method comprising administering to the subject via subcutaneous administration about 3 mL to about 50 mL of a formulation comprising a hyaluronidase enzyme and a therapeutically effective amount of an active ingredient.

Clause 2. The method of clause 1, wherein the hyaluronidase enzyme is a recombinant human hyaluronidase enzyme.

Clause 3. The method of clause 1, wherein the hyaluronidase enzyme is recombinant human hyaluronidase PH20 enzyme.

Clause 4. The method of clause 1, wherein the hyaluronidase enzyme has an activity of about 150 U/mL to about 150 kU/mL.

Clause 5. The method of clauses 1-4, wherein the concentration of the hyaluronidase enzyme in the formulation is about 500 U/mL to about 5,000 U/mL.

Clause 6. The method of any one of clauses 1-5, wherein the concentration of the hyaluronidase enzyme in the formulation is about 1,500 U/mL to about 10,000 U/mL.

Clause 7. The method of any one of clauses 1-6, wherein the active ingredient is a small molecule, a peptide fragment, a biologic, or a nanoparticle.

Clause 8. The method of any one of clauses 1-7, wherein the active ingredient is an antibody, an antibody fragment, or a small molecule antiviral.

Clause 9. The method of any one of clauses 1-8, comprising administering about 10 mL to about 20 mL of the formulation to the subject.

Clause 10. The method of any one of clauses 1-8, comprising administering about 3 mL, about 4 mL, about 5 mL, about 5.5 mL, about 6 mL, about 7 mL, about 8 mL, about 9 mL, about 10 mL, about 11 mL, about 12 mL, about 13 mL, about 14 mL, about 15 mL, about 16 mL, about 17 mL, about 18 mL, about 19 mL, about 20 mL, about 21 mL, about 22 mL, about 23 mL, about 24 mL, or about 25 mL to the subject.

Clause 11. The method of any one of clauses 1-10, comprising administering the formulation using a high volume autoinjector.

Clause 12. The method of any one of clauses 1-11, wherein the formulation is in a prefilled syringe.

Clause 13. The method of clause 12, wherein the prefilled syringe contains 3 mL, about 4 mL, about 5 mL, about 5.5 mL, about 6 mL, about 7 mL, about 8 mL, about 9 mL, about 10 mL, about 11 mL, about 12 mL, about 13 mL, about 14 mL, about 15 mL, about 16 mL, about 17 mL, about 18 mL, about 19 mL, about 20 mL, about 21 mL, about 22 mL, about 23 mL, about 24 mL, or about 25 mL of the formulation.

Clause 14. The method of clause 12 or 13, wherein the prefilled syringe comprises a needle having a gauge of about 20 to about 27.

Clause 15. The method of any one of clauses 12-14, wherein the prefilled syringe comprises a 20 gauge needle, a 21 gauge needle, a 22 gauge needle, a 23 gauge needle, a 24 gauge needle, a 25 gauge needle, a 26 gauge needle, a 27 gauge needle, a 28 gauge needle, a 29 gauge needle, a 30 gauge needle, or a 31 gauge needle.

Clause 16. The method of any one of clauses 1-15, comprising administering the formulation at a rate of about 0.08 to about 0.75 mL/sec.

Clause 17. The method of any one of clauses 1-16, wherein the formulation has a viscosity of about 1 cP to about 50 cP.

Clause 18. The method of any one of clauses 1-17, wherein the administration takes about 20 seconds to about 40 seconds.

Clause 19. The method of any one of clauses 1-18, wherein the administration takes about 26 seconds to about 30 seconds.

Clause 20. The method of any one of clauses 1-19, wherein administration of the formulation is faster than a comparable formulation that does not comprise a hyaluronidase enzyme.

Clause 21. The method of any one of clauses 1-20, wherein administration of the formulation causes fewer side effects in the subject when compared to a similar formulation that does not comprise a hyaluronidase enzyme.

Clause 22. The method of any one of clauses 1-21, wherein administration of the formulation causes less pain and discomfort in the subject when compared to a similar formulation that does not comprise a hyaluronidase enzyme.

Clause 23. The method of any one of clauses 1-22, wherein administration of the formulation causes less back leakage at the injection site when compared to a similar formulation that does not comprise a hyaluronidase enzyme.

Clause 24. The method of clause 23, wherein the back leakage at the injection site is about 85% to about 30% less when compared to a similar formulation that does not comprise a hyaluronidase enzyme.

Clause 25. The method of any one of clauses 1-24, wherein administration of the formulation causes less swelling volume and/or swelling height at the injection site when compared to a similar formulation that does not comprise a hyaluronidase enzyme.

Clause 26. The method of clause 25, wherein the formulation causes about 35% to about 5% less swelling and/or swelling height the injection site when compared to a similar formulation that does not comprise a hyaluronidase enzyme.

Clause 27. The method of any one of clauses 1-26, wherein administration of the formulation yields a lower bleb swelling size, less bleb induration, and/or quicker bleb resolution when compared to a similar formulation that does not comprise a hyaluronidase enzyme.

Clause 28. The method of any one of clauses 1-27, wherein the subject is a human.

Clause 29. The method of any one of clauses 1-28, wherein the subject self-administers the formulation.

Clause 30. The method of any one of clauses 1-28, wherein a healthcare provider or a caregiver administers the formulation to the subject.

Clause 31. The method of any one of clauses 1-30, wherein the subcutaneous administration is a single injection.

Clause 32. The method of any one of clauses 1-30, wherein the subcutaneous administration comprises two or more injections.

Clause 33. The method of any one of clauses 1-30, wherein the subcutaneous administration is delivered via an on body device.

Clause 101. A method of treating a disease or disorder in a subject in need thereof, the method comprising administering to the subject via subcutaneous administration about 3 mL to about 50 mL of a formulation comprising a therapeutically effective amount of an active ingredient selected from a small molecule, a peptide fragment, a biologic, a nanoparticle, an antibody, an antibody fragment, and a small molecule antiviral, wherein the subcutaneous administration occurs via a high volume autoinjector with a starting delivery force of about 5 lbf to about 50 lbf, an ending delivery force of about 5 lbf to about 20 lbf, a starting pressure of about 50 psi to about 200 psi, and/or an ending pressure of about 20 psi to about 75 psi.

Clause 102. The method of claim 101, wherein the formulation further comprises a hyaluronidase enzyme.

Clause 103. The method of claim 102, wherein the hyaluronidase enzyme is a recombinant human hyaluronidase enzyme.

Clause 104. The method of claim 102 or 103, wherein the hyaluronidase enzyme is recombinant human hyaluronidase PH20 enzyme.

Clause 105. The method of any one of claims 102-104, wherein the hyaluronidase enzyme has an activity of about 150 U/mL to about 150 kU/mL.

Clause 106. The method of any one of claims 102-104, wherein the hyaluronidase enzyme has an activity of about 500 U/mL to about 5,000 U/mL.

Clause 107. The method of any one of claims 102-104, wherein the hyaluronidase enzyme has an activity of about 1,500 U/mL to about 10,000 U/mL.

Clause 108. The method of any one of claims 101-107, wherein the active ingredient is a small molecule, a peptide fragment, a biologic, or a nanoparticle.

Clause 109. The method of any one of claims 101-108, wherein the active ingredient is an antibody, an antibody fragment, or a small molecule antiviral.

Clause 110. The method of any one of claims 101-109, comprising administering to the subject about 10 mL to about 20 mL of the formulation.

Clause 111. The method of any one of claims 101-110, comprising administering to the subject about 3 mL to about 15 mL of the formulation.

Clause 112. The method of any one of claims 101-111, comprising administering to the subject about 3 mL, about 3.1 mL, about 3.2 mL, about 3.4 mL, about 3.5 mL, about 3.6 mL, about 3.7 mL, about 3.8 mL, about 3.9 mL, about 4 mL, about 4.1 mL, about 4.2 mL, about 4.3 mL, about 4.4 mL, about 4.5 mL, about 5 mL, about 5.1 mL, about 5.2 mL, about 5.3 mL, about 5.4 mL, about 5.5 mL, about 5.6 mL, about 5.7 mL, about 5.8 mL, about 5.9 mL, about 6 mL, about 6.1 mL, about 6.2 mL, about 6.3 mL, about 6.4 mL, about 6.5 mL, about 6.6 mL, about 6.7 mL, about 6.8 mL, about 6.9 mL, about 7 mL, about 7.1 mL, about 7.2 mL, about 7.3 mL about 7.4 mL, about 7.5 mL, about 7.6 mL, about 7.7 mL, about 7.8 mL, about 7.9 mL, about 8 mL, about 8.1 mL, about 8.2 mL, about 8.3 mL, about 8.4 mL, about 8.5 mL, about 8.6 mL, about 8.7 mL, about 8.8 mL, about 8.9 mL, about 9 mL, about 9.1 mL, about 9.2 mL, about 9.3 mL, about 9.4 mL, about 9.5 mL, about 9.6 mL, about 9.7 mL, about 9.8 mL, about 9.9 mL, about 10 mL, about 10.1 mL, about 10.2 mL, about 10.3 mL, about 10.4 mL, about 10.5 mL, about 10.6 mL, about 10.7 mL, about 10.8 mL, about 10.9 mL, about 11 mL, about 11.1 mL, about 11.2 mL, about 11.3 mL, about 11.4 mL, about 11.5 mL, about 11.6 mL, about 11.7 mL, about 11.8 mL, about 11.9 mL, about 12 mL, about 12.1 mL, about 12.2 mL, about 12.3 mL, about 12.4 mL, about 12.5 mL, about 12.6 mL, about 12.7 mL, about 12.8 mL, about 12.9 mL, about 13 mL, about 13.1 mL, about 13.2 mL, about 13.3 mL, about 13.4 mL, about 13.5 mL, about 13.6 mL, about 13.7 mL, about 13.8 mL, about 13.9 mL, about 14 mL, about 14.1 mL, about 14.2 mL, about 14.3 mL, about 14.4 mL, about 14.5 mL, about 14.6 mL, about 14.7 mL, about 14.8 mL, about 14.9 mL, about 15 mL, about 15.1 mL, about 15.2 mL, about 15.3 mL, about 15.4 mL, about 15.5 mL, about 15.6 mL, about 15.7 mL, about 15.8 mL, about 15.9 mL, about 16 mL, about 16.1 mL, about 16.2 mL, about 16.3 mL, about 16.4 mL, about 16.5 mL, about 16.6 mL, about 16.7 mL, about 16.8 mL, about 16.9 mL about 17 mL, about 17.1 mL, about 17.2 mL, about 17.3 mL, about 17.4 mL, about 17.5 mL, about 17.6 mL, about 17.7 mL, about 17.8 mL, about 17.9 mL, about 18 mL, about 18.1 mL, about 18.2 mL, about 18.3 mL, about 18.4 mL, about 18.5 mL, about 18.6 mL, about 18.7 mL, about 18.8 mL, about 18.9 mL, about 19 mL, about 19.1 mL, about 19.2 mL, about 19.3 mL, about 19.4 mL, about 19.5 mL, about 19.6 mL, about 19.7 mL, about 19.8 mL, about 19.9 mL, about 20 mL, about 20.1 mL, about 20.2 mL, about 20.3 mL, about 20.4 mL, about 20.5 mL, about 20.6 mL, about 20.7 mL, about 20.8 mL, about 20.9 mL, about 21 mL, about 21.1 mL, about 21.2 mL, about 21.3 mL, about 21.4 mL, about 21.5 mL, about 21.6 mL, about 21.7 mL, about 21.8 mL, about 21.9 mL, about 22 mL, about 22.1 mL, about 22.2 mL, about 22.3 mL, about 22.4 mL, about 22.5 mL, about 22.6 mL, about 22.7 mL, about 22.8 mL, about 22.9 mL, about 23 mL, about 23.1 mL, about 23.2 mL, about 23.3 mL, about 23.4 mL, about 23.5 mL, about 23.6 mL, about 23.7 mL, about 23.8 mL, about 23.9 mL, about 24 mL, about 24.1 mL, about 24.2 mL, about 24.3 mL, about 24.4 mL, about 24.5 mL, about 24.6 mL, about 24.7 mL, about 24.8 mL, about 24.9 mL, or about 25 mL.

Clause 113. The method of any one of claims 101-112, comprising administering the formulation using a high volume autoinjector.

Clause 114. The method of any one of claims 101-113, comprising administering the formulation with a starting delivery force of about 3 lbf to about 50 lbf using a high volume autoinjector.

Clause 115. The method of any one of claims 101-114, comprising administering the formulation with an ending delivery force of about 5 lbf to about 20 lbf using a high volume autoinjector.

Clause 116. The method of any one of claims 101-115, comprising administering the formulation with a starting pressure of about 50 psi to about 200 psi using a high volume autoinjector.

Clause 117. The method of any one of claims 101-116, comprising administering the formulation with an ending pressure of about 20 psi to about 75 psi using a high volume autoinjector.

Clause 118. The method of any one of claims 101-117, wherein the formulation is in a prefilled syringe.

Clause 119. The method of claim 118, wherein the prefilled syringe contains about 3 mL, about 3.1 mL, about 3.2 mL, about 3.4 mL, about 3.5 mL, about 3.6 mL, about 3.7 mL, about 3.8 mL, about 3.9 mL, about 4 mL, about 4.1 mL, about 4.2 mL, about 4.3 mL, about 4.4 mL, about 4.5 mL, about 5 mL, about 5.1 mL, about 5.2 mL, about 5.3 mL, about 5.4 mL, about 5.5 mL, about 5.6 mL, about 5.7 mL, about 5.8 mL, about 5.9 mL, about 6 mL, about 6.1 mL, about 6.2 mL, about 6.3 mL, about 6.4 mL, about 6.5 mL, about 6.6 mL, about 6.7 mL, about 6.8 mL, about 6.9 mL, about 7 mL, about 7.1 mL, about 7.2 mL, about 7.3 mL about 7.4 mL, about 7.5 mL, about 7.6 mL, about 7.7 mL, about 7.8 mL, about 7.9 mL, about 8 mL, about 8.1 mL, about 8.2 mL, about 8.3 mL, about 8.4 mL, about 8.5 mL, about 8.6 mL, about 8.7 mL, about 8.8 mL, about 8.9 mL, about 9 mL, about 9.1 mL, about 9.2 mL, about 9.3 mL, about 9.4 mL, about 9.5 mL, about 9.6 mL, about 9.7 mL, about 9.8 mL, about 9.9 mL, about 10 mL, about 10.1 mL, about 10.2 mL, about 10.3 mL, about 10.4 mL, about 10.5 mL, about 10.6 mL, about 10.7 mL, about 10.8 mL, about 10.9 mL, about 11 mL, about 11.1 mL, about 11.2 mL, about 11.3 mL, about 11.4 mL, about 11.5 mL, about 11.6 mL, about 11.7 mL, about 11.8 mL, about 11.9 mL, about 12 mL, about 12.1 mL, about 12.2 mL, about 12.3 mL, about 12.4 mL, about 12.5 mL, about 12.6 mL, about 12.7 mL, about 12.8 mL, about 12.9 mL, about 13 mL, about 13.1 mL, about 13.2 mL, about 13.3 mL, about 13.4 mL, about 13.5 mL, about 13.6 mL, about 13.7 mL, about 13.8 mL, about 13.9 mL, about 14 mL, about 14.1 mL, about 14.2 mL, about 14.3 mL, about 14.4 mL, about 14.5 mL, about 14.6 mL, about 14.7 mL, about 14.8 mL, about 14.9 mL, about 15 mL, about 15.1 mL, about 15.2 mL, about 15.3 mL, about 15.4 mL, about 15.5 mL, about 15.6 mL, about 15.7 mL, about 15.8 mL, about 15.9 mL, about 16 mL, about 16.1 mL, about 16.2 mL, about 16.3 mL, about 16.4 mL, about 16.5 mL, about 16.6 mL, about 16.7 mL, about 16.8 mL, about 16.9 mL about 17 mL, about 17.1 mL, about 17.2 mL, about 17.3 mL, about 17.4 mL, about 17.5 mL, about 17.6 mL, about 17.7 mL, about 17.8 mL, about 17.9 mL, about 18 mL, about 18.1 mL, about 18.2 mL, about 18.3 mL, about 18.4 mL, about 18.5 mL, about 18.6 mL, about 18.7 mL, about 18.8 mL, about 18.9 mL, about 19 mL, about 19.1 mL, about 19.2 mL, about 19.3 mL, about 19.4 mL, about 19.5 mL, about 19.6 mL, about 19.7 mL, about 19.8 mL, about 19.9 mL, about 20 mL, about 20.1 mL, about 20.2 mL, about 20.3 mL, about 20.4 mL, about 20.5 mL, about 20.6 mL, about 20.7 mL, about 20.8 mL, about 20.9 mL, about 21 mL, about 21.1 mL, about 21.2 mL, about 21.3 mL, about 21.4 mL, about 21.5 mL, about 21.6 mL, about 21.7 mL, about 21.8 mL, about 21.9 mL, about 22 mL, about 22.1 mL, about 22.2 mL, about 22.3 mL, about 22.4 mL, about 22.5 mL, about 22.6 mL, about 22.7 mL, about 22.8 mL, about 22.9 mL, about 23 mL, about 23.1 mL, about 23.2 mL, about 23.3 mL, about 23.4 mL, about 23.5 mL, about 23.6 mL, about 23.7 mL, about 23.8 mL, about 23.9 mL, about 24 mL, about 24.1 mL, about 24.2 mL, about 24.3 mL, about 24.4 mL, about 24.5 mL, about 24.6 mL, about 24.7 mL, about 24.8 mL, about 24.9 mL, or about 25 mL of the formulation.

Clause 120. The method of claim 118 or 119, wherein the prefilled syringe comprises a needle having a gauge of about 20 to about 33.

Clause 121. The method of any one of claims 118-120, wherein the prefilled syringe comprises a 20 gauge needle, a 21 gauge needle, a 22 gauge needle, a 23 gauge needle, a 24 gauge needle, a 25 gauge needle, a 26 gauge needle, a 27 gauge needle, a 28 gauge needle, a 29 gauge needle, a 30 gauge needle, a 31 gauge needle, a 32 gauge needle, or a 33 gauge needle.

Clause 122. The method of any one of claims 101-121, comprising administering the formulation at a rate of about 0.08 to about 1.00 mL/sec.

Clause 123. The method of any one of claims 101-122, comprising administering the formulation at a rate of at least about 0.08 to about 1.0 mL/sec.

Clause 124. The method of any one of claims 101-122, comprising administering the formulation at a rate of at least or faster than about 0.08 to about 1.00 mL/sec.

Clause 125. The method of any one of claims 101-124, wherein the administration takes about 10 seconds to about 40 seconds.

Clause 126. The method of any one of claims 101-124, wherein the administration takes at least about 10 seconds to about 40 seconds.

Clause 127. The method of any one of claims 101-124, wherein the administration takes at least or less than about 10 seconds to about 40 seconds.

Clause 128. The method of any one of claims 101-124, wherein the administration takes about 15 seconds to about 30 seconds.

Clause 129. The method of any one of claims 101-124, wherein the administration takes at least about 15 seconds to about 30 seconds.

Clause 130. The method of any one of claims 101-124, wherein the administration takes at least or less than about 15 seconds to about 30 seconds.

Clause 131. The method of any one of claims 101-124, comprising administering about 5 mL of the formulation at a rate of about 0.14 mL/sec to about 0.21 mL/sec.

Clause 132. The method any one of claims 101-124, comprising administering about 10 mL of the formulation at a rate of about 0.32 mL/sec to about 0.42 mL/sec.

Clause 133. The method of any one of claims 101-132 wherein the formulation has a viscosity of about 1 cP to about 50 cP.

Clause 134. The method of any one of claims 101-132, wherein administration of the formulation requires less applied force when compared to a similar formulation that does not comprise a hyaluronidase enzyme.

Clause 135. The method of any one of claims 101-134, comprising administering about 5 mL of the formulation at a rate of about 0.14 mL/sec to about 0.21 mL/sec with an applied force of about 10 N to about 45 N.

Clause 136. The method of claim 135, comprising administering the formulation to the subject using a prefilled syringe comprising a 25 gauge needle.

Clause 137. The method of any one of claims 101-134, comprising administering about 10 mL of the formulation to the subject at a rate of about 0.32 mL/sec to about 0.42 mL/sec with an applied force of about 25 N to about 50 N.

Clause 138. The method of claim 137, comprising administering the formulation to the subject using a prefilled syringe comprising a 25 gauge needle.

Clause 139. The method of any one of claims 102-138, wherein administration of the formulation is faster when compared to a similar formulation that does not comprise a hyaluronidase enzyme.

Clause 140. The method of any one of claims 102-139, wherein administration of the formulation causes fewer side effects in the subject when compared to a similar formulation that does not comprise a hyaluronidase enzyme.

Clause 141. The method of any one of claims 102-140, wherein administration of the formulation causes less pain and discomfort in the subject when compared to a similar formulation that does not comprise a hyaluronidase enzyme.

Clause 142. The method of any one of claims 102-141, wherein administration of the formulation causes less back leakage at the injection site when compared to a similar formulation that does not comprise a hyaluronidase enzyme.

Clause 143. The method of claim 142, wherein the back leakage at the injection site is about 85% to about 30% less when compared to a similar formulation that does not comprise a hyaluronidase enzyme.

Clause 144. The method of any one of claims 102-143, wherein administration of the formulation causes less swelling volume and/or swelling height at the injection site when compared to a similar formulation that does not comprise a hyaluronidase enzyme.

Clause 145. The method of claim 144, wherein the formulation causes about 35% to about 5% less swelling and/or swelling height the injection site when compared to a similar formulation that does not comprise a hyaluronidase enzyme.

Clause 146. The method of any one of claims 102-145, wherein administration of the formulation yields a lower bleb swelling size, less bleb induration, and/or quicker bleb resolution when compared to a similar formulation that does not comprise a hyaluronidase enzyme.

Clause 147. The method of any one of claims 101-146, wherein administration of the formulation yields more consistent delivery times when compared to a similar formulation that does not comprise a hyaluronidase enzyme.

Clause 148. The method of any one of claims 101-147, wherein the subject is human.

Clause 149. The method of any one of claims 101-148, wherein the administering comprises the subject self-administering the formulation.

Clause 150. The method of any one of claims 101-149 wherein the administering comprises a healthcare provider or a caregiver administering the formulation to the subject.

Clause 151. The method of any one of claims 101-150, wherein the subcutaneous administration comprises a single injection.

Clause 152. The method of any one of claims 101-150, wherein the subcutaneous administration comprises two or more injections.

Clause 153. The method of any one of claims 101-152, wherein the subcutaneous administration is delivered via an on body device.

Clause 154. A pharmaceutical kit comprising a high volume autoinjector and about 3 mL to about 50 mL of a formulation comprising a therapeutically effective amount of an active ingredient selected from a small molecule, a peptide fragment, a biologic, a nanoparticle, an antibody, an antibody fragment, and a small molecule antiviral.

Clause 155. The pharmaceutical kit of claim 154, wherein the formulation further comprises a hyaluronidase enzyme.

Clause 156. The pharmaceutical kit of claim 154, further comprising instructions for administering a hyaluronidase enzyme to a subject in need thereof.

Clause 157. The pharmaceutical kit of claim 154, further comprising instructions for administering a hyaluronidase enzyme to a subject in need thereof concurrently or sequentially with the formulation comprising the active ingredient.

Clause 158. The pharmaceutical kit of any one of claims 154-157, wherein the high volume autoinjector is configured to subcutaneously administer the formulation to a subject at a rate of about 0.05 mL/sec to about 1.0 mL/sec.

Clause 159. The pharmaceutical kit of claim 158, wherein the high volume autoinjector is configured to subcutaneously administer the formulation from a prefilled syringe having a volume of about 3 mL to about 15 mL.

Clause 160. The pharmaceutical kit of claim 159, wherein the prefilled syringe comprises a needle having a gauge of about 20 to about 33.

Clause 161. The pharmaceutical kit of any one of claims 154-160, wherein the high volume autoinjector is configured to subcutaneously administer the formulation to a subject at a rate of about 0.05 mL/sec to about 0.10 mL/sec.

Clause 162. The pharmaceutical kit of any one of claims 154-160, wherein the high volume autoinjector is configured to subcutaneously administer the formulation to a subject at a rate of about 0.10 mL/sec to about 0.20 mL/sec.

Clause 163. The pharmaceutical kit of any one of claims 154-160, wherein the high volume autoinjector is configured to subcutaneously administer the formulation to a subject at a rate of about 0.20 mL/sec to about 0.30 mL/sec.

Clause 164. The pharmaceutical kit of any one of claims 154-160, wherein the high volume autoinjector is configured to subcutaneously administer the formulation to a subject at a rate of about 0.30 mL/sec to about 0.40 mL/sec.

Clause 165. The pharmaceutical kit of any one of claims 154-160, wherein the high volume autoinjector is configured to subcutaneously administer the formulation to a subject at a rate of about 0.40 mL/sec to about 0.50 mL/sec.

Clause 166. The pharmaceutical kit of any one of claims 154-160, wherein the high volume autoinjector is configured to subcutaneously administer the formulation to a subject at a rate of about 0.50 mL/sec to about 0.60 mL/sec.

Clause 167. The pharmaceutical kit of any one of claims 154-160, wherein the high volume autoinjector is configured to subcutaneously administer the formulation to a subject at a rate of about 0.60 mL/sec to about 0.70 mL/sec.

Clause 168. The pharmaceutical kit of any one of claims 154-160, wherein the high volume autoinjector is configured to subcutaneously administer the formulation to a subject at a rate of about 0.70 mL/sec to about 0.80 mL/sec.

Clause 169. The pharmaceutical kit of any one of claims 154-160, wherein the high volume autoinjector is configured to subcutaneously administer the formulation to a subject at a rate of about 0.80 mL/sec to about 0.90 mL/sec.

Clause 170. The pharmaceutical kit of any one of claims 154-160, wherein the high volume autoinjector is configured to subcutaneously administer the formulation to a subject at a rate of about 0.90 mL/sec to about 1.00 mL/sec.

Clause 171. The pharmaceutical kit of any one of claims 154-170, wherein the high volume autoinjector is configured to subcutaneously administer the formulation to a subject with an applied force of about 10 N to about 200 N.

Clause 172. The pharmaceutical kit of any one of claims 154-171, wherein the high volume autoinjector is configured to subcutaneously administer the formulation to a subject with an applied force of about 10 N to about 45 N.

Clause 173. The pharmaceutical kit of any one of claims 154-171, wherein the high volume autoinjector is configured to subcutaneously administer the formulation to a subject with an applied force of about 25 N to about 50 N.

Clause 174. The pharmaceutical kit of any one of claims 154-173, wherein the high volume autoinjector is configured for self-administration of the formulation by the subject.

EXAMPLES

Example 1: Assessment of a Ten mL Subcutaneous Vertical Injection Using a 25 G Needle for Development of an Auto-Injector

SUMMARY

This study examined the delivery of an Ig solution formulated at 120 mg/mL using a mock auto-injector. The test solution was delivered with and without rHuPH20 at a concentration of 2,000 U/mL. All injections were performed using a hand-held device that holds a needle in place so that it was inserted vertically into the subcutaneous space at an injection depth of 7.5 mm. The test solution volume was 10 mL and was delivered in 30 seconds using a 20 cc syringe and 25 G needle. The applied force to the syringe barrel was measured throughout the injection by attaching a load cell to the end of the syringe flange. In addition, the back-leakage was collected post-injection and quantified by weight. The post-injection swelling was measured using calipers and 3D imaging. After the injection three independent scorers evaluated the injection site for erythema, swelling size and induration over time (at times T=0, 15, 30 min, 2 h and 24 h) to assess the time for the resolution of the post-injection swelling.

Introduction

Current auto-injectors (AIs) are limited to extremely small volumes (typically ≤2.25 mL), limiting their usefulness for delivery of larger volumes. For larger volumes higher flow rates are required to make use of an AI practical. Currently 30 seconds is a recommended amount of time that a device can be held in place during self-administration to prevent fatigue and potential interruption of the injection.

rHuPH20 has been shown to facilitate the subcutaneous (SC) administration of fluids and drugs by transiently and locally depolymerizing hyaluronan (HA) in the extracellular matrix (ECM). The depolymerization of HA reduces tissue backpressure in the SC space that subsequently allows for rapid, large volume administration of drugs. Previous work has shown that rHuPH20 can facilitate the delivery of large volumes to the SC space at high flow rates using an infusion set.

The mini-pig model has been selected due to the high degree of similarity of the subcutaneous space to that of humans. Previous studies using a mini-pig model have demonstrated the translatability of the model for use in pre-clinical (Kang et al., 2013) and auto-injector studies (Shi et al., 2021).

In summary, the objective of this study was to determine if rHuPH20 may potentiate the development of a high volume AI that is able to deliver clinically relevant volumes to the SC space at high flow rates using the mini-pig as an animal model. In particular, this study assessed the delivery an Ig solution formulated at 120 mg/mL through a 25 G needle when injected vertically into the SC space using a hand-held mock auto-injector device.

Test Articles and Methods

Test Articles

Human Gamma Globulin (Ig-120: 12% solution)
Lot number: 1032-17
Description: Lyophilized powder reconstituted at 120 mg/ml Date of Manufacture: 21 Sep. 2020
Formulation: 10 mM Histidine, 130 mM Sodium Chloride, pH 6.5
Storage Conditions: 2-8° C.
Supplier: BioMed Supply
Formulated by: Halozyme Product Development
Recombinant Human Hyaluronidase rHuPH20
Lot number: 462-022
Description: Clear and colorless solution
Concentration: 10 mg/ml
Date of Manufacture: Dec. 30, 2014
Retest Date: February 2023
Enzyme activity: 1,229,456 U/mL
Storage: ≤70° ° C.
Formulation: 10 mM Histidine, 130 mM sodium chloride, pH 6.5
Handling Conditions: Standard laboratory precautions
Supplier: Halozyme Therapeutics, Inc Formulation
Preparation of Test Solutions The two test solutions administered in this study were Ig-120 alone and Ig-120+rHuPH20. These were prepared by addition of rHuPH20 from a concentrated stock to an Ig solution previously prepared at 120 mg/mL. The final concentration of rHuPH20 in the test solution was 2,000 U/mL.

Ig-120 was thawed at 2-8° C. overnight. The following day test solutions were prepared by adding rHuPH20 to the Ig-120 solution at room temperature. A concentrated stock of rHuPH20 was used for test article preparation (10 mg/mL; 1,229,456 U/mL). To prepare Ig-120+rHuPH20, 488 µL of rHuPH20 was added to 300 mL of Ig-120. 75 mL of each test solution was then aliquoted into individual 100 mL glass vials and stored at 4° C. until used for syringe filling on the day prior to the study.

The Ig-120+rHuPH20 solution was tested for rHuPH20 activity prior to the start of the study using a micro-turbidity assay. The activity of the Ig-120+rHuPH20 test solution was within 10% of target concentration and deemed to be within acceptable range for use in the study. Two vials of each test solution (~150 mL) were reserved for a second follow-on study and stored at 2-8° C.

At the end of the study dose retain samples that were obtained during the study procedure as well as a stock of Ig-120+rHuPH20 that had been used for syringe filling and kept continually at 2-8° C. since being formulated were tested for rHuPH20 activity. The activity of the Ig-120+ rHuPH20 test solutions were deemed to be within acceptable range. These values are summarized in Table 1 and Table 2.

TABLE 1

Pre-study activity testing of rHuPH20 activity in test solutions

| Test Solution | Pre-study Concentration (U/mL ± SD) |
|---|---|
| Pre-study Ig-120 + rHuPH20 | 2167 ± 44 |

TABLE 2

Post-study activity testing of rHuPH20 activity in test solutions

| Test Solution | Post-study Concentration (U/mL ± SD) |
|---|---|
| Dose retain #1: AID #1114L (Ig-120 + rHuPH20) | 1832 ± 67 |
| Dose retain #2: AID #1181R (Ig-120 + rHuPH20) | 1782 ± 74 |

TABLE 2-continued

Post-study activity testing of rHuPH20 activity in test solutions

| Test Solution | Post-study Concentration (U/mL ± SD) |
|---|---|
| Dose retain #3: AID #1184L (Ig-120 + rHuPH20) | 1784 ± 106 |
| Dose retain #4: AID #1185R (Ig-120 + rHuPH20) | 1806 ± 75 |
| Dose retain #5: AID #1107L (Ig-120 alone) | 0 |
| Dose retain #6: AID #1184R (Ig-120 alone) | 0 |
| Master stock of Ig-120 + rHuPH20 (stored at 2-8° C. since prepared) | 1949 ± 73 |

Animal Description
Species: Pig (*Sus scrofa domestica*)
Strain: Yucatan miniature
Sex: Female
Age: >3 months
Body weight: 12-16 kg upon receipt
Quantity: 6
Source: Premier BioSource (Ramona, CA)

Husbandry

Animals were received on 2 Sep. 2022 by the facility and allowed to acclimate prior to study start. Animals were group housed in steel pens with automatic water provided ad libitum. Animals were fed twice daily (AM and PM), except on study day (PM only). Room environment was set to maintain a temperature of ~17-27° C. and a relative humidity of 40-70%, with a 12 hour light/12 hour dark time cycle. Animals were allowed to acclimate to the facility for a minimum of 3 days prior to study onset.

Test Materials

TABLE 3

Summary of test materials

| Test Material | Supplier |
|---|---|
| High pressure syringe pump | KD Scientific, Holliston, MA |
| 25G × 1 inch PrecisionGlide needle | Becton Dickinson, Franklin Lakes, NJ |
| 20 mL Luer-Lok ™ syringe | Becton Dickinson, Franklin Lakes, NJ |
| 21 inch standard bore extension set | B/Braun, Bethlehem, PA |
| Subminiature load cell | Loadstar Sensors; Fremont, CA |
| Load cell interface | Loadstar Sensors; Fremont, CA |
| Load cell software | Loadstar Sensors; Fremont, CA |
| Standard Digital Camera | Canon |
| High Resolution 3D camera | Canfield Sciences, Parsippany, NJ |
| 3D Printed Mock Auto-Injector | Halozyme, Inc. |
| Digital caliper | Fisher Scientific |
| Infrared thermometer | Fisher Scientific |
| Surgical Eye Spear | Becton Dickinson, Franklin Lakes, NJ |

Experimental Design

In this study, two 10 mL injections were administered to the abdomen of a Yucatan miniature pig. On one side of the abdomen a test solution of Ig-120 alone was administered. One the contralateral side of the animal a second test solution of Ig-120+rHuPH20 was administered. All test solutions containing rHuPH20 were formulated at 2000 U/mL. The location of the injection sites was randomized on the left and right sides of an animal. The needle was mounted in a mock auto-injector device handle and the needle inserted vertically into the SC space. The treatments for each animal are summarized in Table 4.

TABLE 4

Description of treatments

| Cohort | N/Cohort | Test Solution (Left) | Volume (mL) | Flow Rate (mL/min) |
|---|---|---|---|---|
| 1 | 6 | Ig-120 alone | 10 | 20 |
| 2 | 6 | Ig-120 + rHuPH20 | 10 | 20 |

Quantitative endpoints included in this study were measurement of applied force to the syringe barrel during the injection, post-injection swelling (bleb) volume, area, and height via digital caliper measurements, and skin temperature changes pre and post-injection were collected via infrared thermometer. In addition, the post-injection back-leakage of test article was collected from the injection site for 30 seconds after the removal of the needle using an eye-spear to absorb any leakage and quantified by weight. The volume of the injection site blebs was also determined by 3D camera. Additional post-injection qualitative injection site evaluations for erythema, swelling and induration were performed immediately post injection (TO) and at 15 minutes post-injection (T15), 30 minutes post-injection (T30), 2 hours post-injection (T2 h) and at approximately 24 hours post-injection (T24 h) post-injection. Qualitative assessments of the injection sites were performed while the animal was under anesthesia for the T0, T15, T30 and T24 h timepoints while the T2 h assessment was performed while the animal was conscious and hand-held by an animal technician. Standard photographs were obtained both pre-injection and at times T0, T15, T30, T2 h and T24 h post-injection. After euthanasia, a 12 mm punch biopsy was obtained from the injection site and fixed in 10% formalin. In summary the endpoints for the study were:

- Applied force during the injection
- Measurement of back-leakage post-injection
- Measurement of bleb size (length/width/height) post-injection (caliper)
- Measurement of bleb size (volume, height, area) using 3D imaging
- Assessment of blebs for erythema, swelling size and induration at times T0, T15, T30, T2 h and T24 h
- Measurement of injection site temperature (pre-injection and post-injection)
- Assessment of injection site post-injection (24 h) by histology Study Procedure Prior to start of the study, animals were assessed for general health, and body weights were collected. On the day prior to the study test articles (~17 mL) were drawn into a 20 ml syringe, capped, and stored at 2-8° C. On the day of the study the syringes were removed from 2-8° C. and brought to room temperature for at least 30 minutes but no more than 4 hours. Dose retains taken during the study procedure were kept at room temperature until transferred back to Product Development.

Animals were anesthetized with isoflurane gas and placed in dorsal recumbence on a foam wedge placed on a heated surgical table and were maintained under isoflurane gas for the entire duration of the procedure. The abdominal region was cleaned with Nolvasan followed by wiping the injection site with gauze containing 70% isopropanol and wiped dry with sterile gauze.

Injection sites were located on the left and right abdominal regions, ~5 cm cranially from the inguinal fold towards the midline and ~3 cm towards the midline of the animal. Each of the injection sites was marked with a permanent marker and then photographed with the standard and 3D cameras prior to needle insertion. The temperature of the skin at the injection site was recorded prior to the start of the injection using an infrared thermometer. The initial injection for each animal was the control solution (Ig-120 alone). The second injection on the contralateral side of the animal was the test solution containing rHuPH20 (Ig-120+rHuPH20).

Assembly of Mock Device

The mock device was prepared by attaching a capped 25 G×1 inch Leur-lok needle to the male end of a 21-inch extension set. The extension set was then routed through the inside of the mock device and the needle was firmly seated in place in the end of the device. Assembly of the mock device was complete when the cap of the device was screwed onto the end of the device. The length of the needle projecting from the end of the mock device was confirmed to be 7.5 mm+0.5 mm. The needle remained capped until just prior to vertical needle insertion. The syringe that contains the test solution was uncapped, attached to the female end of the extension set and then the hardware was primed to the needle tip with the test solution. The syringe was then placed into the syringe pump. The load cell was then attached to the end of the syringe plunger. After zeroing the load cell, the applied force readings were initiated. The pump block was positioned so that it abutted the end of the syringe plunger-load cell with minimal contact force and was then locked into place. The needle was inserted vertically into the marked injection site and held in place by hand at the predetermined depth of ~7.5 mm. Once load cell readings were confirmed the syringe pump was started to begin injection of the test article at the designated flow rate of 20 mL/min. Upon completion of injection the needle was removed, the pressure on the syringe pump block removed and the applied force data collection was stopped. Test solution back-leakage was then absorbed to a tared eye-spear for 30 seconds on the injection site. The weight of the eye spear was recorded using analytical balance with an accuracy of 0.1 mg. The margins of the injection site bleb were marked with a permanent marker and measured for length, width, and height using a digital caliper and recorded then photographed with the standard and 3D cameras immediately post-injection. The injection site was then qualitatively scored by three independent evaluators for appearance and severity of erythema, swelling/bleb size, and firmness (induration) using a 5-point scoring system (a modified Draize Test) based on the 1992 OECD guidelines for grading skin reactions (Table 5, 6, and 7). The evaluators were blinded to each other's scores After the first injection, the procedure was repeated on the contra-lateral side of the animal using the other test solution (Ig-120+rHuPH20).

TABLE 5

Grading scale for erythema formation

| Scale | Description |
|---|---|
| 0 | No erythema |
| 1 | Very slight erythema (barely perceptible) |
| 2 | Well defined erythema |
| 3 | Moderate erythema |
| 4 | Severe erythema (beet redness) to slight eschar formation |

TABLE 6

Grading scale for swelling size formation

| Scale | Description |
|---|---|
| 0 | No swelling |
| 1 | Very slight swelling |
| 2 | Slight swelling |
| 3 | Moderate swelling |
| 4 | Severe swelling |

TABLE 7

Grading scale for swelling firmness (induration)

| Scale | Description |
|---|---|
| 0 | No perceptible difference in firmness after injection |
| 1 | Very slightly firm (barely perceptible) |
| 2 | Mildly firm |
| 3 | Moderately firm |
| 4 | Very firm |

Qualitative scoring for erythema, swelling, and induration were collected by all 3 evaluators again at 15 min., 30 min, 2 hr, and approximately 24 hr post injections. Photographs with the standard camera were collected at each of these timepoints. Following the final assessment, the animal was humanely euthanized using a ready for use solution of sodium pentobarbital and sodium phenytoin (Euthasol®).

Calculations and Statistical Methods

Assessment of Applied Force

Applied force, as measured via a load cell attached to the end of syringe plungers, was recorded using SensorVUE software (Loadstar Sensors), and the mean applied force over the entire injection period was calculated.

Assessment of Local Swelling Volume and Area Using Caliper Measurement and 3D Imaging Volume and area of post-injection swelling were measured using both caliper measurement and 3D camera image analysis. For caliper measurements a digital caliper was utilized to measure length, width, and height of the bleb that formed post-injection. The length and width are defined as the edge-to-edge measurements of the bleb (i.e., diameter) along their longest axes. These values were manually recorded, and the volume determined using the formula for half of an ellipsoid Vol=(2/3)*π*A*B*C where A=Length/2, B=Width/2 and C=Height.

3D imaging was applied as a longitudinal methodology to measure post-injection swelling. By obtaining high definition pre- and post-injection 3D images the distances between two registered surfaces can be determined. The camera captures images using a factory calibrated bifocal imaging system to measure distance between surfaces. Surface registration was performed using multipoint method that utilized common landmarks between the pre-injection image and the post-injection image. Using the proprietary software, the volume, area, and height of the post-injection swelling was calculated for each injection.

Caliper measurement and 3D imaging measurement will yield different values for volume, area, and bleb height. The differences are a result of the difference in the bleb size measurement. The 3D measurement calculates bleb height based from the top of the bleb to the original skin position, while the bleb height from caliper measurements measure from the top of the bleb to the height at the edge of the bleb. Due to skin curvature, this may yield an overall increase in bleb height for the caliper measurements compared to the 3D measurements, resulting in greater bleb volume and height. However, the measurements are consistent with each other and therefore not substantially different.

Results and Discussion

Pre and Post-Injection Quantitative Measurements

Applied force was measured during the injection. Upon completion of the injection any back-leakage of the test solution was collected for 30 seconds and weighed. In addition, the size of the swelling bleb was measured using both calipers and 3D imaging using the method described above. Pre-injection and post-injection temperature readings were also taken to calculate the change in temperature at the injection site.

Assessment of applied force during injection: The applied force was measured during the SC injection by attaching a subminiature load cell to the end of the 20-cc syringe barrel. The load cell provided force data that was electronically recorded throughout the injection via a DI-100U load cell interface at a data capture rate of 2 Hz. Applied forces for each test solution and flow rate are summarized in Table 8 and FIG. 1. Applied force during injection for individual animals at each flow rate is shown in FIG. 2.

TABLE 8

Summary of applied forces during injection

| Flow Rate (mL/min) | Delivery Time (sec) | Mean Applied Force (N) ± SEM | | |
|---|---|---|---|---|
| | | Ig-120 alone | Ig-120 + rHuPH20 | % Decrease |
| 20 | 30 | 93.6 ± 3.4 | 85.2 ± 3.2 | −9.0 |

Figure 3:
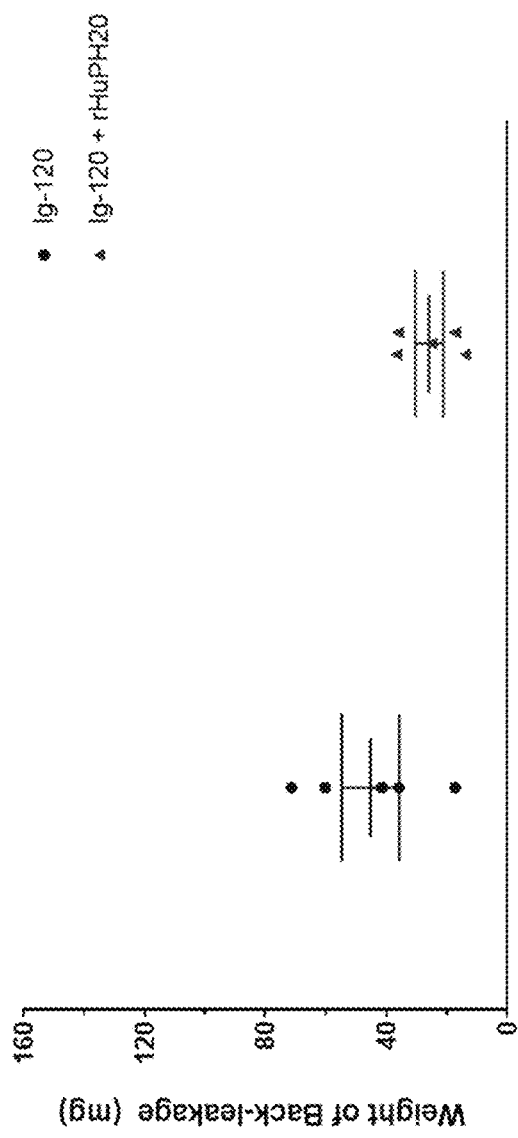
FIG. 3 is a chart of mean (±SEM) and individual weights of back-leakage.

Assessment of post-injection back-leakage: The amount of back-leakage for each injection was measured by collecting post-injection fluid at the site using a surgical eye spear. Prior to collection, the weight of each eye spear was tared on the analytical balance. Post-injection back-leakage from the injection site was collected for an interval of 30 seconds. The eye spear was then immediately weighed, and the weight recorded. The analytical balance had a precision of 0.1 mg. Back-leakage for Ig-120 alone and Ig-120+rHuPH20 are shown in Table 9 and individual animal data with Mean±SEM is shown in FIG. 3.

TABLE 9

Mean weight of back-leakage (mg ± SEM)

| Weight of Back-leakage (mg ± SEM) | | |
|---|---|---|
| Ig-120 alone | Ig-120 + rHuPH20 | % Decrease |
| 45.3 ± 9.4 | 26.0 ± 4.7 | −42.6 | n = (5/group)

Figure 4:
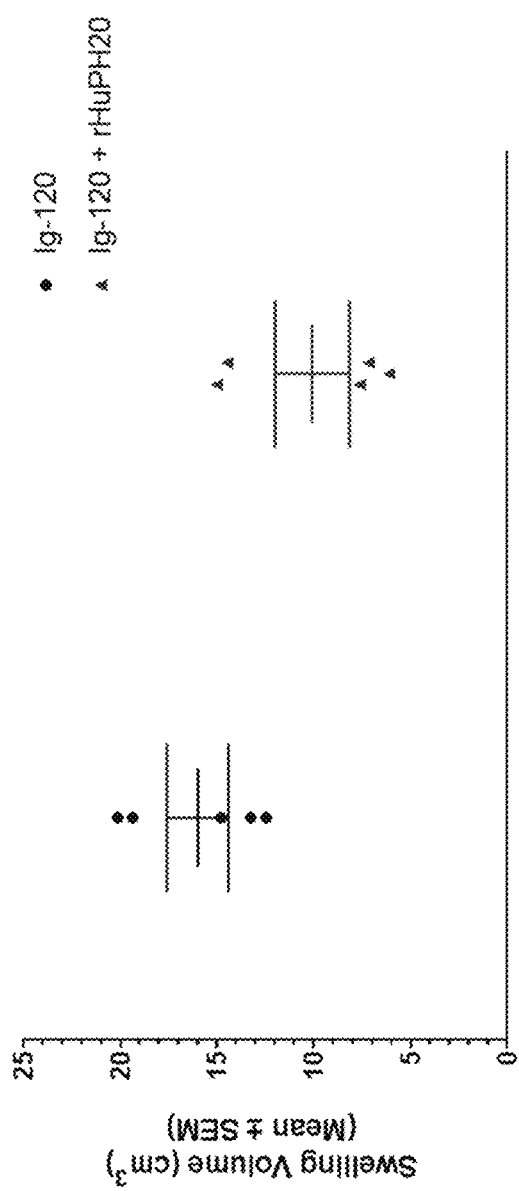
FIG. 4 is a chart of individual swelling volumes ($cm^3$) after SC injection of Ig-120 and Ig-120+rHuPH20—caliper measurement.
Figure 5:
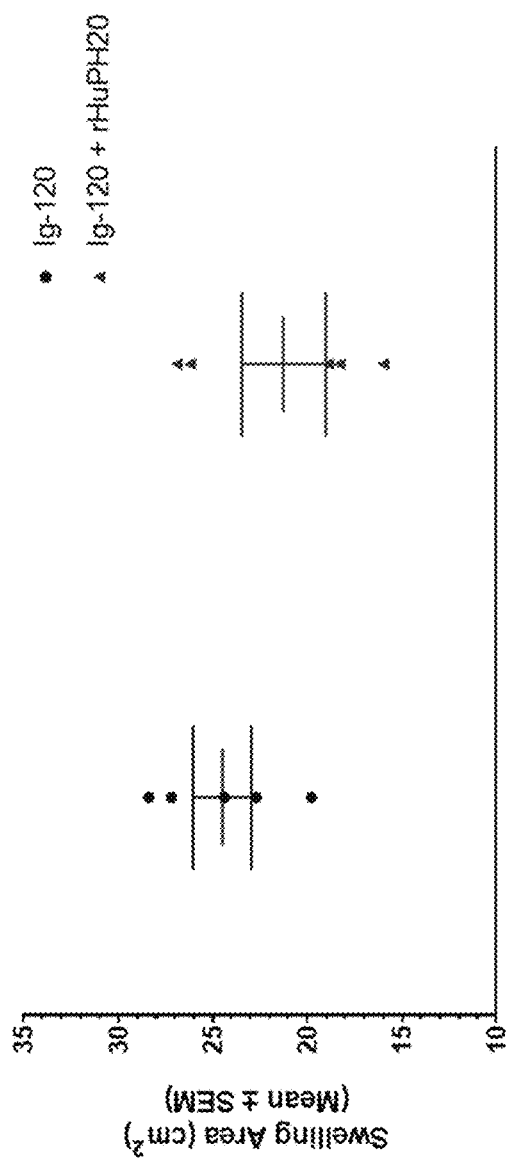
FIG. 5 is a chart of individual swelling areas ($cm^2$) after SC injection of Ig-120 and Ig-120+rHuPH20—caliper measurement.
Figure 6:
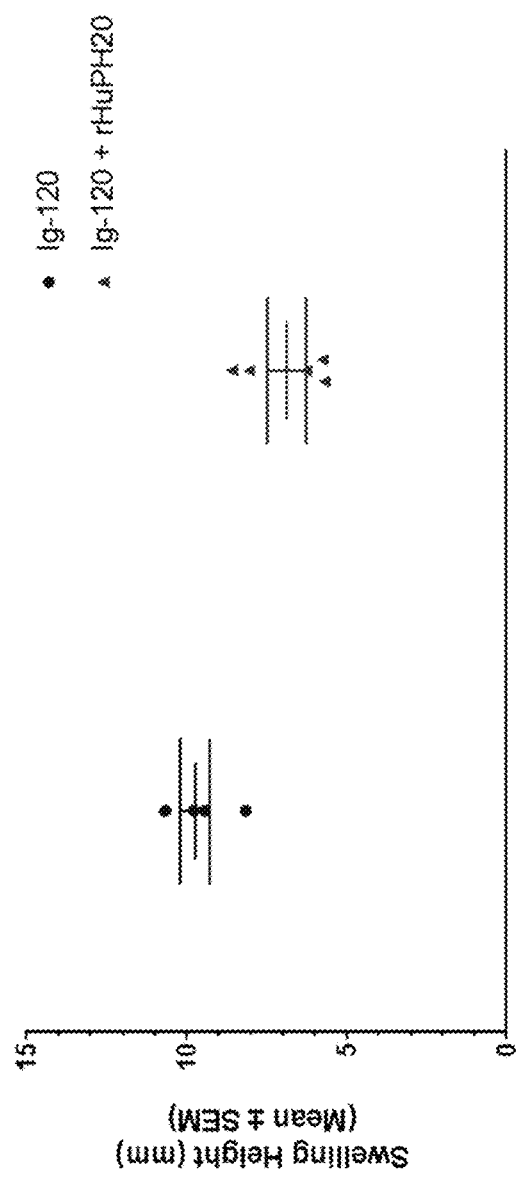
FIG. 6 is a chart of individual swelling heights (mm) after SC injection of Ig-120 and Ig-120+rHuPH20—caliper measurement.

Assessment of post-injection bleb volume, area, and height (caliper measurements): The local injection site swelling was marked and measured using a digital caliper. Bleb volume, dispersion area, and swelling height of each bleb was determined as described above and are summarized in Table 10 for Ig-120 and Ig-120+rHuPH20. Individual post-injection bleb volume, area, and height values are shown in FIGS. 4-6.

TABLE 10

Bleb volume, area, and height after injection of Ig-120 +
rHuPH20 using caliper measurement (Mean ± SEM)

| Test Solution | Volume (mL) | Area (cm2) | Height (mm) |
|---|---|---|---|
| Ig-120 | 16.0 ± 1.6 | 24.5 ± 1.5 | 9.7 ± 0.5 |
| Ig-120 + rHuPH20 | 10.1 ± 1.9 | 21.3 ± 2.2 | 6.9 ± 0.6 |
| % Decrease | −36.9 | −13.1 | −28.9 |

The swelling volume, area, and height of injections of Ig-120+rHuPH20 were found to be reduced 37%, 13% and 29%, respectively compared to injections of Ig-120 alone.

Assessment of post-injection bleb shape, volume, area, and height (3D imaging): Pre- and post-injection photographs were taken using a 3D imaging system. This technology permits point-to-point alignment of these two images through multipoint surface registration. The distance between any two points is then represented using a colorimetric surface contour map. Regions where there is no difference between the two images are displayed in gray. Where the post-injection image is higher than the pre-injection image, the region is displayed in shades of blue. Where the post-injection image is lower than the pre-injection image the distance is displayed in shades of orange. The color intensity is proportional to the amount of distance measured between images and the range that is set for positive and negative measurements. Out of range height measurements are depicted in white (>6 mm). Bleb measurements of volume and height include regions out of range.

Figure 7A:
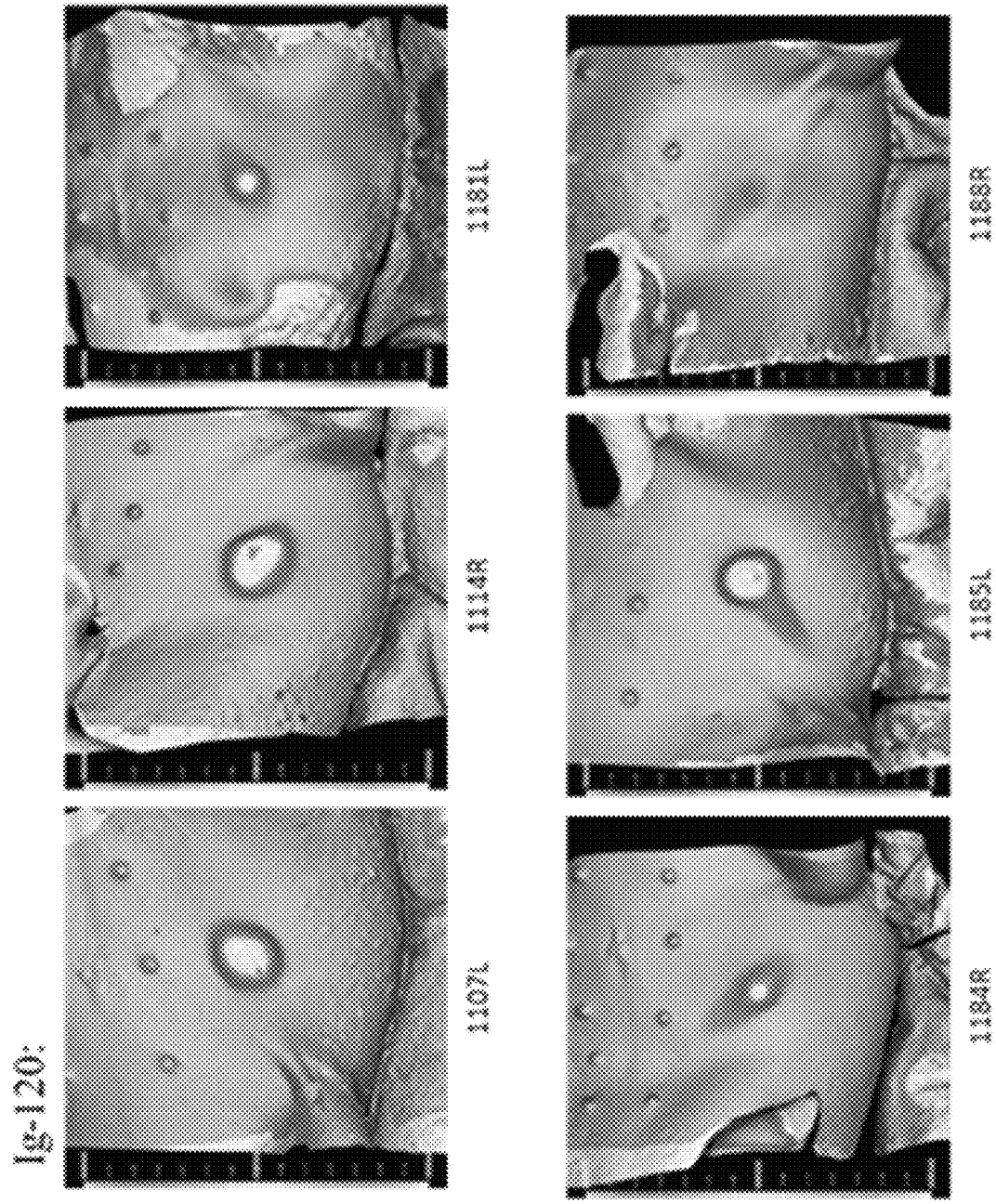
FIGS. 7A-7B are composite 3D images of the minipigs by treatment.
Figure 7B:
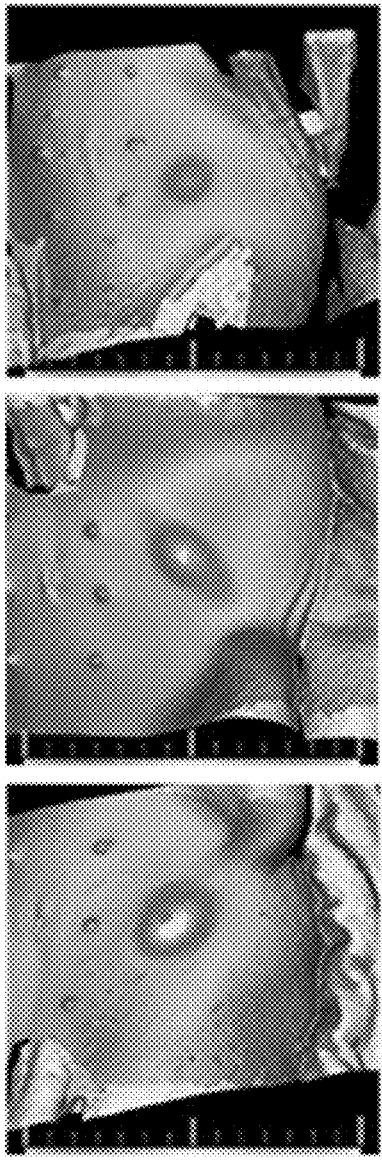

Each animal had a pre-injection 3D image taken of the injection site followed by a second image taken immediately post-injection and these images were mapped to each other using multipoint registration. These registered pre-/post-injection images were then used to calculate the bleb volume, height, circumference, length, and width for each bleb using proprietary software. Colorimetric surface contour maps of each post-injection bleb for Ig-120 and Ig-120+rHuPH20 are shown in FIGS. 7A-7B.

Figure 8:
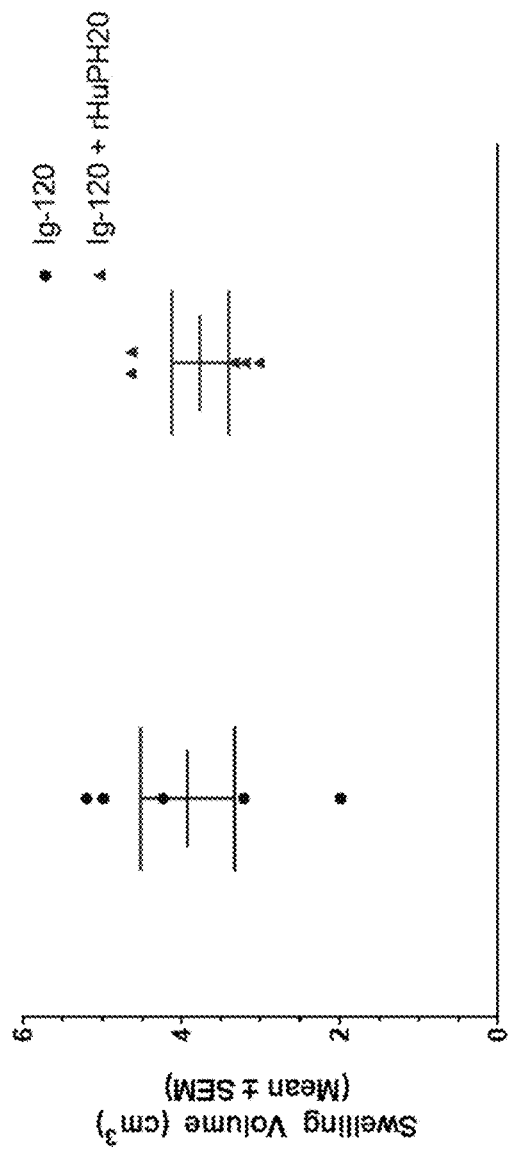
FIG. 8 is a chart of individual bleb volumes ($cm^3$) after SC injection of Ig-120 and Ig-120+rHuPH20—3D imaging.
Figure 9:
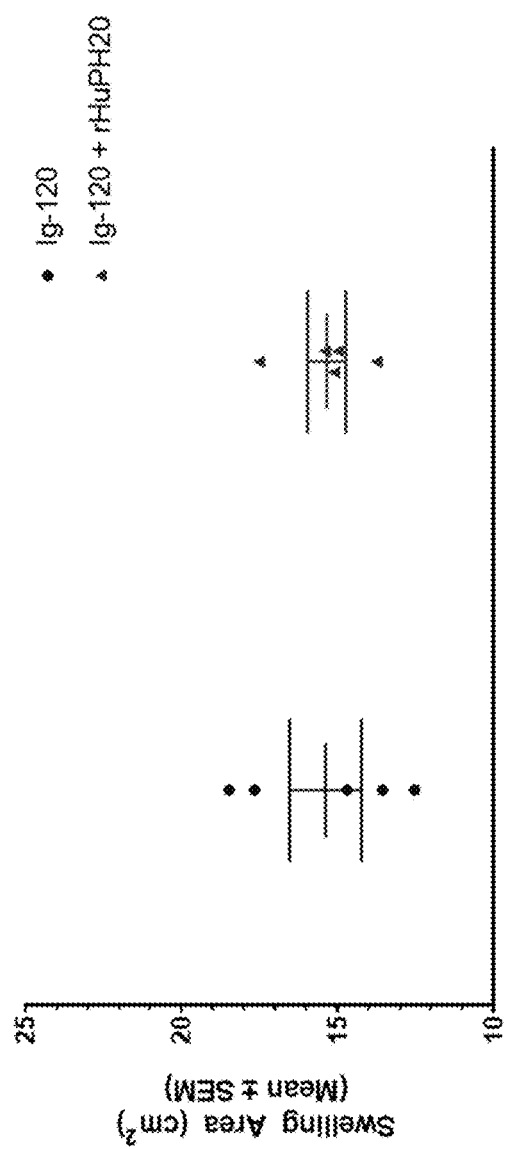
FIG. 9 is a chart of individual bleb areas ($cm^2$) after SC injection of Ig-120 and Ig-120+rHuPH20—3D imaging.
Figure 10:
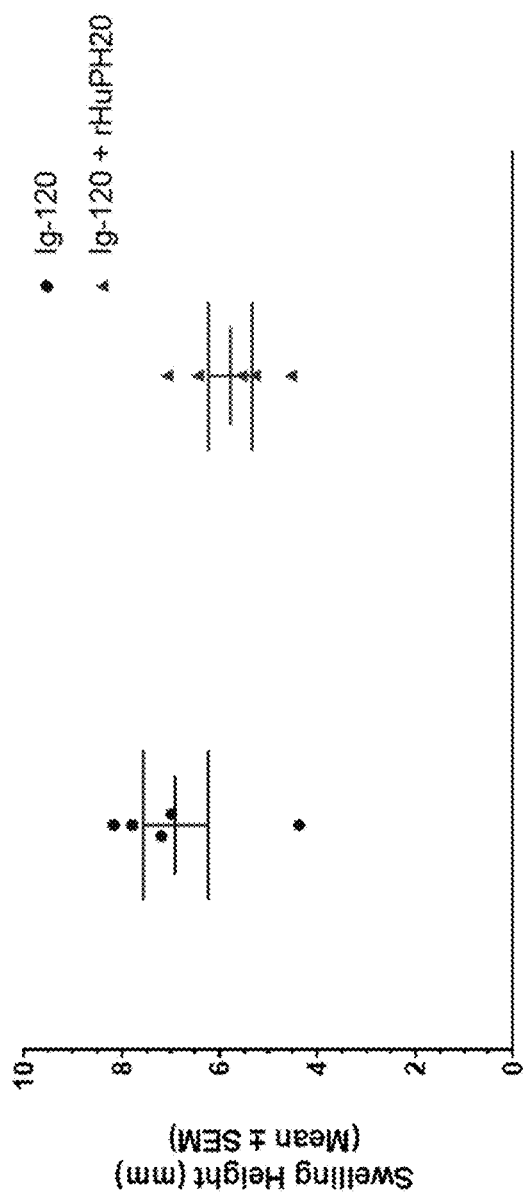
FIG. 10 is a chart of individual bleb heights (mm) after SC injection of Ig-120 and Ig-120+rHuPH20—3D imaging.
Figure 11:
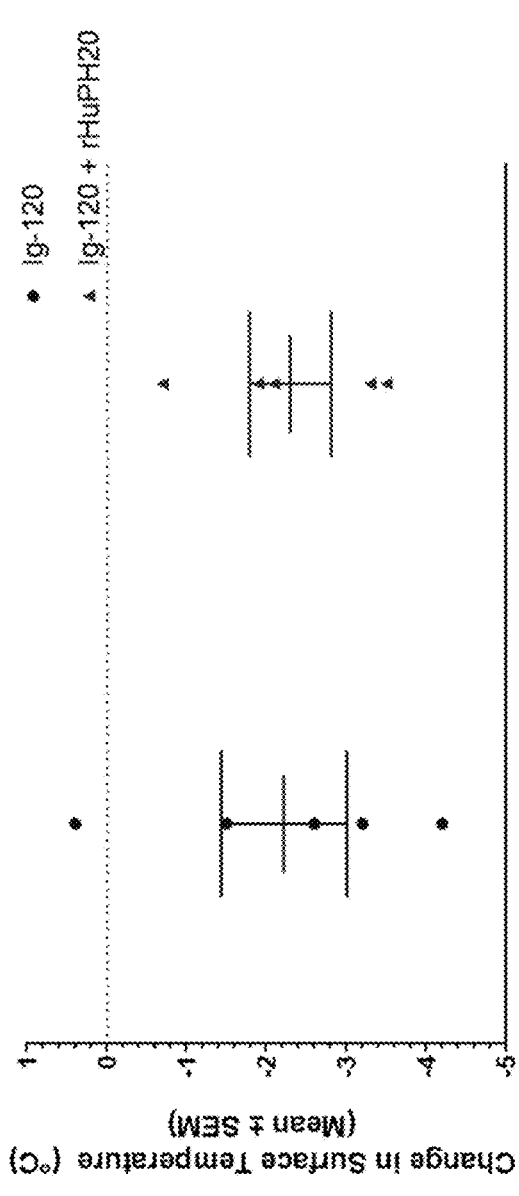
FIG. 11 is a chart of the change in surface temperature: pre- to post-injection.

Post-injection bleb volume, area and height for Ig-120 and Ig-120+rHuPH20 calculated from the 3D images are summarized in Table 11. Individual post-injection bleb volume, area, and height are shown graphically in FIGS. 8-10.

TABLE 11

Bleb volume, area and height after injection of Ig-120 +
rHuPH20 assessed using 3D imaging (Mean ± SEM)

| | Ig-120 + rHuPH20 | | |
|---|---|---|---|
| Flow Rate (mL/min) | Volume (mL) | Area (cm²) | Height (mm) |
| Ig-120 | 3.9 ± 1.3 | 15.4 ± 2.5 | 6.9 ± 1.5 |
| Ig-120 + rHuPH20 | 3.8 ± 0.8 | 15.3 ± 1.4 | 5.8 ± 1.0 |
| % Decrease | −2.6 | −0.6 | −15.9 |

The post-injection swelling volume and height were found to be reduced for injections of Ig-120+rHuPH20 compared to Ig-120 alone. Differences in volume appear to be primarily a result of reduced bleb height for Ig-120+rHuPH20 injections as swelling area was similar for both injections.

Assessment of post-injection temperature changes: The temperature of the injection site was measured immediately prior to needle insertion using an infrared thermometer. It was then re-measured at the end of the injection to determine if any significant changes in temperature may occur as a result of flow rate. Temperature changes are summarized in FIG. 34. While surface temperature variability was greater for Ig-120 alone, the mean changes of surface temperature between the two test solutions were not significantly different.

Qualitative Assessment of Local Injection Sites

Following the completion of the 5 mL injections the qualitative assessments for erythema, swelling size and firmness by the three different scorers was performed as described above.

Qualitative assessment of post-injection erythema: Erythema was minor for both test solutions. It was observed most frequently at the post-injection T15 timepoint but rapidly resolved in all cases with a substantial reduction by the T30 timepoint and near complete resolution by the T2 h timepoint. The scoring by the three evaluators for erythema (Mean±SEM) for each test solution is shown in FIG. 12 and summarized in Table 12.

TABLE 12

Erythema scores post-injection for Ig-120 and
Ig-120 + rHuPH20 (Mean ± SEM)

| Test Solution | Timepoint Post-Injection | | | | |
|---|---|---|---|---|---|
| | T0 | T15 | T30 | T2 h | T24 h |
| Ig-120 | 0.6 ± 0.2 | 0.2 ± 0.1 | 0.0 ± 0.0 | 0.0 ± 0.0 | 0.0 ± 0.0 |
| Ig-120 + rHuPH20 | 0.4 ± 0.1 | 1.1 ± 0.4 | 0.2 ± 0.1 | 0.0 ± 0.0 | 0.0 ± 0.0 |
| % Decrease | −33.3 | +450 | −15.9 | 0 | 0 |

Qualitative assessment of post-injection swelling size: Scoring by the three evaluators for swelling size (Mean±SEM) for each test solution over time is shown in FIG. 13 and summarized in Table 13.

TABLE 13

Swelling scores post-injection for Ig120 +
rHuPH20 (Mean ± SEM)

| Test Solution | Timepoint Post-Injection | | | | |
|---|---|---|---|---|---|
| | T0 | T15 | T30 | T2 h | T24 h |
| Ig-120 | 3.8 ± 0.1 | 3.7 ± 0.1 | 3.5 ± 0.2 | 3.1 ± 0.3 | 0.1 ± 0.1 |
| Ig-120 + rHuPH20 | 3.2 ± 0.2 | 2.6 ± 0.3 | 2.0 ± 0.2 | 1.3 ± 0.2 | 0.0 ± 0.0 |
| % Decrease | −15.8 | −29.7 | −42.9 | −58.1 | −100 |

Injections of Ig-120+rHuPH20 appeared to have a more rapid reduction in bleb swelling size over time and was approaching resolution (≤1) by T2 h whereas injections of Ig-120 alone were still prominent (~3) at the T2 h timepoint.

Qualitative assessment of post-injection firmness (induration): The hardness (induration) of the post-injection blebs were also evaluated by the independent scorers. The scoring for induration (Mean±SEM) for each test solution over time is shown in FIG. 14 and summarized in Table 14.

TABLE 14

Induration scores post-injection for Ig120 + rHuPH20 (Mean ± SEM)

| Test Solution | Timepoint Post-Injection | | | | |
|---|---|---|---|---|---|
| | T0 | T15 | T30 | T2 h | T24 h |
| Ig-120 | 3.9 ± 0.1 | 3.8 ± 0.1 | 3.3 ± 0.2 | 2.9 ± 0.2 | 0.03 ± 0.03 |
| Ig-120 + rHuPH20 | 2.6 ± 0.1 | 2.0 ± 0.1 | 1.5 ± 0.2 | 1.1 ± 0.1 | 0.0 ± 0.0 |
| % Decrease | −33.3 | −47.4 | −54.5 | −62.1 | −100 |

The induration of post-injection swelling was determined to be reduced at T0 for Ig-120+rHuPH20 compared to Ig-120 alone injections. In addition, the induration rapidly resolved for injections of Ig-120+rHuPH20 compared to Ig-120 alone and were near complete resolution (≤1) by T2 h. In contrast, the induration of the post-injection blebs from Ig-120 alone injections was still notable at T2 h.

The injection sites were photographed before and after the 10 mL injection procedure. Photographic images are shown in FIGS. 16A-21B. It should be noted at the 2 hour timepoint (T2 h), the photos of the animal were taken while it was not anesthetized, but rather manually held by an animal technician. Because of the increased stress to the animal, this resulted in some flushing of the skin for some animals. In addition, the injection site may have had some increased tension (skin stretching) when photographed. Therefore, the qualitative scoring is considered the more accurate assessment of the injection site at the 2 h timepoint.

Summary and Conclusions

Test solutions of Ig-120+rHuPH20 required ~9% less applied force for delivery compared to Ig-120 alone.

Back-leakage for Ig-120+rHuPH20 injections was reduced by ~43% compared to Ig-120 alone.

Post-injection swelling volume, area, and bleb height were reduced for injections of Ig-120+rHuPH20 compared to Ig-120 alone (~37%, 13%, and 29%, respectively).

Qualitative assessment of post-injection swelling size and induration over time demonstrated that Ig-120+rHuPH20 were reduced compared to Ig-120 alone and resolved faster than Ig-120 alone with most swelling resolved within 30 minutes.

Example 2: Assessment of a Ten mL Subcutaneous Vertical Injection Using a 23 G Needle for Development of an Auto-Injector Summary This study examined the delivery of an Ig solution formulated at 120 mg/mL using a mock auto-injector. The test solution was delivered with and without rHuPH20 at a concentration of 2,000 U/mL. All injections were performed using a hand-held device that holds a needle in place so that it can be inserted vertically into the subcutaneous space at an injection depth of 7.5 mm. The test solution volume was 10 mL and was delivered in 30 seconds using a 20 cc syringe and 23 G needle. The applied force to the syringe barrel was measured throughout the injection by attaching a load cell to the end of the syringe flange. In addition, the back-leakage was collected post-injection and quantified by weight. The post-injection swelling was measured using calipers and 3D imaging. After the injection three independent scorers evaluated the injection site for erythema, swelling size, and induration over time (at times T=0, 15, 30 min, 2 h, and 24 h) to assess the time for the resolution of the post-injection swelling.

Introduction

Current auto-injectors (AIs) are limited to extremely small volumes (typically ≤ 2.25 mL), limiting their usefulness for delivery of larger volumes. For larger volumes higher flow rates are required to make use of an AI practical. Currently 30 seconds is a recommended amount of time that a device can be held in place during self-administration to prevent fatigue and potential interruption of the injection the device.

rHuPH20 has been shown to facilitate the SC administration of fluids and drugs by transiently and locally depolymerizing hyaluronan (HA) in the extracellular matrix (ECM). The depolymerization of HA reduces tissue backpressure in the SC space that subsequently allows for rapid, large volume administration of drugs. Previous work has shown that rHuPH20 can facilitate the delivery of large volumes to the SC space at high flow rates using an infusion set.

The mini-pig model has been selected due to the high degree of similarity of the subcutaneous space to that of humans. Previous studies using a mini-pig model have demonstrated the translatability of the model for use in pre-clinical (Kang et al., 2013) and auto-injector studies (Shi et al., 2021).

In summary, the objective of this study was to determine if rHuPH20 may potentiate the development of a large volume AI that is able to deliver larger clinically relevant volumes to the SC space at high flow rates using the mini-pig as an animal model. In this study the use of a larger vertically placed 23 G needle was investigated for all injections using a hand-held mock auto-injector device.

Test Articles and Methods

Test Articles

Human Gamma Globulin (Ig-120: 12% solution)
Lot number: 1032-17
Description: Lyophilized powder reconstituted at 120 mg/mL
Date of Manufacture: 21 Sep. 2020
Formulation: 10 mM Histidine, 130 mM Sodium Chloride, pH 6.5
Storage Conditions: 2-8° C.
Supplier: BioMed Supply
Formulated by: Halozyme Product Development
Recombinant Human Hyaluronidase rHuPH20 (ENHANZE™ Drug Product)
Lot number: 462-022
Description: Clear and colorless solution
Concentration: 10 mg/mL
Date of Manufacture: Dec. 30, 2014
Retest Date: February 2023
Enzyme activity: 1,229,456 U/mL
Storage: ≤ 70° C.
Formulation: 10 mM Histidine, 130 mM sodium chloride, pH 6.5
Handling Conditions: Standard laboratory precautions
Supplier: Halozyme Therapeutics, Inc
Ig Dilution Buffer
Description: Clear colorless liquid
Formulation: 20 mM histidine, 130 mM sodium chloride, 0.05% PS 80, pH 6.3
Batch/Lot: 01032-3
Storage Conditions: 2-8° C.
Handling Conditions: Standard laboratory precautions
Supplier: Halozyme Therapeutics, Inc Formulation Preparation of Test Solutions The two test solutions administered in this study were Ig-120 alone and Ig-120+rHuPH20. These were prepared by addition of rHuPH20 from a concentrated stock to an Ig solution previously prepared at 120 mg/mL. The final concentration of rHuPH20 in the test solution was 2,000 U/mL.

Ig-120 was thawed at 2-8° C. overnight. The following day test solutions were prepared by adding rHuPH20 to the Ig-120 solution at room temperature. A concentrated stock of rHuPH20 was used for test article preparation (10 mg/mL; 1,229,456 U/mL). To prepare Ig-120+rHuPH20, 270 µL of rHuPH20 was added to 150 mL of Ig-120 and the test solution stored overnight at 4° C. until used for syringe filling on the day prior to the study.

The Ig-120+rHuPH20 solution was tested for rHuPH20 activity prior to the start of the study using a micro-turbidity assay. The activity of the Ig-120+rHuPH20 test solution was within 10% of target concentration and deemed to be within acceptable range for use in the study. The test solution was prepared and stored at 2-8° C. and tested for enzyme activity prior to study start.

At the end of the study dose retain samples that were obtained during the study procedure were tested for rHuPH20 activity. The activity of the Ig-120+rHuPH20 test solutions were deemed to be within acceptable range. These values are summarized in Table 15 and Table 16.

TABLE 15

Pre-study activity testing of rHuPH20 activity in test solutions

| Test Solution | Pre-study Concentration (U/mL ± SD) |
| --- | --- |
| Pre-study Ig-120 + rHuPH20 | 2077 ± 126 |

TABLE 16

Post-study activity testing of rHuPH20 activity in test solutions

| Test Solution | Post-study Concentration (U/mL ± SD) |
| --- | --- |
| Dose retain #1: AID #1359R (Ig-120 + rHuPH20) | 2064 ± 80 |
| Dose retain #2: AID #1396R (Ig-120 + rHuPH20) | 2066 ± 151 |
| Dose retain #3: AID #1405L (Ig-120 + rHuPH20) | 2016 ± 51 |
| Dose retain #4: AID #1359L (Ig-120 alone) | 0 |
| Dose retain #5: AID #1405R (Ig-120 alone) | 0 |

Animal Description
 Species: Pig (*Sus scrofa domestica*)
 Strain: Yucatan miniature
 Sex: Female
 Age: >3 months
 Body weight: 12-16 kg upon receipt
 Quantity: 6
 Source: Premier BioSource (Ramona, CA)
Husbandry Animals were received by the facility and allowed to acclimate prior to study start. Animals were group housed in steel pens with automatic water provided ad libitum. Animals were fed twice daily (AM and PM), except on study day (PM only). Room environment was set to maintain a temperature of ~17-27° C. and a relative humidity of 40-70%, with a 12 hour light/12 hour dark time cycle. Animals were allowed to acclimate to the facility for a minimum of 3 days prior to study onset.

Test Materials

TABLE 17

Summary of test materials

| Test Material | Supplier |
| --- | --- |
| High pressure syringe pump | KD Scientific, Holliston, MA |
| 23G × 1 inch Precision Glide needle | Becton Dickinson, Franklin Lakes, NJ |
| 20 mL Luer-Lok ™ syringe | Becton Dickinson, Franklin Lakes, NJ |
| 21 inch standard bore extension set | B/Braun, Bethlehem, PA |
| Subminiature load cell | Loadstar Sensors; Fremont, CA |
| Load cell interface | Loadstar Sensors; Fremont, CA |
| Load cell software | Loadstar Sensors; Fremont, CA |
| Standard Digital Camera | Canon |
| High Resolution 3D camera | Canfield Sciences, Parsippany, NJ |
| 3D Printed Mock Auto-Injector | Halozyme, Inc. |
| 3D Printed Auto-Injector Platform | Halozyme, Inc. |
| Digital caliper | Fowler Precision Instruments, Switzerland |
| Infrared thermometer | Fisher Brand |
| Surgical Eye Spear | Becton Dickinson, Franklin Lakes, NJ |

Experimental Design

In this study, two 10 mL injections were administered to the abdomen of a Yucatan miniature pig. On one side of the abdomen a test solution of Ig-120 alone was administered. One the contralateral side of the animal a second test solution of Ig-120+rHuPH20 was administered. All test solutions containing rHuPH20 were formulated at 2000 U/mL. The location of the injection sites was randomized with three injections of each test solution on the left and right sides of an animal. The needle was mounted in a mock auto-injector device handle and the needle inserted vertically into the SC space. The treatments for each animal are summarized in Table 18A, Description of treatments.

TABLE 18A

Description of treatments

| Cohort | N/Cohort | Test Solution (Left) | Volume (mL) | Flow Rate (mL/min) |
| --- | --- | --- | --- | --- |
| 1 | 6 | Ig-120 alone | 10 | 20 |
| 2 | 6 | Ig-120 + rHuPH20 | 10 | 20 |

Quantitative endpoints included in this study were measurement of applied force to the syringe barrel during the injection, post-injection swelling (bleb) volume, area, and height, and skin temperature changes pre and post-injection were collected via infrared thermometer. In addition, the post-injection back-leakage of test article was collected from the injection site for 30 seconds after the removal of the needle using an eye-spear to absorb any leakage and quantified by weight. The volume of the injection site blebs was determined by digital caliper measurement (length, width, and height) as well as by 3D camera imaging. Additional post-injection qualitative injection site evaluations for erythema, swelling and induration were performed immediately post injection (TO) and at 15 minutes post-injection (T15), 30 minutes post-injection (T30), 2 hours post-injection (T2 h), and at approximately 24 hours post-injection (T24 h) post-injection. Qualitative assessments of the injection sites were performed while the animal was under anesthesia for the TO, T15, T30, and T24 h timepoints while the T2 h assessment was performed while the animal was conscious and hand-held by an animal technician. Standard photographs were obtained both pre-injection and at times T0, T15, T30, T2 h, and T24 h post-injection. After euthanasia a 12 mm punch biopsy was obtained from the injection site and fixed in 10% formalin. In summary the endpoints for the study were:

Applied force during the injection
Measurement of back-leakage post-injection
Measurement of bleb size (length/width/height) post-injection (caliper)
Measurement of bleb size (volume, height, area) using 3D imaging
Assessment of blebs for erythema, swelling size and induration at times T0, T15, T30, T2 h and T24 h
Measurement of temperature at injection site both pre and post-injection Study Procedure Prior to start of study, animals were assessed for general health, and body weights were collected. On the day prior to the study test articles (~17 mL) were drawn into a 20 mL syringe, capped, and stored at 2-8° C. On the day of the study the syringes were removed from 2-8° C. and brought to room temperature for at least 30 minutes but no more than 2 hours. Dose retains taken during the study procedure were stored on ice until transferred back to Product Development for enzymatic testing on the day following the study procedure.

Animals were anesthetized with isoflurane gas and placed in dorsal recumbence on a foam wedge placed on a heated surgical table and were maintained under isoflurane gas for the entire duration of the procedure. The abdominal region was cleaned with Nolvasan followed by wiping the injection site with gauze containing 70% isopropanol and wiped dry with sterile gauze.

Injection sites were located on the left and right abdominal regions, ~6 cm cranially from the inguinal fold towards the midline and ~3 cm towards the midline of the animal. Each of the injection sites was marked with a permanent marker and then photographed with the standard and 3D cameras prior to needle insertion. The temperature of the skin at the injection site was recorded prior to the start of the injection using an infrared thermometer. The initial injection for each animal was the control solution (Ig-120 alone). The second injection on the contralateral side of the animal was the test solution containing rHuPH20 (Ig-120+rHuPH20).

Assembly of Mock Device

The mock device was prepared by attaching a capped 23 G×1 inch Luer-lok needle to the male end of a 21-inch extension set. The extension set was then routed through the inside of the mock device and the needle was firmly seated in place in the end of the device. The device with needle attached was then inserted into the platform. The length of the needle projecting from the end of the mock device was confirmed to be 7.5 mm±0.5 mm (providing an injection depth of 7.5 mm). The needle remained capped until just prior to vertical needle insertion. The 20 cc syringe that contains the test solution was uncapped, attached to the female end of the extension set and then the hardware was primed to the needle tip with the test solution and the syringe was placed into the syringe pump. The load cell was then attached to the end of the syringe plunger. Applied force readings were initiated and the load cell was zeroed. The pump block was positioned so that it abutted the end of the syringe plunger-load cell with minimal contact force and was then locked into place. Once applied force readings were confirmed to be recorded the syringe pump was started to begin injection of the test article at the designated flow rate of 20 mL/min. Upon completion of the injection the needle was removed, the pressure on the syringe pump block removed and the applied force data collection was stopped. Test solution back-leakage was then absorbed to a tared eye-spear for 30 seconds by blotting the injection site. The weight of the eye spear was recorded using analytical balance with an accuracy of 0.1 mg. The margins of the injection site bleb were marked with a permanent marker and measured for length, width, and height using a digital caliper and recorded. The injection site was then photographed with the standard and 3D cameras and then qualitatively scored by three independent evaluators for appearance and severity of erythema, swelling/bleb size, and firmness (induration) using a 5-point scoring system (a modified Draize Test) based on the 1992 OECD guidelines for grading skin reactions (Table 18B, 19, and 20). The evaluators were blinded to each other's scores. After the first injection, the procedure was repeated on the contra-lateral side of the animal using the other test solution (Ig-120+rHuPH20).

TABLE 18B

Grading scale for erythema formation

| Scale | Description |
|---|---|
| 0 | No erythema |
| 1 | Very slight erythema (barely perceptible) |
| 2 | Well defined erythema |
| 3 | Moderate erythema |
| 4 | Severe erythema (beet redness) to slight eschar formation |

TABLE 19

Grading scale for swelling size formation

| Scale | Description |
|---|---|
| 0 | No swelling |
| 1 | Very slight swelling |
| 2 | Slight swelling |
| 3 | Moderate swelling |
| 4 | Severe swelling |

TABLE 20

Grading scale for swelling firmness (induration)

| Scale | Description |
|---|---|
| 0 | No perceptible difference in firmness after injection |
| 1 | Very slightly firm (barely perceptible) |
| 2 | Mildly firm |
| 3 | Moderately firm |
| 4 | Very firm |

Qualitative scoring for erythema, swelling, and induration were collected by all 3 evaluators again at 15 min, 30 min, 2 hr, and approximately 24 hr post injections. Photographs with the standard camera were collected at each of these timepoints. Following the final assessment, the animal was humanely euthanized using a ready for use solution of sodium pentobarbital and sodium phenytoin (Euthasolx).

Calculations and Statistical Methods

Assessment of Applied Force

Applied force, as measured via a load cell attached to the end of syringe plungers, was recorded using SensorVUE software (Loadstar Sensors), and the mean applied force over the entire injection period was calculated.

Assessment of Local Swelling Volume and Area Using Caliper Measurement and 3D Imaging Volume and area of post-injection swelling were measured using both caliper measurement and 3D camera image analysis. For caliper measurements a digital caliper was utilized to measure length, width and height of the bleb that formed post-injection. The length and width are defined as the edge-to-edge measurements of the bleb (i.e., diameter) along their longest axes. These values were manually recorded, and the volume determined using the formula for half of an ellipsoid Vol=(⅔)*π*A*B*C where A=Length/2, B=Width/2 and C=Height.

3D imaging was applied as a longitudinal methodology to measure post-injection swelling. By obtaining high definition pre- and post-injection 3D images the distances between two registered surfaces can be determined. The camera captures images using a factory calibrated bifocal imaging system to measure distance between surfaces. Surface registration was performed using multipoint method that utilized common landmarks between the pre-injection image and the post-injection image. Using the proprietary software, the volume, area, and height of the post-injection swelling was calculated for each injection.

Caliper measurement and 3D imaging measurement will yield different values for volume, area, and bleb height. The differences are a result of the difference in the bleb size measurement. The 3D measurement calculates bleb height based from the top of the bleb to the original skin position, while the bleb height from caliper measurements measure from the top of the bleb to the height at the edge of the bleb. Due to skin curvature, this may yield an overall increase in bleb height for the caliper measurements compared to the 3D measurements, resulting in greater bleb volume and height. However, the measurements are consistent with each other and therefore differ only due to the methodology.

Results and Discussion

Pre- and Post-Injection Quantitative Measurements

Quantitative measurements included applied force, back-leakage, bleb size (length, width, & height) and pre- and post-injection temperatures (as described above).

Assessment of applied force during injection: The applied force was measured during the SC injection by attaching a subminiature load cell to the end of the 20-cc syringe barrel. The load cell provided force data that was electronically recorded throughout the injection via a DI-100U load cell interface at a data capture rate of 2 Hz.

Figure 22:
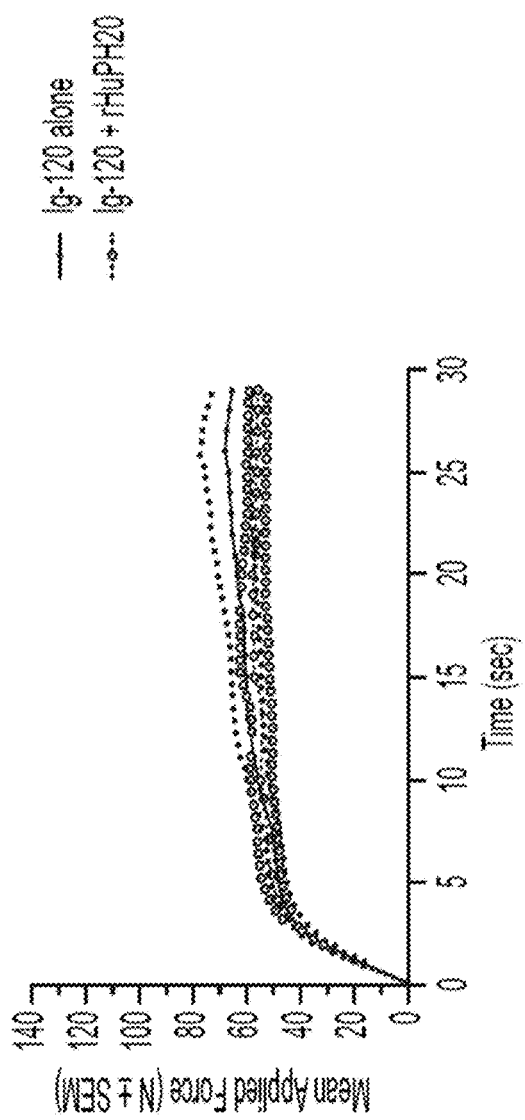
FIG. 22 is a chart of the applied force (N) during injection (Mean±SEM) of Ig-120 and Ig-120+rHuPH20.
Figure 23:
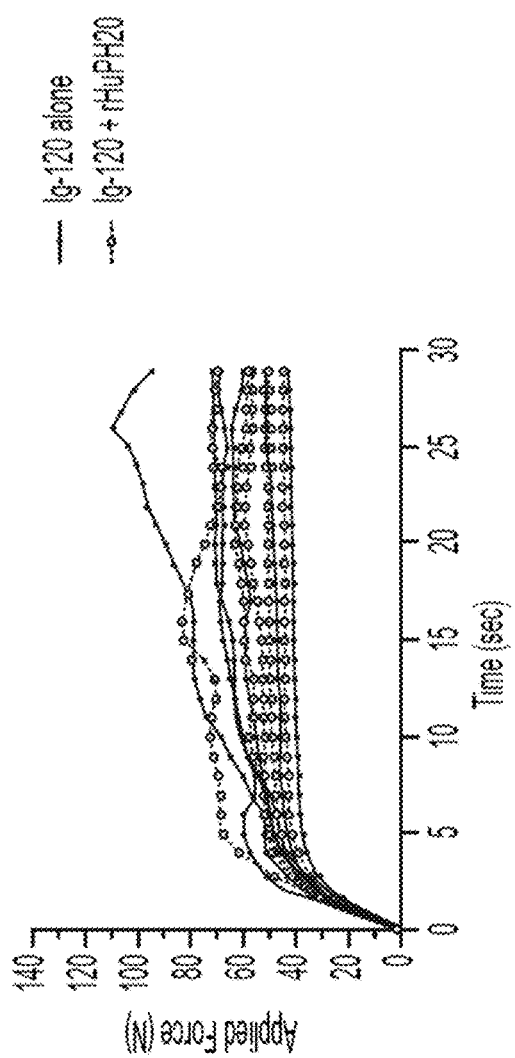
FIG. 23 is a chart of the individual applied force (N) during injection of Ig-120 and Ig-120+rHuPH20.

Applied forces for each test solution and flow rate are summarized in Table 21 and FIG. 22. Applied force during injection for individual animals at each flow rate is shown in FIG. 23.

TABLE 21

Summary of applied forces during injection

| | | Mean Applied Force (N) ± SEM | | |
|---|---|---|---|---|
| Flow Rate (mL/min) | Delivery Time (sec) | Ig-120 alone | Ig-120 + rHuPH20 | % Decrease |
| 20 | 30 | 55.3 ± 1.8 | 51.3 ± 1.5 | −7.2% | n = (5/group)

Figure 24:
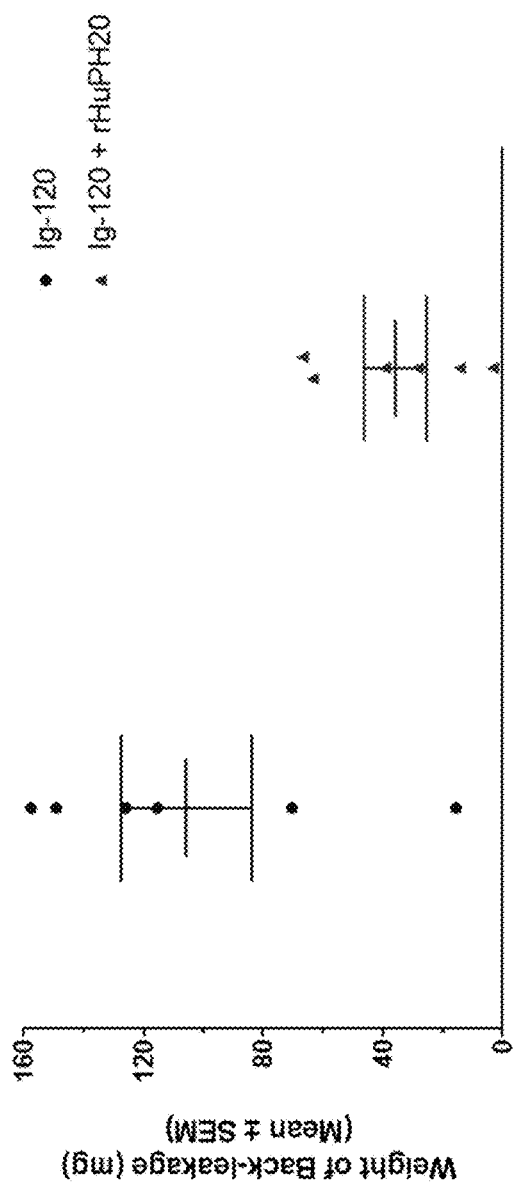
FIG. 24 is a chart of the mean (mg±SEM) and individual weights of back-leakage.

Assessment of post-injection back-leakage: The amount of back-leakage for each injection was measured by collecting post-injection fluid at the site using a surgical eye spear. Prior to collection the weight of each eye spear was tared on the analytical balance. Post-injection back-leakage from the injection site was collected for an interval of 30 seconds. The eye spear was then immediately weighed, and the weight recorded. The analytical balance had a precision of 0.1 mg. Back-leakage for Ig-120 alone and Ig-120+rHuPH20 are shown in Table 22 and individual animal data with Mean±SEM is shown in FIG. 24.

TABLE 22

Mean weight of back-leakage (mg ± SEM)

| Weight of Back-leakage (mg ± SEM) | | |
|---|---|---|
| Ig-120 alone | Ig-120 + rHuPH20 | % Decrease |
| 105.7 ± 21.9 | 36.0 ± 10.5 | −66.0 |

Figure 25:
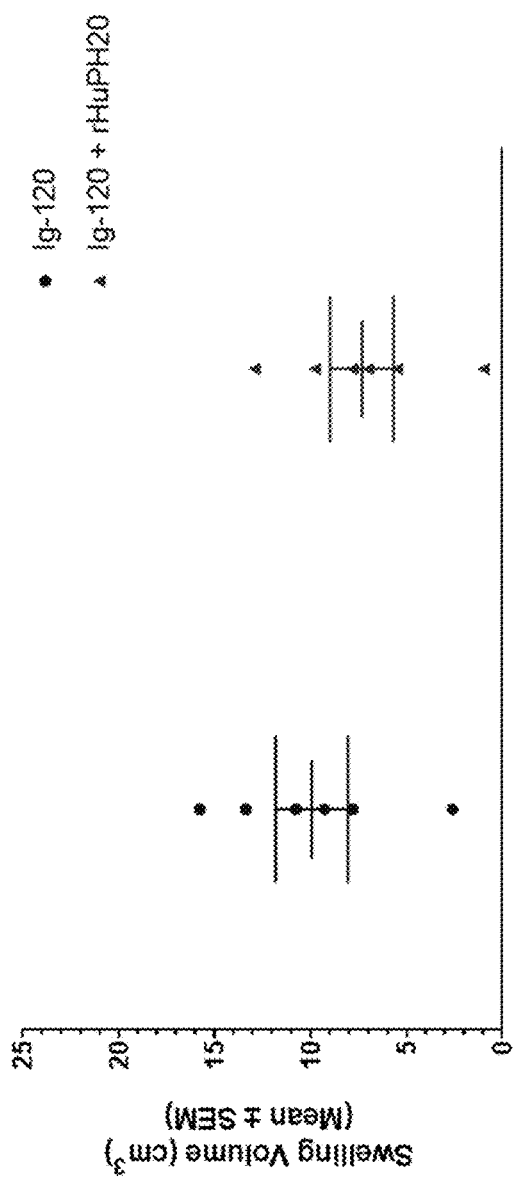
FIG. 25 is a chart of the individual swelling volumes ($cm^3$) after SC injection of Ig-120 and Ig-120+rHuPH20—caliper measurement.
Figure 26:
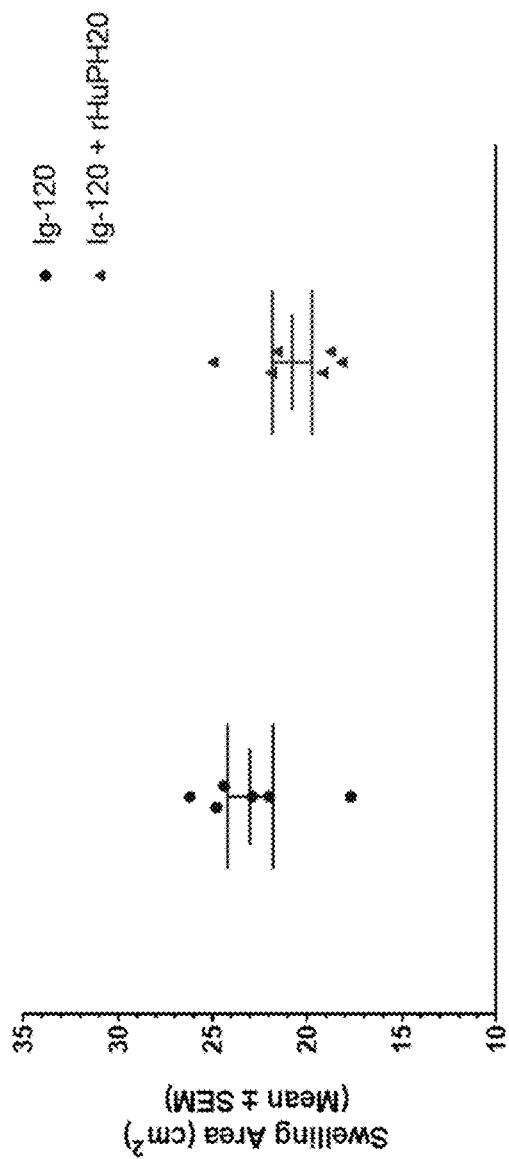
FIG. 26 is a chart of the individual swelling areas ($cm^2$) after SC injection of Ig-120 and Ig-120 +rHuPH20—caliper measurement.
Figure 27:
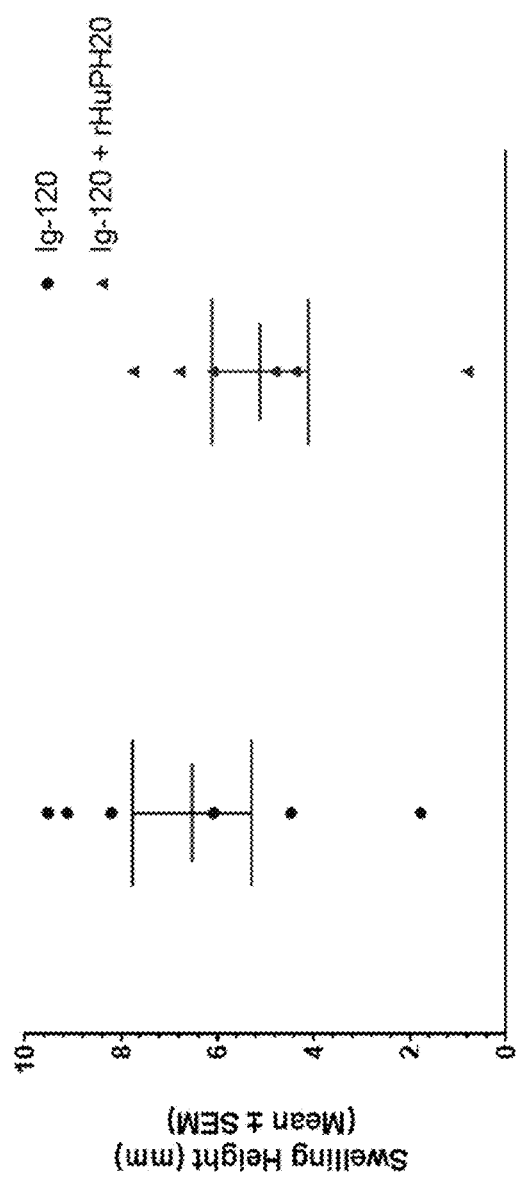
FIG. 27 is a chart of the individual swelling heights (mm) after SC injection of Ig-120 and Ig-120+rHuPH20—caliper measurement.

Assessment of post-injection bleb volume, area, and height (caliper measurements): The local injection site swelling was marked and measured using a digital caliper. Bleb volume, dispersion area, and swelling height of each bleb was determined as described above and are summarized in Table 23 for Ig-120 and Ig-120+rHuPH20. Individual post-injection bleb volume, area, and height values are shown in FIGS. 25-27.

TABLE 23

Bleb volume, area, and height after injection of Ig-120 + rHuPH20 using caliper measurement (Mean ± SEM)

| Test Solution | Volume (mL) | Area (cm$^2$) | Height (mm) |
|---|---|---|---|
| Ig-120 | 9.9 ± 1.9 | 23.0 ± 1.2 | 6.5 ± 1.2 |
| Ig-120 + rHuPH20 | 7.3 ± 1.6 | 20.8 ± 1.0 | 5.1 ± 1.0 |
| % Decrease | −26.3 | −9.6 | −21.5 |

Assessment of Post-Injection Bleb Shape, Volume, Area, and Height (3D Imaging):

Pre- and post-injection photographs were taken using a 3D imaging system. This technology permits point-to-point alignment of these two images through multipoint surface registration. The distance between any two points is then represented using a colorimetric surface contour map. Regions where there is no difference between the two images are displayed in gray. Where the post-injection image is higher than the pre-injection image, the region is displayed in shades of blue. Where the post-injection image is lower than the pre-injection image the distance is displayed in shades of orange. The color intensity is proportional to the amount of distance measured between images and the range that is set for positive and negative measurements. Out of range measurements are depicted in white. Bleb measurements of volume and height include regions out of range.

Figure 28A:
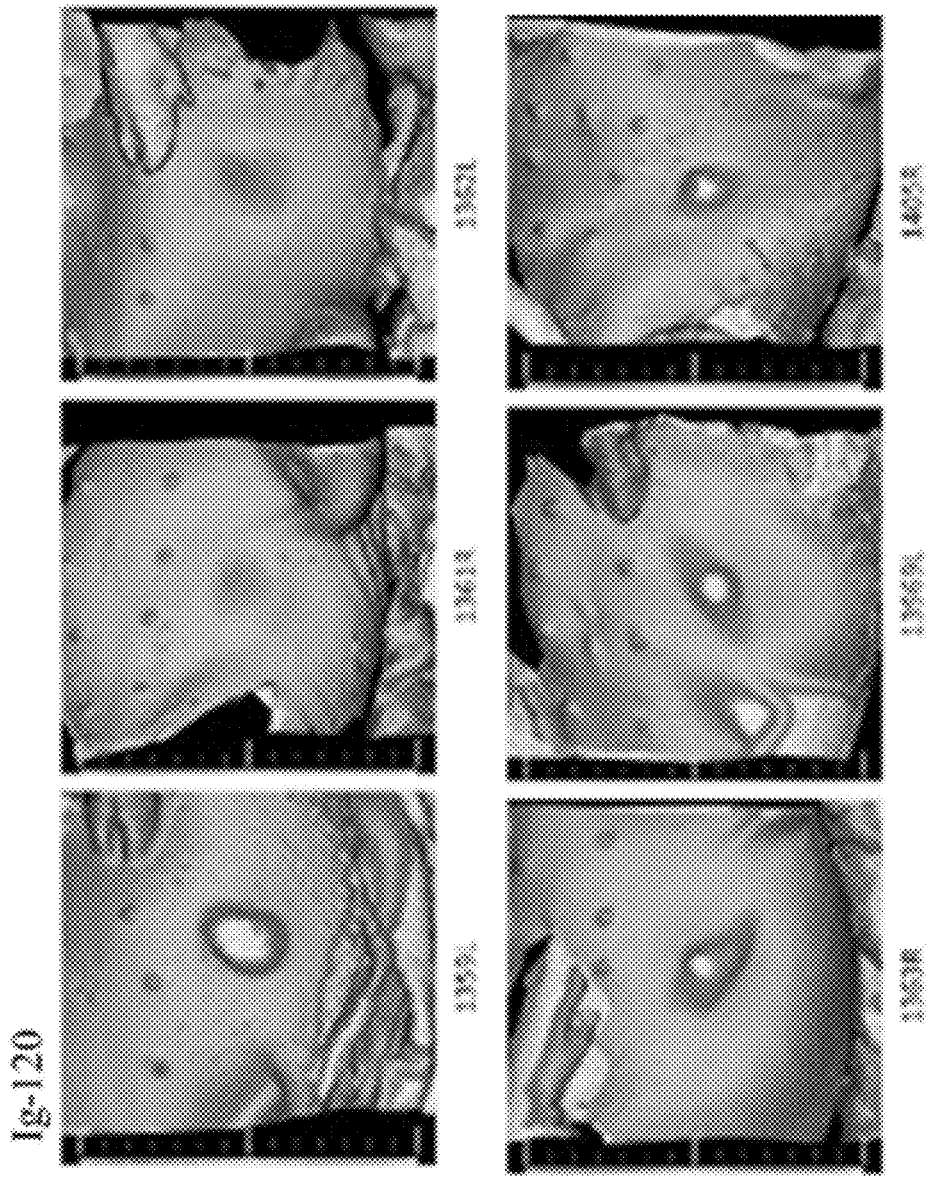
FIGS. 28A-28B are composite 3D images of the minipigs by treatment.
Figure 28B:
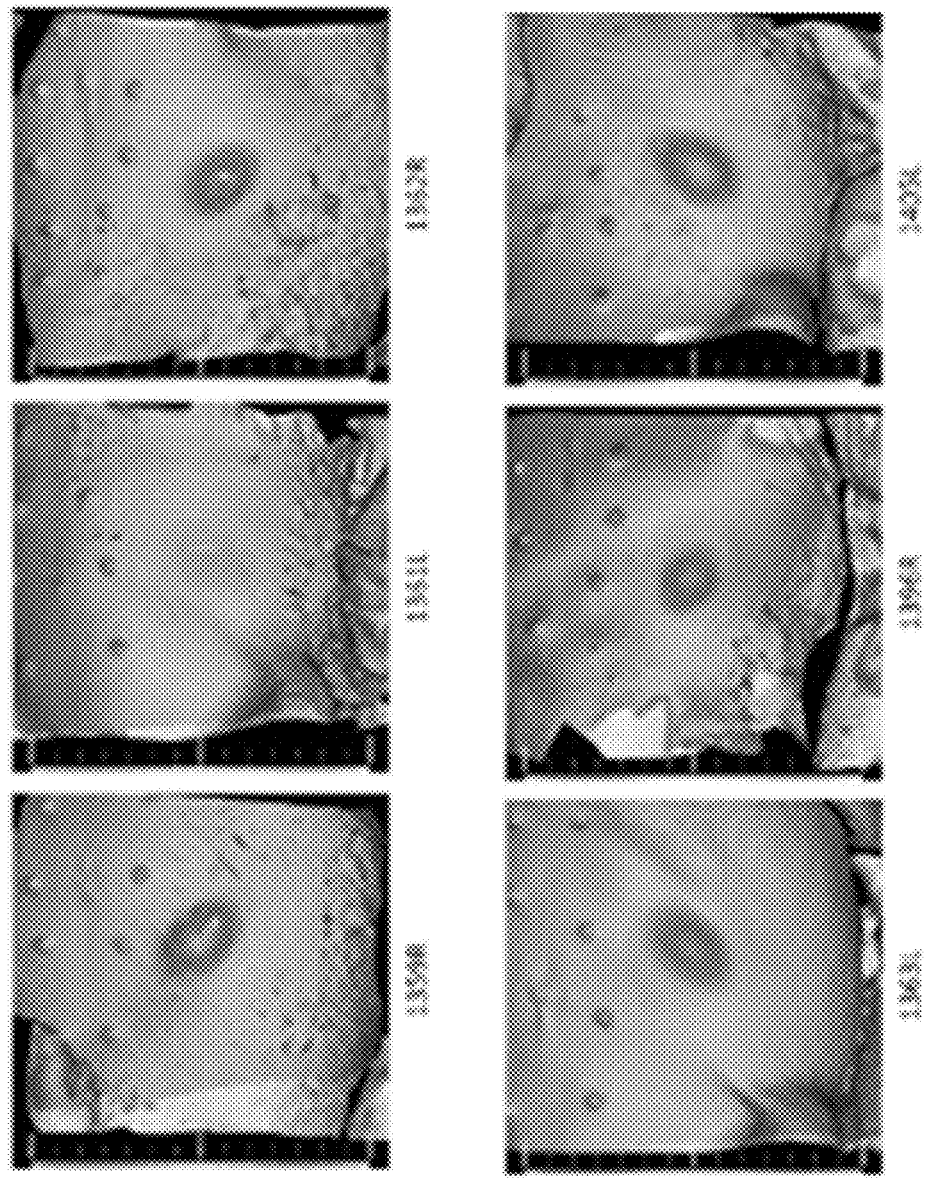

Each animal had a pre-injection 3D image taken of the injection site followed by a second image taken immediately post-injection and these images were mapped to each other using multipoint registration. These registered pre-/post-injection images were then used to calculate the bleb volume, height, circumference, length, and width for each bleb using proprietary software. Colorimetric surface contour maps of each post-injection bleb for Ig-120 and Ig-120+rHuPH20 are shown in FIG. 28A and FIG. 28B, respectively.

Figure 29:
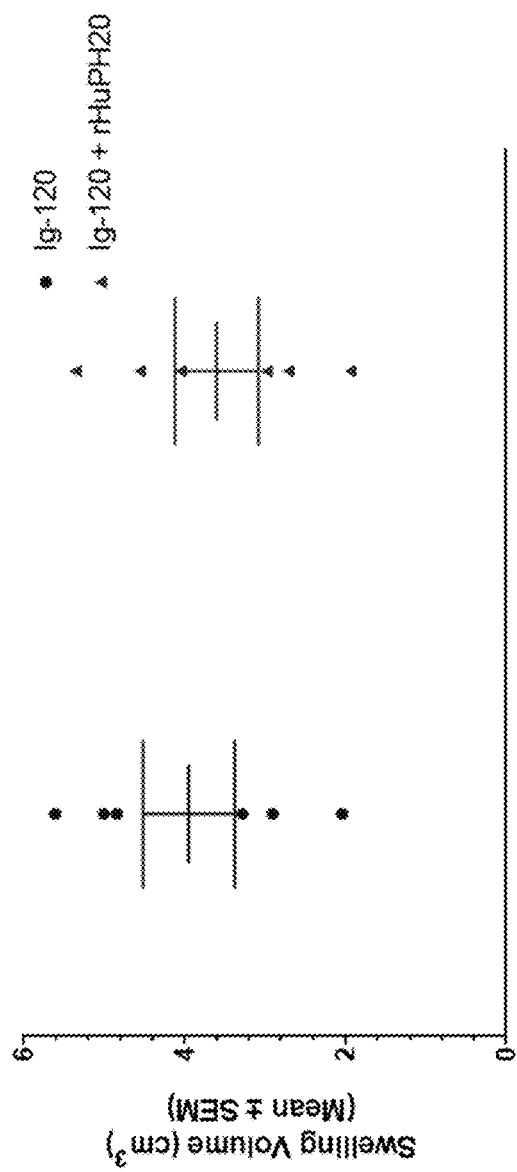
FIG. 29 is a chart of the individual bleb volumes ($cm^3$) after SC injection of Ig-120 and Ig-120+rHuPH20—3D imaging.
Figure 30:
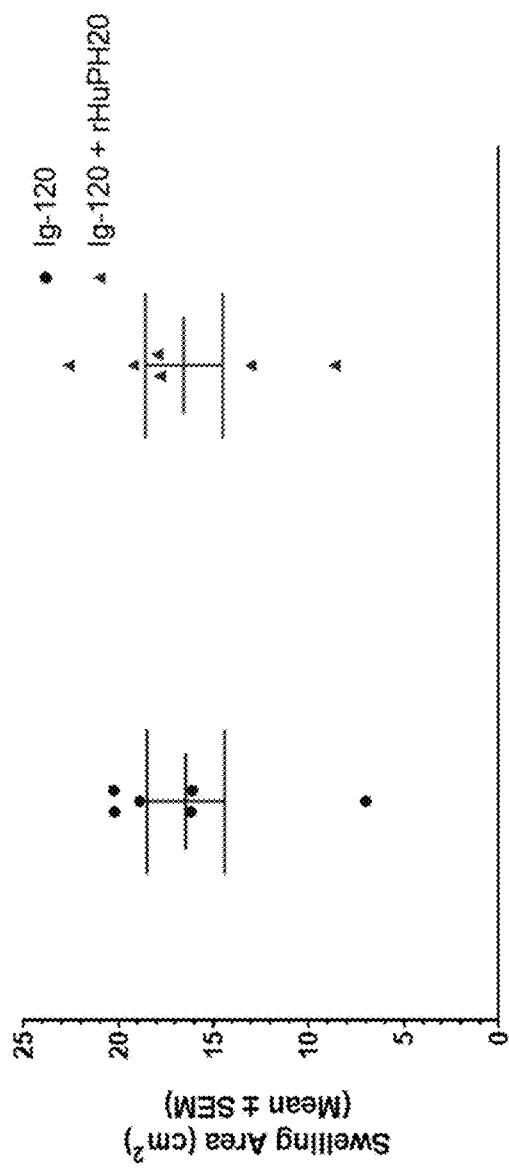
FIG. 30 is a chart of the individual bleb areas ($cm^2$) after SC injection of Ig-120 and Ig-120+rHuPH20—3D imaging.
Figure 31:
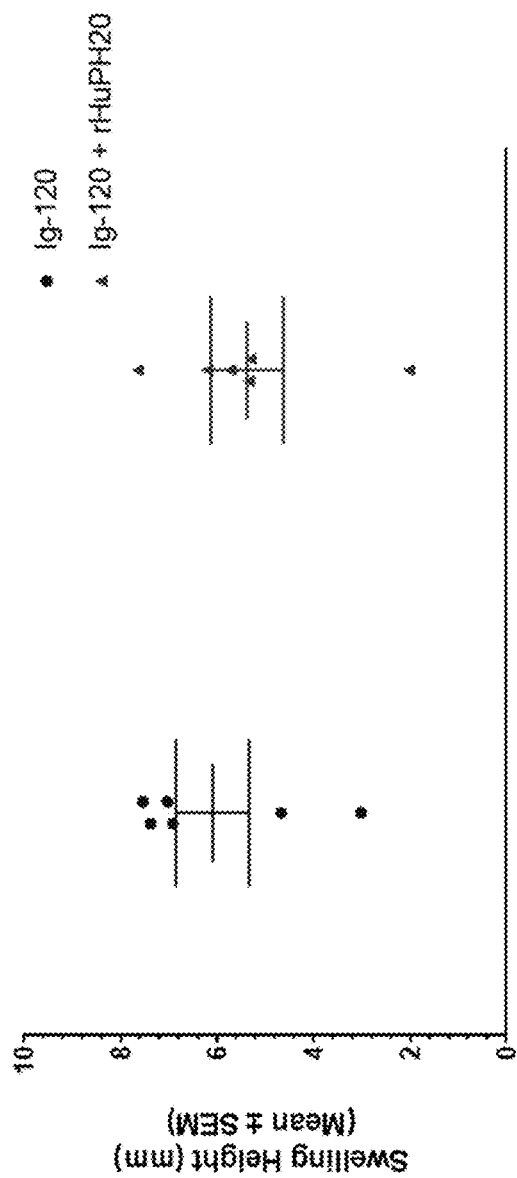
FIG. 31 is a chart of the individual bleb heights (mm) after SC injection of Ig-120 and Ig-120+rHuPH20—3D imaging.

Post-injection bleb volume, area and height for Ig-120 and Ig-120+rHuPH20 calculated from the 3D images are summarized in Table 24. Individual post-injection bleb volume, area, and height are shown graphically in FIGS. 29-31.

TABLE 24

Bleb volume, area and height after injection of Ig-120 +
rHuPH20 assessed using 3D imaging (Mean ± SEM)

| Flow Rate (mL/min) | Ig-120 + rHuPH20 | | |
|---|---|---|---|
| | Volume (mL) | Area (cm²) | Height (mm) |
| Ig-120 | 3.9 ± 0.6 | 16.5 ± 2.0 | 6.1 ± 0.7 |
| Ig-120 + rHuPH20 | 3.6 ± 0.5 | 16.6 ± 2.0 | 5.4 ± 0.8 |
| % Decrease | −7.7 | +0.6 | −11.5 |

Figure 32:
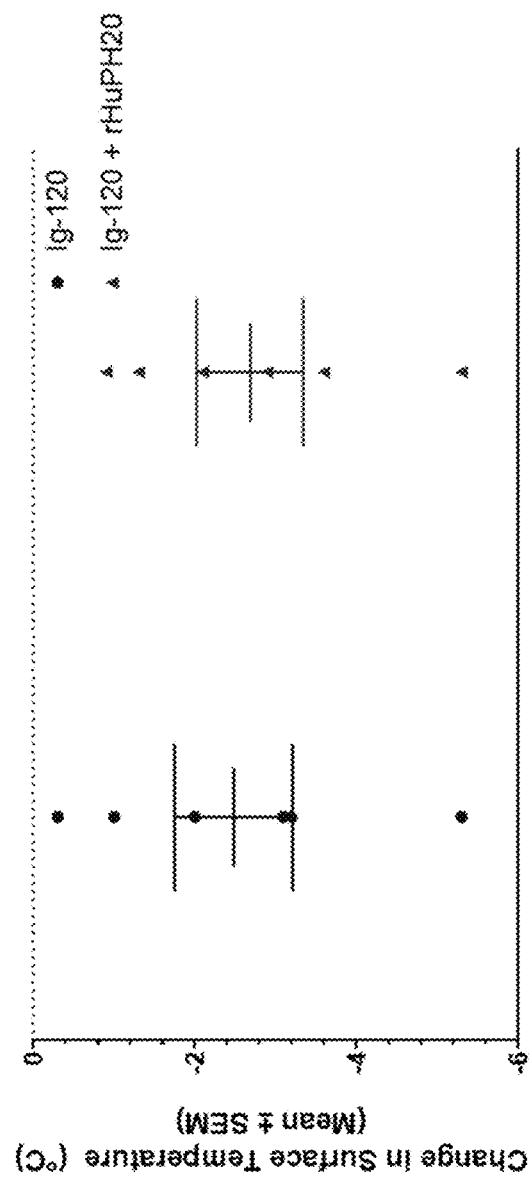
FIG. 32 is a chart of the change in surface temperature: pre to post-injection.

Assessment of post-injection temperature changes: The temperature of the injection site was measured immediately prior to needle insertion using an infrared thermometer. It was then re-measured at the end of the injection to determine if any significant changes in temperature may occur as a result of flow rate. Temperature changes are summarized in FIG. 32. While surface temperature variability was greater for Ig-120 alone, the mean changes of surface temperature between the two test solutions was not significantly different.

Qualitative Assessment of Local Injection Sites

Following the completion of the 10 mL injections the qualitative assessments for erythema, swelling size and firmness by the three different scorers was performed as described above.

Figure 33:
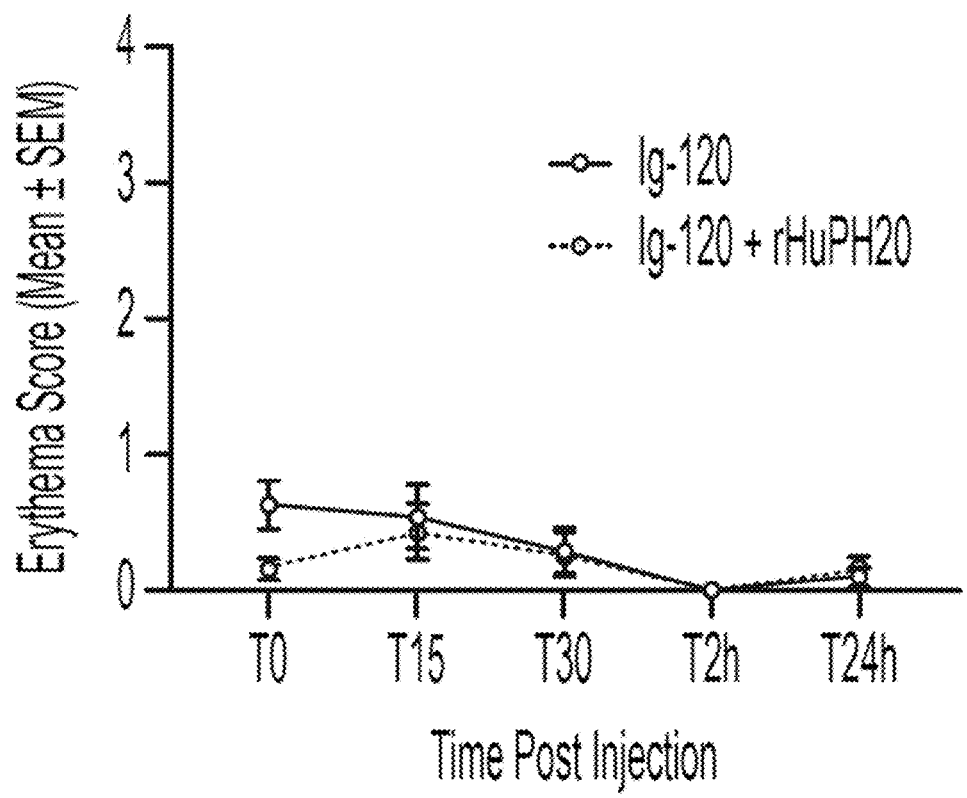
FIG. 33 is a chart of the qualitative assessment of post-injection erythema.

Qualitative assessment of post-injection erythema: Erythema was minor for both test solutions. It was observed most frequently at the post-injection T15 timepoint but rapidly resolved in all cases with a substantial reduction by the T30 timepoint and near complete resolution by the T2 h timepoint. The scoring by the three evaluators for erythema (Mean±SEM) for each test solution is shown in FIG. 33 and summarized in Table 25.

TABLE 25

Erythema scores post-injection for Ig-120 and
Ig-120 + rHuPH20 (Mean ± SEM)

| Test Solution | Timepoint Post-Injection | | | | |
|---|---|---|---|---|---|
| | T0 | T15 | T30 | T2 h | T24 h |
| Ig-120 | 0.6 ± 0.2 | 0.6 ± 0.2 | 0.3 ± 0.2 | 0.0 ± 0.0 | 0.1 ± 0.1 |
| Ig-120 + rHuPH20 | 0.2 ± 0.1 | 0.4 ± 0.2 | 0.3 ± 0.2 | 0.0 ± 0.0 | 0.2 ± 0.1 |
| % Decrease | −66.7 | −33.3 | 0 | 0 | +100 |

Figure 34:
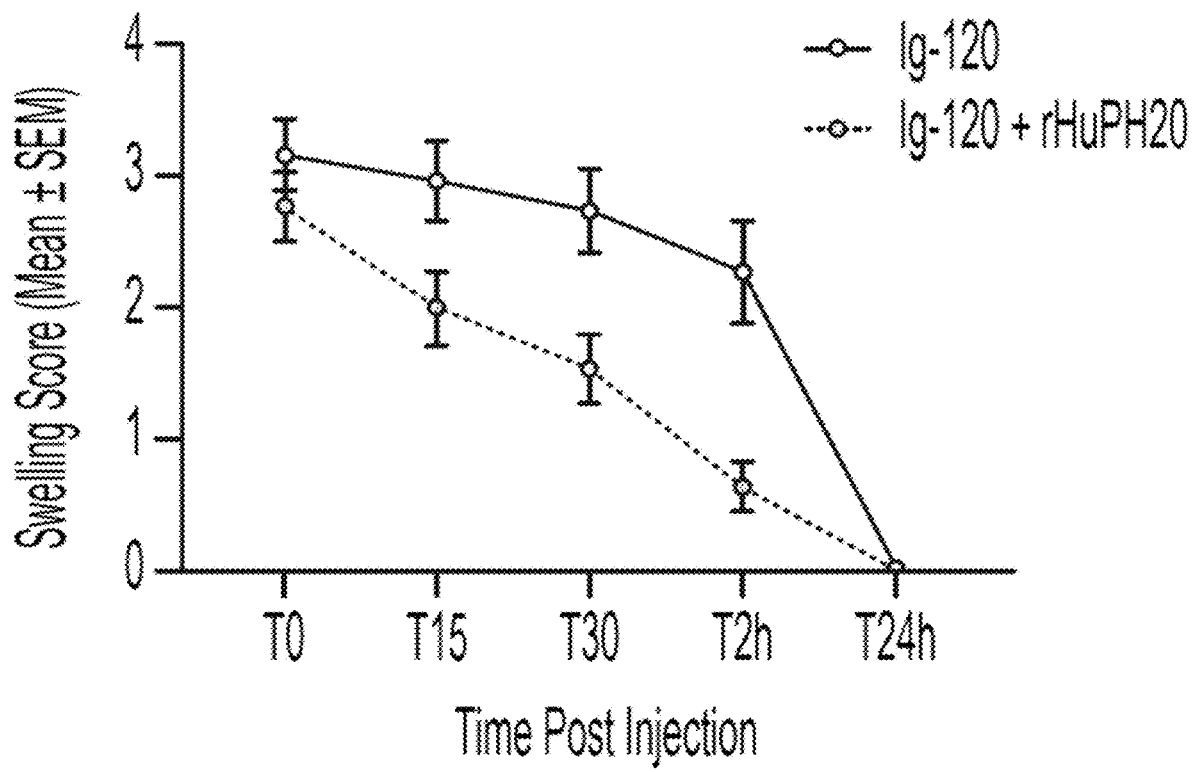
FIG. 34 is a chart of the qualitative assessment of post-injection swelling size.

Qualitative assessment of post-injection swelling size: Scoring by the three evaluators for swelling size (Mean±SEM) for each test solution is shown in FIG. 34 and summarized in Table 26.

TABLE 26

Swelling scores post-injection for Ig120 +
rHuPH20 (Mean ± SEM)

| Test Solution | Timepoint Post-Injection | | | | |
|---|---|---|---|---|---|
| | T0 | T15 | T30 | T2 h | T24 h |
| Ig-120 | 3.2 ± 0.3 | 3.0 ± 0.3 | 2.8 ± 0.3 | 2.3 ± 0.4 | 0.0 ± 0.0 |
| Ig-120 + rHuPH20 | 2.8 ± 0.3 | 2.0 ± 0.3 | 1.5 ± 0.3 | 0.6 ± 0.2 | 0.0 ± 0.0 |
| % Decrease | −12.5 | −33 | −46.4 | −73.9 | 0 |

Figure 35:
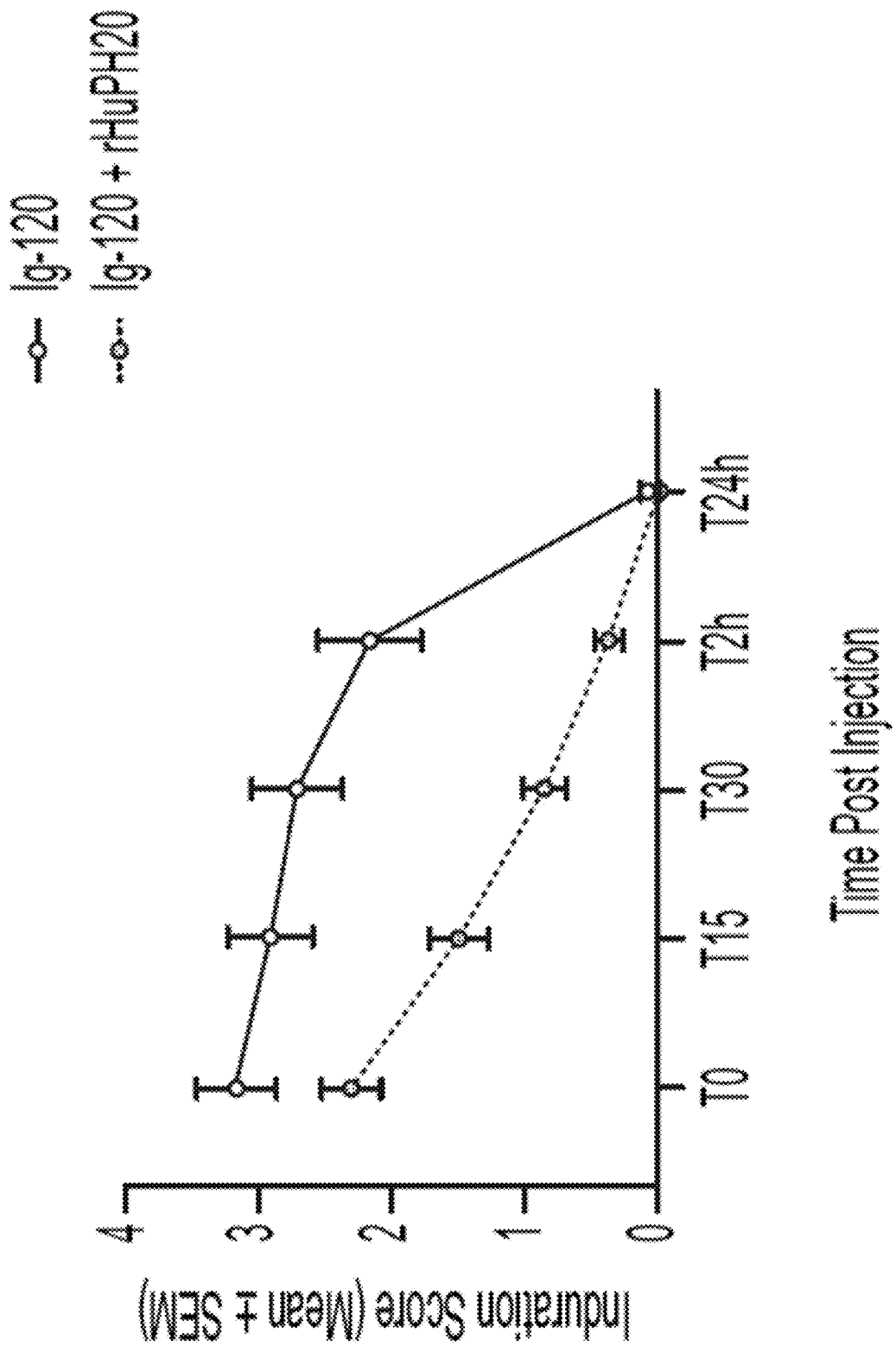
FIG. 35 is a chart of the qualitative assessment of post-injection induration (firmness).
Figure 38:
FIG. 38 provides photographs of the injection site of minipig AID #1361 before and at different intervals after the 10 mL Ig-120+rHuPH20 injection procedure.
Figure 40A:
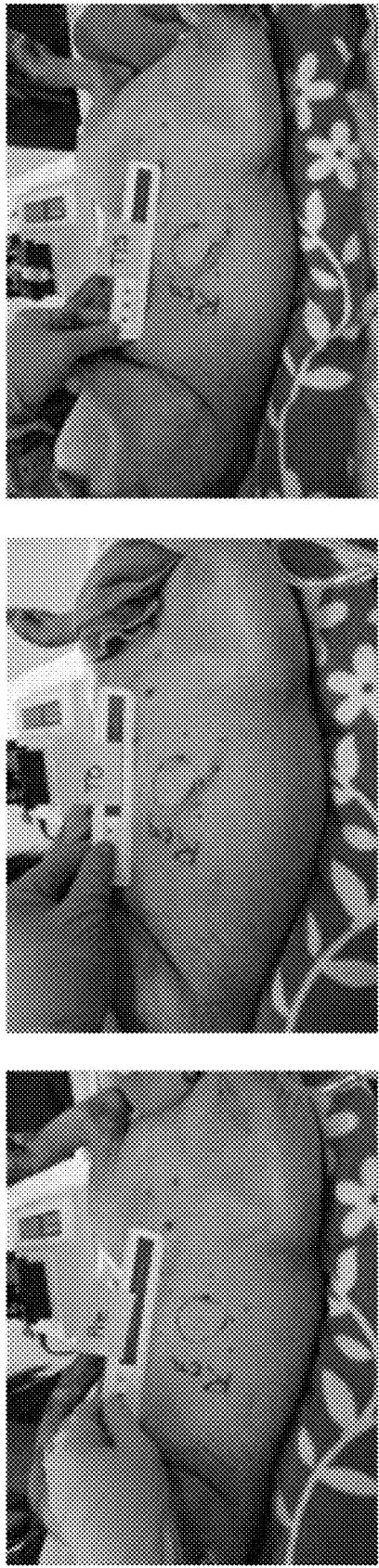

Qualitative assessment of post-injection firmness (induration): The hardness (induration) of the post-injection blebs were also evaluated by the independent scorers. The scoring for induration (Mean±SEM) for each test solution over time is shown in FIG. 35 and summarized in Table 27.

TABLE 27

Induration scores post-injection for Ig120 +
rHuPH20 (Mean ± SEM)

| Test Solution | Timepoint Post-Injection | | | | |
|---|---|---|---|---|---|
| | T0 | T15 | T30 | T2 h | T24 h |
| Ig-120 | 3.2 ± 0.3 | 2.9 ± 0.3 | 2.7 ± 0.3 | 2.2 ± 0.4 | 0.1 ± 0.1 |
| Ig-120 + rHuPH20 | 2.3 ± 0.2 | 1.5 ± 0.2 | 0.9 ± 0.2 | 0.4 ± 0.1 | 0.0 ± 0.0 |
| % Decrease | −28.1 | −48.3 | −66.7 | −81.8 | −100 |

The injection sites were photographed before and after the 10 mL injection procedure. Photographic images are shown in FIGS. 36A-42B. It should be noted at the 2 hour timepoint (T2 h), the photos of the animal were taken while it was anesthetized, but rather manually held by an animal technician. Because of the increased stress to the animal, this resulted in some flushing of the skin for some animals. In addition, the injection site may have had some increased tension (skin stretching) when photographed. Therefore, the qualitative scoring is considered the more accurate assessment of the injection site at the 2 h timepoint.

Summary and Conclusions

Back-leakage was reduced by 66% with the addition of rHuPH20.

Applied force using a 23 G needle was reduced from previous studies with 25 G needles by approximately 40%; addition of rHuPH20 reduced applied force approximately 7% compared to control injections.

Swelling and induration were reduced more rapidly for injections of Ig-120 rHuPH20 compared to injections of Ig-120 alone.

Example 3: Assessment of a Ten mL Subcutaneous Vertical Injection Using a 25 G Needle Using 5000 U/mL of rHuPH20 for Development of an Auto-Injector Summary This study examined the delivery of an Ig solution formulated at 120 mg/mL using a hand-held mock auto-injector. The test solution was delivered with and without rHuPH20 at a concentration of 5,000 U/mL. All injections were performed using a hand-held device that holds a needle in place so that it can be inserted vertically into the subcutaneous space at an injection depth of 7.5 mm. The test solution volume was 10 mL and was delivered in 30 seconds using a 20 cc syringe and 25 G needle. The applied force to the syringe barrel was measured throughout the injection by attaching a load cell to the end of the syringe flange. In addition, the back-leakage was collected post-injection and quantified by weight. The post-injection swelling was measured using calipers and 3D imaging. After the injection three independent scorers evaluated the injection site for erythema, swelling size and induration over time (at times T=0, 15, 30 min, 2 h, and 24 h) to assess the time for the resolution of the post-injection swelling.

Introduction

Current auto-injectors (AIs) are limited to extremely small volumes (typically ≤ 2.25 mL), limiting their usefulness for delivery of larger volumes. For larger volumes higher flow rates are required to make use of an AI practical. Currently 30 seconds is a recommended amount of time that a device can be held in place during self-administration to prevent fatigue and potential interruption of the injection.

rHuPH20 has been shown to facilitate the SC administration of fluids and drugs by transiently and locally depolymerizing hyaluronan (HA) in the extracellular matrix (ECM). The depolymerization of HA reduces tissue backpressure in the SC space that subsequently allows for rapid, large volume administration of drugs. Previous work has shown that rHuPH20 can facilitate the delivery of large volumes to the SC space at high flow rates using an infusion set.

The mini-pig model has been selected due to the high degree of similarity of the subcutaneous space to that of humans. Previous studies using a mini-pig model have demonstrated the translatability of the model for use in pre-clinical (Kang et al., 2013) and auto-injector studies (Shi et al., 2021).

In summary, the objective of this study was to determine if rHuPH20 may potentiate the development of a large volume AI that is able to deliver larger clinically relevant volumes to the SC space at high flow rates using the mini-pig as an animal model. In this study, the use of higher concentrations of rHuPH20 using a 25 G needle was investigated for all injections (5000 U/mL). This study builds upon data from a previous study which also injected Ig-120±rHuPH20 using a vertical needle insertion with a 25 G needle but used a lower concentration of rHuPH20 (2,000 U/mL). All injections for this study were performed via a vertically placed 25 G needle using a hand-held mock auto-injector device at a depth of 7.5 mm.

Test Articles and Methods

Test Articles

Human Gamma Globulin (Ig-120: 12% solution)
Lot number: 1032-17
Description: Lyophilized powder reconstituted at 120 mg/ml
Date of Manufacture: 21 Sep. 2020
Formulation: 10 mM Histidine, 130 mM Sodium Chloride, pH 6.5
Storage Conditions: 2-8° C.
Supplier: BioMed Supply
Formulated by: Halozyme Product Development
Recombinant Human Hyaluronidase rHuPH20 (ENHANZE™ Drug Product)
Lot number: 462-022
Description: Clear and colorless solution
Concentration: 10 mg/mL
Date of Manufacture: Dec. 30, 2014
Retest Date: February 2023
Enzyme activity: 1,229,456 U/mL
Storage: ≤70° C.
Formulation: 10 mM Histidine, 130 mM sodium chloride, pH 6.5
Handling Conditions: Standard laboratory precautions
Supplier: Halozyme Therapeutics, Inc Formulation Preparation of Test Solutions The two test solutions administered in this study were Ig-120 alone and Ig-120+rHuPH20. These were prepared by addition of rHuPH20 from a concentrated stock to an Ig solution previously prepared at 120 mg/mL. The final concentration of rHuPH20 in the test solution was 5,000 U/mL.

Ig-120 was thawed at 2-8° C. overnight. The following day test solutions were prepared by adding rHuPH20 to the Ig-120 solution at room temperature. A concentrated stock of rHuPH20 was used for test article preparation (10 mg/mL; 1,229,456 U/mL). To prepare Ig-120+rHuPH20, 675 µL of rHuPH20 was added to 150 mL of Ig-120 and the test solution immediately used for syringe filling on the day prior to the study.

The Ig-120+rHuPH20 solution was tested for rHuPH20 activity prior to the start of the study using a micro-turbidity assay. The activity of the Ig-120+rHuPH20 test solution was within 10% of target concentration and deemed to be within acceptable range for use in the study. The test solution was stored at 2-8° C. until study start. rHuPH20 activity values are summarized in Table 28.

TABLE 28

Pre-Study activity testing of rHuPH20 activity in test solution

| Test Solution | Pre-study Concentration (U/mL ± SD) |
|---|---|
| Pre-study Ig-120 + rHuPH20 | 4941 ± 84 |

At the end of the study, dose retain samples that were obtained during the study procedure were tested for rHuPH20 activity. After administration of the test solution the remaining solution in the syringe was stored at 2-5° ° C. (on ice) until transported back for activity testing on the following day. The activity of the Ig-120+rHuPH20 test solutions are summarized in Table 29.

TABLE 29

Post-study activity testing of rHuPH20 activity in test solution

| Test Solution | Post-study Concentration (U/mL ± SD) |
|---|---|
| Dose retain #1: AID #1535L (Ig-120 alone) | 0 |
| Dose retain #2: AID #1536R (Ig-120 alone) | 0 |
| Dose retain #3: AID #1535R (Ig-120 + rHuPH20) | 4805 ± 77 |
| Dose retain #4: AID #1537R (Ig-120 + rHuPH20) | 4745 ± 50 |
| Dose retain #5: AID #1539L (Ig-120 + rHuPH20) | 4701 ± 51 |
| Dose retain #6: AID #1543L (Ig-120 + rHuPH20) | 4761 ± 51 |

Animal Description
Species: Pig (Sus scrofa domestica)
Strain: Yucatan miniature
Sex: Female
Age: >3 months
Body weight: 12-16 kg upon receipt
Quantity: 6
Source: Premier BioSource (Ramona, CA)

Husbandry

Animals were received on 9 Sep. 2022 by the facility and allowed to acclimate prior to study start. Animals were group housed in steel pens with automatic water provided ad libitum. Animals were fed twice daily (AM and PM), except on study day (PM only). Room environment was set to maintain a temperature of ~17-27° ° C. and a relative humidity of 40-70%, with a 12 hour light/12 hour dark time cycle. Animals were allowed to acclimate to the facility 4 days prior to study onset.

Test Materials

TABLE 30
Summary of test materials

| Test Material | Supplier |
| --- | --- |
| High pressure syringe pump | KD Scientific, Holliston, MA |
| 25G × 1 inch Precision Glide needle | Becton Dickinson, Franklin Lakes, NJ |
| 20 mL Luer-Lok ™ syringe | Becton Dickinson, Franklin Lakes, NJ |
| 21 inch standard bore extension set | B/Braun, Bethlehem, PA |
| Subminiature load cell | Loadstar Sensors; Fremont, CA |
| Load cell interface | Loadstar Sensors; Fremont, CA |
| Load cell software | Loadstar Sensors; Fremont, CA |
| Standard Digital Camera | Canon |
| High Resolution 3D camera | Canfield Sciences, Parsippany, NJ |
| 3D Printed Mock Auto-Injector | Halozyme, Inc. |
| 3D Printed Auto-Injector Platform | Halozyme, Inc. |
| Digital caliper | Fowler Precision Instruments, Switzerland |
| Infrared thermometer | Fisher Brand |
| Surgical Eye Spear | Becton Dickinson, Franklin Lakes, NJ |

Experimental Design

In this study, two 10 mL injections were administered to the abdomen of a Yucatan miniature pig. On one side of the abdomen a test solution of Ig-120 alone was administered. One the contralateral side of the animal a second test solution of Ig-120+rHuPH20 (5000 U/mL) was administered. The location of the injection sites was randomized with three injections of each test solution on the left side and right sides of an animal. The needle was mounted in a hand-held mock auto-injector device and the needle inserted vertically into the SC space. The treatments for each animal are summarized in Table 31, Description of treatments.

TABLE 31
Description of treatments

| Cohort | N/Cohort | Test Solution (Left) | Volume (mL) | Flow Rate (mL/min) | [rHuPH20] (U/mL) |
| --- | --- | --- | --- | --- | --- |
| 1 | 6 | Ig-120 alone | 10 | 20 | 0 |
| 2 | 6 | Ig-120 + rHuPH20 | 10 | 20 | 5000 |

Quantitative endpoints included in this study were measurement of applied force to the syringe barrel during the injection, post-injection swelling (bleb) volume, area, and height, and skin temperature changes pre and post-injection were collected via infrared thermometer. In addition, the post-injection back-leakage of test article was collected from the injection site for 30 seconds after the removal of the needle using an eye-spear to absorb any leakage and quantified by weight. The volume of the injection site blebs was determined by digital caliper measurement (length, width, and height) as well as by 3D camera imaging. At 15 minutes post-injection (T15) and 30 minutes post-injection (T30) the dimensions of the bleb were again measured using a digital caliper. Additional post-injection qualitative injection site evaluations for erythema, swelling, and induration was performed immediately post injection (T0) and at T15, T30, 2 hours post-injection (T2 h) and at approximately 24 hours post-injection (T24 h) post-injection.

Qualitative assessments of the injection sites were performed while the animal was under anesthesia for the T0, T15, T30, and T24 h timepoints while the T2 h assessment was performed while the animal was conscious and hand-held by an animal technician. Standard photographs were obtained both pre-injection and at times T0, T15, T30, T2 h, and T24 h post-injection. After euthanasia, a 12 mm punch biopsy was obtained from the injection site and fixed in 10% formalin. In summary, the endpoints for the study were:
- Applied force during the injection
- Measurement of back-leakage post-injection
- Measurement of bleb size (length/width/height) post-injection (caliper) over time (T0, T15, T30)
- Measurement of bleb size (volume, height, area) using 3D imaging (T0 only) Assessment of blebs for erythema, swelling size and induration at times T0, T15, T30, T2 h and T24 h
- Measurement of temperature at injection site both pre- and post-injection Study Procedure Prior to start of study, animals were assessed for general health, and body weights were collected. On the day prior to the study, test articles (~17 mL) were drawn into a 20 mL syringe, capped, and stored at 2-8° C. On the day of the study, two syringes containing the test solutions for each animal were removed from 2-8° C. and brought to room temperature for at least 45 minutes and administered within 1.5 hours. Dose retains taken during the study procedure were stored on ice until transferred back to Product Development for enzymatic testing on the day following the study procedure.

Animals were anesthetized with isoflurane gas and placed in dorsal recumbence on a foam wedge placed on a heated surgical table and were maintained under isoflurane gas for the entire duration of the procedure. The abdominal region was cleaned with Nolvasan followed by wiping the injection site with gauze containing 70% isopropanol and wiped dry with sterile gauze.

Injection sites were located on the left and right abdominal regions, ~6 cm cranially from the inguinal fold towards the midline and ~3 cm towards the midline of the animal. Each of the injection sites was marked with a permanent marker and then photographed with the standard and 3D cameras prior to needle insertion. The temperature of the skin at the injection site was recorded prior to the start of the injection using an infrared thermometer. The initial injection for each animal was the control solution (Ig-120 alone). The second injection on the contralateral side of the animal was the test solution containing rHuPH20 (Ig-120+rHuPH20).

Assembly of Mock Device

The mock device was prepared by attaching a capped 25 G×1 inch Leur-lok needle to the male end of a 21-inch extension set. The extension set was then routed through the inside of the mock device and the needle was firmly seated in place in the end of the device. The device with needle attached was then inserted into the platform. The length of the needle projecting from the end of the mock device was confirmed to be 7.5 mm+0.5 mm (providing an injection depth of 7.5 mm). The needle remained capped until just prior to vertical needle insertion. The 20 cc syringe that contains the test solution was uncapped, attached to the female end of the extension set and then the hardware was primed to the needle tip with the test solution and the syringe was placed into the syringe pump. The load cell was then attached to the end of the syringe plunger and the syringe mounted into the syringe pump. After loading the syringe, the load cell was zeroed. The pump block was positioned so that it abutted the end of the syringe plunger-load cell with minimal contact force and was then locked into place.

Pre-injection temperature measurements of the injection site were taken using a digital thermometer. Once applied force readings were confirmed to be recorded the syringe pump was started to begin injection of the test article at the designated flow rate of 20 mL/min. Upon completion of the injection, the needle was removed, the pressure on the syringe pump block removed, and the applied force data collection was stopped. Test solution back-leakage was then absorbed to a tared eye-spear for 30 seconds by blotting the injection site. The weight of the eye spear was recorded using analytical balance with an accuracy of 0.1 mg. Post injection temperature was collected at the injection site. The margins of the injection site bleb were marked with a permanent marker and measured for length, width, and height using a digital caliper and recorded. The injection site was then photographed with the standard and 3D cameras and then qualitatively scored by three independent evaluators for appearance and severity of erythema, swelling/bleb size, and firmness (induration) using a 5-point scoring system (a modified Draize Test) based on the 1992 OECD guidelines for grading skin reactions (Table 32, 33, and 34). The evaluators were blinded to each other's scores. After the first injection, the procedure was repeated on the contralateral side of the animal using the other test solution (Ig-120+rHuPH20).

TABLE 32

Grading scale for erythema formation

| Scale | Description |
| --- | --- |
| 0 | No erythema |
| 1 | Very slight erythema (barely perceptible) |
| 2 | Well defined erythema |
| 3 | Moderate erythema |
| 4 | Severe erythema (beet redness) to slight eschar formation |

TABLE 33

Grading scale for swelling size formation

| Scale | Description |
| --- | --- |
| 0 | No swelling |
| 1 | Very slight swelling |
| 2 | Slight swelling |
| 3 | Moderate swelling |
| 4 | Severe swelling |

TABLE 34

Grading scale for swelling firmness (induration)

| Scale | Description |
| --- | --- |
| 0 | No perceptible difference in firmness after injection |
| 1 | Very slightly firm (barely perceptible) |
| 2 | Mildly firm |
| 3 | Moderately firm |
| 4 | Very firm |

Qualitative scoring for erythema, swelling, and induration were collected by all 3 evaluators again at 15 min., 30 min, 2 hr, and approximately 24 hr post injections. Photographs with the standard camera were collected at each of these timepoints. Following the final assessment, the animal was humanely euthanized using a ready for use solution of sodium pentobarbital and sodium phenytoin (Euthasol®).

Calculations and Statistical Methods
Assessment of Applied Force
Applied force, as measured via a load cell attached to the end of syringe plungers, was recorded using SensorVUE software (Loadstar Sensors), and the mean applied force over the entire injection period was calculated.

Assessment of Local Swelling Volume and Area Using Caliper Measurement and 3D Imaging
Volume and area of post-injection swelling were measured using both caliper measurement and 3D camera image analysis. For caliper measurements a digital caliper was utilized to measure length, width and height of the bleb that formed post-injection. The length and width are defined as the edge to edge measurements of the bleb (i.e., diameter) along their longest axes. These values were manually recorded, and the volume determined using the formula for half of an ellipsoid $Vol=(2/3)*\pi*A*B*C$ where A=Length/2, B=Width/2 and C=Height.

3D imaging was applied as a longitudinal methodology to measure post-injection swelling. By obtaining high definition pre- and post-injection 3D images the distances between two registered surfaces can be determined. The camera captures images using a factory calibrated bifocal imaging system to measure distance between surfaces. Surface registration was performed using multipoint method that utilized common landmarks between the pre-injection image and the post-injection image. Using the proprietary software the volume, area and height of the post-injection swelling was calculated for each injection.

Caliper measurement and 3D imaging measurement will yield different values for volume, area, and bleb height. The differences are a result of the difference in the bleb size measurement. The 3D measurement calculates bleb height based from the top of the bleb to the original skin position, while the bleb height from caliper measurements measure from the top of the bleb to the height at the edge of the bleb. Due to skin curvature, this may yield an overall increase in bleb height for the caliper measurements compared to the 3D measurements, resulting in greater bleb volume and height. However, the measurements are consistent with each other and therefore differ only due to the methodology.

Results and Discussion
Pre- and Post-Injection Quantitative Measurements
Quantitative measurements included applied force, back-leakage, bleb size (length, width, & height) and pre- and post-injection temperatures (as described above).

Assessment of applied force during injection: The applied force was measured during the SC injection by attaching a subminiature load cell to the end of the 20-cc syringe barrel. The load cell provided force data that was electronically recorded throughout the injection via a DI-100U load cell interface at a data capture rate of 2 Hz.

Figure 43:
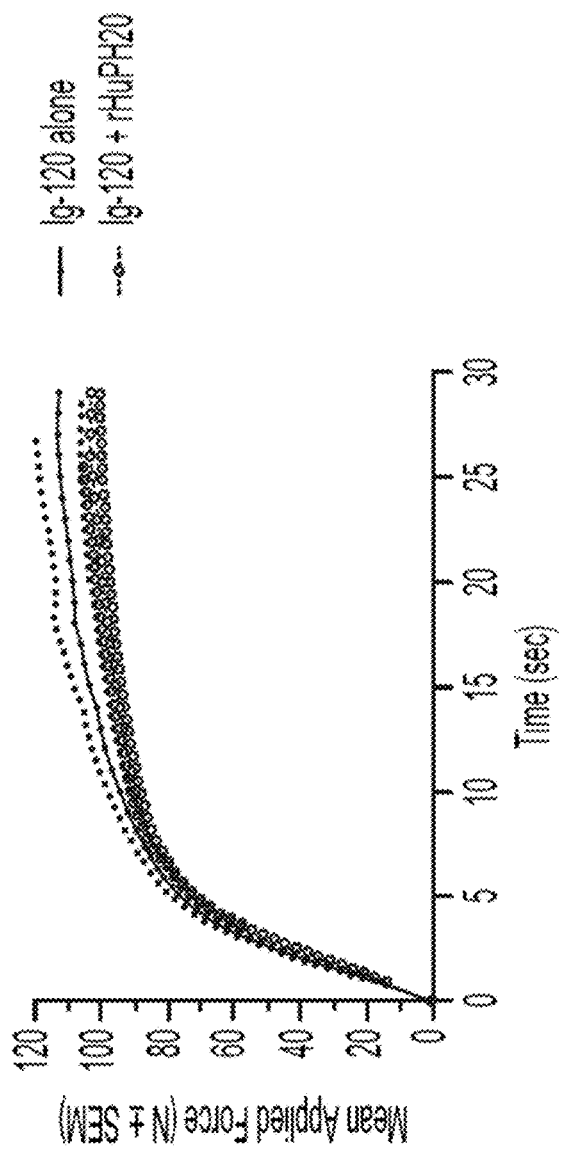
FIG. 43 is a chart of the is a chart of the applied force (N) during injection (Mean±SEM) of Ig-120 and Ig-120+rHuPH20.
Figure 44:
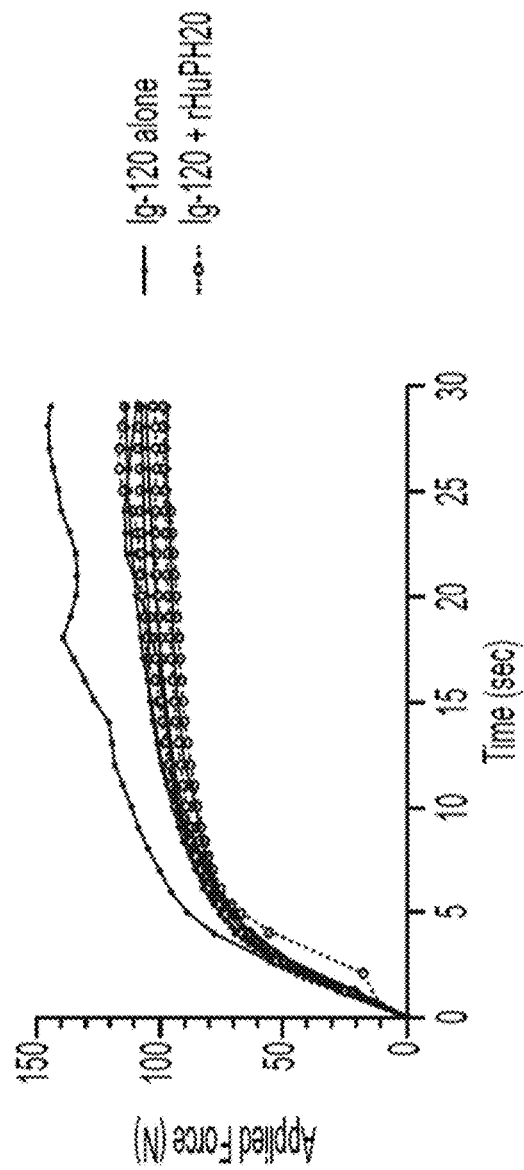
FIG. 44 is a chart of the individual applied force (N) during injection of Ig-120 and Ig-120+rHuPH20.

Applied forces for each test solution and flow rate are summarized in Table 35 and FIG. 43. Applied force during injection for individual animals at each flow rate is shown in FIG. 44.

TABLE 35

Summary of applied forces during injection

| Flow Rate | Delivery Time | Mean Applied Force (N) ± SEM | |
| --- | --- | --- | --- |
| (mL/min) | (sec) | Ig-120 alone | Ig-120 + rHuPH20 |
| 20 | 30 | 92.7 ± 3.5 | 85.9 ± 3.2 |

Figure 45A:
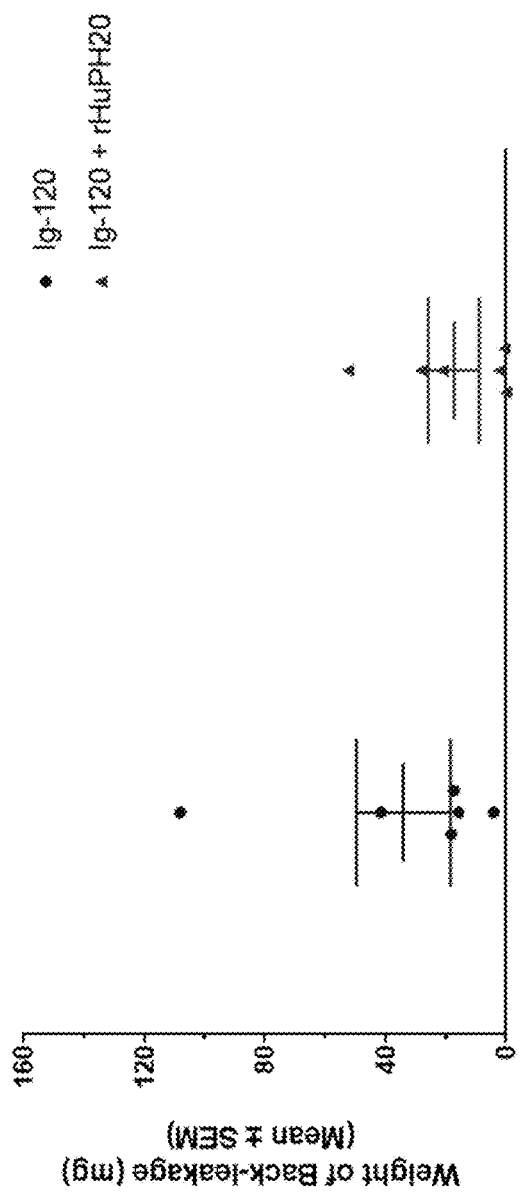
FIG. 45A is a chart of the mean (mg±SEM) and individual weights of back-leakage.
Figure 45B:
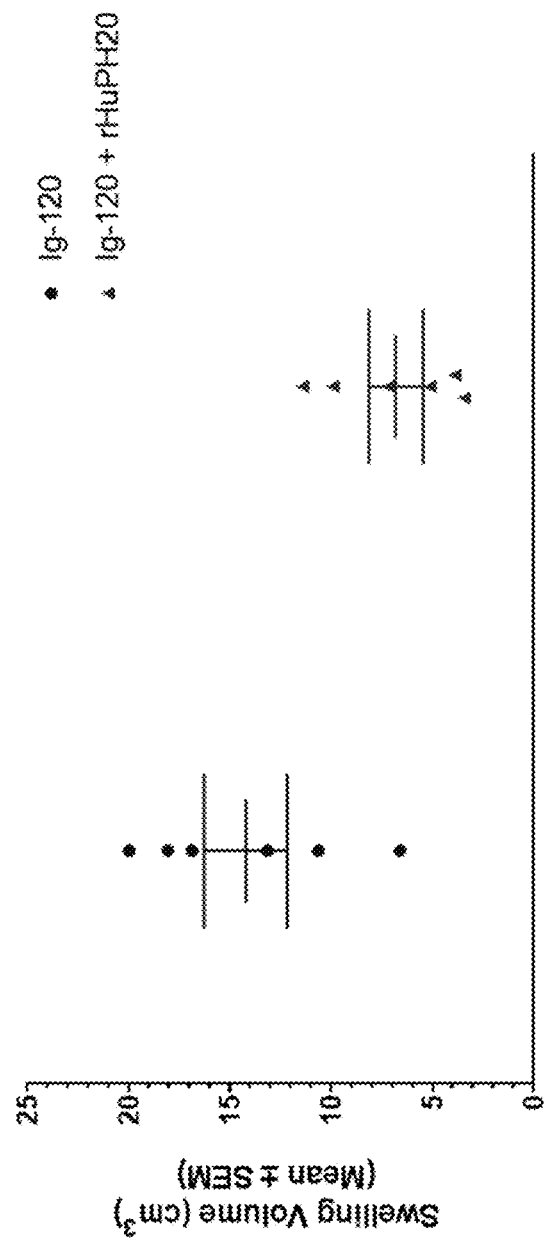
FIG. 45B is a chart of the individual swelling volumes ($cm^3$) after SC injection of Ig-120 and Ig-120+rHuPH20—caliper measurement.

Assessment of post-injection back-leakage: The amount of back-leakage for each injection was measured by collecting post-injection fluid at the site using a surgical eye spear. Prior to collection, the weight of each eye spear was tared on the analytical balance. Post-injection back-leakage from the injection site was collected for an interval of 30 seconds. The eye spear was then immediately weighed, and the weight recorded. The analytical balance had a precision of 0.1 mg. Back-leakage for Ig-120 alone and Ig-120+rHuPH20 are shown in Table 36 and individual animal data with Mean±SEM is shown in FIG. 45.

TABLE 36

Mean weight of back-leakage (mg ± SEM)
Weight of Back-leakage (mg ± SEM)

| Ig-120 alone | Ig-120 + rHuPH20 |
|---|---|
| 34.2 ± 15.6 | 17.4 ± 8.5 |

Figure 46:
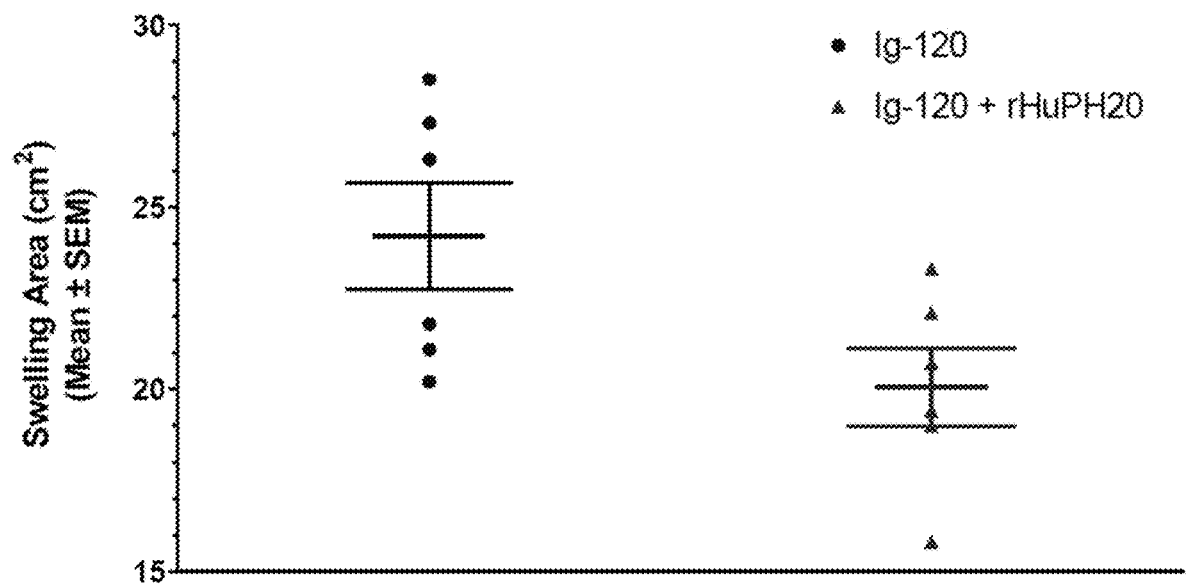
FIG. 46 is a chart of the individual swelling areas ($cm^2$) after SC injection of Ig-120 and Ig-120+rHuPH20—caliper measurement.
Figure 47:
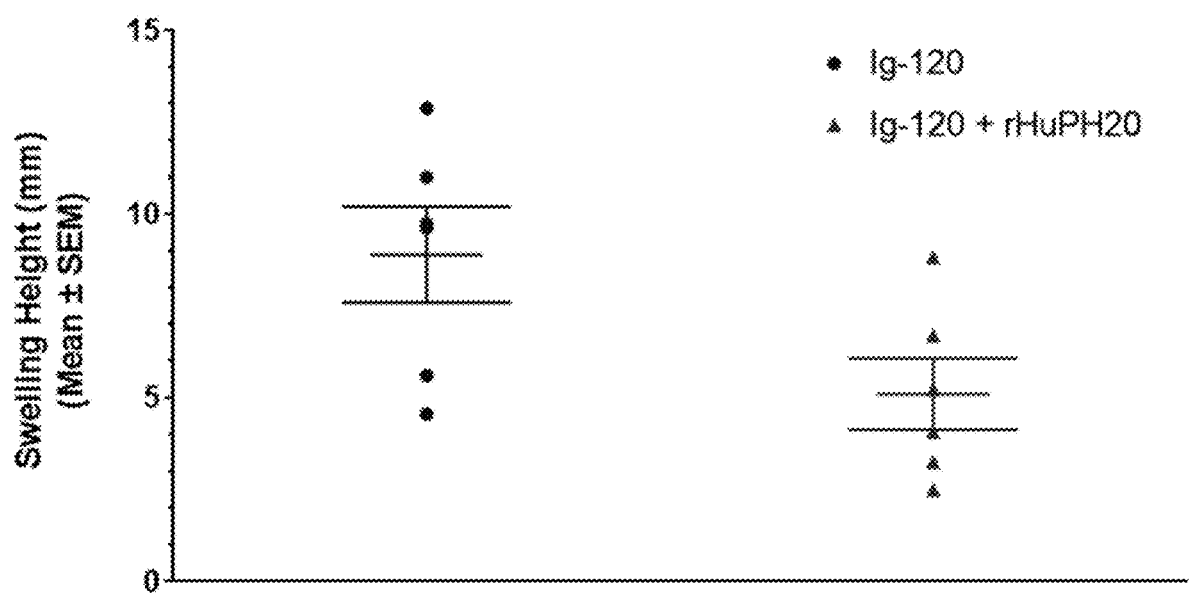
FIG. 47 is a chart of the individual swelling heights (mm) after SC injection of Ig-120 and Ig-120+rHuPH20—caliper measurement.

Assessment of post-injection bleb volume, area, and height (caliper measurements): The local injection site swelling was marked and measured using a digital caliper. Bleb volume, dispersion area, and swelling height of each bleb was determined as described above and are summarized in Table 37 for Ig-120 and Ig-120+rHuPH20. Individual post-injection bleb volume, area, and height values are shown in FIGS. 45-47.

TABLE 37

Bleb volume, area and height after injection of Ig-120 + rHuPH20 using caliper measurement (Mean ± SEM)

| Test Solution | Volume (mL) | Area (cm$^2$) | Height (mm) |
|---|---|---|---|
| Ig-120 | 14.2 ± 2.1 | 24.2 ± 1.5 | 8.9 ± 1.3 |
| Ig-120 + rHuPH20 | 6.8 ± 1.4 | 20.1 ± 1.1 | 5.1 ± 1.0 |

Figure 48:
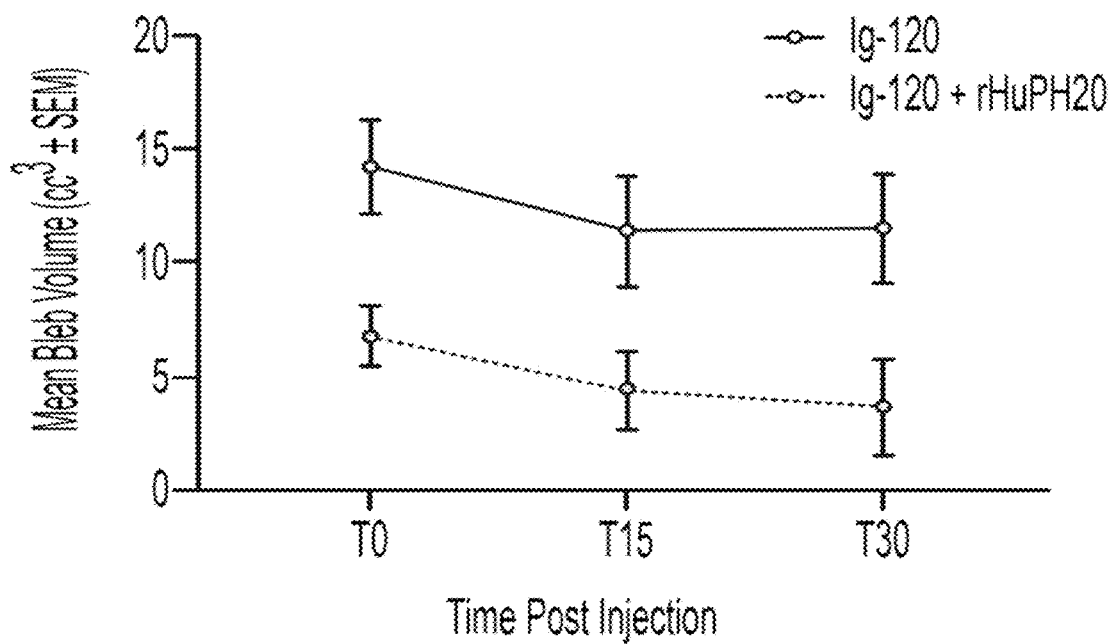
FIG. 48 is a chart of the bleb volume over time (T0-T15-T30).

The dimensions (length, width and height) of the bleb was measured at T15 and T30 post-injection in addition to the T0 timepoint (caliper measurements only) which was used to calculate the volume over time which is shown in FIG. 48.

Figure 49:
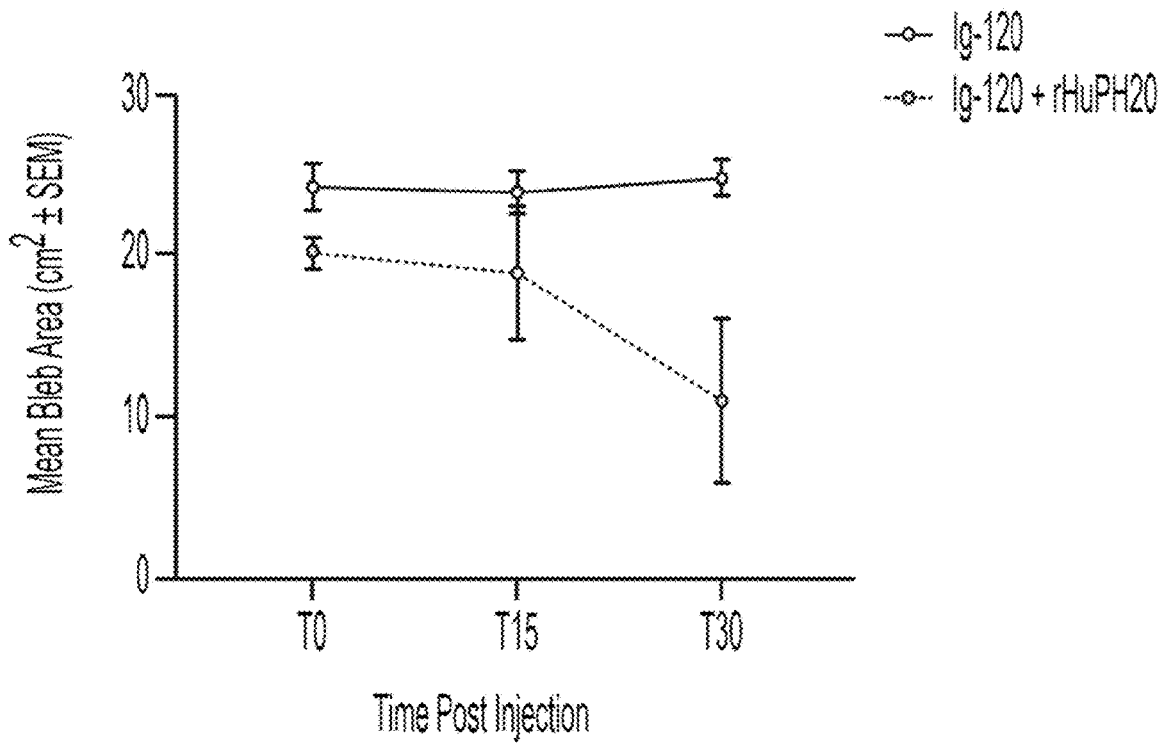
FIG. 49 is a chart of the bleb area over time (T0-T15-T30).

The area of the bleb was measured at T15 and T30 post-injection in addition to the T0 timepoint (caliper measurements only) and the area over time is shown in FIG. 49.

Figure 50:
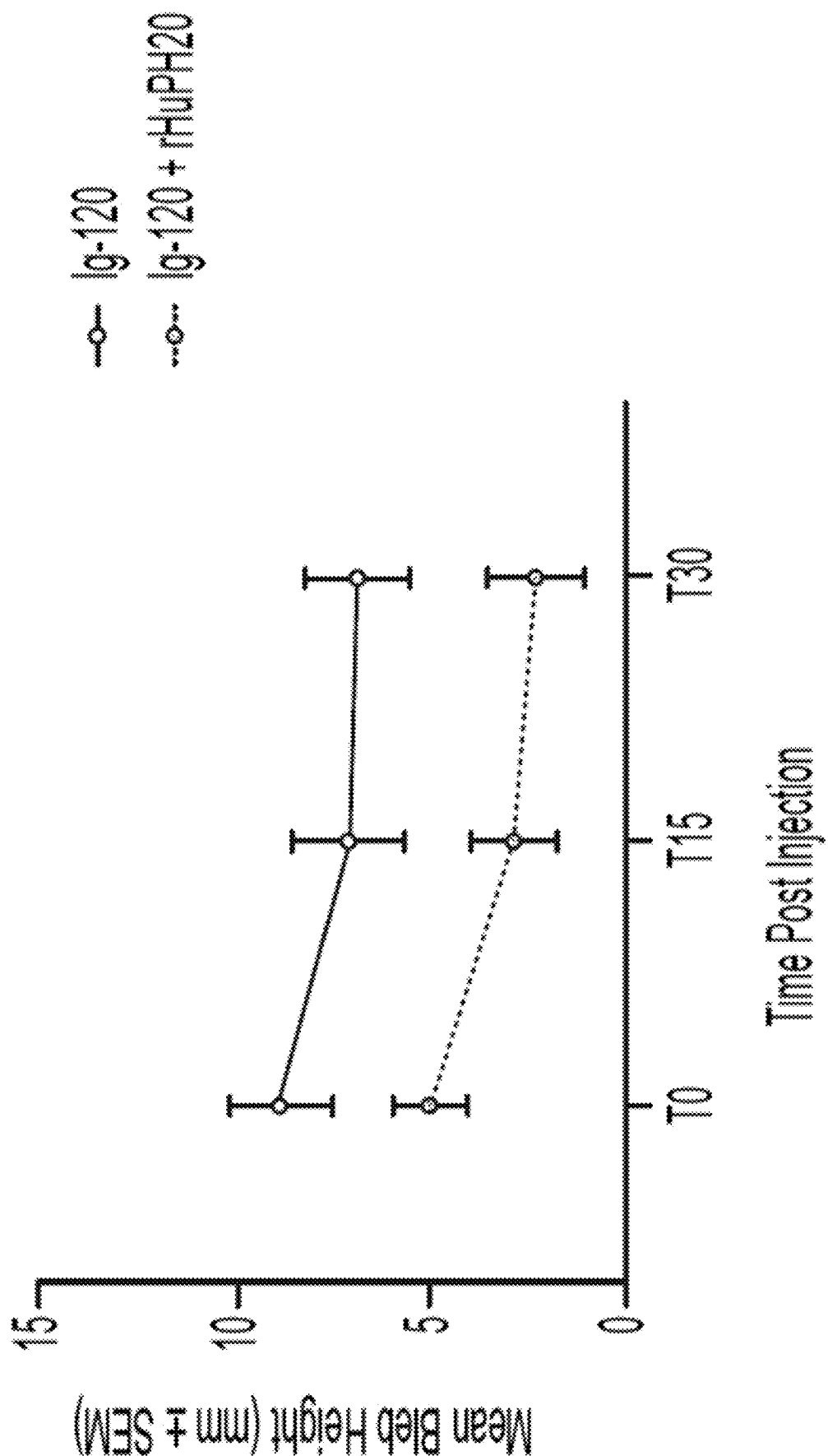
FIG. 50 is a chart of the bleb height over time (T0-T15-T30).

The height of the bleb was measured at T15 and T30 post-injection in addition to the T0 timepoint (caliper measurements only) and the height over time is shown in FIG. 50.

Assessment of post-injection bleb shape, volume, area, and height (3D imaging): Pre- and post-injection photographs were taken using a 3D imaging system. This technology permits point-to-point alignment of these two images through multipoint surface registration. The distance between any two points is then represented using a colorimetric surface contour map. Regions where there is no difference between the two images are displayed in gray. Where the post-injection image is higher than the pre-injection image, the region is displayed in shades of blue. Where the post-injection image is lower than the pre-injection image the distance is displayed in shades of orange. The color intensity is proportional to the amount of distance measured between images and the range that is set for positive and negative measurements. Out of range measurements are depicted in white. Bleb measurements of volume and height include regions out of range.

Each animal had a pre-injection 3D image taken of the injection site followed by a second image taken immediately post-injection and these images were mapped to each other using multipoint registration. These registered pre-/post-injection images were then used to calculate the bleb volume, height, circumference, length, and width for each bleb using proprietary software. Colorimetric surface contour maps of each post-injection bleb for Ig-120 and Ig-120+rHuPH20 are shown in FIGS. 51A-51B.

Figure 52:
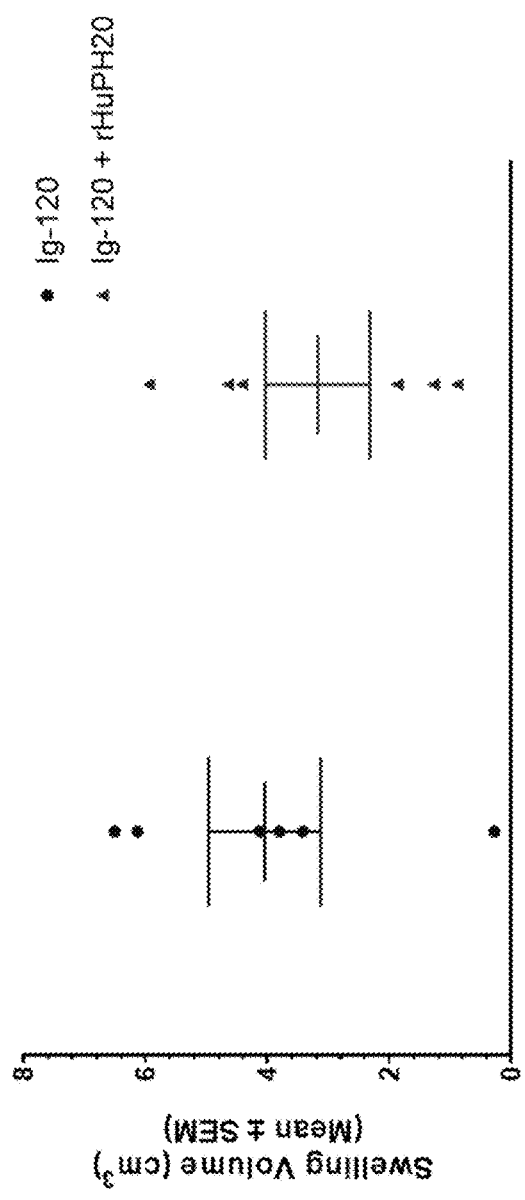
FIG. 52 is a chart of the individual bleb volumes ($cm^3$) after SC injection of Ig-120 and Ig-120+rHuPH20—3D imaging.
Figure 53:
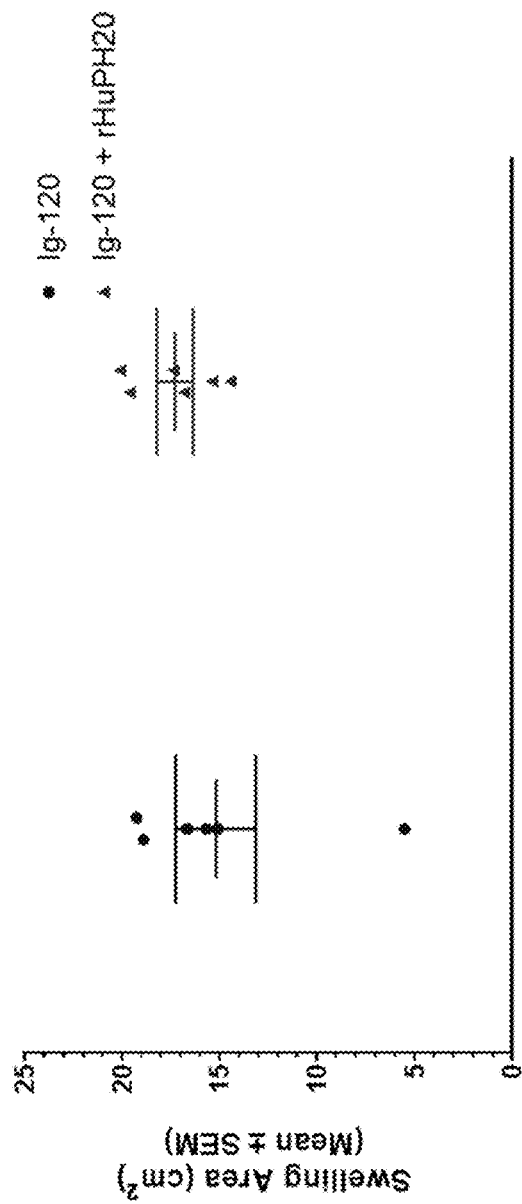
FIG. 53 is a chart of the individual bleb areas ($cm^2$) after SC injection of Ig-120 and Ig-120+rHuPH20—3D imaging.
Figure 54:
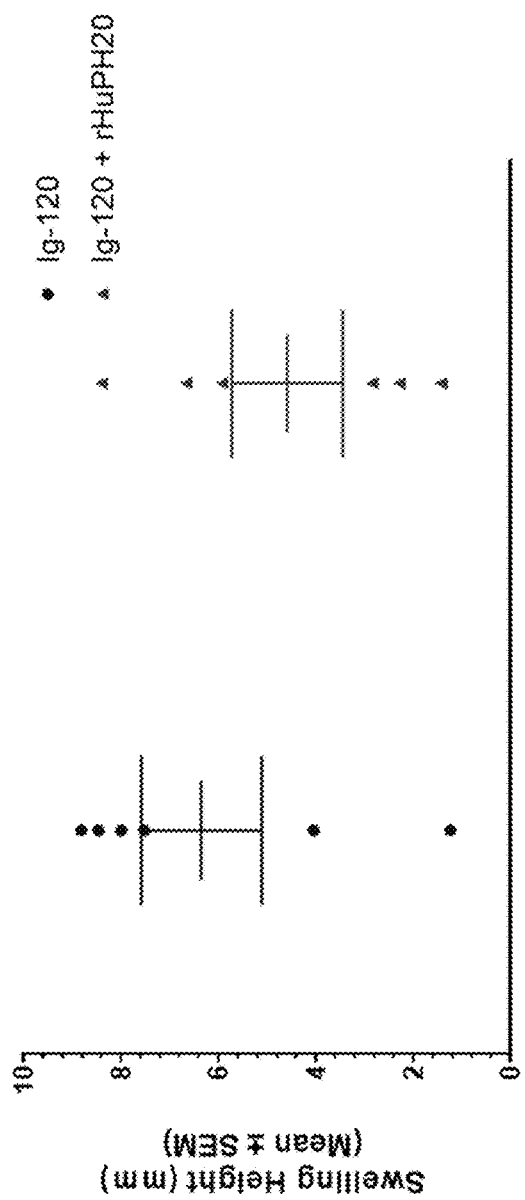
FIG. 54 is a chart of the individual bleb heights (mm) after SC injection of Ig-120 and Ig-120+rHuPH20—3D imaging.

Post-injection bleb volume, area and height for Ig-120 and Ig-120+rHuPH20 calculated from the 3D images are summarized in Table 38. Individual post-injection bleb volume, area, and height are shown graphically in FIGS. 52-54.

TABLE 38

Bleb volume, area, and height after injection of Ig-120 + rHuPH20 assessed using 3D imaging (Mean ± SEM)

| | Ig-120 + rHuPH20 | | |
|---|---|---|---|
| Test Solution | Volume (mL) | Area (cm$^2$) | Height (mm) |
| Ig-120 | 4.0 ± 0.9 | 15.2 ± 2.1 | 6.4 ± 1.2 |
| Ig-120 + rHuPH20 | 3.2 ± 0.9 | 17.3 ± 0.9 | 4.6 ± 1.1 |

Figure 55:
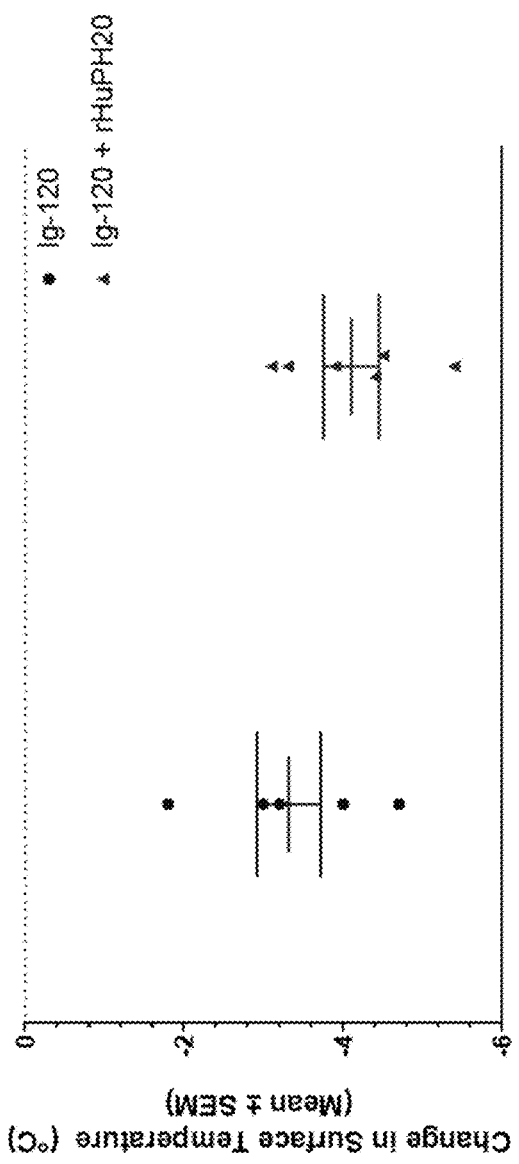
FIG. 55 is a chart of the change in surface temperature: pre- to post-injection.

Assessment of post-injection temperature changes: The temperature of the injection site was measured immediately prior to needle insertion using an infrared thermometer. It was then re-measured at the end of the injection to determine if any significant changes in temperature may occur as a result of flow rate. The changes in surface temperature between pre- and post-injection are provided in Table 39 and FIG. 55.

TABLE 39

Mean changes in surface temperature (° C. ± SEM)
Test Solution

| Ig-120 | Ig-120 + rHuPH20 |
|---|---|
| −3.3 ± 0.4 | −4.1 ± 0.3 |

Qualitative Assessment of Local Injection Sites

Following the completion of the 10 mL injections, the qualitative assessments for erythema, swelling size and firmness by the three different scorers was performed as described above.

Figure 56:
FIG. 56 is a chart of the qualitative assessment of post-injection erythema.

Qualitative assessment of post-injection erythema: Erythema was minor for both test solutions. Erythema for both test solutions was both mild and transient. The scoring by the three evaluators for erythema (Mean±SEM) for each test solution are summarized in Table 40 and shown in FIG. 56.

TABLE 40

Erythema scores post-injection for Ig-120 and
Ig-120 + rHuPH20 (Mean ± SEM)

| Test Solution | Timepoint Post-Injection | | | | |
|---|---|---|---|---|---|
| | T0 | T15 | T30 | T2 h | T24 h |
| Ig-120 | 0.3 ± 0.2 | 0.3 ± 0.2 | 0.1 ± 0.1 | 0.0 ± 0.0 | 0.0 ± 0.0 |
| Ig-120 + rHuPH20 | 0.3 ± 0.1 | 0.3 ± 0.1 | 0.2 ± 0.1 | 0.0 ± 0.0 | 0.0 ± 0.0 |

Figure 57:
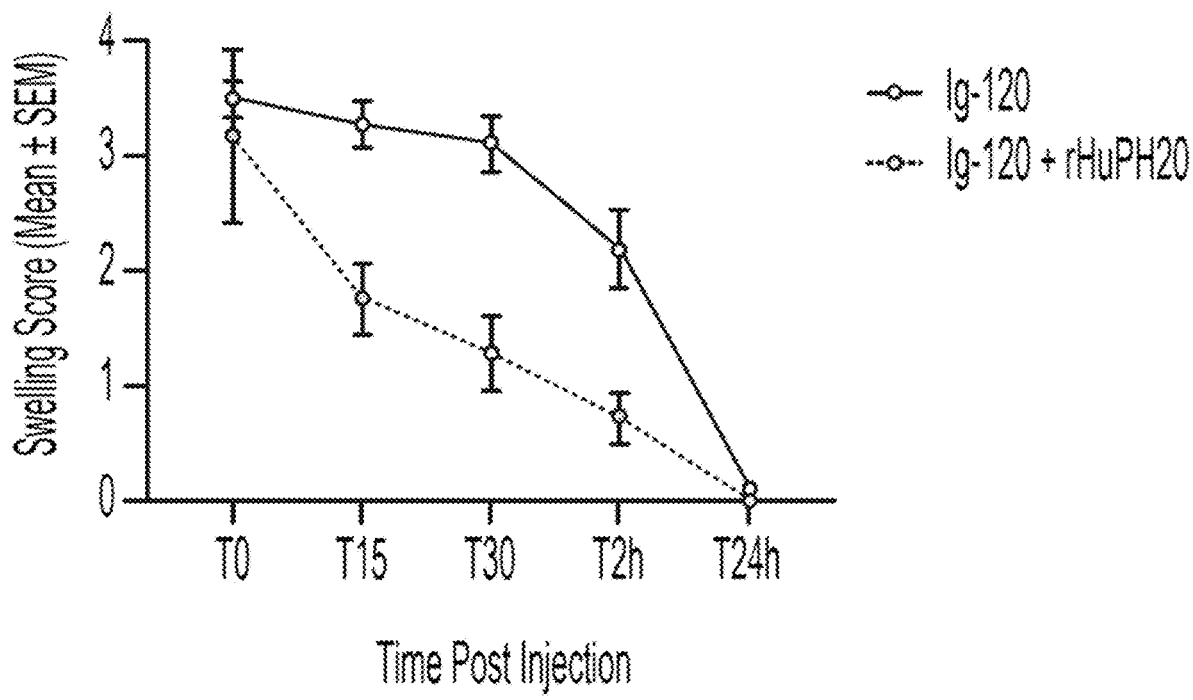
FIG. 57 is a chart of the qualitative assessment of post-injection swelling size.

Qualitative assessment of post-injection swelling size: Post injection swelling size was mild to moderate for all injections with rapid swelling resolution over time for injections containing rHuPH20. Scoring by the three evaluators for swelling size (Mean±SEM) for each test solution over time are summarized in Table 41 and shown in FIG. 57.

TABLE 41

Swelling scores post-injection for Ig120 + rHuPH20 (Mean ± SEM)

| Test Solution | Timepoint Post-Injection | | | | |
|---|---|---|---|---|---|
| | T0 | T15 | T30 | T2 h | T24 h |
| Ig-120 | 3.5 ± 0.2 | 3.3 ± 0.2 | 3.1 ± 0.2 | 2.2 ± 0.3 | 0.1 ± 0.1 |
| Ig-120 + rHuPH20 | 3.2 ± 0.8 | 1.8 ± 0.3 | 1.3 ± 0.3 | 0.7 ± 0.2 | 0.0 ± 0.0 |

Figure 58:
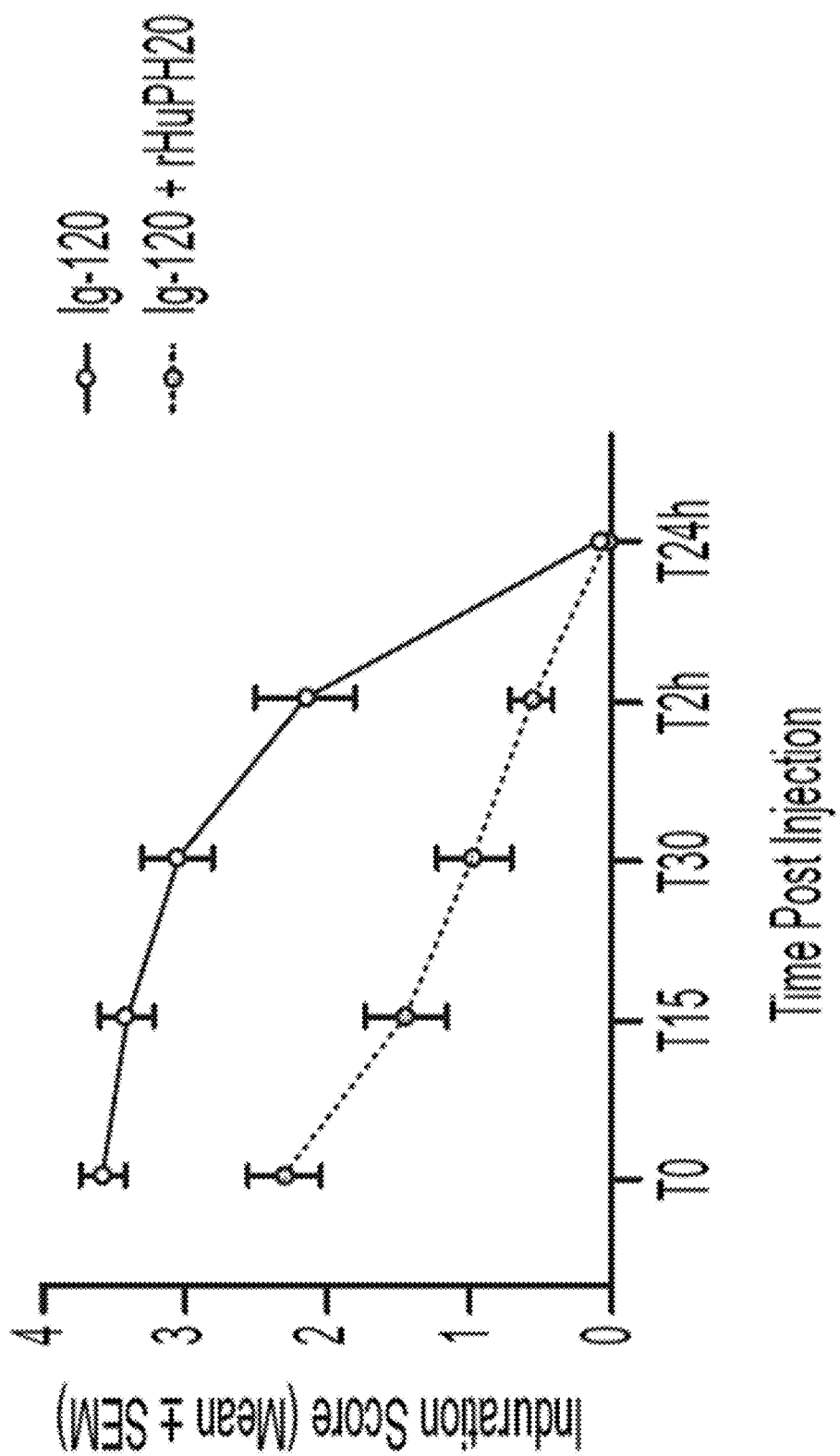
FIG. 58 is a chart of the qualitative assessment of post-injection induration (firmness).
Figure 63A:
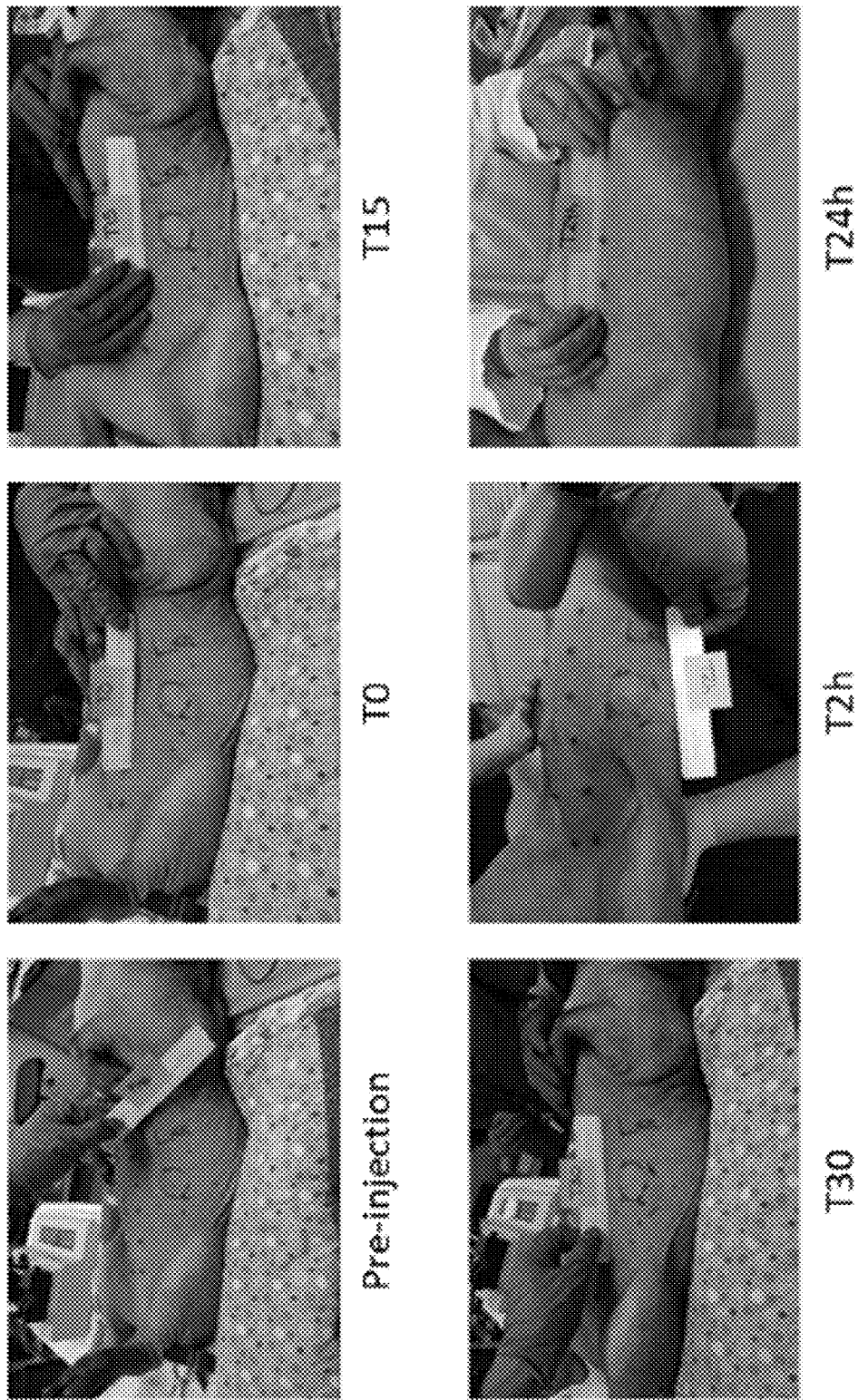
FIGS. 63A-63B provide photographs of minipig AID #1542 before and at different intervals after the 10 mL injection procedure.
Figure 63B:
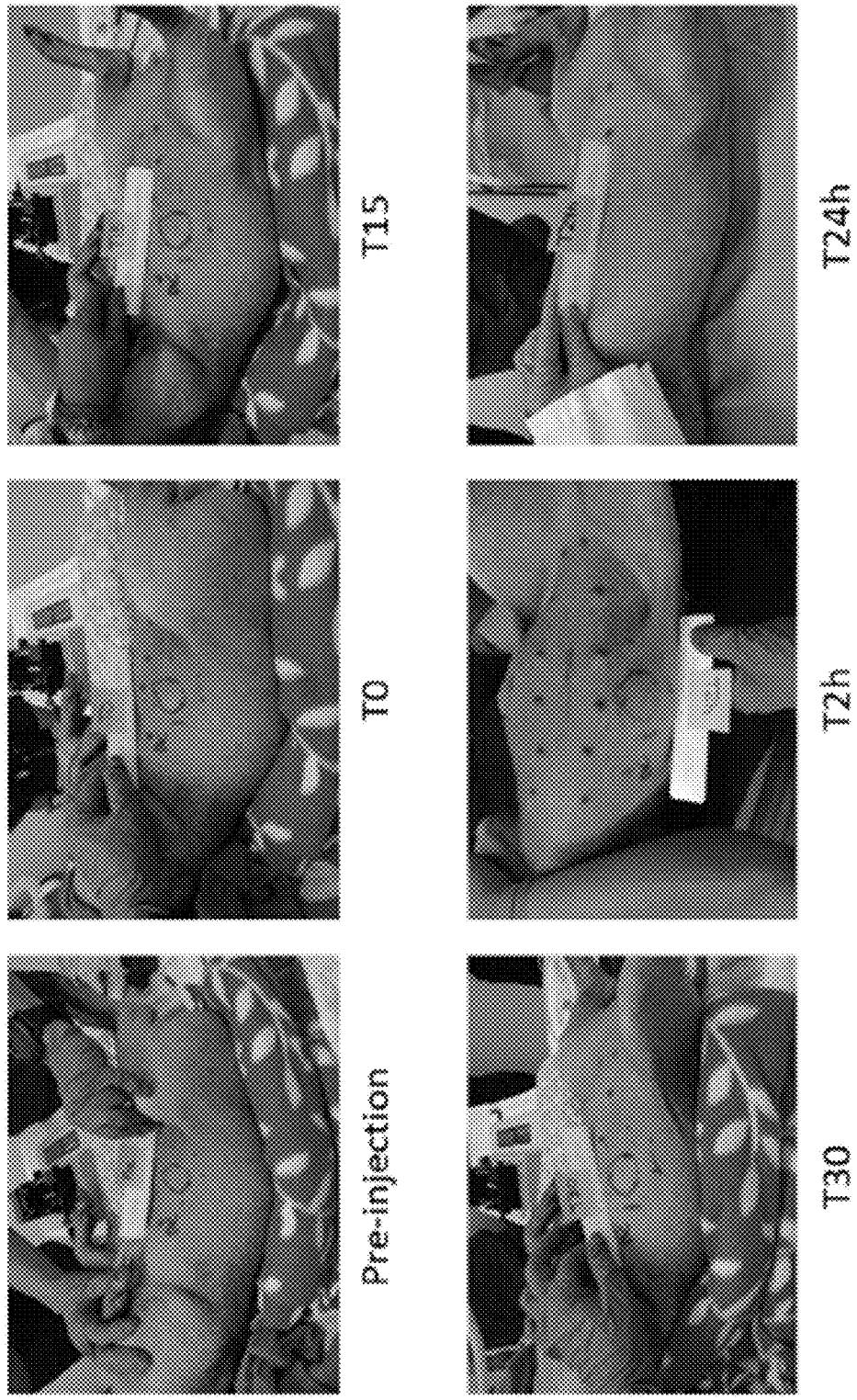

Qualitative assessment of post-injection firmness (induration): The hardness (induration) of the post-injection blebs were also evaluated by the independent scorers. The induration of the post-injection blebs for injections containing rHuPH20 was mild to moderate immediately after injection. Over time the induration of control injections persisted to 30 minutes (T30) and beyond while the induration for injections containing rHuPH20 decreased rapidly over time and was <1 (very slightly firm (barely perceptible) by 30 minutes post-injection. The scoring for induration (Mean±SEM) for each test solution over time are summarized in Table 42 and shown in FIG. 58.

TABLE 42

Induration scores post-injection for Ig120 + rHuPH20 (Mean ± SEM)

| Test Solution | Timepoint Post-Injection | | | | |
|---|---|---|---|---|---|
| | T0 | T15 | T30 | T2 h | T24 h |
| Ig-120 | 3.6 ± 0.2 | 3.4 ± 0.2 | 3.0 ± 0.3 | 2.1 ± 0.4 | 0.1 ± 0.04 |
| Ig-120 + rHuPH20 | 2.3 ± 0.3 | 1.4 ± 0.3 | 0.9 ± 0.3 | 0.6 ± 0.2 | 0.0 ± 0.0 |

The injection sites were photographed before and after the 10 mL injection procedure. Photographic images are shown in FIGS. 59A-64B. It should be noted at the 2 hour timepoint (T2 h), the photos of the animal were taken while it was anesthetized, but rather manually held by an animal technician. Because of the increased stress to the animal, this resulted in some flushing of the skin for some animals. In addition, the injection site may have had some increased tension (skin stretching) when photographed. Therefore, the qualitative scoring is considered the more accurate assessment of the injection site at the 2 h timepoint.

Summary and Conclusions

Back-leakage was reduced ~50% for injections that contained rHuPH20 compared to control injections of Ig-120.

Swelling volume and bleb height were reduced for injections that contained rHuPH20 by 52% and 43%, respectively when using caliper measurement and 20% and 28%, respectively when using 3D imaging.

Injections of Ig-120 with rHuPH20 had a 9% reduction in applied force compared to control injections.

Post-injection swelling was more rapidly resolved for injections that contained rHuPH20 compared to control injections of Ig-120.

Initial post-injection induration was less for rHuPH20-containing injections compared to control injections of Ig-120 and resolved more rapidly than control injections.

Example 4: Assessment of a Prototype High Volume Auto-Injector (HVAI) for Subcutaneous Administration of an Ig Solution Using a 23 G or 25 G Needle and 2000 U/mL of rHuPH20

Summary

This study assessed the ability of a hand-held high volume auto-injector (HVAI) to deliver a polyclonal Ig solution (12%) formulated either alone (Ig-120) or with recombinant human hyaluronidase PH20 (rHuPH20) at 2000 U/mL (Ig-120+rHuPH20). The prototype HVAI device was used to deliver a 10 mL dose of each test solution to the lower abdominal region of a Yucatan minipig. One side of the animal received an injection of Ig-120 and, on the contralateral side, received an injection of Ig-120+rHuPH20. Two needle gauges were tested in this study, 23 gauge (G) and 25 G. Endpoints included measuring the duration of the injection, the amount of back-leakage after the injection, swelling area and volume over time, qualitative scoring for erythema, swelling size and induration over time, as well as skin temperature changes pre and post-injection.

HVAI devices with a 23 G needle had shorter delivery times compared to the HVAI with a 25 G needle. The addition of rHuPH20 reduced injection times compared to the control injections for both needle gauges. Back-leakage was significantly reduced for all injections that contained rHuPH20. Swelling volumes and heights were reduced for HVAI devices that contained rHuPH20, and swelling size and induration resolved more quickly over time for HVAI devices that contained rHuPH20.

Introduction

Current auto-injectors (AIs) are limited to smaller volumes (typically ≤5 mL). In order to achieve high volume injections at a single site, a hand-held HVAI that has the potential to deliver volumes up to 10 mL was developed.

rHuPH20 has been shown to facilitate the subcutaneous (SC) administration of fluids and drugs by transiently and locally depolymerizing hyaluronan (HA) in the extracellular matrix (ECM). The depolymerization of HA reduces tissue backpressure in the SC space that subsequently allows for rapid, high volume administration of drugs. Previous work has shown that rHuPH20 can facilitate the delivery of high volumes to the SC space at high flow rates using an injection set.

The mini-pig model has been selected due to the high degree of similarity of the subcutaneous space to that of humans. Previous studies using a mini-pig model have demonstrated the translatability of the model for use in pre-clinical (Kang et al., 2013) and auto-injector studies (Shi et al., 2021).

In summary, the objective of this study was to assess the performance of a HVAI for its ability to deliver a 10 mL volume of Ig using a vertical needle insertion utilizing either a 23 G or 25 G needle.

Test Articles and Methods

Test Articles

Human Gamma Globulin (Ig-120: 12% Solution)
  Lot number: 1032-71
  Description: Lyophilized powder reconstituted at 120 mg/mL
  Date of Manufacture: Sep. 21, 2020
  Formulation: 10 mM Histidine, 130 mM Sodium Chloride, pH 6.5

Storage Conditions: 2-8° C.
Supplier: BioMed Supply
Formulated by: Halozyme Product Development
Recombinant Human Hyaluronidase rHuPH20 (ENHANZE™ Drug Product)
Lot number: SSRM-1
Description: Clear and colorless solution
Concentration: 1.01 mg/mL
Date of Manufacture: Dec. 30, 2014
Retest Date: February 2023
Enzyme activity: 120 kU/mL
Storage: ≤70° C.
Formulation: 10 mM Histidine, 130 mM sodium chloride, pH 6.5
Handling Conditions: Standard laboratory precautions
Supplier: Halozyme Therapeutics, Inc
Ig Dilution Buffer
Description: Clear colorless liquid
Formulation: 20 mM histidine, 130 mM sodium chloride, 0.05% PS 80, pH 6.3
Batch/Lot: 01032-3
Storage Conditions: 2-8° C.
Handling Conditions: Standard laboratory precautions
Supplier: Halozyme Therapeutics, Inc Formulation Preparation of Test Solutions The two test solutions administered in this study were Ig-120 and Ig-120+rHuPH20. Ig-120 comes from a concentrated stock of an Ig solution previously prepared at 120 mg/mL. The solution for Ig-120+rHuPH20 was prepared by adding rHuPH20 to the same previous stock of Ig-120. The final concentration of rHuPH20 in the test solution was targeted to be 2,000 U/mL. To prepare Ig-120+rHuPH20, Ig-120 was thawed at 2-8° C. overnight. The following day the Ig-120+rHuPH20 test solution was prepared by adding 3.64 mL rHuPH20 to 196.36 mL Ig-120 solution. A stock of rHuPH20 was used for test article preparation (Lot #SSRM-1; 1.01 mg/mL; 120,000 U/mL). The target final concentration for Ig-120+rHuPH20 was 2,000 U/mL.

Pre-Study Enzymatic Activity Testing of rHuPH20

The Ig-120+rHuPH20 solution was prepared and tested for rHuPH20 activity one day prior to the start of the study using a micro-turbidity assay. The activity of the Ig-120+rHuPH20 test solution was within 10% of target concentration and were deemed to be within acceptable range for use in the study. These values are summarized in Table 43.

TABLE 43

Pre-study enzymatic activity testing of rHuPH20 in test solutions

| Test Solution | Pre-study Concentration (U/mL ± SD) |
|---|---|
| Pre-study Ig-120 + rHuPH20 | 2154 ± 61 |

Post-Study Enzymatic Activity Testing of rHuPH20

At the end of the study, dose retain samples were collected from unused devices and tested for rHuPH20 enzymatic activity. The device was injected into a 15 mL Falcon tube and the sample placed on wet ice until transported to a refrigerator set to maintain 2-8° C., and then tested for enzymatic activity on the following day. Intended enzymatic activity was observed for all tested samples (within 10% of the original target concentration of 2,000 U/mL). The values for enzymatic activity are provided in Table 44.

TABLE 44

Post-study enzymatic activity testing of rHuPH20 in test solutions

| Test Solution | Post-study Concentration (U/mL ± SD) |
|---|---|
| Dose retain #1: AID # (Ig-120 alone) | 0 |
| Dose retain #2: AID # (Ig-120 + rHuPH20) | 2076 ± 65 |
| Dose retain #3: AID # (Ig-120 + rHuPH20) | 2034 ± 56 |
| Dose retain #4: AID # (Ig-120 + rHuPH20) | 1988 ± 48 |
| Dose retain #5: AID # (Ig-120 + rHuPH20) | 1968 ± 61 |

Preparation of AI Devices

One day prior to the study, devices were assembled using proprietary jigs. Syringes that fit the HVAI were filled with ~10.2 mL of either Ig-120 or Ig-120+rHuPH20. Once the syringe was filled, a sterile rubber stopper was inserted into the barrel end of the syringe. The syringe was then inverted with the tip upward, and the syringe cap removed and replaced with either a 23 G or a 25 G capped needle. The filled syringe with attached needle was then placed onto a proprietary jig that allowed for further insertion of the rubber stopper into the syringe barrel to the predetermined depth that allowed for priming and a final delivery volume of 10 mL. The filled syringe was then loaded into a spring-driven powerpack, and the external components of the AI device assembled around the syringe. Once each device was assembled, it was stored in a refrigerator set to maintain 2-8° C. in a vertical position (needle up) so that no leakage of test solution would occur during storage.

Animal Description
    Species: Pig (*Sus scrofa domestica*)
    Strain: Yucatan miniature
    Sex: Female
    Age: >3 months
    Body weight: 12-16 kg upon receipt
    Quantity: 6
    Source: Premier BioSource (Ramona, CA)

Husbandry

Animals were received by the animal facility and allowed to acclimate prior to study start. Animals were group housed in steel pens with automatic water provided ad libitum. Animals were fed twice daily (AM and PM), except on study day (PM only). Room environment was set to maintain a temperature of ~17-27° C. and a relative humidity of 40-70%, with a 12 hour light/12 hour dark time cycle. Animals were allowed to acclimate to the facility for 6 days prior to study onset.

Test Materials

TABLE 45

Summary of test materials

| Test Material | Supplier |
|---|---|
| 23G × 1 inch Precision Glide needle | Becton Dickinson, Franklin Lakes, NJ |
| 25G × 1 inch Precision Glide needle | Becton Dickinson, Franklin Lakes, NJ |
| 20 mL Luer-Lok ™ syringe | Becton Dickinson, Franklin Lakes, NJ |
| Standard Digital Camera | Canon |
| High Resolution 3D camera | Canfield Sciences, Parsippany, NJ |
| Hand-held HVAI | Halozyme |
| Digital caliper | Fisher Scientific |
| Infrared thermometer | Fisher Scientific |
| Surgical Eye Spear | Becton Dickinson, Franklin Lakes, NJ |
| Digital Stopwatch | Fisher Scientific |

Experimental Design

In this study, two 10 mL injections were administered to the abdomen of a Yucatan miniature pig using a prototype HVAI. Test solution of Ig-120 alone was administered on one side, and the contralateral side was injection with Ig-120+rHuPH20 (2000 U/mL). The Ig-120 alone injection was always administered prior to the Ig-120+rHuPH20 injection. Description of cohorts are summarized in Table 46.

TABLE 46

Description of cohorts

| Cohort | N/Cohort | Test Solution (Left) | Volume (mL) | Needle Gauge | [rHuPH20] (U/mL) |
|---|---|---|---|---|---|
| 1 | 3 | Ig-120 alone | 10 | 23 | 0 |
| 2 | 3 | Ig-120 + rHuPH20 | 10 | | 2000 |
| 3 | 3 | Ig-120 alone | 10 | 25 | 0 |
| 4 | 3 | Ig-120 + rHuPH20 | 10 | | 2000 |

Quantitative study endpoints included duration of the injection (time) collected via stopwatch and high-speed video imaging, skin temperature changes pre and post-injection which were collected via infrared thermometer. Post-injection back-leakage of test article was collected from the injection site for 30 seconds after the removal of the needle using an eye-spear to absorb any leakage and quantified by weight. The area and volume of the swelling blebs at the injection site were determined by digital caliper measurement (length, width, and height), as well as by 3D camera imaging immediately after the injection (T0), at 15 minutes (T15), and at 30 minutes (T30) post-injection. Qualitative study endpoints included scoring for erythema, swelling size, and induration assessed at each of these previously described timepoints as well as at 2 hours (T2 h) and at approximately 24 hours post-injection (T24 h) post-injection. Qualitative assessments of the injection sites were performed while the animal was under anesthesia for the T0, T15, T30 and T24 h timepoints, while the T2 h assessment was performed while the animal was conscious and held by an animal technician. Standard photographs were obtained pre-injection and at timepoints T0, T15, T30, T2 h and T24 h post-injection. In summary, the endpoints for the study were:

- Measurement of injection duration;
- Measurement of back-leakage post-injection;
- Measurement of swelling area and volume (length/width/height) post-injection over time (T0, T15, T30) using caliper measurements and 3D imaging;
- Assessment of swelling blebs for erythema, size and induration at times T0, T15, T30, T2 h and T24 h; and
- Measurement of skin temperature at injection site both pre and post-injection.

Study Procedure

Prior to study start, animals were assessed for general health and body weights were collected. On study day, the devices were taken out of 2-8° C. storage and placed on ice in an insulated container for transport to the animal facility. A device of each type (Ig-120 and Ig-120+rHuPH20) was removed approximately 45 minutes prior to use. The amount of time that each injector was at room temperature prior to injection was recorded on data sheets for each animal.

Animals were anesthetized with isoflurane gas and placed in dorsal recumbence on a foam wedge placed on a heated surgical table, and they were maintained under isoflurane gas for the entire duration of the procedure. The abdominal region was cleaned with Nolvasan followed by wiping the injection site with gauze containing 70% isopropanol and wiped dry with sterile gauze. Injection sites were located on the left and right abdominal regions, ~6 cm cranially from the inguinal fold towards the midline and ~3 cm towards the midline of the animal. Each of the injection sites was marked with a permanent marker and then photographed with the standard and 3D cameras prior to needle insertion. The temperature of the skin at the injection site was recorded prior to the start of the injection using an infrared thermometer. The initial injection for each animal from the AI device was the control solution (Ig-120 alone). The second injection was on the contralateral side of the animal and was the test solution containing rHuPH20 (Ig-120+rHuPH20).

Injections using the HVAI were recorded using high-speed video. The duration of the injection was measured by using a hand-held stopwatch and also by video recording. At the end of the injection the device was removed, and video recording stopped.

Test solution back-leakage was then absorbed to a tared eye-spear for 30 seconds by blotting the injection site. The weight of the eye spear was recorded using analytical balance with an accuracy of 0.1 mg. The margins of the injection site swelling were marked with a permanent marker and measured for length, width, and height using a digital caliper and recorded. Post injection skin temperature was also collected using the infrared thermometer.

Qualitative Scoring of Post-Injection Swelling

The injection site was then photographed with the standard and 3D cameras and then qualitatively scored by three independent evaluators for appearance and severity of erythema, swelling/bleb size, and firmness (induration) using a 5-point scoring system (a modified Draize Test) based on the 1992 OECD guidelines for grading skin reactions (Table 47, Table 48, and Table 49). The evaluators were blinded to each other's scores. After the first injection, the procedure was repeated on the contra-lateral side of the animal using the other test solution (Ig-120+rHuPH20). These swelling measurements, imaging and qualitative assessments were conducted immediately post-injection (T0) as well as at 15 minutes post-injection (T15) and 30 minutes post-injection (T30). After the T30 swelling measurements, imaging and qualitative scoring, the animals were allowed to recover and were returned to their home pens. Images taken at the 2 hour timepoint (T2 h) were from non-anesthetized animals. Qualitative scoring was also conducted at T2 h, and approximately 24 hr post injections. Photographs with the standard camera were collected at each of these timepoints. Following the final assessment, the animal was humanely euthanized using a ready for use solution of sodium pentobarbital and sodium phenytoin (Euthasol®).

TABLE 47

Grading scale for erythema formation

| Scale | Description |
|---|---|
| 0 | No erythema |
| 1 | Very slight erythema (barely perceptible) |
| 2 | Well defined erythema |
| 3 | Moderate erythema |
| 4 | Severe erythema (beet redness) to slight eschar formation |

TABLE 48

Grading scale for swelling size formation

| Scale | Description |
|---|---|
| 0 | No swelling |
| 1 | Very slight swelling |
| 2 | Slight swelling |
| 3 | Moderate swelling |
| 4 | Severe swelling |

TABLE 49

Grading scale for swelling firmness (induration)

| Scale | Description |
|---|---|
| 0 | No perceptible difference in firmness after injection |
| 1 | Very slightly firm (barely perceptible) |
| 2 | Mildly firm |
| 3 | Moderately firm |
| 4 | Very firm |

Calculations And Statistical Methods
Assessment of Injection Time

The duration of the injection was calculated based upon measurements collected using a stopwatch and by video recording during the injection. The video frame for the start and end of the injection was identified and the total length of the injection was calculated using the formula: (Total #of frames)/Frame rate=Injection Time. In this instance, the total #of frames was equal to the (ending frame #minus the starting frame #+1) and the video frame rate was 29.98 frames per second.

Assessment of Injection Time, Local Swelling Volume and Area Using Caliper Measurement and 3D Imaging Volume and area of post-injection swelling were measured using both caliper measurement and 3D camera image analysis. For caliper measurements a digital caliper was utilized to measure length, width and height of the bleb that formed post-injection. The length and width are defined as the edge-to-edge measurements of the swelling bleb (i.e., diameter) along their longest axes. These values were manually recorded, and the volume determined using the formula for half of an ellipsoid Vol=(2/3)*π*A*B*C where A=Length/2, B=Width/2 and C=Height.

3D imaging was applied as a longitudinal methodology to measure post-injection swelling. By obtaining high definition pre- and post-injection 3D images the distances between two registered surfaces can be determined. The camera captures images using a factory calibrated bifocal imaging system to measure distance between surfaces. Surface registration was performed using multipoint method that utilized common landmarks between the pre-injection image and the post-injection image. Using the proprietary software, the volume, area, and height of the post-injection swelling was calculated for each injection (Canfield Biosciences, Inc.).

Caliper measurement and 3D imaging measurement will yield different values for volume, area, and swelling height. The differences are a result of the difference in the measurement of swelling/bleb size. The 3D measurement calculates swelling height based on the top of the swelling bleb to the original skin position, while the swelling height from caliper measurements measure from the top of the swelling bleb to the height at the edge of the bleb. Due to skin curvature, this may yield an overall increase in swelling height for the caliper measurements compared to the 3D measurements, resulting in greater swelling volume and height. However, the measurements are consistent with each other and therefore differ only due to the methodology.

Results And Discussion
Pre and Post-Injection Quantitative Measurements

Figure 65:
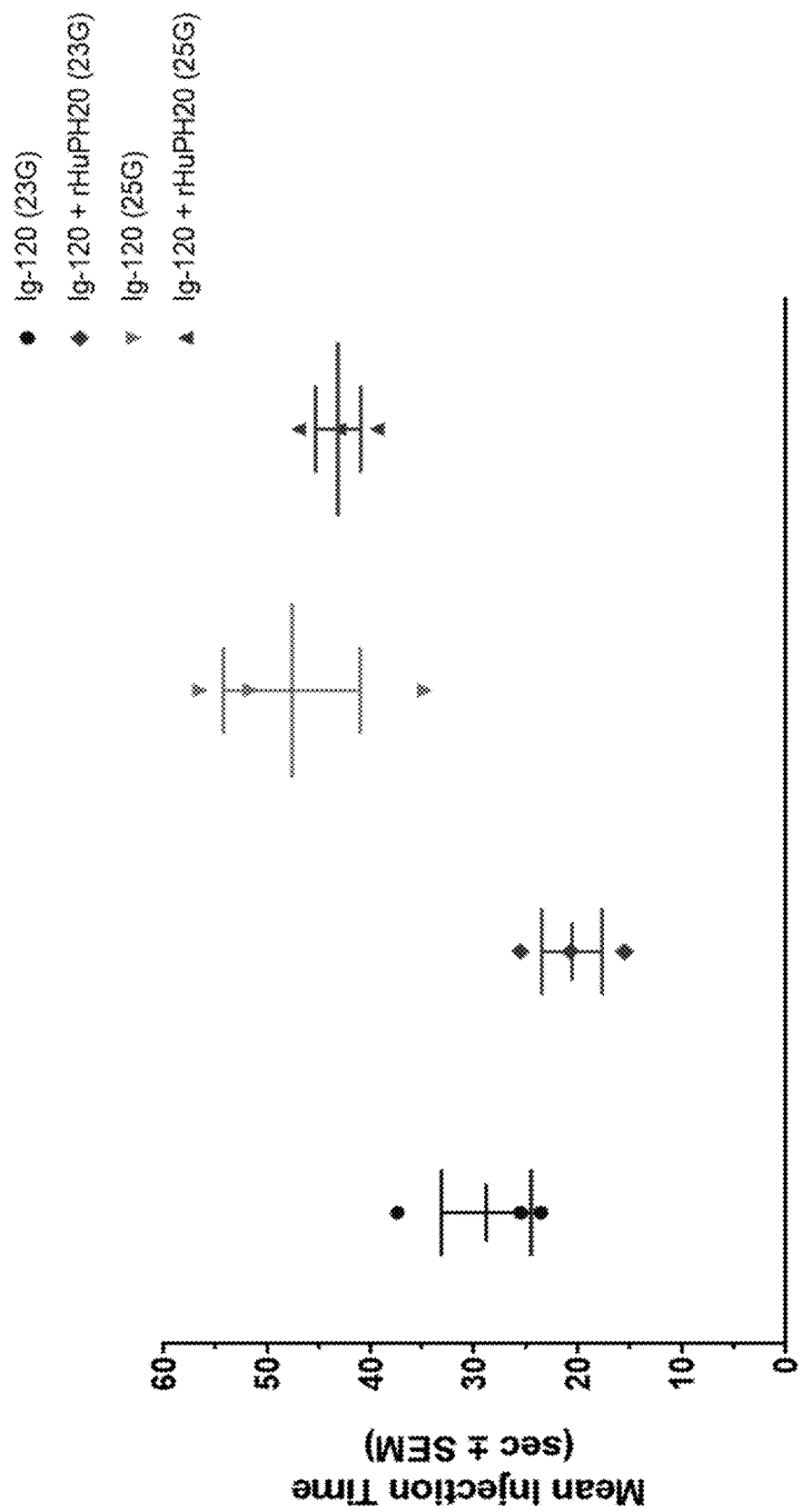
FIG. 65 is a chart depicting individual animal injection times (Mean±SEM) calculated by video analysis for each configuration of high volume autoinjector (HVAI).

Duration of injection: Injection times (seconds) were recorded via two orthogonal methods, one by utilizing a hand-held stopwatch and closely monitoring the start and completion of the injection, the second method was by high-speed video recording analysis. Mean injection times, calculated by video analysis for each configuration of HVAI, are shown in Table 50 and individual animal data (Mean±SEM) are shown in FIG. 65. Injection times were comparable between both methods of analysis, with the mean injection times calculated by stopwatch being 28.8 seconds (Ig-120) and 20.6 seconds (Ig-120+rHuPH20) for the HVAI with a 23 G needle and 47.6 seconds (Ig-120) and 43.1 seconds (Ig-120+rHuPH20) for the HVAI with a 25 G needle. A comparison of the injection times for both the video analyses and the times using a stopwatch are provided in Table 51. The decrease in injection times compared to the control was about 28.5% for the 23 G needle and about 9.4% for the 25 G needle.

TABLE 50

Mean injection time from video analyses (seconds ± SEM)

| Needle Gauge | Ig-120 | Ig-120 + rHuPH20 |
|---|---|---|
| 23G | 29.0 ± 4.4 | 20.8 ± 2.9 |
| 25G | 47.8 ± 6.7 | 43.4 ± 2.3 |

TABLE 51

Comparison of injection time (sec) - video analyses vs. stopwatch

| | | | Delivery Time (sec) | |
|---|---|---|---|---|
| Animal ID # | Needle Gauge | Test Solution | Video | Stopwatch |
| 1865L | 23G | Ig-120 | 25.52 | 25.48 |
| 1865R | | Ig-120 + rHuPH20 | 15.78 | 15.50 |
| 1866R | | Ig-120 | 37.63 | 37.38 |
| 1866L | | Ig-120 + rHuPH20 | 20.78 | 20.72 |
| 1867L | | Ig-120 | 23.75 | 23.58 |
| 1867R | | Ig-120 + rHuPH20 | 25.72 | 25.53 |
| 1869R | 25G | Ig-120 | 56.84 | 56.52 |
| 1869L | | Ig-120 + rHuPH20 | 43.16 | 43.08 |
| 1870L | | Ig-120 | 51.70 | 51.62 |
| 1870R | | Ig-120 + rHuPH20 | 39.56 | 39.39 |
| 1926R | | Ig-120 | 34.79 | 34.70 |
| 1926L | | Ig-120 + rHuPH20 | 47.40 | 46.98 |

Figure 66:
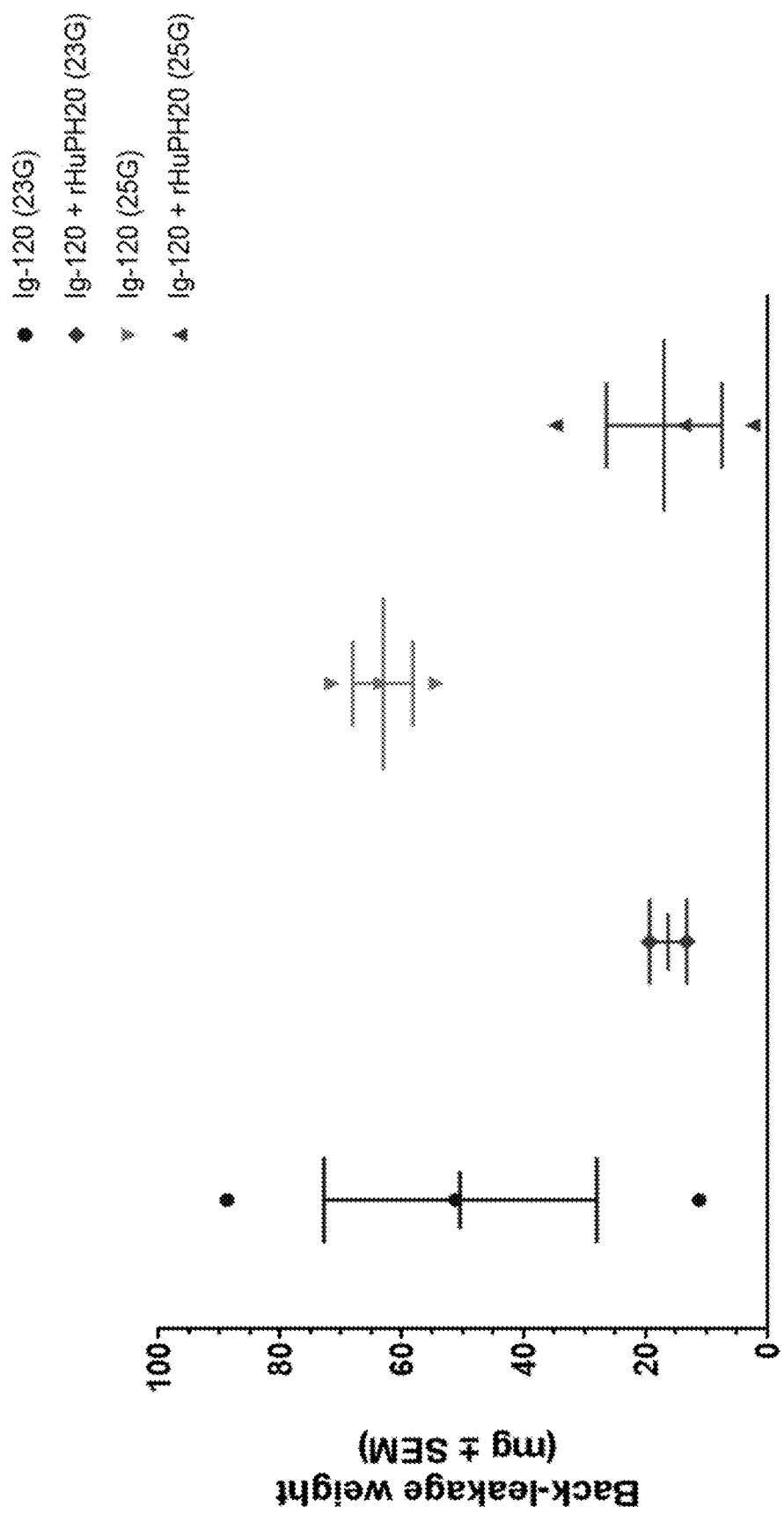
FIG. 66 is a chart depicting mean (mg±SEM) and individual weights of back-leakage.

Assessment of post-injection back-leakage: The amount of back-leakage for each injection was measured by collecting post-injection fluid from the injection site using a surgical eye spear for 30 seconds immediately following needle removal. Prior to collection the weight of each eye spear was tared on the analytical balance, and then re-weighed following fluid collection. The analytical balance had a precision of 0.1 mg. Back-leakage for Ig-120 alone and Ig-120+rHuPH20 are shown in Table 52 and individual animal data (Mean±SEM) is shown in FIG. 66. It should be noted that for one of the injections of Ig-120+rHuPH20 (AID #1869R; 23 G needle) there was leakage at an unidentified site inside the device that resulted in leakage not related to the injection site. Leakage occurred within a few seconds after the start of the injection. The value was excluded for this injection for back-leakage analysis.

TABLE 52

Mean weight of back-leakage (mg ± SEM)

| Needle Gauge | Test Solution | |
|---|---|---|
| | Ig-120 | Ig-120 + rHuPH20 |
| 23G | 50.4 ± 22.4 | 16.3 ± 3.1 |
| 25G | 63.1 ± 5.0 | 17.0 ± 9.5 |

Figure 67:
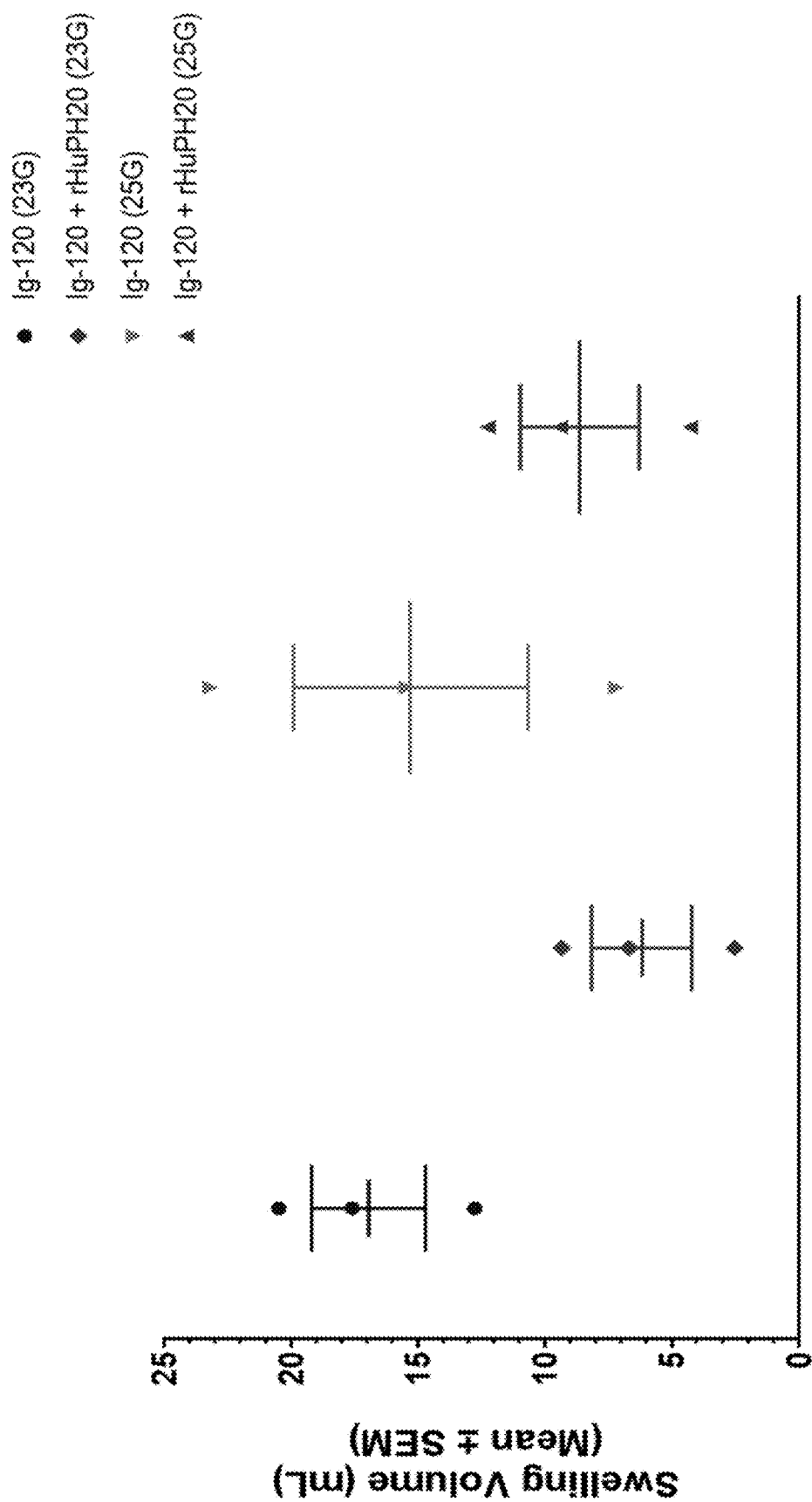
FIG. 67 is a chart depicting individual swelling volumes (mL) after SC injection of Ig-120 and Ig-120+rHuPH20 determined using caliper measurements.
Figure 68:
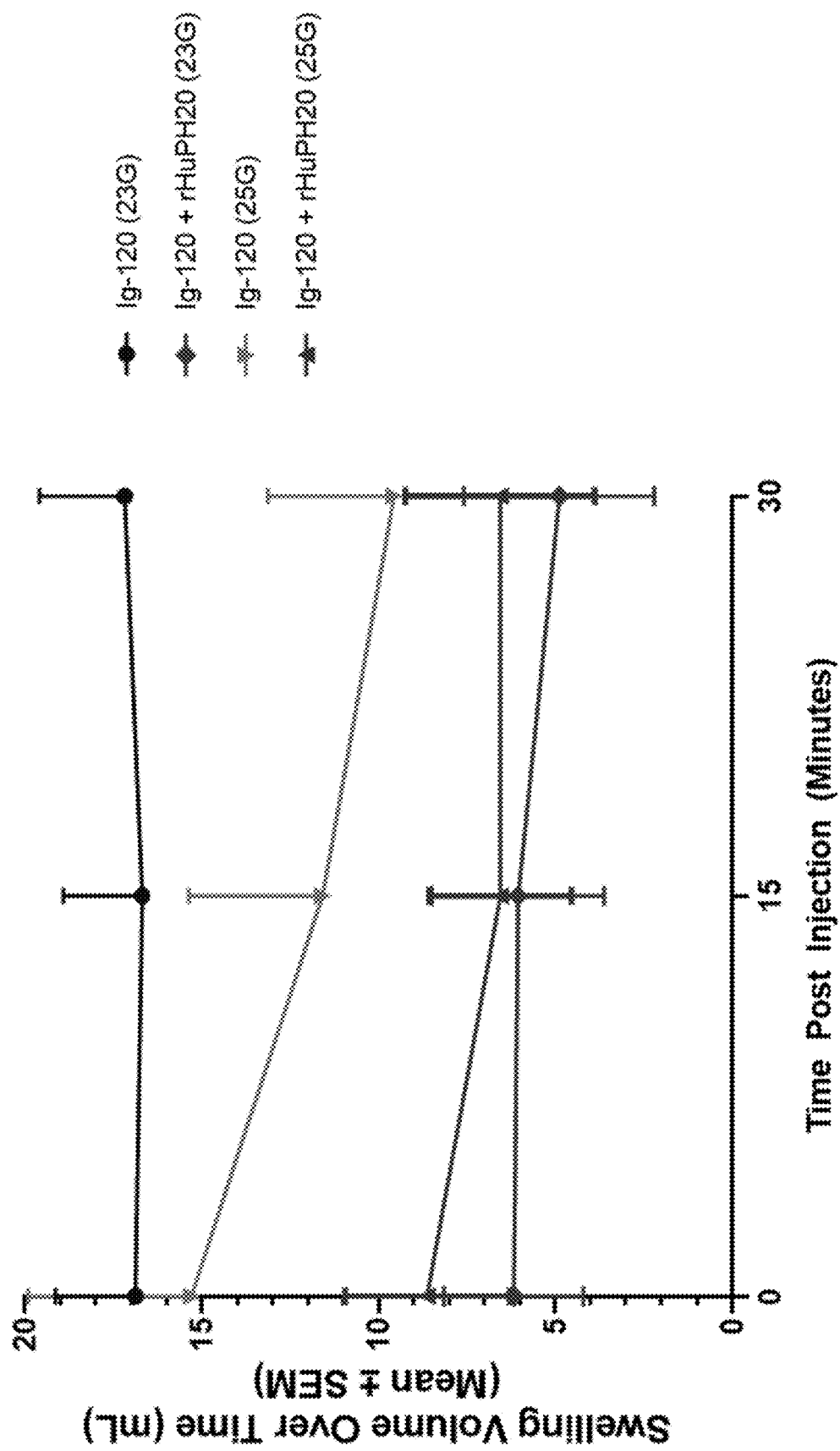
FIG. 68 is a chart depicting swelling (bleb) volume over time at the T0, T15, and T30 time points.
Figure 69:
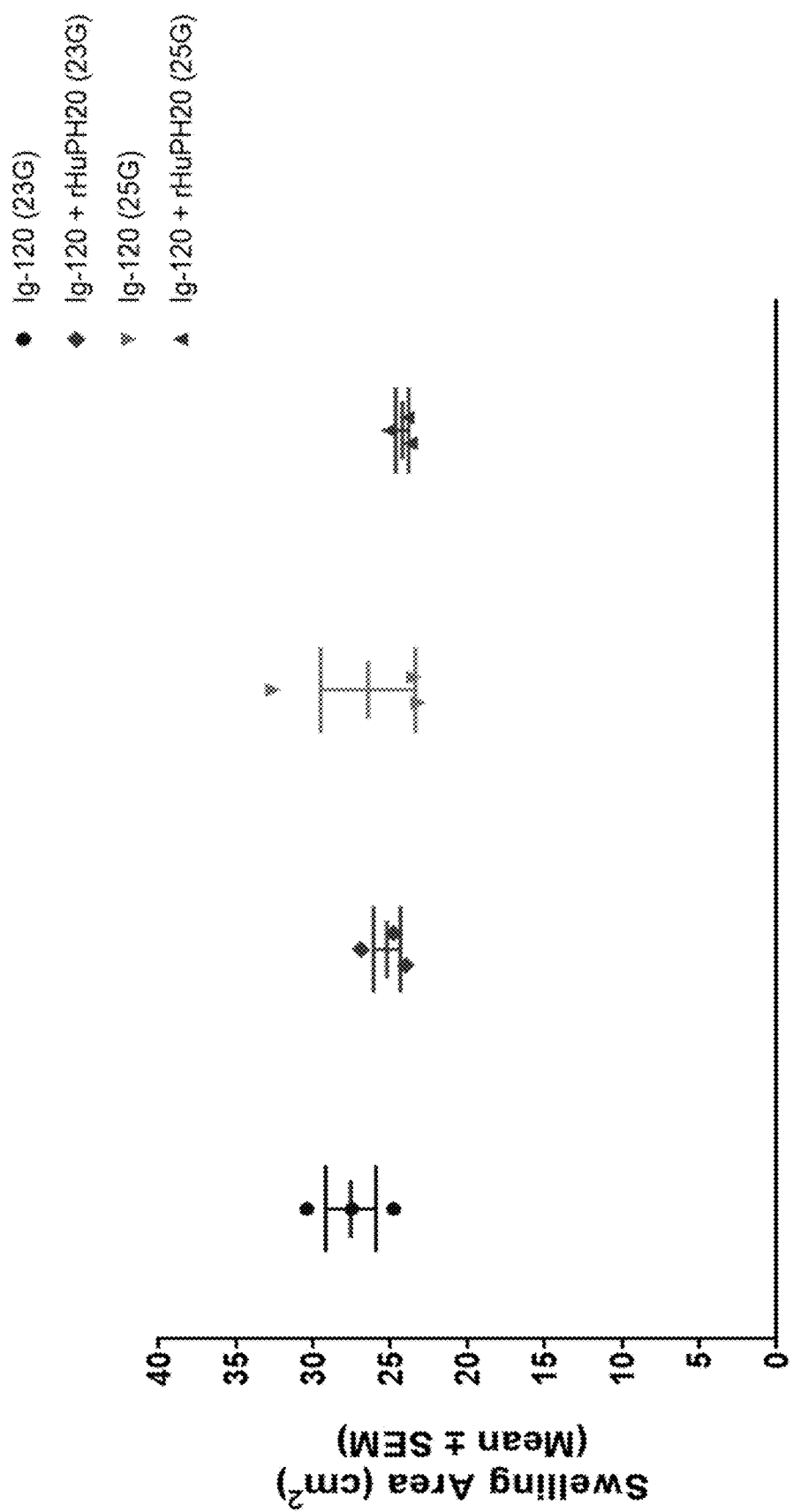
FIG. 69 is a chart depicting individual swelling areas (cm$^2$) after SC injection of Ig-120 and Ig-120+rHuPH20 determined using caliper measurements.

Assessment of post-injection swelling volume, area, and height (caliper measurements): The local injection site swelling (bleb) was marked and measured using a digital caliper. Swelling volume, dispersion area and swelling height of each bleb was determined as described above and are summarized in Table 53, Table 54, and Table 55 for Ig-120 and Ig-120+rHuPH20. Individual post-injection swelling volume, area and height values are shown in FIGS. 67, 68, and 69. Swelling volume was decreased about 63.3% using the HVAI with the 23 G needle and about 43.8% using the HVAI with the 25 G needle (Table 53 and FIG. 67). Swelling dispersion area was decreased about 8.7% using the HVAI with the 23 G needle and about 8.3% using the LVA with the 25 G needle (Table 54 and FIG. 68). Swelling height was decreased about 58.2% using the HVAI with the 23 G needle and about 36.9% using the HVAI with the 25 G needle (Table 55 and FIG. 69).

TABLE 53

Swelling volume after injection of Ig-120 and Ig-120 + rHuPH20
over time using caliper measurement (Mean ± SEM)
Volume of Post-injection Swelling (mL)

| Test Solution | Needle Gauge | Time after injection (minutes) | | |
|---|---|---|---|---|
| | | T0 | T15 | T30 |
| Ig-120 | 23G | 16.9 ± 2.3 | 16.7 ± 2.2 | 17.2 ± 2.4 |
| Ig-120 + rHuPH20 | | 6.2 ± 2.0 | 6.1 ± 2.4 | 4.9 ± 2.7 |
| Ig-120 | 25G | 15.3 ± 4.6 | 11.6 ± 3.8 | 9.6 ± 3.6 |
| Ig-120 + rHuPH20 | | 8.6 ± 2.3 | 6.6 ± 2.0 | 6.6 ± 2.7 |

TABLE 54

Swelling area after injection of Ig-120 and Ig-120 + rHuPH20
over time using caliper measurement (Mean ± SEM)
Area of Post-injection Swelling ($mm^2$ ± SEM)

| Test Solution | Needle Gauge | Time after injection (minutes) | | |
|---|---|---|---|---|
| | | T0 | T15 | T30 |
| Ig-120 | 23G | 27.6 ± 1.6 | 28.0 ± 2.4 | 32.0 ± 4.2 |
| Ig-120 + rHuPH20 | | 25.2 ± 0.9 | 31.0 ± 3.2 | 21.2 ± 10.6 |
| Ig-120 | 25G | 26.4 ± 3.1 | 26.4 ± 2.3 | 29.9 ± 3.6 |
| Ig-120 + rHuPH20 | | 24.2 ± 0.4 | 30.3 ± 2.5 | 31.7 ± 2.0 |

TABLE 55

Swelling Height After Injection of Ig-120 and Ig-120 + rHuPH20
Over Time Using Caliper Measurement (Mean ± SEM)
Height of Post-injection Swelling (mm ± SEM)

| Test Solution | Needle Gauge | Time after injection (minutes) | | |
|---|---|---|---|---|
| | | T0 | T15 | T30 |
| Ig-120 | 23G | 9.1 ± 0.7 | 8.9 ± 0.6 | 8.1 ± 0.8 |
| Ig-120 + rHuPH20 | | 3.8 ± 1.3 | 2.8 ± 0.9 | 2.3 ± 1.2 |

TABLE 55-continued

Swelling Height After Injection of Ig-120 and Ig-120 + rHuPH20
Over Time Using Caliper Measurement (Mean ± SEM)
Height of Post-injection Swelling (mm ± SEM)

| Test Solution | Needle Gauge | Time after injection (minutes) | | |
|---|---|---|---|---|
| | | T0 | T15 | T30 |
| Ig-120 | 25G | 8.4 ± 1.9 | 6.6 ± 2.2 | 4.9 ± 2.1 |
| Ig-120 + rHuPH20 | | 5.3 ± 1.4 | 3.2 ± 0.8 | 3.0 ± 1.1 |

Figure 70:
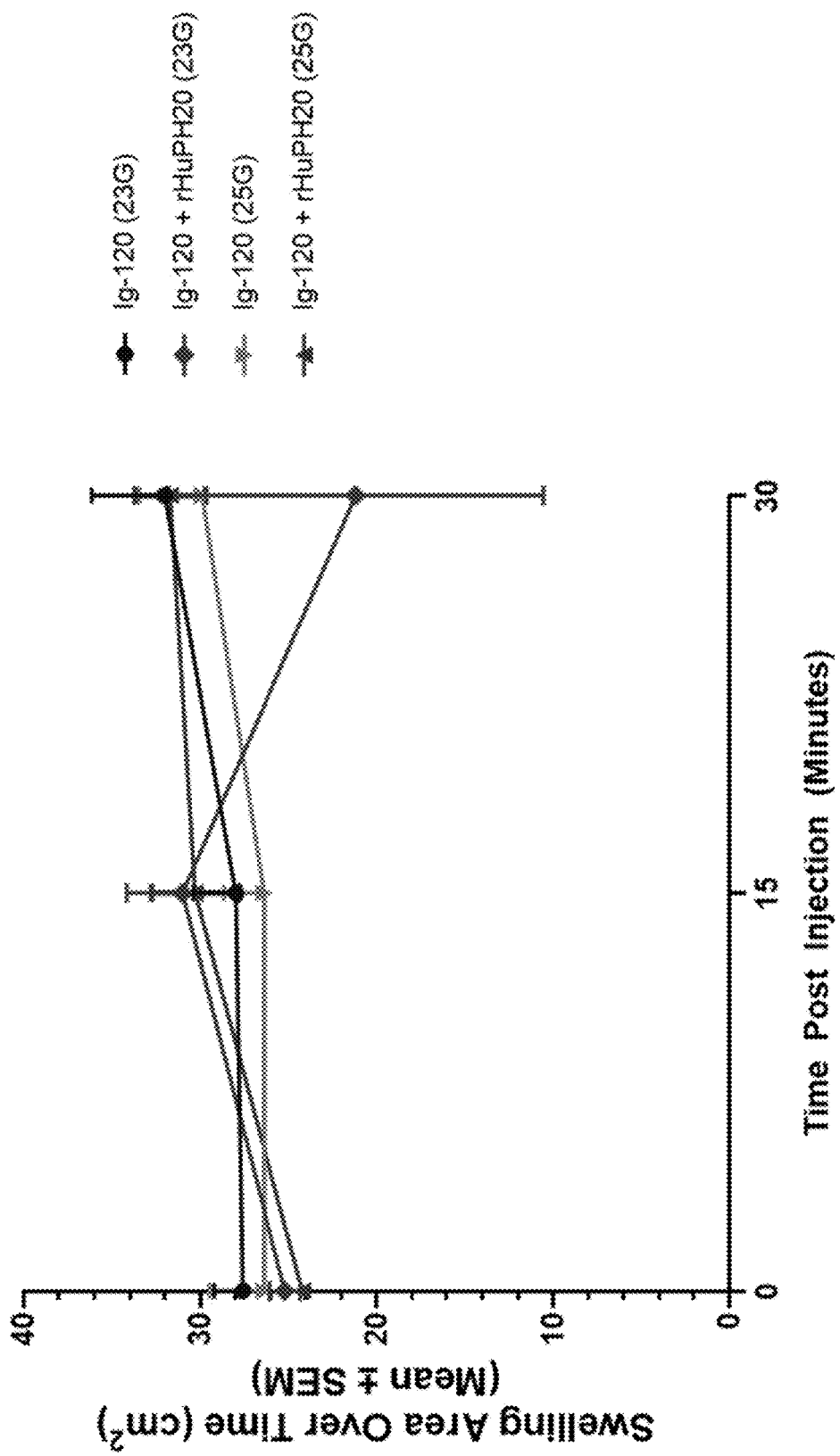
FIG. 70 is a chart depicting swelling area over time at the T0, T15, and T30 time points.
Figure 71:
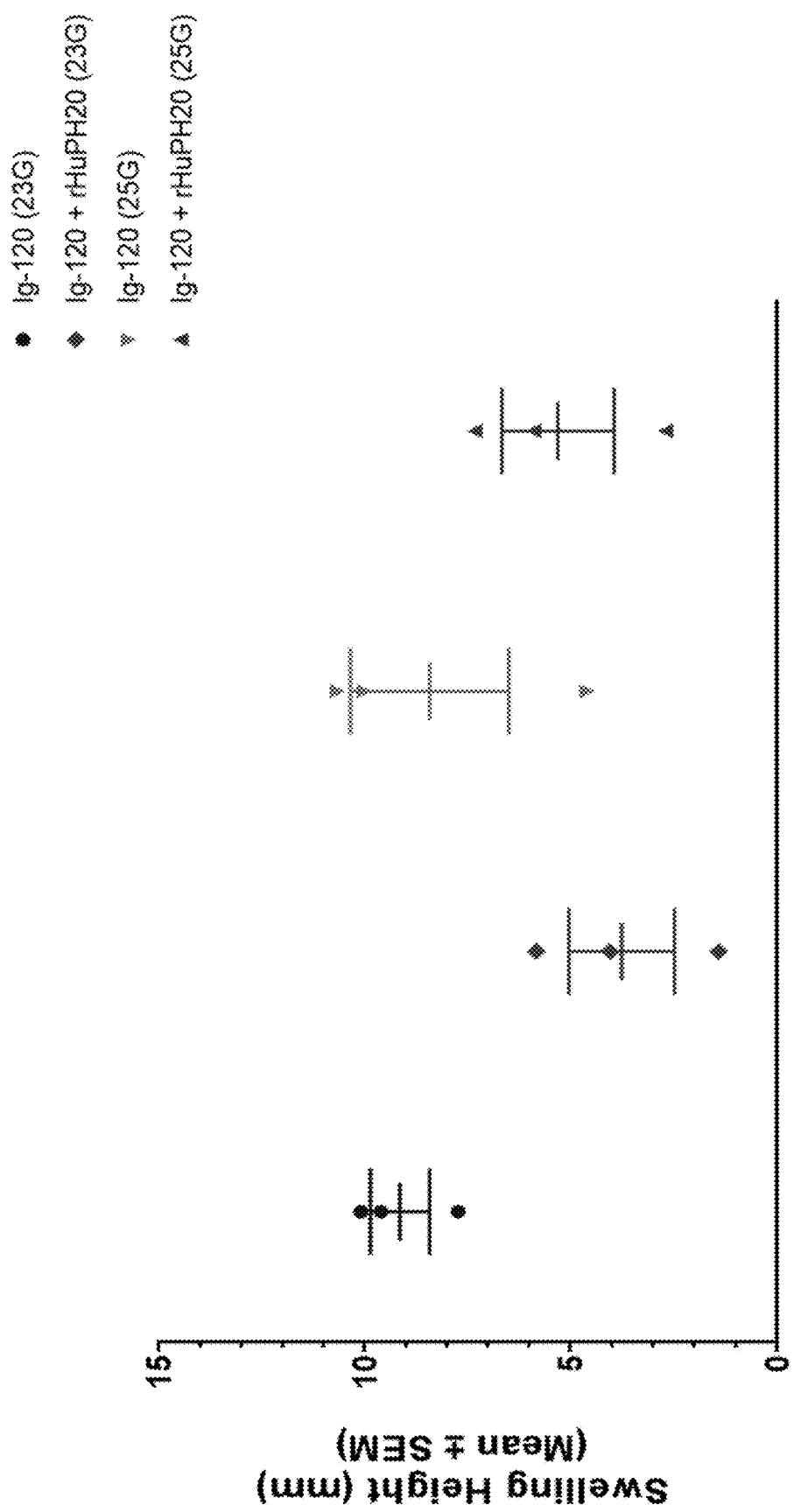
FIG. 71 is a chart depicting individual swelling bleb heights (mm) after SC injection of Ig-120 and Ig-120+rHuPH20 determined using caliper measurements.
Figure 72:
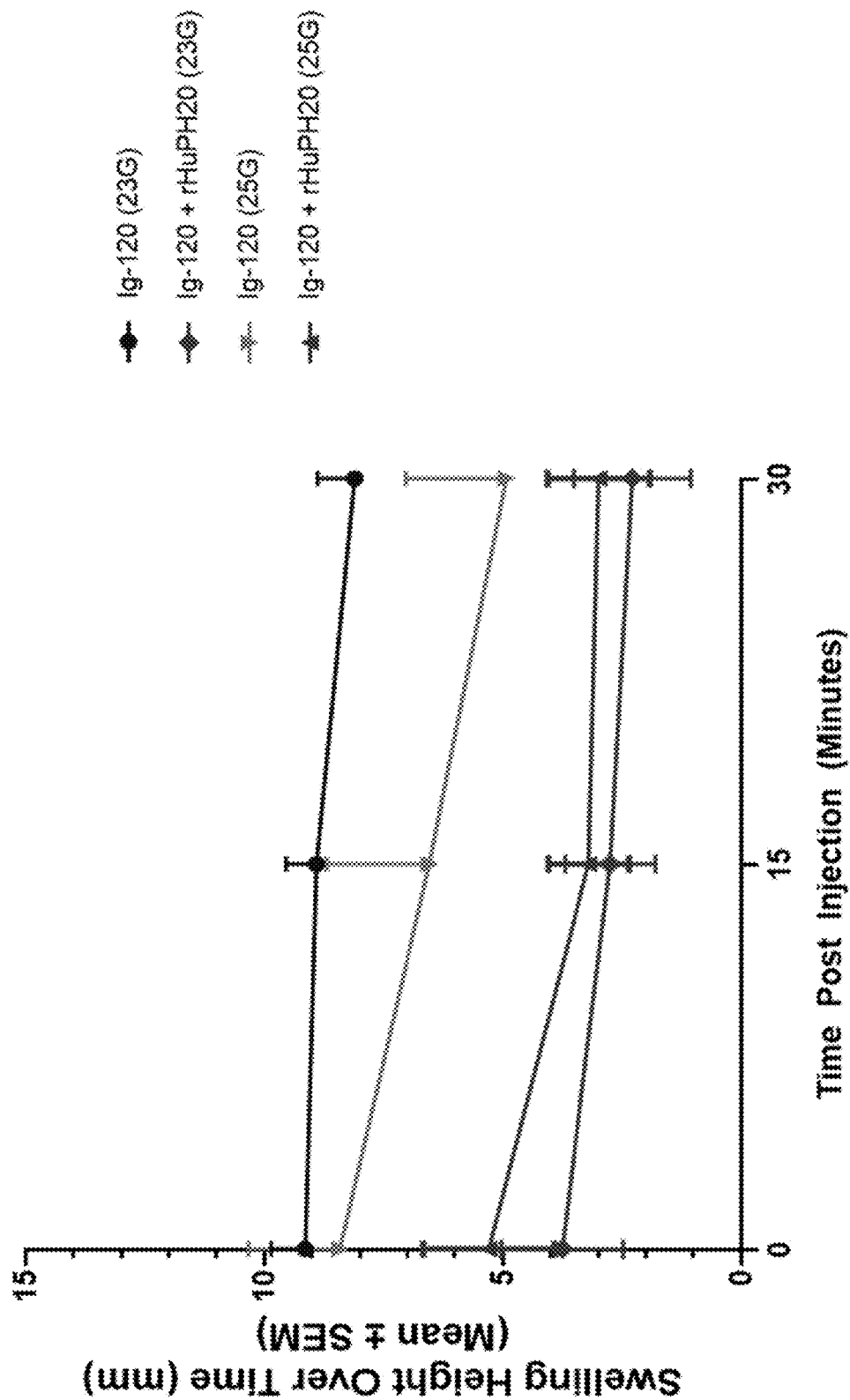
FIG. 72 is a chart depicting swelling height over time at the T0, T15, and T30 time points.

Dimensions (length, width and height) of the swelling were measured at T15 and T30 post-injection in addition to the T0 timepoint (caliper measurements only) which were used to calculate the volume over time which are shown in FIG. 68. The area of the swelling bleb was measured at T15 and T30 post-injection in addition to the T0 timepoint (caliper measurements only) and the area over time is shown in FIG. 70. The height of the swelling bleb was measured at T15 and T30 post-injection in addition to the T0 timepoint (caliper measurements only) and the height over time is shown in FIG. 72.

Assessment of post-injection bleb shape, volume, area, and height (3D imaging): Pre- and post-injection photographs were taken using a 3D imaging system (Canfield Scientific). This technology permits point-to-point alignment of these two images through multipoint surface registration. The distance between any two points is then represented using a colorimetric surface contour map. Regions where there is no difference between the two images are displayed in gray. Where the post-injection image is higher than the pre-injection image, the region is displayed in shades of blue. Where the post-injection image is lower than the pre-injection image the distance is displayed in shades of orange. The color intensity is proportional to the amount of distance measured between images with darker blue color indicating greater distance from the pre-injection image. Out of range measurements (distances greater than 6 mm) are depicted in white. Swelling measurements of volume and height include regions out of range.

Figure 73A:
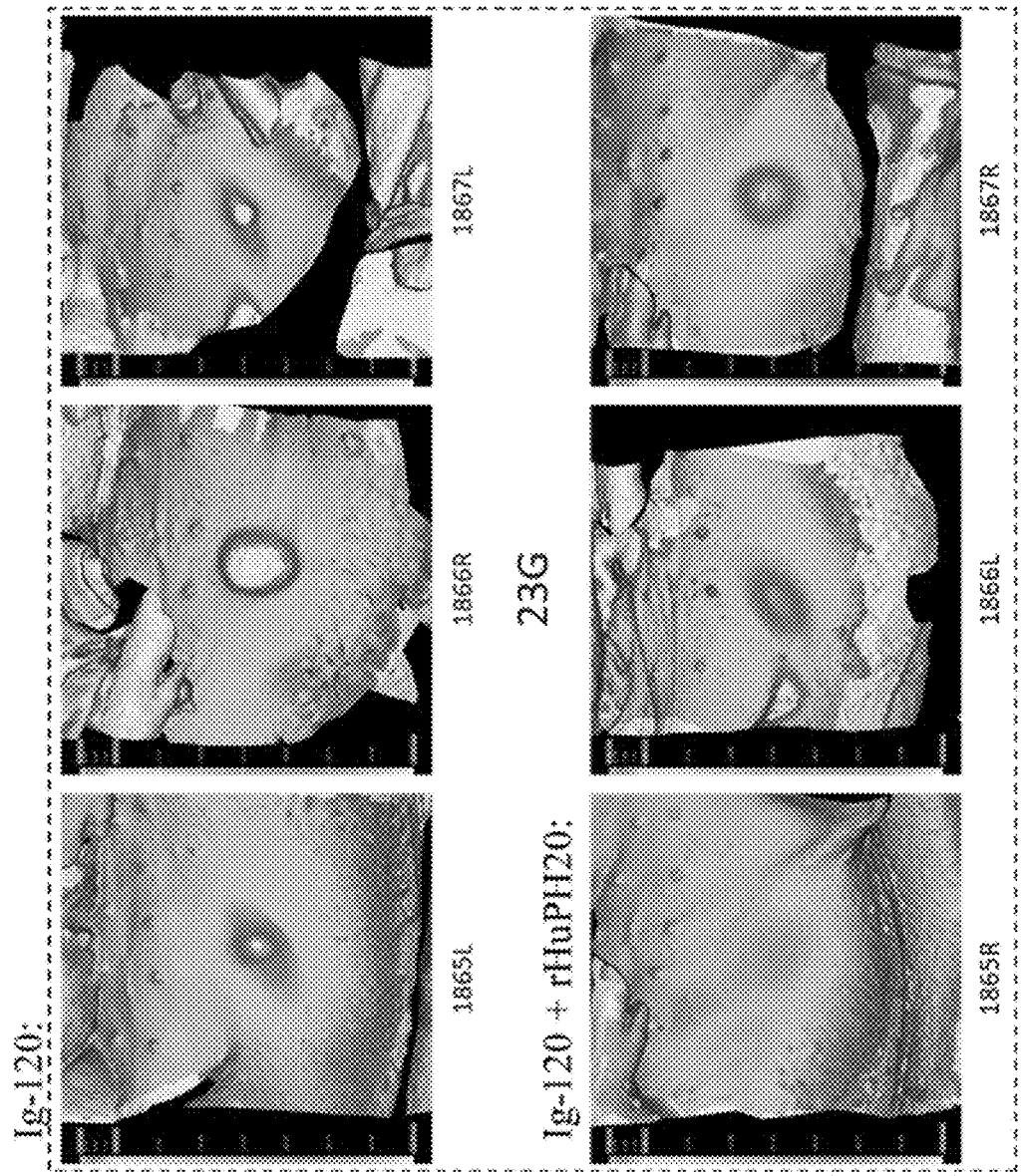
FIGS. 73A-73B are composite of 3D images (colorimetric surface contour maps) of each post-injection bleb for Ig-120 and Ig-120+rHuPH20 administered with a HVAI and a 23 G needle (FIG. 73A) and administered with a HVAI and a 25 G needle (FIG. 73B).
Figure 73B:
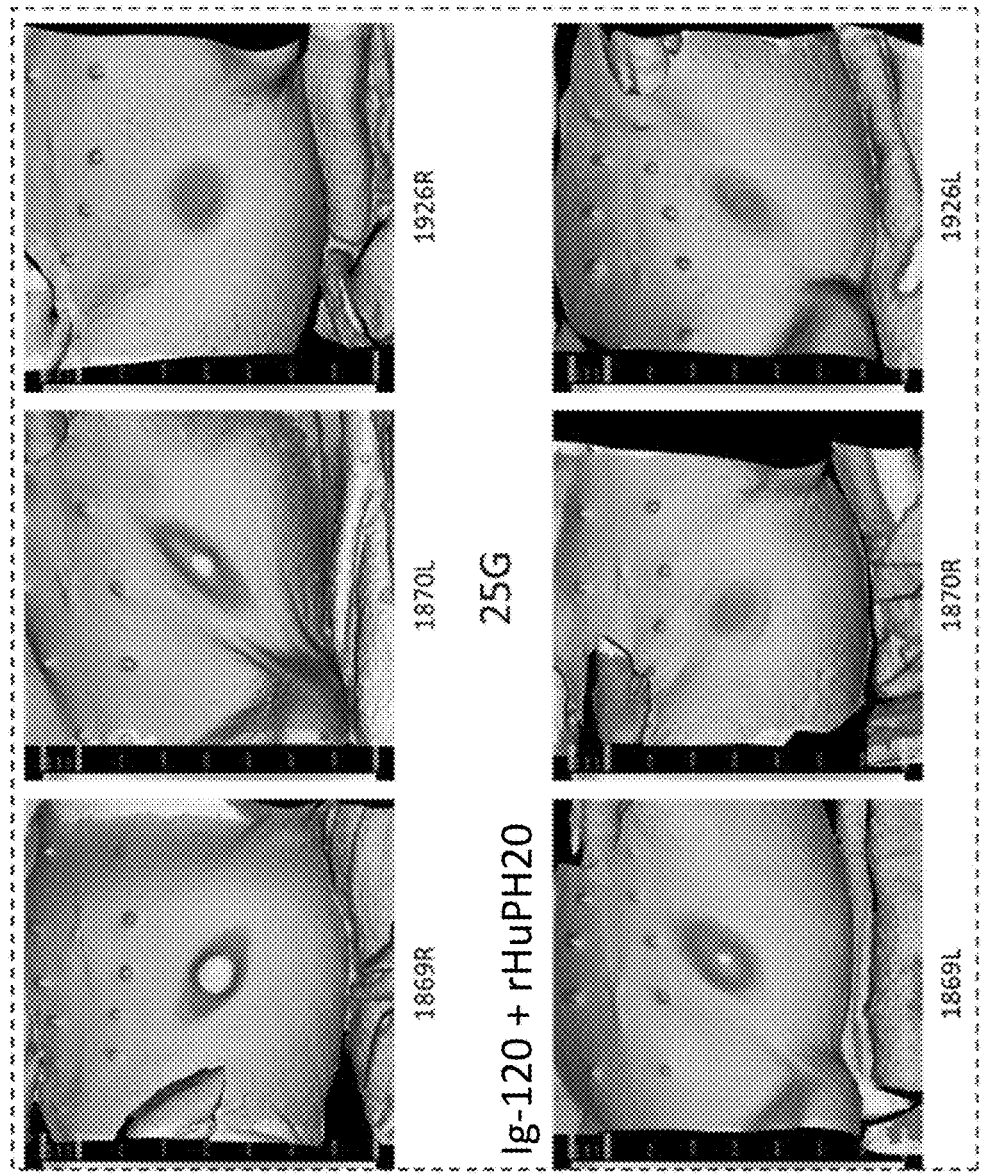

Each animal had a pre-injection 3D image taken of the injection site followed by a second image taken immediately post-injection and these images were mapped to each other using multipoint registration. These registered pre-/post-injection images were then used to calculate the swelling volume, height, circumference, length, and width for each swelling bleb using proprietary software (Vectra H1 software; Canfield Sciences). Colorimetric surface contour maps of each post-injection swelling bleb for Ig-120 and Ig-120+rHuPH20 are shown in FIGS. 73A-73B.

Figure 74:
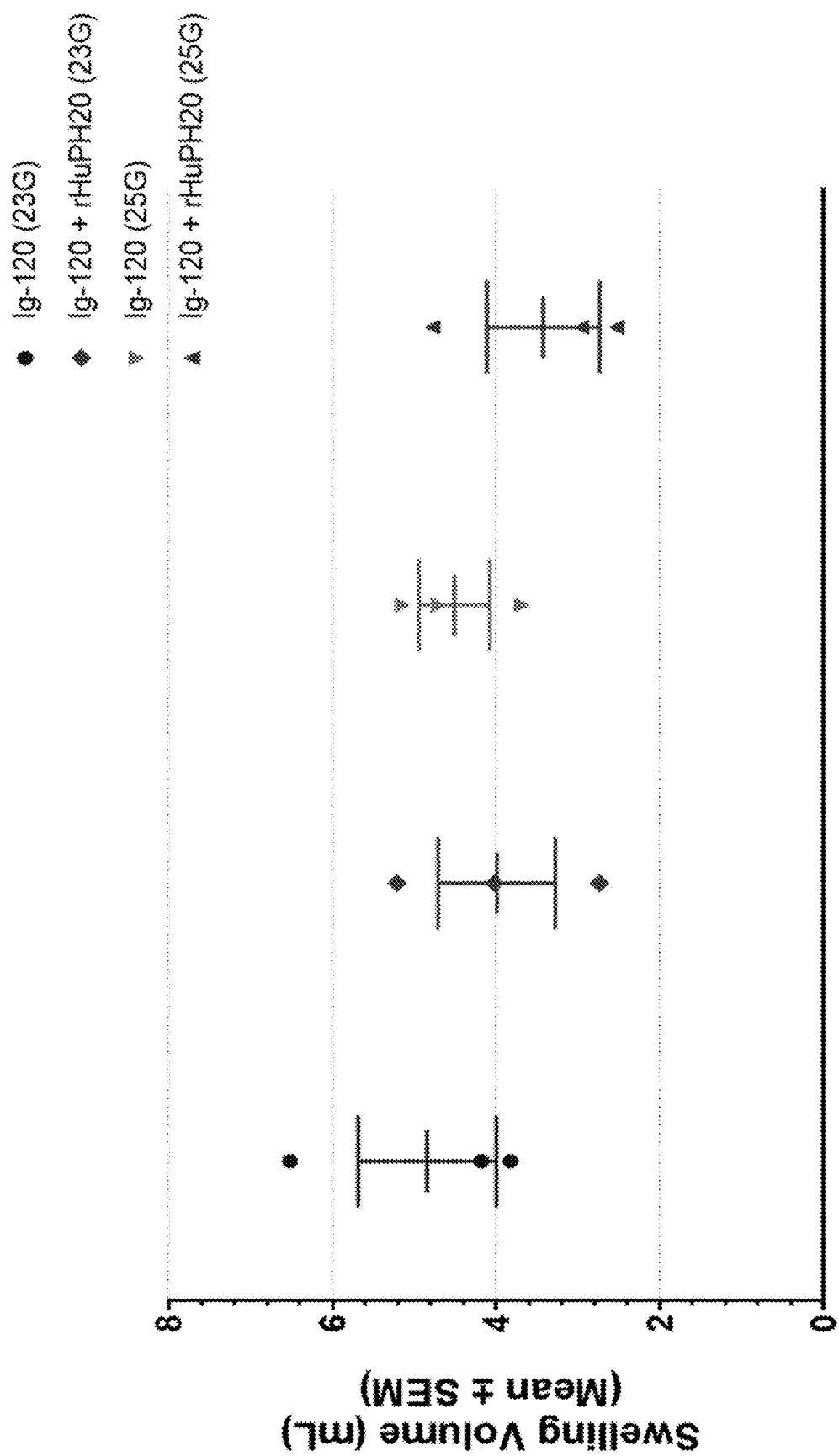
FIG. 74 is a chart of individual swelling volumes (mL) after SC injection of Ig-120 and Ig-120+rHuPH20 determined using 3D imaging.
Figure 75:
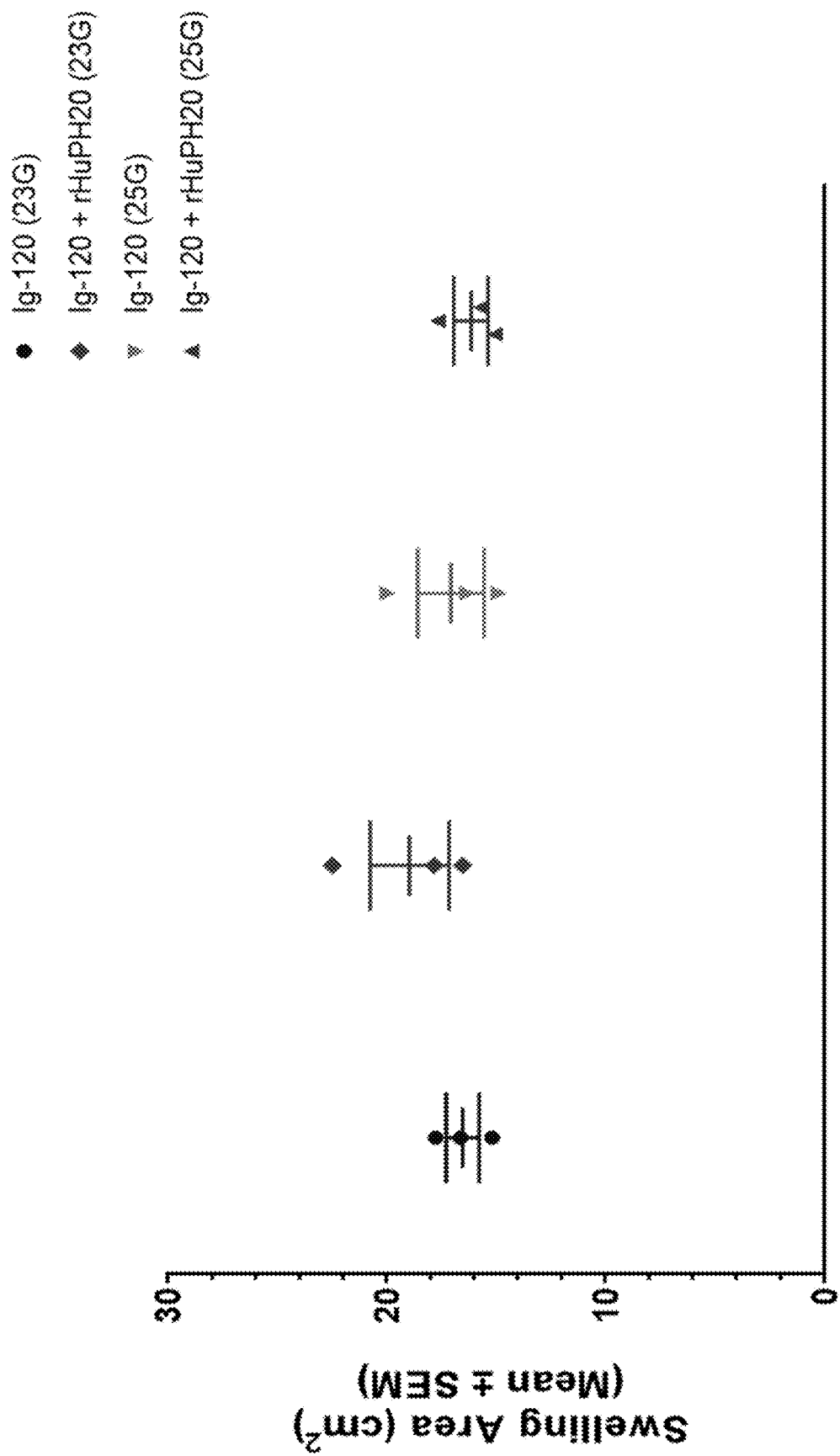
FIG. 75 is a chart of individual swelling bleb areas (cm$^2$) after SC injection of Ig-120 and Ig-120+rHuPH20 determined using 3D imaging.
Figure 76:
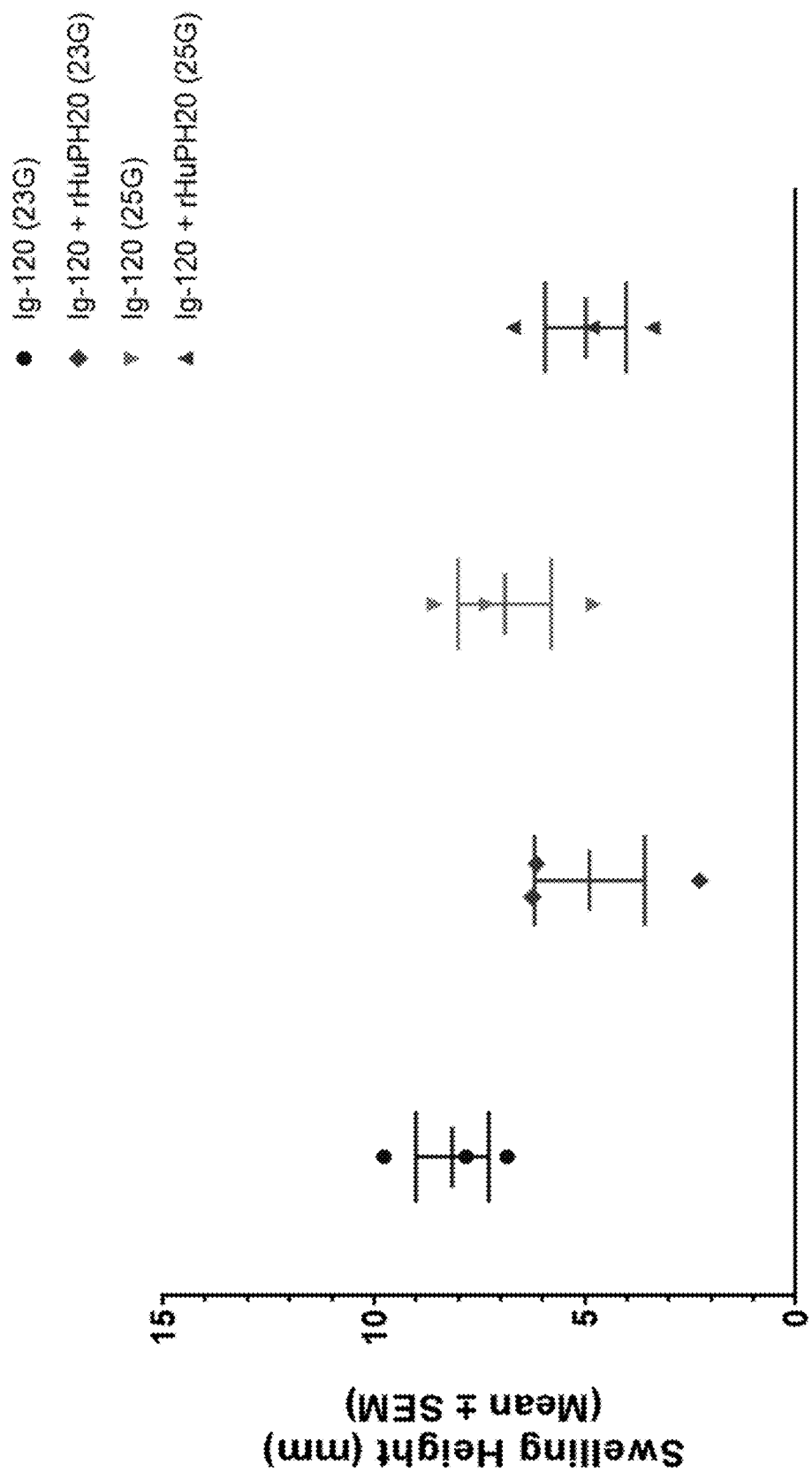
FIG. 76 is a chart of individual swelling bleb heights (mm) after SC injection of Ig-120 and Ig-120+rHuPH20 determined using 3D imaging.

Post-injection swelling volume, area, and height for Ig-120 and Ig-120+rHuPH20 calculated from the 3D images are summarized in Table 56. Individual post-injection swelling bleb volume, area and height are shown graphically in FIGS. 74, 75, and 76. Further analyses of timepoints T15 and T30 indicated that the excessive movement of the animal between imaging timepoints made surface registration problematic and therefore no further analyses were performed for these later timepoints.

TABLE 56

Swelling volume, area, and height after injection of Ig-120 + rHuPH20 assessed using 3D imaging (Mean ± SEM)
Ig-120 + rHuPH20

| Test Solution | Needle Gauge | Volume (mL) | Area (cm$^2$) | Height (mm) |
|---|---|---|---|---|
| Ig-120 | 23G | 4.8 ± 0.8 | 16.5 ± 0.7 | 8.1 ± 0.9 |
| Ig-120 + rHuPH20 | | 2.7 ± 0.7 | 19.0 ± 1.8 | 4.9 ± 1.3 |
| Ig-120 | 25G | 4.5 ± 0.4 | 17.1 ± 1.5 | 6.9 ± 1.1 |
| Ig-120 + rHuPH20 | | 3.4 ± 0.7 | 16.1 ± 0.8 | 5.0 ± 1.0 |

Figure 77:
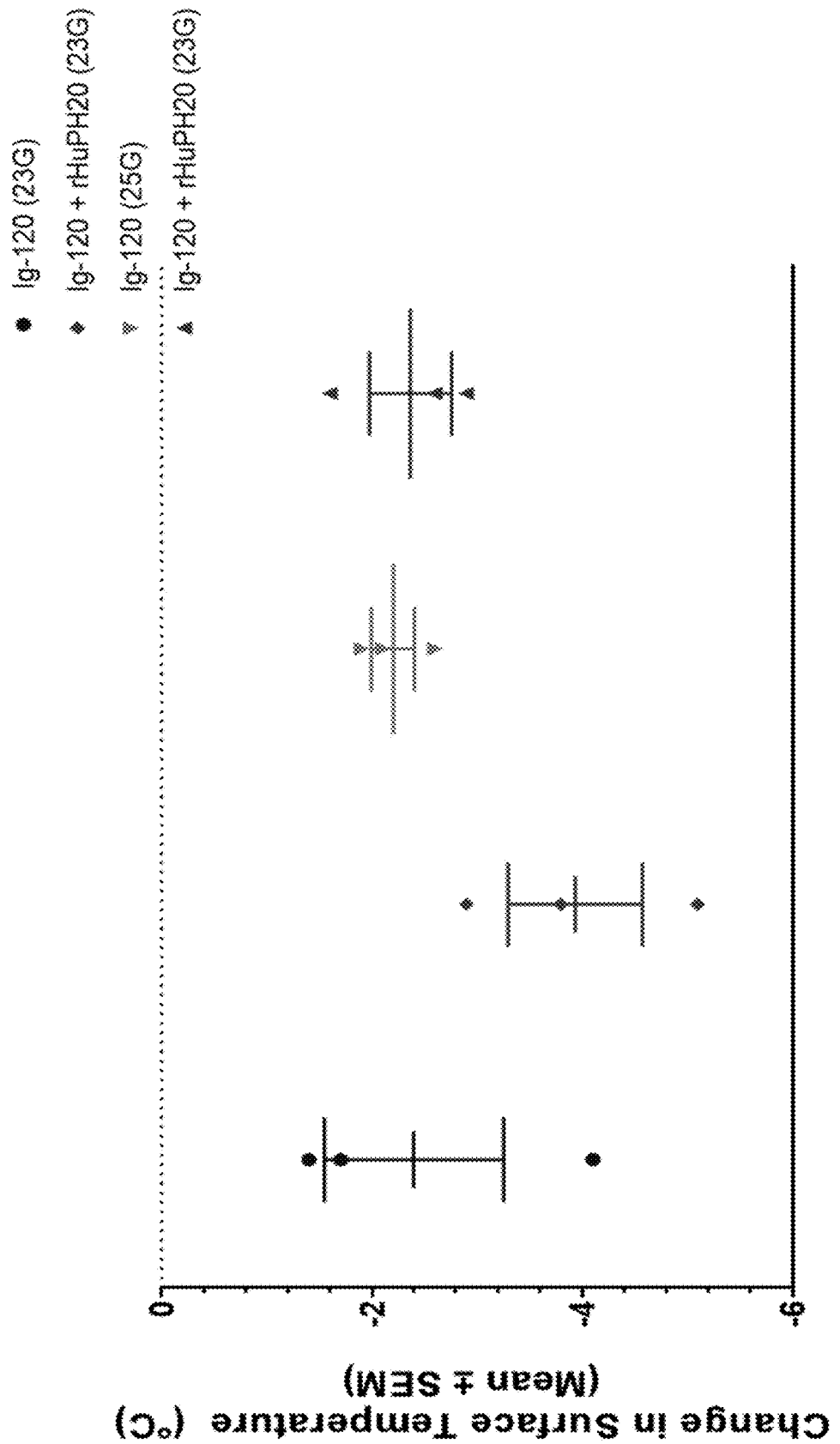
FIG. 77 is a chart of change in skin temperature from pre to post-injection.

Assessment of post-injection temperature changes: Skin temperature of the injection site was measured immediately prior to needle insertion using an infrared thermometer. It was then re-measured at the end of the injection to determine if any significant changes in temperature may occur following injection. The changes in skin temperature between pre- and post-injection decreased by approximately 2.2-3.9° C. and are provided in Table 57 and FIG. 77.

TABLE 57

Mean changes in skin temperature (° C. ± SEM)

| | Test Solution | |
|---|---|---|
| Needle Gauge | Ig-120 | Ig-120 + rHuPH20 |
| 23G | −2.4 ± 0.9 | −3.9 ± 0.6 |
| 25G | −2.2 ± 0.2 | −2.4 ± 0.4 |

Qualitative Assessment of Local Injection Sites

Post-injection erythema: Erythema for both test solutions was very slight and transient. The scoring by the three evaluators for erythema (Mean±SEM) for each test solution are summarized in Table 58 and shown in FIG. 78.

TABLE 58

Erythema scores post-injection for Ig-120 and Ig-120 + rHuPH20 (Mean ± SEM)

| Test Solution | Needle Gauge | T0 | T15 | T30 | T2 h | T24 h |
|---|---|---|---|---|---|---|
| Ig-120 | 23G | 0.7 ± 0.3 | 0.3 ± 0.1 | 0.0 ± 0.0 | 0.0 ± 0.0 | 0.8 ± 0.4 |
| Ig-120 + rHuPH20 | | 0.3 ± 0.2 | 0.0 ± 0.0 | 0.0 ± 0.0 | 0.0 ± 0.0 | 0.0 ± 0.0 |
| Ig-120 | 25G | 0.3 ± 0.1 | 0.2 ± 0.1 | 0.0 ± 0.0 | 0.0 ± 0.0 | 0.8 ± 0.4 |
| Ig-120 + rHuPH20 | | 0.2 ± 0.1 | 0.4 ± 0.2 | 0.1 ± 0.1 | 0.0 ± 0.0 | 0.3 ± 0.2 |

Post-injection swelling size: Post injection swelling size, for Ig-120 alone, was moderate to severe and for Ig-120+rHuPH20 was slight to moderate. All bleb swelling size decreased over time. Scoring by the three evaluators for swelling size (Mean±SEM) are summarized in Table 59 and shown in FIG. 79.

TABLE 59

Swelling size scores post-injection for Ig120 + rHuPH20 (Mean ± SEM)

| Test Solution | Needle Gauge | T0 | T15 | T30 | T2 h | T24 h |
|---|---|---|---|---|---|---|
| Ig-120 | 23G | 3.8 ± 0.1 | 3.8 ± 0.1 | 3.8 ± 0.1 | 3.4 ± 0.3 | 0.6 ± 0.3 |
| Ig-120 + rHuPH20 | | 2.4 ± 0.6 | 2.1 ± 0.6 | 1.6 ± 0.5 | 0.9 ± 0.4 | 0.1 ± 0.1 |
| Ig-120 | 25G | 3.4 ± 0.3 | 3.1 ± 0.3 | 2.8 ± 0.4 | 2.5 ± 0.5 | 0.2 ± 0.1 |
| Ig-120 + rHuPH20 | | 2.9 ± 0.3 | 2.1 ± 0.3 | 1.8 ± 0.2 | 0.9 ± 0.3 | 0.0 ± 0.0 |

Post-injection firmness (induration): The hardness (induration) of the post-injection swelling blebs for Ig-120 alone were moderate to severely firm, and for Ig-120+rHuPH20 post-injection swelling blebs were mild to moderately firm. All swelling bleb induration decreased over time and scoring (Mean±SEM) is summarized in Table 60 and shown in FIG. 80.

The injection sites were photographed before and at different intervals after the 10 mL injection procedure. Photographic images are shown in FIGS. 81A-86B. It should be noted at the 2 hour timepoint (T2 h), the photos of the animal were taken while it was manually held by an animal technician. Because of the increased stress to the animal, this resulted in some flushing of the skin for some animals. In addition, the injection site may have had some increased tension (skin stretching) when photographed. Therefore, the qualitative scoring is considered the more accurate assessment of the injection site at the 2 h timepoint

TABLE 60

Induration scores post-injection for Ig120 + rHuPH20 (Mean ± SEM)

| Test Solution | Needle Gauge | T0 | T15 | T30 | T2 h | T24 h |
|---|---|---|---|---|---|---|
| Ig-120 | 23G | 3.9 ± 0.1 | 3.9 ± 0.1 | 3.8 ± 0.1 | 3.2 ± 0.2 | 0.6 ± 0.3 |
| Ig-120 + rHuPH20 | | 2.2 ± 0.5 | 1.6 ± 0.5 | 1.3 ± 0.5 | 0.8 ± 0.4 | 0.1 ± 0.1 |
| Ig-120 | | 3.6 ± 0.3 | 3.2 ± 0.3 | 2.8 ± 0.4 | 2.3 ± 0.5 | 0.2 ± 0.1 |
| Ig-120 + rHuPH20 | 25G | 2.6 ± 0.3 | 1.6 ± 0.2 | 1.2 ± 0.2 | 0.7 ± 0.3 | 0.0 ± 0.0 |

Summary and Conclusions

The addition of rHuPH20 to the Ig test solution showed that an HVAI can successfully deliver a 10 mL volume and showed that the delivery time can be modulated by using different needle gauges. In addition, this study showed:
  HVAI devices that contained rHuPH20 had a reduced time of delivery compared to control HVAI devices (23 G: ~ 29%; 25 G: ~ 9%);
  Larger needle gauge (23 G) reduced time of delivery for both control injections (~39%) and rHuPH20 injections (~52%);
  Back-leakage was reduced for all HVAI devices that contained rHuPH20 (23 G: ~ 67%; 25 G: ~73%);
  Post-injection swelling volume and height were reduced for all HVAI devices that contained rHuPH20 compared to control injections; and
  Bleb swelling size and induration were lower at T0 for rHuPH20-containing injections and had more rapid resolution compared to control HVAI devices (Ig-120 alone).

Example 5: Assessment of Subcutaneous Injection of GAMMAGARD LIQUID with rHuPH20 (4000 U/mL) Using Various Needle Gauges Summary The objective of this study was to determine the injection dynamics of subcutaneous (SC) administration of GAMMAGARD LIQUID (GGL) with and without recombinant human hyaluronidase (rHuPH20) using a 3D printed mock auto injector. Four cohorts were compared in this study each consisting of six SC injections. Cohort #1 evaluated the delivery of 10 mL of the GGL solution without rHuPH20 using a 25 Gauge (25 G) Terumo thin walled (TW) needle (25 G-Terumo). Cohort #2, 3, and 4 evaluated the delivery of 10 mL of the GGL solution with rHuPH20 using either a 25 G-Terumo thin walled needle, a 23 G Becton Dickinson (23 G-BD) needle, or a 25 G Becton Dickinson needle (25 G-BD). All test solutions containing rHuPH20 were formulated at 4000 U/mL Yucatan miniature pigs were used in this study due to the similarity of the SC skin architecture with humans and their ability to receive clinically relevant dose volumes. Each animal received two vertical 10 mL SC injections into the lower abdominal regions. The test solution was delivered using a syringe pump connected to a 30-inch extension set which was mounted in a 3D printed handle that held the needle at an injection depth of 10 mm. All injections were delivered at 20 mL/min (30 second injection).

Endpoints included measurement of applied force during delivery as well as post-injection back-leakage, swelling size area and volume (measured by caliper and 3D imaging) and qualitative assessment of the injection site over time for erythema, swelling size and induration (at times T=0, 15, 30 min, 2 h, and 24 h). The study provides guidance about the dynamics of injection of GGL+rHuPH20 comparable to what is anticipated for use in a human clinical trial.

Introduction

Current auto-injectors (AIs) are limited to extremely small volumes (typically ≤ 2.25 mL), limiting their usefulness for delivery of larger volumes. For larger volumes higher flow rates are required to make use of an AI practical. Currently 30 seconds is a recommended amount of time that a device can be held in place during self-administration to prevent fatigue and potential interruption of the injection.

rHuPH20 has been shown to facilitate the SC administration of fluids and drugs by transiently and locally depolymerizing hyaluronan (HA) in the extracellular matrix (ECM). The depolymerization of HA reduces tissue back-pressure in the SC space that subsequently allows for rapid, large volume administration of drugs. Previous work has shown that rHuPH20 can facilitate the delivery of large volumes to the SC space at high flow rates using an infusion set.

The mini-pig model has been selected due to the high degree of similarity of the subcutaneous space to that of humans. Previous studies using a mini-pig model have demonstrated the translatability of the model for use in pre-clinical and auto-injector studies.

In summary, the objective of this study was to determine if rHuPH20 may potentiate the development of a large volume AI that is able to deliver larger clinically relevant volumes to the SC space at high flow rates using the mini-pig as an animal model. The study design was created to model a potential clinical trial that would utilize a commercially available antibody solution (GammaGard; GGL) co-mixed with recombinant human hyaluronidase (rHuPH20). For this study recombinant human hyaluronidase Enhanze Drug Product (EDP) was used for preparation of the co-mix. EDP is a solution of rHuPH20 (1 mg/mL) that is approved for early clinical studies.

Test Articles and Methods
Test Articles
  Gammagard Liquid
  Lot number: BE12C18748
  Description: Clear liquid reconstituted from lyophilized powder
  Concentration: 10%
  Storage Conditions: 2-8° C.
  Handling Conditions: Standard laboratory precautions
  Supplier: Myonex
  ENHANZE™ Drug Product (EDP; Recombinant Human Hyaluronidase rHuPH20)
  Lot number: 1-FIN-3426
  Description: Clear and colorless solution
  Concentration: 0.97 mg/mL
  Date of Manufacture: Oct. 6, 2021

Retest Date: July 2024
Enzyme activity: 106 kU/mL
Storage: 2-8° C.
Formulation: 10 mM Histidine, 130 mM Sodium Chloride, 10 mM L-Methionine, 0.02% Polysorbate-80, pH 6.5
Handling Conditions: Standard laboratory precautions
Supplier: Halozyme Therapeutics, Inc Formulation Preparation of Test Solutions: Two test solutions were used in this study GAMMAGARD LIQUID (GGL) alone and GGL co-mixed with Enhanze Drug Product (EDP). EDP is a solution of recombinant human hyaluronidase PH20 (rHuPH20). The first test solution of GGL alone was prepared from a stock vial of GGL that was not diluted prior to syringe filling. The second test solution of GGL+EDP was prepared by co-mixing the GGL with EDP to make a test solution having an activity of 4000 U/mL. Because the study was conducted over two different days two preparations of GGL+EDP were prepared. Twelve syringes were prepared on the day prior to use for dosing day 1 and twelve syringes were prepared on the day prior to use for dosing day 2.

To prepare the co-mix of GGL+EDP six separate co-mix vials were prepared for dosing day 1 and six additional co-mix vials were prepared for dosing day 2. Each co-mix vial contained 36.6 mL of GGL mixed with 1.4 mL of EDP to provide a total of 38 mL. Because the syringe fill volume was 16 mL, then each vial of co-mix was able to fill (2) syringes.

The GGL+EDP solution was tested for rHuPH20 activity prior to the start of the study using a micro-turbidity assay. The activity of the GGL+EDP test solutions were deemed to be within acceptable range for use in the study. The syringes were stored in a refrigerator set to maintain 2-8° C. and transferred on ice to the study site. Activity values are summarized in Table 61.

TABLE 61

Pre-study activity testing of GGL + EDP

| Study Day | Co-mix vial # | Pre-study Concentration (U/mL ± SD) |
|---|---|---|
| 1 | 1 | 4109 ± 108 |
| 1 | 2 | 3856 ± 122 |
| 1 | 3 | 3855 ± 129 |
| 1 | 4 | 3897 ± 110 |
| 1 | 5 | 3765 ± 96 |
| 1 | 6 | 3422 ± 79 |

TABLE 61-continued

Pre-study activity testing of GGL + EDP

| Study Day | Co-mix vial # | Pre-study Concentration (U/mL ± SD) |
|---|---|---|
| 2 | 1 | 3815 ± 80 |
| 2 | 2 | 3753 ± 84 |
| 2 | 3 | 3786 ± 71 |
| 2 | 4 | 3982 ± 82 |
| 2 | 5 | 3554 ± 80 |

After administration of the test solution dose retain samples were obtained by storing the remaining solution in the syringe on ice until transported back for activity testing. Three dose samples were retained for each dosing day. The activity of the GGL+EDP test solutions for dose retains are summarized in Table 62.

TABLE 62

Post-study activity testing of rHuPH20 activity in test solution

| Study Day | Co-mix vial # | Syringe # | Post-study Concentration (U/mL ± SD) |
|---|---|---|---|
| 1 | 5 | 5b | 4133 ± 91 |
| 1 | 6 | 6a | 4110 ± 128 |
| 1 | 6 | 6b | 4085 ± 80 |
| 2 | 1 | 1a | 4097 ± 91 |
| 2 | 2 | 2a | 4107 ± 77 |
| 2 | 3 | 3a | 4149 ± 75 |

Animal Description
 Species: Pig (*Sus scrofa domestica*)
 Strain: Yucatan miniature
 Sex: Female
 Age: >3 months
 Body weight: 12-16 kg upon receipt
 Quantity: 12
 Source: Premier BioSource (Ramona, CA)
 Husbandry: Animals were received by the facility and allowed to acclimate prior to study start. Animals were group housed in steel pens with automatic water provided ad libitum. Animals were fed twice daily (AM and PM), except on study day (PM only). Room environment was set to maintain a temperature of ~17-27° C. and a relative humidity of 40-70%, with a 12 hour light/12 hour dark time cycle. Animals were allowed to acclimate to the facility 4 days prior to study onset.

Test Materials

TABLE 63

Summary of test materials

| Test Material | Supplier |
|---|---|
| High pressure syringe pump | KD Scientific, Holliston, MA |
| 25G × 1 inch Precision Glide needle | Becton Dickinson, Franklin Lakes, NJ |
| 23G × 1 inch Precision Glide needle | Becton Dickinson, Franklin Lakes, NJ |
| 25G × 1 inch hypodermic thin-walled needle | Terumo Medical Corporation; Somerset, NJ |
| 20 mL Luer-Lok™ syringe | Becton Dickinson, Franklin Lakes, NJ |
| 30-inch standard bore extension set | B/Braun, Bethlehem, PA |
| Subminiature load cell | Loadstar Sensors; Fremont, CA |
| Load cell interface | Loadstar Sensors; Fremont, CA |
| Load cell software | Loadstar Sensors; Fremont, CA |
| Standard Digital Camera | Canon |
| High Resolution 3D camera | Canfield Sciences, Parsippany, NJ |
| 3D Printed Mock Auto-Injector | Halozyme, Inc. |

TABLE 63-continued

Summary of test materials

| Test Material | Supplier |
|---|---|
| Digital caliper | Fisher Scientific, Los Angeles, CA |
| Surgical Eye Spear | Becton Dickinson, Franklin Lakes, NJ |

Experimental Design

In this study, two 10 mL injections were administered to the abdomen of a Yucatan miniature pig. Twelve animals were placed on study. Two test solutions were used for the injections: GGL alone and GGL co-mixed with Enhanze Drug Product™ (EDP). EDP is a solution of recombinant human hyaluronidase (rHuPH20) suitable for early clinical applications and is provided at a concentration of ~105 kU/mL (~1 mg/mL). The final concentration of the co-mix was 4000 U/mL.

The GGL alone solution was delivered using only a 25 G-Terumo needle while the GGL+EDP solutions were delivered using all three different needles: 25 G-Terumo, 25 G-BD and 23 G-BD. A summary of the cohorts for the study is shown in Table 64. Injections were randomized to ensure equal distribution of cohort combinations over the 12 animals.

TABLE 64

Description of treatments

| Cohort # | N/Cohort | Test Solution | Needle | Volume (mL) | Flow Rate (mL/min) | [rHuPH20] U/mL |
|---|---|---|---|---|---|---|
| 1 | 6 | GGL | 25G-Terumo | 10 | 20 | 0 |
| 2 | 6 | GGL + EDP | 25G-Terumo | 10 | 20 | 4000 |
| 3 | 6 | GGL + EDP | 23G-BD | 10 | 20 | 4000 |
| 4 | 6 | GGL + EDP | 25G-BD | 10 | 20 | 4000 |

Quantitative endpoints of this study included measurement of applied force to the syringe plunger during the injection, post-injection swelling (bleb) volume, area, and height. Post-injection back-leakage of test article was collected from the injection site for 30 seconds after the removal of the needle using an eye-spear to absorb any leakage and quantified by weight. The volume of the injection site blebs was determined by digital caliper measurement (length, width, and height) as well as by 3D camera imaging immediately post-injection (T0), as well as at 15 and 30 minutes post-injection (T15 and T30, respectively). Additional post-injection qualitative injection site evaluations for erythema, swelling, and induration were performed at T0, T15 and T30 minutes post-injection, as well as at 2 hours (T2 h) and at approximately 24 hours post-injection (T24 h) post-injection. Qualitative assessments of the injection sites were performed while the animal was under anesthesia for the T0, T15, T30 and T24 h timepoints while the T2 h assessment was performed while the animal was conscious and hand-held by an animal technician. Standard photographs were obtained both pre-injection and at times T0, T15, T30, T2 h and T24 h post-injection. In summary the endpoints for the study were:

Applied force during the injection
Measurement of back-leakage post-injection
Measurement of bleb size (length/width/height) post-injection (caliper) at T0, T15, T30
Measurement of bleb size (volume, height, area) using 3D imaging at T0, T15, T30
Assessment of blebs for erythema, swelling size and induration at times T0, T15, T30, T2 h and T24 h by three independent assessors.

Study Procedure

Prior to study start, animals were assessed for general health, and body weights were collected. On the day prior to the study test articles were drawn into a 20 ml syringe, capped, and stored in a refrigerator set to maintain 2-8° C. On the day of the study the syringes were removed from 2-8° C. and brought to room temperature for at least 30 minutes prior to dosing.

Animals were anesthetized with isoflurane gas and placed in dorsal recumbence on a foam wedge on a heated surgical table and were maintained under isoflurane gas for the entire duration of the procedure. The abdominal region was cleaned with Nolvasan followed by wiping the injection site with gauze containing 70% isopropanol and wiped dry with sterile gauze. M Injection sites were located on the left and right abdominal regions, ~6 cm cranially from the inguinal fold towards the midline and ~3 cm towards the midline of the animal. Each of the injection sites was marked with a permanent marker and then photographed with the standard and 3D cameras prior to needle insertion.

Assembly of 3D Printed Handle:

The handle was prepared by initially attaching a 1-inch Luer-lok needle (either 25 G-Terumo, 25 G-BD or 23 G-BD) to the male end of a 30-inch extension set. The needle hub was then mounted into the proximal end of the 3D printed handle and firmly seated. The extension set tubing was routed through the inside of the handle exiting out the distal end of the handle. The length of the projecting needle was confirmed to be 10.0 mm±0.5 mm. The female end of the extension set was then attached to the male end of a 20 ml syringe previously filled with 16 mL of the test solution. The hardware was primed to the needle tip with the test solution and the syringe was placed into the syringe pump. The load cell was then attached to the end of the syringe plunger and the syringe mounted into the syringe pump. After loading the syringe into the pump, the load cell was zeroed and applied force recordings were initiated. The pump block was positioned so that it abutted the end of the syringe plunger-load cell with minimal contact force and was then locked into place. The needle remained capped until just prior to dosing.

The needle cap was removed, and the needle inserted into the SC space using a pinch method with vertical needle insertion. After the needle was inserted the syringe pump was started to begin injection of the test article at 20 mL/min. Upon completion of the injection the needle was removed, the pressure on the syringe pump block removed and the applied force data collection was stopped. Test solution back-leakage was absorbed to a pre-tared eye-spear for 30 seconds post-injection by blotting the injection site. The weight of the eye spear was recorded using analytical balance with an accuracy of 0.1 mg. The margins of the injection site bleb were marked with a permanent marker and measured for length, width, and height using a digital caliper and recorded. The injection site was then photographed with the standard and 3D cameras immediately post-injection (T0). The injection site was then qualitatively scored by three independent evaluators for appearance and severity of erythema, swelling/bleb size, and firmness (induration) using a 5-point scoring system (a modified Draize Test) based on the 1992 OECD guidelines for grading skin reactions (Table 65, Table 66, and Table 67).

TABLE 65

Grading scale for erythema formation

| Scale | Description |
|---|---|
| 0 | No erythema |
| 1 | Very slight erythema (barely perceptible) |
| 2 | Well defined erythema |
| 3 | Moderate erythema |
| 4 | Severe erythema (beet redness) to slight eschar formation |

TABLE 66

Grading scale for swelling size formation

| Scale | Description |
|---|---|
| 0 | No swelling |
| 1 | Very slight swelling |
| 2 | Slight swelling |
| 3 | Moderate swelling |
| 4 | Severe swelling |

TABLE 67

Grading scale for swelling firmness (induration)

| Scale | Description |
|---|---|
| 0 | No perceptible difference in firmness after injection |
| 1 | Very slightly firm (barely perceptible) |
| 2 | Mildly firm |
| 3 | Moderately firm |
| 4 | Very firm |

The evaluators were blinded to each other's scores. Caliper measurements and 3D images were also obtained at 15 minutes post-injection (T15) and 30 minutes post-injection (T30). Qualitative scoring for erythema, swelling, and induration was also collected at T15, T30, 2 hours and approximately 24 hours post-injection (T2 h and T24 h, respectively). Standard images of the injection site were also taken at T15, T30, T2 h and T24 h. After the first injection, the procedure was repeated on the contra-lateral side of the animal using the other test solution or needle type. Following the final 24 h assessment, the animal was humanely euthanized using a ready for use solution of sodium pentobarbital and sodium phenytoin (Euthasol®).

Calculations And Statistical Methods
Assessment of Applied Force

Applied force, as measured via a load cell attached to the end of syringe plungers, was recorded using SensorVUE software, and the mean applied force over the entire injection period was calculated.

Assessment of Local Swelling Volume and Area Using Caliper Measurement and 3D Imaging Volume and area of post-injection swelling were measured using both caliper measurement and 3D camera image analysis. For caliper measurements a digital caliper was utilized to measure length, width and height of the bleb that formed post-injection. The length and width are defined as the edge to edge measurements of the bleb (i.e., diameter) along their longest axes. These values were manually recorded, and the volume determined using the formula for half of an ellipsoid Vol=$(2/3)*\pi*A*B*C$ where A=Length/2, B=Width/2 and C=Height.

3D imaging was applied as an orthogonal methodology to measure post-injection swelling. By obtaining high definition pre- and post-injection 3D images the distances between two registered surfaces can be determined. The camera captures images using a factory calibrated bifocal imaging system to measure distance between surfaces. Surface registration was performed using multipoint method that utilized common landmarks between the pre-injection image and the post-injection image. Using the proprietary software, the volume, area and height of the post-injection swelling was calculated for each injection.

Caliper measurement and 3D imaging measurement will yield different values for volume, area, and bleb height. The differences are a result of the difference in the bleb size measurement. The 3D measurement calculates bleb height based from the top of the bleb to the original skin position, while the bleb height from caliper measurements measure from the top of the bleb to the height at the edge of the bleb. Due to skin curvature, this may yield an overall increase in bleb height for the caliper measurements compared to the 3D measurements, resulting in greater bleb volume and height. However, the measurements are consistent with each other and therefore differ only due to the methodology.

Results and Discussion
Pre and Post-Injection Quantitative Measurements

Quantitative measurements included measurement of applied force during the injection, back-leakage for 30 seconds post-injection, and bleb size collection at T0, T15, and T30 (as described above).

Figure 88A:
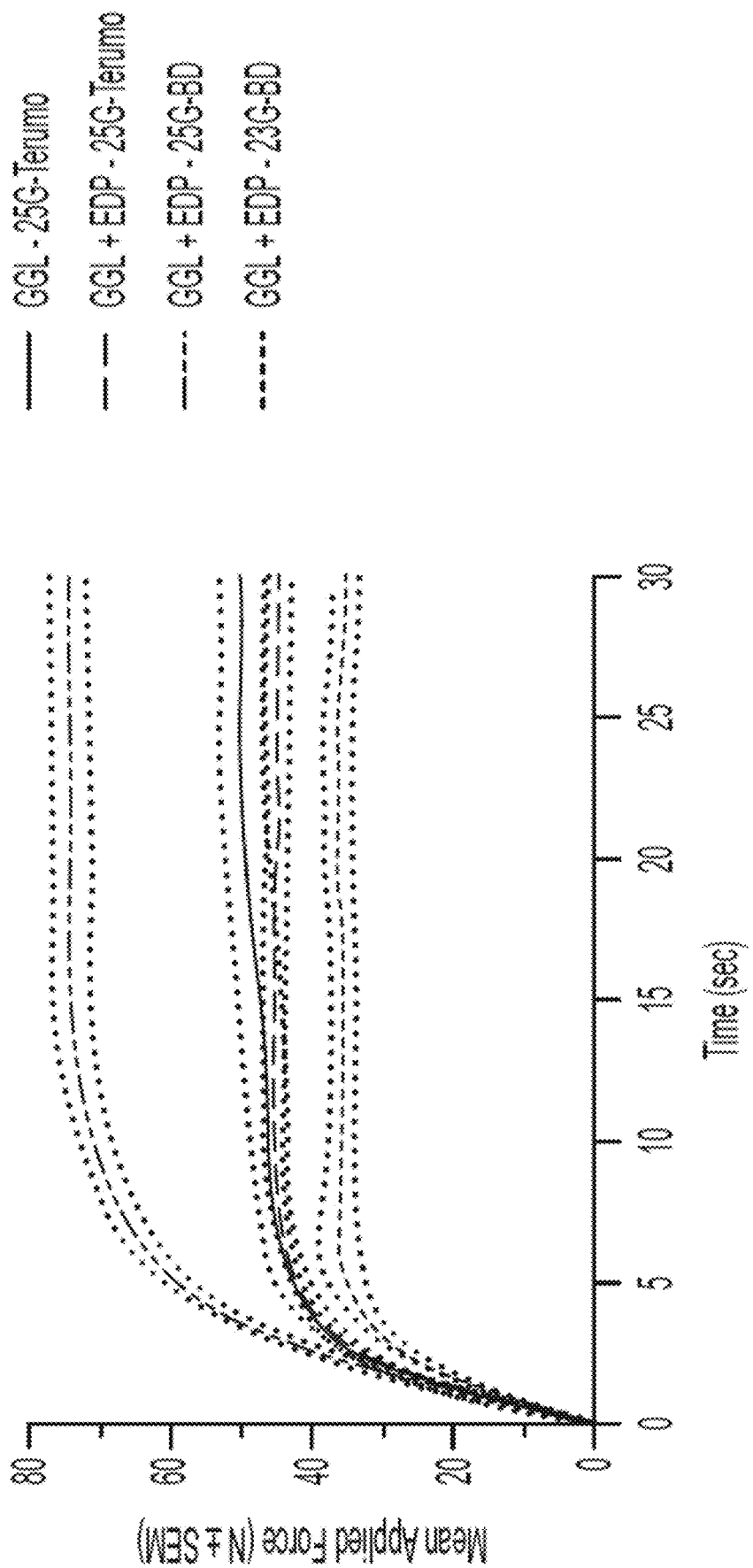
FIG. 88A is a graph of applied force (N) during the injection (Mean±SEM) of GAMMAGARD LIQUID (GGL) and GGL+Enhanze Drug Product (EDP).
Figure 88B:
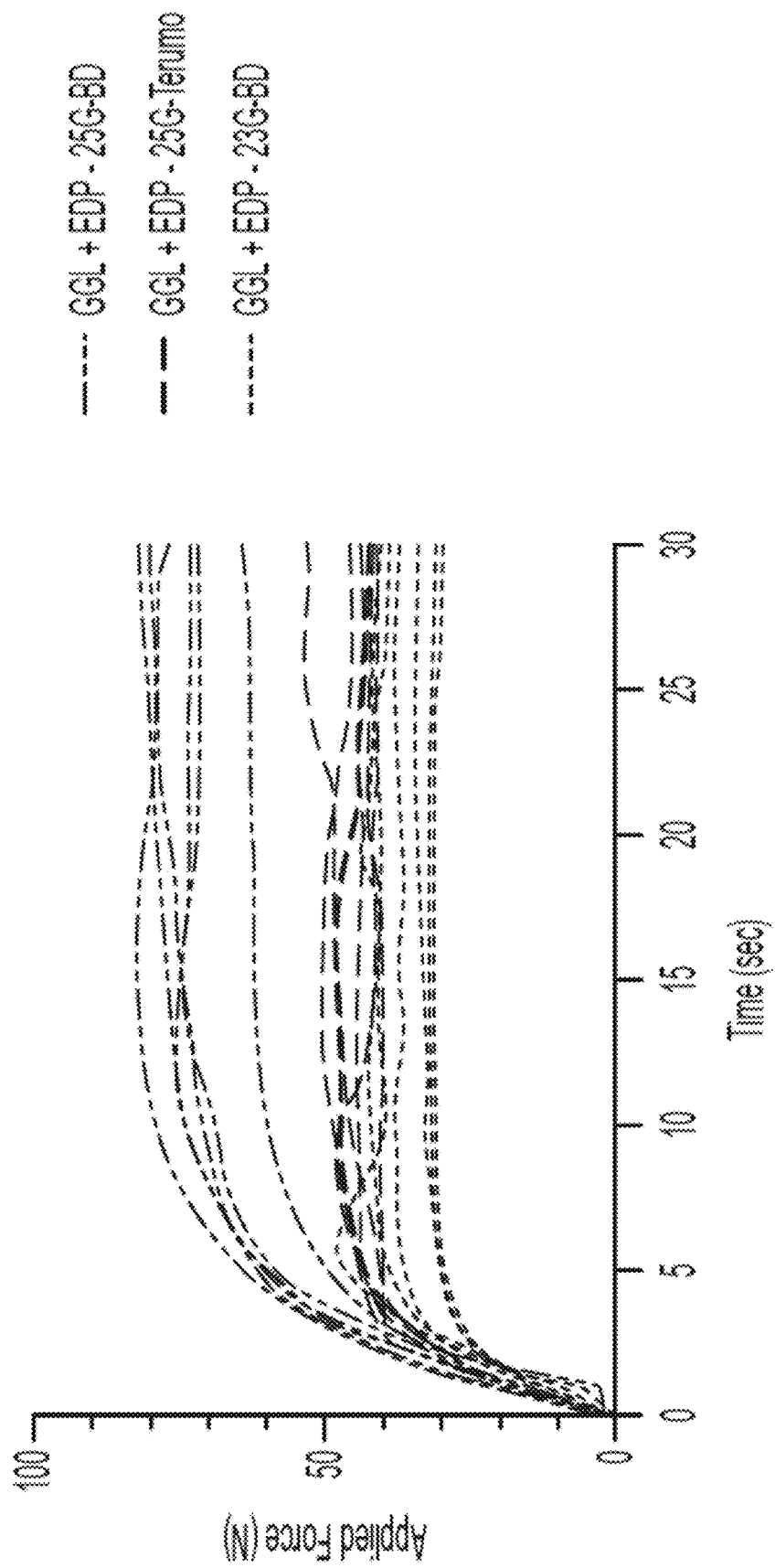
FIG. 88B is a graph of individual applied force (N) during the injection of GGL+EDP.

Assessment of applied force during injection: The applied force was measured during the SC injection by attaching a subminiature load cell to the end of the 20 ml syringe barrel. The load cell provided force data that was electronically recorded throughout the injection via a DI-100U load cell interface at a data capture rate of 2 Hz. Applied forces for each test solution and flow rate are summarized in Table 68 and FIG. 88A. Applied force during injection for individual animals at each flow rate is shown in FIG. 88B.

TABLE 68

Summary of applied forces during injection

| Cohort # | Test Solution | Needle | [rHuPH20] | Mean Applied Force (N) ± SEM |
|---|---|---|---|---|
| 1 | GGL | 25G-Terumo | 0 | 43.3 ± 1.2 |
| 2 | GGL + EDP | 25G-Terumo | 4000 | 42.6 ± 1.1 |
| 3 | GGL + EDP | 23G-BD | 4000 | 34.1 ± 0.8 |
| 4 | GGL + EDP | 25G-BD | 4000 | 67.4 ± 2.1 |

Figure 89:
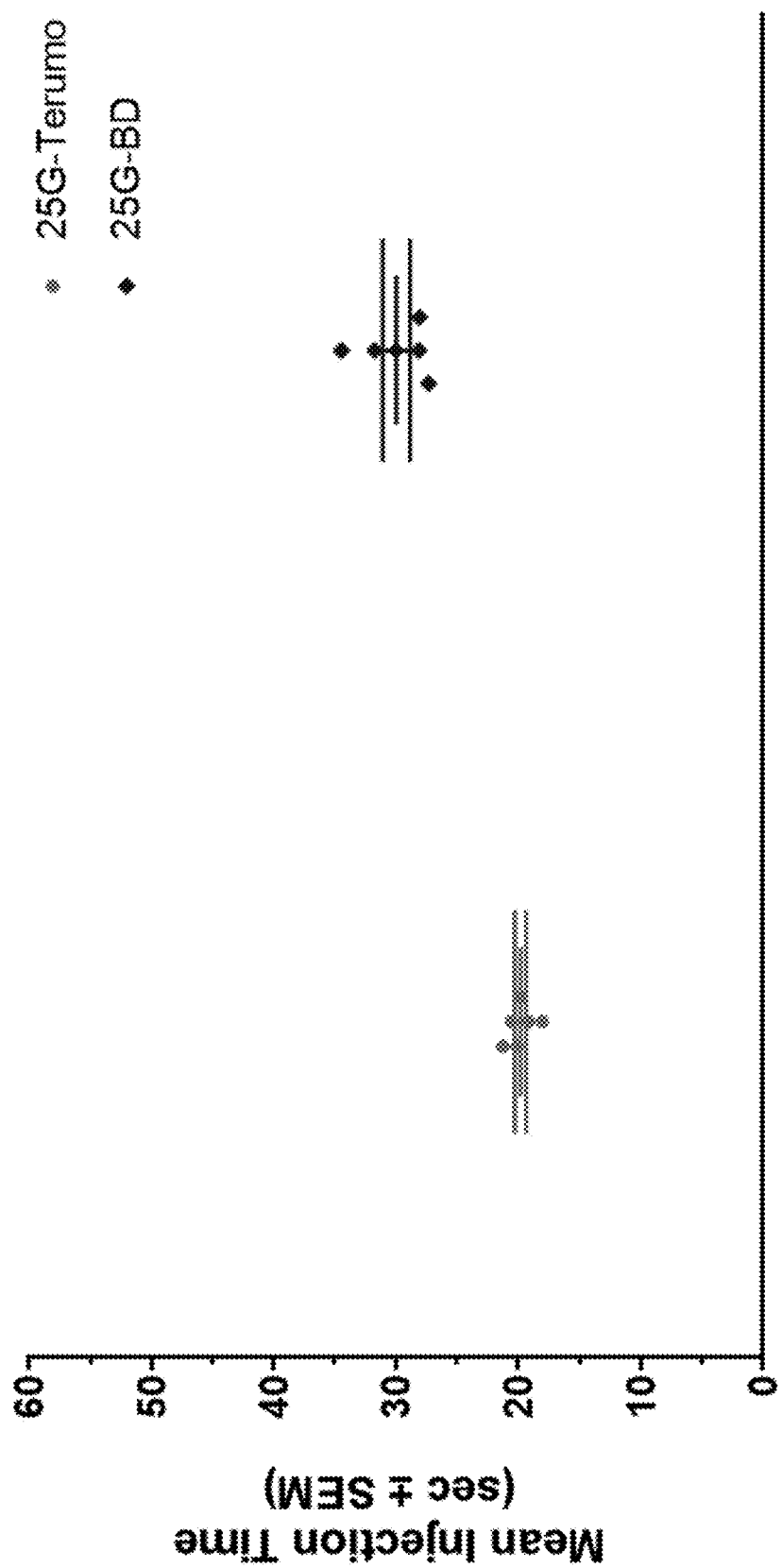
FIG. 89 is a graph of mean injection time (seconds±SEM) for the 25 G-Terumo needle versus the 25 G-BD needle.

Duration of injection: Injection times (seconds) were utilizing a hand-held stopwatch and closely monitoring the start and completion of the injection. Individual injection times are shown in FIG. 89 and mean injection times are summarized in Table 68B. The mean injection time for the 25 G-Terumo needle group was approximately 33% faster than the mean injection time for the 25 G-BD needle group.

TABLE 68B

Mean injection time (seconds ± SEM)

| Needle Gauge | Injection Time (sec ± SEM) | |
| --- | --- | --- |
| | 25G-Terumo | 25G-BD |
| | 19.8 ± 0.5 | 30.0 ± 1.1 |

Figure 90:
FIG. 90 is graph of mean (mg±SEM) and individual weights of back-leakage.

Assessment of post-injection back-leakage: The amount of back-leakage for each injection was measured by collecting post-injection fluid at the site using a surgical eye spear. Prior to collection the weight of each eye spear was tared on the analytical balance. Post-injection back-leakage from the injection site was collected for an interval of 30 seconds. The eye spear was then immediately weighed, and the weight recorded. The analytical balance had a precision of 0.1 mg. Back-leakage for Ig-120 alone and Ig-120+rHuPH20 are shown in Table 69 and FIG. 90.

TABLE 69

Mean weight of back-leakage (mg ± SEM)

| Cohort # | Test Solution | Needle | [rHuPH20] | Weight of Back-leakage (mg ± SEM) |
| --- | --- | --- | --- | --- |
| 1 | GGL | 25G-Terumo | 0 | 62.1 ± 34.1 |
| 2 | GGL + EDP | 25G-Terumo | 4000 | 10.6 ± 4.1 |
| 3 | | 25G-BD | 4000 | 25.2 ± 11.8 |
| 4 | | 23G-BD | 4000 | 42.0 ± 16.6 |

The back-leakage was greatest for the GGL delivered without rHuPH20. For injections that contained rHuPH20 the 25 G-Terumo needle had the least back-leakage and the 23 G-BD had the greatest. Overall, the back-leakage was very modest for all injections that contained rHuPH20.

Assessment of post-injection bleb volume, area, and height (caliper measurements): The local injection site swelling was marked and measured using a digital caliper. Bleb volume, dispersion area, and swelling height of each bleb was determined as described above and are summarized in Table 70, Table 71, and Table 72 for GGL and GGL+EDP at the T0, T15 and T30 timepoints, respectively.

TABLE 70

Bleb volume over time after injection of GGL and GGL + EDP - caliper measurements (Mean ± SEM)

| | | Volume (mL ± SEM) | | |
| --- | --- | --- | --- | --- |
| Test Solution | Needle Gauge | T0 | T15 | T30 |
| GGL | 25G-Terumo | 9.6 ± 1.5 | 7.1 ± 1.7 | 5.1 ± 1.4 |
| GGL + EDP | 25G-Terumo | 9.0 ± 1.7 | 2.8 ± 1.1 | 2.0 ± 0.7 |
| | 25G-BD | 6.9 ± 1.5 | 4.3 ± 1.2 | 3.6 ± 1.3 |
| | 23G-BD | 6.8 ± 0.6 | 2.7 ± 0.5 | 1.7 ± 0.6 |

TABLE 71

Bleb area over time after injection of GGL and GGL + EDP - caliper measurements (Mean ± SEM)

| | | Area (cm² ± SEM) | | |
| --- | --- | --- | --- | --- |
| Test Solution | Needle Gauge | T0 | T15 | T30 |
| GGL | 25G-Terumo | 21.4 ± 1.9 | 24.1 ± 2.4 | 25.8 ± 4.0 |
| GGL + EDP | 25G-Terumo | 22.6 ± 2.2 | 18.2 ± 5.4 | 15.6 ± 5.6 |
| | 25G-BD | 22.2 ± 1.6 | 23.0 ± 1.5 | 22.3 ± 1.6 |
| | 23G-BD | 22.6 ± 1.6 | 23.3 ± 1.5 | 19.8 ± 4.1 |

TABLE 72

Bleb height over time after injection of GGL and GGL + EDP - caliper measurements (Mean ± SEM)

| | | Height (mm ± SEM) | | |
| --- | --- | --- | --- | --- |
| Test Solution | Needle Gauge | T0 | T15 | T30 |
| GGL | 25G-Terumo | 6.6 ± 1.0 | 4.3 ± 1.1 | 3.0 ± 0.8 |
| GGL + EDP | 25G-Terumo | 5.8 ± 1.0 | 1.8 ± 0.5 | 1.3 ± 0.5 |
| | 25G-BD | 4.5 ± 0.9 | 2.7 ± 0.6 | 2.3 ± 0.8 |
| | 23G-BD | 4.6 ± 0.6 | 1.8 ± 0.4 | 1.1 ± 0.4 |

Figure 91:
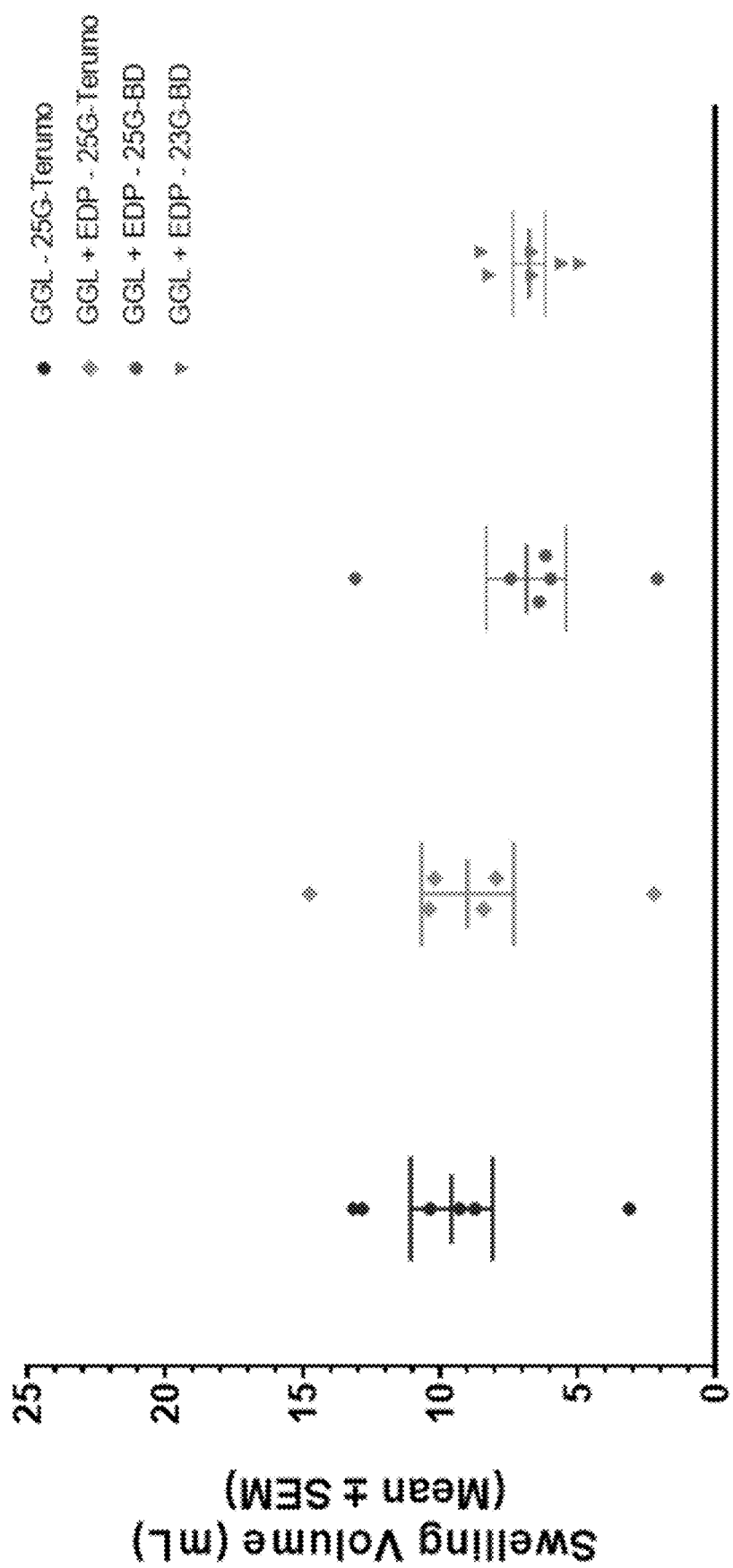
FIG. 91 is a graph of individual swelling volumes (mL) after SC injection of GGL & GGL+EDP—caliper measurement (TO).
Figure 92:
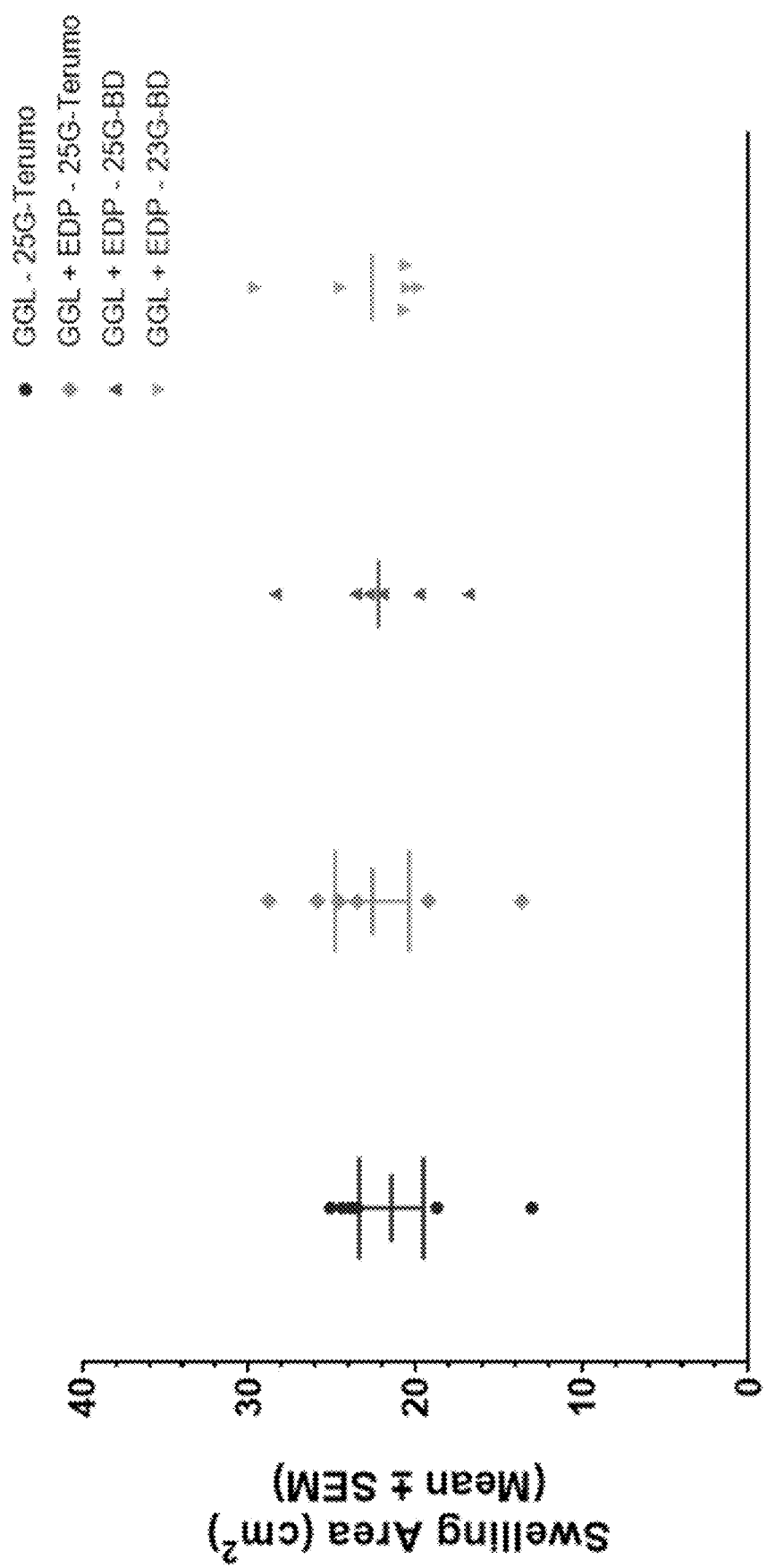
FIG. 92 is a graph of individual swelling areas (cm$^2$) after SC injection of GGL and GGL+EDP—caliper measurement (TO).
Figure 93:
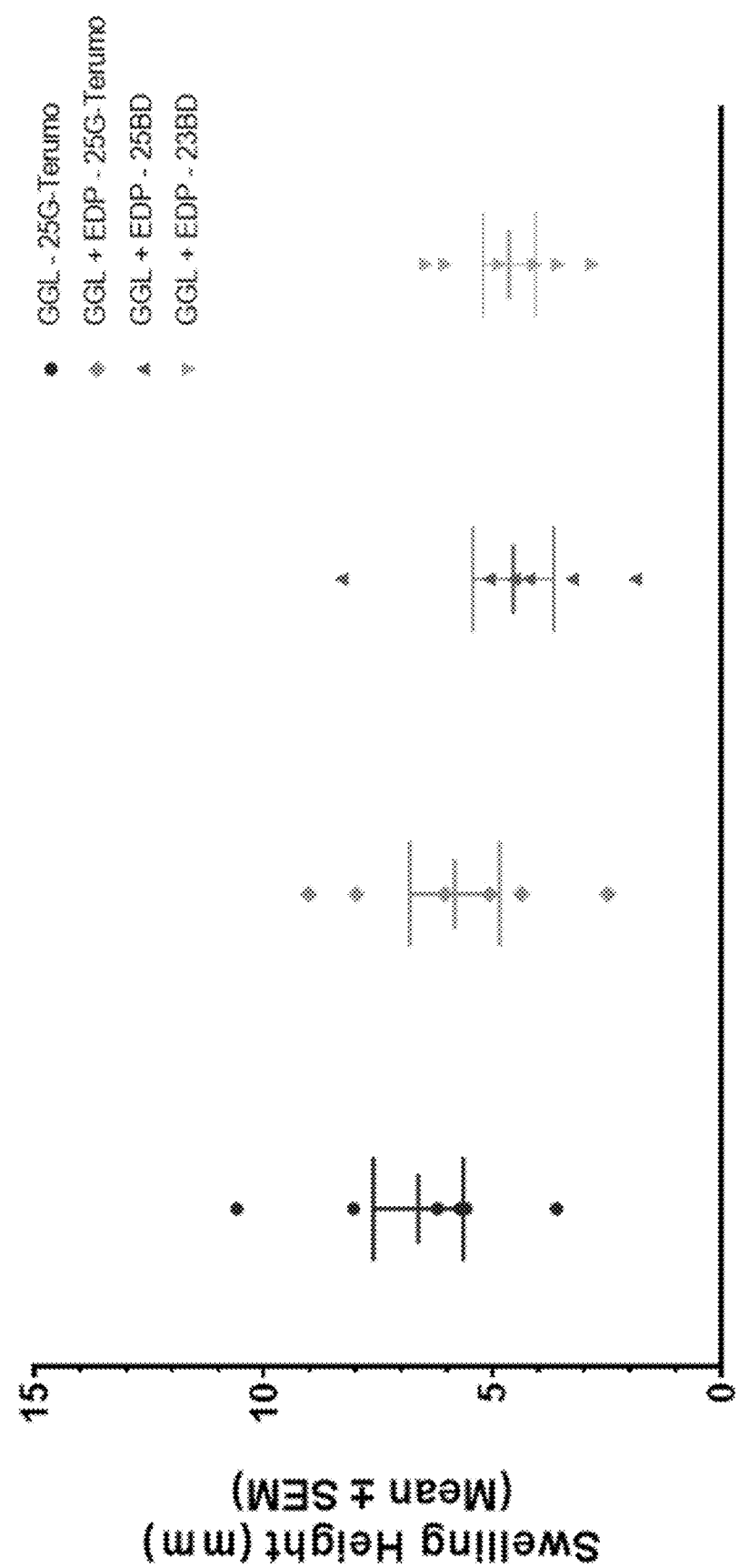
FIG. 93 is a graph of individual swelling heights (mm) after SC injection of GGL and GGL+EDP—caliper measurement (TO).
Figure 94:
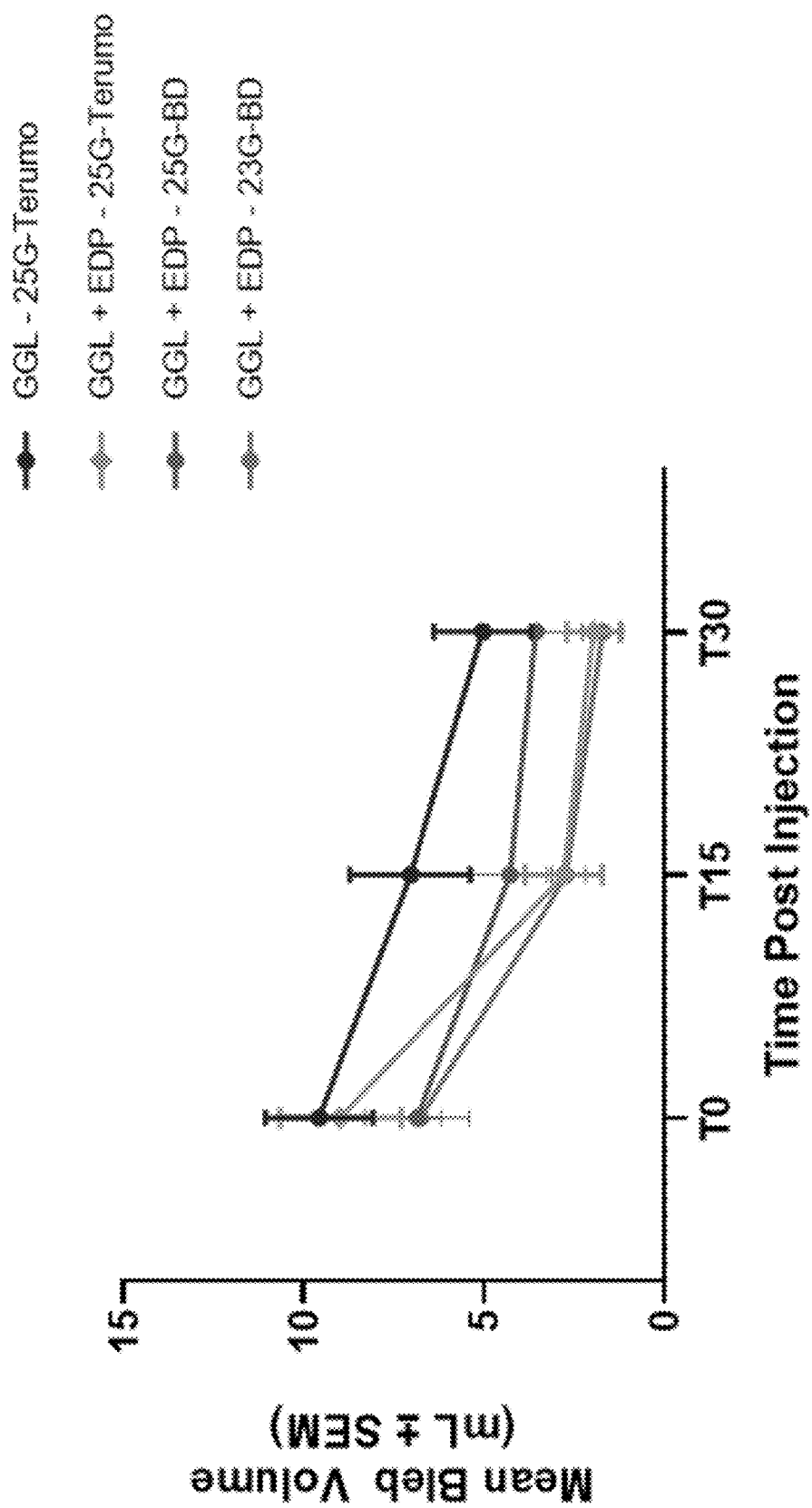
FIG. 94 is a graph of mean bleb volume over time (T0-T15-T30)—caliper measurement.
Figure 95:
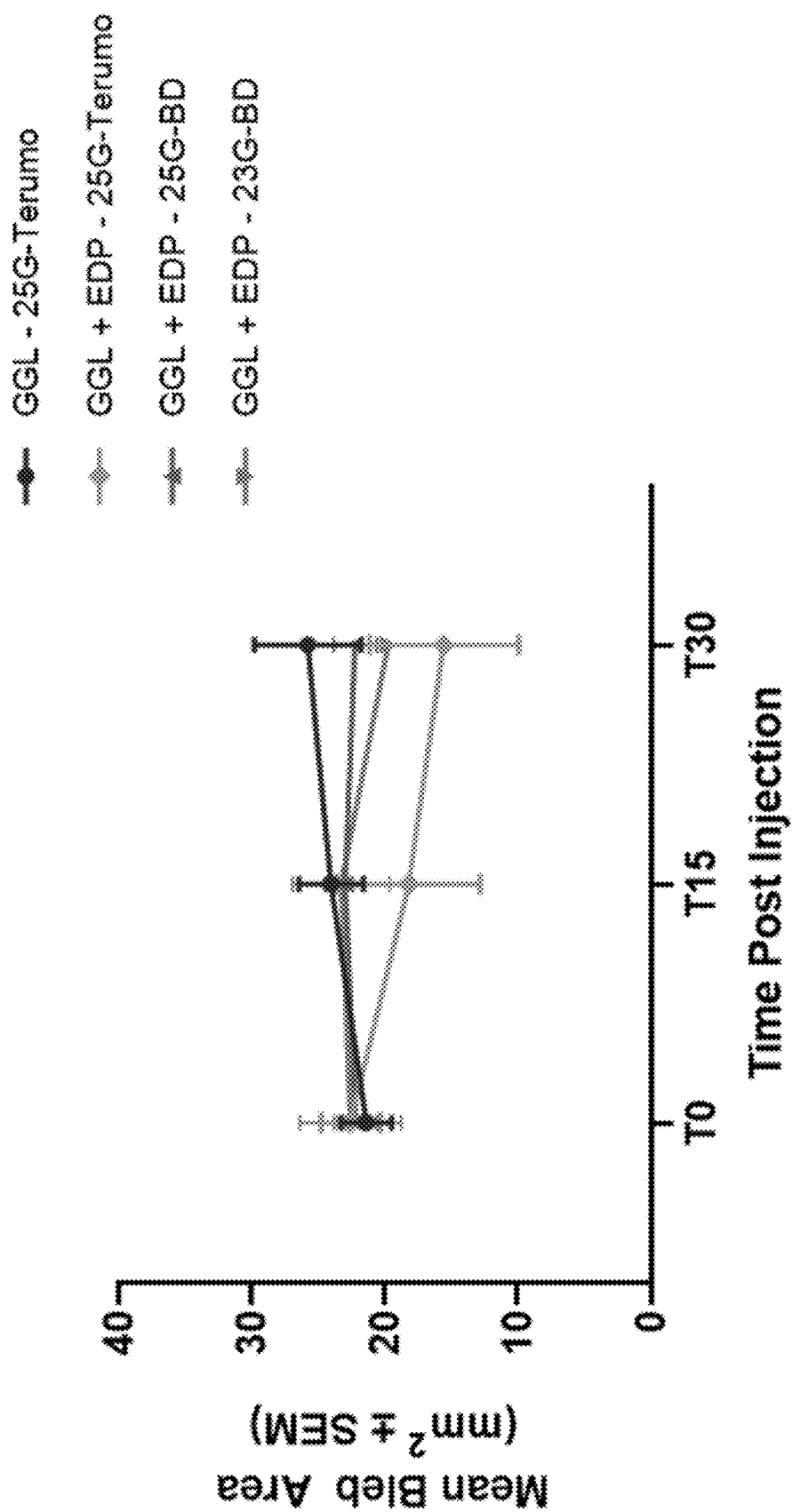
FIG. 95 is a graph of mean bleb volume over time (T0-T15-T30)—caliper measurement.
Figure 96:
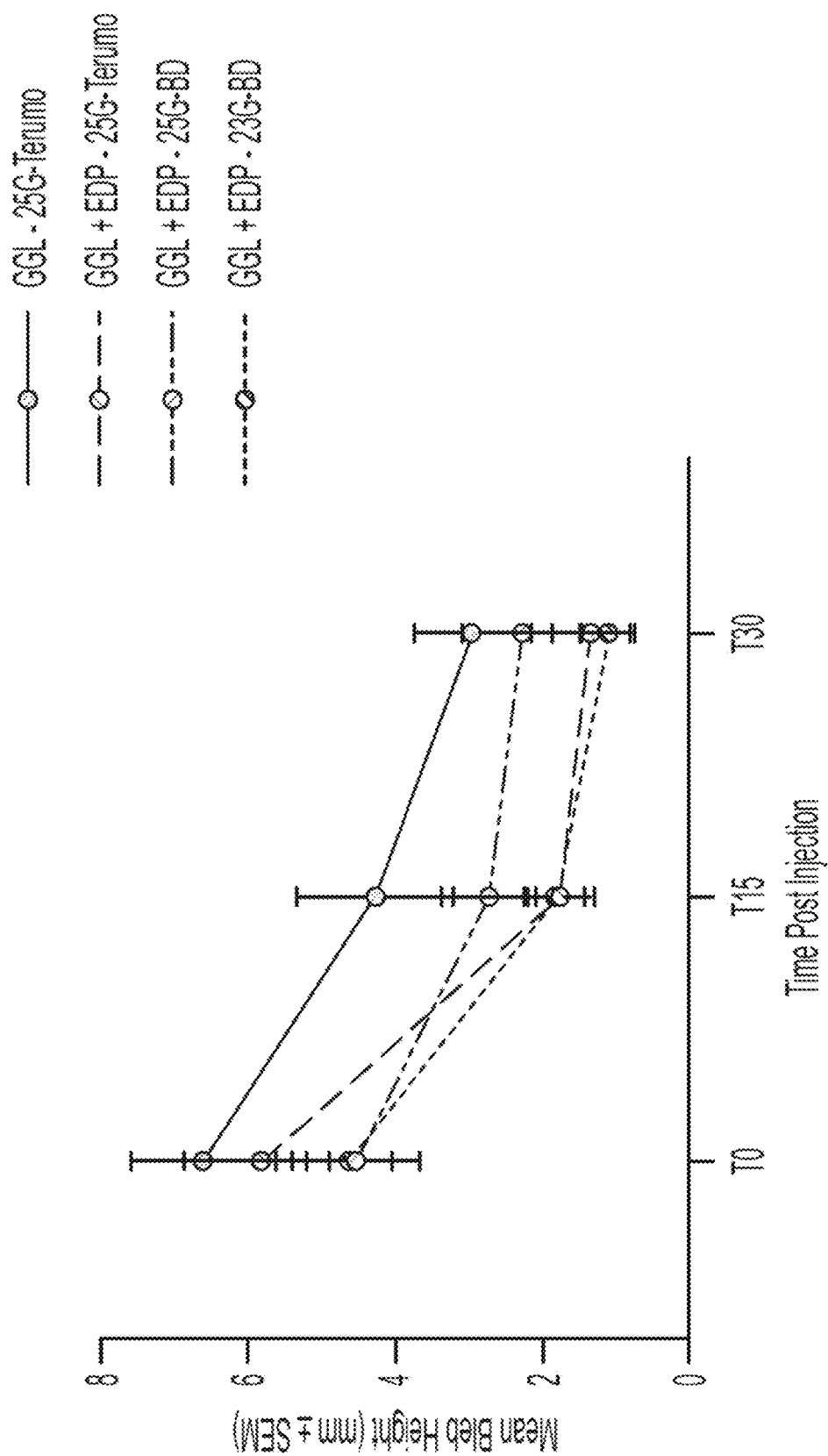
FIG. 96 is a graph of mean bleb area over time (T0-T15-T30)—caliper measurement.
Figure 97:
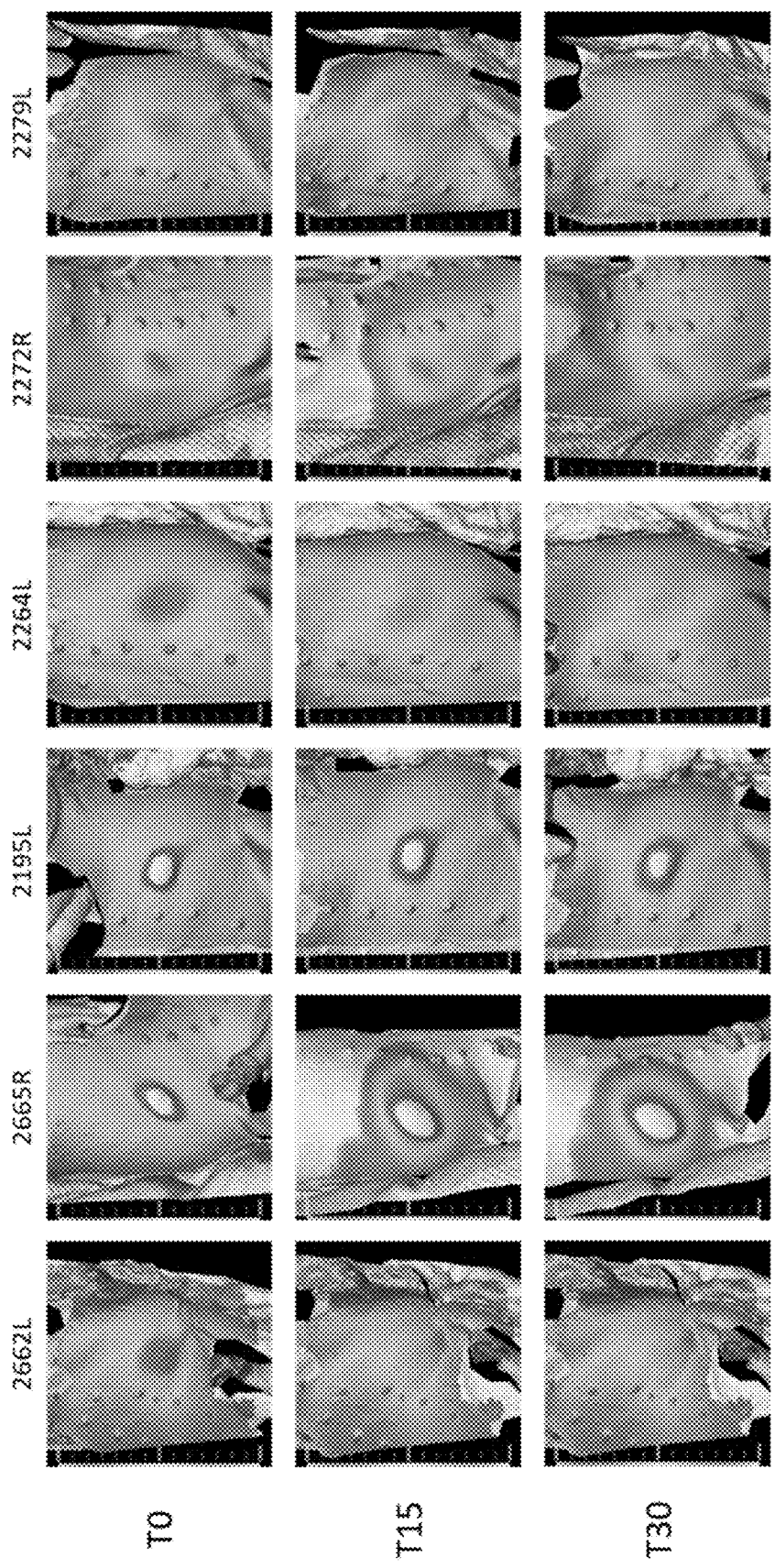
FIG. 97 provides a composite of 3D Images (T0-T15-T30) of GGL—25 G-Terumo.
Figure 98:
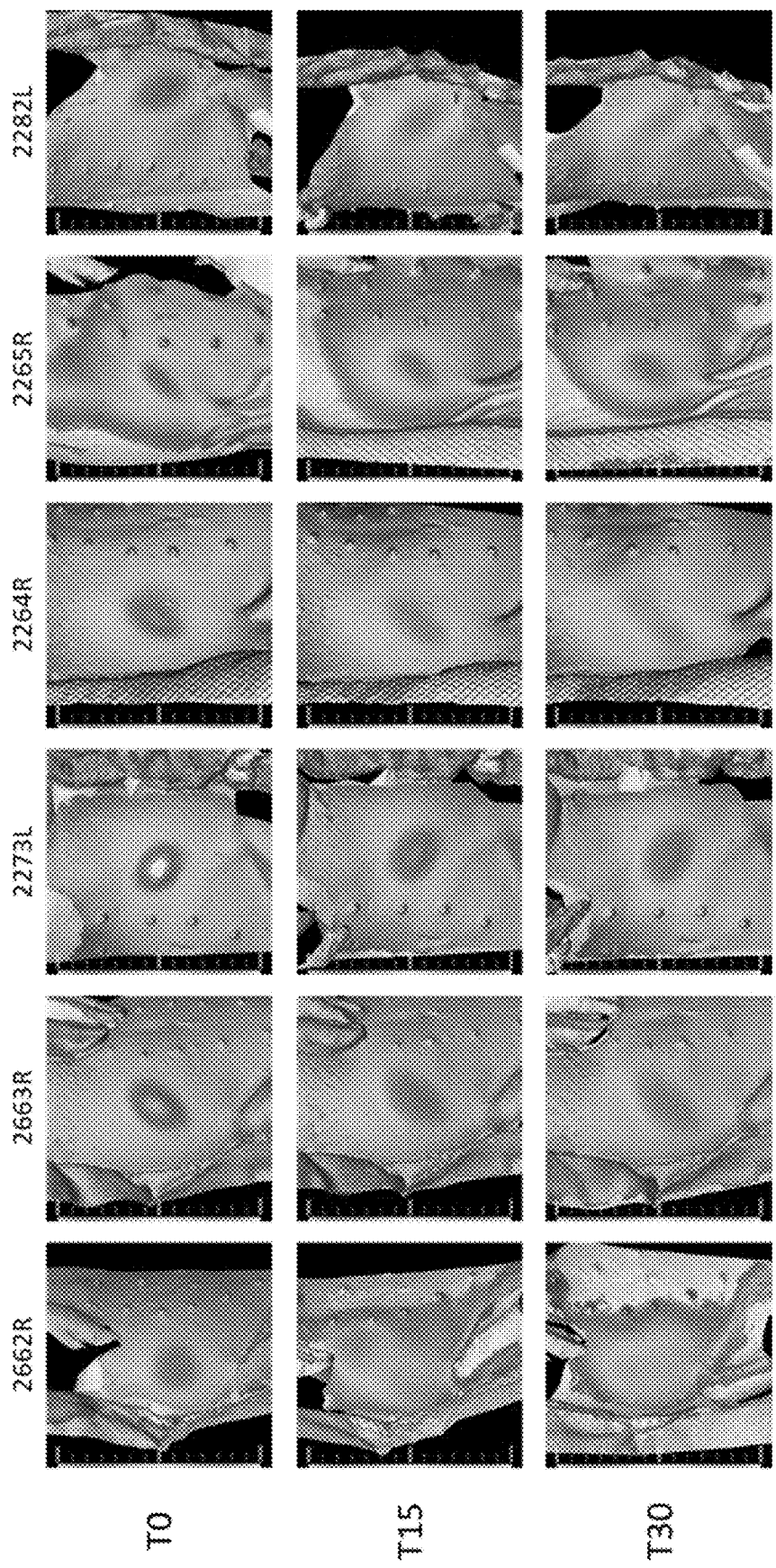
FIG. 98 provides a composite of 3D Images (T0-T15-T30) of GGL+EDP—25 G-Terumo.
Figure 99:
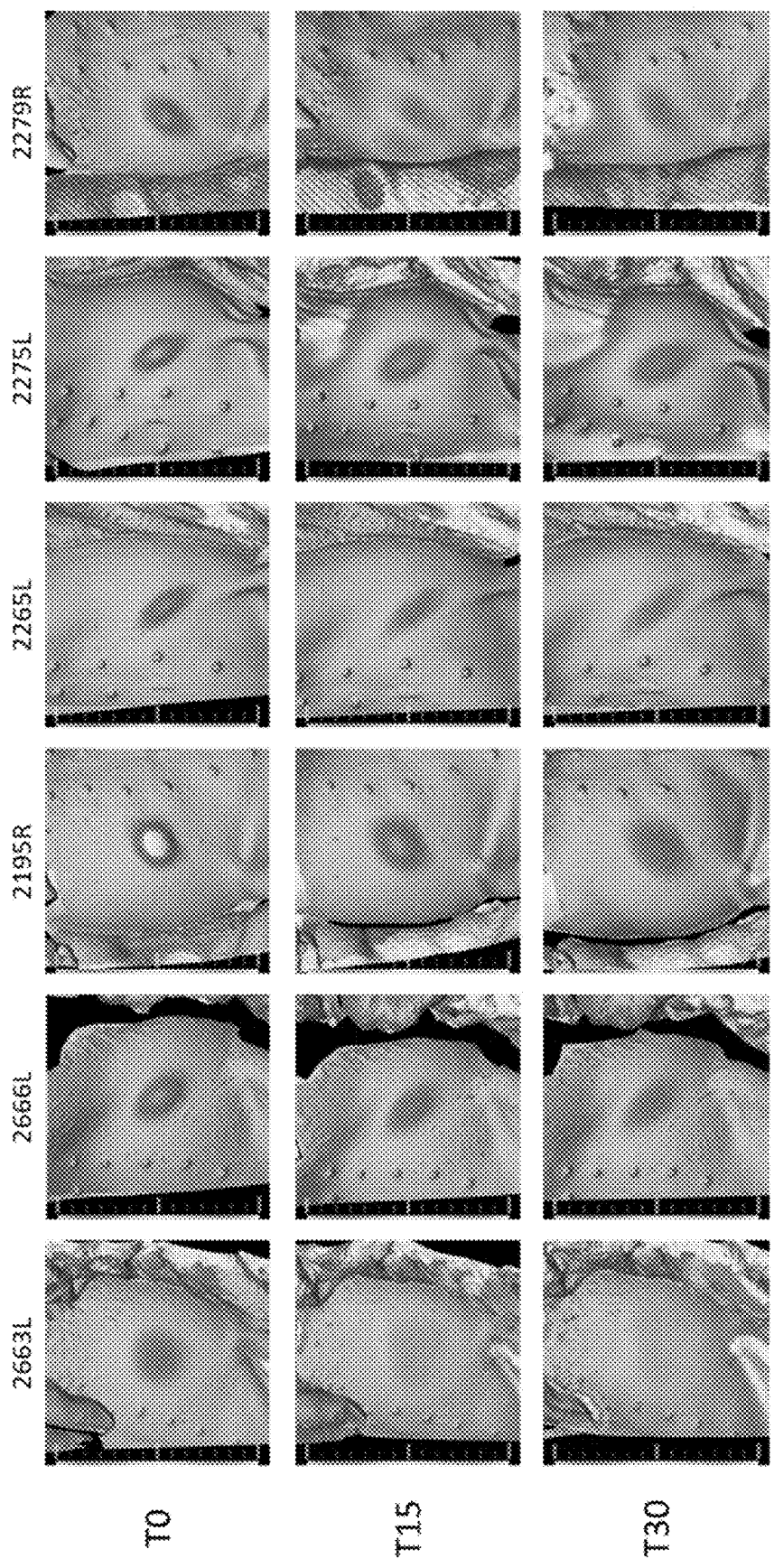
FIG. 99 provides a composite of 3D images (T0-T15-T30) of GGL+EDP—25 G-BD.
Figure 100:
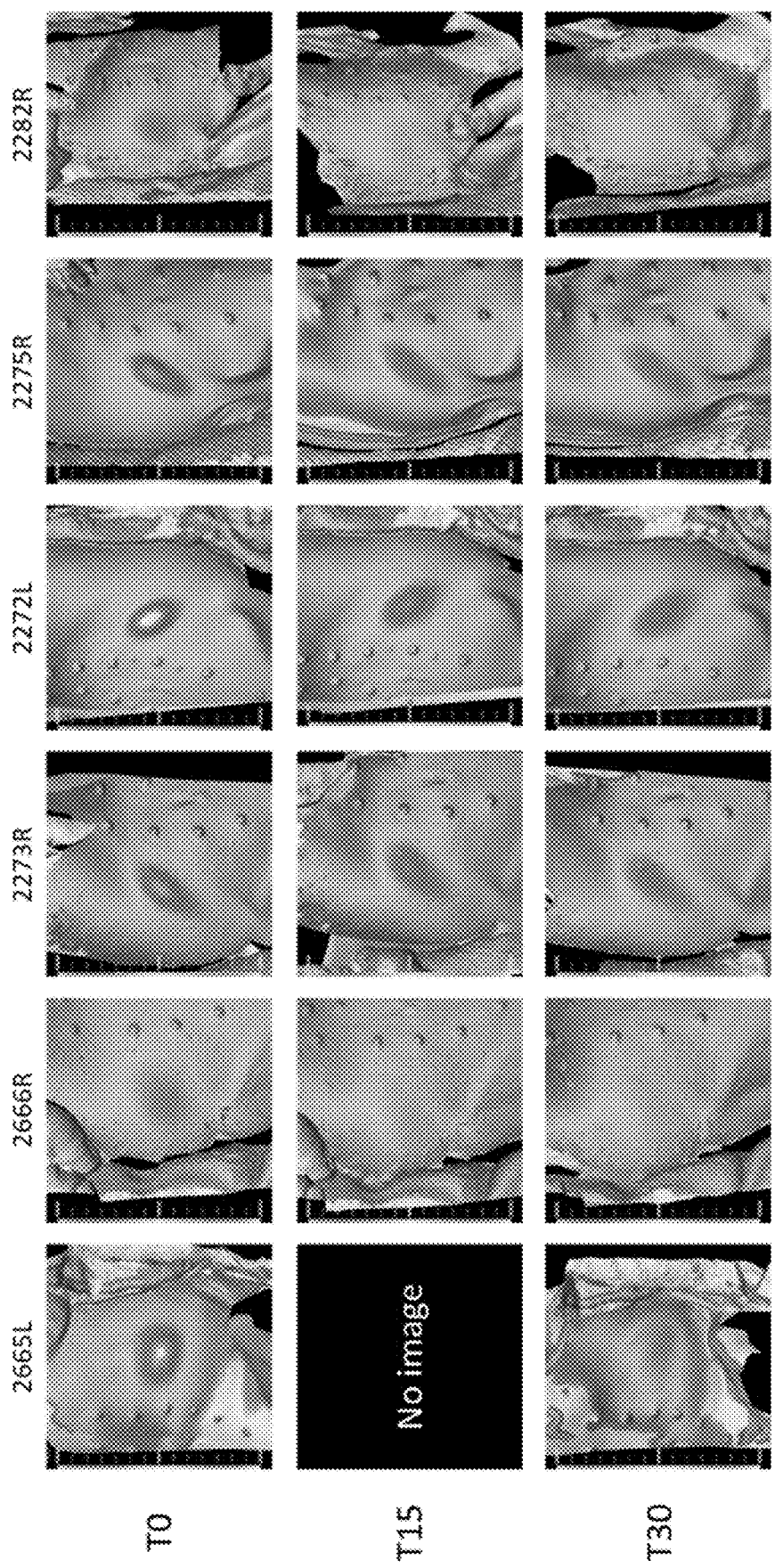
FIG. 100 provides a composite of 3D images (T0-T15-T30) of GGL+EDP—23 G-BD.

Individual post-injection bleb volume, area, and height at time T0 are shown in FIG. 91, FIG. 92, and FIG. 93, respectively. Mean bleb volume, area, and height (mean±SEM) over time (T0-T15-T30) are shown in FIGS. 94-96.

Assessment of post-injection bleb volume, area, and height (3D imaging). Pre- and post-injection photographs were taken using a 3D imaging system. This technology permits point-to-point alignment of these two images through multipoint surface registration. The distance between any two points is then represented using a colorimetric surface contour map. Regions where there is no difference between the two images are displayed in gray. Where the post-injection image is higher than the pre-injection image, the region is displayed in shades of blue. Where the post-injection image is lower than the pre-injection image the distance is displayed in shades of orange. The color intensity is proportional to the amount of distance measured between images and the range that is set for positive and negative measurements. Out of range measurements are depicted in white. Bleb measurements of volume and height include regions out of range.

Each animal had a pre-injection 3D image taken of the injection site followed by a second image taken immediately post-injection and these images were mapped to each other using multipoint registration. These registered pre-/post-injection images were then used to calculate the bleb volume, height, circumference, length, and width for each bleb using proprietary software. Colorimetric surface contour maps of each post-injection bleb for GGL using the 25 G-Terumo needle as well as GGL+EDP using the 25 G-Terumo, 25 G-BD and 23 G-BD needles at T0, T15 & T30 are shown in FIG. 97, FIG. 98, FIG. 99, and FIG. 100, respectively. Injections including rHuPH20 showed greater resolution by the 15 minute timepoint compared to injections without rHuPH20. Injections without rHuPH20 remained relatively static at the 15 minute timepoint, showing some resolution at 30 minutes.

Post-injection bleb volume, area, and height for GGL and GGL+EDP using the various needle configurations was calculated from the 3D images and is summarized in Table 73, Table 74, and Table 75 at time T0, T15, and T30.

TABLE 73

Bleb volume over time after injection of GGL + EDP measured using 3D imaging (Mean ± SEM)

| | | Volume (mL ± SEM) | | |
|---|---|---|---|---|
| | | T0 | T15 | T30 |
| GGL | 25G-Terumo | 4.9 ± 0.9 | 5.4 ± 2.1 | 5.1 ± 2.2 |
| GGL + EDP | 25G-Terumo | 5.6 ± 0.5 | 4.3 ± 0.7 | 3.6 ± 0.9 |
| | 25G-BD | 5.8 ± 0.4 | 5.4 ± 0.7 | 5.4 ± 0.6 |
| | 23G-BD | 5.9 ± 0.6 | 4.4 ± 1.0 | 4.0 ± 0.9 |

TABLE 74

Bleb area over time after injection of GGL + EDP measured using 3D imaging (Mean ± SEM)

| | | Area (cm$^2$ ± SEM) | | |
|---|---|---|---|---|
| | | T0 | T15 | T30 |
| GGL | 25G-Terumo | 23.6 ± 3.5 | 30.3 ± 4.9 | 29.0 ± 7.2 |
| GGL + EDP | 25G-Terumo | 26.8 ± 2.0 | 28.4 ± 1.7 | 24.1 ± 5.2 |
| | 25G-BD | 26.9 ± 1.8 | 31.7 ± 4.0 | 34.4 ± 2.8 |
| | 23G-BD | 28.3 ± 1.4 | 29.0 ± 2.4 | 27.9 ± 2.8 |

TABLE 75

Bleb height over time after injection of GGL + EDP measured using 3D imaging (Mean ± SEM)

| | | Height (mm ± SEM) | | |
|---|---|---|---|---|
| | | T0 | T15 | T30 |
| GGL | 25G-Terumo | 5.3 ± 1.0 | 4.4 ± 1.5 | 3.9 ± 1.5 |
| GGL + EDP | 25G-Terumo | 5.0 ± 0.4 | 3.5 ± 0.5 | 2.7 ± 0.7 |
| | 25G-BD | 5.7 ± 0.5 | 4.4 ± 0.5 | 3.8 ± 0.5 |
| | 23G-BD | 5.2 ± 0.6 | 3.5 ± 0.8 | 3.0 ± 0.6 |

Figure 101:
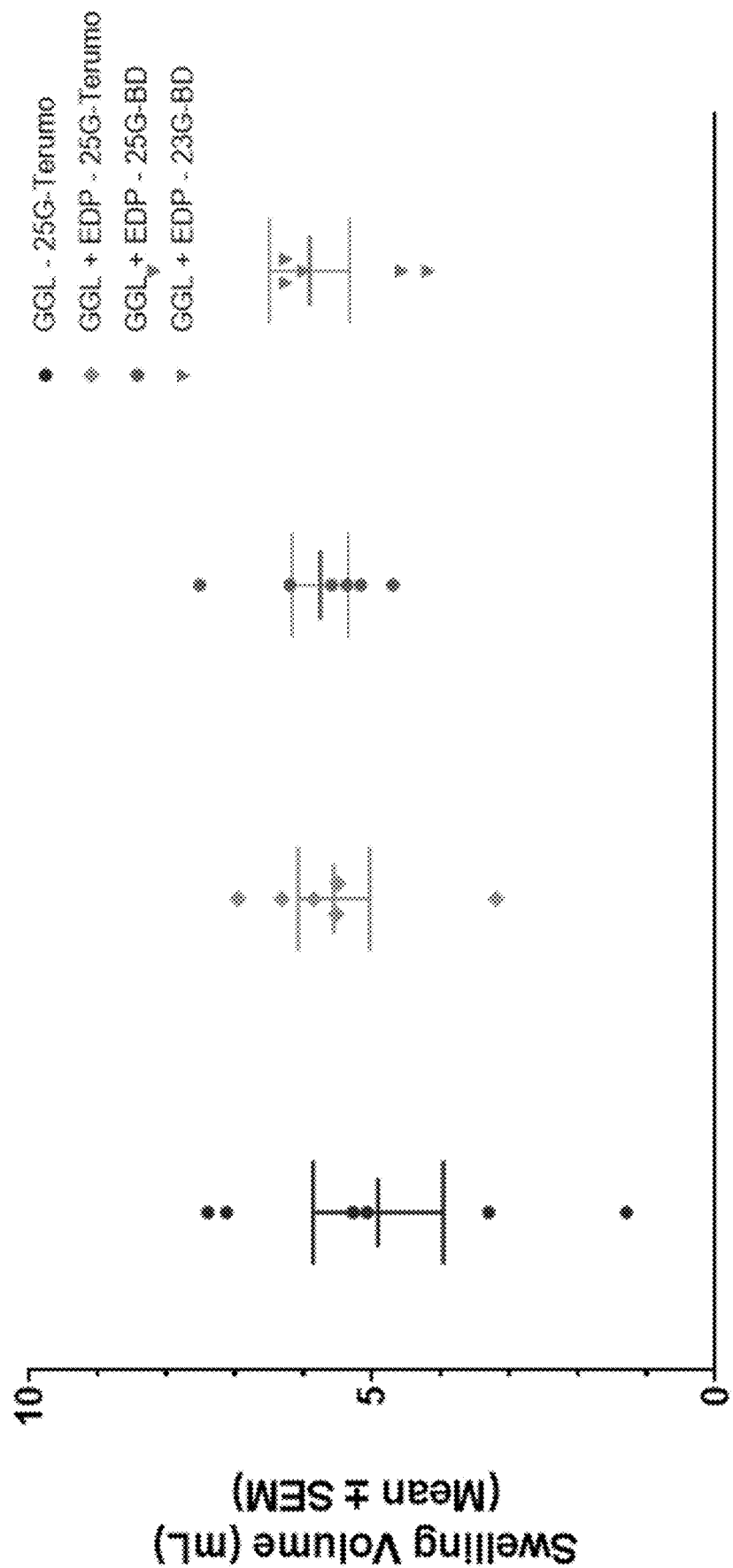
FIG. 101 is a graph of individual bleb volumes ($cm^3$) after SC injection of GGL and GGL+EDP—3D imaging.
Figure 102:
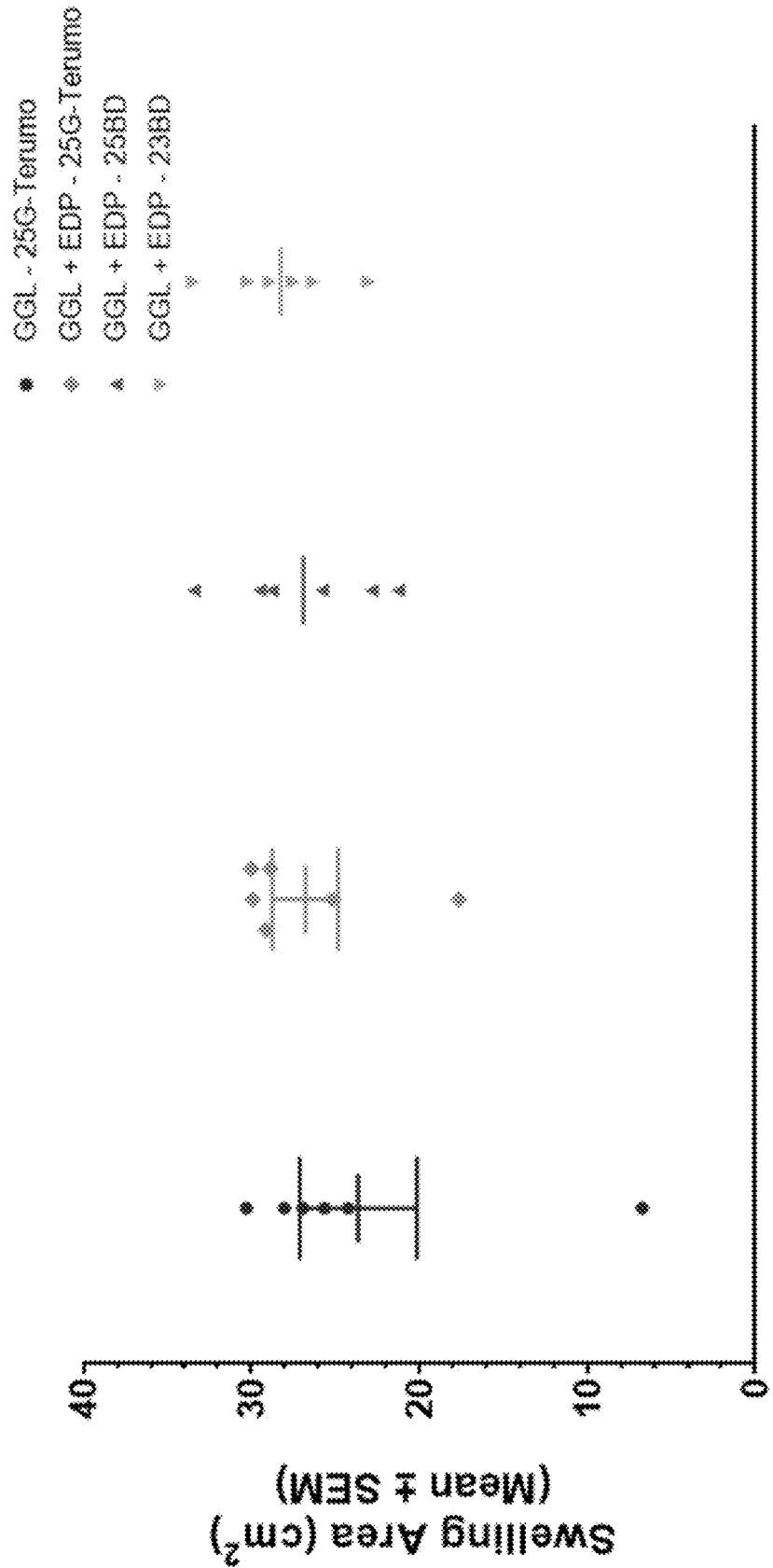
FIG. 102 is a graph of individual bleb areas ($cm^2$) after SC injection of GGL and GGL+EDP-3D imaging.
Figure 103:
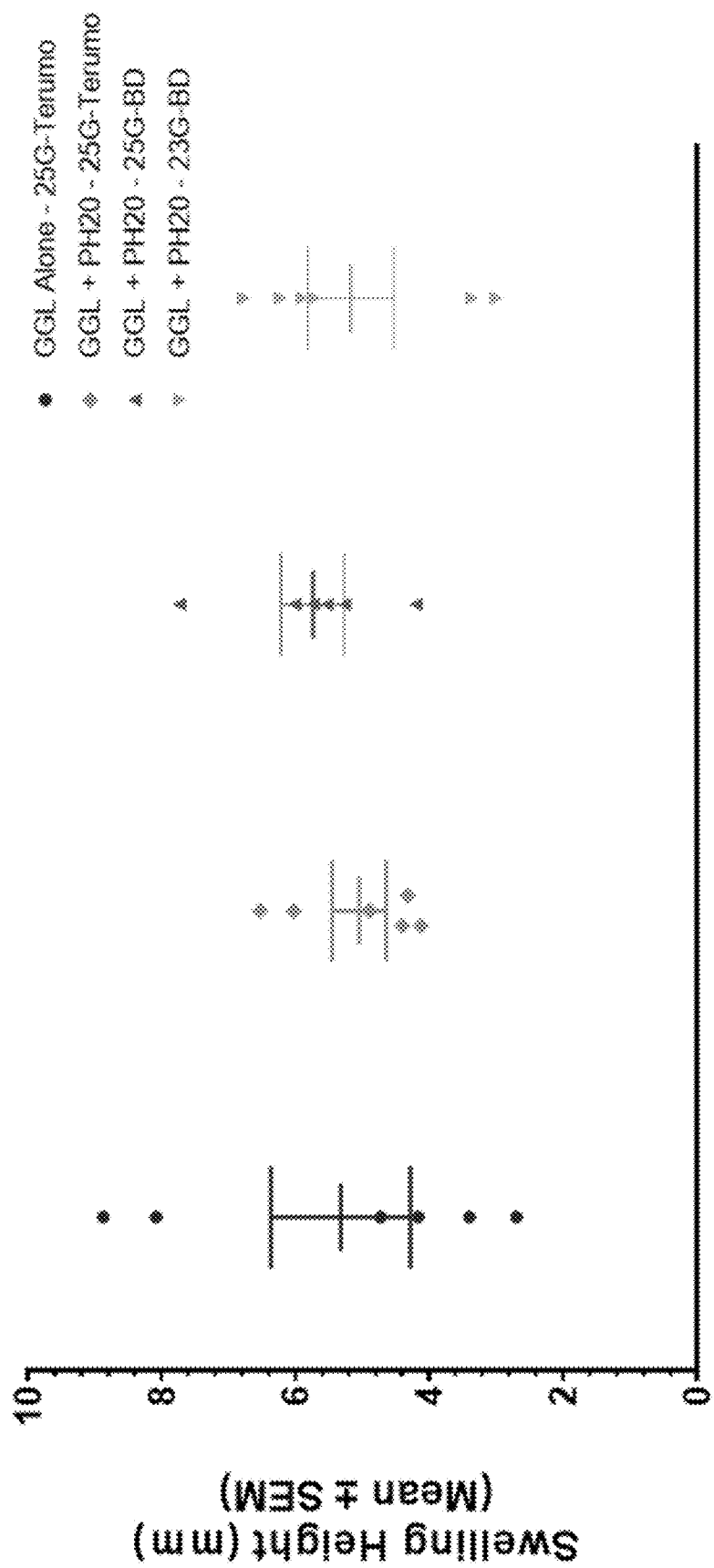
FIG. 103 is a graph of individual bleb heights (mm) after SC injection of GGL and GGL+EDP-3D imaging.
Figure 104:
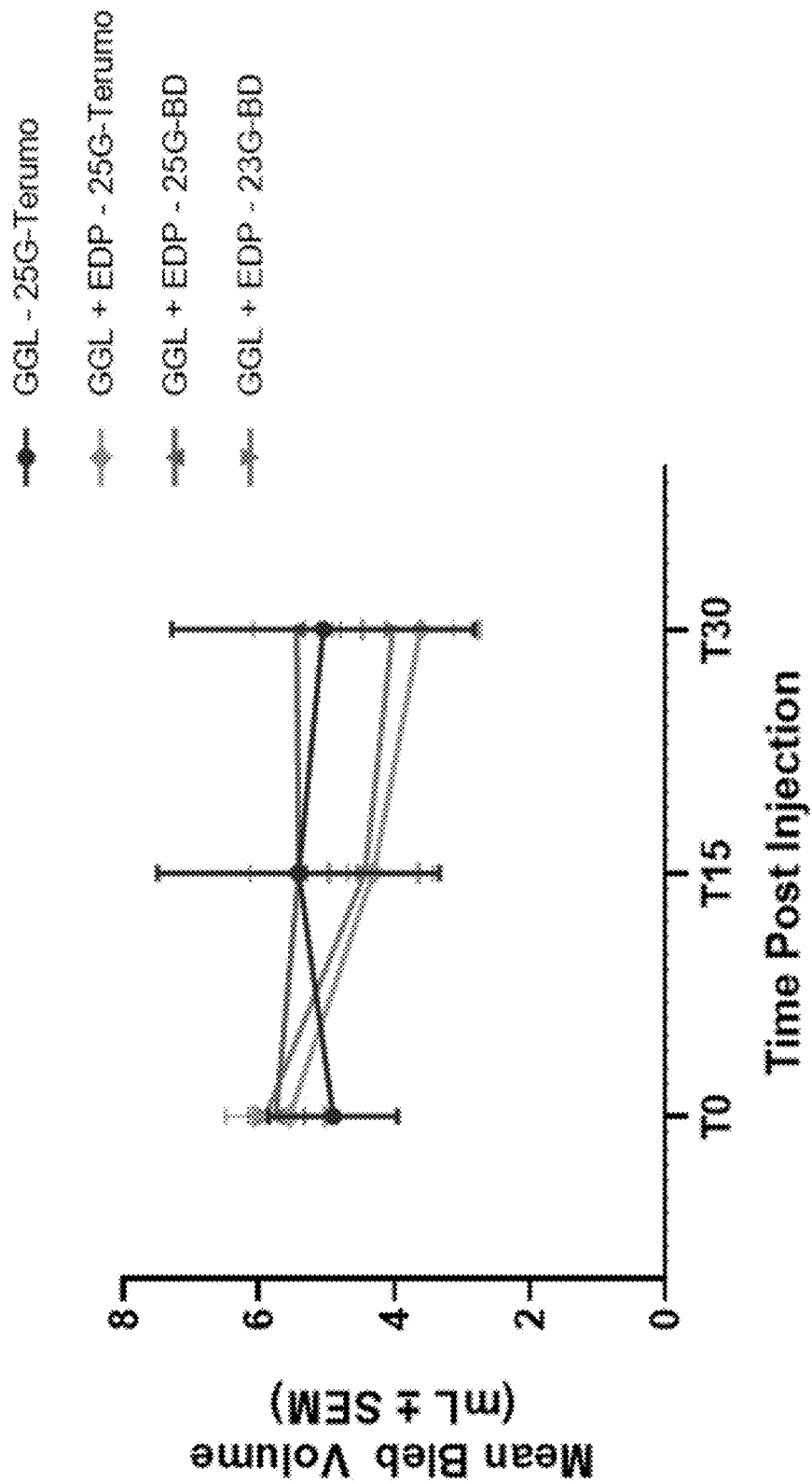
FIG. 104 is a graph of mean bleb volume over time (T0-T15-T30)—3D imaging.
Figure 105:
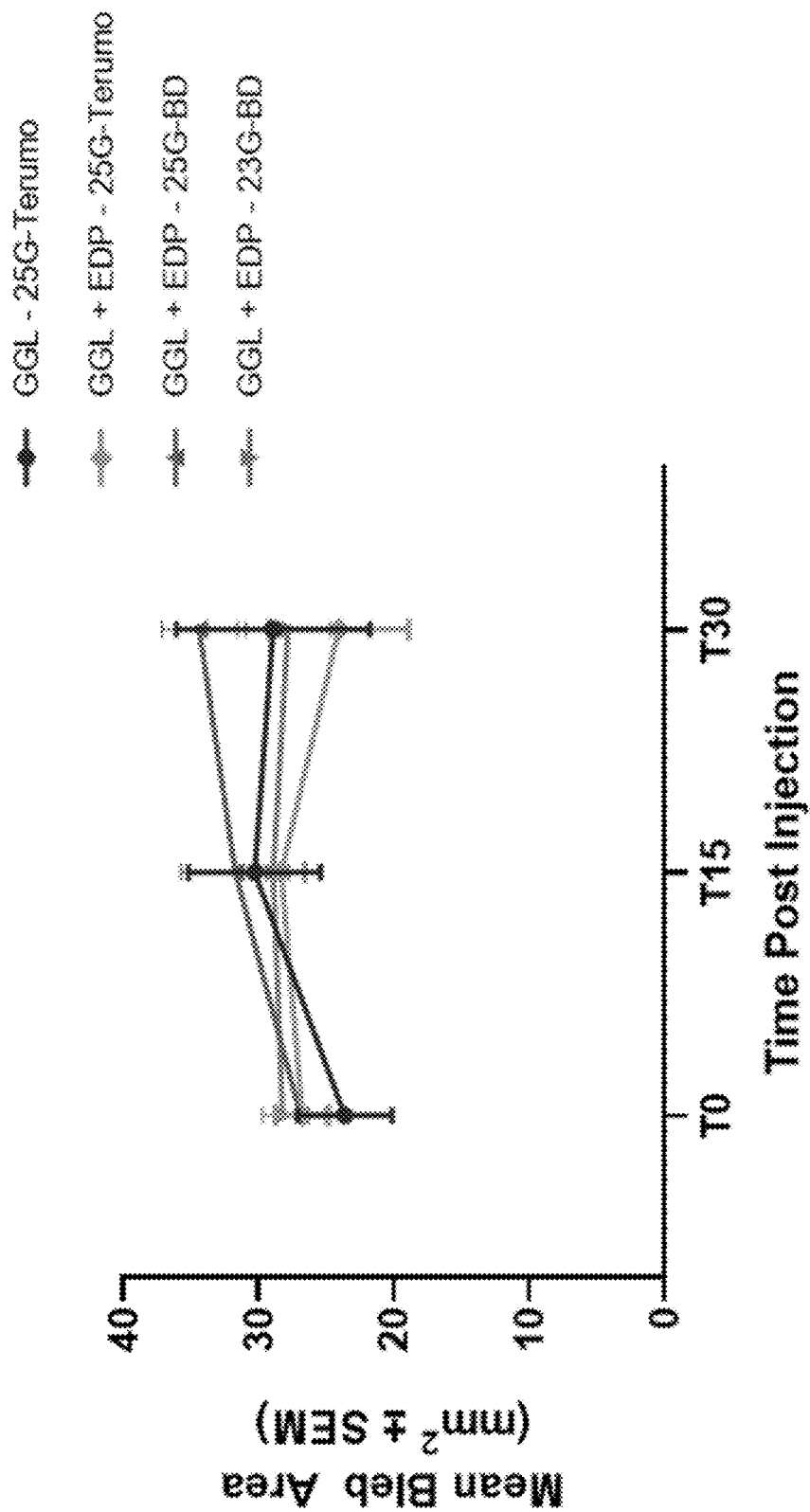
FIG. 105 is a graph of mean bleb area over time (T0-T15-T30)—3D imaging.
Figure 106:
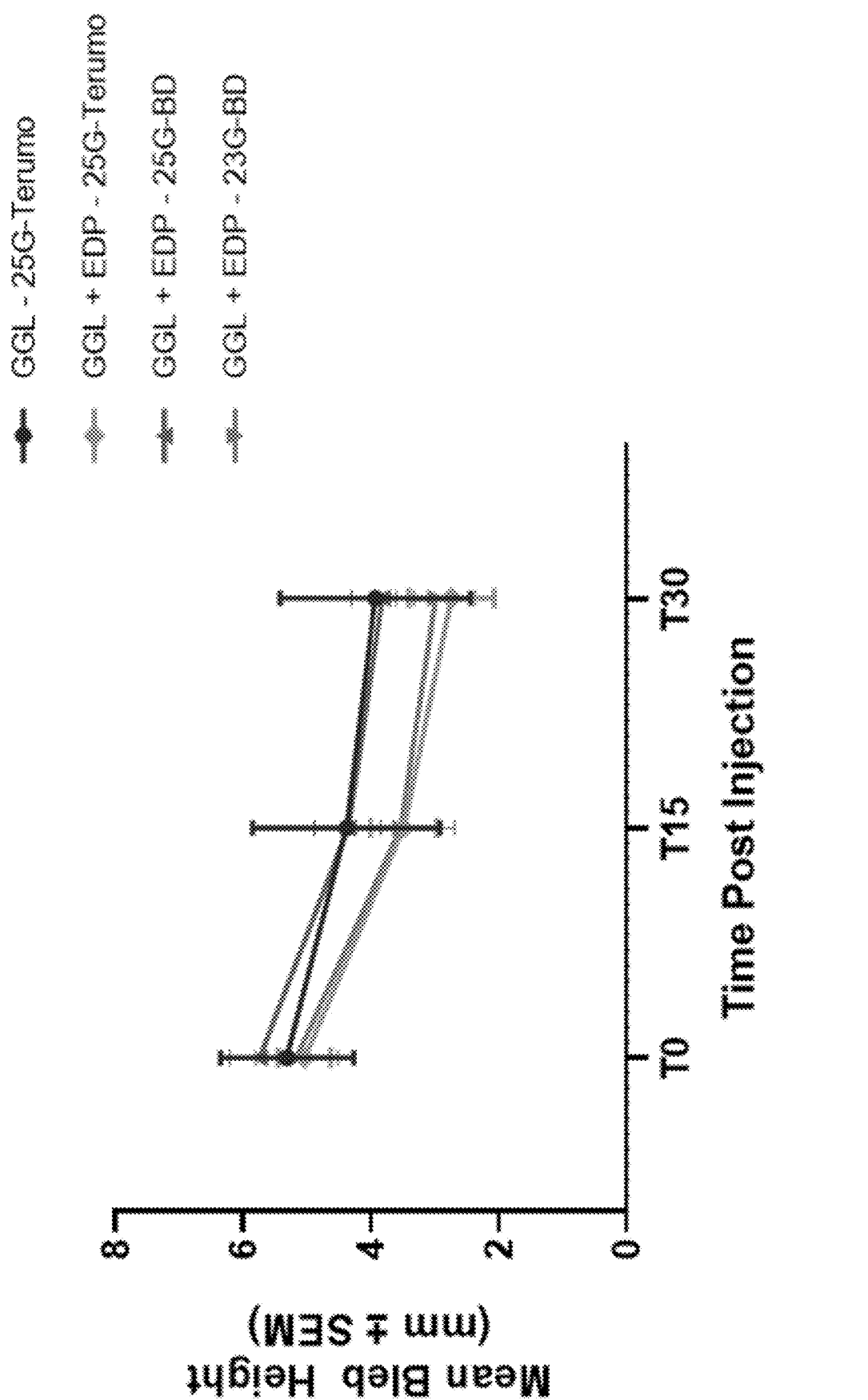
FIG. 106 is a graph of mean bleb height over time (T0-T15-T30)—3D imaging.

Individual post-injection bleb volume, area, and height at time T0 are shown graphically in FIG. 101, FIG. 102, and FIG. 103, respectively. Mean bleb volume, area, and height over time (T0-T15-T30) are shown in FIG. 104, FIG. 105, and FIG. 106.

Qualitative Assessment of Local Injection Sites

Following the completion of the 10 mL injections the qualitative assessments for erythema, swelling size, and firmness by the three different scorers was performed as described above.

Figure 107:
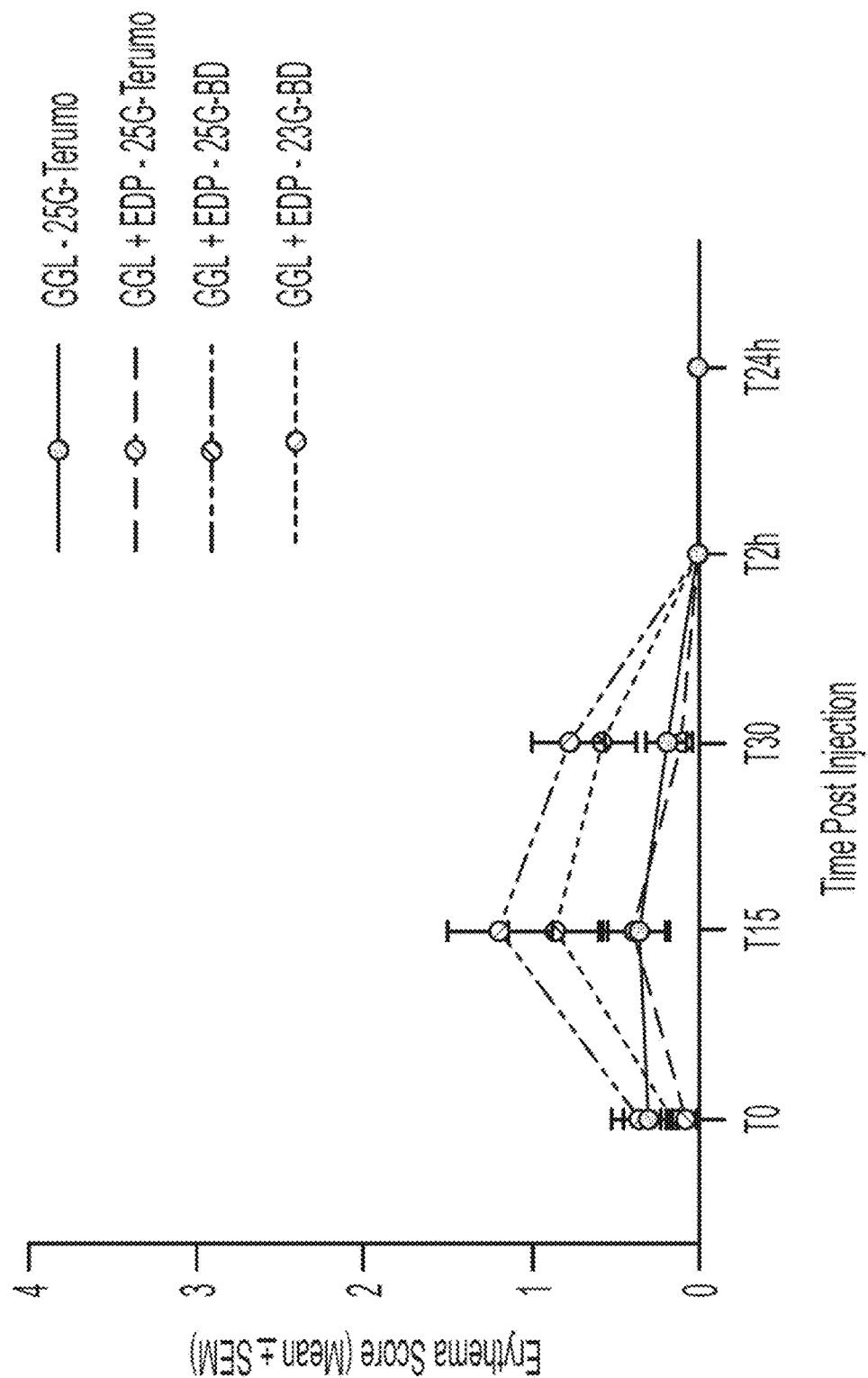
FIG. 107 is a graph of the qualitative assessment of post-injection erythema.

Qualitative assessment of post-injection erythema: Erythema was minor for both test solutions. Erythema for both test solutions was mild and transient. The scoring by the three evaluators for erythema (Mean±SEM) for each test solution are summarized in Table 76 and shown in FIG. 107.

TABLE 76

Erythema scores post-injection for GGL and GGL + EDP (Mean ± SEM)

| Test Solution | Needle | Timepoint Post-Injection | | | | |
|---|---|---|---|---|---|---|
| | | T0 | T15 | T30 | T2 h | T24 h |
| GGL | 25G-Terumo | 0.3 ± 0.1 | 0.4 ± 0.2 | 0.2 ± 0.1 | 0.0 ± 0.0 | 0.0 ± 0.0 |
| GGL + EDP | 25G-Terumo | 0.1 ± 0.1 | 0.4 ± 0.2 | 0.1 ± 0.1 | 0.0 ± 0.0 | 0.0 ± 0.0 |
| | 25G-BD | 0.4 ± 0.2 | 1.2 ± 0.3 | 0.8 ± 0.2 | 0.0 ± 0.0 | 0.0 ± 0.0 |
| | 23G-BD | 0.2 ± 0.1 | 0.9 ± 0.3 | 0.6 ± 0.2 | 0.0 ± 0.0 | 0.0 ± 0.0 |

Figure 108:
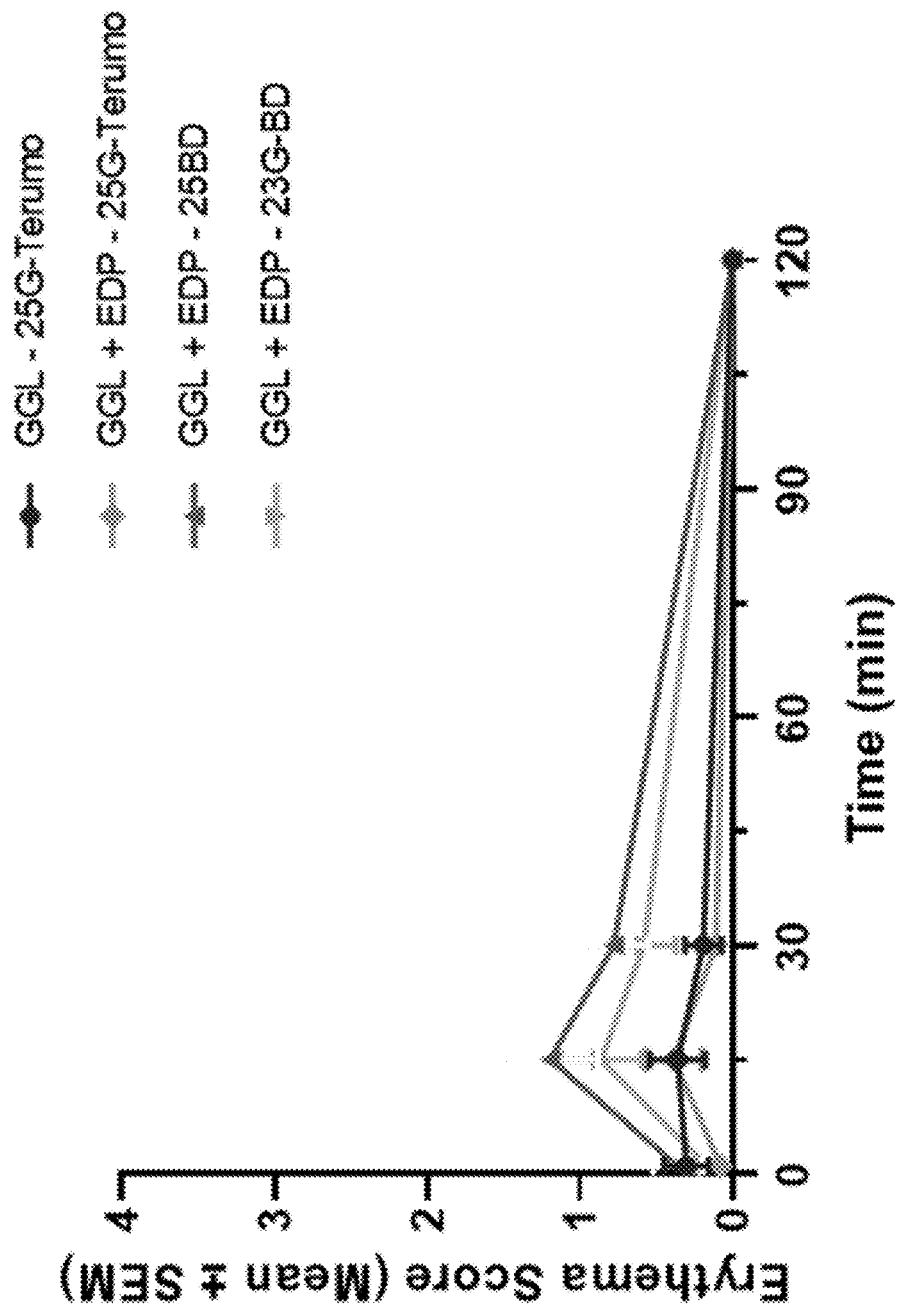
FIG. 108 is a graph of the qualitative assessment of post-injection erythema (0-120 min).

By T24 h all post-injection erythema was resolved. Therefore, a plot of the erythema scores over the first two hours using a linear timescale is shown in FIG. 108.

Figure 109:
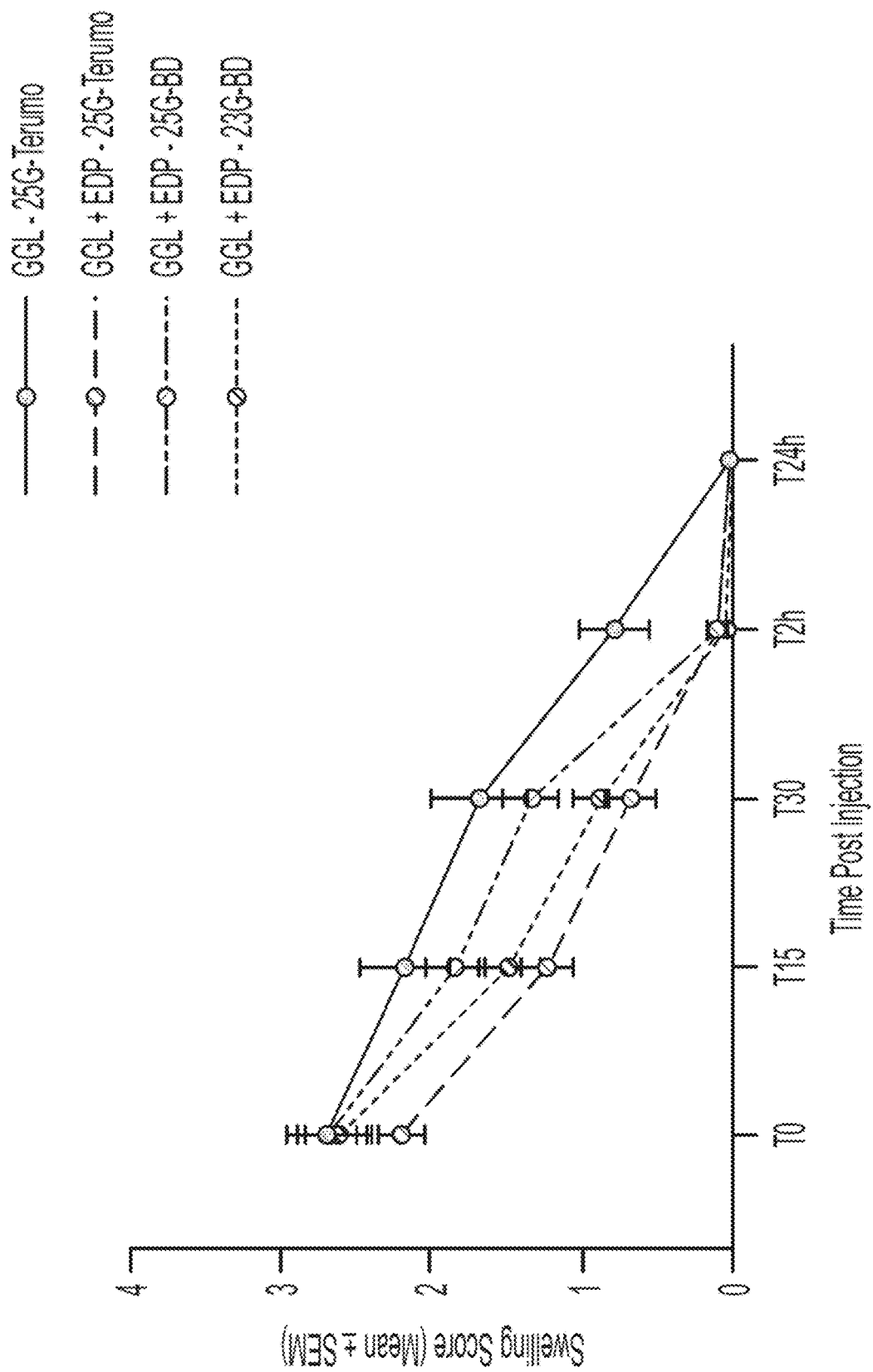
FIG. 109 is a graph of the qualitative assessment of post-injection swelling size.

Qualitative assessment of post-injection swelling size: Post injection swelling size was mild to moderate for all injections with rapid swelling resolution over time for injections containing rHuPH20. Scoring by the three evaluators for swelling size (Mean±SEM) for each test solution over time are summarized in Table 77 and shown in FIG. 109.

TABLE 77

Swelling scores post-injection for GGL and GGL + EDP (Mean ± SEM)

| Test Solution | Needle | Timepoint Post-Injection | | | | |
|---|---|---|---|---|---|---|
| | | T0 | T15 | T30 | T2 h | T24 h |
| GGL | 25G-Terumo | 2.7 ± 0.3 | 2.2 ± 0.3 | 1.7 ± 0.3 | 0.8 ± 0.2 | 0.0 ± 0.0 |
| GGL + EDP | 25G-Terumo | 2.2 ± 0.2 | 1.2 ± 0.2 | 0.7 ± 0.2 | 0.1 ± 0.1 | 0.0 ± 0.0 |
| | 25G-BD | 2.7 ± 0.2 | 1.8 ± 0.2 | 1.3 ± 0.2 | 0.1 ± 0.1 | 0.0 ± 0.0 |
| | 23G-BD | 2.6 ± 0.2 | 1.5 ± 0.2 | 0.9 ± 0.2 | 0.0 ± 0.0 | 0.0 ± 0.0 |

Figure 110:
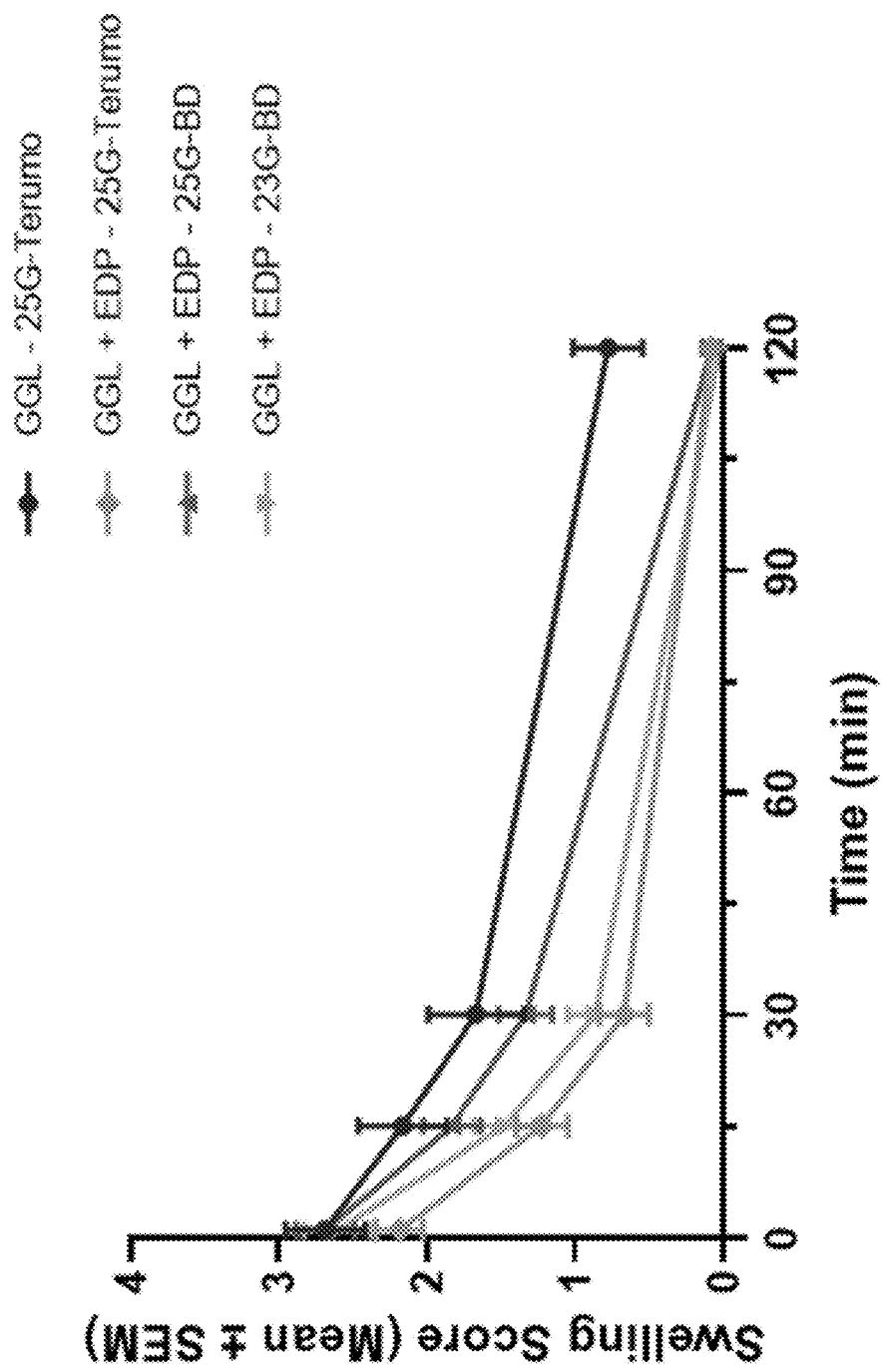
FIG. 110 is a graph of the qualitative scoring of post-injection swelling (0-120 min).

By T2 h post-injection swelling was resolved for all groups except GGL alone. Therefore, a plot of the swelling scores over the first two hours using a linear timescale is shown in FIG. 110.

Qualitative assessment of post-injection firmness (induration): The hardness (induration) of the post-injection blebs were also evaluated by the independent scorers. The induration of the post-injection blebs for injections containing rHuPH20 was slight to mild immediately after injection. The induration of the post-injection blebs for injections without rHuPH20 was mild to moderate immediately after injection. Over time the induration of control injections persisted to 30 minutes (T30) and beyond while the induration for injections containing rHuPH20 decreased rapidly over time and was barely perceptible by 30 minutes post-injection. The scoring for induration (Mean±SEM) for each test solution over time are summarized in Table 78 and shown in FIG. 108.

TABLE 78

Induration scores post-injection for GGL and GGL + EDP (Mean ± SEM)

| Test Solution | Needle | T0 | T15 | T30 | T2 h | T24 h |
|---|---|---|---|---|---|---|
| GGL | 25G-Terumo | 2.3 ± 0.3 | 1.8 ± 0.3 | 1.3 ± 0.3 | 0.6 ± 0.2 | 0.0 ± 0.0 |
| GGL + EDP | 25G-Terumo | 1.5 ± 0.1 | 0.9 ± 0.1 | 0.3 ± 0.1 | 0.0 ± 0.0 | 0.0 ± 0.0 |
|  | 25G-BD | 1.9 ± 0.1 | 1.3 ± 0.2 | 0.9 ± 0.2 | 0.1 ± 0.1 | 0.0 ± 0.0 |
|  | 23G-BD | 1.7 ± 0.2 | 0.9 ± 0.2 | 0.4 ± 0.1 | 0.0 ± 0.0 | 0.0 ± 0.0 |

Figure 111:
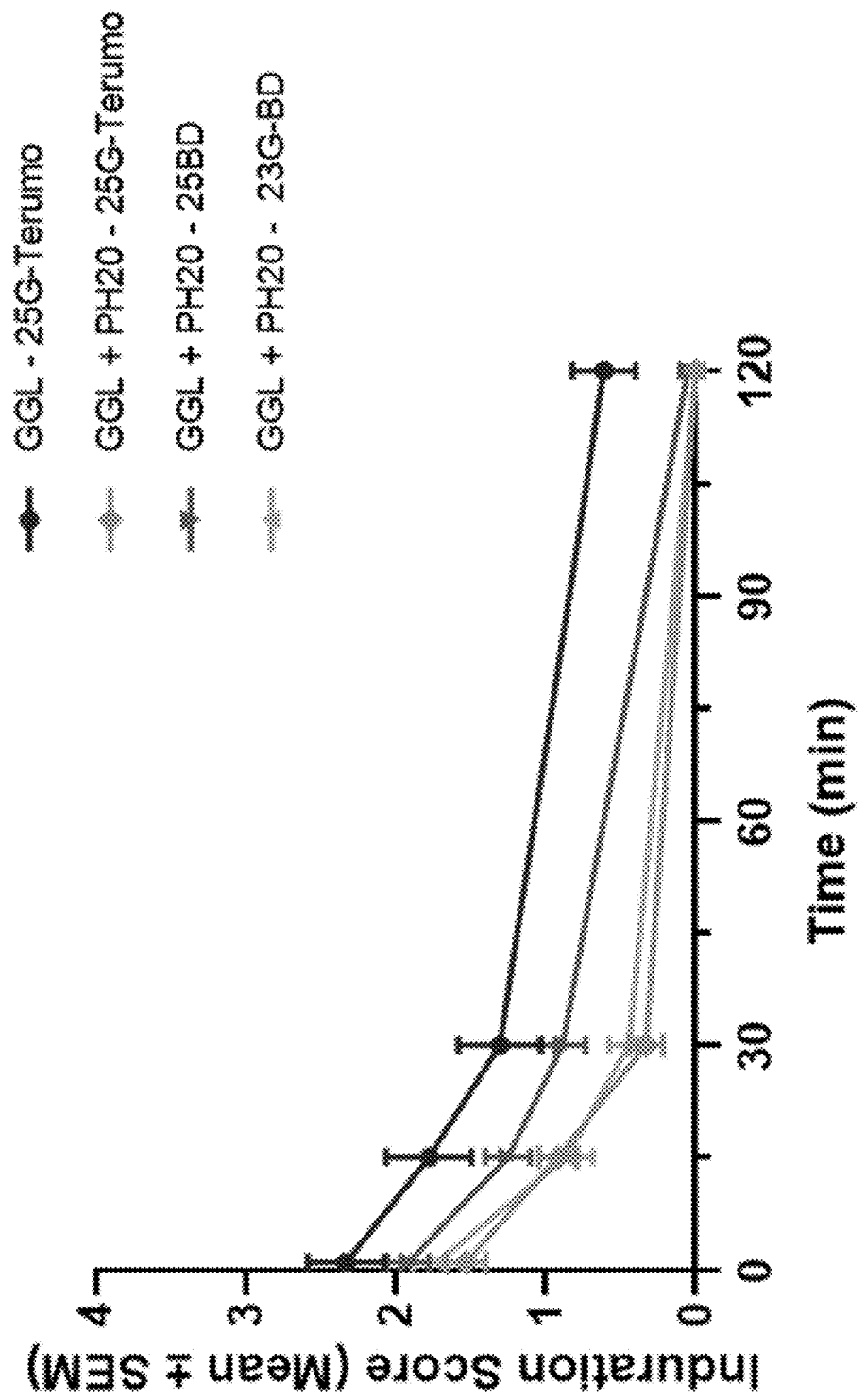
FIG. 111 is a graph of the qualitative assessment of post-injection induration (firmness).
Figure 113A:
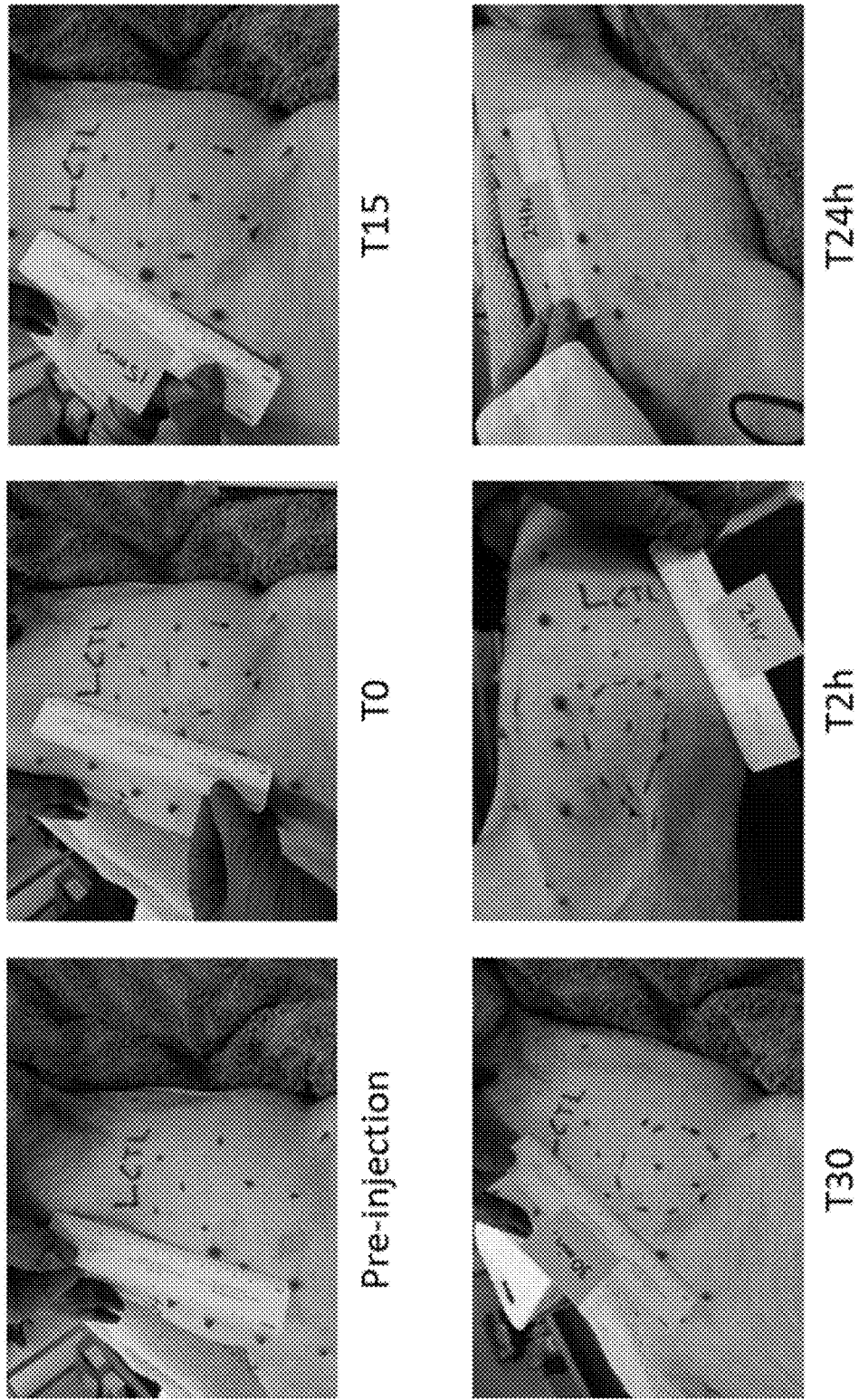
FIGS. 113A-113B provide photographs of minipig AID #2662 before and at different intervals after the 10 mL injection procedure.
Figure 113B:
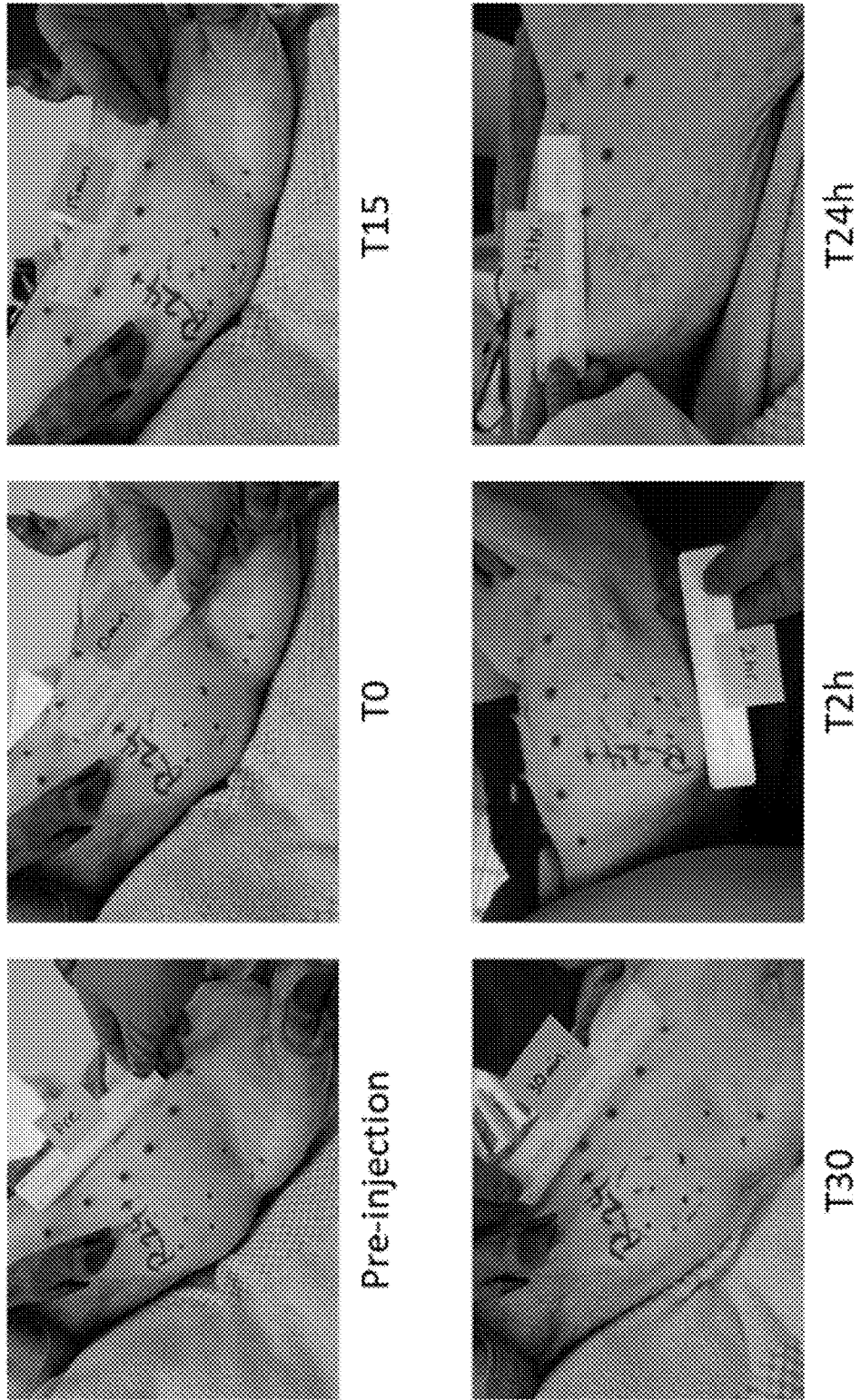
Figure 114A:
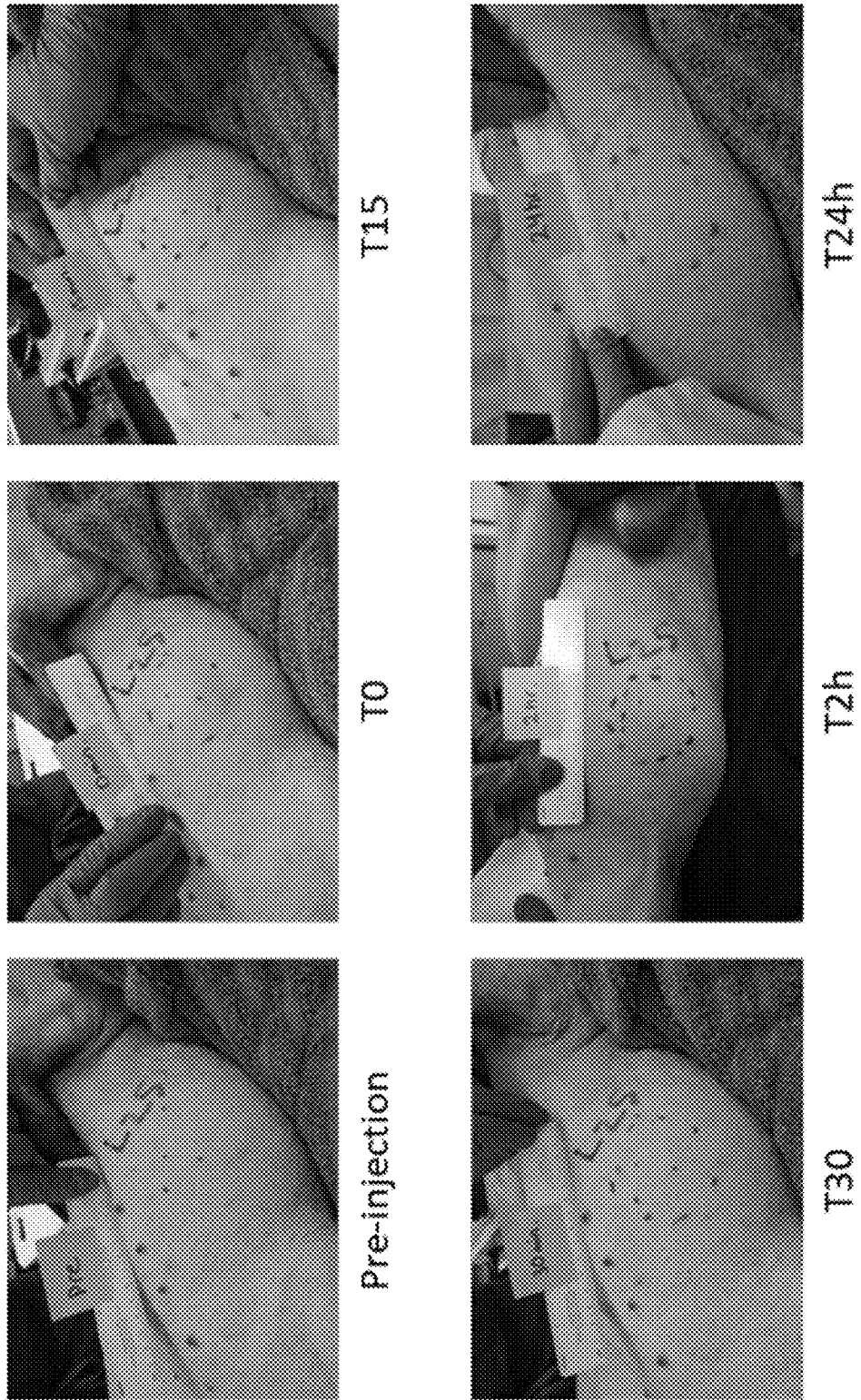
FIGS. 114A-114B provide photographs of minipig AID #2663 before and at different intervals after the 10 mL injection procedure.
Figure 114B:
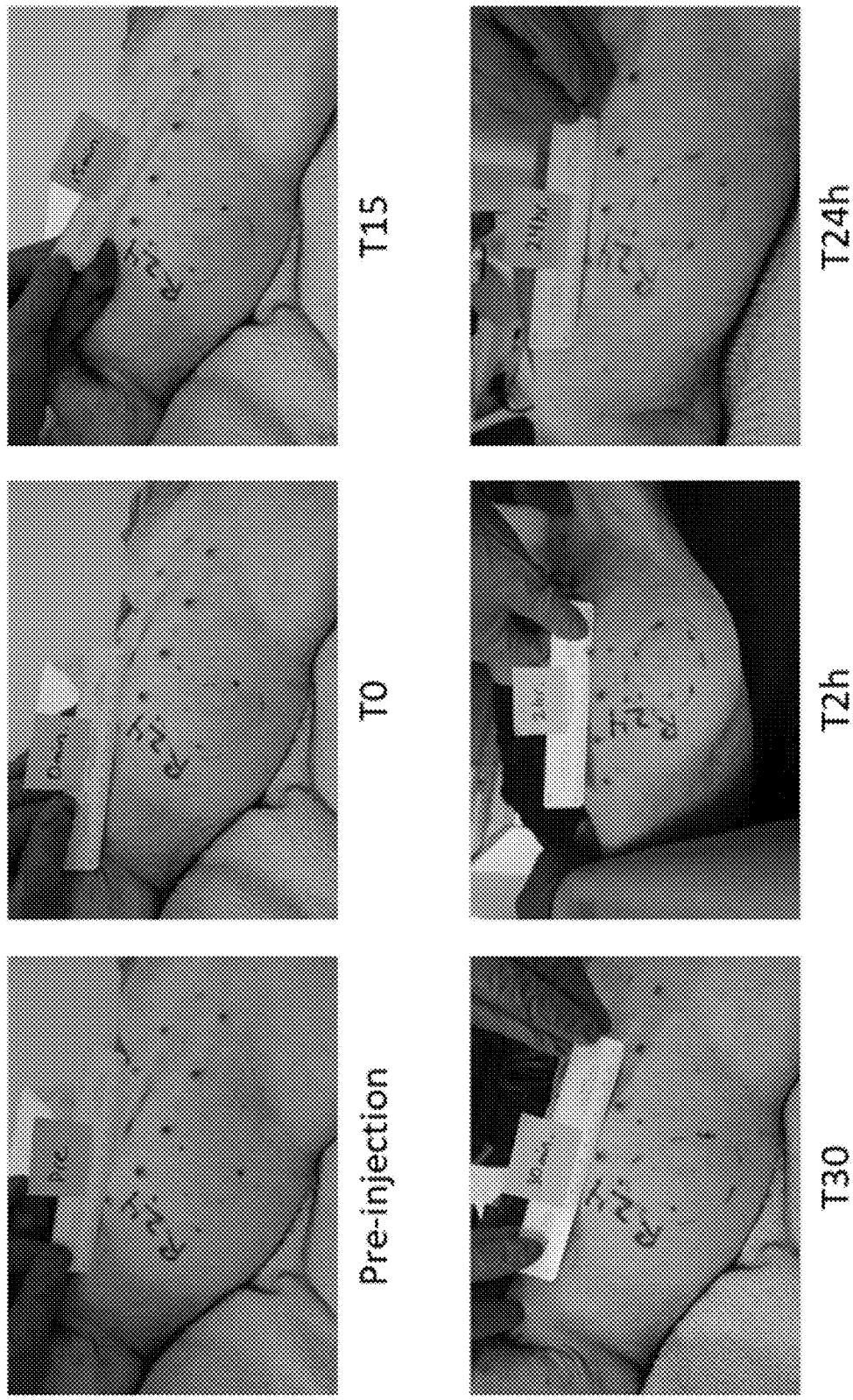
Figure 115A:
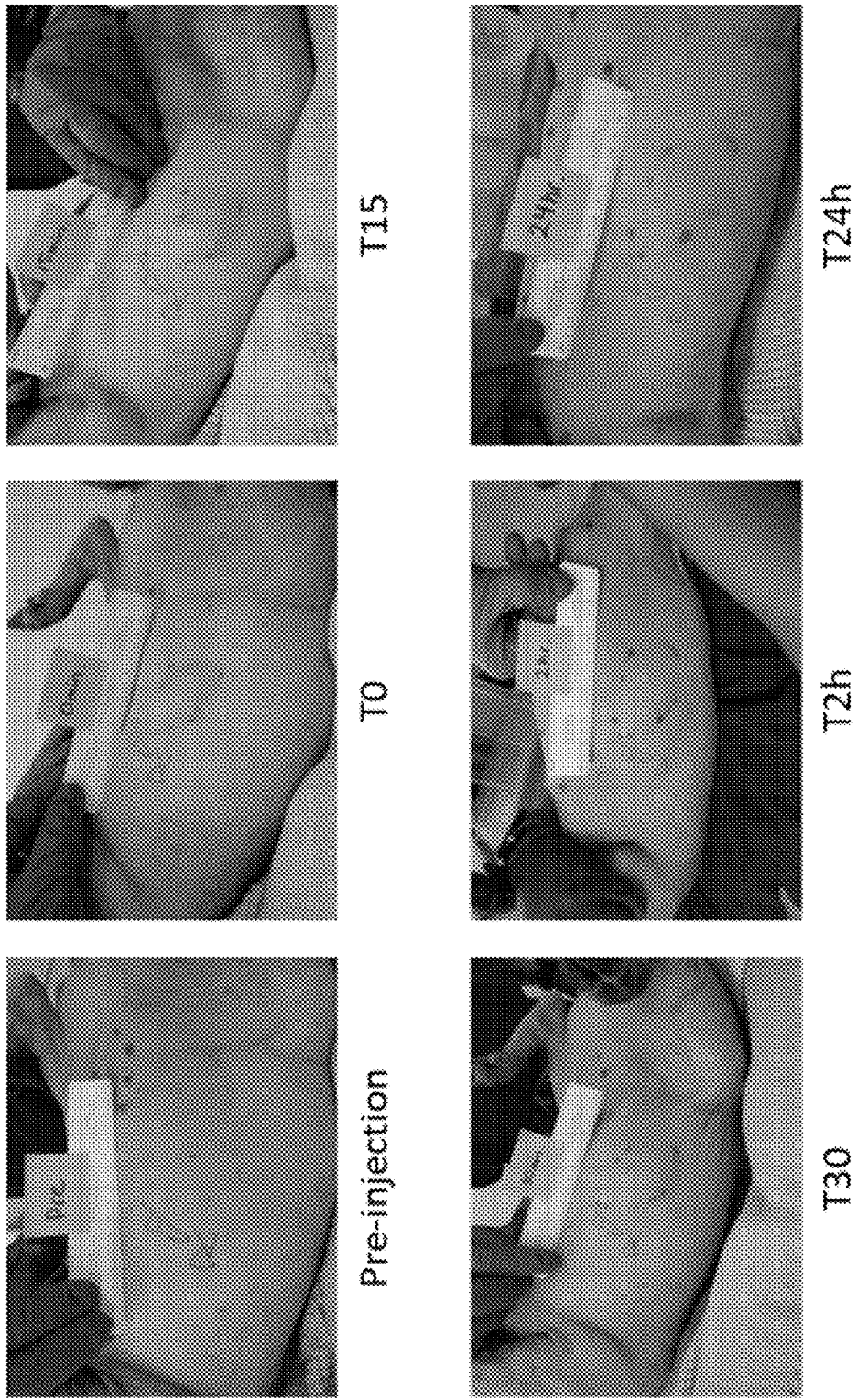
FIGS. 115A-115B provide photographs of minipig AID #2665 before and at different intervals after the 10 mL injection procedure.
Figure 115B:
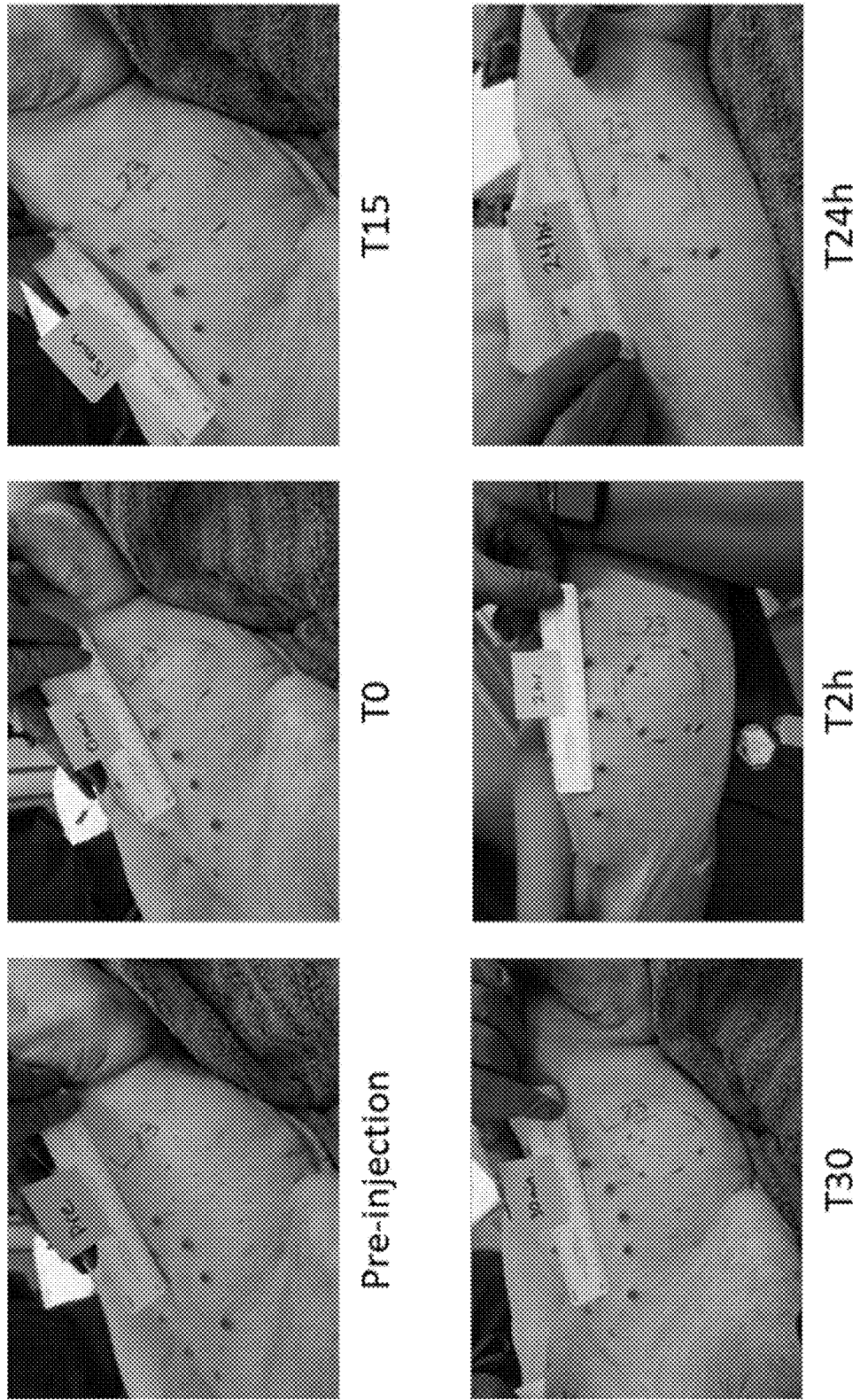
Figure 116A:
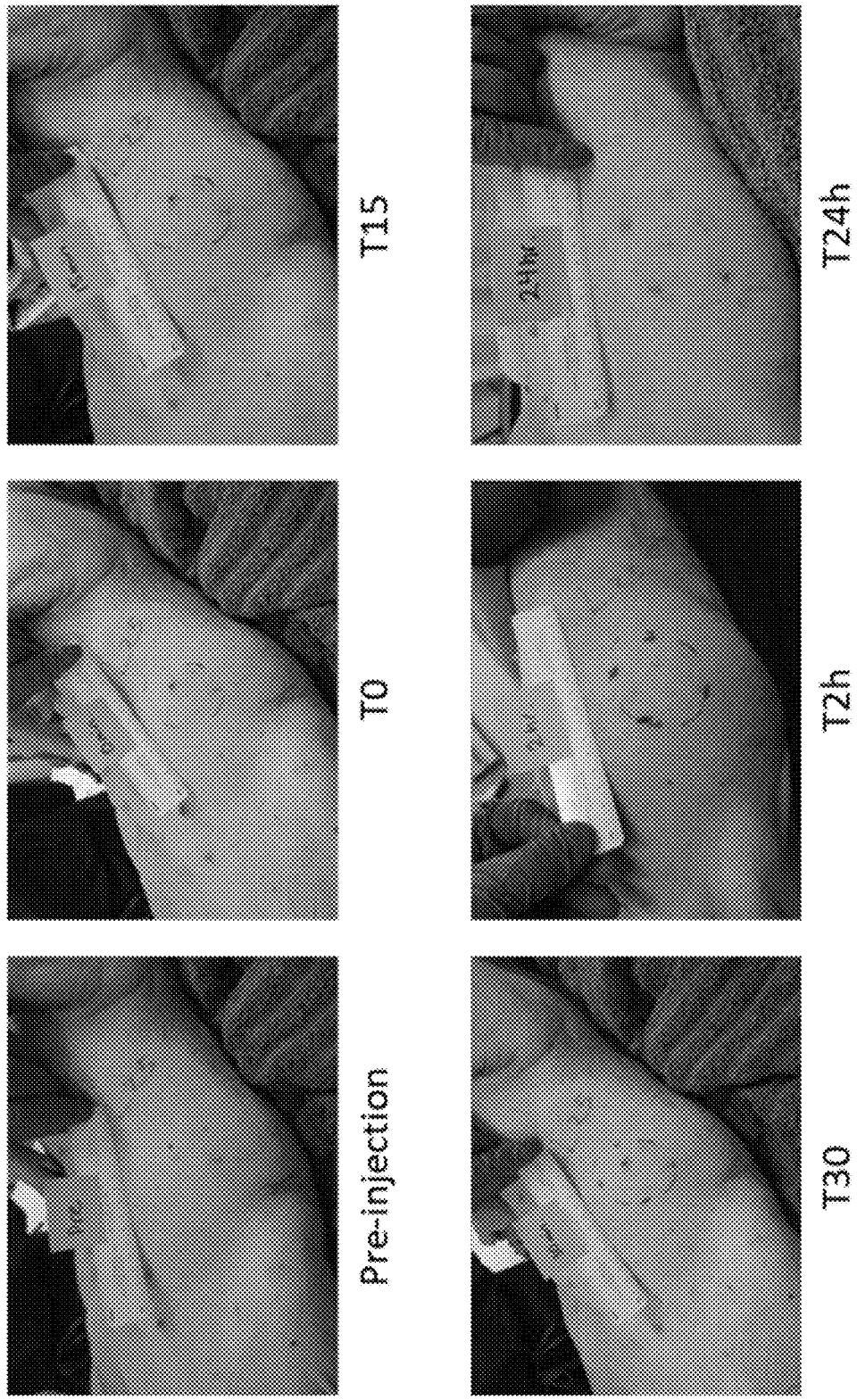
FIGS. 116A-116B provide photographs of minipig AID #2666 before and at different intervals after the 10 mL injection procedure.
Figure 116B:
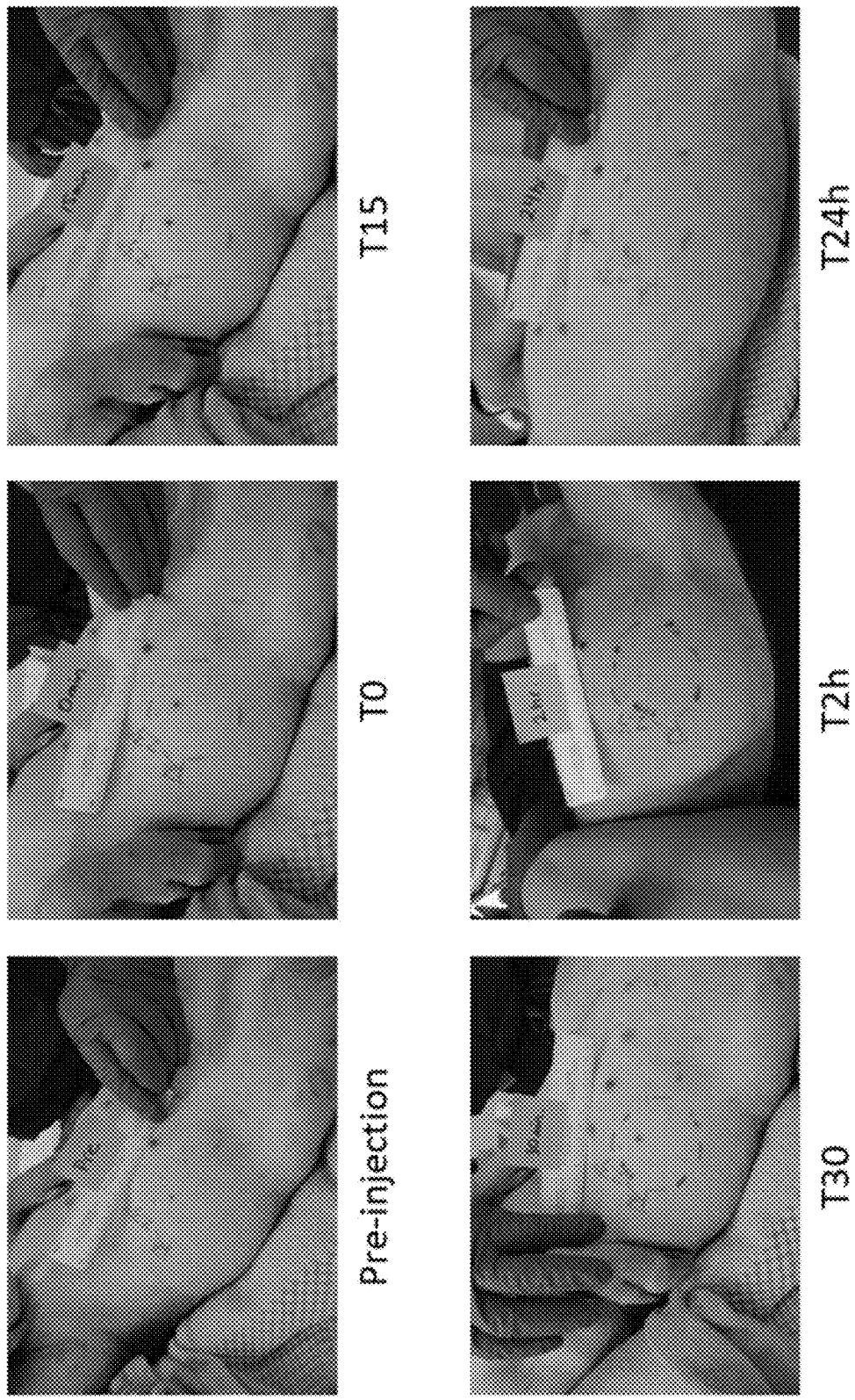
Figure 117A:
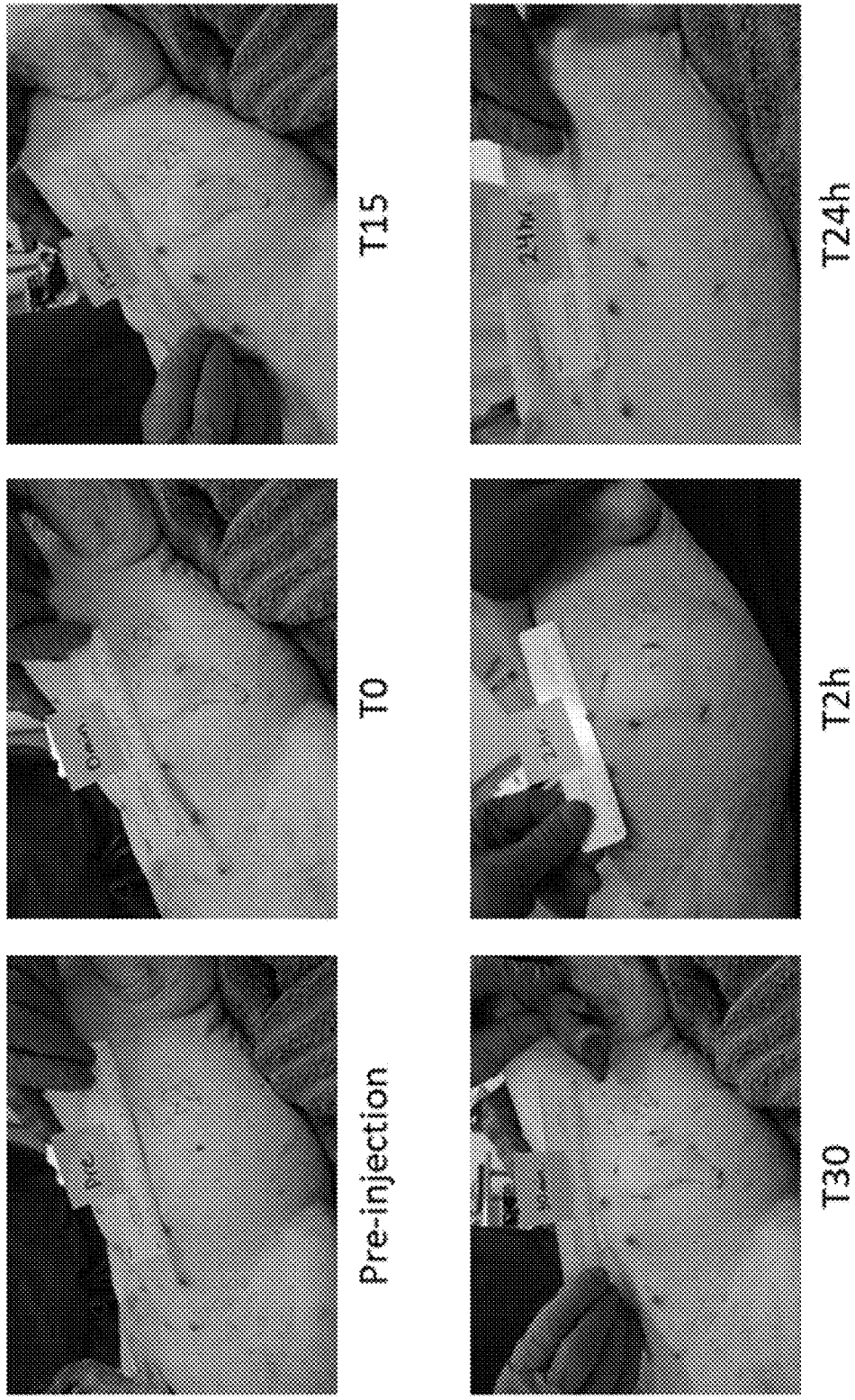
FIGS. 117A-117B provide photographs of minipig AID #2195 before and at different intervals after the 10 mL injection procedure.
Figure 117B:
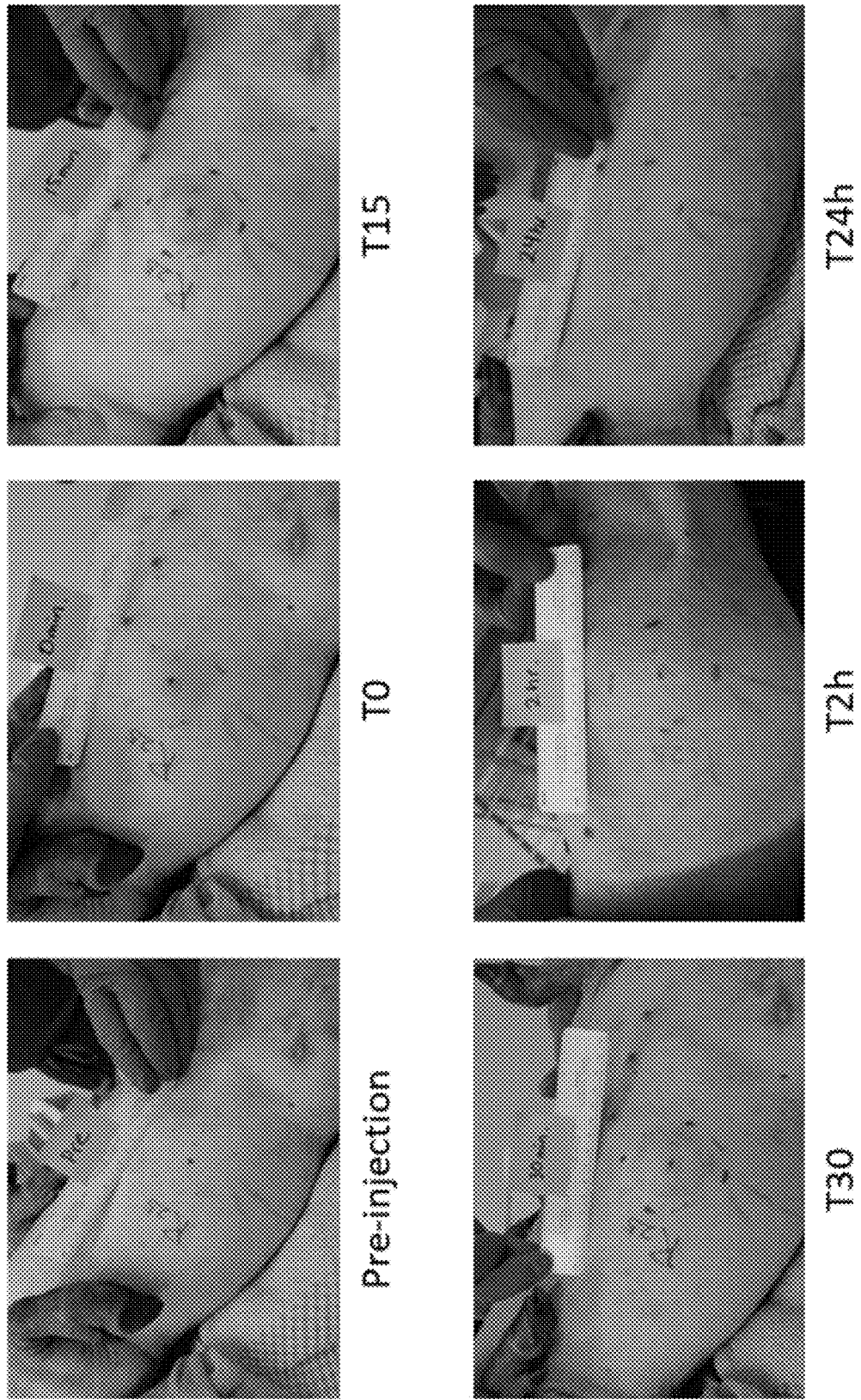

By T2 h post-injection induration was resolved for all groups except GGL alone. Therefore, a plot of the swelling scores over the first two hours using a linear timescale is shown in FIG. 111.

FIG. 112 is the certificate of analysis of the Enhanze™ drug product used for the studies of Example 6. The injection sites were photographed before and after the 10 mL injection procedure. Photographic images are shown in FIGS. 113A-124B. It should be noted at the 2 hour timepoint (T2 h), the photos of the animal were taken while it was anesthetized, but rather manually held by an animal technician. Because of the increased stress to the animal, this resulted in some flushing of the skin for some animals. In addition, the injection site may have had some increased tension (skin stretching) when photographed. Therefore, the qualitative scoring is considered the more accurate assessment of the injection site at the 2 h timepoint.

Summary and Conclusions

The applied force required to use the 23 G-BD needle was the lowest compared to the 25 G-Terumo (30% greater force required) and 25 G-BD needle (~197% greater force required).

Back-leakage was greatest for injections of GGL without rHuPH20 (25 G-Terumo needle only tested). For injections of GGL+EDP, the 25 G-Terumo needle had the least back-leakage (~83% less than control injections). Injections using the 23 G-BD needle had the greatest back-leakage (~32% less than control injections) and the 25 G-BD needle had an intermediate amount of back-leakage (~59% less than control injections).

Post-injection swelling volume assessed by caliper measurement was greatest for injections of GGL alone. Injections of GGL+EDP performed using the 23 G-BD and 25 G-BD needles had the least post-injection swelling volume compared to the control (~29% and 28% reduction, respectively). Injections of GGL+EDP performed using the 25 G-Terumo needle showed slightly less swelling volume compared to the control (~6% reduction). Swelling areas were similar for all injections.

Swelling height of injections using the 25 G-BD and 23 G-BD had less swelling height compared to the control injections (32% and 30%, respectively).

Qualitative assessments of post-injection swelling and induration were greatest for control injections of GGL alone. Injections of GGL+EDP were scored initially as smaller in size, and with less induration than the control injections. GGL+EDP injections were found to resolve more rapidly compared to the control injections. Qualitative assessments of erythema for all injections were transient and barely perceptible.

Example 6: Study to Investigate the Tolerability of Different Volumes and Injection Rates of Subcutaneous, Rapid Administration of a 10% Solution of Immunoglobulin G with Recombinant Human Hyaluronidase (rHuPH20) in Healthy Volunteers Introduction Background and Rationale Study rationale: This exploratory clinical study was conducted to: 1) Confirm the tolerability of 10% IgG (5 or 10 mL) with rHuPH20 (4000 U/mL) at different volumes and rates to determine the appropriate volume and rate of injection for an HVAI; 2) Assess injection site reactions; 3) Assess three dimensional swelling/bleb before and after the injection and time to resolution of the swelling; 4) Assess leakage at the injection site; 5) Measure injection forces during pump administration; 6) Assess injection duration using the HVAI; and 7) assess study participants' perception of the HVAI.

Rapid, high volume (>2.25 mL) SC injections are limited by the presence of hyaluronan (HA) in in the SC space which acts as a barrier to bulk fluid flow. This reduces the rate at which SC injections can be administered. The addition of rHuPH20 to a SC injection temporarily removes the HA barrier, facilitating rapid SC injections.

Current autoinjectors are limited to approximately 2.25 mL due to the factors described above and volumes greater than this are generally administered by slow SC injection or by the use of an infusion device. With the addition of rHuPH20, it is feasible to inject a volume up to 10 mL or more in an autoinjector over a short period of time. This may allow for the self-administration of higher doses and volumes of drugs using an autoinjector providing a convenient way of administering medicines and reducing healthcare costs. The HVAI for use in this clinical study performed well in nonclinical minipig studies, delivering 10 mL of IgG (120 mg/mL) with rHuPH20 (2000 U/mL) at rates up to 30 mL/min with minimal injection back-leakage, bleb size, and bleb induration along with rapid resolution of all measured endpoints at the injection site.

The use of 10% IgG serves the role of a representative large protein molecule therapeutic (LPMT), which at a 10% concentration provides a viscosity typical of many biologic candidates for SC injection and so is a suitable product with which to combine with rHuPH20 to test the hypothesis of rapid high-volume injections. IgG has been studied in healthy volunteers in the past. 20% IgG plus rHuPH20 was administered to healthy volunteers at doses of 0.4-1.0 g/kg in a single dose (NCT05059977). HYQVIA (IgG and rHuPH20) was administered to healthy volunteers in multiple doses up to 1.0 g/kg (NCT04578535). For reference, the dose of IgG utilized in the present study are considerably lower at a maximum single dose of 1 g and a maximum individual subject exposure is 2 g (total, not per kg of weight) over two administrations. In addition, previous studies have been conducted combining 10% IgG with rHuPH20.

HYQVIA is approved in the U.S. for the treatment of primary immunodeficiency (PI) in adults. HYQVIA consists of 10% IgG which is administered SC at volumes up to 600 mL, preceded by an injection of rHuPH20. More than 98% of local reactions were either mild or moderate and consisted of discomfort, erythema, swelling, and pruritus. These were transient and resolved without sequelae.

rHuPH20 was administered at a concentration of 4000 U/mL, resulting in a dose of 20,000 to 40,000U per injection. The dose/concentration of rHuPH20 may be adjusted for viscosity, volume, and rate of injection of the solution to be injected. The approved monoclonal antibodies co-formulated with rHuPH20 have a viscosity of ~5 cP and volumes of 5 to 15 mL per injection and utilize concentrations of 2000 U/mL of rHuPH20 delivered at a rate of up to 5 mL/min.

Based on the injection volume and rate of injection in this study, a concentration of 4000 U/mL was appropriate to obtain sufficient dispersion of the volume injected at up to 20 mL/minute. rHuPH20 has been administered SC as a single injection at doses of 96,000U (rHuPH20 IB) and as repeat dosing at doses of 45,000U. At a dose of 96,000U, adverse events (AEs) were predominantly mild injection site reactions. There were no deaths, serious adverse events (SAEs), or discontinuations due to AEs. With repeat dosing of 45,000U, all injection site reactions were Grade 1 in severity and resolved without intervention within 2 hours.

The bioavailability of rHuPH20 when administered SC is low and at doses of 30,000U, there was no measurable systemic exposure. In a study of healthy volunteers, up to 30,000U was well tolerated when administered intravenously, with a half-life of less than 10 minutes. No SAEs, deaths, or discontinuations due to an AE were reported during this study. One subject (30,000U treatment group) experienced a treatment-emergent AE of Grade 1 hypotension assessed as unlikely related to rHuPH20. Another subject (10,000U treatment group) experienced an AE of catheter site pain (Grade 1, not related). This event occurred at the time of catheter placement and prior to administration of the study treatment.

As of Dec. 1, 2022, 1,592 subjects were exposed to HYLENEX and other rHuPH20 drug products in 30 clinical studies conducted under Investigational New Drug (IND) 66,888 or in post-marketing Phase 4 studies. In partnered trials with co-administered therapeutics, more than 9000 subjects were exposed. Subjects/subjects in these clinical studies have been exposed to doses ranging from 15 U-96,000U, which have been generally well tolerated.

Given the acceptable safety profile of rHuPH20 of single doses up to 96,000U and with repeat dosing of 45,000U SC, combined with the low bioavailability, short systemic half-life and the safety profile of intravenous injection of high doses of rHuPH20, it is acceptable to dose patients in this study at doses up to 40,000.

Hyaluronidases and rHuPH20: Hyaluronidase products temporarily increase the permeability of tissues by depolymerizing hyaluronan. Hyaluronan is a large, repeating sugar found in interstitial tissue that acts as a barrier to the movement of molecules through the interstitial space. Posterior head protein 20 (PH20) hyaluronidases, including bovine PH20, ovine PH20, and recombinant human PH20 (rHuPH20), depolymerize hyaluronan by hydrolysis of the β-1,4 linkage between the C1 position of N-acetylglucosamine and the C4 position of glucuronic acid. The final products of this depolymerization are small, tetra and hexa-saccharide sugars.

The human genome contains several hyaluronidase genes, but only PH20 possesses enzyme activity under physiologic conditions and acts as a spreading factor in vivo. Mammalian hyaluronidase preparations differing in source, species, and manufacturing process have been the subject of multiple investigations and regulatory approvals in Europe, the United States, and Asia, collectively encompassing more than 60 years of use in humans. The extent of administration of these products to patients in the U.S. alone has been estimated to be in the tens of millions of doses.

When other drugs are injected with hyaluronidase, dispersion and absorption of the co-injected drugs are enhanced. By depolymerizing hyaluronan, hyaluronidase temporarily facilitates dispersion by reducing the viscosity of interstices. The permeability barrier in these tissues is restored to pre-injection levels within 24 to 48 hours after injection of hyaluronidase. In animals, the extent of drug dispersion is proportional to the concentration of hyaluronidase injected and the volume of the material injected.

rHuPH20 is a single chain glycoprotein with up to 447 amino acids. rHuPH20 is synthesized in Chinese hamster ovary (CHO) cells that have been transfected with a plasmid containing the deoxyribonucleic acid (DNA) sequence encoding human PH20 hyaluronidase. The protein is purified through a series of chromatographic steps that results in a purified protein with high specific activity.

rHuPH20 is the active ingredient of the commercial product HYLENEX® recombinant (hyaluronidase human injection). HYLENEX obtained regulatory agency approval for marketed use in the United States in December 2005. After its approval, the FDA transitioned HYLENEX to a licensed biologic on 23 Mar. 2020. HYLENEX is indicated as an adjuvant in subcutaneous (SC) fluid administration for achieving hydration, to increase the dispersion and absorption of other injected drugs. The cumulative patient exposure to HYLENEX from Dec. 5, 2005, to Dec. 1, 2022 is estimated to be 4,048,932, excluding subjects exposed during clinical trials. This figure is based on the total number of vials distributed, less those returned during recall, and on the presumed dose of 150 U rHuPH20 per treated patient.

Three completed clinical studies assessed safety and tolerability of rHuPH20 in combination with 10% IgG (CARIMMUNE). The first 2 studies were conducted in Phase I units with 75 healthy volunteer subjects. The third trial was conducted in a Phase I unit with 30 healthy volunteer subjects.

Immune Globulin Intravenous (Human) GAMMAGARD LIQUID® and Other IgG Products: The IgG product, GAMMAGARD LIQUID, is used as an injection solution for this study. In the context of this protocol, GAMMAGARD LIQUID is mentioned when discussing the physical and chemical characteristics, as well as the clinical indications of this IgG product; however, for subject dosing, this product is referred to as 10% IgG.

GAMMAGARD LIQUID is a ready-for-use sterile, liquid preparation of highly purified polyvalent antibody product containing in concentrated form all the IgG antibodies that regularly occur in the donor population. GAMMAGARD LIQUID is prepared from human plasma through fractionation and purification steps. GAMMAGARD LIQUID contains a broad spectrum of antibody specificities against bacterial, viral, parasitic, and *mycoplasma* antigens that are capable of both opsonization and neutralization of microbes and toxins. GAMMAGARD LIQUID is indicated for the maintenance treatment of subjects with primary immunodeficiencies (PI), and as a maintenance therapy to improve muscle strength and disability in adult patients with Multifocal Motor Neuropathy (MMN).

GAMMAGARD LIQUID is supplied as a ready-to-use liquid in various size vials (10 mL, 25 mL, 50 mL, 100 mL, and 200 mL) containing 100 milligram/mL protein. At least 98% of the protein is immune globulin. Glycine (0.25 M) serves as a stabilizing and buffering agent. There are no added sugars, sodium or preservatives. The pH is 4.6 to 5.1. The osmolality is 240 to 300 mOsmol/kg, which is similar to physiological osmolality (285 to 295 mOsmol/kg). GAMMAGARD LIQUID should be stored at refrigerated (2° to 8° C.) or room temperature (up to 25° C.). The median serum half-life of GAMMAGARD LIQUID is 35 days and is similar to those reported for other human immune globulin products.

Study Objectives
Primary Objective

To confirm the tolerability of the subcutaneous (SC) administration of a 10% solution of immunoglobulin G (IgG) in combination with recombinant human hyaluronidase (rHuPH20) of different volumes and injection rates in healthy volunteers to determine the appropriate volume and injection rate for use in a high-volume autoinjector (HVAI).

Secondary Objectives
1) To assess injection site reactions as evaluated by the subject and Investigator.
2) To assess swelling/bleb formation at the injection site before and after the injection and time to resolution of swelling/bleb.
3) To evaluate leakage at the injection site for syringe pump and HVAI.
4) To measure injection forces during syringe pump administration.
5) To assess study participants' perception of the HVAI.

Investigational Plan
Overall Study Design

This was an open-label, multiple cohort study evaluating the tolerability of various volumes and injection rates of 10% IgG solution with rHuPH20 administered SC via syringe pump (Injection Visit 1) and HVAI (Injection Visit 2) to 24 eligible healthy volunteers. The study was conducted at a Phase I unit of a contract research organization (CRO) with emergency equipment (including epinephrine) readily available in case of suspected anaphylaxis.

Eligibility screening was performed between 1 and 14 day(s) before the subject's first injection day. Screening included obtaining informed consent, a medical and medication history, physical examination, urine pregnancy test for female subjects, clinical chemistry and hematology laboratory analysis, Urine Drug Screen (UDS) for substances of abuse, a nasal swab coronavirus disease 2019 (COVID-19) test, and a review of the inclusion/exclusion criteria. The total duration of the study was up to 14 weeks, including a screening period of up to 14 days, a treatment period of up to 4 weeks during which each subject receives 2 injections on 2 separate days, and an 8-week safety Follow-Up period (or until all adverse events [AEs] have resolved), whichever is longer. An overview of the study design is shown in FIG. 125.

Injection Visit 1: syringe pump: Twenty-four eligible subjects were assigned to receive 1 of 2 volume/rate injections of 10% IgG solution with rHuPH20, SC into the abdomen using a syringe pump, in 2 cohorts of 12 subjects each as follows:
1) Cohort A (12 subjects): 4000 U/mL rHuPH20 in 10% IgG solution for a total of 5 mL in 30 sec;
2) Cohort B (12 subjects): 4000 U/mL rHuPH20 in 10% IgG solution for a total of 10 mL in 30 sec;

If the injection for Cohort B is not tolerated, a third cohort (12 subjects) is added:
3) Cohort C: 4000 U/mL rHuPH20 in 10% IgG solution for a total of 10 mL in 45 sec.

A targeted physical exam (to assess injection site for skin pigmentation, tattoos, and scars), UDS, COVID-19 test, and a pregnancy test for female subjects is conducted, medical history and concomitant medications was updated, and eligibility is confirmed prior to the subject's first injection.

On the first 3 days of dosing, 1 of 3 sentinel subjects received a single injection per day; subjects were dosed at least 24 hours apart. The Sponsor, Medical Monitor, and Investigator assess tolerability prior to injection of the next subject. All sentinel subjects remained in the clinic for observation for 24 hours post-injection. Tolerability was defined as the ability for a study subject to receive the full Investigational Product (IP) dose/volume combination within the specified time and did not meet any of the criteria listed for pausing and stopping below. If tolerated by the 3 sentinel subjects, the remaining 9 subjects in Cohort A received their injection at least 24 hours after the third sentinel subject is dosed and the tolerability assessment completed.

The Sponsor assessed subject tolerability before proceeding to Cohort B dosing. The injection for Cohort A was not considered tolerated if any of the following criteria were met:
  Two or more subjects have Grade 2 (per CTCAE version 5) allergic reaction, injection-site reaction, or injection site reaction.
  Any subject in a cohort has:
  Grade 3 or higher (per CTCAE version 5) allergic reaction or injection-site reaction
  Any grade 4 or higher AE (regardless of attribution to treatment)
  Any signs or symptoms of thrombosis, hemolysis, or acute kidney injury If the Sponsor, Medical Monitor, and Investigator determine Cohort A tolerated the injection of 5 mL/30 sec, dosing continued for Cohort B at 10 mL/30 sec according to the same schedule used for Cohort A (3 sentinel subjects dosed 24 hours apart, followed by the remaining subjects at least 24 hours later). If subjects in Cohort B did not tolerate 10 mL/30 sec, a Cohort C was added evaluating 10 mL/45 sec on the same schedule as Cohort B. Once dosing was complete for Cohort B (or Cohort C, if applicable), the Sponsor, Medical Monitor, and Investigator determine the tolerability of Cohort B (or C) using the criteria described above before proceeding to dosing at Injection Visit 2.

The site of injection, start and stop time of each injection, the times and details of any interruptions or discontinuations, and the times of assessments were recorded.

Three-dimensional imaging was taken of the injection site approximately 10 minutes pre-injection, and at 4-, 20-, 35-, 60-, and 125-, minutes post-injection, then hourly (up to 6 hours post-injection) until resolution as determined by Draize scoring in a subset of subjects. Injection was documented in the subject's source documents per site policy. Immediately after needle insertion but before the injection had started, the subject made a self-assessment of discomfort on a 0- to 10-point numeric rating scale (NRS), with 0 being no discomfort and 10 being the worst imaginable discomfort. The Investigator conducted injection site observations (ISO), including monitoring for symptoms of injection-site reactions and allergic reactions or anaphylaxis; vital signs were collected, and NRS was performed approximately 5 minutes pre-injection, immediately after the injection, and at 5-, 10-, 15-, 30-, 45-, 60-, 90-, 120-, 180-, 240-, 300-, and 360 minutes post-injection. If the injection was interrupted, the subject completed the NRS, and the Investigator conducted the ISO. After completion of all injection visit safety assessments, including assessment of AEs, vital signs, and observations and imaging, subjects who showed no signs of allergic or other concerning reactions were allowed to leave the unit no earlier than 6 hours post-injection. The subject then returned to the unit for Injection Visit 2.

Injection Visit 2: high-volume autoinjector: A targeted physical exam, UDS, COVID-19 test, and a pregnancy test for female subjects, ISO and NRS and review of concomitant medications was conducted, and findings were recorded in each subject's source records prior to the injection. Each subject was then dosed according to their assigned cohort, SC via HVIA at an alternate abdominal injection site to that used at Injection Visit 1.

If, after completing Injection Visit 1, the volume/rate for Cohort B (10 mL/30 sec) was tolerated, subjects in Cohort B received their second injection at the same volume/rate using the HVAI. On the first 2 days of dosing, 1 of 2 sentinel subjects received a single injection per day; subjects were spaced at least 24 hours apart. The Sponsor, Medical Monitor, and Investigator assessed tolerability prior to injection of the next subject. Tolerability was defined as the ability for a study subject to receive the full IP dose/volume combination within the specified time. If tolerated by the 2 sentinel subjects, the remaining 10 subjects in Cohort B received their injection at least 24 hours after the second sentinel subject had been dosed and the tolerability assessment completed.

If 10 mL/30 sec was not tolerated by Cohort B at Injection Visit 1, but Cohort C tolerated mL/45 sec with the syringe pump, Cohort C received 10 mL/45 sec with the HVAI at Injection Visit 2 on the schedule described above (2 sentinel subjects dosed 24 hours apart, followed by the remaining 10 subjects at least 24 hours later). If 10 mL/30 sec was tolerated by Cohort B at Injection Visit 1 (syringe pump), but not during injection visit 2 (HVAI), Cohort C was evaluated at 10 mL/45 sec with the syringe pump on the Cohort B schedule for Injection Visit 1. If Cohort C tolerated 10 mL/45 sec using the syringe pump, the HVAI dose for Cohort B was 10 mL/45 sec at Injection Visit 2.

If 10 mL/30 sec was tolerated using the HVAI (injection visit 2/Cohort B), then the volume for Cohort A at Injection Visit 2 increased to 10 mL/30 sec (or the highest tolerated volume/rate combination). The dosing schedule for Cohort A was the same as that described above for Cohort B for Injection Visit 2 (2 sentinel subjects dosed 24 hours apart, followed by the remaining 10 subjects at least 24 hours later).

Three-dimensional imaging, ISO (including monitoring for symptoms of injection-site reactions and allergic reactions or anaphylaxis)/NRS, and vital sign assessments of all subjects were taken at the same timepoints as during Injection Visit 1. Subjects were also given a participant-reported outcome (PRO) question to be answered regarding their experience with receiving the dose via the HVAI.

The safety and tolerability of the subcutaneous injections was monitored throughout the study. Safety was based on incidence, severity, duration, causality, seriousness, and types of AEs, and changes in physical examination findings as detailed in the Assessment of Safety section below. Adverse events were graded by the Investigator using the National Cancer Institute (NCI) CTCAE scoring system (NCI CTCAE v 5.0). Injections were paused for a cohort if a Grade 3 or higher injection site reaction occurred to allow further assessment prior to restarting injections.

Follow-up visits: Safety follow up occurred over 8 weeks after a subject's last injection, or until resolution of all AEs (whichever is longer) at 7 days, 4 weeks, and 8 weeks after the last injection.

Number of Subjects

Up to 24 subjects were enrolled to provide a total of 20 evaluable subjects. Twelve additional subjects were enrolled in Cohort C if subjects in Cohort B did not tolerate the injection. Subjects were replaced if they were assigned to a cohort but did not receive the injection, or if the device (syringe pump or HVAI) failed and the injection was not repeated.

Treatment Assignment

An overview of the treatments administered at each injection visit is shown in FIG. 125.

"Dosing days" did not reflect actual consecutive calendar days and may include a weekend where there is no dosing; but rather, denote sequence of dosing. In other words, the Cohort A Sentinel Subject 1 dosed on Dosing Day 1 was dosed prior to the Cohort A Sentinel Subject 2 dosed on Dosing Day 2, and so forth. All three sentinel subjects on Dosing Days 1-3 were dosed prior to the remainder of the cohort on dosing Day 4. Similarly for Injection Visit 1 Cohort B. After data was evaluated as described in the protocol, Injection Visits 2 commence, with the 2 Sentinel Subjects from Cohort B on Dosing Days 10-11 and the remainder of the cohort on Day 12, and similarly for Cohort A on Dosing Days 13-15.

Injection Visit 1: Eligible subjects were assigned to receive one of 2 combinations of volume of 4,000 U/mL rHuPH20 in 10% IgG solution and duration of injection. All Visit 1 injections were administered into the lower left or right quadrant of the abdomen. There are 2 dosing volume/duration cohorts at Injection Visit 1:

A) 5 mL 4000 U/mL rHuPH20 in 10% IgG solution over 30 seconds,
B) 10 mL 4000 U/mL rHuPH20 in 10% IgG solution over 30 seconds.

If B is not tolerated, a third cohort is added:
C) 10 mL 4000 U/mL rHuPH20 in 10% IgG solution over 45 seconds.

For each cohort at Injection Visit 1, 3 sentinel subjects were dosed followed by the remaining 9 subjects. The first sentinel subject in Cohort A received an injection, followed by a 24-hour observation period for tolerability. If the Sponsor, Medical Monitor, and Investigator determined that the first sentinel subject tolerated the injection, the second sentinel subject was dosed, followed by a 24-hour observation period. If the Sponsor, Medical Monitor, and Investigator determined that the second sentinel subject tolerated the injection, the third sentinel subject was dosed, followed by a 24-hour observation period. The remaining 9 subjects in the cohort received their injection after the Sponsor, Medical Monitor, and Investigator determined that the third sentinel subject tolerated the injection.

Cohort A was dosed on Days 1 through 4 and Cohort B was dosed on Days 5 through 8. No treatment was administered on Day 9. If subjects in Cohort B did not tolerate 10 mL/30 sec, a Cohort C was added evaluating 10 mL/45 sec on the same schedule as Cohort B. Once dosing was complete for Cohort B (or Cohort C, if applicable), the Sponsor, Medical Monitor, and Investigator determine the tolerability of Cohort B (or C) before proceeding to dosing at Injection Visit 2.

The subject was injected into the lower left or right quadrant of the abdomen with the dosing volume/duration appropriate to the assigned cohort through a 23- or 25-gauge needle attached via 30 inches of tubing connected to the syringe. The start and stop time of each injection, the times and details of any interruptions or discontinuations, and the times of assessments were recorded in each subject's source notes and subsequently transcribed into the Electronic Case Report Form (eCRF). Table 79 illustrates when each injection site was deemed resolved (bold in table).

TABLE 79

| ICON Screen No | YOB | Gender | Photo Date | Photo Time | Photo Visit |
|---|---|---|---|---|---|
| 101-1001 | 1990 | M | 2023 Jun. 26 | 8:10:21 | Before Injection |
| 101-1001 | 1990 | M | 2023 Jun. 26 | 8:15:42 | 1 Minute |
| 101-1001 | 1990 | M | 2023 Jun. 26 | 8:31:24 | 15 Minutes |
| 101-1001 | 1990 | M | 2023 Jun. 26 | 8:46:23 | 30 Minutes |
| 101-1001 | 1990 | M | 2023 Jun. 26 | 9:16:23 | 60 Minutes |
| 101-1001 | 1990 | M | 2023 Jun. 26 | 10:14:29 | 120 Minutes |
| 101-1001 | 1990 | M | 2023 Jun. 26 | 14:15:39 | 360 Minutes |
| 101-1002 | 1982 | F | 2023 Jun. 27 | 8:10:57 | Before Injection |
| 101-1002 | 1982 | F | 2023 Jun. 27 | 8:24:44 | 1 Minute |
| 101-1002 | 1982 | F | 2023 Jun. 27 | 8:40:46 | 15 Minutes |
| 101-1002 | 1982 | F | 2023 Jun. 27 | 8:55:46 | 30 Minutes |
| 101-1002 | 1982 | F | 2023 Jun. 27 | 9:26:09 | 60 Minutes |
| 101-1002 | 1982 | F | 2023 Jun. 27 | 10:25:37 | 120 Minutes |
| 101-1003 | 1961 | M | 2023 Jun. 28 | 8:27:52 | Before Injection |
| 101-1003 | 1961 | M | 2023 Jun. 28 | 8:35:25 | 1 Minute |
| 101-1003 | 1961 | M | 2023 Jun. 28 | 8:51:27 | 15 Minutes |
| 101-1003 | 1961 | M | 2023 Jun. 28 | 9:06:34 | 30 Minutes |
| 101-1003 | 1961 | M | 2023 Jun. 28 | 9:36:43 | 60 Minutes |
| 101-1004 | 1964 | F | 2023 Jun. 29 | 8:38:24 | Before Injection |
| 101-1004 | 1964 | F | 2023 Jun. 29 | 8:45:07 | 1 Minute |
| 101-1004 | 1964 | F | 2023 Jun. 29 | 9:01:41 | 15 Minutes |
| 101-1004 | 1964 | F | 2023 Jun. 29 | 9:15:43 | 30 Minutes |
| 101-1004 | 1964 | F | 2023 Jun. 29 | 9:45:22 | 60 Minutes |
| 101-1005 | 1979 | M | 2023 Jun. 29 | 8:31:59 | Before Injection |
| 101-1005 | 1979 | M | 2023 Jun. 29 | 8:46:08 | 1 Minute |
| 101-1005 | 1979 | M | 2023 Jun. 29 | 9:01:24 | 15 Minutes |
| 101-1005 | 1979 | M | 2023 Jun. 29 | 9:16:27 | 30 Minutes |
| 101-1005 | 1979 | M | 2023 Jun. 29 | 9:46:22 | 60 Minutes |
| 101-1006 | 1984 | M | 2023 Jun. 29 | 9:50:49 | Before Injection |
| 101-1006 | 1984 | M | 2023 Jun. 29 | 10:04:24 | 1 Minute |
| 101-1006 | 1984 | M | 2023 Jun. 29 | 10:20:17 | 15 Minutes |
| 101-1006 | 1984 | M | 2023 Jun. 29 | 10:35:22 | 30 Minutes |
| 101-1006 | 1984 | M | 2023 Jun. 29 | 11:05:30 | 60 Minutes |
| 101-1007 | 1998 | F | 2023 Jun. 29 | 9:51:34 | Before Injection |
| 101-1007 | 1998 | F | 2023 Jun. 29 | 10:05:39 | 1 Minute |
| 101-1007 | 1998 | F | 2023 Jun. 29 | 10:21:25 | 15 Minutes |
| 101-1007 | 1998 | F | 2023 Jun. 29 | 10:36:27 | 30 Minutes |
| 101-1007 | 1998 | F | 2023 Jun. 29 | 11:06:24 | 60 Minutes |
| 101-1008 | 1973 | F | 2023 Jun. 29 | 11:15:11 | Before Injection |
| 101-1008 | 1973 | F | 2023 Jun. 29 | 11:24:27 | 1 Minute |
| 101-1008 | 1973 | F | 2023 Jun. 29 | 11:40:17 | 15 Minutes |
| 101-1008 | 1973 | F | 2023 Jun. 29 | 11:55:25 | 30 Minutes |
| 101-1008 | 1973 | F | 2023 Jun. 29 | 12:26:08 | 60 Minutes |
| 101-1009 | 1982 | F | 2023 Jun. 29 | 11:11:44 | Before Injection |
| 101-1009 | 1982 | F | 2023 Jun. 29 | 11:25:23 | 1 Minute |
| 101-1009 | 1982 | F | 2023 Jun. 29 | 11:41:25 | 15 Minutes |
| 101-1009 | 1982 | F | 2023 Jun. 29 | 11:56:27 | 30 Minutes |
| 101-1009 | 1982 | F | 2023 Jun. 29 | 12:26:26 | 60 Minutes |
| 101-1010 | 1987 | F | 2023 Jun. 29 | 12:32:07 | Before Injection |
| 101-1010 | 1987 | F | 2023 Jun. 29 | 12:44:28 | 1 Minute |
| 101-1010 | 1987 | F | 2023 Jun. 29 | 13:00:31 | 15 Minutes |
| 101-1010 | 1987 | F | 2023 Jun. 29 | 13:15:05 | 30 Minutes |
| 101-1010 | 1987 | F | 2023 Jun. 29 | 13:45:26 | 60 Minutes |
| 101-1012 | 1968 | M | 2023 Jun. 29 | 13:54:48 | Before Injection |
| 101-1012 | 1968 | M | 2023 Jun. 29 | 14:04:27 | 1 Minute |
| 101-1012 | 1968 | M | 2023 Jun. 29 | 14:22:12 | 15 Minutes |
| 101-1012 | 1968 | M | 2023 Jun. 29 | 14:35:35 | 30 Minutes |
| 101-1012 | 1968 | M | 2023 Jun. 29 | 15:05:25 | 60 Minutes |
| 101-1013 | 1963 | M | 2023 Jun. 29 | 12:32:43 | Before Injection |

TABLE 79-continued

| ICON Screen No | YOB | Gender | Photo Date | Photo Time | Photo Visit |
|---|---|---|---|---|---|
| 101-1013 | 1963 | M | 2023 Jun. 29 | 12:45:17 | 1 Minute |
| 101-1013 | 1963 | M | 2023 Jun. 29 | 13:01:28 | 15 Minutes |
| 101-1013 | 1963 | M | 2023 Jun. 29 | 13:16:24 | 30 Minutes |
| 101-1013 | 1963 | M | 2023 Jun. 29 | 13:46:28 | 60 Minutes |
| 101-1028 | 2001 | M | 2023 Jul. 5 | 7:22:17 | Before Injection |
| 101-1028 | 2001 | M | 2023 Jul. 5 | 7:36:07 | 1 Minute |
| 101-1028 | 2001 | M | 2023 Jul. 5 | 7:51:32 | 15 Minutes |
| 101-1028 | 2001 | M | 2023 Jul. 5 | 8:08:52 | 30 Minutes |
| 101-1028 | 2001 | M | 2023 Jul. 5 | 8:36:32 | 60 Minutes |
| 101-1028 | 2001 | M | 2023 Jul. 5 | 9:36:31 | 120 Minutes |
| 101-1033 | 1969 | F | 2023 Jul. 6 | 7:33:11 | Before Injection |
| 101-1033 | 1969 | F | 2023 Jul. 6 | 7:45:19 | 1 Minute |
| 101-1033 | 1969 | F | 2023 Jul. 6 | 8:00:44 | 15 Minutes |
| 101-1033 | 1969 | F | 2023 Jul. 6 | 8:15:44 | 30 Minutes |
| 101-1033 | 1969 | F | 2023 Jul. 6 | 8:45:43 | 60 Minutes |
| 101-1033 | 1969 | F | 2023 Jul. 6 | 9:45:58 | 120 Minutes |
| 101-1029 | 2004 | F | 2023 Jul. 7 | 7:47:42 | Before Injection |
| 101-1029 | 2004 | F | 2023 Jul. 7 | 7:56:43 | 1 Minute |
| 101-1029 | 2004 | F | 2023 Jul. 7 | 8:12:29 | 15 Minutes |
| 101-1029 | 2004 | F | 2023 Jul. 7 | 8:26:31 | 30 Minutes |
| 101-1029 | 2004 | F | 2023 Jul. 7 | 8:56:20 | 60 Minutes |
| 101-1029 | 2004 | F | 2023 Jul. 7 | 9:57:48 | 120 Minutes |
| 101-1031 | 1970 | M | 2023 Jul. 10 | 7:23:36 | Before Injection |
| 101-1031 | 1970 | M | 2023 Jul. 10 | 7:36:44 | 1 Minute |
| 101-1031 | 1970 | M | 2023 Jul. 10 | 7:52:36 | 15 Minutes |
| 101-1031 | 1970 | M | 2023 Jul. 10 | 8:07:33 | 30 Minutes |
| 101-1031 | 1970 | M | 2023 Jul. 10 | 8:37:35 | 60 Minutes |
| 101-1031 | 1970 | M | 2023 Jul. 10 | 9:38:36 | 120 Minutes |
| 101-1034 | 1998 | M | 2023 Jul. 10 | 7:26:08 | Before Injection |
| 101-1034 | 1998 | M | 2023 Jul. 10 | 7:35:38 | 1 Minute |
| 101-1034 | 1998 | M | 2023 Jul. 10 | 7:51:39 | 15 Minutes |
| 101-1034 | 1998 | M | 2023 Jul. 10 | 8:06:38 | 30 Minutes |
| 101-1030 | 1962 | F | 2023 Jul. 10 | 8:42:42 | Before Injection |
| 101-1030 | 1962 | F | 2023 Jul. 10 | 8:54:38 | 1 Minute |
| 101-1030 | 1962 | F | 2023 Jul. 10 | 9:10:43 | 15 Minutes |
| 101-1030 | 1962 | F | 2023 Jul. 10 | 9:25:39 | 30 Minutes |
| 101-1030 | 1962 | F | 2023 Jul. 10 | 9:55:42 | 60 Minutes |
| 101-1030 | 1962 | F | 2023 Jul. 10 | 10:58:39 | 120 Minutes |
| 101-1035 | 1975 | F | 2023 Jul. 10 | 8:41:40 | Before Injection |
| 101-1035 | 1975 | F | 2023 Jul. 10 | 8:55:37 | 1 Minute |
| 101-1035 | 1975 | F | 2023 Jul. 10 | 9:11:38 | 15 Minutes |
| 101-1035 | 1975 | F | 2023 Jul. 10 | 9:27:03 | 30 Minutes |
| 101-1037 | 1966 | F | 2023 Jul. 10 | 10:05:27 | Before Injection |
| 101-1037 | 1966 | F | 2023 Jul. 10 | 10:14:35 | 1 Minute |
| 101-1037 | 1966 | F | 2023 Jul. 10 | 10:30:46 | 15 Minutes |
| 101-1037 | 1966 | F | 2023 Jul. 10 | 10:45:37 | 30 Minutes |
| 101-1037 | 1966 | F | 2023 Jul. 10 | 11:15:34 | 60 Minutes |
| 101-1037 | 1966 | F | 2023 Jul. 10 | 12:19:00 | 120 Minutes |
| 101-1037 | 1966 | F | 2023 Jul. 10 | 13:15:54 | 180 Minutes |
| 101-1038 | 1976 | F | 2023 Jul. 10 | 10:01:38 | Before Injection |
| 101-1038 | 1976 | F | 2023 Jul. 10 | 10:15:37 | 1 Minute |
| 101-1038 | 1976 | F | 2023 Jul. 10 | 10:31:38 | 15 Minutes |
| 101-1038 | 1976 | F | 2023 Jul. 10 | 10:46:32 | 30 Minutes |
| 101-1040 | 1960 | F | 2023 Jul. 10 | 11:23:01 | Before Injection |
| 101-1040 | 1960 | F | 2023 Jul. 10 | 11:34:43 | 1 Minute |
| 101-1040 | 1960 | F | 2023 Jul. 10 | 11:50:41 | 15 Minutes |
| 101-1040 | 1960 | F | 2023 Jul. 10 | 12:05:35 | 30 Minutes |
| 101-1040 | 1960 | F | 2023 Jul. 10 | 12:36:14 | 60 Minutes |
| 101-1040 | 1960 | F | 2023 Jul. 10 | 13:38:22 | 120 Minutes |
| 101-1040 | 1960 | F | 2023 Jul. 10 | 14:35:15 | 180 Minutes |
| 101-1041 | 1980 | F | 2023 Jul. 10 | 11:21:37 | Before Injection |
| 101-1041 | 1980 | F | 2023 Jul. 10 | 11:35:35 | 1 Minute |
| 101-1041 | 1980 | F | 2023 Jul. 10 | 11:51:33 | 15 Minutes |
| 101-1041 | 1980 | F | 2023 Jul. 10 | 12:10:07 | 30 Minutes |
| 101-1041 | 1980 | F | 2023 Jul. 10 | 12:36:23 | 60 Minutes |
| 101-1041 | 1980 | F | 2023 Jul. 10 | 13:37:52 | 120 Minutes |
| 101-1043 | 1975 | F | 2023 Jul. 10 | 12:44:10 | Before Injection |
| 101-1043 | 1975 | F | 2023 Jul. 10 | 12:54:39 | 1 Minute |
| 101-1043 | 1975 | F | 2023 Jul. 10 | 13:10:53 | 15 Minutes |
| 101-1043 | 1975 | F | 2023 Jul. 10 | 13:25:37 | 30 Minutes |
| 101-1043 | 1975 | F | 2023 Jul. 10 | 13:55:42 | 60 Minutes |
| 101-1043 | 1975 | F | 2023 Jul. 10 | 14:57:43 | 120 Minutes |
| 101-1028 | 2001 | M | 2023 Jul. 12 | 7:01:28 | Before Injection |
| 101-1028 | 2001 | M | 2023 Jul. 12 | 7:15:45 | 1 Minute |
| 101-1028 | 2001 | M | 2023 Jul. 12 | 7:31:16 | 15 Minutes |
| 101-1028 | 2001 | M | 2023 Jul. 12 | 7:46:32 | 30 Minutes |
| 101-1028 | 2001 | M | 2023 Jul. 12 | 8:16:39 | 60 Minutes |
| 101-1028 | 2001 | M | 2023 Jul. 12 | 9:16:15 | 120 Minutes |

TABLE 79-continued

| ICON Screen No | YOB | Gender | Photo Date | Photo Time | Photo Visit |
|---|---|---|---|---|---|
| 101-1033 | 1969 | F | 2023 Jul. 13 | 7:10:37 | Before Injection |
| 101-1033 | 1969 | F | 2023 Jul. 13 | 7:24:33 | 1 Minute |
| 101-1033 | 1969 | F | 2023 Jul. 13 | 7:40:35 | 15 Minutes |
| 101-1033 | 1969 | F | 2023 Jul. 13 | 7:55:29 | 30 Minutes |
| 101-1033 | 1969 | F | 2023 Jul. 13 | 8:25:38 | 60 Minutes |
| 101-1033 | 1969 | F | 2023 Jul. 13 | 9:25:34 | 120 Minutes |
| 101-1029 | 2004 | F | 2023 Jul. 14 | 7:21:41 | Before Injection |
| 101-1029 | 2004 | F | 2023 Jul. 14 | 7:35:39 | 1 Minute |
| 101-1029 | 2004 | F | 2023 Jul. 14 | 7:51:37 | 15 Minutes |
| 101-1029 | 2004 | F | 2023 Jul. 14 | 8:06:37 | 30 Minutes |
| 101-1029 | 2004 | F | 2023 Jul. 14 | 8:36:29 | 60 Minutes |
| 101-1029 | 2004 | F | 2023 Jul. 14 | 9:38:52 | 120 Minutes |
| 101-1031 | 1970 | M | 2023 Jul. 14 | 7:25:30 | Before Injection |
| 101-1031 | 1970 | M | 2023 Jul. 14 | 7:39:20 | 1 Minute |
| 101-1031 | 1970 | M | 2023 Jul. 14 | 7:50:45 | 15 Minutes |
| 101-1031 | 1970 | M | 2023 Jul. 14 | 8:10:30 | 30 Minutes |
| 101-1031 | 1970 | M | 2023 Jul. 14 | 8:35:23 | 60 Minutes |
| 101-1034 | 1998 | M | 2023 Jul. 14 | 8:41:54 | Before Injection |
| 101-1034 | 1998 | M | 2023 Jul. 14 | 8:55:44 | 1 Minute |
| 101-1034 | 1998 | M | 2023 Jul. 14 | 9:11:33 | 15 Minutes |
| 101-1034 | 1998 | M | 2023 Jul. 14 | 9:26:34 | 30 Minutes |
| 101-1034 | 1998 | M | 2023 Jul. 14 | 9:56:34 | 60 Minutes |
| 101-1030 | 1962 | F | 2023 Jul. 14 | 8:41:58 | Before Injection |
| 101-1030 | 1962 | F | 2023 Jul. 14 | 8:54:44 | 1 Minute |
| 101-1030 | 1962 | F | 2023 Jul. 14 | 9:13:56 | 15 Minutes |
| 101-1030 | 1962 | F | 2023 Jul. 14 | 9:29:47 | 30 Minutes |
| 101-1035 | 1975 | F | 2023 Jul. 14 | 10:00:41 | Before Injection |
| 101-1035 | 1975 | F | 2023 Jul. 14 | 10:15:45 | 1 Minute |
| 101-1035 | 1975 | F | 2023 Jul. 14 | 10:31:32 | 15 Minutes |
| 101-1035 | 1975 | F | 2023 Jul. 14 | 10:46:35 | 30 Minutes |
| 101-1035 | 1975 | F | 2023 Jul. 14 | 11:16:42 | 60 Minutes |
| 101-1037 | 1966 | F | 2023 Jul. 14 | 10:00:36 | Before Injection |
| 101-1037 | 1966 | F | 2023 Jul. 14 | 10:14:39 | 1 Minute |
| 101-1037 | 1966 | F | 2023 Jul. 14 | 10:30:41 | 15 Minutes |
| 101-1037 | 1966 | F | 2023 Jul. 14 | 10:45:31 | 30 Minutes |
| 101-1037 | 1966 | F | 2023 Jul. 14 | 11:15:52 | 60 Minutes |
| 101-1038 | 1976 | F | 2023 Jul. 14 | 11:22:24 | Before Injection |
| 101-1038 | 1976 | F | 2023 Jul. 14 | 11:35:41 | 1 Minute |
| 101-1038 | 1976 | F | 2023 Jul. 14 | 11:51:47 | 15 Minutes |
| 101-1038 | 1976 | F | 2023 Jul. 14 | 12:06:44 | 30 Minutes |
| 101-1038 | 1976 | F | 2023 Jul. 14 | 12:36:34 | 60 Minutes |
| 101-1040 | 1960 | F | 2023 Jul. 14 | 11:22:55 | Before Injection |
| 101-1040 | 1960 | F | 2023 Jul. 14 | 11:34:43 | 1 Minute |
| 101-1040 | 1960 | F | 2023 Jul. 14 | 11:50:28 | 15 Minutes |
| 101-1040 | 1960 | F | 2023 Jul. 14 | 12:08:05 | 30 Minutes |
| 101-1040 | 1960 | F | 2023 Jul. 14 | 12:35:35 | 60 Minutes |
| 101-1040 | 1960 | F | 2023 Jul. 14 | 13:35:43 | 120 Minutes |
| 101-1041 | 1980 | F | 2023 Jul. 14 | 12:42:22 | Before Injection |
| 101-1041 | 1980 | F | 2023 Jul. 14 | 12:55:36 | 1 Minute |
| 101-1041 | 1980 | F | 2023 Jul. 14 | 13:11:52 | 15 Minutes |
| 101-1041 | 1980 | F | 2023 Jul. 14 | 13:26:29 | 30 Minutes |
| 101-1041 | 1980 | F | 2023 Jul. 14 | 13:56:37 | 60 Minutes |
| 101-1043 | 1975 | F | 2023 Jul. 14 | 12:45:13 | Before Injection |
| 101-1043 | 1975 | F | 2023 Jul. 14 | 12:54:44 | 1 Minute |
| 101-1043 | 1975 | F | 2023 Jul. 14 | 13:10:35 | 15 Minutes |
| 101-1043 | 1975 | F | 2023 Jul. 14 | 13:25:39 | 30 Minutes |
| 101-1043 | 1975 | F | 2023 Jul. 14 | 13:55:44 | 60 Minutes |
| 101-1001 | 1990 | M | 2023 Jul. 17 | 7:05:01 | Before Injection |
| 101-1001 | 1990 | M | 2023 Jul. 17 | 7:15:56 | 1 Minute |
| 101-1001 | 1990 | M | 2023 Jul. 17 | 7:33:02 | 15 Minutes |
| 101-1001 | 1990 | M | 2023 Jul. 17 | 7:47:20 | 30 Minutes |
| 101-1001 | 1990 | M | 2023 Jul. 17 | 8:16:54 | 60 Minutes |
| 101-1002 | 1982 | F | 2023 Jul. 18 | 7:15:07 | Before Injection |
| 101-1002 | 1982 | F | 2023 Jul. 18 | 7:24:39 | 1 Minute |
| 101-1002 | 1982 | F | 2023 Jul. 18 | 7:41:04 | 15 Minutes |
| 101-1002 | 1982 | F | 2023 Jul. 18 | 7:55:58 | 30 Minutes |
| 101-1002 | 1982 | F | 2023 Jul. 18 | 8:26:18 | 60 Minutes |
| 101-1002 | 1982 | F | 2023 Jul. 18 | 9:21:35 | 120 Minutes |
| 101-1003 | 1961 | M | 2023 Jul. 19 | 7:26:45 | Before Injection |
| 101-1003 | 1961 | M | 2023 Jul. 19 | 7:35:59 | 1 Minute |
| 101-1003 | 1961 | M | 2023 Jul. 19 | 7:52:58 | 15 Minutes |
| 101-1003 | 1961 | M | 2023 Jul. 19 | 8:06:57 | 30 Minutes |
| 101-1003 | 1961 | M | 2023 Jul. 19 | 8:37:28 | 60 Minutes |
| 101-1004 | 1964 | F | 2023 Jul. 19 | 7:22:48 | Before Injection |
| 101-1004 | 1964 | F | 2023 Jul. 19 | 7:35:08 | 1 Minute |
| 101-1004 | 1964 | F | 2023 Jul. 19 | 7:50:58 | 15 Minutes |
| 101-1004 | 1964 | F | 2023 Jul. 19 | 8:06:38 | 30 Minutes |
| 101-1004 | 1964 | F | 2023 Jul. 19 | 8:35:51 | 60 Minutes |

TABLE 79-continued

| ICON Screen No | YOB | Gender | Photo Date | Photo Time | Photo Visit |
|---|---|---|---|---|---|
| 101-1005 | 1979 | M | 2023 Jul. 19 | 8:42:54 | Before Injection |
| 101-1005 | 1979 | M | 2023 Jul. 19 | 8:55:50 | 1 Minute |
| 101-1005 | 1979 | M | 2023 Jul. 19 | 9:12:00 | 15 Minutes |
| 101-1005 | 1979 | M | 2023 Jul. 19 | 9:33:07 | 30 Minutes |
| 101-1005 | 1979 | M | 2023 Jul. 19 | 9:56:57 | 60 Minutes |
| 101-1008 | 1973 | F | 2023 Jul. 19 | 10:00:26 | Before Injection |
| 101-1008 | 1973 | F | 2023 Jul. 19 | 10:16:14 | 1 Minute |
| 101-1008 | 1973 | F | 2023 Jul. 19 | 10:30:36 | 15 Minutes |
| 101-1008 | 1973 | F | 2023 Jul. 19 | 10:45:41 | 30 Minutes |
| 101-1008 | 1973 | F | 2023 Jul. 19 | 11:16:11 | 60 Minutes |
| 101-1007 | 1998 | F | 2023 Jul. 19 | 10:03:05 | Before Injection |
| 101-1007 | 1998 | F | 2023 Jul. 19 | 10:17:12 | 1 Minute |
| 101-1007 | 1998 | F | 2023 Jul. 19 | 10:35:43 | 15 Minutes |
| 101-1007 | 1998 | F | 2023 Jul. 19 | 10:54:57 | 30 Minutes |
| 101-1007 | 1998 | F | 2023 Jul. 19 | 11:16:52 | 60 Minutes |
| 101-1010 | 1987 | F | 2023 Jul. 19 | 11:22:48 | Before Injection |
| 101-1010 | 1987 | F | 2023 Jul. 19 | 11:35:07 | 1 Minute |
| 101-1010 | 1987 | F | 2023 Jul. 19 | 11:52:29 | 15 Minutes |
| 101-1010 | 1987 | F | 2023 Jul. 19 | 12:05:39 | 30 Minutes |
| 101-1010 | 1987 | F | 2023 Jul. 19 | 12:36:12 | 60 Minutes |
| 101-1009 | 1982 | F | 2023 Jul. 19 | 11:27:34 | Before Injection |
| 101-1009 | 1982 | F | 2023 Jul. 19 | 11:37:14 | 1 Minute |
| 101-1009 | 1982 | F | 2023 Jul. 19 | 11:51:23 | 15 Minutes |
| 101-1009 | 1982 | F | 2023 Jul. 19 | 12:08:03 | 30 Minutes |
| 101-1009 | 1982 | F | 2023 Jul. 19 | 12:36:28 | 60 Minutes |
| 101-1009 | 1982 | F | 2023 Jul. 19 | 13:37:24 | 120 Minutes |
| 101-1012 | 1968 | F | 2023 Jul. 19 | 12:54:50 | Before Injection |
| 101-1012 | 1968 | F | 2023 Jul. 19 | 12:59:14 | 1 Minute |
| 101-1012 | 1968 | F | 2023 Jul. 19 | 13:10:41 | 15 Minutes |
| 101-1012 | 1968 | F | 2023 Jul. 19 | 13:26:14 | 30 Minutes |
| 101-1013 | 1963 | M | 2023 Jul. 19 | 12:42:58 | Before Injection |
| 101-1013 | 1963 | M | 2023 Jul. 19 | 12:55:50 | 1 Minute |
| 101-1013 | 1963 | M | 2023 Jul. 19 | 13:11:54 | 15 Minutes |
| 101-1013 | 1963 | M | 2023 Jul. 19 | 13:27:03 | 30 Minutes |
| 101-1013 | 1963 | M | 2023 Jul. 19 | 13:56:49 | 60 Minutes |

Injection Visit 2: The first sentinel subject in Cohort B (or Cohort C, if B is not tolerated) are requested to return on Day 10 to receive an injection via an HVAI, followed by a 24-hour observation period for tolerability. If the Sponsor, Medical Monitor, and Investigator determine that the first sentinel subject tolerated the injection, the second sentinel subject is dosed, followed by a 24-hour observation period. The remaining 10 subjects in the cohort receive their injection after the Sponsor, Medical Monitor, and Investigator determine that the second sentinel subject tolerated the injection. The maximum volume/rate combination is used with the HVAI for Cohort A, using the same schedule described above for Injection Visit 2 (2 sentinel subjects dosed 24 hours apart, followed by the remaining 10 subjects at least 24 hours later). Cohort B (or C, if B is not tolerated) is dosed on Days 10 through 12 and Cohort A is dosed on Days 13 through 15.

The subject is injected into the contralateral lower quadrant of the abdomen (at an alternate abdominal injection site to that used in Injection Visit 1) through an HVAI, preset to deliver the dose over the optimum time. The start and stop time of each injection, the times and details of any interruptions or discontinuations, and the times of assessments are recorded into the subject's source notes and transcribed into the eCRF.

Pausing and Stopping Rules
Cohort Pausing Rules

Injections are paused for a cohort to allow time for the Sponsor, Medical Monitor, and Investigator to assess any of the following potential outcomes, irrespective of attribution to study treatment: any subject death, any Common Terminology Criteria for Adverse Events (CTCAE) Grade 4 AE in any subject; CTCAE Grade 2 or higher injection site reaction or allergic reaction in any 2 subjects in a study cohort; CTCAE Grade 3 or higher injection site reaction or allergic reaction in any subject; or thrombosis or hemolysis in any study subject.

Injections may resume for a cohort after the Sponsor, Medical Monitor, and Investigator review the events and determine none of the criteria have been met.

Individual Subject Stopping Rules

An injection is stopped, and no further injections allowed for an individual subject for any of the following reasons: CTCAE Grade 2 or higher injection-site reaction (moderate pain or that is interfering with activities of daily living, lipodystrophy, edema, phlebitis) or allergic reaction; any CTCAE Grade 3 AE that is within 48 hours of product administration, regardless of attribution to treatment; any signs or symptoms of thrombosis, hemolysis, or acute kidney injury; severe anxiety; vasovagal reaction; severe pain; or at the subject request for any reason, or at the investigator's discretion that stopping is at the best interest of the subject.

Criteria for Study Termination

Reasons for terminating the study include, but are not limited to, the following: the incidence or severity of AEs in this or other studies indicates a potential health hazard to subjects; subject enrollment is unsatisfactory; data recording is inaccurate or incomplete; or the Investigator does not adhere to the protocol or applicable regulatory guidelines in conducting the study.

TABLE 80

Schedule of assessments

| | | Injection Visits | | Safety Follow-Up[1] | | |
|---|---|---|---|---|---|---|
| | Screening | Injection Visit 1 | Injection Visit 2 | Follow-Up Visit 1 | Follow-Up Visit 2 | Follow-Up Visit 3 |
| | | | Study Day | | | |
| | Days −14 to −1 | Days 1-8 | Days 10-15 | Day 22 (±2 days) | Day 43 (±7 days) | Day 71 (±7 days) |
| Signed and dated informed consent | X | | | | | |
| Review of inclusion/exclusion criteria | X | X | | | | |
| Medical and medication history | X | X | | X | X | X |
| Physical examination | X | | | | | |
| Vital signs (BP, HR, respiratory rate, temperature) | X | X | X | X | X | X |
| Height and weight | X | | | | | |
| Electrocardiogram | X | | | | | |
| Clinical chemistry, hematology, urinalysis and serum IgA level | X | | | | | |
| Urine pregnancy test[2] | X | X | X | | | |
| Toxicology, Hepatitis B and C, and HIV test | X | | | | | |
| Assignment to dosing cohort | X | | | | | |
| Targeted physical exam[3] | | X | X | X | X | X |
| Urine Drug Screen (UDS) | X | X | X | | | |
| COVID-19 test (nasal swab) | X | X | X | | | |
| Injection | | X | X | | | |
| Injection Site 3-D Imaging | | X | X | | | |
| Numeric Rating Scale (NRS), Injection Site Observations (ISO), and symptoms of allergic reaction/anaphylaxis[4] | | X | X | X | X | X |
| Prior & concomitant medications | X | X | X | X | X | X |
| AEs/toxicity assessment[5] | | X | X | X | X | X |
| Device/pump constituent failures/malfunctions | | X | X | | | |

[1] Safety Follow-Up continues for 8 weeks after the last injection or until AEs have resolved, whichever is longer.
[2] A negative urine pregnancy test is required for female subjects during Screening and at each Injection Visit.
[3] Targeted physical examination is an evaluation of positives on a review of systems and follow-up of previous physical exam findings. Also includes an examination of the prior injection site.
[4] Please see Table 81 for all assessments and assessment timepoints.
[5] Any AE associated with device or pump failures is also included here

TABLE 81

Timepoints for injection site assessments and subject questions

| | 5 Minutes Prior to Needle Placement (±2 min) | After Needle Placement, Before Start of Injection | Immediately After Injection | 5 Minutes After the Injection (±30 sec) | 10 Minutes After the Injection (±2 min) | 15 Minutes After the Injection (±2 min) | 30 Minutes After the Injection (±5 min) | 45, 60, 90, 120, and 180 Minutes After the Injection (±5 min) | 240, 300, and 360 Minutes After the Injection (±10 min) |
|---|---|---|---|---|---|---|---|---|---|
| Visit 2 injection duration[1] | | X | X | | | | | | |
| Back-leakage collection[2] | | | X | | | | | | |
| Assess Visit 1 Applied Force[3] | | X | X | | | | | | |
| Investigator Injection Site Observations | X[4] | | X | X | X | X | X | X | X |
| Vital Signs | X[4] | | X | X | X | X | X | X | X |
| Injection Site 3-D Imaging | X[5] | | X[5] | | X[5] | | X[5] | X[5] | X[5] |
| Numeric Rating Scale | X[4] | | X | X | X | X | X | X | X |
| Participant-Reported Experience with Device | | | | | | | | X[6] | |

[1] Collected by staff at Visit 2 only
[2] Collect back-leakage for 30 seconds by dabbing injection site with pre-weighed eye spear at Injection Visits 1 and 2
[3] Collected by staff at Visit 1 only
[4] Conducted 5 minutes prior to the injections at Injection Visits 1 and 2.
[5] Injection site 3-D imaging is conducted 10 minutes before the injection and at 4-, 20-, 35-, 65-, and 125-minutes post-injection (to prevent overlap with vital signs assessments), then hourly (5 minutes after the hour) for up to 6 hours until resolution is determined by Draize scoring (see Three-Dimensional Imaging section below).
[6] Conducted after the second injection (only at Injection Visit 2).

Selection and Withdrawal of Subjects

Subjects should meet all inclusion criteria and none of the exclusion criteria before enrollment.

Subject Inclusion Criteria

Subjects must meet all of the following criteria to be eligible to participate in this study:
- provide informed consent;
- healthy male or female subject between 18 and 65 years of age, inclusive;
- intact normal skin without potentially obscuring tattoos, pigmentation or lesions in the area intended for injection, and is willing to have their hair locally shaved;
- vital signs (BP, HR, temperature, respiratory rate) within normal range or, if out of range, assessed by the Investigator as not clinically significant and it is mutually agreed by both Investigator and Sponsor Medical Monitor that the subject need not be excluded from the study;
- within 14 days prior to administration, clinical chemistry, hematology, urinalysis within the laboratory normal reference range or, if out of range, assessed by the Investigator as not clinically significant and it is mutually agreed by both Investigator and Sponsor's medical monitor;
- negative urine pregnancy test, if female, at screening, and prior to first and second injection visits;
- negative toxicology screen test;
- adequate venous access in at least one upper extremity;
- baseline general pain scores <4 on a NRS; and
- negative nasal swab COVID-19 test.

Subject Exclusion Criteria

Subjects who are determined by the Investigator to meet any of the following criteria are not eligible to participate in this study:
- contraindication to IgG, such as known history of anaphylactic or severe systemic reaction to immune globulin preparations, or selective immunoglobulin A deficiency with known antibody against IgA;
- any clinical laboratory evidence of renal insufficiency or renal failure, diabetes mellitus, volume depletion, sepsis, paraproteinemia, and subjects receiving known nephrotoxic drugs; any pain at abdominal injection site;
- hyperpigmentation, tattoo, or scar located at injection site(s);
- known allergy to hyaluronidase or any other ingredient in the study formulation or to IgG, GAMMAGARD LIQUID, Immune Globulin Injection (Human), 10% Solution, or its ingredients;
- pregnant, planning to become pregnant, or breast-feeding female;
- are not willing to use highly effective birth control (e.g., male and female sterilization, intra-uterine devices, hormonal implants, oral contraceptives, and consistent use of female hormonal injections, vaginal rings, patches and a diaphragm with spermicide) throughout the study;
- females or males of reproductive potential who do not accept potential risks to current or future fertility;
- known clinically significant cardiovascular, respiratory, gastrointestinal (GI), hepatic, neurological, psychiatric, endocrine, cancer, human immunodeficiency virus (HIV) infection, Hepatitis B or C infection, diabetes mellitus, intercurrent illness or any other major systemic disease that would unduly risk the subject's safety or interfere with the completion of the study or interpretation of results;
- has a high risk of thrombosis or hemolysis;
- chronic pain condition (such as fibromyalgia, etc.) or history of drug abuse;
- participation in a study of any investigational drug or device within 30 days or 5 half-lives of investigational drug prior to enrollment in this study, whichever is longer; or having taken anticoagulants or analgesics within 12 hours of injections.

Subject Withdrawal Criteria

The Investigator must guard the subject's welfare and should discontinue the injection and/or study participation at any time that this action appears to be in the subject's best interest.

Injection may be discontinued, and subjects may withdraw or be removed from the study at any time. Reasons for subject withdrawal from the study may include, but are not limited to, the following:
- subject chooses to withdraw from the study;
- unacceptable toxicity occurs;
- unwillingness or inability to comply with the study requirements;
- other reasons as determined by the Investigator; or
- sponsor discontinues the study for any reason.

Safety and tolerability of the injections are determined largely on the basis of clinical observations, especially local injection site signs and symptoms. Cohort stopping rules and criteria for study termination are described above.

Once a study subject receives any study drug (10% IgG solution with rHuPH20), the subject is monitored for safety as specified in the protocol. If a subject has an injection that is discontinued, that should not necessarily require withdrawal of the subject from the study; the subject may not receive further injections but should still undergo all protocol-specified assessments and be followed for safety and toxicity, as much as possible.

If a study subject withdraws from the study, every effort is made to document the reason(s) for premature withdrawal and obtain follow-up safety information as appropriate. The specific reason(s) for and date of the withdrawal is documented in the CRFs.

Those subjects who do not complete an injection due to injection site pain may continue in the study and are considered evaluable. For the tolerability assessment, an evaluable subject is a subject who completes at least 1 of the 2 Injection Visits and has an assessment of the tolerability of the administration. An enrolled subject found not evaluable due to device or delivery failure is not replaced, and the subject may have a repeat injection.

Treatment of Subjects

Description of Study Drug

10% IgG solution for subcutaneous administration: GAMMAGARD LIQUID vials are stored in accordance with the package insert.

Recombinant human hyaluronidase: ENHANZE™ Drug Product (EDP, Ajinomoto Althea, Inc) is a purified preparation of rHuPH20 supplied as a sterile, clear, colorless, non-preserved, ready-for-use solution provided at a concentration of 1 mg/ml (~110,000 U/mL). The solution is filled to 0.5 mL in a 2-mL clear glass vial and is to be stored as labeled, either at −20° C.±5° C. or 5° C.±3° C. and protected from light. The solution has a pH of approximately 6.5 and contains 130 mM sodium chloride, 10 mM L-histidine/hydrochloride as a buffer, and 10 mM L-methionine, 0.02% w/w PS80.

Co-mixture of 10% IgG and 4000 U/mL rHuPH20 solution for subcutaneous administration: Details of the co-mixed investigational product are provided in Table 81.

TABLE 82

| Investigational product | | |
|---|---|---|
| | Co-Mixed Investigational Product | |
| Product name: | 10% IgG solution | rHuPH20 |
| Dosage form: | Liquid | Liquid |
| Unit dose | 100 mg/mL | 4000 U/mL |
| Route of administration | Subcutaneous injection | Subcutaneous injection |
| Physical description | Clear or slightly opalescent, colorless or pale-yellow solution | Clear liquid |
| Manufacturer | Shire/Takeda. | Ajinomoto Althea, Inc for Halozyme Therapeutics |
| Excipients | Glycine | Sodium chloride, histidine/hydrochloride as a buffer, and L-methionine, polysorbate 80 |

Concomitant Medications

All concomitant medications from 14 days prior to the Screening visit through the final study visit are recorded in the CRFs. Recording of concomitant medications includes the name of the drug (generic drug names preferred, except for combination drug, for which brand name is preferred), and start date and stop date (or ongoing at end of study), frequency, dose, route of administration, and indication.

Concomitant medications are updated at each visit according to the Schedule of Assessments (Table 80), including any medication taken to treat an AE. At each study visit, subjects are asked if there has been any change in the medications they have taken since their last study visit.

Randomization and Blinding

This is an open-label study with subjects assigned to receive 1 of 2 dosing volumes/rate combinations of 10% IgG solution with 4000 U/mL rHuPH20 administered into the abdomen at Injection Visit 1. Subjects in Cohort B are to receive the same dosing volumes/rate combination administered at Injection Visit 1 at Injection Visit 2 unless the volume/rate combination is not tolerated using the HVAI. Subjects in Cohort A receive the highest tolerated volume/rate combination determined for Cohort B (or C, if applicable) at Injection Visit 2.

Study Drug Materials and Management

Study Drug Packaging and Labeling

Labeling of the study products are in accordance with local law and study requirements. Study materials are unblinded such that the pharmacist knows the identity of the study products.

Study Drug Storage

All unused study drugs are stored at the clinical study site. Used, empty vials are stored at room temperature and should be stored separately from unused study drug to avoid confusion. They are discarded as per site SOP following accountability by the CRA.

No study drugs are dispensed to any person not enrolled in the study. All study drugs are secured in a locked, limited access location.

Administration

Single doses of 5 or 10 mL of 10% IgG solution with 4000 U/mL rHuPH20 are administered SC on 2 separate Injection Visits using a syringe pump or HVAI. The injection is administered in either lower right or left quadrant of the abdomen according to the dosing cohort using a syringe pump at Injection Visit 1 and in the contralateral lower quadrant at the determined volume/rate using an HVAI at Injection Visit 2. The HVAI device is shown in FIG. 126. The autoinjector is a reusable, fixed dose, spring powered, disposable auto-injector designed to accommodate a 10-mL syringe to deliver a specified volume. The autoinjector has a 2-step operating mechanism. The autoinjector is first unlocked by rotating the activation button and then the injection is made by pressing the button. A needle depth gauge is used with the autoinjector to determine the depth of the needle into the injection site. The auto injector is designed to deliver the entire pre-filled volume. The autoinjector components are assembled around the pre-filled syringe (PFS) subassembly to become a single use autoinjector. There is no contact between the autoinjector components and the drug product.

Study Drug Accountability

A record of all study drug received and dispensed is documented. Documentation of the study drugs dispensation consists of a dosing record including the identification of the subjects to whom the drug is dosed, the quantity and the calendar date of dosing, and any unused drug remaining on site. Used and unused drug are reconciled with the drug inventory record.

Study Drug Disposal

All unused and used vials of study drug are, after reconciliation by the Sponsor or designee, properly disposed or destroyed in accordance with local regulations. The reconciled drug inventory record is provided to the Sponsor and a copy is retained at the site.

Study Methods and Procedures

The Schedule of Assessments (Table 80) is given as an aid to subject management. This section describes evaluations performed at each study visit.

After the subject receives the injection, there is an observation period of at least 24 hours for sentinel subjects and 6 hours for all other subjects during which assessments are made at listed intervals.

If additional safety follow-up visits are required to monitor the resolution of injection site related AEs, the procedures listed in Follow-up Visits section are completed. Any AEs or malfunctions/failures related to the device/pump are captured in the subject's source notes, evaluated by the Investigator, and transcribed to the e-CRF.

Study Methods by Visit

Screening Visit: Before any screening procedure takes place, potential study subjects are provided with written and oral information about the study and the procedures involved.

Subjects are fully informed of all the procedures involved in the study, the possible risks and disadvantages of the study drugs and study procedures, and their rights and responsibilities while participating in the study. They are allowed sufficient time to consider their participation in the study and have the opportunity to ask questions and have those questions answered. If the subject wishes to participate in the study, the subject signs and dates the informed consent form (ICF) and is provided a copy prior to any screening or study-related procedures. Screening is performed within 14 days prior to the first injection visit:

Obtain signed and dated informed consent
Inclusion/exclusion criteria review
Medical history
Medication history within 14 days of screening
Physical exam, including assessment of injection sites
Vital signs including body temperature
Height and weight
Electrocardiogram (ECG)
Clinical chemistry, hematology, urinalysis, and IgA level
Urine pregnancy test
Toxicology screening, Hepatitis B & C, HIV test
Urine Drug Screen (UDS)
COVID-19 test (nasal swab)
Assignment of Dosing Cohort Injection Visits 1 and 2: The start and stop times of each injection are recorded electronically, via pump computer (Injection Visit 1), or via stopwatch (provided by Sponsor) in the subject's source notes. If the injection is interrupted, the stop time and reason is recorded. All observations are recorded in the subject's source notes unless it is noted that a measurement is collected electronically. All source notes are transcribed into the eCRF within 5 days following the subject's visit.

Before injection, the following are performed:
Confirm eligibility
Review medical history
Vital signs including body temperature
Targeted physical exam (including assessment of injection area, both Injection Visits) including examination of the previous injection site and follow-up of AE related to the previous injection (Injection Visit 2 only)
Shaving injection site, if necessary
Adverse event and concomitant medication review
Urine pregnancy test
Urine Drug Screen (UDS)
COVID-19 test (nasal swab)
Marking the injection site with a sharpie (or equivalent)
3-D photographic images approximately 10 minutes prior to the start of the injection
NRS approximately 5 minutes prior to the start of the injection
ISO assessment approximately 5 minutes prior to the start of injection (includes edema, erythema, and induration).

After needle placement and before start of injection, the following are performed:
Collection of applied force for Injection Visit 1 only
Collection of the start of the duration of the injection for Injection Visit 2 only
NRS Immediately after injection, the needle is to be removed from the injection site. Then the following are assessed:
Back-leakage from the injection site is collected for 30 seconds with pre-weighed wicking spear.
Collection of applied force for Injection Visit 1 only
Collection of the end of the duration of the injection for Injection Visit 2 only
Vital signs and temperature
ISO assessment
Documentation of device failure (if applicable at Injection Visit 2 only)

5-, 10-, 15-, 30-, 45-, 60-, 90-, 120-, 180-, 240-, 300, and 360—minutes after each injection, the following assessments are performed:
ISO assessment
Vital signs
3-D photographic image of the injection site for a subset of subjects (4-, 20-, 35-, 65, 125-, and then hourly [5 minutes after the hour for up to 6 hours post-injection] until resolution as determined by Draize scoring)
NRS 30 minutes after the second injection, a PRO question assessment is performed (only at Injection Visit 2)

Follow-up visits 7 days (+2 days), 4 weeks and 8 weeks (+7 days) post-injection are conducted via in-person visit to clinic. The subjects are provided with information regarding signs/symptoms to monitor for and who to contact for concerns about AEs between study visits. The follow-up visits also include the following assessments:
Medical history, adverse event, and concomitant medication review
Targeted physical examination
Visualization of Injection Site 2
Vital signs
ISO
NRS Study Procedures Informed consent: The Investigator or designee presents and explains the study protocol to prospective study subjects prior to any screening procedures. Once the subject has an opportunity to read the ICF, the Investigator (or designee) is available to answer any questions the subject may have regarding the study protocol and procedures.

Inclusion/exclusion criteria review: Review the inclusion/exclusion criteria (see above) to ensure the subject qualifies for this study at the Screening Visit.

Medical history: A complete medical history is collected at the Screening Visit and updated prior to the injection at Injection Visit 1. Demographic information, including the subject's initials, date of birth, gender, race, and ethnic origin is also collected at the Screening Visit.

Medication history/concomitant medication: The medication history is collected for the 14 days prior to the Screening Visit and updated prior to the injection at Injection Visit 1. Any medication stopped before the first injection is recorded in the medication history. The concomitant medications are all medications taken from the first visit through the final follow-up visit and are reviewed at each study visit.

Physical exam: Physical examination, including ears/eyes/nose/throat/neck, respiratory, cardiovascular, gastrointestinal including mouth, musculo-skeletal, central, and peripheral nervous system and dermatological assessments is performed by the Investigator or designee at the Screening Visit.

Vital signs: Assessment of vital signs includes the measurement of blood pressure (systolic and diastolic), pulse rate, and body temperature. Blood pressure and pulse is measured with the subject at rest and in semi-recumbent position for at least 5 minutes prior to recording the pre-injection vitals. Blood pressure, pulse rate, and body temperature are recorded at Screening and both injection visits at the times specified in Table 81 and prior to discharge from the unit, and at the Safety Follow-Up visits. Clinical Research Site SOPs are followed to facilitate determination of out-of-range vital signs. Principal Investigator must evaluate out-of-range values and determine clinical significance (clinically significant or not clinically significant).

Height and weight Height and body weight are measured at the Screening Visit.

ECG: The ECG is done at the Screening Visit to help determine if there are any unknown cardiac conditions.

Clinical chemistry, hematology, urinalysis, and IgA levels: The Investigator evaluates all results outside the reference range and determines the clinical significance (clinically significant or not clinically significant). Clinical Research Site SOPs are followed to facilitate determination of out-of-range clinical chemistry, hematology, urinalysis, and IgA levels. The results from the laboratory assays are part of the clinical study database. Lab results are transferred to the EDC. Chemistry: BUN, creatinine, AST (aspartate transaminase), ALT (alanine transaminase), alkaline phosphatase, total bilirubin, direct bilirubin, and albumin, are measured at the screening visit. Hematology: Hemoglobin, hematocrit, red blood cell count, white blood cell count, and platelet count are measured at the screening visit. Serum IgA is measured at the screening visit. Urinalysis: Bilirubin, blood, glucose, ketones, nitrite, pH, protein, specific gravity, urine clarity, urine color, and urobilinogen are measured at the screening visit.

Immunogenicity samples: No immunogenicity sampling is performed in this study because of the large clinical database that exists for rHuPH20 subcutaneous doses at similar ranges and lack of any correlation of anti-rHuPH20 antibodies and adverse safety events.

Hypersensitivity: No blood sampling is expected to occur during this study.

However, in the event of a suspected hypersensitivity reaction (allergic reactions or anaphylaxis defined below), standard of care medical practices are followed to treat subjects experiencing a hypersensitivity reaction, as necessary, per investigator instructions. Blood is also collected at the time of the reaction (between 15 min.-3 hours post injection) per the Sponsor's instructions to confirm the reaction (e.g., rHuPH20-specific immunoglobulin E [IgE] and serum tryptase levels). An allergic reaction is a disorder characterized by an adverse local or general response from exposure to an allergen. Anaphylaxis is a disorder characterized by an acute inflammatory reaction resulting from the release of histamine and histamine-like substances from mast cells, causing a hypersensitivity immune response. Clinically, it presents with breathing difficulty, dizziness, hypotension, cyanosis, and loss of consciousness and may lead to death.

The study is performed in a medical facility with emergency equipment (including epinephrine) readily available in case of suspected anaphylaxis. The study site staff are trained to recognize and manage anaphylaxis. Prior to discharge from the treatment unit, subjects are ensured have no signs of allergic or other concerning reactions and normal vital sign measurements.

Pregnancy test: For all females, urine pregnancy testing is performed at the Screening visit and prior to subject dosing at each injection visit.

Toxicology, hepatitis, and HIV test: The toxicology, Hepatitis B surface antigen, Hepatitis C antibody, and HIV 1 and 2 antibodies test sample are collected at the screening visit and a negative result for all must be received prior to the first injection.

Urine Drug Screen (UDS): Urine Drug Screen for substances with the potential for abuse: cannabinoids, opiates, amphetamines/methamphetamine, methadone, barbiturates, benzodiazepines, cocaine, alcohol, and MDMA is performed during Screening and prior to Injection Visits 1 and 2.

Dose cohort assignment, visit 1: This is an open-label study with each subject being assigned to one of two combinations of dose/volume of 10% IgG plus rHuPH20. Cohort assignment occurs after all Screening assessments have been performed and results reviewed by appropriate site staff and prior to Injection Visit 1.

Targeted physical exam: The targeted physical exam includes injection site assessment (hyperpigmentation, excessive tattoos, hairiness—including the need to shave the injection site), evaluation of positives on a review of systems, and follow-up findings on previous physical exams. A targeted physical exam is performed at every visit following Screening.

Sentinel dosing: At Injection Visit 1, one of 3 sentinel subjects receives a single injection per day for the first 3 days of each cohort; subjects are dosed at least 24 hours apart. The Sponsor, Medical Monitor, and Investigator assess tolerability prior to injection of the next subject. Tolerability is defined as the ability for a study subject to receive the full dose/volume combination within the specified time for each cohort and do not meet any of the criteria listed in the individual subject stopping rules section above. If tolerated by sentinel subjects, the remaining 9 subjects in the cohort receive their injection at least 24 hours after the third sentinel subject has been dosed and the tolerability assessment completed. At Injection Visit 2, one of 2 sentinel subjects is dosed 24 hours apart, followed by the remaining 10 subjects in a cohort at least 24 hours after the second sentinel subject is dosed and the tolerability assessment completed.

Individual subject tolerability is assessed for 24 hours following each injection for the sentinel subjects. The injection is stopped, and no further injections are permitted for an individual who meets any of the criteria in the individual subject stopping rules section above.

Injection Visit 1: The injection is 5 or 10 mL per 30 seconds into the posterior right or left lower quadrant of the abdomen with a syringe pump. All start and stop times of the injection and any interruptions are recorded. The staff is trained to observe the injections as they are ongoing and are instructed to turn off the pump if there is any undue pain or discomfort as manifested by the subject.

Injection Visit 2: The injection is 10 mL per 30 seconds (or 45 seconds, if 30 seconds is not tolerated) into the abdomen, into the contralateral quadrant compared to the Injection from Injection Visit 1 with a HVAI. All start and stop times of the injection and any interruptions are recorded. The staff are trained to observe the injections as they are ongoing and are instructed to withdraw the HVAI if there is any undue pain or discomfort as manifested by the subject.

Injection site observation assessment: The Investigator, or qualified Sub-Investigator designee conducts Injection Site Observations (ISO) using modified Draize scoring (Tables 83-85). The Investigator is specifically asked to assess erythema, edema/swelling, and induration at the injection site. The ISO is performed approximately 5 minutes prior to the start of the injection, immediately after the injection, and 5-, 10-, 15-, 30-, 45-, 60-, 90-, 120-, 180-, 240-, 300-, and 360-minutes after each injection, and at follow-up visits 7 days, 4 weeks, and 8 weeks after the last injection, or after all AEs have resolved (whichever is longer). All other AEs observed at the injection site are assessed as per the NCI CTCAE Version 5 criteria for severity (see the Classification of Adverse Events by Severity section below).

TABLE 83

Grading scale for local injection site erythema

| Scale | Description |
| --- | --- |
| 0 | No erythema |
| 1 | Very slight erythema (barely perceptible) |
| 2 | Well defined erythema |
| 3 | Moderate to severe erythema |
| 4 | Severe erythema (beet redness) to slight eschar formation |

TABLE 84

Grading scale for local injection site swelling

| Scale | Description |
| --- | --- |
| 0 | No swelling |
| 1 | Very slight swelling |
| 2 | Slight swelling |
| 3 | Moderate swelling |
| 4 | Severe swelling |

TABLE 85

Grading scale for local injection site induration (firmness)

| Scale | Description |
| --- | --- |
| 0 | No perceptible difference in firmness after injection |
| 1 | Very slightly firm (barely perceptible) |
| 2 | Mildly firm |
| 3 | Moderately firm |
| 4 | Very firm |

Numeric Rating Scale (NRS): Discomfort at the injection site is self-assessed by the subject on a 0 to 10 NRS, on which 0 represents no discomfort and 10 represents the worst imaginable discomfort. Subjects are requested to report discomfort in whole numbers only (not N.5 or between N & M). The NRS for the subject's assessment of discomfort is explained to the subject prior to the injection so that they fully understand in advance how to properly respond to the question. The NRS is assessed immediately after needle insertion prior to the start of injection, immediately after the injection, and 5-, 10-, 15-, 30-, 45-, 60-, 90-, 120-, 180-, 240-, 300-, and 360-minutes after each injection, and at follow-up visits 7 days, 4 weeks, and 8 weeks after the last injection, or after all AEs have resolved (whichever is longer).

Participant-Reported Outcome question: The PRO question (I would be willing to have this injection by the autoinjector again. Yes/No) is answered on Injection Visit 2, 30 minutes after the completion of the second injection.

Three-dimensional imaging: Three-dimensional imaging is taken of the injection site approximately 10 minutes pre-injection, and at 4-, 20-, 35-, 65-, 125-minutes post-injection, then hourly (five minutes past the hour up to 6 hours post-injection) until resolution as determined by Draize scoring in a subset of subjects as follows:

- The 3 sentinel subjects in each cohort using the syringe pump for a total of 6 subjects at Injection Visit 1
- The 2 sentinel subjects in Cohort B (HVAI) at Injection Visit 2
- Every other subject for the remaining 10 subjects in Cohort B at Injection Visit 2, for a total of 5 subjects.
- The 2 sentinel subjects in Cohort A (HVAI) at Injection Visit 2 (if needed)

Back leakage: Back-leakage is collected immediately following the injection by dabbing at the injection site following Injection Visits 1 and 2 with a pre-weighed eye spear for 30 seconds. The eye spear is then re-weighed on a sensitive (to 2-decimal places) analytical balance and the pre- and post-weights recorded in the subject's source notes. Back leakage is an expected occurrence and dependent on individual skin characteristics and are not captured as an AE.

Concomitant medications: Medications taken 14 days prior to Injection Visit 1 through the last follow-up visit are recorded in each subject's source notes.

Adverse events: Assess subject's adverse events (and any events associated with device/pump failures or malfunctions), based on the criteria in the adverse event definition section at all study visits after the screening visit. Any adverse reactions that occur subsequent to signing of the informed consent but prior to study drug dosing unless related to medical procedures related to the study are recorded in the medical history.

Assessment of Safety

Safety parameters that are collected and monitored during this study include adverse events (AEs), concomitant medications, laboratory measurements, physical examination findings, vital signs, pregnancy test results, and local tolerability at injection sites. For this study, any event associated with device/pump constituent failure/malfunction are captured as well.

All AEs that occur during the study are treated appropriately to protect and ensure the subject's well-being. If such treatment constitutes a deviation from this protocol, the Investigator complies with applicable Institutional Review Board (IRB) reporting requirements.

Adverse Event Definitions

An adverse event (AE) is the development or increased severity of an undesirable medical condition or the worsening of a pre-existing medical condition during or following exposure to a pharmaceutical product, whether or not considered casually related to study drug.

A serious adverse event (SAE) is any adverse event that:
Results in death
Is life-threatening
A life-threatening SAE is any adverse event that places the subject at immediate risk of death from the reaction as it occurred, as assessed by the Investigator. This definition does not include a reaction that might have caused death if it occurred in a more severe form.
Requires in-patient hospitalization or prolongs existing hospitalization
For the purposes of this protocol, any hospital admission is considered in-patient hospitalization, regardless of duration. An emergency room visit without hospital admission is not recorded as a SAE under this criterion, nor will hospitalization for a procedure scheduled prior to study enrollment. However, unexpected complications that occur during elective surgery are recorded as AEs and assessed for seriousness.
Results in persistent or significant disability or incapacity
Results in a congenital anomaly or birth defect, or
Is any other Important Medical Event
Other medical events are considered SAEs when, based upon appropriate medical judgment, they may jeopardize the subject and may require medical or surgical intervention to prevent one of the other outcomes listed in this definition. Examples include allergic bronchospasm requiring intensive treatment in an emergency room or at home, blood dyscrasias or convulsions that do not result in hospitalization of the subject/patient, or the development of drug dependency or drug abuse.

Serious Adverse Events

All SAEs are reported within one business day of discovery or notification of the event. Event information is recorded on a SAE Report Form. The minimum required information for an initial report is: reporter's name and contact information, protocol number, site and subject identification information, and event term(s) (with a brief summary of the event[s] and the causality assessment).

If additional follow-up information is required or becomes available for a previously reported SAE, a follow-up SAE Report Form is prepared with the new information and emailed within 1 business day.

For hospitalizations, all attempts to obtain the hospital record are documented. An SAE Report Form is completed with any known information, however minimal, about the hospitalization.

Classification of Adverse Events by Severity

The Investigator categorizes the severity of each AE using the National Cancer Institute (NCI) Common Terminology Criteria for Adverse Events (CTCAE), Version 5.0, as a guide:

Mild (Grade 1): Symptoms or signs may exist, but are transient and easily tolerated. Intervention is not indicated.

Moderate (Grade 2): The symptoms limit some activities of daily living (e.g., preparing meals, shopping for groceries, using the telephone, managing money, etc.). Minimal, local, or noninvasive intervention is indicated to avert subject/patient discomfort.

Severe (Grade 3 or higher): The symptoms are incapacitating. Hospitalization or other urgent intervention may be indicated.

It is important to distinguish between serious and severe AEs. Severity is a measure of intensity whereas seriousness is defined by the criteria above. A severe AE may or may not be considered serious.

Classification of Adverse Events by Relationship to Study Drug

For each AE, the Investigator decides, based on his or her medical judgment, whether there is a reasonable possibility that the event was caused by administration of study drug. The Investigator makes this decision after careful consideration of the following questions:

Does the AE follow a reasonable temporal sequence from administration of study drug?

Can the AE be reasonably explained by the known characteristics of the subject's/patient's clinical state, environmental or toxic factors, or other modes of therapy administered to the subject/patient?

Do the AE symptoms disappear or decrease on cessation of study drug or reduction in study drug dose? (There are exceptions when an AE does not disappear upon discontinuation of the drug, yet drug relatedness clearly exists [e.g., bone marrow depression, fixed drug eruptions, tardive dyskinesia, etc.]).

Does the AE reappear or worsen when study drug is re-administered?

Does the AE follow an expected response pattern based on the established pharmacological and toxicological effects of the product?

Does the AE follow an expected response pattern based on the known effects of other products in the same class?

For this assessment, the Investigator classifies each AE as one of the following:

Yes, Related: The AE is definitely related to study drug administration.

Probably Related: There is a high degree of certainty that the AE is related to study drug administration.

Possibly Related: The AE could be related to either study drug administration or concurrent disease/medication.

Unlikely Related: There is a high degree of certainty that the AE is NOT related to study drug administration.

Not Related: The AE is clearly due to other causes (e.g., concurrent medication, underlying disease, etc.).

For the purposes of expedited reporting to regulatory authorities, AEs assessed as "Yes, Related," "Probably Related," or "Possibly Related" are considered causally related to study drug.

Recording Adverse Events

Events that occur prior to the first administration of study drug are not considered AEs, by definition (see above), and are captured on the subject's Medical History CRF.

Subjects are questioned and examined by the Investigator or a qualified designee for evidence of AEs. Information gathering for AEs does not begin with specific questions about the presence or absence of individual AEs, rather, initial questions are general (e.g., "How have you been feeling since your last visit?"). All AEs are recorded on the subject's AE CRF. If a previously reported AE increases in severity, a new AE is recorded.

Wherever possible, syndromes, rather than individual symptoms, are recorded in the AE CRF to avoid duplication and facilitate meaningful interpretation of data. For example, a subject presenting with rhinitis, fever, and headache is reported as having "flu-like symptoms," without independently noting each accompanying sign. Where no clearly recognizable clinical syndrome can be described, individual clinical signs and symptoms are recorded.

All SAEs and deaths are immediately reported to Drug Safety and Pharmacovigilance. This includes deaths within 30 days of the last dose of study drug, or prior to the last formal follow-up contact with the subject, whichever occurs later.

The Investigator is responsible for determining whether or not an AE is of sufficient severity to require the subject's removal from treatment. A subject may also voluntarily withdraw from treatment because of an AE. If either occurs, the subject undergoes an end of study assessment and is given appropriate care under medical supervision. The subject returns to the study site for follow-up evaluations until the AE is resolved or stabilized at an acceptable level. All AEs, serious or not, that result in the subject's permanent withdrawal from study drug are immediately reported.

Laboratory Abnormalities and Immunogenicity Findings

Laboratory abnormalities may occur within the context of a reported adverse event (AE) that describes a clinical syndrome (e.g., elevated BUN and creatinine in the setting of an AE of renal failure, or elevated SGOT/SGPT in the setting of an AE of hepatitis). In these cases, the abnormality itself is not recorded as an AE.

However, in the absence of an AE that encompasses the observed laboratory abnormality, the abnormality is reported as an AE if it is judged by the Investigator to be clinically significant for that subject.

Similarly, in the absence of an observable clinical effect, findings of immunogenicity via a measurable antibody titer to study drug are not recorded as an AE unless judged by the Investigator to be clinically significant for the subject.

For the purposes of this study, the criteria for a "clinically significant" laboratory abnormality or antibody titer are:
  It leads to a dose-limiting toxicity, or
  It results in any therapeutic intervention (i.e., concomitant medication or therapy), or
  It is judged by the Investigator to be of other particular clinical relevance.

Pregnancy

Pregnancy in a study subject must be reported to Drug Safety and Pharmacovigilance within 1 business day of discovery or notification. Available information is recorded on a Pregnancy Report Form and faxed along with the pregnancy test results, if available, and any other pertinent information. As additional information becomes available for a previously reported pregnancy, a follow-up Pregnancy Report Form is prepared with the new information.

Pregnancy itself is not regarded as an AE unless there is suspicion that the study drug may have interfered with the effectiveness of a contraceptive medication. If a non-serious AE occurs in the course of the pregnancy, the AE CRF should be completed and faxed with a follow-up Pregnancy Report Form.

Female subjects who become pregnant during the study do not receive any additional injections of study drug and are withdrawn from the study. The reason for withdrawal is documented in the CRF as a protocol violation. These subjects are required to return to the clinical study site for early study termination procedures. In addition, the Investigator monitors and follows the pregnancy until final resolution (e.g., delivery, miscarriage, or early termination). Follow-up occurs at least monthly and is documented. Spontaneous miscarriage or congenital anomaly is reported as an SAE.

Reporting of Safety Information to the Institutional Review Board

The Investigator informs the study center's Institutional Review Board (IRB) of SAEs and other safety information in accordance with the IRB's requirements. At the completion or early termination of the study, the investigator submits a final report to the IRB within the applicable IRB time frames.

Concomitant Medications

Any medication taken during the study other than study drug is regarded as concomitant medication. Concomitant medications taken during the period beginning at the screening visit and ending at the final follow-up visit are recorded in the Concomitant Medications CRF. Subjects are queried regarding both prescription and over-the-counter medications.

Concomitant medications, including any medication taken to treat an AE, are updated at each subsequent visit according to the schedule of events. At each study visit, subjects are asked if there has been any change in the medications they have taken since their last study visit.

Subjects may receive medical care during the study, including but not limited to antibiotics, analgesics, antipyretics, etc., when clinically indicated. Whenever possible, the subject should avoid starting any new medications during the treatment period of this study (including over-the-counter medications) unless the Investigator deems such medication medically necessary.

Statistics

Sample Size Determination

Up to 24 subjects are enrolled to provide a total of 20 evaluable subjects. For the tolerability assessment, an evaluable subject is one who has received an injection and has undergone sufficient assessments to allow an assessment of the safety and tolerability of the administration. Subjects who are unable to complete the injection due to any clinical reason (e.g., pain, vasovagal response, etc.) which leads to a verbal request to stop the injection are still considered evaluable. Subjects are also considered evaluable if the injection cannot be completed because the volume cannot be fully injected. Subjects unable to complete injection due to failure of the device (syringe pump or HVIA) are not considered evaluable and may have a repeat injection or be replaced if they do not agree to a repeat injection.

This is an exploratory study. A sample size of 20 evaluable subjects provides adequate data to assess the safety and tolerability of each treatment and is sufficient to evaluate via descriptive statistics.

Overview

The results of this study are reported using summary tables, figures, and data listings. Standard descriptive summaries summarize demographic characteristics (e.g., means and standard deviations for continuous variables such as age and percentages for categorical variables such as gender). Standard descriptive summaries summarize each treatment arm's tolerability and numeric rating scale. Full details of the statistical methods used are provided in a separate Statistical Analysis Plan (SAP), which is generated prior to database lock and unblinding. Any deviations from statistical methods provided here are outlined in the SAP, and any deviations from the SAP are described in the clinical study report.

Analysis Sets

The primary analysis data set for all safety endpoint parameters is the safety analysis set, defined as all subjects who received an injection of any amount of study drug (10% IgG with rHuPH20). The primary analysis data set for all tolerability endpoint parameters (e.g., preference, and pain) is all evaluable subjects. An evaluable subject is one who has completed at least one of the injections at either Injection Visit 1 or 2 and has undergone sufficient assessments to allow an assessment of the tolerability of the administration. Tolerability data is also summarized using the safety analysis set and the intent-to-treat analysis set, which includes all subjects.

Primary and Secondary Endpoints

Primary: Ability to receive entire dose of IgG solution with rHuPH20 with a goal of ≥75% of subjects being able to complete their respective doses within the indicated time (which is considered tolerability for the purposes of this study).

Secondary:
  Subject perception of discomfort during both injections using the NRS.
  Subject discomfort during needle insertion compared with discomfort during injection of study drug product.
  Proportion of subjects requiring analgesia for treatment of discomfort following each injection and time to resolution of discomfort.
  Proportion of subjects who had interruption and/or premature discontinuations of injection due to complication, intolerance, or technical issues.
  Investigator-assessed ISO (i.e., erythema, bleb formation, induration, including rates and severity using Modified Draize scoring).
  Three-dimensional volumetric assessment of the bleb/swelling at the injection site.
  Time to resolution of swelling (i.e., bleb formation).
  Leakage of fluid at the injection site following each injection.
  Injection force during syringe pump administration.

Participant responses to questions regarding their experience with receiving a dose of IgG solution with rHuPH20 via an HVAI.

Assess injection duration using the HVAI.

Analysis Methods

Primary and secondary analyses: The primary analysis for the tolerability endpoint parameters is the completion of an injection at Injection Visit 1 and Injection Visit 2.

Secondary analyses include injection site assessment by the Investigator post-injection for appearance and severity of erythema, bleb formation, and induration using a 5-point modified Draize scoring scale. Subject discomfort with injections is analyzed by comparing the NRS score with needle insertion to the NRS score with drug product injection. This is also analyzed by calculating the percentage of subjects that required analgesia. The proportion of subjects who had premature discontinuations of their injection is determined as a percentage. The injection sites are photographed with a 3-dimensional camera and then analyzed using proprietary software to determine swelling volume over time as well as time to resolution. Injection applied forces for Injection Visit 1 are analyzed using a miniature load cell and means are calculated. Injection site leakage is collected immediately following completion of injection and is quantified by weight and means are calculated. Injection duration for Injection Visit 2 is collected manually using a stopwatch and means are calculated. Lastly, subject responses to the PRO question for acceptability of the autoinjector are analyzed.

Safety analysis: All safety data is examined, including AEs (including incidence), physical examination findings including injection site signs and symptoms, and vital signs. Descriptive statistics (frequency and percentage for categorical variables; univariate descriptive statistics for continuous variables) are used to summarize all safety variables by treatment cohorts. The incidence of subjects with AEs is tabulated by MedDRA System Organ Class (SOC), Preferred Term, and grade or severity, and relationship to study drug. SAEs are also listed and summarized separately. All safety endpoints are provided in data listings. Additional details of the safety analyses are provided in the SAP.

Tolerability analysis: Evaluations of treatment groups are performed using a Freidman U test with post hoc tests (Wilcoxon tests) including Bonferroni adjustment. These analyses are performed using the evaluable and safety analysis sets. Additional statistical models using the raw data from each treatment, rather than the differences, are also explored.

Handling of Missing Data

Only observed data is included in the summary tables and listings and in statistical comparisons. Missing data is not imputed.

Results

TABLE 86

| ICON Screen No | YOB | Gender | Canfield No | HVAI Injection Time (sec) |
|---|---|---|---|---|
| 101-1028 | 2001 | M | 001-201 | 31.15 |
| 101-1033 | 1969 | F | 001-202 | 31.38 |
| 101-1029 | 2004 | F | 001-203 | 29.47 |
| 101-1031 | 1970 | M | 001-204 | 33.72 |
| 101-1034 | 1998 | M | 001-205 | 28.96 |
| 101-1030 | 1962 | F | 001-206 | 27.57 |
| 101-1035 | 1975 | F | 001-207 | 28.61 |
| 101-1037 | 1966 | F | 001-208 | 24.49 |
| 101-1038 | 1976 | F | 001-209 | 29.07 |
| 101-1040 | 1975 | F | 001-210 | 24.05 |
| 101-1041 | 1980 | F | 001-211 | 32.15 |
| 101-1043 | 1975 | F | 001-212 | 24.16 |
| 101-1001 | 1990 | M | 001-213 | 33.11 |
| 101-1002 | 1982 | F | 001-214 | 24.51 |
| 101-1003 | 1961 | M | 001-215 |  |
| 101-1004 | 1964 | F | 001-216 | 24.17 |
| 101-1005 | 1979 | M | 001-217 | 34.49 |
| 101-1008 | 1973 | F | 001-218 | 24.36 |
| 101-1007 | 1998 | F | 001-219 | 24.97 |
| 101-1010 | 1987 | F | 001-220 | 22.91 |
| 101-1009 | 1982 | F | 001-221 | 24.63 |
| 101-1012 | 1968 | M | 001-222 | 23.84 |
| 101-1013 | 1963 | M | 001-223 | 32.60 |
|  |  |  | average | 27.93 |
|  |  |  | STDev | 3.77 |

Tables 87 and 88 provide the applied force data from Injection visit #1—Cohort A (5 mL/30 seconds) and Cohort B (10 mL/30 seconds). Applied force was measured at these two different flow rates (10 mL/min and 20 mL/min) when injecting either 5 mL (Table 87) or 10 mL (Table 88) in 30 seconds.

Tables 89-93 provide overviews of the data from the human clinical trials, including adverse events (Table 89), demographics (Table 90), informed consent (Table 91), injection visits (Table 92), and follow-up visits (Table 93).

TABLE 87

Applied force data from Injection visit #1 - Cohort A measured at a flow rate of 10 mL/min (when injecting 5 mL in 30 seconds).
Cohort A - 5 mL/30 s

| Time (sec) | 25G-Terumo | | | | | | |
|---|---|---|---|---|---|---|---|
|  | 1001 | 1002 | 1003 | 1004 | 1005 | 1006 | 1007 |
| 0 | −0.001 | −0.003 | 0.063 | 0.615 | −0.021 | 0.068 | 0.002 |
|  | 0.322 | 5.208 | 0.212 | 8.983 |  | 4.824 | 3.288 |
|  | 7.350 | 10.775 | 5.225 | 13.535 |  | 8.108 | 3.461 |
|  | 10.161 | 14.358 | 8.229 | 15.207 |  | 10.538 | 3.392 |
| 1 | 12.961 | 15.882 | 11.200 | 16.771 | 3.496 | 13.307 | 4.135 |
|  | 14.910 | 17.728 | 13.139 | 18.127 |  | 15.943 | 4.688 |
|  | 16.557 | 19.183 | 14.607 | 19.347 |  | 18.008 | 5.242 |
|  | 18.069 | 20.629 | 15.661 | 20.074 |  | 19.972 | 5.757 |
| 2 | 19.130 | 21.902 | 16.354 | 20.802 | 6.531 | 21.779 | 6.015 |
|  | 20.027 | 22.891 | 17.053 | 21.295 |  | 23.238 | 6.325 |
|  | 20.872 | 23.810 | 17.662 | 21.648 |  | 24.534 | 6.611 |
|  | 21.431 | 24.513 | 18.099 | 22.011 |  | 25.508 | 6.589 |

TABLE 87-continued

Applied force data from Injection visit #1 - Cohort A measured
at a flow rate of 10 mL/min (when injecting 5 mL in 30 seconds).
Cohort A - 5 mL/30 s

| | | | | | | | |
|---|---|---|---|---|---|---|---|
| 3 | 21.904 | 25.153 | 18.600 | 22.358 | 13.702 | 26.005 | 6.885 |
| | 22.413 | 25.744 | 18.870 | 22.676 | | 26.618 | 7.168 |
| | 22.775 | 26.151 | 19.010 | 23.017 | | 27.209 | 8.018 |
| | 23.106 | 26.478 | 19.251 | 23.295 | | 27.708 | 8.432 |
| 4 | 23.409 | 26.891 | 19.429 | 23.497 | 16.325 | 27.987 | 9.417 |
| | 23.702 | 27.196 | 19.552 | 23.781 | | 28.276 | 10.378 |
| | 23.981 | 27.445 | 19.718 | 24.069 | | 28.596 | 11.060 |
| | 24.190 | 27.765 | 19.925 | 24.256 | | 28.873 | 11.859 |
| 5 | 24.490 | 28.019 | 20.008 | 24.445 | 17.941 | 29.051 | 12.534 |
| | 24.727 | 28.213 | 20.077 | 24.711 | | 29.257 | 13.020 |
| | 24.886 | 28.439 | 20.141 | 24.891 | | 29.415 | 13.438 |
| | 25.070 | 28.713 | 20.168 | 25.012 | | 29.466 | 13.822 |
| 6 | 25.219 | 28.843 | 20.222 | 25.164 | 18.902 | 29.498 | 14.215 |
| | 25.264 | 28.958 | 20.232 | 25.333 | | 29.643 | 14.561 |
| | 25.320 | 29.088 | 20.263 | 25.476 | | 29.688 | 14.873 |
| | 25.473 | 29.191 | 20.322 | 25.661 | | 29.731 | 15.129 |
| 7 | 25.543 | 29.269 | 20.359 | 25.896 | 19.653 | 29.789 | 15.363 |
| | 25.630 | 29.361 | 20.386 | 26.009 | | 29.799 | 15.479 |
| | 25.699 | 29.460 | 20.442 | 26.071 | | 29.795 | 15.577 |
| | 25.690 | 29.512 | 20.479 | 26.109 | | 29.740 | 15.769 |
| 8 | 25.690 | 29.598 | 20.444 | 26.102 | 20.061 | 29.732 | 15.909 |
| | 25.638 | 29.669 | 20.367 | 26.085 | | 29.683 | 16.059 |
| | 25.623 | 29.723 | 20.420 | 26.028 | | 29.650 | 16.191 |
| | 25.539 | 29.762 | 20.395 | 25.992 | | 29.592 | 16.282 |
| 9 | 25.416 | 29.674 | 20.278 | 25.854 | 20.425 | 29.525 | 16.374 |
| | 25.257 | 29.508 | 20.229 | 25.686 | | 29.545 | 16.418 |
| | 25.020 | 29.333 | 20.187 | 25.472 | | 29.467 | 16.435 |
| | 24.691 | 29.074 | 20.116 | 25.237 | | 29.317 | 16.535 |
| 10 | 24.280 | 28.699 | 20.036 | 24.957 | 20.845 | 29.082 | 16.648 |
| | 23.751 | 28.294 | 20.114 | 24.508 | | 28.811 | 16.756 |
| | 23.133 | 27.843 | 20.048 | 24.106 | | 28.474 | 16.805 |
| | 22.573 | 27.085 | 19.995 | 23.681 | | 28.189 | 16.835 |
| 11 | 22.113 | 26.214 | 20.017 | 23.201 | 20.962 | 27.996 | 16.811 |
| | 21.679 | 24.892 | 19.963 | 22.724 | | 27.740 | 16.771 |
| | 21.340 | 23.450 | 19.910 | 22.312 | | 27.492 | 16.855 |
| | 21.122 | 22.818 | 19.873 | 21.894 | | 27.380 | 16.900 |
| 12 | 20.899 | 22.300 | 19.935 | 20.935 | 21.233 | 27.187 | 16.997 |
| | 20.843 | 21.727 | 19.923 | 20.543 | | 26.907 | 17.053 |
| | 20.727 | 21.120 | 19.930 | 20.530 | | 26.728 | 17.071 |
| | 20.589 | 20.562 | 19.923 | 20.239 | | 26.623 | 17.045 |
| 13 | 20.499 | 20.239 | 19.858 | 19.961 | 21.318 | 26.535 | 17.004 |
| | 20.430 | 19.955 | 19.829 | 19.919 | | 26.452 | 17.075 |
| | 20.370 | 19.847 | 19.837 | 19.771 | | 26.477 | 17.129 |
| | 20.273 | 19.854 | 19.862 | 19.629 | | 26.391 | 17.257 |
| 14 | 20.306 | 19.807 | 19.893 | 19.536 | 21.420 | 26.313 | 17.291 |
| | 20.238 | 19.786 | 19.905 | 19.530 | | 26.305 | 17.325 |
| | 20.168 | 19.808 | 19.910 | 19.522 | | 26.184 | 17.294 |
| | 20.197 | 19.869 | 19.920 | 19.484 | | 26.122 | 17.267 |
| 15 | 20.133 | 19.907 | 19.954 | 19.526 | 21.221 | 26.112 | 17.312 |
| | 20.079 | 19.911 | 19.895 | 19.517 | | 26.059 | 17.343 |
| | 20.074 | 19.950 | 19.830 | 19.493 | | 26.026 | 17.476 |
| | 20.083 | 19.966 | 19.896 | 19.474 | | 25.977 | 17.533 |
| 16 | 20.076 | 20.016 | 19.870 | 19.506 | 21.070 | 25.883 | 17.581 |
| | 20.066 | 20.048 | 19.786 | 19.478 | | 25.786 | 17.587 |
| | 20.091 | 20.088 | 19.812 | 19.469 | | 25.771 | 17.579 |
| | 20.069 | 20.213 | 19.825 | 19.468 | | 25.832 | 17.645 |
| 17 | 20.075 | 20.264 | 19.820 | 19.410 | 21.159 | 25.846 | 17.671 |
| | 20.054 | 20.281 | 19.802 | 19.370 | | 25.824 | 17.794 |
| | 20.052 | 20.325 | 19.874 | 19.355 | | 25.803 | 17.854 |
| | 20.098 | 20.374 | 19.832 | 19.344 | | 25.701 | 17.868 |
| 18 | 20.134 | 20.394 | 19.751 | 19.376 | 21.009 | 25.652 | 17.861 |
| | 20.085 | 20.415 | 19.772 | 19.253 | | 25.551 | 17.821 |
| | 20.072 | 20.532 | 19.736 | 19.053 | | 25.345 | 17.813 |
| | 20.080 | 20.595 | 19.669 | 19.017 | | 25.160 | 17.871 |
| 19 | 20.063 | 20.595 | 19.614 | 18.976 | 21.057 | 25.077 | 17.920 |
| | 20.060 | 20.696 | 19.656 | 18.878 | | 24.887 | 18.007 |
| | 20.152 | 20.774 | 19.616 | 18.808 | | 24.657 | 18.058 |
| | 20.179 | 20.789 | 19.640 | 18.840 | | 24.736 | 18.081 |
| 20 | 20.127 | 20.836 | 19.754 | 18.791 | 20.955 | 24.793 | 18.050 |
| | 20.168 | 20.996 | 19.792 | 18.670 | | 24.782 | 18.015 |
| | 20.174 | 21.017 | 19.814 | 18.688 | | 24.805 | 18.085 |
| | 20.151 | 21.055 | 19.887 | 18.645 | | 24.876 | 18.117 |
| 21 | 20.141 | 21.118 | 19.937 | 18.595 | 21.107 | 24.894 | 18.228 |
| | 20.226 | 21.154 | 20.001 | 18.586 | | 24.840 | 18.260 |
| | 20.187 | 21.202 | 20.019 | 18.643 | | 24.875 | 18.258 |
| | 20.118 | 21.317 | 20.015 | 18.616 | | 24.812 | 18.181 |

TABLE 87-continued

Applied force data from Injection visit #1 - Cohort A measured at a flow rate of 10 mL/min (when injecting 5 mL in 30 seconds).
Cohort A - 5 mL/30 s

| | | | | | | | | |
|---|---|---|---|---|---|---|---|---|
| 22 | | 20.165 | 21.465 | 20.060 | 18.582 | 21.079 | 24.738 | 18.125 |
| | | 20.134 | 21.589 | 20.106 | 18.642 | | 24.691 | 18.175 |
| | | 20.096 | 21.699 | 20.088 | 18.656 | | 24.707 | 18.197 |
| | | 20.129 | 21.833 | 20.084 | 18.645 | | 24.673 | 18.287 |
| 23 | | 20.165 | 21.903 | 20.152 | 18.627 | 21.166 | 24.660 | 18.309 |
| | | 20.162 | 21.927 | 20.167 | 18.688 | | 24.706 | 18.263 |
| | | 20.148 | 21.971 | 20.095 | 18.655 | | 24.697 | 18.149 |
| | | 20.181 | 22.011 | 20.129 | 18.642 | | 24.762 | 18.034 |
| 24 | | 20.210 | 22.072 | 20.138 | 18.661 | 21.075 | 24.811 | 18.029 |
| | | 20.232 | 22.142 | 20.126 | 18.637 | | 24.814 | 17.984 |
| | | 20.203 | 22.179 | 20.125 | 18.627 | | 24.881 | 18.021 |
| | | 20.188 | 22.286 | 20.241 | 18.640 | | 24.945 | 18.045 |
| 25 | | 20.212 | 22.403 | 20.249 | 18.652 | 21.181 | 24.977 | 18.026 |
| | | 20.219 | 22.492 | 20.188 | 18.686 | | 25.019 | 17.961 |
| | | 20.174 | 22.613 | 20.257 | 18.731 | | 25.048 | 17.884 |
| | | 20.174 | 22.887 | 20.259 | 18.764 | | 24.999 | 17.826 |
| 26 | | 20.196 | 23.102 | 20.212 | 18.834 | 21.115 | 24.894 | 17.841 |
| | | 20.197 | 23.249 | 20.181 | 18.919 | | 24.864 | 17.854 |
| | | 20.199 | 23.489 | 20.225 | 18.916 | | 24.701 | 17.892 |
| | | 20.273 | 23.619 | 20.244 | 18.907 | | 24.500 | 17.895 |
| 27 | | 20.297 | 23.678 | 20.272 | 18.961 | 21.116 | 24.503 | 17.871 |
| | | 20.270 | 23.718 | 20.335 | 18.982 | | 24.450 | 17.826 |
| | | 20.356 | 23.988 | 20.329 | 18.914 | | 24.395 | 17.758 |
| | | 20.385 | 24.080 | 20.291 | 18.946 | | 24.332 | 17.802 |
| 28 | | 20.382 | 24.224 | 20.330 | 18.936 | 21.573 | 24.324 | 17.829 |
| | | 20.368 | 24.509 | 20.328 | 18.923 | | 24.291 | 17.880 |
| | | 20.457 | 24.674 | 20.378 | 18.913 | | 24.232 | 17.896 |
| | | 20.485 | 24.812 | 20.392 | 19.010 | | 24.280 | 17.879 |
| 29 | | 20.472 | 24.958 | 20.380 | 19.030 | 21.859 | 24.213 | 17.813 |
| | Avg. | 20.76 | 22.97 | 19.12 | 20.54 | 18.68 | 25.36 | 15.33 |
| | SD | 3.92 | 4.61 | 3.31 | 3.53 | 5.54 | 4.57 | 4.37 |
| | SEM | 0.36 | 0.43 | 0.31 | 0.33 | 0.51 | 0.42 | 0.40 |

| | | 25G-Terumo | | 25G-BD | | |
|---|---|---|---|---|---|---|
| Time (sec) | | 1008 | 1009 | 1010 | 1011 | 1012 |
| 0 | | 0.752 | 0.093 | −0.024 | 0.754 | 0.244 |
| | | 3.158 | 2.488 | 1.161 | 3.736 | 5.222 |
| | | 10.836 | 3.666 | 9.595 | 7.028 | 10.526 |
| | | 12.566 | 4.318 | 12.333 | 7.804 | 12.717 |
| 1 | | 14.977 | 4.931 | 16.288 | 9.789 | 15.133 |
| | | 17.059 | 5.422 | 19.901 | 11.421 | 17.136 |
| | | 18.470 | 6.899 | 23.233 | 12.445 | 18.991 |
| | | 19.503 | 8.613 | 25.960 | 13.527 | 20.631 |
| 2 | | 20.418 | 10.225 | 29.014 | 14.636 | 22.200 |
| | | 21.290 | 11.967 | 31.275 | 15.524 | 23.505 |
| | | 21.861 | 13.271 | 33.456 | 16.290 | 24.626 |
| | | 22.438 | 14.285 | 35.032 | 17.049 | 25.706 |
| 3 | | 22.852 | 15.196 | 36.669 | 17.769 | 26.522 |
| | | 23.119 | 15.920 | 38.204 | 18.313 | 27.352 |
| | | 23.413 | 16.469 | 39.107 | 18.904 | 28.073 |
| | | 23.754 | 16.984 | 39.936 | 19.314 | 28.778 |
| 4 | | 23.970 | 17.485 | 40.779 | 19.787 | 29.314 |
| | | 24.252 | 17.913 | 41.686 | 20.099 | 29.850 |
| | | 24.489 | 18.242 | 42.429 | 20.477 | 30.220 |
| | | 24.681 | 18.505 | 43.120 | 20.945 | 30.659 |
| 5 | | 24.964 | 18.690 | 43.803 | 21.489 | 31.134 |
| | | 25.213 | 18.833 | 44.330 | 21.993 | 31.543 |
| | | 25.460 | 18.931 | 44.837 | 22.395 | 31.944 |
| | | 25.671 | 19.156 | 44.179 | 22.802 | 32.344 |
| 6 | | 25.821 | 19.248 | 44.613 | 23.145 | 32.685 |
| | | 25.900 | 19.442 | 45.204 | 23.554 | 32.950 |
| | | 25.986 | 19.540 | 45.662 | 23.859 | 33.180 |
| | | 26.080 | 19.585 | 46.166 | 24.113 | 33.401 |
| 7 | | 26.104 | 19.569 | 46.547 | 24.225 | 33.511 |
| | | 26.106 | 19.544 | 46.880 | 24.443 | 33.589 |
| | | 26.072 | 19.616 | 47.320 | 24.746 | 33.732 |
| | | 25.971 | 19.682 | 47.645 | 24.932 | 33.615 |
| 8 | | 25.834 | 19.812 | 47.898 | 25.197 | 33.319 |
| | | 25.730 | 19.861 | 48.014 | 25.455 | 33.266 |
| | | 25.551 | 19.884 | 48.230 | 25.678 | 33.379 |
| | | 25.336 | 19.858 | 48.361 | 25.855 | 33.486 |

TABLE 87-continued

Applied force data from Injection visit #1 - Cohort A measured at a flow rate of 10 mL/min (when injecting 5 mL in 30 seconds).
Cohort A - 5 mL/30 s

| | | | | | |
|---|---|---|---|---|---|
| 9 | 25.077 | 19.781 | 48.373 | 25.957 | 33.590 |
| | 24.836 | 19.716 | 48.257 | 26.046 | 33.787 |
| | 24.429 | 19.709 | 48.032 | 26.217 | 33.876 |
| | 23.996 | 19.793 | 47.817 | 26.360 | 33.906 |
| 10 | 23.535 | 19.799 | 47.654 | 26.551 | 33.907 |
| | 23.088 | 19.807 | 47.473 | 26.649 | 33.889 |
| | 22.666 | 19.802 | 47.249 | 26.723 | 33.801 |
| | 22.198 | 19.760 | 46.928 | 26.758 | 33.648 |
| 11 | 21.783 | 19.721 | 46.466 | 26.759 | 33.569 |
| | 21.495 | 19.738 | 46.060 | 26.852 | 33.318 |
| | 21.407 | 19.773 | 45.658 | 26.947 | 32.979 |
| | 21.266 | 19.802 | 45.327 | 27.065 | 32.758 |
| 12 | 21.102 | 19.787 | 44.941 | 27.149 | 32.389 |
| | 21.027 | 19.741 | 44.637 | 27.232 | 32.080 |
| | 20.921 | 19.684 | 44.287 | 27.279 | 31.817 |
| | 20.801 | 19.658 | 44.102 | 27.303 | 31.637 |
| 13 | 20.701 | 19.685 | 44.029 | 27.343 | 31.522 |
| | 20.614 | 19.711 | 43.940 | 27.423 | 31.407 |
| | 20.513 | 19.778 | 43.852 | 27.519 | 31.335 |
| | 20.396 | 19.775 | 43.772 | 27.634 | 31.266 |
| 14 | 20.319 | 19.764 | 43.752 | 27.690 | 31.208 |
| | 20.203 | 19.691 | 43.493 | 27.718 | 31.114 |
| | 20.176 | 19.619 | 43.192 | 27.740 | 31.061 |
| | 20.229 | 19.672 | 42.904 | 27.768 | 31.144 |
| 15 | 20.173 | 19.687 | 42.677 | 27.860 | 31.117 |
| | 20.093 | 19.812 | 42.451 | 27.974 | 31.007 |
| | 20.095 | 19.847 | 42.306 | 28.083 | 30.986 |
| | 20.063 | 19.878 | 42.353 | 28.163 | 30.929 |
| 16 | 19.982 | 19.902 | 42.383 | 28.159 | 30.865 |
| | 19.931 | 19.935 | 42.409 | 28.151 | 30.792 |
| | 19.989 | 19.999 | 42.437 | 28.155 | 30.843 |
| | 19.934 | 20.029 | 42.405 | 28.216 | 30.805 |
| 17 | 19.836 | 20.100 | 42.323 | 28.277 | 30.697 |
| | 19.803 | 20.152 | 42.257 | 28.357 | 30.700 |
| | 19.755 | 20.193 | 42.239 | 28.388 | 30.671 |
| | 19.648 | 20.203 | 42.237 | 28.385 | 30.594 |
| 18 | 19.481 | 20.213 | 42.268 | 28.343 | 30.587 |
| | 19.391 | 20.292 | 42.263 | 28.280 | 30.656 |
| | 19.301 | 20.423 | 42.297 | 28.306 | 30.646 |
| | 19.158 | 20.564 | 42.321 | 28.339 | 30.643 |
| 19 | 19.104 | 20.717 | 42.294 | 28.388 | 30.668 |
| | 19.041 | 20.793 | 42.241 | 28.390 | 30.636 |
| | 18.984 | 20.778 | 42.290 | 28.366 | 30.623 |
| | 18.993 | 20.765 | 42.311 | 28.320 | 30.634 |
| 20 | 19.018 | 20.859 | 42.295 | 28.262 | 30.663 |
| | 18.980 | 20.908 | 42.423 | 28.285 | 30.713 |
| | 19.026 | 20.967 | 42.505 | 28.296 | 30.730 |
| | 18.975 | 21.068 | 42.564 | 28.333 | 30.706 |
| 21 | 18.986 | 21.159 | 42.601 | 28.366 | 30.719 |
| | 18.973 | 21.186 | 42.781 | 28.384 | 30.730 |
| | 18.933 | 21.183 | 42.808 | 28.375 | 30.701 |
| | 18.860 | 21.170 | 42.810 | 28.317 | 30.695 |
| 22 | 18.905 | 21.222 | 42.924 | 28.323 | 30.735 |
| | 18.912 | 21.193 | 42.957 | 28.333 | 30.734 |
| | 18.845 | 21.237 | 42.987 | 28.353 | 30.698 |
| | 18.894 | 21.184 | 42.999 | 28.405 | 30.724 |
| 23 | 18.873 | 21.097 | 43.098 | 28.427 | 30.723 |
| | 18.834 | 20.989 | 43.031 | 28.399 | 30.679 |
| | 18.827 | 20.937 | 42.924 | 28.356 | 30.639 |
| | 18.938 | 20.936 | 42.973 | 28.324 | 30.748 |
| 24 | 18.932 | 20.941 | 43.002 | 28.358 | 30.723 |
| | 18.863 | 20.982 | 43.034 | 28.420 | 30.663 |
| | 18.913 | 20.967 | 43.096 | 28.529 | 30.699 |
| | 18.929 | 20.963 | 43.254 | 28.562 | 30.683 |
| 25 | 18.878 | 20.890 | 43.395 | 28.556 | 30.649 |
| | 18.833 | 20.833 | 43.491 | 28.520 | 30.641 |
| | 18.939 | 20.790 | 43.515 | 28.493 | 30.703 |
| | 18.886 | 20.778 | 43.604 | 28.527 | 30.701 |
| 26 | 18.891 | 20.837 | 43.689 | 28.593 | 30.714 |
| | 18.904 | 20.890 | 43.707 | 28.696 | 30.742 |
| | 18.884 | 20.919 | 43.734 | 28.720 | 30.748 |
| | 18.863 | 20.764 | 43.857 | 28.709 | 30.743 |
| 27 | 18.878 | 20.553 | 43.909 | 28.667 | 30.773 |
| | 18.870 | 20.350 | 43.881 | 28.631 | 30.826 |
| | 18.894 | 20.195 | 43.999 | 28.642 | 30.876 |
| | 18.905 | 20.156 | 44.052 | 28.657 | 30.878 |

TABLE 87-continued

Applied force data from Injection visit #1 - Cohort A measured at a flow rate of 10 mL/min (when injecting 5 mL in 30 seconds).
Cohort A - 5 mL/30 s

|    |      |       |       |       |       |        |
|----|------|-------|-------|-------|-------|--------|
| 28 |      | 18.841 | 20.190 | 44.049 | 28.723 | 30.855 |
|    |      | 18.850 | 20.158 | 44.098 | 28.782 | 30.843 |
|    |      | 18.855 | 20.042 | 44.269 | 28.797 | 30.866 |
|    |      | 18.803 | 19.962 | 44.257 | 28.759 | 30.886 |
| 29 |      | 18.773 | 19.881 | 44.252 | 28.717 | 30.945 |
|    | Avg. | 20.52 | 18.65 | 41.37 | 25.11 | 29.81 |
|    | SD   | 3.76  | 4.25  | 8.47  | 5.70  | 5.34  |
|    | SEM  | 0.35  | 0.39  | 0.78  | 0.52  | 0.49  |

| For entire series: | 25G-Terumo | 25G-BD |
|---|---|---|
| Avg. | 20.4 | 32.1 |
| SD | 4.9 | 9.5 |
| SEM | 0.2 | 0.5 |

TABLE 88

Applied force data from Injection visit #1 - Cohort B measured at a flow rate of 20 mL/min (when injecting 10 mL in 30 seconds).

| Time (sec) | 1013 | 1014 | 1015 | 1016 | 1017 | 1018 |
|---|---|---|---|---|---|---|
| 0 | 1.576 | 0.151 | 0.106 | −0.311 | 0.488 | 1.587 |
|   | 7.232 | 0.514 | 7.250 | 6.397 | 2.101 | 7.881 |
|   | 12.904 | 9.324 | 8.734 | 12.539 | 11.951 | 16.006 |
|   | 16.621 | 13.721 | 13.803 | 16.541 | 14.315 | 21.124 |
| 1 | 21.367 | 17.597 | 17.185 | 18.235 | 16.996 | 25.059 |
|   | 25.011 | 19.791 | 19.522 | 20.494 | 19.930 | 27.821 |
|   | 27.403 | 21.845 | 21.831 | 22.225 | 22.520 | 30.126 |
|   | 29.665 | 23.811 | 23.776 | 24.126 | 24.434 | 31.888 |
| 2 | 31.712 | 25.305 | 25.025 | 24.631 | 26.542 | 30.743 |
|   | 33.343 | 26.411 | 26.742 | 26.276 | 28.458 | 32.490 |
|   | 34.689 | 27.796 | 28.423 | 27.534 | 29.929 | 33.629 |
|   | 36.020 | 29.268 | 29.744 | 28.699 | 31.262 | 34.659 |
| 3 | 37.032 | 30.413 | 30.858 | 29.736 | 32.366 | 35.440 |
|   | 37.655 | 31.225 | 31.897 | 30.699 | 33.275 | 36.213 |
|   | 38.163 | 32.097 | 32.831 | 31.539 | 33.984 | 36.809 |
|   | 38.795 | 32.797 | 33.532 | 32.294 | 34.532 | 37.073 |
| 4 | 39.205 | 33.270 | 34.131 | 32.984 | 35.215 | 37.507 |
|   | 39.488 | 33.871 | 34.822 | 33.606 | 35.776 | 37.838 |
|   | 39.861 | 34.412 | 35.277 | 34.102 | 36.203 | 38.151 |
|   | 40.337 | 34.712 | 35.583 | 34.503 | 36.606 | 38.119 |
| 5 | 40.565 | 35.054 | 35.977 | 34.870 | 37.113 | 38.062 |
|   | 40.709 | 35.535 | 36.459 | 35.067 | 37.421 | 37.836 |
|   | 41.034 | 35.873 | 36.696 | 35.212 | 37.654 | 37.705 |
|   | 41.247 | 35.993 | 36.866 | 35.352 | 38.030 | 37.549 |
| 6 | 41.318 | 36.230 | 37.173 | 35.356 | 38.289 | 37.472 |
|   | 41.502 | 36.547 | 37.428 | 35.511 | 38.426 | 37.507 |
|   | 41.782 | 36.626 | 37.494 | 35.560 | 38.568 | 37.568 |
|   | 41.828 | 36.692 | 37.647 | 35.687 | 38.854 | 37.645 |
| 7 | 41.777 | 36.872 | 37.916 | 35.779 | 39.070 | 37.658 |
|   | 41.976 | 37.006 | 38.038 | 35.767 | 39.187 | 37.756 |
|   | 42.103 | 36.982 | 38.005 | 35.813 | 39.265 | 37.746 |
|   | 42.044 | 37.023 | 38.151 | 35.862 | 39.470 | 37.822 |
| 8 | 42.084 | 37.242 | 38.377 | 35.984 | 39.426 | 37.789 |
|   | 42.251 | 37.326 | 38.386 | 36.019 | 39.230 | 37.878 |
|   | 42.258 | 37.319 | 38.419 | 36.152 | 39.239 | 37.893 |
|   | 42.191 | 37.438 | 38.523 | 36.239 | 39.401 | 37.847 |
| 9 | 42.316 | 37.558 | 38.522 | 36.347 | 39.427 | 37.909 |
|   | 42.465 | 37.520 | 38.412 | 36.364 | 39.493 | 37.892 |
|   | 42.410 | 37.486 | 38.476 | 36.448 | 39.687 | 37.981 |
|   | 42.413 | 37.605 | 38.665 | 36.377 | 39.716 | 37.965 |
| 10 | 42.557 | 37.617 | 38.670 | 36.166 | 39.626 | 38.063 |
|   | 42.594 | 37.512 | 38.661 | 36.143 | 39.773 | 38.122 |
|   | 42.486 | 37.563 | 38.824 | 36.034 | 39.878 | 38.125 |
|   | 42.537 | 37.745 | 38.948 | 36.051 | 39.907 | 38.212 |
| 11 | 42.732 | 37.726 | 38.931 | 36.060 | 39.864 | 38.173 |
|   | 42.713 | 37.642 | 38.905 | 36.134 | 40.025 | 38.272 |
|   | 42.648 | 37.756 | 39.008 | 36.160 | 40.015 | 38.217 |
|   | 42.753 | 37.822 | 39.058 | 36.250 | 39.940 | 38.291 |

TABLE 88-continued

Applied force data from Injection visit #1 - Cohort B measured
at a flow rate of 20 mL/min (when injecting 10 mL in 30 seconds).

| | | | | | | |
|---|---|---|---|---|---|---|
| 12 | 42.851 | 37.735 | 38.958 | 36.294 | 39.954 | 38.222 |
| | 42.789 | 37.707 | 39.000 | 36.397 | 40.155 | 38.240 |
| | 42.769 | 37.892 | 39.119 | 36.474 | 40.178 | 38.193 |
| | 42.963 | 37.933 | 39.041 | 36.477 | 40.145 | 38.242 |
| 13 | 42.972 | 37.860 | 38.888 | 36.578 | 40.246 | 38.188 |
| | 42.845 | 37.975 | 38.844 | 36.601 | 40.385 | 38.117 |
| | 42.867 | 38.117 | 38.827 | 36.665 | 40.347 | 38.068 |
| | 43.010 | 38.110 | 38.744 | 36.640 | 40.337 | 37.988 |
| 14 | 42.977 | 38.095 | 38.665 | 36.756 | 40.462 | 37.958 |
| | 42.914 | 38.215 | 38.738 | 36.815 | 40.473 | 37.932 |
| | 43.033 | 38.316 | 38.689 | 36.795 | 40.336 | 38.017 |
| | 43.105 | 38.215 | 38.549 | 36.882 | 40.341 | 38.056 |
| 15 | 42.992 | 38.244 | 38.589 | 36.910 | 40.452 | 38.092 |
| | 42.957 | 38.381 | 38.736 | 36.922 | 40.423 | 38.117 |
| | 43.107 | 38.373 | 38.733 | 36.903 | 40.349 | 38.230 |
| | 43.117 | 38.303 | 38.736 | 37.004 | 40.433 | 38.332 |
| 16 | 42.991 | 38.395 | 38.922 | 37.010 | 40.538 | 38.344 |
| | 43.031 | 38.492 | 39.030 | 37.049 | 40.469 | 38.522 |
| | 43.141 | 38.458 | 38.919 | 37.024 | 40.494 | 38.573 |
| | 43.036 | 38.459 | 38.907 | 37.103 | 40.679 | 38.641 |
| 17 | 42.994 | 38.609 | 39.008 | 37.108 | 40.700 | 38.612 |
| | 43.080 | 38.696 | 38.943 | 37.123 | 40.649 | 38.666 |
| | 43.154 | 38.606 | 38.857 | 37.186 | 40.720 | 38.631 |
| | 43.088 | 38.652 | 38.927 | 37.221 | 40.764 | 38.588 |
| 18 | 43.075 | 38.771 | 39.020 | 37.260 | 40.708 | 38.555 |
| | 43.180 | 38.728 | 38.949 | 37.196 | 40.622 | 38.604 |
| | 43.149 | 38.695 | 38.952 | 37.272 | 40.698 | 38.635 |
| | 43.044 | 38.765 | 39.116 | 37.290 | 40.727 | 38.634 |
| 19 | 43.109 | 38.825 | 39.177 | 37.252 | 40.639 | 38.733 |
| | 43.214 | 38.763 | 39.144 | 37.193 | 40.655 | 38.760 |
| | 43.148 | 38.787 | 39.244 | 37.208 | 40.710 | 38.847 |
| | 43.144 | 38.900 | 39.389 | 37.174 | 40.608 | 38.876 |
| 20 | 43.239 | 38.925 | 39.401 | 37.096 | 40.487 | 39.007 |
| | 43.275 | 38.843 | 39.434 | 37.109 | 40.450 | 39.055 |
| | 43.171 | 38.895 | 39.541 | 37.073 | 40.489 | 39.124 |
| | 43.223 | 38.966 | 39.636 | 37.085 | 40.393 | 39.204 |
| 21 | 43.327 | 38.905 | 39.612 | 37.035 | 40.353 | 39.209 |
| | 43.288 | 38.880 | 39.645 | 37.078 | 40.464 | 39.257 |
| | 43.192 | 38.942 | 39.759 | 37.075 | 40.465 | 39.199 |
| | 43.240 | 38.954 | 39.756 | 37.007 | 40.372 | 39.287 |
| 22 | 43.294 | 38.810 | 39.749 | 36.971 | 40.382 | 39.287 |
| | 43.193 | 38.741 | 39.820 | 36.901 | 40.448 | 39.284 |
| | 43.179 | 38.785 | 39.999 | 36.909 | 40.336 | 39.331 |
| | 43.256 | 38.772 | 39.932 | 36.822 | 40.283 | 39.282 |
| 23 | 43.254 | 38.664 | 39.854 | 36.795 | 40.418 | 39.309 |
| | 43.130 | 38.694 | 39.892 | 36.770 | 40.442 | 39.226 |
| | 43.205 | 38.788 | 39.886 | 36.766 | 40.337 | 39.242 |
| | 43.296 | 38.679 | 39.776 | 36.584 | 40.295 | 39.213 |
| 24 | 43.243 | 38.638 | 39.812 | 36.547 | 40.364 | 39.193 |
| | 43.289 | 38.711 | 39.945 | 36.530 | 40.315 | 39.147 |
| | 43.294 | 38.707 | 39.958 | 36.385 | 40.192 | 39.158 |
| | 43.318 | 38.622 | 39.911 | 36.375 | 40.226 | 39.008 |
| 25 | 43.195 | 38.604 | 39.944 | 36.346 | 40.340 | 38.894 |
| | 43.144 | 38.637 | 40.038 | 36.305 | 40.281 | 38.838 |
| | 43.199 | 38.544 | 39.935 | 36.173 | 40.173 | 38.782 |
| | 43.126 | 38.483 | 39.882 | 36.147 | 40.176 | 38.788 |
| 26 | 43.029 | 38.530 | 39.913 | 36.085 | 40.193 | 38.684 |
| | 43.021 | 38.613 | 39.844 | 35.983 | 40.050 | 38.688 |
| | 42.999 | 38.493 | 39.665 | 35.900 | 40.036 | 38.596 |
| | 42.890 | 38.420 | 39.586 | 35.824 | 40.109 | 38.553 |
| 27 | 42.788 | 38.362 | 39.586 | 35.774 | 40.043 | 38.442 |
| | 42.805 | 38.265 | 39.464 | 35.633 | 39.945 | 38.408 |
| | 42.760 | 38.129 | 39.399 | 35.499 | 39.936 | 38.316 |
| | 42.631 | 38.063 | 39.421 | 35.350 | 39.935 | 38.215 |
| 28 | 42.649 | 38.034 | 39.418 | 35.270 | 39.756 | 38.162 |
| | 42.646 | 37.914 | 39.285 | 35.136 | 39.712 | 38.003 |
| | 42.579 | 37.816 | 39.235 | 35.129 | 39.734 | 37.905 |
| | 42.521 | 37.826 | 39.236 | 35.240 | 39.712 | 37.759 |
| 29 | 42.504 | 37.817 | 39.177 | 35.262 | 39.600 | 37.758 |
| | 42.486 | 37.721 | 39.040 | 35.238 | 39.658 | 37.709 |
| | 42.310 | 37.726 | 39.002 | 35.060 | 39.764 | 37.749 |
| 20.22 | 40.51 | 35.68 | 36.55 | 34.35 | 37.52 | 36.90 |
| | 6.887144 | 6.880416 | 6.886747 | 5.975815 | 7.113836 | 5.36626 |
| | 0.631343 | 0.630727 | 0.631307 | 0.547802 | 0.652124 | 0.491924 |

TABLE 88-continued

Applied force data from Injection visit #1 - Cohort B measured at a flow rate of 20 mL/min (when injecting 10 mL in 30 seconds).

| Time (sec) | 1019 | 1020 | 1021 | 1022 | 1023 | 1024 |
|---|---|---|---|---|---|---|
| 0 | 0.156 | 0.683 | 0.033 | 0.956 | 0.457 | 1.043 |
|  | 0.731 | 7.932 | 5.078 | 11.147 | 0.945 | 7.564 |
|  | 8.485 | 14.973 | 11.550 | 16.792 | 10.067 | 15.882 |
|  | 13.956 | 19.883 | 16.592 | 19.993 | 13.832 | 21.115 |
| 1 | 18.872 | 21.457 | 21.195 | 22.676 | 17.431 | 25.015 |
|  | 21.725 | 22.657 | 24.943 | 25.705 | 20.173 | 28.182 |
|  | 25.971 | 25.740 | 28.447 | 27.686 | 22.519 | 30.686 |
|  | 29.214 | 27.808 | 30.954 | 30.597 | 24.122 | 32.811 |
| 2 | 33.711 | 29.695 | 33.283 | 33.011 | 25.373 | 34.492 |
|  | 37.516 | 31.307 | 35.475 | 35.409 | 26.871 | 36.153 |
|  | 40.812 | 32.608 | 37.067 | 37.264 | 27.995 | 37.394 |
|  | 43.429 | 33.861 | 38.537 | 39.081 | 29.197 | 38.303 |
| 3 | 45.202 | 34.489 | 40.038 | 40.648 | 29.700 | 39.126 |
|  | 46.543 | 35.391 | 41.170 | 41.916 | 30.640 | 39.738 |
|  | 47.249 | 36.197 | 42.044 | 43.115 | 31.277 | 40.296 |
|  | 47.574 | 36.800 | 43.129 | 44.308 | 31.982 | 40.722 |
| 4 | 47.860 | 37.201 | 44.305 | 45.152 | 32.711 | 41.135 |
|  | 48.174 | 37.522 | 45.176 | 45.914 | 33.148 | 41.339 |
|  | 48.343 | 37.577 | 45.873 | 46.586 | 33.450 | 41.423 |
|  | 48.467 | 37.496 | 46.762 | 47.013 | 33.988 | 41.362 |
| 5 | 48.743 | 37.300 | 47.447 | 47.398 | 34.440 | 41.246 |
|  | 49.025 | 37.226 | 47.921 | 47.562 | 34.633 | 40.800 |
|  | 49.106 | 37.226 | 48.489 | 47.700 | 34.910 | 40.425 |
|  | 49.216 | 37.367 | 49.311 | 47.732 | 35.230 | 40.200 |
| 6 | 49.493 | 37.528 | 49.840 | 48.079 | 35.387 | 40.170 |
|  | 49.592 | 37.726 | 50.329 | 48.296 | 35.482 | 40.079 |
|  | 49.685 | 37.893 | 50.865 | 48.508 | 35.766 | 40.026 |
|  | 49.927 | 38.028 | 51.378 | 48.714 | 36.064 | 40.043 |
| 7 | 50.175 | 38.211 | 51.620 | 48.886 | 36.135 | 40.007 |
|  | 50.291 | 38.358 | 51.817 | 49.054 | 36.276 | 40.081 |
|  | 50.411 | 38.504 | 52.234 | 49.150 | 36.546 | 40.127 |
|  | 50.544 | 38.665 | 52.498 | 49.362 | 36.591 | 40.371 |
| 8 | 50.749 | 38.798 | 52.694 | 49.508 | 36.610 | 40.614 |
|  | 50.807 | 38.915 | 53.026 | 49.791 | 36.777 | 40.790 |
|  | 50.888 | 38.983 | 53.236 | 49.980 | 36.839 | 41.070 |
|  | 51.091 | 39.119 | 53.482 | 50.213 | 36.847 | 41.144 |
| 9 | 51.126 | 39.171 | 53.825 | 50.278 | 36.812 | 41.300 |
|  | 51.012 | 39.227 | 54.444 | 50.407 | 36.916 | 41.327 |
|  | 50.987 | 39.258 | 54.736 | 50.675 | 36.991 | 41.499 |
|  | 51.012 | 39.378 | 55.007 | 50.214 | 36.949 | 41.543 |
| 10 | 50.929 | 39.373 | 55.568 | 49.617 | 36.972 | 41.532 |
|  | 50.842 | 39.451 | 56.433 | 49.100 | 37.140 | 41.579 |
|  | 50.897 | 39.450 | 56.834 | 48.669 | 37.141 | 41.525 |
|  | 50.931 | 39.586 | 56.767 | 48.283 | 37.069 | 41.521 |
| 11 | 50.853 | 39.620 | 55.957 | 47.967 | 37.142 | 41.474 |
|  | 50.905 | 39.639 | 55.548 | 47.735 | 37.256 | 41.525 |
|  | 51.093 | 39.744 | 54.837 | 47.601 | 37.197 | 41.498 |
|  | 51.081 | 39.763 | 54.165 | 47.373 | 37.146 | 41.484 |
| 12 | 51.076 | 39.840 | 53.596 | 47.075 | 37.275 | 41.487 |
|  | 51.191 | 39.877 | 52.999 | 46.900 | 37.238 | 41.569 |
|  | 51.206 | 39.971 | 52.404 | 46.595 | 37.052 | 41.595 |
|  | 51.071 | 39.994 | 51.950 | 46.458 | 37.009 | 41.682 |
| 13 | 51.045 | 40.062 | 51.695 | 46.303 | 37.022 | 41.800 |
|  | 51.093 | 40.126 | 51.253 | 46.222 | 36.898 | 41.927 |
|  | 50.762 | 40.196 | 50.667 | 46.037 | 36.802 | 42.027 |
|  | 50.471 | 40.300 | 50.107 | 45.867 | 36.947 | 42.115 |
| 14 | 50.351 | 40.342 | 49.594 | 45.671 | 36.938 | 42.215 |
|  | 50.269 | 40.445 | 49.334 | 45.345 | 36.888 | 42.228 |
|  | 50.146 | 40.500 | 48.912 | 44.942 | 36.859 | 42.231 |
|  | 50.009 | 40.544 | 48.725 | 44.535 | 37.020 | 42.184 |
| 15 | 50.032 | 40.603 | 48.581 | 44.273 | 37.104 | 42.200 |
|  | 50.006 | 40.639 | 48.388 | 43.991 | 37.070 | 42.174 |
|  | 49.802 | 40.670 | 48.279 | 43.844 | 37.153 | 42.135 |
|  | 49.672 | 40.641 | 47.495 | 43.698 | 37.300 | 42.218 |
| 16 | 49.679 | 40.701 | 46.266 | 43.681 | 37.291 | 42.217 |
|  | 49.640 | 40.758 | 45.105 | 43.653 | 37.216 | 42.293 |
|  | 49.645 | 40.790 | 44.361 | 43.625 | 37.293 | 42.331 |
|  | 49.800 | 40.802 | 43.792 | 43.751 | 37.344 | 42.458 |
| 17 | 49.986 | 40.903 | 43.161 | 43.812 | 37.241 | 42.497 |
|  | 49.957 | 40.858 | 42.622 | 43.933 | 37.190 | 42.555 |
|  | 49.893 | 40.902 | 42.303 | 43.928 | 37.266 | 42.683 |
|  | 49.894 | 40.867 | 41.967 | 43.981 | 37.254 | 42.721 |

TABLE 88-continued

Applied force data from Injection visit #1 - Cohort B measured at a flow rate of 20 mL/min (when injecting 10 mL in 30 seconds).

| | | | | | | |
|---|---|---|---|---|---|---|
| 18 | 49.653 | 40.955 | 41.621 | 43.875 | 37.214 | 42.799 |
| | 49.174 | 40.962 | 41.478 | 43.724 | 37.287 | 42.797 |
| | 49.012 | 40.958 | 41.409 | 43.640 | 37.435 | 42.920 |
| | 48.919 | 41.042 | 41.230 | 43.455 | 37.433 | 42.934 |
| 19 | 48.393 | 41.041 | 41.108 | 43.336 | 37.494 | 42.906 |
| | 47.838 | 41.139 | 41.114 | 43.241 | 37.685 | 42.908 |
| | 47.462 | 41.075 | 41.086 | 43.226 | 37.699 | 42.939 |
| | 46.988 | 41.164 | 40.954 | 43.139 | 37.693 | 42.883 |
| 20 | 46.515 | 41.181 | 40.916 | 43.162 | 37.793 | 42.847 |
| | 46.127 | 41.169 | 40.970 | 43.114 | 37.899 | 42.777 |
| | 45.795 | 41.227 | 40.869 | 43.188 | 37.842 | 42.799 |
| | 45.401 | 41.172 | 40.750 | 43.271 | 37.840 | 42.697 |
| 21 | 45.142 | 41.188 | 40.764 | 43.319 | 37.981 | 42.633 |
| | 45.124 | 41.159 | 40.755 | 43.395 | 38.012 | 42.640 |
| | 45.129 | 41.253 | 40.640 | 43.430 | 38.003 | 42.520 |
| | 44.909 | 41.206 | 40.566 | 43.454 | 38.063 | 42.492 |
| 22 | 44.628 | 41.246 | 40.478 | 43.405 | 38.126 | 42.431 |
| | 44.304 | 41.202 | 40.334 | 43.367 | 38.174 | 42.458 |
| | 43.892 | 41.314 | 40.175 | 43.248 | 38.120 | 42.399 |
| | 43.315 | 41.331 | 40.144 | 43.154 | 38.148 | 42.323 |
| 23 | 42.974 | 41.380 | 40.134 | 43.023 | 38.240 | 42.349 |
| | 42.761 | 41.483 | 40.044 | 42.953 | 38.189 | 42.259 |
| | 42.423 | 41.512 | 39.965 | 42.785 | 38.139 | 42.268 |
| | 42.012 | 41.559 | 39.996 | 42.631 | 38.192 | 42.206 |
| 24 | 41.728 | 41.563 | 40.031 | 42.578 | 38.231 | 42.226 |
| | 41.498 | 41.635 | 39.864 | 42.389 | 38.136 | 42.118 |
| | 41.181 | 41.660 | 39.696 | 42.338 | 38.151 | 41.973 |
| | 40.953 | 41.621 | 39.707 | 42.204 | 38.262 | 41.891 |
| 25 | 40.771 | 41.639 | 39.628 | 42.167 | 38.271 | 41.673 |
| | 40.382 | 41.626 | 39.426 | 42.026 | 38.215 | 41.552 |
| | 40.001 | 41.623 | 39.384 | 41.893 | 38.253 | 41.362 |
| | 39.763 | 41.503 | 39.366 | 41.780 | 38.350 | 41.302 |
| 26 | 39.619 | 41.553 | 39.267 | 41.657 | 38.287 | 41.188 |
| | 39.339 | 41.489 | 39.172 | 41.625 | 38.242 | 41.047 |
| | 39.118 | 41.446 | 39.177 | 41.442 | 38.321 | 40.954 |
| | 38.918 | 41.282 | 39.116 | 41.420 | 38.274 | 40.909 |
| 27 | 38.666 | 41.262 | 39.013 | 41.207 | 38.168 | 40.595 |
| | 38.402 | 41.121 | 38.996 | 41.007 | 38.139 | 40.368 |
| | 38.102 | 41.006 | 38.970 | 40.723 | 38.123 | 40.336 |
| | 37.970 | 40.907 | 38.824 | 40.548 | 37.931 | 40.203 |
| 28 | 37.798 | 40.792 | 38.776 | 40.307 | 37.845 | 40.030 |
| | 37.567 | 40.663 | 38.746 | 40.107 | 37.847 | 39.997 |
| | 37.466 | 40.488 | 38.703 | 40.032 | 37.823 | 39.903 |
| | 37.359 | 40.409 | 38.626 | 39.847 | 37.701 | 39.903 |
| 29 | 37.175 | 40.310 | 38.566 | 39.734 | 37.670 | 39.616 |
| | 37.056 | 40.297 | 38.593 | 39.551 | 37.762 | 39.345 |
| | 37.035 | 40.079 | 38.569 | 39.515 | 37.815 | 39.306 |
| 20.22 | 44.27 | 38.24 | 43.22 | 42.74 | 35.04 | 39.93 |
| | 9.571879 | 6.349773 | 9.514916 | 7.457884 | 6.605388 | 6.119232 |
| | 0.877453 | 0.582083 | 0.872231 | 0.683663 | 0.605515 | 0.560949 |

| 25G-Terumo | |
|---|---|
| Avg. | 38.7 |
| SD | 7.8 |
| SEM | 0.2 |

TABLE 89

Human clinical trial adverse event overview

| SUBJID | VISIT NUM | DataPage Name | PageRepeat Number | Record Position | MinCreated | MaxUpdated | SaveTS | AEYN | AETERM | AESTDAT |
|---|---|---|---|---|---|---|---|---|---|---|
| 1013 | 11 | Adverse Events | 0 | 1 | Jul. 26, 2023 19:55 | Jul. 27, 2023 5:47 | Jul. 27, 2023 6:11 | Y | ISR #2 (INJECTION SITE #2 RASH) | 20 JUL. 2023 |
| 1009 | 11 | Adverse Events | 0 | 1 | Jul. 26, 2023 20:06 | Jul. 26, 2023 20:10 | Jul. 26, 2023 20:10 | Y | PRURITIS | 29 JUN. 2023 |

TABLE 89-continued

Human clinical trial adverse event overview

| 1007 | 11 | Adverse Events | 0 | 1 | Jul. 25, 2023 15:16 | Jul. 25, 2023 15:16 | Jul. 25, 2023 15:16 | Y | PRURITUS | 29 JUN. 2023 |
| 1009 | 11 | Adverse Events | 0 | 3 | Jul. 26, 2023 20:10 | Jul. 31, 2023 11:07 | Aug. 1, 2023 1:04 | Y | EAR INFECTION | 29 JUL. 2023 |
| 1009 | 11 | Adverse Events | 0 | 2 | Jul. 26, 2023 20:08 | Jul. 27, 2023 7:19 | Jul. 28, 2023 1:04 | Y | PRURITIS | 19 JUL. 2023 |

| SUBJID | AESTTIM | AESTDTTM | AEENRTPT | AEENDAT | AEENTIM | AEENDTTM | AEREL | AESEV | AEACN |
|---|---|---|---|---|---|---|---|---|---|
| 1013 | 09:00 | 20 JUL. 2023 09:00 | | 21 JUL. 2023 | 12:00 | 21 JUL. 2023 12:00 | DEFINITELY RELATED | MILD | DOSE NOT CHANGED |
| 1009 | 11:25 | 29 JUN. 2023 11:25 | | 29 JUN. 2023 | 11:51 | 29 JUN. 2023 11:51 | PROBABLY RELATED | MILD | NOT APPLICABLE |
| 1007 | 10:05 | 29 JUN. 2023 10:05 | | 29 JUN. 2023 | 10:22 | 29 JUN. 2023 10:22 | PROBABLY RELATED | MILD | NOT APPLICABLE |
| 1009 | 17:30 | 29 JUL. 2023 17:30 | ONGOING | | | | UNLIKELY RELATED | MILD | DOSE NOT CHANGED |
| 1009 | 11:30 | 19 JUL. 2023 11:30 | | 19 JUL. 2023 | 12:07 | 19 JUL. 2023 12:07 | DEFINITELY RELATED | MILD | NOT APPLICABLE |

| SUBJID | AEACN | AECONTRT | AEOUT | AESER | NOW |
|---|---|---|---|---|---|
| 1013 | DOSE NOT CHANGED | N | RECOVERED/RESOLVED | N | 26 JUL. 2023 14:55:56 |
| 1009 | NOT APPLICABLE | N | RECOVERED/RESOLVED | N | 26 JUL. 2023 15:10:24 |
| 1007 | NOT APPLICABLE | | RECOVERED/RESOLVED | N | 25 JUL. 2023 09:16:19 |
| 1009 | DOSE NOT CHANGED | N | | N | 26 JUL. 2023 15:10:24 |
| 1009 | NOT APPLICABLE | N | RECOVERED RESOLVED | N | 26 JUL. 2023 15:10:24 |

TABLE 90

Human clinical trial demographic overview

| SUBJID | VISIT | VISIT NUM | DataPage Name | Page Repeat Number | Record Position | Min Created | Max Updated | SaveTS | BRTH YEAR | AGE | SEX |
|---|---|---|---|---|---|---|---|---|---|---|---|
| 1002 | Screening | 1 | Demographics | 0 | 0 | Jul. 10, 2023 20:20 | Jul. 13, 2023 21:23 | Jul. 14, 2023 1:06 | 1982 | 41 | F |
| 1004 | Screening | 1 | Demographics | 0 | 0 | Jul. 10, 2023 22:42 | Jul. 20, 2023 18:31 | Jul. 21, 2023 1:06 | 1964 | 58 | F |
| 1006 | Screening | 1 | Demographics | 0 | 0 | Jul. 11, 2023 20:39 | Jul. 27, 2023 6:00 | Jul. 27, 2023 6:11 | 1984 | 39 | M |
| 1007 | Screening | 1 | Demographics | 0 | 0 | Jul. 11, 2023 22:00 | Jul. 31, 2023 20:09 | Aug. 1, 2023 1:04 | 1998 | 24 | F |
| 1009 | Screening | 1 | Demographics | 0 | 0 | Jul. 12, 2023 16:53 | Jul. 31, 2023 20:32 | Aug. 1, 2023 1:04 | 1982 | 40 | F |
| 1013 | Screening | 1 | Demographics | 0 | 0 | Jul. 12, 2023 17:49 | Jul. 12, 2023 17:49 | Jul. 12, 2023 17:49 | 1963 | 60 | M |
| 1008 | Screening | 1 | Demographics | 0 | 0 | Jul. 12, 2023 15:30 | Jul. 20, 2023 19:33 | Jul. 21, 2023 1:06 | 1973 | 49 | F |
| 1010 | Screening | 1 | Demographics | 0 | 0 | Jul. 12, 2023 17:41 | Jul. 31, 2023 20:46 | Aug. 1, 2023 1:04 | 1987 | 35 | F |
| 1012 | Screening | 1 | Demographics | 0 | 0 | Jul. 12, 2023 19:41 | Jul. 31, 2023 21:06 | Aug. 1, 2023 1:04 | 1968 | 54 | M |
| 1029 | Screening | 1 | Demographics | 0 | 0 | Jul. 13, 2023 15:43 | Jul. 19, 2023 16:19 | Jul. 20, 2023 1:05 | 2004 | 19 | F |

TABLE 90-continued

| | | | | | | | | | | | |
|---|---|---|---|---|---|---|---|---|---|---|---|
| 1034 | Screening | 1 | Demographics | 0 | 0 | Jul. 13, 2023 17:49 | Jul. 20, 2023 20:19 | Jul. 21, 2023 1:06 | 1998 | 24 | M |
| 1033 | Screening | 1 | Demographics | 0 | 0 | Jul. 14, 2023 14:04 | Jul. 19, 2023 20:10 | Jul. 20, 2023 1:05 | 1969 | 54 | F |
| 1028 | Screening | 1 | Demographics | 0 | 0 | Jul. 14, 2023 17:11 | Jul. 14, 2023 17:11 | Jul. 14, 2023 17:11 | 2001 | 22 | M |
| 1030 | Screening | 1 | Demographics | 0 | 0 | Jul. 17, 2023 17:49 | Jul. 17 2023 17:49 | Jul. 17, 2023 17:49 | 1962 | 60 | F |
| 1001 | Screening | 1 | Demographics | 0 | 0 | Jul. 10, 2023 19:26 | | Jul. 14, 2023 1:06 | 1990 | 33 | M |
| 1003 | Screening | 1 | Demographics | 0 | 0 | Jul. 10, 2023 21:51 | | Jul. 21, 2023 1:06 | 1961 | 61 | M |
| 1005 | Screening | 1 | Demographics | 0 | 0 | Jul. 11, 2023 16:43 | | Jul. 21, 2023 1:06 | 1979 | 43 | M |
| 1038 | Screening | 1 | Demographics | 0 | 0 | Jul. 17, 2023 19:56 | | Jul. 20, 2023 1:05 | 1976 | 46 | F |
| 1043 | Screening | 1 | Demographics | 0 | 0 | Jul. 18, 2023 14:33 | | Jul. 21, 2023 1:06 | 1975 | 48 | F |
| 1031 | Screening | 1 | Demographics | 0 | 0 | Jul. 18, 2023 17:47 | | Jul. 20, 2023 1:05 | 1970 | 53 | M |
| 1040 | Screening | 1 | Demographics | 0 | 0 | Jul. 19, 2023 16:02 | | Jul. 21, 2023 1:06 | 1960 | 62 | F |
| 1035 | Screening | 1 | Demographics | 0 | 0 | Jul. 19, 2023 17:42 | | Jul. 19, 2023 17:42 | 1975 | 48 | F |
| 1041 | Screening | 1 | Demographics | 0 | 0 | Jul. 19, 2023 19:45 | | Jul, 21, 2023 1:06 | 1980 | 42 | F |
| 1037 | Screening | 1 | Demographics | 0 | 0 | Jul. 20, 2023 15:36 | | Jul. 20, 2023 15:36 | 1966 | 56 | F |
| | | | | | | | | Male | | | 9 |
| | | | | | | | | Female | | | 15 |
| | | | | | | | | Hispanic//Latino | | | 13 |
| | | | | | | | | Not Hispanic/Latino | | | 11 |
| | | | | | | | | Black/African American | | | 4 |
| | | | | | | | | White | | | 17 |
| | | | | | | | | Other | | | 3 |
| | | | | | | | | Age Minimum | | | 19 |
| | | | | | | | | Age Maximum | | | 62 |

| SUBJID | ETHNIC | RACE | RACEOTH | COHORT |
|---|---|---|---|---|
| 1002 | NOT HISPANIC OR LATINO | WHITE | | Cohort A Sentinel 2 |
| 1004 | HISPANIC OR LATINO | WHITE | | Cohort A Sentinel 3 |
| 1006 | NOT HISPANIC OR LATINO | OTHER | MIXED | Cohort A Non-Sentinel |
| 1007 | NOT HISPANIC OR LATINO | OTHER | LEFT BLANK | Cohort A Non-Sentinel |
| 1009 | HISPANIC OR LATINO | WHITE | | Cohort A Non-Sentinel |
| 1013 | NOT HISPANIC OR LATINO | WHITE | | Cohort A Non-Sentinel |
| 1008 | HISPANIC OR LATINO | WHITE | | Cohort A Non-Sentinel |
| 1010 | NOT HISPANIC OR LATINO | NATIVE HAWAIIAN OR OTHER PACIFIC ISLANDER | | Cohort A Non-Sentinel |
| 1012 | NOT HISPANIC OR LATINO | BLACK OR AFRICAN AMERICAN | | Cohort A Non-Sentinel |
| 1029 | HISPANIC OR LATINO | WHITE | | Cohort B Sentinel 3 |
| 1034 | NOT HISPANIC OR LATINO | WHITE | | Cohort B Non-Sentinel |
| 1033 | HISPANIC OR LATINO | WHITE | | Cohort B Sentinel 2 |
| 1028 | HISPANIC OR LATINO | WHITE | | Cohort B Sentinel 1 |
| 1030 | NOT HISPANIC OR LATINO | WHITE | | Cohort B Non-Sentinel |
| 1001 | HISPANIC OR LATINO | WHITE | | Cohort A Sentinel 1 |
| 1003 | HISPANIC OR LATINO | WHITE | | Cohort A Sentinel 3 |
| 1005 | NOT HISPANIC OR LATINO | BLACK OR AFRICAN AMERICAN | | Cohort A Non-Sentinel |
| 1038 | NOT HISPANIC OR LATINO | BLACK OR AFRICAN AMERICAN | | Cohort B Sentinel 3 |
| 1043 | HISPANIC OR LATINO | WHITE | | Cohort B Non-Sentinel |
| 1031 | HISPANIC OR LATINO | WHITE | | Cohort B Non-Sentinel |
| 1040 | HISPANIC OR LATINO | WHITE | | Cohort B Non-Sentinel |
| 1035 | HISPANIC OR LATINO | WHITE | | Cohort B Non-Sentinel |
| 1041 | HISPANIC OR LATINO | WHITE | | Cohort B Non-Sentinel |
| 1037 | NOT HISPANIC OR LATINO | BLACK OR AFRICAN AMERICAN | | Cohort B Non-Sentinel |

TABLE 91

| | | | | | Human clinical trial informed consent overview | | | | | |
|---|---|---|---|---|---|---|---|---|---|---|
| SUBJID | SITEID | VISIT | VISITNUM | Data Page Name | Page Repeat Number | Record Position | Min Created | Max Updated | SaveTS | DSYN |
| 1001 | 101_21080079 | Screening | 1 | Informed Consent | 0 | 0 | Jul. 10, 2023 19:26 | Jul. 19, 2023 10:33 | Jul. 24, 2023 8:31 | Y |
| 1002 | 101_21080079 | Screening | 1 | Informed Consent | 0 | 0 | Jul. 10, 2023 20:19 | Jul. 19, 2023 10:33 | Jul. 24, 2023 8:31 | Y |
| 1003 | 101_21080079 | Screening | 1 | Informed Consent | 0 | 0 | Jul. 10, 2023 21:51 | Jul. 20, 2023 17:53 | Jul. 24, 2023 8:31 | Y |
| 1004 | 101_21080079 | Screening | 1 | Informed Consent | 0 | 0 | Jul. 10, 2023 22:41 | Jul. 20, 2023 18:30 | Jul. 24, 2023 8:31 | Y |
| 1005 | 101_21080079 | Screening | 1 | Informed Consent | 0 | 0 | Jul. 11, 2023 16:35 | Jul. 20, 2023 18:51 | Jul. 24, 2023 8:32 | Y |
| 1006 | 101_21080079 | Screening | 1 | Informed Consent | 0 | 0 | Jul. 11, 2023 20:39 | Jul. 20, 2023 19:15 | Jul. 24, 2023 8:31 | Y |
| 1007 | 101_21080079 | Screening | 1 | Informed Consent | 0 | 0 | Jul. 11, 2023 21:59 | Jul. 31, 2023 20:08 | Aug. 1, 2023 1:04 | Y |
| 1008 | 101_21080079 | Screening | 1 | Informed Consent | 0 | 0 | Jul. 12, 2023 15:30 | Jul. 20, 2023 19:33 | Jul. 24, 2023 8:32 | Y |
| 1009 | 101_21080079 | Screening | 1 | Informed Consent | 0 | 0 | Jul. 12, 2023 16:52 | Jul. 31, 2023 20:31 | Aug. 1, 2023 1:04 | Y |
| 1010 | 101_21080079 | Screening | 1 | Informed Consent | 0 | 0 | Jul. 12, 2023 17:40 | Jul. 31, 2023 20:45 | Aug. 1, 2023 1:04 | Y |
| 1013 | 101_21080079 | Screening | 1 | Informed Consent | 0 | 0 | Jul. 12, 2023 17:47 | Jul. 19, 2023 10:33 | Jul. 24, 2023 8:32 | Y |
| 1012 | 101_21080079 | Screening | 1 | Informed Consent | 0 | 0 | Jul. 12, 2023 19:41 | Jul. 31, 2023 21:06 | Aug. 1, 2023 1:04 | Y |
| 1029 | 101_21080079 | Screening | 1 | Informed Consent | 0 | 0 | Jul. 13, 2023 15:42 | Jul. 19, 2023 16:18 | Jul. 24, 2023 8:32 | Y |
| 1034 | 101_21080079 | Screening | 1 | Informed Consent | 0 | 0 | Jul. 13, 2023 17:26 | Jul. 20, 2023 20:18 | Jul. 24, 2023 8:32 | Y |
| 1033 | 101_21080079 | Screening | 1 | Informed Consent | 0 | 0 | Jul. 14, 2023 14:03 | Jul. 19, 2023 20:10 | Jul. 24, 2023 8:32 | Y |
| 1028 | 101_21080079 | Screening | 1 | Informed Consent | 0 | 0 | Jul. 14, 2023 17:09 | Jul. 19, 2023 10:33 | Jul. 24, 2023 8:32 | Y |
| 1030 | 101_21080079 | Screening | 1 | Informed Consent | 0 | 0 | Jul. 17, 2023 17:49 | Jul. 17, 2023 19:55 | Jul. 24, 2023 8:32 | Y |
| 1038 | 101_21080079 | Screening | 1 | Informed Consent | 0 | 0 | Jul. 17, 2023 19:56 | Jul. 17, 2023 21:15 | Jul. 24, 2023 8:32 | Y |
| 1043 | 101_21080079 | Screening | 1 | Informed Consent | 0 | 0 | Jul. 18, 2023 14:32 | Jul. 20, 2023 21:01 | Jul. 24, 2023 8:32 | Y |
| 1031 | 101_21080079 | Screening | 1 | Informed Consent | 0 | 0 | Jul. 18, 2023 17:46 | Jul. 19, 2023 18:20 | Jul. 24, 2023 8:32 | Y |
| 1040 | 101_21080079 | Screening | 1 | Informed Consent | 0 | 0 | Jul. 19, 2023 16:01 | Jul. 20, 2023 20:32 | Jul. 24, 2023 8:32 | Y |
| 1035 | 101_21080079 | Screening | 1 | Informed Consent | 0 | 0 | Jul. 19, 2023 17:41 | Jul. 20, 2023 15:06 | Jul. 24, 2023 8:32 | Y |
| 1041 | 101_21080079 | Screening | 1 | Informed Consent | 0 | 0 | Jul. 19, 2023 19:44 | Jul. 20, 2023 20:46 | Jul. 24, 2023 8:32 | Y |
| 1037 | 101_21080079 | Screening | 1 | Informed Consent | 0 | 0 | Jul. 20, 2023 15:35 | Jul. 20, 2023 17:17 | Jul. 24, 2023 8:32 | Y |

| SaveTS | Study Env Site Number | DSYN | DSSTDAT | DSTIM | DSDTTM | DSDECOD |
|---|---|---|---|---|---|---|
| Jul. 24, 2023 8:31 | 101_21080079 | Y | 15 JUN. 2023 | 07:15 | 15 JUN. 2023 07:15 | INFORMED CONSENT OBTAINED |
| Jul. 24, 2023 8:31 | 101_21080079 | Y | 15 JUN. 2023 | 07:40 | 15 JUN. 2023 07:40 | INFORMED CONSENT OBTAINED |
| Jul. 24, 2023 8:31 | 101_21080079 | Y | 15 JUN. 2023 | 08:11 | 15 JUN. 2023 08:11 | INFORMED CONSENT OBTAINED |
| Jul. 24, 2023 8:31 | 101_21080079 | Y | 15 JUN. 2023 | 08:35 | 15 JUN. 2023 08:35 | INFORMED CONSENT OBTAINED |
| Jul. 24, 2023 8:32 | 101_21080079 | Y | 15 JUN. 2023 | 09:09 | 15 JUN. 2023 09:09 | INFORMED CONSENT OBTAINED |
| Jul. 24, 2023 8:31 | 101_21080079 | Y | 15 JUN. 2023 | 09:29 | 15 JUN. 2023 09:29 | INFORMED CONSENT OBTAINED |
| Aug. 1, 2023 1:04 | 101_21080079 | Y | 15 JUN. 2023 | 09:46 | 15 JUN. 2023 09:46 | INFORMED CONSENT OBTAINED |
| Jul. 24, 2023 8:32 | 101_21080079 | Y | 15 JUN. 2023 | 10:22 | 15 JUN. 2023 10:22 | INFORMED CONSENT OBTAINED |
| Aug. 1, 2023 1:04 | 101_21080079 | Y | 15 JUN. 2023 | 10:39 | 15 JUN. 2023 10:39 | INFORMED CONSENT OBTAINED |
| Aug. 1, 2023 1:04 | 101_21080079 | Y | 15 JUN. 2023 | 10:54 | 15 JUN. 2023 10:54 | INFORMED CONSENT OBTAINED |
| Jul. 24, 2023 8:32 | 101_21080079 | Y | 16 JUN. 2023 | 09:03 | 16 JUN. 2023 09:03 | INFORMED CONSENT OBTAINED |

TABLE 91-continued

| | | | | | | | |
|---|---|---|---|---|---|---|---|
| Aug. 1, 2023 1:04 | 101_21080079 | Y | 15 JUN. 2023 | 11:50 | 15 JUN. 2023 11:50 | | INFORMED CONSENT OBTAINED |
| Jul. 24, 2023 8:32 | 101_21080079 | Y | 26 JUN. 2023 | 08:13 | 26 JUN. 2023 08:13 | | INFORMED CONSENT OBTAINED |
| Jul. 24, 2023 8:32 | 101_21080079 | Y | 26 JUN. 2023 | 10:50 | 26 JUN. 2023 10:50 | | INFORMED CONSENT OBTAINED |
| Jul. 24, 2023 8:32 | 101_21080079 | Y | 26 JUN. 2023 | 10:29 | 26 JUN. 2023 10:29 | | INFORMED CONSENT OBTAINED |
| Jul. 24, 2023 8:32 | 101_21080079 | Y | 26 JUN. 2023 | 07:49 | 26 JUN. 2023 07:49 | | INFORMED CONSENT OBTAINED |
| Jul. 24, 2023 8:32 | 101_21080079 | Y | 26 JUN. 2023 | 08:54 | 26 JUN. 2023 08:54 | | INFORMED CONSENT OBTAINED |
| Jul. 24, 2023 8:32 | 101_21080079 | Y | 26 JUN. 2023 | 12:13 | 26 JUN. 2023 12:13 | | INFORMED CONSENT OBTAINED |
| Jul. 24, 2023 8:32 | 101_21080079 | Y | 28 JUN. 2023 | 08:46 | 28 JUN. 2023 08:46 | | INFORMED CONSENT OBTAINED |
| Jul. 24, 2023 8:32 | 101_21080079 | Y | 26 JUN. 2023 | 09:55 | 26 JUN. 2023 09:55 | | INFORMED CONSENT OBTAINED |
| Jul. 24, 2023 8:32 | 101_21080079 | Y | 28 JUN. 2023 | 07:50 | 28 JUN. 2023 07:50 | | INFORMED CONSENT OBTAINED |
| Jul. 24, 2023 8:32 | 101_21080079 | Y | 26 JUN. 2023 | 12:05 | 26 JUN. 2023 12:05 | | INFORMED CONSENT OBTAINED |
| Jul. 24, 2023 8:32 | 101_21080079 | Y | 28 JUN. 2023 | 07:58 | 28 JUN. 2023 07:58 | | INFORMED CONSENT OBTAINED |
| Jul. 24, 2023 8:32 | 101_21080079 | Y | 26 JUN. 2023 | 12:12 | 26 JUN. 2023 12:12 | | INFORMED CONSENT OBTAINED |

TABLE 92

Human clinical trial injection visit overview

| SUBJID | VISIT | VISIT NUM | Data Page Name | Page Repeat Number | Record Position | Min Created | Max Updated | SaveTS | EXTRT |
|---|---|---|---|---|---|---|---|---|---|
| 1001 | Injection Visit 1 | 2 | Injection Visit 1 | 0 | 1 | Jul. 10, 2023 19:45 | Jul. 13, 2023 20:16 | Jul. 14, 2023 1:06 | 10% IgG plus rHuPH20 |
| 1002 | Injection Visit 1 | 2 | Injection Visit 1 | 0 | 1 | Jul. 10, 2023 21:03 | Jul. 31, 2023 18:35 | Aug. 1, 2023 1:04 | 10% IgG plus rHuPH20 |
| 1003 | Injection Visit 1 | 2 | Injection Visit 1 | 0 | 1 | Jul. 10, 2023 22:18 | Jul. 20, 2023 21:19 | Jul. 21, 2023 1:06 | 10% IgG plus rHuPH20 |
| 1004 | Injection Visit 1 | 2 | Injection Visit 1 | 0 | 1 | Jul. 10, 2023 23:14 | Jul. 19, 2023 11:13 | Jul. 20, 2023 1:05 | 10% IgG plus rHuPH20 |
| 1005 | Injection Visit 1 | 2 | Injection Visit 1 | 0 | 1 | Jul. 11, 2023 17:28 | Jul. 12, 2023 11:36 | Jul.13, 2023 1:05 | 10% IgG plus rHuPH20 |
| 1006 | Injection Visit 1 | 2 | Injection Visit 1 | 0 | 1 | Jul. 11, 2023 20:57 | Jul. 12, 2023 11:36 | Jul. 13, 2023 1:05 | 10% IgG plus rHuPH20 |
| 1007 | Injection Visit 1 | 2 | Injection Visit 1 | 0 | 1 | Jul. 11, 2023 22:21 | Jul. 12, 2023 11:36 | Jul.13, 2023 1:05 | 10% IgG plus rHuPH20 |
| 1008 | Injection Visit 1 | 2 | Injection Visit 1 | 0 | 1 | Jul. 12, 2023 16:07 | Jul. 26, 2023 11:22 | Jul. 27, 2023 1:05 | 10% IgG plus rHuPH20 |
| 1009 | Injection Visit 1 | 2 | Injection Visit 1 | 0 | 1 | Jul. 12, 2023 17:06 | Jul. 26, 2023 11:23 | Jul. 27, 2023 1:05 | 10% IgG plus rHuPH20 |
| 1010 | Injection Visit 1 | 2 | Injection Visit 1 | 0 | 1 | Jul. 12, 2023 20:04 | Jul. 26, 2023 11:03 | Jul. 27, 2023 1:05 | 10% IgG plus rHuPH20 |
| 1013 | Injection Visit 1 | 2 | Injection Visit 1 | 0 | 1 | Jul. 12, 2023 18:34 | Jul. 26, 2023 11:06 | Jul. 27, 2023 1:05 | 10% IgG plus rHuPH20 |
| 1012 | Injection Visit 1 | 2 | Injection Visit 1 | 0 | 1 | Jul. 12, 2023 21:24 | Jul. 26, 2023 11:05 | Jul. 27, 2023 1:05 | 10% IgG plus rHuPH20 |

TABLE 92-continued

Human clinical trial injection visit overview

| 1029 | Injection Visit 1 | 2 | Injection Visit 1 | 0 | 1 | Jul. 13, 2023 16:07 | Jul. 26, 2023 11:11 | Jul. 27, 2023 1:05 | 10% IgG plus rHuPH20 |
|---|---|---|---|---|---|---|---|---|---|
| 1034 | Injection Visit 1 | 2 | Injection Visit 1 | 0 | 1 | Jul. 13, 2023 21:28 | Jul. 26, 2023 11:16 | Jul. 27, 2023 1:05 | 10% IgG plus rHuPH20 |
| 1033 | Injection Visit 1 | 2 | Injection Visit 1 | 0 | 1 | Jul. 14, 2023 14:37 | Jul. 26, 2023 11:15 | Jul. 27, 2023 1:05 | 10% IgG plus rHuPH20 |
| 1028 | Injection Visit 1 | 2 | Injection Visit 1 | 0 | 1 | Jul. 14, 2023 17:51 | Jul. 14, 2023 19:25 | Jul. 15, 2023 1:05 | 10% IgG plus rHuPH20 |
| 1030 | Injection Visit 1 | 2 | Injection Visit 1 | 0 | 1 | Jul. 17, 2023 19:55 | Jul. 26, 2023 11:13 | Jul. 27, 2023 1:05 | 10% IgG plus rHuPH20 |
| 1038 | Injection Visit 1 | 2 | Injection Visit 1 | 0 | 1 | Jul. 18, 2023 11:52 | Jul. 26, 2023 11:18 | Jul. 27, 2023 1:05 | 10% IgG plus rHuPH20 |
| 1043 | Injection Visit 1 | 2 | Injection Visit 1 | 0 | 1 | Jul. 18, 2023 16:00 | Jul. 26, 2023 11:21 | Jul. 27, 2023 1:05 | 10% IgG plus rHuPH20 |
| 1031 | Injection Visit 1 | 2 | Injection Visit 1 | 0 | 1 | Jul. 18, 2023 19:04 | Jul. 26, 2023 11:14 | Jul. 27, 2023 1:05 | 10% IgG plus rHuPH20 |
| 1040 | Injection Visit 1 | 2 | Injection Visit 1 | 0 | 1 | Jul. 19, 2023 17:25 | Jul. 26, 2023 11:19 | Jul. 27, 2023 1:05 | 10% IgG plus rHuPH20 |
| 1035 | Injection Visit 1 | 2 | Injection Visit 1 | 0 | 1 | Jul. 20, 2023 15:06 | Jul. 20, 2023 15:06 | Jul. 20, 2023 15:06 | 10% IgG plus rHuPH20 |
| 1041 | Injection Visit 1 | 2 | Injection Visit 1 | 0 | 1 | Jul. 19, 2023 20:01 | Jul. 19, 2023 20:09 | Jul. 19, 2023 20:09 | 10% IgG plus rHuPH20 |
| 1037 | Injection Visit 1 | 2 | Injection Visit 1 | 0 | 1 | Jul. 20, 2023 17:17 | Jul. 26, 2023 11:17 | Jul. 27, 2023 1:05 | 10% IgG plus rHuPH20 |
| 1001 | Injection Visit 2 | 3 | Injection Visit 2 | 0 | 1 | Jul. 24, 2023 17:28 | Aug. 1, 2023 19:48 | Aug. 1, 2023 19:48 | 10% IgG plus rHuPH20 |
| 1002 | Injection Visit 2 | 3 | Injection Visit 2 | 0 | 1 | Jul. 25, 2023 20:37 | Jul. 31, 2023 19:14 | Aug. 1, 2023 1:04 | 10% IgG plus rHuPH20 |
| 1003 | Injection Visit 2 | 3 | Injection Visit 2 | 0 | 1 | Jul. 25, 2023 20:08 | Aug. 31, 2023 6:31 | Jul. 31, 2023 7:15 | 10% IgG plus rHuPH20 |
| 1004 | Injection Visit 2 | 3 | Injection Visit 2 | 0 | 1 | Jul. 25, 2023 19:49 | Jul. 25, 2023 19:49 | Jul. 25, 2023 19:50 | 10% IgG plus rHuPH20 |
| 1005 | Injection Visit 2 | 3 | Injection Visit 2 | 0 | 1 | Jul. 25, 2023 18:53 | Jul. 25, 2023 18:53 | Jul. 25, 2023 18:53 | 10% IgG plus rHuPH20 |
| 1006 | Injection Visit 2 | 3 | Injection Visit 2 | 0 | 1 | Jul. 25, 2023 14:21 | Jul. 25, 2023 14:38 | Jul. 25, 2023 14:39 | 10% IgG plus rHuPH20 |
| 1007 | Injection Visit 2 | 3 | Injection Visit 2 | 0 | 1 | Jul. 24, 2023 21:42 | Jul. 26, 2023 17:45 | Jul. 26, 2023 17:45 | 10% IgG plus rHuPH20 |
| 1008 | Injection Visit 2 | 3 | Injection Visit 2 | 0 | 1 | Jul. 25, 2023 16:00 | Jul. 25, 2023 16:00 | Jul. 25, 2023 16:00 | 10% IgG plus rHuPH20 |
| 1009 | Injection Visit 2 | 3 | Injection Visit 2 | 0 | 1 | Jul. 25, 2023 15:16 | Jul. 31, 2023 11:15 | Aug. 1, 2023 1:04 | 10% IgG plus rHuPH20 |
| 1010 | Injection Visit 2 | 3 | Injection Visit 2 | 0 | 1 | Jul. 25, 2023 15:41 | Aug. 1, 2023 19:50 | Aug. 1, 2023 19:50 | 10% IgG plus rHuPH20 |
| 1013 | Injection Visit 2 | 3 | Injection Visit 2 | 0 | 1 | Jul. 25, 2023 16:45 | Aug. 1, 2023 19:51 | Aug 1, 2023 19:51 | 10% IgG plus rHuPH20 |
| 1012 | Injection Visit 2 | 3 | Injection Visit 2 | 0 | 1 | Jul. 24, 2023 20:20 | Aug. 1, 2023 19:50 | Aug. 1, 2023 19:50 | 10% IgG plus rHuPH20 |
| 1029 | Injection Visit 2 | 3 | Injection Visit 2 | 0 | 1 | Jul. 26, 2023 14:38 | Jul. 26, 2023 14:38 | Jul. 26, 2023 14:38 | 10% IgG plus rHuPH20 |
| 1034 | Injection Visit 2 | 3 | Injection Visit 2 | 0 | 1 | Jul. 18, 2023 15:31 | Jul. 26, 2023 11:16 | Jul. 27, 2023 1:05 | 10% IgG plus rHuPH20 |

TABLE 92-continued

Human clinical trial injection visit overview

| 1033 | Injection Visit 2 | 3 | Injection Visit 2 | 0 | 1 | Jul. 14, 2023 15:27 | Jul. 26, 2023 11:15 | Jul. 27, 2023 1:05 | 10% IgG plus rHuPH20 |
|---|---|---|---|---|---|---|---|---|---|
| 1028 | Injection Visit 2 | 3 | Injection Visit 2 | 0 | 1 | Jul. 14, 2023 19:52 | Jul. 26, 2023 11:11 | Jul. 27, 2023 1:05 | 10% IgG plus rHuPH20 |
| 1030 | Injection Visit 2 | 3 | Injection Visit 2 | 0 | 1 | Jul. 17, 2023 21:50 | Jul. 26, 2023 11:13 | Jul. 27, 2023 1:05 | 10% IgG plus rHuPH20 |
| 1038 | Injection Visit 2 | 3 | Injection Visit 2 | 0 | 1 | Jul. 18, 2023 13:49 | Jul. 26, 2023 11:19 | Jul. 27, 2023 1:05 | 10% IgG plus rHuPH20 |
| 1043 | Injection Visit 2 | 3 | Injection Visit 2 | 0 | 1 | Jul. 18, 2023 17:38 | Jul. 26, 2023 11:21 | Jul. 27, 2023 1:05 | 10% IgG plus rHuPH20 |
| 1031 | Injection Visit 2 | 3 | Injection Visit 2 | 0 | 1 | Jul. 18, 2023 19:12 | Jul. 26, 2023 11:14 | Jul. 27, 2023 1:05 | 10% IgG plus rHuPH20 |
| 1040 | Injection Visit 2 | 3 | Injection Visit 2 | 0 | 1 | Jul. 19, 2023 17:52 | Jul. 26, 2023 11:19 | Jul. 27, 2023 1:05 | 10% IgG plus rHuPH20 |
| 1035 | Injection Visit 2 | 3 | Injection Visit 2 | 0 | 1 | Jul. 20, 2023 15:16 | Jul. 26, 2023 11:17 | Jul. 27, 2023 1:05 | 10% IgG plus rHuPH20 |
| 1041 | Injection Visit 2 | 3 | Injection Visit 2 | 0 | 1 | Jul. 19, 2023 20:07 | Jul. 26, 2023 11:20 | Jul. 27, 2023 1:05 | 10% IgG plus rHuPH20 |
| 1037 | Injection Visit 2 | 3 | Injection Visit 2 | 0 | 1 | Jul. 20, 2023 17:24 | Jul. 26, 2023 11:18 | Jul. 27, 2023 1:05 | 10% IgG plus rHuPH20 |

| SUBJID | EXADJYN | EXDOSE | EXDOSFRM | EXROUTE | EXSTDAT | EXSTTIM | EXSTDTTM | EXENTIM | EXENDTTM |
|---|---|---|---|---|---|---|---|---|---|
| 1001 | Y | 5 mL in 30 sec | Liquid | SUBCUTANEOUS | 26 JUN. 2023 | 08:10:00 | 26 JUN. 2023 08:10:00 | 08:10:30 | 26 JUN. 2023 08:10:30 |
| 1002 | Y | 5 mL in 30 sec | Liquid | SUBCUTANEOUS | 27 JUN. 2023 | 08:20:01 | 27 JUN. 2023 08:20:01 | 08:20:31 | 27 JUN. 2023 08:20:31 |
| 1003 | Y | 5 mL in 30 sec | Liquid | SUBCUTANEOUS | 28 JUN. 2023 | 08:30:00 | 28 JUN. 2023 08:30:00 | 08:30:30 | 28 JUN. 2023 08:30:30 |
| 1004 | Y | 5 mL in 30 sec | Liquid | SUBCUTANEOUS | 29 JUN. 2023 | 08:41:11 | 29 JUN. 2023 08:41:11 | 08:41:42 | 29 JUN. 2023 08:41:42 |
| 1005 | Y | 5 mL in 30 sec | Liquid | SUBCUTANEOUS | 29 JUN. 2023 | 08:40:38 | 29 JUN. 2023 08:40:38 | 08:41:09 | 29 JUN. 2023 08:41:09 |
| 1006 | Y | 5 mL in 30 sec | Liquid | SUBCUTANEOUS | 29 JUN. 2023 | 10:00:00 | 29 JUN. 2023 10:00:00 | 10:00:30 | 29 JUN. 2023 10:00:30 |
| 1007 | Y | 5 mL in 30 sec | Liquid | SUBCUTANEOUS | 29 JUN. 2023 | 10:00:01 | 29 JUN. 2023 10:00:01 | 10:00:32 | 29 JUN. 2023 10:00:32 |
| 1008 | Y | 5 mL in 30 sec | Liquid | SUBCUTANEOUS | 29 JUN. 2023 | 11:20:04 | 29 JUN. 2023 11:20:04 | 11:20:34 | 29 JUN. 2023 11:20:34 |
| 1009 | Y | 5 mL in 30 sec | Liquid | SUBCUTANEOUS | 29 JUN. 2023 | 11:20:01 | 29 JUN. 2023 11:20:01 | 11:20:32 | 29 JUN. 2023 11:20:32 |
| 1010 | Y | 5 mL in 30 sec | Liquid | SUBCUTANEOUS | 29 JUN. 2023 | 12:40:00 | 29 JUN. 2023 12:40:00 | 12:40:30 | 29 JUN. 2023 12:40:30 |
| 1013 | Y | 5 mL in 30 sec | Liquid | SUBCUTANEOUS | 29 JUN. 2023 | 12:40:01 | 29 JUN. 2023 12:40:01 | 12:40:31 | 29 JUN. 2023 12:40:31 |
| 1012 | Y | 5 mL in 30 sec | Liquid | SUBCUTANEOUS | 29 JUN. 2023 | 14:00:00 | 29 JUN. 2023 14:00:00 | 14:00:30 | 29 JUN. 2023 14:00:30 |
| 1029 | Y | 10 mL in 30 sec | Liquid | SUBCUTANEOUS | 07 JUL. 2023 | 07:50:00 | 07 JUL.2023 07:50:00 | 07:50:30 | 07 JUL. 2023 07:50:30 |
| 1034 | Y | 10 mL in 30 sec | Liquid | SUBCUTANEOUS | 10 JUL. 2023 | 07:31:03 | 10 JUL. 2023 07:31:03 | 07:31:34 | 10 JUL. 2023 07:31:34 |
| 1033 | Y | 10 mL in 30 sec | Liquid | SUBCUTANEOUS | 06 JUL. 2023 | 07:40:00 | 06 JUL. 2023 07:40:00 | 07:40:30 | 06 JUL. 2023 07:40:30 |
| 1028 | Y | 5 mL in 30 sec | Liquid | SUBCUTANEOUS | 05 JUL. 2023 | 07:30:00 | 05 JUL. 2023 07:30:00 | 07:30:30 | 05 JUL. 2023 07:30:30 |
| 1030 | Y | 10 mL in 30 sec | Liquid | SUBCUTANEOUS | 10 JUL. 2023 | 08:50:00 | 10 JUL. 2023 08:50:00 | 08:50:31 | 10 JUL. 2023 08:50:31 |
| 1038 | Y | 10 mL in 30 sec | Liquid | SUBCUTANEOUS | 10 JUL. 2023 | 10:10:01 | 10 JUL. 2023 10:10:01 | 10:10:31 | 10 JUL. 2023 10:10:31 |
| 1043 | Y | 10 mL in 30 sec | Liquid | SUBCUTANEOUS | 10 JUL. 2023 | 12:50:00 | 10 JUL. 2023 12:50:00 | 12:50:33 | 10 JUL. 2023 12:50:33 |
| 1031 | Y | 10 mL in 30 sec | Liquid | SUBCUTANEOUS | 10 JUL. 2023 | 07:32:00 | 10 JUL. 2023 07:32:00 | 07:32:30 | 10 JUL. 2023 07:32:30 |
| 1040 | Y | 10 mL in 30 sec | Liquid | SUBCUTANEOUS | 10 JUL. 2023 | 11:30:00 | 10 JUL. 2023 11:30:00 | 11:30:31 | 10 JUL. 2023 11:30:31 |

TABLE 92-continued

Human clinical trial injection visit overview

| 1035 | Y | 5 mL in 30 sec | Liquid | SUBCUTANEOUS | 10 JUL. 2023 | 08:50:01 | 10 JUL. 2023 08:50:01 | 08:50:40 | 10 JUL. 2023 08:50:40 |
| 1041 | Y | 5 mL in 30 sec | Liquid | SUBCUTANEOUS | 10 JUL. 2023 | 11:30:00 | 10 JUL. 2023 11:30:00 | 11:30:31 | 10 JUL. 2023 11:30:31 |
| 1037 | Y | 10 mL in 30 sec | Liquid | SUBCUTANEOUS | 10 JUL. 2023 | 10:10:24 | 10 JUL. 2023 10:10:24 | 10:10:54 | 10 JUL. 2023 10:10:54 |
| 1001 | Y | 10 mL in 30 sec | Liquid | SUBCUTANEOUS | 17 JUL. 2023 | 07:10:01 | 17 JUL. 2023 07:10:01 | 07:10:34 | 17 JUL. 2023 07:10:34 |
| 1002 | Y | 10 mL in 30 sec | Liquid | SUBCUTANEOUS | 18 JUL. 2023 | 07:20:00 | 18 JUL. 2023 07:20:00 | 07:20:24 | 18 JUL. 2023 07:20:24 |
| 1003 | Y | 10 mL in 30 sec | Liquid | SUBCUTANEOUS | 19 JUL. 2023 | 07:30:00 | 19 JUL. 2023 07:30:00 | 07:30:30 | 19 JUL. 2023 07:30:30 |
| 1004 | Y | 10 mL in 30 sec | Liquid | SUBCUTANEOUS | 19 JUL. 2023 | 07:30:01 | 19 JUL. 2023 07:30:01 | 07:30:25 | 19 JUL. 2023 07:30:25 |
| 1005 | Y | 10 mL in 30 sec | Liquid | SUBCUTANEOUS | 19 JUL. 2023 | 08:50:00 | 19 JUL. 2023 08:50:00 | 08:50:34 | 19 JUL. 2023 08:50:34 |
| 1006 | | | Liquid | SUBCUTANEOUS | | | | | |
| 1007 | Y | 10 mL in 30 sec | Liquid | SUBCUTANEOUS | 19 JUL. 2023 | 10:10:00 | 19 JUL. 2023 10:10:00 | 10:10:24 | 19 JUL. 2023 10:10:24 |
| 1008 | Y | 10 mL in 30 sec | Liquid | SUBCUTANEOUS | 19 JUL. 2023 | 10:10:01 | 19 JUL. 2023 10:10:01 | 10:10:26 | 19 JUL. 2023 10:10:26 |
| 1009 | Y | 10 mL in 30 sec | Liquid | SUBCUTANEOUS | 19 JUL. 2023 | 11:30:00 | 19 JUL. 2023 11:30:00 | 11:30:24 | 19 JUL. 2023 11:30:24 |
| 1010 | Y | 10 mL in 30 sec | Liquid | SUBCUTANEOUS | 19 JUL. 2023 | 11:30:01 | 19 JUL. 2023 11:30:01 | 11:30:23 | 19 JUL. 2023 11:30:23 |
| 1013 | Y | 10 mL in 30 sec | Liquid | SUBCUTANEOUS | 19 JUL. 2023 | 12:50:01 | 19 JUL. 2023 12:50:00 | 12:50:32 | 19 JUL. 2023 12:50:32 |
| 1012 | Y | 10 mL in 30 sec | Liquid | SUBCUTANEOUS | 19 JUL. 2023 | 12:50:00 | 19 JUL. 2023 12:50:00 | 12:50:24 | 19 JUL. 2023 12:50:24 |
| 1029 | Y | 10 mL in 30 sec | Liquid | SUBCUTANEOUS | 14 JUL. 2023 | 07:30:00 | 14 JUL. 2023 07:30:00 | 07:30:33 | 14 JUL. 2023 07:30:33 |
| 1034 | Y | 10 mL in 30 sec | Liquid | SUBCUTANEOUS | 14 JUL. 2023 | 08:50:01 | 14 JUL. 2023 08:50:01 | 08:50:30 | 14 JUL. 2023 08:50:30 |
| 1033 | Y | 10 mL in 30 sec | Liquid | SUBCUTANEOUS | 13 JUL. 2023 | 07:20:02 | 13 JUL. 2023 07:20:02 | 07:20:33 | 13 JUL. 2023 07:20:33 |
| 1028 | Y | 10 mL in 30 sec | Liquid | SUBCUTANEOUS | 12 JUL. 2023 | 07:10:00 | 12 JUL. 2023 07:10:00 | 07:10:30 | 12 JUL. 2023 07:10:30 |
| 1030 | Y | 10 mL in 30 sec | Liquid | SUBCUTANEOUS | 14 JUL. 2023 | 07:30:01 | 14 JUL. 2023 07:30:01 | 07:30:35 | 14 JUL. 2023 07:30:35 |
| 1038 | Y | 10 mL in 30 sec | Liquid | SUBCUTANEOUS | 14 JUL. 2023 | 11:30:01 | 14 JUL. 2023 11:30:01 | 11:30:31 | 14 JUL. 2023 11:30:31 |
| 1043 | Y | 10 mL in 30 sec | Liquid | SUBCUTANEOUS | 14 JUL. 2023 | 12:50:01 | 14 JUL. 2023 12:50:01 | 12:50:25 | 14 JUL. 2023 12:50:25 |
| 1031 | Y | 10 mL in 30 sec | Liquid | SUBCUTANEOUS | 14 JUL. 2023 | 07:30:01 | 14 JUL. 2023 07:30:01 | 07:30:35 | 14 JUL. 2023 07:30:35 |
| 1040 | Y | 10 mL in 30 sec | Liquid | SUBCUTANEOUS | 14 JUL. 2023 | 11:30:01 | 14 JUL. 2023 11:30:01 | 11:30:25 | 14 JUL. 2023 11:30:25 |
| 1035 | Y | 10 mL in 30 sec | Liquid | SUBCUTANEOUS | 14 JUL. 2023 | 10:10:02 | 14 JUL. 2023 10:10:02 | 10:10:30 | 14 JUL. 2023 10:10:30 |
| 1041 | Y | 10 mL in 30 sec | Liquid | SUBCUTANEOUS | 14 JUL. 2023 | 12:50:01 | 14 JUL. 2023 12:50:01 | 12:50:34 | 14 JUL. 2023 12:50:34 |
| 1037 | Y | 10 mL in 30 sec | Liquid | SUBCUTANEOUS | 14 JUL. 2023 | 10:10:01 | 14 JUL. 2023 10:10:01 | 10:10:25 | 14 JUL. 2023 10:10:25 |

| SUBJID | EXINTP | EXYIND | EXCOMPL | EXLOC | EXINDUR | EXINTSPY |
|---|---|---|---|---|---|---|
| 1001 | N | | Y | Lower Right Quadrant of the Abdomen | 30 | |
| 1002 | N | | Y | Lower Right Quadrant of the Abdomen | 30 | |
| 1003 | N | | Y | Lower Right Quadrant of the Abdomen | 30 | |
| 1004 | Y | 71 | Y | Lower Right Quadrant of the Abdomen | 30 | DOSE WAS NOT PROPERLY SET BY TECHNICIAN, RESTARTED |
| 1005 | N | | Y | Lower Right Quadrant of the Abdomen | 30 | |
| 1006 | N | | Y | Lower Right Quadrant of the Abdomen | 30 | |
| 1007 | | | Y | Lower Right Quadrant of the Abdomen | 30 | |
| 1008 | N | | Y | Lower Right Quadrant of the Abdomen | 30 | |
| 1009 | N | | Y | Lower Right Quadrant of the Abdomen | 30 | |
| 1010 | N | | Y | Lower Right Quadrant of the Abdomen | 30 | |
| 1013 | N | | Y | Lower Right Quadrant of the Abdomen | 30 | |
| 1012 | N | | Y | Lower Right Quadrant of the Abdomen | 30 | |
| 1029 | N | | Y | Lower Right Quadrant of the Abdomen | 30 | |
| 1034 | N | | Y | Lower Right Quadrant of the Abdomen | 30 | |
| 1033 | N | | Y | Lower Right Quadrant of the Abdomen | 30 | |
| 1028 | N | | Y | Lower Right Quadrant of the Abdomen | 30 | |
| 1030 | N | | Y | Lower Right Quadrant of the Abdomen | 30 | |
| 1038 | N | | Y | Lower Right Quadrant of the Abdomen | 30 | |
| 1043 | N | | Y | Lower Right Quadrant of the Abdomen | 30 | |
| 1031 | N | | Y | Lower Right Quadrant of the Abdomen | 30 | |
| 1040 | N | | Y | Lower Right Quadrant of the Abdomen | 30 | |

TABLE 92-continued

Human clinical trial injection visit overview

| | | | | |
|---|---|---|---|---|
| 1035 | N | Y | Lower Right Quadrant of the Abdomen | 30 |
| 1041 | N | Y | Lower Right Quadrant of the Abdomen | 30 |
| 1037 | N | Y | Lower Right Quadrant of the Abdomen | 30 |
| 1001 | N | Y | Lower Left Quadrant of the Abdomen | 33 |
| 1002 | N | Y | Lower Left Quadrant of the Abdomen | 24 |
| 1003 | N | Y | Lower Left Quadrant of the Abdomen | 30 |
| 1004 | N | Y | Lower Left Quadrant of the Abdomen | 24 |
| 1005 | N | Y | Lower Left Quadrant of the Abdomen | 34 |
| 1006 | | | | |
| 1007 | N | Y | Lower Left Quadrant of the Abdomen | 24 |
| 1008 | N | Y | Lower Left Quadrant of the Abdomen | 24 |
| 1009 | N | Y | Lower Left Quadrant of the Abdomen | 24 |
| 1010 | N | Y | Lower Left Quadrant of the Abdomen | 22 |
| 1013 | N | Y | Lower Left Quadrant of the Abdomen | 32 |
| 1012 | N | Y | Lower Left Quadrant of the Abdomen | 23 |
| 1029 | N | Y | Lower Left Quadrant of the Abdomen | 29 |
| 1034 | N | Y | Lower Left Quadrant of the Abdomen | 28 |
| 1033 | N | Y | Lower Left Quadrant of the Abdomen | 31 |
| 1028 | N | Y | Lower Left Quadrant of the Abdomen | 31 |
| 1030 | N | Y | Lower Left Quadrant of the Abdomen | 34 |
| 1038 | N | Y | Lower Left Quadrant of the Abdomen | 30 |
| 1043 | N | Y | Lower Left Quadrant of the Abdomen | 24 |
| 1031 | N | Y | Lower Left Quadrant of the Abdomen | 33 |
| 1040 | N | Y | Lower Left Quadrant of the Abdomen | 24 |
| 1035 | N | Y | Lower Left Quadrant of the Abdomen | 28 |
| 1041 | N | Y | Lower Left Quadrant of the Abdomen | 32 |
| 1037 | N | Y | Lower Left Quadrant of the Abdomen | 24 |
| | | | Average Inj Visit 2 | 27.91304348 |
| | | | Minimum Injection Time | 22 |
| | | | Maximum Injection Time | 34 |

TABLE 93

Human clinical trial follow-up visit overview

| SUBJID | VISIT | VISITNUM | Data Page Name | Page Repeat Number | RecordId | Record Position | Min Created | Max Updated | SaveTS |
|---|---|---|---|---|---|---|---|---|---|
| 1001 | Follow-Up Visit 1 | 4 | Injection Site Observation Assessment | 0 | 30218166 | 1 | Jul. 24, 2023 18:04 | Jul. 31, 2023 17:47 | Aug. 1, 2023 1:04 |
| 1002 | Follow-Up Visit 1 | 4 | Injection Site Observation Assessment | 0 | 30218763 | 1 | Jul. 26, 2023 20:37 | Jul. 31, 2023 19:58 | Aug. 1, 2023 1:04 |
| 1003 | Follow-Up Visit 1 | 4 | Injection Site Observation Assessment | 0 | 30219335 | 1 | Jul. 26, 2023 17:26 | Jul. 26, 2023 17:26 | Jul. 26, 2023 17:26 |
| 1004 | Follow-Up Visit 1 | 4 | Injection Site Observation Assessment | 0 | 30219559 | 1 | Jul. 26, 2023 17:22 | Jul. 26, 2023 17:22 | Jul. 26, 2023 17:22 |
| 1005 | Follow-Up Visit 1 | 4 | Injection Site Observation Assessment | 0 | 30269306 | 1 | Jul. 26, 2023 17:04 | Jul. 26, 2023 17:04 | Jul. 26, 2023 17:05 |
| 1007 | Follow-Up Visit 1 | 4 | Injection Site Observation Assessment | 0 | 30345087 | 1 | Jul. 26, 2023 17:02 | Jul. 26, 2023 17:02 | Jul. 26, 2023 17:02 |
| 1008 | Follow-Up Visit 1 | 4 | Injection Site Observation Assessment | 0 | 30583342 | 1 | Jul. 26, 2023 17:11 | Jul. 26, 2023 17:11 | Jul. 26, 2023 17:11 |
| 1009 | Follow-Up Visit 1 | 4 | Injection Site Observation Assessment | 0 | 30586168 | 1 | Jul. 26, 2023 20:04 | Jul. 26, 2023 20:04 | Jul. 26, 2023 20:04 |
| 1010 | Follow-Up Visit 1 | 4 | Injection Site Observation Assessment | 0 | 30586455 | 1 | Jul. 26, 2023 20:14 | Jul. 26, 2023 20:14 | Jul. 26, 2023 20:15 |
| 1013 | Follow-Up Visit 1 | 4 | Injection Site Observation Assessment | 0 | 30586717 | 1 | Jul. 26, 2023 19:50 | Jul. 26, 2023 19:50 | Jul. 26, 2023 19:50 |
| 1012 | Follow-Up Visit 1 | 4 | Injection Site Observation Assessment | 0 | 30587802 | 1 | Jul. 26, 2023 17:19 | Jul. 26, 2023 17:19 | Jul. 26, 2023 17:19 |

TABLE 93-continued

Human clinical trial follow-up visit overview

| 1029 | Follow-Up Visit 1 | 4 | Injection Site Observation Assessment | 0 | 30746045 | 1 | Jul. 26, 2023 20:24 | Jul. 26, 2023 20:24 | Jul. 26, 2023 20:25 |
|---|---|---|---|---|---|---|---|---|---|
| 1034 | Follow-Up Visit 1 | 4 | Injection Site Observation Assessment | 0 | 30748452 | 1 | Jul. 26, 2023 20:48 | Jul. 26, 2023 20:48 | Jul. 26, 2023 20:49 |
| 1033 | Follow-Up Visit 1 | 4 | Injection Site Observation Assessment | 0 | 30888438 | 1 | Jul. 26, 2023 20:35 | Jul. 26, 2023 20:35 | Jul. 26, 2023 20:35 |
| 1028 | Follow-Up Visit 1 | 4 | Injection Site Observation Assessment | 0 | 30894028 | 1 | Jul. 26, 2023 20:28 | Jul. 26, 2023 20:28 | Jul. 26, 2023 20:28 |
| 1030 | Follow-Up Visit 1 | 4 | Injection Site Observation Assessment | 0 | 30972373 | 1 | Jul. 26, 2023 20:32 | Jul. 26, 2023 20:32 | Jul. 26, 2023 20:32 |
| 1038 | Follow-Up Visit 1 | 4 | Injection Site Observation Assessment | 0 | 30975154 | 1 | Jul. 26, 2023 20:44 | Jul. 26, 2023 20:44 | Jul. 26, 2023 20:44 |
| 1043 | Follow-Up Visit 1 | 4 | Injection Site Observation Assessment | 0 | 31028480 | 1 | Jul. 26, 2023 20:43 | Jul. 26, 2023 20:43 | Jul. 26, 2023 20:43 |
| 1040 | Follow-Up Visit 1 | 4 | Injection Site Observation Assessment | 0 | 31087768 | 1 | Jul. 26, 2023 20:46 | Jul. 26, 2023 20:46 | Jul. 26, 2023 20:47 |
| 1035 | Follow-Up Visit 1 | 4 | Injection Site Observation Assessment | 0 | 31089347 | 1 | Jul. 26, 2023 20:22 | Jul. 26, 2023 20:22 | Jul. 26, 2023 20:22 |
| 1041 | Follow-Up Visit 1 | 4 | Injection Site Observation Assessment | 0 | 31093125 | 1 | Jul. 26, 2023 20:19 | Jul. 26, 2023 20:19 | Jul. 26, 2023 20:19 |
| 1037 | Follow-Up Visit 1 | 4 | Injection Site Observation Assessment | 0 | 31156238 | 1 | Jul. 26, 2023 20:30 | Jul. 26, 2023 20:30 | Jul. 26, 2023 20:30 |
| 1001 | Follow-Up Visit 1 | 4 | Numeric Rating Scale | 0 | 30218176 | 1 | Jul. 24, 2023 18:05 | Jul. 24, 2023 18:05 | Jul. 24, 2023 18:05 |
| 1002 | Follow-Up Visit 1 | 4 | Numeric Rating Scale | 0 | 30218773 | 1 | Jul. 26, 2023 20:37 | Jul. 31, 2023 19:56 | Aug. 1, 2023 1:04 |
| 1003 | Follow-Up Visit 1 | 4 | Numeric Rating Scale | 0 | 30219345 | 1 | Jul. 26, 2023 17:27 | Jul. 26, 2023 17:27 | Jul. 26, 2023 17:27 |
| 1004 | Follow-Up Visit 1 | 4 | Numeric Rating Scale | 0 | 30219569 | 1 | Jul. 26, 2023 17:22 | Jul. 26, 2023 17:22 | Jul. 26, 2023 17:22 |
| 1005 | Follow-Up Visit 1 | 4 | Numeric Rating Scale | 0 | 30269316 | 1 | Jul. 26, 2023 17:05 | Jul. 26, 2023 17:05 | Jul. 26, 2023 17:05 |
| 1007 | Follow-Up Visit 1 | 4 | Numeric Rating Scale | 0 | 30345097 | 1 | Jul. 26, 2023 17:02 | Jul. 26, 2023 17:03 | Jul. 26, 2023 17:03 |
| 1008 | Follow-Up Visit 1 | 4 | Numeric Rating Scale | 0 | 30583352 | 1 | Jul. 26, 2023 17:08 | Jul. 26, 2023 17:08 | Jul. 26, 2023 17:08 |
| 1009 | Follow-Up Visit 1 | 4 | Numeric Rating Scale | 0 | 30586178 | 1 | Jul. 26, 2023 20:04 | Jul. 26, 2023 20:04 | Jul. 26, 2023 20:04 |
| 1010 | Follow-Up Visit 1 | 4 | Numeric Rating Scale | 0 | 30586465 | 1 | Jul. 26, 2023 20:15 | Jul. 26, 2023 20:15 | Jul. 26, 2023 20:15 |
| 1013 | Follow-Up Visit 1 | 4 | Numeric Rating Scale | 0 | 30586727 | 1 | Jul. 26, 2023 19:50 | Jul. 26, 2023 19:50 | Jul. 26, 2023 19:51 |
| 1012 | Follow-Up Visit 1 | 4 | Numeric Rating Scale | 0 | 30587812 | 1 | Jul. 26, 2023 17:18 | Jul. 26, 2023 17:18 | Jul. 26, 2023 17:18 |
| 1029 | Follow-Up Visit 1 | 4 | Numeric Rating Scale | 0 | 30746055 | 1 | Jul. 26, 2023 20:25 | Jul. 26, 2023 20:25 | Jul. 26, 2023 20:25 |
| 1034 | Follow-Up Visit 1 | 4 | Numeric Rating Scale | 0 | 30748462 | 1 | Jul. 26, 2023 20:48 | Jul. 26, 2023 20:48 | Jul. 26, 2023 20:49 |
| 1033 | Follow-Up Visit 1 | 4 | Numeric Rating Scale | 0 | 30888448 | 1 | Jul. 26, 2023 20:33 | Jul. 26, 2023 20:33 | Jul. 26, 2023 20:33 |
| 1028 | Follow-Up Visit 1 | 4 | Numeric Rating Scale | 0 | 30894038 | 1 | Jul. 26, 2023 20:28 | Jul. 26, 2023 20:28 | Jul. 26, 2023 20:28 |

TABLE 93-continued

Human clinical trial follow-up visit overview

| 1030 | Follow-Up Visit 1 | 4 | Numeric Rating Scale | 0 | 30972383 | 1 | Jul. 26, 2023 20:32 | Jul. 26, 2023 20:32 | Jul. 26, 2023 20:32 |
|------|-------------------|---|----------------------|---|----------|---|---------------------|---------------------|---------------------|
| 1038 | Follow-Up Visit 1 | 4 | Numeric Rating Scale | 0 | 30975164 | 1 | Jul. 26, 2023 20:44 | Jul. 26, 2023 20:44 | Jul. 26, 2023 20:44 |
| 1043 | Follow-Up Visit 1 | 4 | Numeric Rating Scale | 0 | 31028490 | 1 | Jul. 26, 2023 20:43 | Jul. 26, 2023 20:43 | Jul. 26, 2023 20:43 |
| 1040 | Follow-Up Visit 1 | 4 | Numeric Rating Scale | 0 | 31087778 | 1 | Jul. 26, 2023 20:46 | Jul. 26, 2023 20:46 | Jul. 26, 2023 20:47 |
| 1035 | Follow-Up Visit 1 | 4 | Numeric Rating Scale | 0 | 31089357 | 1 | Jul. 26, 2023 20:22 | Jul. 26, 2023 20:22 | Jul. 26, 2023 20:22 |
| 1041 | Follow-Up Visit 1 | 4 | Numeric Rating Scale | 0 | 31093135 | 1 | Jul. 26, 2023 20:19 | Jul. 26, 2023 20:19 | Jul. 26, 2023 20:19 |
| 1037 | Follow-Up Visit 1 | 4 | Numeric Rating Scale | 0 | 31156248 | 1 | Jul. 26, 2023 20:30 | Jul. 27, 2023 8:06 | Jul. 28, 2023 1:04 |

| SUBJID | QSDAT | QSTIM | QSDTTM | QSPAIN |
|--------|-------|-------|--------|--------|
| 1001 | 24 JUL. 2023 | 08:05 | 24 JUL. 2023 08:05 | |
| 1002 | 25 JUL. 2023 | 07:16 | 25 JUL. 2023 07:16 | |
| 1003 | 26 JUL. 2023 | 07:09 | 26 JUL. 2023 07:09 | |
| 1004 | 26 JUL. 2023 | 07:24 | 26 JUL. 2023 07:24 | |
| 1005 | 26 JUL. 2023 | 07:46 | 26 JUL. 2023 07:46 | |
| 1007 | 26 JUL. 2023 | 09:48 | 26 JUL. 2023 09:48 | |
| 1008 | 26 JUL. 2023 | 09:30 | 26 JUL. 2023 09:30 | |
| 1009 | 26 JUL. 2023 | 11:48 | 26 JUL. 2023 11:48 | |
| 1010 | 26 JUL. 2023 | 11:41 | 26 JUL. 2023 11:41 | |
| 1013 | 26 JUL. 2023 | 12:40 | 26 JUL. 2023 12:40 | |
| 1012 | 26 JUL. 2023 | 10:19 | 26 JUL. 2023 10:19 | |
| 1029 | 21 JUL. 2023 | 08:42 | 21 JUL. 2023 08:42 | |
| 1034 | 21 JUL. 2023 | 09:43 | 21 JUL. 2023 09:43 | |
| 1033 | 20 JUL. 2023 | 08:02 | 20 JUL. 2023 08:02 | |
| 1028 | 19 JUL. 2023 | 09:41 | 19 JUL. 2023 09:41 | |
| 1030 | 20 JUL. 2023 | 09:30 | 20 JUL. 2023 09:30 | |
| 1038 | 21 JUL. 2023 | 11:24 | 21 JUL. 2023 11:24 | |
| 1043 | 21 JUL. 2023 | 12:35 | 21 JUL. 2023 12:35 | |
| 1040 | 21 JUL. 2023 | 11:17 | 21 JUL. 2023 11:17 | |
| 1035 | 21 JUL. 2023 | 11:20 | 21 JUL. 2023 11:20 | |
| 1041 | 26 JUL. 2023 | 08:48 | 26 JUL. 2023 08:48 | |
| 1037 | 21 JUL. 2023 | 10:35 | 21 JUL. 2023 10:35 | |
| 1001 | 24 JUL. 2023 | 08:03 | 24 JUL. 2023 08:03 | 0 |
| 1002 | 25 JUL. 2023 | 07:15 | 25 JUL. 2023 07:15 | 0 |
| 1003 | 26 JUL. 2023 | 07:06 | 26 JUL. 2023 07:06 | 0 |
| 1004 | 26 JUL. 2023 | 07:14 | 26 JUL. 2023 07:14 | 0 |
| 1005 | 26 JUL. 2023 | 07:44 | 26 JUL. 2023 07:44 | 0 |
| 1007 | 26 JUL. 2023 | 09:45 | 26 JUL. 2023 09:45 | 0 |
| 1008 | 26 JUL. 2023 | 09:37 | 26 JUL. 2023 09:37 | 0 |
| 1009 | 26 JUL. 2023 | 11:47 | 26 JUL. 2023 11:47 | 0 |
| 1010 | 26 JUL. 2023 | 11:40 | 26 JUL. 2023 11:40 | 0 |
| 1013 | 26 JUL. 2023 | 12:26 | 26 JUL. 2023 12:26 | 0 |
| 1012 | 26 JUL. 2023 | 10:17 | 26 JUL. 2023 10:17 | 0 |
| 1029 | 21 JUL. 2023 | 08:41 | 21 JUL. 2023 08:41 | 0 |
| 1034 | 21 JUL. 2023 | 09:43 | 21 JUL. 2023 09:43 | 0 |
| 1033 | 20 JUL. 2023 | 07:51 | 20 JUL. 2023 07:51 | 0 |
| 1028 | 19 JUL. 2023 | 09:39 | 19 JUL. 2023 09:39 | 0 |
| 1030 | 20 JUL. 2023 | 09:28 | 20 JUL. 2023 09:28 | 0 |
| 1038 | 21 JUL. 2023 | 11:23 | 21 JUL. 2023 11:23 | 0 |
| 1043 | 21 JUL. 2023 | 12:34 | 21 JUL. 2023 12:34 | 0 |
| 1040 | 21 JUL. 2023 | 11:16 | 21 JUL. 2023 11:16 | 0 |
| 1035 | 21 JUL. 2023 | 11:20 | 21 JUL. 2023 11:20 | 0 |
| 1041 | 26 JUL. 2023 | 08:47 | 26 JUL. 2023 08:47 | 0 |
| 1037 | 21 JUL. 2023 | | | 0 |

Duration of injection: Injection times (seconds) were measured utilizing a hand-held stopwatch and closely monitoring the start and completion of the injection. Individual injection times are shown in FIG. 89 and mean injection times are summarized in Table 94. The mean injection time for the 25 G-Terumo needle group was approximately 33% faster than the mean injection time for the 25 G-BD needle group.

TABLE 94

| Needle Gauge | Mean injection time (seconds ± SEM) | |
|---|---|---|
| | Injection Time (sec ± SEM) | |
| | 25 G-Terumo | 25 G-BD |
| | 19.9 ± 0.5 | 30.0 ± 1.1 |

FIGS. 143-149B provide an overview of the human clinical trial as well as the data collected thus far. FIG. 143 demonstrates that all HVAI injections were completed (n=23) and well tolerated, with a mean injection time of 27.9±0.8 seconds (range of 22.9-34.5 seconds). Although not wishing to be limited by theory, these results demonstrate that the injection time may be controlled by volume, needle gauge, and/or test solution viscosity. FIG. 144 demonstrates the rapid time to resolution for the HVAI injections using HCPs qualitative assessment scoring of combined bleb/swelling size, induration, and erythema over time until complete injection site resolution. Resolution was defined when HCP determined that all three qualitative scores were ≤1 (very slight). Most injections (~74%) were resolved by 30 minutes and 100% were resolved by 60 minutes. FIG. 145 provides modified-Draize scores for erythema, swelling, and induration with HVAI injections. FIGS. 146A-146B provide data demonstrating that the modified-Draize score for erythema, swelling, and induration were low and resolved quickly (score ≤1). FIGS. 147-149B provide data using a numeric rating scale (NRS, 0-10 scale) demonstrating that subjects had minimal pain with the injection and rapid resolution of the pain.

Both 5 mL (n=12) and 10 mL (n=12) injection volumes delivered by pump in 30 seconds were well tolerated. All injection parameters studied were resolved rapidly after the completion of the injection. The delivery of 10 mL in 30 seconds via HVAI (n=23) was well tolerated. The average injection time was 28±0.8 seconds. HCP determined qualitative Draize scores for erythema, swelling, and induration were low and resolved quickly. The pain/discomfort was ≤1 by 45 minutes (91% at 0 by 45 minutes).

FIG. 150 provides a rendering of a patient friendly auto-injector for use with the disclosed formulation.

REFERENCES

1) GAMMAGARD LIQUID (immune globulin infusion [human] 10%). Baxalta US Inc. https://www.shirecontent.com/PI/PDFs/Gamliquid_USA_ENG.pdf. Published March 2021. Accessed 22 Feb. 2023.

2) Connor R, Kang D, Nekoroski T. Assessment of a Prototype Large Volume Auto-Injector (LVAI) for Subcutaneous Administration of an Ig Solution Using a 23 G Needle and 2000 U/mL of rHuPH20. Study Report 22148. On File at Halozyme Therapeutics, Inc. 27 Jan. 2023.

3) Frost G. Recombinant Human Hyaluronidase (rHuPH20): An Enabling Platform for Subcutaneous Drug and Fluid Administration. Expert Opin. Drug Deliv. 2007. 4(4):427-440.

4) HYLENEX recombinant (hyaluronidase human injection). Halozyme Therapeutics, Inc. https://dailymed.nlm.nih.gov/dailymed/fda/fdaDrugXsl.cfm?setid=3023 cc56-ed4b-4e87-b3a1-81b20943f658&type=display. Approved 2005, revised April 2021. Accessed 23 Feb. 2023.

5) HYQVIA [Immune Globulin Infusion 10% (Human) with Recombinant Human Hyaluronidase] Solution for subcutaneous administration. Baxalta US Inc. https://dailymed.nlm.nih.gov/dailymed/fda/fdaDrugXsl.cfm?setid=7ca2c26f-4be2-48cd-be5b-486e350654ba&type=display. Approved 2014, revised March 2021. Accessed 23 Feb. 2023.

6) Investigator's Brochure. Recombinant Human Hyaluronidase PH20 (rHuPH20). Edition 11.0. Halozyme, Inc. 21 Feb. 2023.

7) Karcioglu O, Topacoglu H, Dikme O, Dikme O. A systematic review of the pain scales in adults: Which to use? Am J Emerg Med. 2018 April; 36(4): 707-714.

8) Kirschbrown W P, Wynne C, Kågedal M, Wada R, Li H, Wang B, et al. Development of a Subcutaneous Fixed-Dose Combination of Pertuzumab and Trastuzumab: Results From the Phase Ib Dose-Finding Study. J Clin Pharmacol. 2019 May; 59(5): 702-716.

9) Printz M A, Dychter S S, DeNoia E P, Harrigan R, Sugarman B J, Zepeda M, Souratha J, Kang D W, Maneval D C. A Phase I Study to Evaluate the Safety, Tolerability, Pharmacokinetics, and Pharmacodynamics of Recombinant Human Hyaluronidase PH20 Administered Intravenously in Healthy Volunteers. Curr Ther Res Clin Exp. 2020 Aug. 19; 93:100604.

10) Printz M A, Sugarman B J, Paladini R D, Jorge M C, Wang Y, Kang D W, Maneval D C, LaBarre M J. Risk Factors, Hyaluronidase Expression, and Clinical Immunogenicity of Recombinant Human Hyaluronidase PH20, an Enzyme Enabling Subcutaneous Drug Administration. AAPS J. 2022 Oct. 20; 24(6):110.

11) Rosengren S, Dychter S S, Printz M A, Huang L, Schiff R I, Schwarz H P, McVey J K, Drake F H, Maneval D C, Kennard D A, Frost G I, Sugarman B J, Muchmore D B. Clinical Immunogenicity of rHuPH20, a Hyaluronidase Enabling Subcutaneous Drug Administration. AAPS J. 2015 September; 17(5):1144-56.

12) Usmani S Z, Nahi H, Mateos M V, van de Donk N W C J, Chari A, Kaufman J L, Moreau P, et al. Subcutaneous delivery of daratumumab in relapsed or refractory multiple myeloma. Blood. 2019 Aug. 22; 134(8):668-677.

Example 7: Summary of Data from Examples 1-5

| [rHuPH20] Applied Force | 4000 U/mL | | | | 2000 U/mL | | | | 5000 U/mL | | | |
|---|---|---|---|---|---|---|---|---|---|---|---|---|
| | GGL | GGL + rHuPH20 | % Change from Baseline | Example | Ig-120 | Ig-120 + rHuPH20 | % Change from Baseline | Example | Ig-120 | Ig-120 + rHuPH20 | % Change from Baseline | Example |
| 23G-BD | | 34.1 ± 0.8 | | 5 | 55.3 ± 1.8 | 51.3 ± 1.5 | −7.2 | 2 | | | | |
| 25G-Terumo | 43.2 ± 1.2 | 42.6 ± 1.1 | −1.4 | | | | | | | | | |
| 25G-BD | | 67.4 ± 2.1 | | | 93.6 ± 3.4 | 85.2 ± 3.2 | −9.0 | 1 | 92.7 ± 3.5 | 85.9 ± 3.2 | −7.3 | 3 |

| [rHuPH20] Back-Leakage | 4000 U/mL | | | | 2000 U/mL | | | | 5000 U/mL | | | |
|---|---|---|---|---|---|---|---|---|---|---|---|---|
| | GGL | GGL + rHuPH20 | % Change from Baseline | Example | Ig-120 | Ig-120 + rHuPH20 | % Change from Baseline | Example | Ig-120 | Ig-120 + rHuPH20 | % Change from Baseline | Example |
| 23G-BD | | 42.0 ± 16.6 | −32.4 | 5 | 105.7 ± 21.9 | 36.0 ± 10.5 | −65.9 | 2 | | | | |
| 25G-Terumo | 62.1 ± 34.1 | 10.6 ± 4.1 | −82.9 | | | | | | | | | |
| 25G-BD | | 25.2 ± 11.8 | −59.4 | | 45.3 ± 9.4 | 26.0 ± 4.7 | −42.6 | 1 | 34.2 ± 15.6 | 17.4 ± 8.5 | −49.0 | 3 |

| [rHuPH20] Volume | 4000 U/mL | | | | 2000 U/mL | | | | 5000 U/mL | | | |
|---|---|---|---|---|---|---|---|---|---|---|---|---|
| | GGL | GGL + rHuPH20 | % Change from Baseline | Example | Ig-120 | Ig-120 + rHuPH20 | % Change from Baseline | Example | Ig-120 | Ig-120 + rHuPH20 | % Change from Baseline | Example |
| 23G-BD | | 6.8 ± 0.6 | −29.2 | 5 | 9.9 ± 1.9 | 7.3 ± 1.6 | −26.3 | 2 | | | | |
| 25G-Terumo | 9.6 ± 1.5 | 9.0 ± 1.7 | −6.3 | | | | | | | | | |
| 25G-BD | | 6.9 ± 1.5 | −28.1 | | 16.0 ± 1.6 | 10.1 ± 1.9 | −36.9 | 1 | 14.2 ± 2.1 | 6.8 ± 1.4 | −52.1 | 3 |

| [rHuPH20] Height | 4000 U/mL | | | | 2000 U/mL | | | | 5000 U/mL | | | |
|---|---|---|---|---|---|---|---|---|---|---|---|---|
| | GGL | GGL + rHuPH20 | % Change from Baseline | Example | Ig-120 | Ig-120 + rHuPH20 | % Change from Baseline | Example | Ig-120 | Ig-120 + rHuPH20 | % Change from Baseline | Example |
| 23G-BD | | 4.6 ± 0.6 | −30.3 | 5 | 6.5 ± 1.2 | 5.1 ± 1.0 | −21.5 | 2 | | | | |
| 25G-Terumo | 6.6 ± 1.0 | 5.8 ± 1.0 | −12.1 | | | | | | | | | |
| 25G-BD | | 4.5 ± 0.9 | −31.8 | | 9.7 ± 0.5 | 6.9 ± 0.6 | −28.9 | 1 | 8.9 ± 1.3 | 5.1 ± 1.0 | −42.7 | 3 |

| [rHuPH20] Swelling Size - T0 | 4000 U/mL | | | | 2000 U/mL | | | | 5000 U/mL | | | |
|---|---|---|---|---|---|---|---|---|---|---|---|---|
| | GGL | GGL + rHuPH20 | % Change from Baseline | Example | Ig-120 | Ig-120 + rHuPH20 | % Change from Baseline | Example | Ig-120 | Ig-120 + rHuPH20 | % Change from Baseline | Example |
| 23G-BD | | 2.6 ± 0.2 | −3.7 | 5 | 3.2 ± 0.3 | 2.8 ± 0.3 | −12.5 | 2 | | | | |
| 25G-Terumo | 2.7 ± 0.3 | 2.2 ± 0.2 | −18.5 | | | | | | | | | |
| 25G-BD | | 2.7 ± 0.2 | 0.0 | | 3.8 ± 0.1 | 3.2 ± 0.2 | −15.8 | 1 | 3.5 ± 0.2 | 3.2 ± 0.8 | −8.6 | 3 |

| [rHuPH20] Swelling Induration - T0 | 4000 U/mL | | | | 2000 U/mL | | | | 5000 U/mL | | | |
|---|---|---|---|---|---|---|---|---|---|---|---|---|
| | GGL | GGL + rHuPH20 | % Change from Baseline | Example | Ig-120 | Ig-120 + rHuPH20 | % Change from Baseline | Example | Ig-120 | Ig-120 + rHuPH20 | % Change from Baseline | Example |
| 23G-BD | | 1.7 ± 0.2 | −26.1 | 5 | 3.2 ± 0.3 | 2.3 ± 0.2 | −28.1 | 2 | | | | |
| 25G-Terumo | 2.3 ± 0.3 | 1.5 ± 0.1 | −34.8 | | | | | | | | | |
| 25G-BD | | 1.9 ± 0.1 | −17.4 | | 3.9 ± 0.1 | 2.6 ± 0.1 | −33.3 | 1 | 3.6 ± 0.2 | 2.3 ± 0.3 | −36.1 | 3 |

| Example 5 | 25G-BD/25G-Ter/23G-BD T0 | | | T15 | | | T30 | | | T2 h | | |
|---|---|---|---|---|---|---|---|---|---|---|---|---|
| | 25G-Terumo | 25G-BD | 23G-BD | 25G-Terumo | 25G-BD | 23G-BD | 25G-Terumo | 25G-BD | 23G-BD | 25G-Terumo | 25G-BD | 23G-BD |
| GGL | 2.7 ± 0.3 | | | 2.2 ± 0.3 | | | 1.7 ± 0.3 | | | 0.8 ± 0.2 | | |
| GGL + EDP | 2.2 ± 0.2 | 2.7 ± 0.2 | 2.6 ± 0.2 | 1.2 ± 0.2 | 1.8 ± 0.2 | 1.5 ± 0.2 | 0.7 ± 0.2 | 1.3 ± 0.2 | 0.9 ± 0.2 | 0.1 ± 0.1 | 0.1 ± 0.1 | 0.0 ± 0.0 |
| % Decrease | −18.5 | 0.0 | −3.7 | −45.5 | −18.2 | −31.8 | −58.8 | −23.5 | −47.1 | −87.5 | −87.5 | −100.0 |

| Example 1: 25 G-BD 2000 U/mL | | | | | |
|---|---|---|---|---|---|
| Swelling Size | Timepoint Post-Injection | | | | |
| Test Solution | T0 | T15 | T30 | T2 h | T24 h |
| Ig-120 | 3.8 ± 0.1 | 3.7 ± 0.1 | 3.5 ± 0.2 | 3.1 ± 0.3 | 0.1 ± 0.1 |
| Ig-120 + rHuPH20 | 3.2 ± 0.2 | 2.6 ± 0.3 | 2.0 ± 0.2 | 1.3 ± 0.2 | 0.0 ± 0.0 |
| % Decrease | −15.8 | −29.7 | −42.9 | −58.1 | −100 |
| Induration | Timepoint Post-Injection | | | | |
| Test Solution | T0 | T15 | T30 | T2 h | T24 h |
| Ig-120 | 3.9 ± 0.1 | 3.8 ± 0.1 | 3.3 ± 0.2 | 2.9 ± 0.2 | 0.03 ± 0.03 |
| Ig-120 + rHuPH20 | 2.6 ± 0.1 | 2.0 ± 0.1 | 1.5 ± 0.2 | 1.1 ± 0.1 | 0.0 ± 0.0 |
| % Decrease | −33.3 | −47.4 | −54.5 | −62.1 | −100 |

Example 2: 23 G-BD 2000 U/mL

| Swelling Size | Timepoint Post-Injection | | | | |
|---|---|---|---|---|---|
| Test Solution | T0 | T15 | T30 | T2 h | T24 h |
| Ig-120 | 3.2 ± 0.3 | 3.0 ± 0.3 | 2.8 ± 0.3 | 2.3 ± 0.4 | 0.0 ± 0.0 |
| Ig-120 + rHuPH20 | 2.8 ± 0.3 | 2.0 ± 0.3 | 1.5 ± 0.3 | 0.6 ± 0.2 | 0.0 ± 0.0 |
| % Decrease | −12.5 | −33 | −46.4 | −73.9 | 0 |

| Induration | Timepoint Post-Injection | | | | |
|---|---|---|---|---|---|
| Test Solution | T0 | T15 | T30 | T2 h | T24 h |
| Ig-120 | 3.2 ± 0.3 | 2.9 ± 0.3 | 2.7 ± 0.3 | 2.2 ± 0.4 | 0.1 ± 0.1 |
| Ig-120 + rHuPH20 | 2.3 ± 0.2 | 1.5 ± 0.2 | 0.9 ± 0.2 | 0.4 ± 0.1 | 0.0 ± 0.0 |
| % Decrease | −28.1 | −48.3 | −66.7 | −81.8 | −100 |

Example 3: 25 G-BD 5000 U/mL

| Swelling Size | Timepoint Post-Injection | | | | |
|---|---|---|---|---|---|
| Test Solution | T0 | T15 | T30 | T2 h | T24 h |
| Ig-120 | 3.5 ± 0.2 | 3.3 ± 0.2 | 3.1 ± 0.2 | 2.2 ± 0.3 | 0.1 ± 0.1 |
| Ig-120 + rHuPH20 | 3.2 ± 0.8 | 1.8 ± 0.3 | 1.3 ± 0.3 | 0.7 ± 0.2 | 0.0 ± 0.0 |
| % Decrease | −8.6 | −45.5 | −58.1 | −68.2 | −100 |

| Induration | Timepoint Post-Injection | | | | |
|---|---|---|---|---|---|
| Test Solution | T0 | T15 | T30 | T2 h | T24 h |
| Ig-120 | 3.6 ± 0.2 | 3.4 ± 0.2 | 3.0 ± 0.3 | 2.1 ± 0.4 | 0.1 ± 0.04 |
| Ig-120 + rHuPH20 | 2.3 ± 0.3 | 1.4 ± 0.3 | 0.9 ± 0.3 | 0.6 ± 0.2 | 0.0 ± 0.0 |
| % Decrease | −36.1 | −58.8 | −70.0 | −71.4 | −100 |

FIGS. 151-153 provide an overview of the swelling and induration in minipigs who were administered the disclosed formulation using an HVAI/HVAI protype.

Example 8: Assessment of a Prototype High Volume Auto-Injector (HVAI) for Subcutaneous Administration of GAMMAGARD LIQUID with rHuPH20 (4000 U/mL) Using Various Needle Gauges The objective of this study was to assess the performance of a prototype high volume auto-injector (HVAI) for the administration of GAMMAGARD LIQUID (GGL) with ENHNAZE™ Drug Product (EDP). EDP is a solution used for early human clinical applications that contains recombinant human hyaluronidase PH20 (rHuPH20).

Two cohorts were compared in this study each consisting of six subcutaneous (SC) injections. Cohort #1 evaluated the delivery of 10 mL of GGL+EDP solution using a 25 Gauge (G) Terumo thin-walled needle (25 G-Terumo); cohort #2 evaluated the delivery of 10 mL of the GGL+EDP solution using a 25 G Becton-Dickinson (25 G-BD) needle. All test solutions were formulated at 4000 U/mL on the day prior to the in-vivo assessments.

Yucatan miniature pigs were used in this study due to the similarity of the subcutaneous skin architecture with humans. Each animal received two vertical 10 mL SC injections into the lower abdominal region using the prototype device. One side received an injection of GGL+EDP using the 25 G-Terumo needle and the contralateral side of the animal received an injection of GGL+EDP using the 25 G-BD needle. Injection depth was ~8 mm for the 25 G-Terumo needle and ~10 mm for the 25 G-BD needle. Endpoints included measuring the duration of the injection, the amount of back-leakage after the injection, bleb area and volume over time, qualitative scoring for erythema, swelling size, and induration over time.

HVAI devices with a 25 G-Terumo needle had a shorter mean delivery time of 19.8 seconds compared to 30.0 seconds for the HVAI with a 25 G-BD needle. Back-leakage was greater with the 25 G-Terumo needle with a mean weight of 40.0 mg compared to 14.7 mg with the 25 G-BD needle. Post-injection swelling size decreased with both needles, with the qualitative assessments for erythema, bleb size, and induration reaching a modified Draize score of ~1 (very slight/barely perceptible by 30 minutes).

Overall, this proof-of-concept study showed that the HVAI was successful in subcutaneously delivering the intended 10 mL volume of GGL+EDP in ~30 seconds or less with rapid resolution of injection site swelling in miniature pigs. The results warrant further development of the HVAI including clinical investigation.

Introduction

The development of HVAIs requires information about the performance of the device using a relevant translatable animal species prior to human clinical use. Because the performance is dependent upon the hardware chosen for use in the design of the HVAI, selection of the proper hardware (e.g. needle gauge) is critical in order to ensure clinical success.

rHuPH20 has been shown to facilitate the SC administration of fluids and drugs by transiently and locally depolymerizing hyaluronan (HA) in the extracellular matrix (ECM). The depolymerization of HA reduces tissue backpressure in the SC space that subsequently allows for rapid, large volume administration of drugs. Previous work has shown that rHuPH20 can facilitate the delivery of large volumes to the SC space at high flow rates.

The minipig model has been selected due to the high degree of similarity of the subcutaneous space to that of humans. Previous studies using a minipig model have demonstrated the translatability of the model for use in pre-clinical and auto-injector studies.

The primary objective of the study was to assess the performance of a prototype HVAI for administration of GGL with EDP using either a 25 G-Terumo, or a 25 G-BD needle. The inside diameter of the 25 G-Terumo needle is larger than the 25 G-BD needle resulting in higher flow rates and lower pressure.

Test Articles and Methods
  Gammagard Liquid (GGL; 10% solution)
    Lot number: BE12C18748
    Storage Conditions: 2-8° C.
    Handling Conditions: Standard laboratory precautions
    Refrigerated expiration date: 30 Oct. 2025
    Supplier: Myonex
  ENHANZE Drug Product (EDP)—Recombinant human hyaluronidase PH20
    Lot number: 1-FIN-3426
    Concentration: 1.01 mg/mL
    Date of Manufacture: Dec. 30, 2014
    Retest Date: February 2023
    Enzyme activity: 105 kU/mL
    Storage: ≤70° C.
    Formulation: 10 mM Histidine, 130 mM sodium chloride, pH 6.5
    Handling Conditions: Standard laboratory precautions
    Supplier: Halozyme Therapeutics, Inc.
Formulation
Preparation of Test Solutions In this study all injections utilized one test solution of GGL+EDP (4000 U/mL). m The test solution was prepared on the day prior to the in vivo assessments. GGL was obtained and stored at 2-8° C. until used for preparation of the co-mix (never frozen). EDP was obtained and stored at 2-8° C. until used for preparation of the co-mix as well.

To prepare 38 mL of the co-mix, 36.6 mL of GGL was withdrawn from its source vial and added to a 50-mL co-mix vial. Two withdrawals from the GGL stock were required: 1×30-mL and 1×6.6-mL. Once the GGL was in the co-mix vial 1.4 mL of EDP was added to the 50-mL co-mix vial. This yielded 38 mL of the co-mix with an approximate activity of 4000 U/mL. To obtain 1.4 mL of EDP the contents of four EDP vials were combined into a 3-mL syringe prior to addition to the GGL. Each co-mix vial was used to fill (3) device COC syringes (10.1 mL/syringe). Because (12) COC syringes were required for the in-vivo assessments four bottles of the co-mix were prepared in the first week of dosing. Six COC syringes were required on the second week of dosing so three bottles of the co-mix were prepared one day prior to dosing. Each co-mix vial was used for filling three device COC syringes with 10.1 mL of the GGL+EDP test solution.

Pre-Study Enzymatic Activity Testing of rHuPH20: Week 1

Because of device issues the study was conducted on two separate days one week apart. For each study day the GGL+EDP solutions were prepared and tested for rHuPH20 activity one day prior to the start of the study using a micro-turbidity assay. These values are summarized in Table 95.

TABLE 95

Pre-study enzymatic activity testing of rHuPH20 in test solutions

| Test Solution | Dose Week | Pre-study Concentration (U/mL ± SD) |
|---|---|---|
| Co-mix vial #1 | 1 | 3955 ± 79 |
| Co-mix vial #2 | 1 | 3882 ± 100 |
| Co-mix vial #3 | 1 | 3807 ± 39 |
| Co-mix vial #4 | 1 | 3780 ± 65 |
| Co-mix vial #5 | 2 | 3723 ± 83 |
| Co-mix vial #6 | 2 | 3881 ± 110 |
| Co-mix vial #7 | 2 | 3897 ± 108 |

Post-Study Enzymatic Activity Testing of rHuPH20

At the end of each study day, dose retain samples were collected from unused devices and tested for rHuPH20 enzymatic activity. The device was injected into a 15 mL conical tube and the sample placed on wet ice until transported to a refrigerator set to maintain 2-8° C., and then tested for enzymatic activity on the following day. The values for enzymatic activity are provided in Table 96.

TABLE 96

Post-Study Enzymatic Activity Testing of Test Solutions

| Test Solution | Dose Week | Post-study Concentration (U/mL ± SD) |
|---|---|---|
| Dose retain #1 | 1 | 3966 ± 89 |
| Dose retain #2 | 1 | 3925 ± 103 |
| Dose retain #3 | 2 | 3952 ± 133 |
| Dose retain #4 | 2 | 3904 ± 141 |
| Dose retain #5 | 2 | 3894 ± 109 |

Preparation of AI Devices

One day prior to the study, devices were assembled using proprietary jigs. Syringes that fit the HVAI were filled with ~10.2 mL of either Ig-120 or Ig-120+rHuPH20. Once the syringe was filled, a sterile rubber stopper was inserted into the barrel end of the syringe. The syringe was then inverted with the tip upward, and the syringe cap removed and replaced with either a 23 G or a 25 G capped needle. The filled syringe with attached needle was then placed onto a proprietary jig that allowed for further insertion of the rubber stopper into the syringe barrel to the predetermined depth that allowed for priming and a final delivery volume of 10 mL. The filled syringe was then loaded into a spring-driven powerpack, and the external components of the AI device assembled around the syringe. Once each device was assembled, it was stored in a refrigerator set to maintain 2-8° C. in a vertical position (needle up) so that no leakage of test solution would occur during storage.

Animal Description
  Species: Pig (Sus scrofa domestica)
  Strain: Yucatan miniature
  Sex: Female
  Age: >3 months
  Body weight: 16-20 kg upon receipt
  Quantity: 6
  Source: Premier BioSource (Ramona, CA)
Husbandry Animals were received by the animal facility and allowed to acclimate prior to study start. Animals were group housed in steel pens with automatic water provided ad libitum. Animals were fed twice daily (AM and PM), except on study day (PM only). Room environment was set to maintain a temperature of ~17-27° C. and a relative humidity of 40-70%, with a 12 hour light/12 hour dark time cycle. Animals were allowed to acclimate to the facility for 6 days prior to study onset.

Test Materials

TABLE 97

Summary of test materials

| Test Material | Supplier | Catalog No. |
|---|---|---|
| 25 G × 1 inch Thin-walled needle | Terumo, | NN2525R |
| 25 G × 1 inch Precision Glide needle | Becton Dickinson, Franklin Lakes, NJ | 305125 |
| 18 G × 1½ inch needle | Becton Dickinson, Franklin Lakes, NJ | 305196 |
| 30 mL Luer-Lok ™ syringe | Becton Dickinson, Franklin Lakes, NJ | 305167 |
| 20 mL Luer-Lok ™ syringe | Becton Dickinson, Franklin Lakes, NJ | 302830 |
| 10 mL Luer-Lok ™ syringe | Becton Dickinson, Franklin Lakes, NJ | 302995 |
| 3 mL Luer-Lok ™ syringe | Becton Dickinson, Franklin Lakes, NJ | 309657 |
| High Volume Auto-Injector device | Halozyme, Inc. | N/A |
| Cyclic olefin copolymer (COC) syringes | SCHOTT Pharma | 101-787-TAB - 10 mL TOPPAC Syringe |
| Plunger for COC syringe | SCHOTT Pharma | 101-788-001 - 10 mL TOPPAC plunger |
| Digital Stopwatch | Fisher Scientific | 14-648 |

Experimental Design

In this study, two 10 mL injections of GGL+EDP were administered to the abdomen of a Yucatan miniature pig using a prototype HVAI device. Two devices were tested on each animal—one device had a 25 G-Terumo needle attached while a second device had a 25 G-BD needle attached that was used for injection on the contralateral side of the animal. A description of cohorts is summarized in Table 98.

TABLE 98

Description of Cohorts

| Cohort | N/Cohort | Test Solution | Volume (mL) | HVAI Needle Gauge | [EDP] (U/mL) |
|---|---|---|---|---|---|
| 1 | 6 | GGL + EDP | 10 | 25 G-Terumo | 4000 |
| 2 | 6 | GGL + EDP | 10 | 25 G-BD | |

Quantitative study endpoints included duration of the injection (time) collected via stopwatch and quantification of post-injection back-leakage. Back-leakage was collected for a period of 30 seconds following the removal of the needle from the skin using an eye-spear to absorb any leakage and quantified by weight.

Prior to study start, animals were assessed for general health and body weights were collected. On study day devices were removed from 2-8° C. storage and placed on ice in an insulated container for transport to the animal facility. Devices were removed approximately 45 minutes prior to use. The amount of time that each injector was at room temperature prior to injection was recorded on data sheets for each animal.

Animals were anesthetized with isoflurane gas and placed in dorsal recumbence on a foam wedge placed on a heated surgical table, and they were maintained under isoflurane gas for the entire duration of the procedure. The abdominal region was cleaned with Nolvasan followed by wiping the injection site with gauze containing 70% isopropanol and wiped dry with sterile gauze. Injection sites were located on the left and right abdominal regions, ~6 cm cranially from the inguinal fold towards the midline and ~3 cm towards the midline of the animal. Each of the injection sites was marked with a permanent marker and then photographed with the standard and 3D cameras prior to needle insertion.

Each animal had an injection from a device with a 25 G-Terumo needle attached and one device with a 25 G-BD needle attached on the contralateral side of the abdomen.

The duration of each injection using the HVAI was measured by using a hand-held stopwatch.

Test solution back-leakage was then absorbed to a pre-tared eye-spear for 30 seconds by blotting the injection site. The weight of the eye spear was recorded using analytical balance with an accuracy of 0.1 mg.

Calculations and Statistical Methods

Assessment of Injection Time

The duration of the injection was calculated based upon measurements collected using a stopwatch.

Results and Discussion

Injection Depth

The needle length for injection depth was measure for each HVAI prior to use. The length of the needle for HVAI attached to the 25 G-Terumo needle was found to be approximately 8 mm (7.9±0.1 mm) whereas the length of the needle for the HVAI attached to the 25 G-BD needle was found to be approximately 10 mm (9.9±0.1 mm).

Duration of Injection

Injection times (seconds) were measured utilizing a hand-held stopwatch and closely monitoring the start and completion of the injection. Mean injection times, calculated by video analysis for each configuration of HVAI, are shown in Table 99 and individual animal data (Mean±SEM) are shown in FIG. 171.

TABLE 99

Comparison of injection time (sec)

| | Injection Time (sec ± SEM) | |
|---|---|---|
| Needle Gauge | 25 G-Terumo | 25 G-BD |
| | 19.10 ± 0.5 | 30.0 ± 1.1 |

Assessment of post-injection back-leakage: The amount of back-leakage for each injection was measured by collecting post-injection fluid from the injection site using a surgical eye spear for 30 seconds immediately following needle removal. Prior to collection the weight of each eye spear was tared on the analytical balance, and then re-weighed following fluid collection. The analytical balance had a precision of 0.1 mg. Back-leakage for devices using a 25 G-Terumo needle and a 25 G-BD needle for individual animal is shown in Table 100 and individual animal data (Mean±SEM) is shown in FIG. 172.

TABLE 100

Mean weight of back-leakage (mg ± SEM)

| | Needle Gauge | |
|---|---|---|
| Needle Gauge | 25 G-Terumo | 25 GBD |
| 25 G | 40.0 ± 15.4 | 14.7 ± 5.9 |

SUMMARY AND CONCLUSIONS

The HVAI devices with a 25 G-Terumo thin-walled needle attached had a reduced time of delivery compared to HVAI devices attached to a 25 G-BD needle: (20 sec vs. 30 sec.) likely a result of the wider bore of the 25 G-Terumo needle.

Back-leakage was reduced for all HVAI devices attached to a 25 G-BD needle compared to the HVAI device attached to a 25 G-Terumo needle (15 mg vs. 40 mg).

The invention claimed is:

1. A method of subcutaneous administration of a hyaluronidase PH20 enzyme formulation to a subject in need thereof,
the method comprising subcutaneously administering to the subject in need thereof about 3 mL to about 50 mL of a formulation comprising recombinant human hyaluronidase PH20 enzyme comprising a sequence having at least 95% amino acid sequence identity to an amino acid sequence selected from any of SEQ ID NO: 1 through 7, and having an activity of about 500 U/mL to about 5,000 U/mL, and an antibody,
wherein the subcutaneous administration occurs via a high volume autoinjector at a rate of about 0.10 mL/sec to about 1.0 mL/sec and with a starting delivery force of about 3 lbf to about 50 lbf, an ending delivery force of about 5 lbf to about 20 lbf, a starting pressure of about 50 psi to about 200 psi, and/or an ending pressure of about 20 psi to about 75 psi.

2. The method of claim 1, comprising administering to the subject about 10 mL to about 20 mL of the formulation.

3. The method of claim 1, comprising administering to the subject about 3 mL to about 15 mL of the formulation.

4. The method of claim 1, wherein the high volume autoinjector comprises a prefilled syringe containing the formulation.

5. The method of claim 4, wherein the prefilled syringe comprises a needle having a gauge of about 20 to about 33.

6. The method of claim 1, wherein the formulation has a viscosity of about 1 cP to about 50 cP.

7. The method of claim 1, wherein administration of the formulation requires less applied force when compared to a similar formulation that does not comprise a hyaluronidase enzyme.

8. The method of claim 1, wherein administration of the formulation is faster when compared to a similar formulation that does not comprise a hyaluronidase enzyme.

9. The method of claim 1, wherein administration of the formulation causes fewer side effects, less pain, and less discomfort in the subject when compared to a similar formulation that does not comprise a hyaluronidase enzyme.

10. The method of claim 1, wherein administration of the formulation causes less back leakage at the injection site when compared to a similar formulation that does not comprise a hyaluronidase enzyme.

11. The method of claim 1, wherein administration of the formulation causes less swelling volume and/or swelling height at the injection site when compared to a similar formulation that does not comprise a hyaluronidase enzyme.

12. The method of claim 1, wherein the administering comprises the subject self-administering the formulation.

* * * * *